US009216980B2

(12) United States Patent
Chen et al.

(10) Patent No.: US 9,216,980 B2
(45) Date of Patent: *Dec. 22, 2015

(54) METHODS OF USE OF DIAZACARBAZOLES FOR TREATING CANCER

(71) Applicant: Genentech, Inc., South San Francisco, CA (US)

(72) Inventors: Huifen Chen, Burlingame, CA (US); Hazel Joan Dyke, Harlow (GB); Charles Ellwood, Harlow (GB); Emanuela Gancia, Harlow (GB); Lewis J. Gazzard, Belmont, CA (US); Simon Goodacre, Harlow (GB); Samuel Kintz, Redwood City, CA (US); Joseph Lyssikatos, Piedmont, CA (US); Calum MacLeod, Harlow (GB); Karen Williams, Harlow (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/255,898

(22) Filed: Apr. 17, 2014

(65) Prior Publication Data

US 2015/0087630 A1 Mar. 26, 2015

Related U.S. Application Data

(63) Continuation of application No. 13/890,949, filed on May 9, 2013, now abandoned, which is a continuation of application No. 12/997,066, filed as application No. PCT/US2009/003492 on Jun. 10, 2009, now Pat. No. 8,501,765.

(60) Provisional application No. 61/148,001, filed on Jan. 28, 2009, provisional application No. 61/060,746, filed on Jun. 11, 2008.

(51) Int. Cl.
| | |
|---|---|
| A61K 31/437 | (2006.01) |
| A61K 31/496 | (2006.01) |
| C07D 471/14 | (2006.01) |
| A61K 31/4375 | (2006.01) |
| A61K 31/497 | (2006.01) |
| A61K 31/501 | (2006.01) |
| A61K 31/506 | (2006.01) |
| A61K 31/519 | (2006.01) |
| A61K 31/5377 | (2006.01) |
| A61K 31/541 | (2006.01) |
| A61K 45/06 | (2006.01) |
| C07D 491/107 | (2006.01) |
| C07D 495/04 | (2006.01) |
| C07D 513/04 | (2006.01) |
| A61K 31/55 | (2006.01) |
| A61K 31/553 | (2006.01) |
| C07D 519/00 | (2006.01) |

(52) U.S. Cl.
CPC .......... *C07D 471/14* (2013.01); *A61K 31/4375* (2013.01); *A61K 31/496* (2013.01); *A61K 31/497* (2013.01); *A61K 31/501* (2013.01); *A61K 31/506* (2013.01); *A61K 31/519* (2013.01); *A61K 31/5377* (2013.01); *A61K 31/541* (2013.01); *A61K 31/55* (2013.01); *A61K 31/553* (2013.01); *A61K 45/06* (2013.01); *C07D 491/107* (2013.01); *C07D 495/04* (2013.01); *C07D 513/04* (2013.01); *C07D 519/00* (2013.01)

(58) Field of Classification Search
USPC ........................................ 514/293, 253, 232.8
See application file for complete search history.

(56) References Cited

U.S. PATENT DOCUMENTS

| | | | |
|---|---|---|---|
| 8,501,765 B2* | 8/2013 | Chen et al. ............. | 514/293 |
| 2002/0099068 A1 | 7/2002 | Ritzeler et al. | |
| 2006/0264493 A1 | 11/2006 | Vanotti et al. | |
| 2009/0232885 A1 | 9/2009 | Venkatesh et al. | |
| 2011/0178053 A1 | 7/2011 | Arendt et al. | |
| 2012/0208809 A1 | 8/2012 | Babin et al. | |

FOREIGN PATENT DOCUMENTS

| | | |
|---|---|---|
| JP | 2003-527394 | 9/2003 |
| JP | 2011-513498 | 4/2011 |

(Continued)

OTHER PUBLICATIONS

Bahekar et al. et al., "Synthesis of 3,8,9-trisubstitued-1,7,9-triaza-fluorene-6-carboxylic acid derivatives as a new class of insulin secretagogues" Bioorg Med Chem 15(17):5950-64 (Sep. 2007).
Bartek and Lukas, "Chk1 and Chk2 kinases in checkpoint control and cancer" Cancer Cell 3(5):421-9 (2003).
Bartek et al., "CHK2 kinase—a busy messenger" Nat Rev Mol Cell Biol. 2(12);877-86 (2001).
Bhatti et al. et al., "Pyrolysis of 1-substituted pyrazoles and chloroform at 550 C: formation of α-carboline from 1-benzylpyrazoles" J Chem Soc 1997:3581-5 ( 1997).

(Continued)

*Primary Examiner* — Charanjit Aulakh
(74) *Attorney, Agent, or Firm* — Viksnins Harris & Padys PLLP

(57) ABSTRACT

Methods of use of compounds of formula (I) for treating cancer:

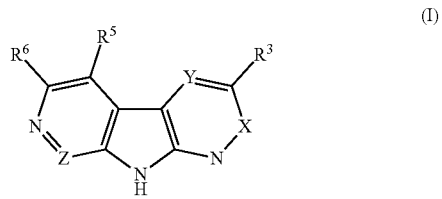

(I)

wherein X, Y, X, $R^3$, $R^5$ and $R^6$ are as defined herein.

37 Claims, No Drawings

(56) References Cited

FOREIGN PATENT DOCUMENTS

| WO | 01/68648 A1 | 9/2001 |
| WO | WO 03/022849 | 3/2003 |
| WO | WO 2006/131552 | 12/2006 |
| WO | 2007/044779 A1 | 4/2007 |
| WO | 2008/045834 | 4/2008 |
| WO | 2008/054956 | 5/2008 |
| WO | 2009/004329 A1 | 1/2009 |
| WO | 2009/129401 | 10/2009 |
| WO | 2010/015589 | 2/2010 |

OTHER PUBLICATIONS

Hartwell et al., "Checkpoints: controls that ensure the order of cell cycle events" Science 246(4930):629-34 (Nov. 1989).

Hayakawa et al., "Synthesis and biological evaluation of pyrido[3',2':4,5]furo[3,2-d]pyrimidine derivatives as novel PI3 kinase p110α inhibitors" Bioorg Med Chem Lett 17(9):2438-42 (May 2007).

International Search Report, Written Opinion, and International Preliminary Report on Patentability for PCT/US2009/003492, mailed Oct. 7, 2009.

* cited by examiner

METHODS OF USE OF DIAZACARBAZOLES FOR TREATING CANCER

CROSS REFERENCE TO RELATED APPLICATIONS

This application is a continuation of U.S. patent application Ser. No. 13/890,949 filed May 9, 2013 which is a continuation of U.S. patent application Ser. No. 12/997,066 filed Jun. 10, 2009, which is a U.S. National Phase Entry of PCT Patent Application PCT/US2009/003492 filed Jun. 10, 2009, which claims priority to U.S. Provisional Application No. 61/060,746, filed Jun. 11, 2008 and U.S. Provisional Application No. 61/148,001, filed Jan. 28, 2009, the disclosures of which are all incorporated herein by reference in their entirety.

The invention relates to 1,7-diazacarbazole compounds which are useful as kinase inhibitors, more specifically useful as checkpoint kinase 1 (chk1) inhibitors, thus useful as cancer therapeutics. The invention also relates to compositions, more specifically pharmaceutical compositions comprising these compounds and methods of using the same to treat various forms of cancer and hyperproliferative disorders, as well as methods of using the compounds for in vitro, in situ, and in vivo diagnosis or treatment of mammalian cells, or associated pathological conditions.

Individual cells replicate by making an exact copy of their chromosomes, and then segregating these into separate cells. This cycle of DNA replication, chromosome separation and division is regulated by mechanisms within the cell that maintain the order of the steps and ensure that each step is precisely carried out. Involved in these processes are the cell cycle checkpoints (Hartwell et al., Science, Nov. 3, 1989, 246(4930):629-34) where cells may arrest to ensure DNA repair mechanisms have time to operate prior to continuing through the cycle into mitosis. There are two such checkpoints in the cell cycle—the G1/S checkpoint that is regulated by p53 and the G2/M checkpoint that is monitored by the serine/threonine kinase checkpoint kinase 1 (chk1).

Chk1 and chk2 are structurally unrelated yet functionally overlapping serine/threonine kinases activated in response to genotoxic stimuli (reviewed in Bartek et al., Nat. Rev. Mol. Cell Biol. 2001, vol. 2, pp. 877-886). Chk1 and chk2 relay the checkpoint signals from the ATM and ATR, which phosphorylate and activate them. Chk2 is a stable protein expressed throughout the cell cycle, activated mainly by ATM in response to double-strand DNA breaks (DSBs). In contrast, Chk1 protein expression is largely restricted to S and G2 phases. In response to DNA damage, ChK1 is phosphorylated and activated by ATM/ATR, resulting in cell cycle arrest in the S and G2/M phases to allow for repair of DNA damage (reviewed in Cancer Cell, Bartek and Lukas, Volume 3, Issue 5, May 2003, Pages 421-429. Inhibition of Chk1 has been shown to abrogate cell cycle arrest leading to enhanced tumor cell death following DNA damage by a range of chemotherapeutics. Cells lacking intact G1 checkpoints are particularly dependent on S and G2/M checkpoints and are therefore expected to be more sensitive to chemotherapeutic treatment in the presence of a chk1 inhibitor, whereas normal cells with functional G1 checkpoints would be predicted to undergo less cell death.

The invention relates to 1,7-diazacarbazoles of Formula (I), (I-a), and/or (I-b) (and/or solvates, hydrates and/or salts thereof) with kinase inhibitory activity, more specifically with chk1 inhibitory activity. The compounds of the present invention are also useful as inhibitors of Glycogen Synthase Kinase-3 (GSK-3), KDR kinase, and FMS-like tyrosine kinase 3 (FLT3). Accordingly, the compounds of the invention and compositions thereof are useful in the treatment of hyperproliferative disorders such as cancer.

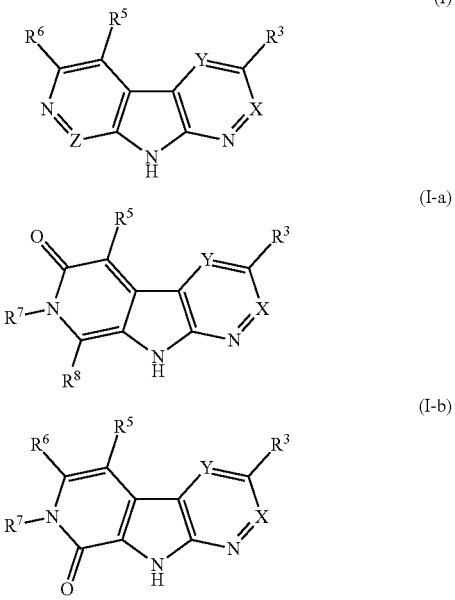

X is $CR^2$ or N;
Y is $CR^4$ or N;
Z is $CR^8$ or N; provided that no more than one of X, Y and Z is N at the same time;
$R^2$ is H, halo, CN, $CF_3$, —$OCF_3$, OH, —$NO_2$, $C_1$-$C_5$ alkyl, —$O(C_1$-$C_5$ alkyl), —$S(C_1$-$C_5$ alkyl), or $N(R^{22})_2$;
$R^3$ is H, halo, CN, —O—$R^9$, —$N(R^{22})$—$R^9$, —$S(O)_p$—$R^9$, or $R^9$;
p is 0, 1 or 2;
$R^4$ is H, halo, CN, $CF_3$, —$OCF_3$, OH, —$NO_2$, —$(CR^{14}R^{15})_nC(=Y')OR^{11}$, —$(CR^{14}R^{15})_nC(=Y')NR^{11}R^{12}$, —$(CR^{14}R^{15})_nNR^{11}R^{12}$, —$(CR^{14}R^{15})_nOR^{11}$, —$(CR^{14}R^{15})_nS(O)_pR^{11}$, —$(CR^{14}R^{15})_nNR^{12}C(=Y')R^{11}$, —$(CR^{14}R^{15})_nNR^{12}C(=Y')OR^{11}$, —$(CR^{14}R^{15})_nNR^{12}C(=Y')NR^{11}R^{12}$, —$(CR^{14}R^{15})_nNR^{12}SO_2R^{11}$, —$(CR^{14}R^{15})_nOC(=Y')R^{11}$, —$(CR^{14}R^{15})_nOC(=Y')NR^{11}R^{12}$, —$(CR^{14}R^{15})_nS(O)_2NR^{11}R^{12}$, alkyl, alkenyl, alkynyl, cycloalkyl, heterocyclyl, aryl, or heteroaryl wherein said alkyl, alkenyl, alkynyl, cycloalkyl, heterocyclyl, aryl and heteroaryl are optionally substituted with one to four $R^{13}$ groups;
each n is independently 0-5;
$R^5$ is H, halo, CN, $CF_3$, —$OCF_3$, OH, —$NO_2$, —$(CR^{14}R^{15})_nC(=Y')OR^{11}$, —$(CR^{14}R^{15})_nC(=Y')NR^{11}R^{12}$, —$(CR^{14}R^{15})_nNR^{12}C(=Y')R^{11}$, —$(CR^{14}R^{15})_nNR^{11}NR^{12}$, —$(CR^{14}R^{15})_nOR^{11}$, —$(CR^{14}R^{15})_nS(O)_pR^{11}$, —$(CR^{14}R^{15})_nNR^{12}C(=Y')OR^{11}$, —$(CR^{14}R^{15})_nNR^{12}C(=Y')NR^{11}R^{12}$, —$(CR^{14}R^{15})_nNR^{12}SO_2R^{11}$, —$(CR^{14}R^{15})_nOC(=Y')R^{11}$, —$(CR^{14}R^{15})_nOC(=Y')NR^{11}R^{12}$, —$(CR^{14}R^{15})_nS(O)_2NR^{11}R^{12}$, alkyl, alkenyl, alkynyl, cycloalkyl, heterocyclyl, aryl, heteroaryl wherein the said alkyl, alkenyl, alkynyl, cycloalkyl, heterocyclyl, aryl and heteroaryl are optionally substituted with one to four $R^{13}$ groups;
$R^6$ is H, CN, —$CF_3$, —$OCF_3$, halo, —$C(=Y')OR^{11}$, —$C(=Y')NR^{11}R^{12}$, —$OR^{11}$, —$OC(=Y')R^{11}$, —$NR^{11}R^{12}$, —$NR^{12}C(=Y')R^{11}$, —$NR^{12}C(=Y')NR^{12}S$ $-(O)_qR^{11}$, $-SR^{11}$, $-S(O)R^{11}$, $-S(O)_2R^{11}$, $-OC(=Y')NR^{11}R^{12}$, $-S(O)_2NR^{11}R^{12}$, alkyl, alkenyl, alkynyl, cycloalkyl, heterocyclyl, aryl, or heteroaryl wherein said alkyl, alkenyl, alkynyl, cycloalkyl, heterocyclyl, aryl and heteroaryl are optionally substituted by one to four $R^{13}$ groups;

$R^7$ is H, OH, CN, $O(C_1$-$C_3$ alkyl), or $C_1$-$C_4$ alkyl, wherein each said alkyl is optionally substituted with one to three groups independently selected from halo, $N(R^{22})_2$ or $OR^{22}$;

$R^8$ is H, halo, CN, $NO_2$, $N(R^{22})_2$, OH, $O(C_1$-$C_3$ alkyl), or $C_1$-$C_3$ alkyl, wherein each said alkyl is optionally substituted with one to three fluoro groups;

each $R^9$ is independently alkyl, alkenyl, alkynyl, cycloalkyl, heterocyclyl, aryl, heteroaryl, wherein each member of $R^9$ is independently substituted with one to three $R^{10}$ groups;

each $R^{10}$ is independently H, CN, $-CF_3$, $-OCF_3$, $-NO_2$, halo, $R^{11}$, $-OR^{11}$, $-NR^{12}C(=Y')R^{11}$, $-NR^{12}C(=NR^{12})R^{11}$, $-NR^{12}S(O)_qR^{11}$, $-SR^{11}$, $-NR^{11}R^{12}$, oxo, $-C(=Y')OR^{11}$, $-C(=Y')NR^{11}R^{12}$, $-S(O)_qR^{11}$, $-NR^{12}C(=Y')OR^{11}$, $-NR^{12}C(=Y')NR^{11}R^{12}$, $-OC(=Y')R^{11}$, $-OC(=Y')NR^{11}R^{12}$, or $-S(O)_2NR^{11}R^{12}$;

each q independently is 1 or 2;

$R^{11}$ and $R^{12}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{13}$ groups, wherein two geminal $R^{13}$ groups are optionally taken together with the atom to which they are attached to form a 3-6 membered ring having additional 0-2 heteroatoms selected from O, S, and N, said ring being optionally substituted with one to four $R^{18}$ groups;

$R^{11}$ and $R^{12}$ are optionally taken together with the attached N atom to form a 4-7 membered ring having additional 0-2 heteroatoms selected from O, S, and N, said ring being optionally substituted with one to four $R^{13}$ groups;

each $R^{13}$ is independently halo, CN, $CF_3$, $-OCF_3$, $-NO_2$, oxo, $-(CR^{14}R^{15})_nC(=Y')R^{16}$, $-(CR^{14}R^{15})_nC(=Y')OR^{16}$, $-(CR^{14}R^{15})_nC(=Y')NR^{16}R^{17}$, $-(CR^{14}R^{15})_nNR^{16}R^{17}$, $-(CR^{14}R^{15})_nOR^{16}$, $-(CR^{14}R^{15})_nSR^{16}$, $-(CR^{14}R^{15})_nNR^{16}C(=Y')R^{17}$, $-(CR^{14}R^{15})_nNR^{16}C(=Y')OR^{17}$, $-(CR^{14}R^{15})_nNR^{17}C(=Y')NR^{16}R^{17}$, $-(CR^{14}R^{15})_nNR^{17}SO_2R^{16}$, $-(CR^{14}R^{15})_nOC(=Y')R^{16}$, $-(CR^{14}R^{15})_nOC(=Y')NR^{16}R^{17}$, $-(CR^{14}R^{15})_nS(O)R^{16}$, $-(CR^{14}R^{15})_nS(O)_2R^{16}$, $-(CR^{14}R^{15})_nS(O)_2NR^{16}R^{17}$, or $R^{16}$;

$R^{14}$ and $R^{15}$ are independently selected from H, alkyl, cycloalkyl, heterocyclyl, aryl or heteroaryl, wherein said alkyl, cycloalkyl, heterocyclyl, aryl and heteroaryl are optionally substituted with one to four $R^{18}$ groups;

$R^{16}$ and $R^{17}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{18}$ groups;

$R^{16}$ and $R^{17}$ are optionally taken together with the attached N atom to form a 5-6 membered ring having additional 0-2 heteroatoms selected from O, S, and N, said ring being optionally substituted with one to four $R^{18}$ groups;

each $R^{18}$ is independently H, alkyl, cycloalkyl, heterocyclyl, aryl, heteroaryl, halo, CN, $CF_3$, $-OCF_3$, $-NO_2$, oxo, $-(CR^{19}R^{20})_nC(=Y')R^{23}$, $-(CR^{19}R^{20})_nC(=Y')OR^{23}$, $-(CR^{19}R^{20})_nC(=Y')NR^{23}R^{24}$, $-(CR^{19}R^{20})_nNR^{23}R^{24}$, $-(CR^{19}R^{20})_nOR^{23}$, $-(CR^{19}R^{20})_nSR^{23}$, $-(CR^{19}R^{20})_nNR^{24}C(=Y')R^{23}$, $-(CR^{19}R^{20})_nNR^{24}C(=Y')OR^{23}$, $-(CR^{19}R^{20})_nNR^{22}C(=Y')NR^{23}R^{24}$, $-(CR^{19}R^{20})_nNR^{24}SO_2R^{23}$, $-(CR^{19}R^{20})_nOC(=Y')R^{23}$, $-(CR^{19}R^{20})_nOC(=Y')NR^{23}R^{24}$, $-(CR^{19}R^{20})_nS(O)R^{23}$, $-(CR^{19}R^{20})_nS(O)_2R^{23}$, or $-(CR^{19}R^{20})_nS(O)_2NR^{23}R^{24}$, wherein said alkyl, cycloalkyl, heterocyclyl, aryl, and heteroaryl are optionally substituted with one to four $R^{21}$ groups;

$R^{19}$ and $R^{20}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{25}$ groups;

$R^{23}$ and $R^{24}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{21}$ groups;

$R^{23}$ and $R^{24}$ are optionally taken together with the attached N atom to form a 5-6 membered ring having additional 0-2 heteroatoms selected from O, S, and N, said ring being optionally substituted with one to four $R^{21}$ groups;

each $R^{21}$ is independently H, alkyl, cycloalkyl, heterocyclyl, aryl, heteroaryl, halo, CN, $CF_3$, $-OCF_3$, $-NO_2$, oxo, $-C(=Y')R^{25}$, $-C(=Y')OR^{25}$, $-C(=Y')NR^{25}R^{26}$, $-NR^{25}R^{26}$, $-OR^{25}$, $-SR^{25}$, $-NR^{26}C(=Y')R^{25}$, $-NR^{26}C(=Y')OR^{25}$, $-NR^{22}C(=Y')NR^{25}R^{26}$, $-NR^{26}SO_2R^{25}$, $-OC(=Y')R^{25}$, $-OC(=Y')NR^{25}R^{26}$, $-S(O)R^{25}$, $-S(O)_2R^{25}$, or $-S(O)_2NR^{25}R^{26}$, wherein said alkyl, cycloalkyl, heterocyclyl, aryl, and heteroaryl are optionally substituted with one to four $R^{25}$ groups;

each $R^{25}$ and $R^{26}$ is independently H, alkyl, cycloalkyl, heterocyclyl, aryl, or heteroaryl, wherein said alkyl, cycloalkyl, heterocyclyl, aryl, or heteroaryl is optionally substituted with one to four groups selected from halo, $-CN$, $-OCF_3$, $-CF_3$, $-NO_2$, $-C_1$-$C_6$ alkyl, $-OH$, oxo, $-SH$, $-O(C_1$-$C_6$ alkyl), $-S(C_1$-$C_6$ alkyl), $-NH_2$, $-NH(C_1$-$C_6$ alkyl), $-N(C_1$-$C_6$ alkyl)$_2$, $-SO_2(C_1$-$C_6$ alkyl), $-CO_2H$, $-CO_2(C_1$-$C_6$ alkyl), $-C(O)NH_2$, $-C(O)NH(C_1$-$C_6$ alkyl), $-C(O)N(C_1$-$C_6$ alkyl)$_2$, $-N(C_1$-$C_6$ alkyl)C(O)(C_1$-$C_6$ alkyl), $-NHC(O)(C_1$-$C_6$ alkyl), $-NHSO_2(C_1$-$C_6$ alkyl), $-N(C_1$-$C_6$ alkyl)SO_2(C_1$-$C_6$ alkyl), $-SO_2NH_2$, $-SO_2NH(C_1$-$C_6$ alkyl), $-SO_2N(C_1$-$C_6$ alkyl)$_2$, $-OC(O)NH_2$, $-OC(O)NH(C_1$-$C_6$ alkyl), $-OC(O)N(C_1$-$C_6$ alkyl)$_2$, $-NHC(O)NH(C_1$-$C_6$ alkyl), $-NHC(O)N(C_1$-$C_6$ alkyl)$_2$, $-N(C_1$-$C_6$ alkyl)C(O)NH(C_1$-$C_6$ alkyl), $-N(C_1$-$C_6$ alkyl)C(O)N(C_1$-$C_6$ alkyl)$_2$, $-NHC(O)NH(C_1$-$C_6$ alkyl), $-NHC(O)N(C_1$-$C_6$ alkyl)$_2$, $-NHC(O)O(C_1$-$C_6$ alkyl), and $-N(C_1$-$C_6$ alkyl)C(O)O(C_1$-$C_6$ alkyl);

$R^{25}$ and $R^{26}$ are optionally taken together with the attached N atom to form a 5-6 membered ring having additional 0-2 heteroatoms selected from O, S, and N, said ring being optionally substituted with one to four groups selected from halo, $-CN$, $-OCF_3$, $CF_3$, $-NO_2$, $-C_1$-$C_6$ alkyl, $-OH$, oxo, $-SH$, $-O(C_1$-$C_6$ alkyl), $-S(C_1$-$C_6$ alkyl), $-NH_2$, $-NH(C_1$-$C_6$ alkyl), $-N(C_1$-$C_6$ alkyl)$_2$, $-SO_2(C_1$-$C_6$ alkyl), $-CO_2H$, $-CO_2(C_1$-$C_6$ alkyl), $-C(O)NH_2$, $-C(O)NH(C_1$-$C_6$ alkyl), $-C(O)N(C_1$-$C_6$ alkyl)$_2$, $-N(C_1$-$C_6$ alkyl)C(O)(C_1$-$C_6$ alkyl), $-NHC(O)(C_1$-$C_6$ alkyl), $-NHSO_2(C_1$-$C_6$ alkyl), $-N(C_1$-$C_6$ alkyl)SO_2(C_1$-$C_6$ alkyl), $-SO_2NH_2$, $-SO_2NH(C_1$-$C_6$ alkyl), $-SO_2N(C_1$-$C_6$ alkyl)$_2$, $-OC(O)NH_2$, $-OC(O)NH(C_1$-$C_6$ alkyl), $-OC(O)N(C_1$-$C_6$ alkyl)$_2$, $-NHC(O)NH(C_1$-$C_6$ alkyl), $-NHC(O)N(C_1$-$C_6$ alkyl)$_2$, $-N(C_1$-$C_6$ alkyl)C(O)NH(C_1$-$C_6$ alkyl), $-N(C_1$-$C_6$ alkyl)C(O)N(C_1$-$C_6$ alkyl)$_2$, $-NHC(O)NH(C_1$-$C_6$ alkyl), $-NHC(O)N(C_1$-$C_6$ alkyl)$_2$, $-NHC(O)O(C_1$-$C_6$ alkyl), and $-N(C_1$-$C_6$ alkyl)C(O)O(C_1$-$C_6$ alkyl);

Y' is independently O, $NR^{22}$, or S; and each $R^{22}$ is independently H or $C_1$-$C_5$ alkyl.

The present invention includes a composition (e.g., a pharmaceutical composition) comprising a compound of Formula (I), (I-a), and/or (I-b) (and/or solvates, hydrates and/or salts thereof) and a carrier (a pharmaceutically acceptable carrier). The present invention also includes a composition (e.g., a pharmaceutical composition) comprising a compound of Formula (I), (I-a), and/or (I-b) (and/or solvates, hydrates and/or salts thereof) and a carrier (a pharmaceutically acceptable carrier), further comprising a second chemotherapeutic agent. The present compositions are therefore useful for inhibiting abnormal cell growth or treating a hyperproliferative disorder in a mammal (e.g., human), such as cancer.

The present invention includes a method of inhibiting abnormal cell growth or treating a hyperproliferative disorder in a mammal (e.g., human) such as cancer comprising administering to said mammal a therapeutically effective amount of a compound of Formula (I), (I-a), and/or (I-b) (and/or solvates, hydrates and/or salts thereof) or a composition thereof, alone or in combination with a second chemotherapeutic agent.

The present invention includes a method of using the present compounds for in vitro, in situ, and in vivo diagnosis or treatment of mammalian cells, organisms, or associated pathological conditions. Also included are methods for making the present compounds.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

The term "alkyl" as used herein refers to a saturated linear or branched-chain monovalent hydrocarbon radical of one to twelve carbon atoms. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl (—C≡CH), propynyl (propargyl, —CH$_2$C≡CH), and the like.

The term "cycloalkyl" refers to a monovalent non-aromatic, saturated or partially unsaturated ring having 3 to 12 carbon atoms as a monocyclic ring or 6 to 12 carbon atoms as a bicyclic ring. Bicyclic carbocycles having 6 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-14 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like.

The terms "heterocycle," "heterocyclyl" and "heterocyclic ring" are used interchangeably herein and refer to a saturated or a partially unsaturated (i.e., having one or more double bonds within the ring) carbocyclic radical of 3 to 14 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, and S) or a bicycle having 6 to 10 ring members (4 to 9 carbon atoms and 1 to 6 heteroatoms selected from N, O, and S), for example: a bicyclo[4,5], [5,5], [5,6], or [6,6] system or a bridged [2.1.1], [2.2.1], [2.2.2] or [3.2.2] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-16 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, tetrahydrothiophene, pyrrole or pyrrolidine, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, 2-oxo-1,2-dihydropyridine, or 4-oxo-1,4-dihydropyridine; position 2 of a isoindole, or isoindoline; position 4 of a morpholine; and position 9 of a carbazole, or β-carboline.

The term "halo" refers to F, Cl, Br or I. The heteroatoms present in heteroaryl or heterocyclyl include the oxidized forms such as $N^+\rightarrow O^-$, $S(O)$ and $S(O)_2$.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "abnormal cell growth" and "hyperproliferative disorder" are used interchangeably in this application. "Abnormal cell growth", as used herein, unless otherwise indicated, refers to cell growth that is independent of normal regulatory mechanisms. This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Tumors include solid and liquid tumors. Examples of cancer include, but are not limited to, carcinoma, lymphoma, blastoma, sarcoma, myeloma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, malignant brain tumors, melanoma, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, as well as acute myelogenous leukemia (AML).

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), Leucovorin, Rapamycin (Sirolimus, RAPAMUNE®, Wyeth), Lapatinib (TYKERB®, GSK572016, Glaxo Smith Kline), Lonafamib (SCH 66336), Sorafenib (BAY43-9006, Bayer Labs), and Gefitinib (IRESSA®, AstraZeneca), AG1478, AG1571 (SU 5271; Sugen), alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; am inolevulinic acid; eniluracil; bestrabucil; bisantrene; edatraxate; defofamine; demecolcine; diaziquone; elfornithine; elliptinium acetate; an epothilone; etoglucid; gallium nitrate; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); chloranmbucil; 6-thioguanine; mercaptopurine; ifosfamide; mitoxantrone; novantrone; edatrexate; daunomycin; aminopterin; capecitabine (XELODA®); ibandronate; CPT-11; difluoromethylornithine (DMFO); and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Other examples of "chemotherapeutic agents" that can be used in combination with the present compounds include inhibitors of MEK (MAP kinase kinase), such as XL518 (Exelixis, Inc.) and AZD6244 (Astrazeneca); inhibitors of Raf, such as XL281 (Exelixis, Inc.), PLX4032 (Plexxikon), and ISIS5132 (Isis Pharmaceuticals); inhibitors of mTor (mammalian target of rapamycin), such as rapamycin, AP23573 (Ariad Pharmaceuticals), temsirolimus (Wyeth Pharmaceuticals) and RAD001 (Novartis); inhibitors of PI3K (phosphoinositide-3 kinase), such as SF-1126 (PI3K inhibitor, Semafore Pharmaceuticals), BEZ-235 (PI3K inhibitor, Novartis), XL-147 (PI3K inhibitor, Exelixis, Inc.), and GDC-0941 (Genentech); inhibitors of cMet, such as PHA665752 (Pfizer), XL-880 (Exelixis, Inc.), ARQ-197 (ArQule), and CE-355621; and pharmaceutically acceptable salts, acids and derivatives of any of the above.

Examples of a "chemotherapeutic agent" also include a DNA damaging agent such as thiotepa and CYTOXAN® cyclosphosphamide; alkylating agents (for example cis-platin; carboplatin; cyclophosphamide; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; busulphan; nitrosoureas such as carmustine, chlorozotocin, fotemustine, lomustine, nimustine, and ranimnustine; and temozolomide); antimetabolites (for example antifolates such as fluoropyrimidines like 5-fluorouracil (5-FU) and tegafur, raltitrexed, methotrexate, cytosine arabinoside, hydroxyurea and GEMZAR® (gemcitabine); antitumour antibiotics such as the enediyne antibiotics (e.g., calicheamicin, especially calicheamicin gamma 1I and calicheamicin omegaII (Angew Chem. Intl. Ed. Engl. (1994) 33:183-186); anthracyclines like adriamycin; dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin, epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; antimitotic agents (for example vinca alkaloids like vincristine, vinblastine, vindesine and NAVELBINE® (vinorelbine) and taxoids like taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); topoisomerase inhibitors (for example RFS 2000, epipodophyllotoxins like etoposide and teniposide, amsacrine, a camptothecin (including the synthetic analog topotecan), and irinotecan and SN-38) and cytodifferentiating agents (for example retinoids such as all-trans retinoic acid, 13-cis retinoic acid and fenretinide); and pharmaceutically acceptable salts, acids and derivatives of any of the above.

A "chemotherapeutic agent" also includes an agent that modulates the apoptotic response including inhibitors of IAP (inhibitor of apoptosis proteins) such as AEG40826 (Aegera Therapeutics); and inhibitors of bcl-2 such as GX15-070 (Gemin X Biotechnologies), CNDO103 (Apogossypol;

Coronado Biosciences), HA14-1 (ethyl 2-amino-6-bromo-4-(1-cyano-2-ethoxy-2-oxoethyl)-4H-chromene-3-carboxylate), AT101 (Ascenta Therapeutics), ABT-737 and ABT-263 (Abbott); and pharmaceutically acceptable salts, acids and derivatives of any of the above.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as chk inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons. For example, any reference to a structure of 2-hydroxypyridine include its tautomer 2-oxo-1,2-dihydropyridine, also known as 2-pyridone, and vice versa. Similarly, compounds of Formula (I-a) include the tautomeric form, i.e., Formula (I-c) and compounds of Formula (I-b) include the tautomeric form, i.e., Formula (I-d).

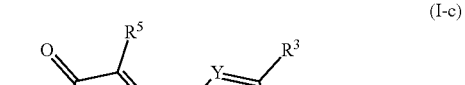

(I-c)

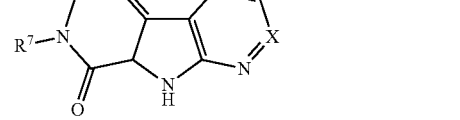

(I-d)

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, methanesulfonic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ), 2-(trimethylsilyl) ethoxymethyl (SEM) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and t-butyldimethylsilyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention", "compounds of Formula (I), (I-a), or (I-b)" and "compounds of Formula (I), (I-a), and/or (I-b)", unless otherwise indicated, include compounds of Formula (I), (I-a), or (I-b) and stereoisomers, geometric isomers, tautomers, solvates, metabolites, salts (e.g., pharmaceutically acceptable salts) and prodrugs thereof. Unless otherwise stated, structures depicted herein are also meant to include compounds that differ only in the presence of one or more isotopically enriched atoms. For example, compounds of Formula (I), (I-a), or (I-b), wherein one or more hydrogen atoms are replaced deuterium or tritium, or one or more carbon atoms are replaced by a $^{13}$C- or $^{14}$C-enriched carbon are within the scope of this invention.

The present invention provides 1,7-diazacarbazoles of Formula (I), (I-a), and/or (I-b) (and/or solvates, hydrates and/or salts thereof) as described above with kinase inhibitory activity, such as chk1, GSK-3, KDR and/or FLT3 inhibitory activities. The present compounds are particularly useful as chk1 kinase inhibitors.

In certain embodiments of the present invention, X is $CR^2$, and all other variables are as defined in Formula (I), (I-a), or (I-b). In certain embodiments of the present invention, $R^2$ is H, $CF_3$, $C_1$-$C_5$ alkyl, or $O(C_1$-$C_5$ alkyl), and all other variables are as defined in Formula (I), (I-a), or (I-b). In certain embodiments of the present invention, $R^2$ is H, $CF_3$, $C_1$-$C_3$ alkyl, or $O(C_1$-$C_3$ alkyl), and all other variables are as defined in Formula (I), (I-a), or (I-b). In certain embodiments of the present invention, $R^2$ is H, and all other variables are as defined in Formula (I), (I-a), or (I-b).

In certain embodiments of the present invention, X is N, and all other variables are as defined in Formula (I), (I-a), or (I-b).

In certain embodiments of the present invention, Y is $CR^4$, and all other variables are as defined in Formula (I), (I-a), or (I-b), or as defined in any one of the embodiments herein.

In certain embodiments of the present invention, $R^4$ is H, and all other variables are as defined in Formula (I), (I-a), or (I-b), or as defined in any one of the embodiments herein. In certain embodiments of the present invention, Y is N, and all other variables are as defined in Formula (I), (I-a), or (I-b), or as defined in any one of the embodiments herein.

In certain embodiments of the present invention, Z is $CR^8$, and all other variables are as defined in Formula (I), (I-a), or (I-b), or as defined in any one of the embodiments herein. In certain embodiments of the present invention, $R^8$ is H, and all other variables are as defined in Formula (I), (I-a), or (I-b), or as defined in any one of the embodiments herein.

In certain embodiments of the present invention, Z is N, and all other variables are as defined in Formula (I), (I-a), or (I-b), or as defined in any one of the embodiments herein.

In certain embodiments of the present invention, $R^3$ is H; and all other variables are as defined in Formula (I), (I-a), or (I-b), or as defined in any one of the embodiments herein.

In certain embodiments of the present invention, $R^3$ is halo, —O—$R^9$, —N($R^{22}$)—$R^9$, —S(O)$_p$—$R^9$, or $R^9$; and all other variables are as defined in Formula (I), (I-a), or (I-b), or as defined in any one of the embodiments herein.

In certain embodiments of the present invention, $R^3$ is halo, and all other variables are as defined in Formula (I), (I-a), or (I-b), or as defined in any one of the embodiments herein. In certain embodiments of the present invention, $R^3$ is Br, and all other variables are as defined in Formula (I), (I-a), or (I-b), or as defined in any one of the embodiments herein. In certain embodiments of the present invention, $R^3$ is F or Cl, and all other variables are as defined in Formula (I), (I-a), or (I-b), or as defined in any one of the embodiments herein.

In certain embodiments of the present invention, $R^3$ is CN, and all other variables are as defined in Formula (I), (I-a), or (I-b), or as defined in any one of the embodiments herein.

In certain embodiments of the present invention, $R^9$ is alkyl, alkynyl, cycloalkyl, heterocyclyl, aryl, or heteroaryl and wherein each member of $R^9$ is independently substituted with one to three $R^{10}$ groups; and all other variables are as defined in Formula (I), (I-a), or (I-b), or as defined in any one of the embodiments herein.

In certain embodiments of the present invention, $R^9$ is $C_1$-$C_6$ alkyl, $C_2$-$C_3$ alkynyl, $C_6$ cycloalkyl, 5-6-membered heterocyclyl having 1 to 2 nitrogen ring atoms, $C_6$ aryl, or 5-6 membered monocyclic or 8-10-membered bicyclic heteroaryl and wherein each member of $R^9$ is independently substituted with one to two $R^{10}$ groups; and all other variables are as defined in Formula (I), (I-a) or (I-b), or as defined in any one of the embodiments herein.

In certain embodiments of the present invention, $R^9$ is $C_1$-$C_6$ alkyl, $C_2$-$C_3$ alkynyl, $C_6$ aryl, or 5-6 membered monocyclic or 8-10-membered bicyclic heteroaryl having 1 to 2 ring atoms selected from N, O and S; and wherein each member of $R^9$ is independently substituted with one to two $R^{10}$ groups; and all other variables are as defined in Formula (I), (I-a), or (I-b), or as defined in any one of the embodiments herein.

In certain embodiments of the present invention, $R^9$ is isopropyl, propynyl, phenyl, pyrazolyl, furanyl, thienyl, pyridyl, imidazolyl, pyrimidinyl, benzothienyl, thiazolyl, tetrahydrothienopyridinyl, tetrahydrothiazolopyridinyl, isothiazolyl, tetrahydropyridinyl, tetrahydroisoquinolinyl, triazolyl, dihydrobenzodioxinyl, dihydroindolyl, or oxazolyl, wherein each member of $R^9$ is independently substituted with one to two $R^{10}$ groups; and all other variables are as defined in Formula (I), (I-a) or (I-b), or as defined in any one of the embodiments herein.

In certain embodiments of the present invention, $R^9$ is cyclohexyl or piperidinyl, and wherein each member of $R^9$ is independently substituted with one to two $R^{10}$ groups; and all other variables are as defined in Formula (I), (I-a) or (I-b), or as defined in any one of the embodiments herein.

In certain embodiments of the present invention, $R^3$ is $R^9$ and $R^9$ is as defined in any one of the embodiments herein, and all other variables are as defined in Formula (I), (I-a) or (I-b), or as defined in any one of the embodiments herein.

In certain embodiments of the present invention, $R^3$ is O$R^9$, and all other variables are as defined in Formula (I), (I-a) or (I-b), or as defined in any one of the embodiments herein.

In certain embodiments of the present invention, $R^3$ is O$R^9$ and $R^9$ is as defined in any one of the embodiments herein, and all other variables are as defined in Formula (I), (I-a) or (I-b), or as defined in any one of the embodiments herein.

In certain embodiments of the present invention, $R^3$ is O$R^9$ and $R^9$ is phenyl optionally substituted with one to three $R^{10}$ groups; and all other variables are as defined in Formula (I), (I-a) or (I-b), or as defined in any one of the embodiments herein.

In certain embodiments of the present invention, $R^3$ is O$R^9$, and $R^9$ is alkyl or heterocyclyl wherein said alkyl or heterocyclyl is optionally substituted with one to three $R^{10}$ groups; and all other variables are as defined in Formula (I), (I-a) or (I-b), or as defined in any one of the embodiments herein.

In certain embodiments of the present invention, $R^3$ is O$R^9$, and $R^9$ is $C_1$-$C_2$ alkyl optionally substituted with one to two $R^{10}$ groups selected from N(Me)$_2$, NHEt, N-methylpiperidinyl and OCH$_3$; and all other variables are as defined in Formula (I), (I-a) or (I-b), or as defined in any one of the embodiments herein.

In certain embodiments of the present invention, $R^3$ is O$R^9$, and $R^9$ is piperidinyl or pyrrolidinyl wherein piperidinyl or pyrrolidinyl is optionally substituted with one to three $R^{10}$ groups; and all other variables are as defined in Formula (I), (I-a) or (I-b), or as defined in any one of the embodiments herein.

In certain embodiments of the present invention, $R^3$ is —N($R^{22}$)—$R^9$, and $R^9$ is defined in any one of the embodiments herein; and all other variables are as defined in Formula (I), (I-a) or (I-b), or as defined in any one of the embodiments herein.

In certain embodiments of the present invention, $R^3$ is —N($R^{22}$)—$R^9$, and $R^9$ is alkyl optionally substituted with one to three $R^{10}$ groups; and all other variables are as defined in Formula (I), (I-a) or (I-b), or as defined in any one of the embodiments herein.

In certain embodiments of the present invention, $R^3$ is —N($R^{22}$)—$R^9$, and $R^9$ is $C_1$-$C_2$ alkyl optionally substituted with one to two $R^{10}$ groups selected from oxo, N$R^{11}R^{12}$; and all other variables are as defined in Formula (I), (I-a) or (I-b), or as defined in any one of the embodiments herein. In certain embodiments of the present invention, $R^3$ is NH-ethyl or NHC(O)(N-pyrrolidinyl); and all other variables are as defined in Formula (I), (I-a) or (I-b), or as defined in any one of the embodiments herein.

In certain embodiments of the present invention, $R^3$ is hydrogen, fluoro, chloro, bromo, cyano, trifluoromethyl, methyl, (2-propyl), (2-hydroxy-2-propyl), (2-fluoro-2-propyl), cyclopropyl, methoxy, ethoxy, difluoromethoxy, trifluoromethoxy, (2-hydroxyethyl)oxy, (2,2,2-trifluoroethyl)oxy, methylsulfonyl, or aminosulfonyl; all other variables are as defined in Formula (I), (I-a) or (I-b), or as defined in any one of the embodiments herein.

In certain embodiments of the present invention, $R^3$ is $R^9$ wherein $R^9$ is alkyl, alkynyl, cycloalkyl, heterocyclyl, aryl, or heteroaryl and wherein each member of $R^9$ is independently substituted with one to three $R^{10}$ groups; and all other variables are as defined in Formula (I), (I-a) or (I-b), or as defined in any one of the embodiments herein.

In certain embodiments of the present invention, $R^3$ is $R^9$ wherein $R^9$ is $C_1$-$C_6$ alkyl, $C_2$-$C_3$ alkynyl, $C_4$-$C_6$ cycloalkyl, $C_6$ aryl, 4-6 membered heterocyclyl or 5-6 membered monocyclic or 8-10-membered bicyclic heteroaryl having 1 to 2 ring atoms selected from N, O and S; and wherein each member of $R^9$ is independently substituted with one to two $R^{10}$ groups; and all other variables are as defined in Formula (I), (I-a) or (I-b), or as defined in any one of the embodiments herein.

In certain embodiments of the present invention, $R^3$ is $R^9$ wherein $R^9$ is $C_1$-$C_6$ alkyl, $C_2$-$C_3$ alkynyl, $C_6$ aryl, or 5-6 membered monocyclic or 8-10-membered bicyclic heteroaryl having 1 to 2 ring atoms selected from N, O and S; and wherein each member of $R^9$ is independently substituted with one to two $R^{10}$ groups; and all other variables are as defined in Formula (I), (I-a) or (I-b), or as defined in any one of the embodiments herein.

In certain embodiments of the present invention, $R^3$ is $R^9$ wherein $R^9$ is isopropyl, propynyl, phenyl, pyrazolyl, furanyl, thienyl, pyridyl, imidazolyl, pyrimidinyl, benzothienyl, thiazolyl, tetrahydrothienopyridinyl, tetrahydrothiazolopyridinyl, isothiazolyl, tetrahydropyridinyl, tetrahydroisoquinolinyl, triazolyl, dihydrobenzodioxinyl, dihydroindolyl, oxazolyl, or tetrahydrobenzothienyl, wherein each member of $R^9$ is independently substituted with one to two $R^{10}$ groups; and all other variables are as defined in Formula (I), (I-a) or (I-b), or as defined in any one of the embodiments herein.

In certain embodiments of the present invention, $R^3$ is $R^9$ wherein $R^9$ is cyclohexyl or piperidinyl, wherein each member of $R^9$ is independently substituted with one to two $R^{10}$ groups; and all other variables are as defined in Formula (I), (I-a) or (I-b) or as defined in any one of the embodiments herein.

In certain embodiments of the present invention, $R^{10}$ is H, halo, $R^{11}$, —$OR^{11}$, CN, —$CF_3$, —$OCF_3$, —$NR^{12}C(=O)R^{11}$, —$NR^{12}S(O)_qR^{11}$, —$SR^{11}$, —$NR^{11}R^{12}$, —$C(=O)NR^{11}R^{12}$, oxo, —$S(O)_qR^{11}$, —$S(O)_2NR^{11}R^{12}$, or —$C(=O)OR^{11}$, wherein $R^{11}$ and $R^{12}$ are optionally taken together with the attached N atom to form a 4-7 membered ring having additional 0-2 heteroatoms selected from O, S, and N, said ring being optionally substituted with one to four $R^{13}$ groups; and all other variables are as defined in Formula (I), (I-a) or (I-b), or as defined in any one of the embodiments herein.

In certain embodiments of the present invention, $R^{10}$ is halo, $R^{11}$, —$OR^{11}$, CN, —$CF_3$, —$OCF_3$, —$NR^{12}C(=O)R^{11}$, —$NR^{12}S(O)_qR^{11}$, —$SR^{11}$, —$NR^{11}R^{12}$, —$C(=O)NR^{11}R^{12}$, oxo, —$S(O)_qR^{11}$, —$S(O)_2NR^{11}R^{12}$, or —$C(=O)OR^{11}$, wherein $R^{11}$ and $R^{12}$ are optionally taken together with the attached N atom to form a 4-7 membered ring having additional 0-2 heteroatoms selected from O, S, and N, said ring being optionally substituted with one to four $R^{13}$ groups; and all other variables are as defined in Formula (I), (I-a) or (I-b), or as defined in any one of the embodiments herein.

In certain embodiments of the present invention, $R^{10}$ is halo; CN; —$CF_3$; —$OCF_3$; —$NR^{12}C(O)R^{11}$ wherein $R^{12}$ is H and $R^{11}$ is $C_1$-$C_4$ alkyl; —$NR^{12}S(O)_2R^{11}$ wherein $R^{12}$ is H and $R^{11}$ is $C_1$-$C_4$ alkyl; —$SR^{11}$ wherein $R^{11}$ is H or $C_1$-$C_4$ alkyl; —$NR^{11}R^{12}$ wherein $R^{11}$ and $R^{12}$ are independently H or $C_1$-$C_4$ alkyl and $R^{11}$ and $R^{12}$ are optionally taken together with the attached N atom to form a 6-membered ring having additional 0-2 heteroatoms selected from O, S, and N, said ring being optionally substituted with one $R^{22}$ group; —$C(=Y')NR^{11}R^{12}$ wherein $R^{11}$ and $R^{12}$ are independently H or $C_1$-$C_4$ alkyl; oxo; —$S(O)_2R^{11}$ wherein $R^{11}$ is $C_1$-$C_4$ alkyl, $C_5$-$C_6$ cycloalkyl or a 5-6 membered heterocyclyl having 1 to 2 heteroatoms selected from N and O; or —$S(O)_2NR^{11}R^{12}$ wherein $R^{11}$ and $R^{12}$ are independently H or $C_1$-$C_4$ alkyl; and all other variables are as defined in Formula (I), (I-a), or (I-b), or as defined in any one of the embodiments herein.

In certain embodiments of the present invention, $R^{10}$ is F, Cl, CN, —$CF_3$, —$OCF_3$, —OH, —$NHC(O)CH_3$, —$NHS(O)_2CH_3$, —$SCH_3$, —$NH_2$, —$N(Et)_2$, —$C(O)NH_2$, —$C(O)NH(p-methoxybenzyl)$, —$C(O)N(Et)_2$, oxo, —$S(O)_2CH_3$, —$S(O)_2N(CH_3)_2$, N-morpholinyl, N-piperidinyl, N-piperazinyl, or $CO_2H$, and all other variables are as defined in Formula (I), (I-a) or (I-b), or as defined in any one of the embodiments herein.

In certain embodiments of the present invention, $R^{10}$ is $R^{11}$, and all other variables are as defined in Formula (I), (I-a) or (I-b), or as defined in any one of the embodiments herein.

In certain embodiments of the present invention, $R^{10}$ is $R^{11}$ wherein $R^{11}$ is alkyl or heterocyclyl, wherein said alkyl and heterocyclyl are optionally substituted with one to four $R^{13}$ groups, wherein two geminal $R^{13}$ groups are optionally taken together with the atom to which they are attached to form a 3-6 membered ring having additional 0-2 heteroatom selected from O, S, and N, said ring being optionally substituted with one to four $R^{18}$ groups; and all other variables are as defined in Formula (I), (I-a) or (I-b), or as defined in any one of the embodiments herein.

In certain embodiments of the present invention, $R^{10}$ is $R^{11}$ wherein $R^{11}$ is $C_1$-$C_6$ alkyl, or 4-6 membered (e.g., 5-6 membered) monocyclic or 8-10-membered bicyclic heterocyclyl having 1 to 2 heteroatoms selected from N and O, wherein said alkyl and heterocyclyl are optionally substituted with one to four $R^{13}$ groups, wherein two geminal $R^{13}$ groups are optionally taken together with the atom to which they are attached to form a six-membered ring having 0-2 heteroatom selected from O, S, and N, said ring being optionally substituted with one to four $R^{18}$ groups; and all other variables are as defined in Formula (I), (I-a) or (I-b), or as defined in any one of the embodiments herein.

In certain embodiments of the present invention, $R^{10}$ is $R^{11}$ wherein $R^{11}$ is $C_1$-$C_6$ alkyl, or 4-6 membered (e.g., 5-6 membered) monocyclic or 8-10-membered bicyclic heterocyclyl having 1 to 2 heteroatoms selected from N and O, wherein said alkyl and heterocyclyl are optionally substituted with one to two $R^{13}$ groups and wherein each $R^{13}$ is independently halo, CN, $CF_3$, —$OCF_3$, oxo, —$(CR^{14}R^{15})_nC(O)OR^{16}$, —$(CR^{14}R^{15})_nC(O)NR^{16}R^{17}$, —$(CR^{14}R^{15})_nNR^{16}R^{17}$, —$(CR^{14}R^{15})_nOR^{16}$, —$(CR^{14}R^{15})_nNR^{16}C(O)R^{17}$, —$(CR^{14}R^{15})_nS(O)_2NR^{16}R^{17}$, or $R^{16}$; and all other variables are as defined in Formula (I), (I-a) or (I-b), or as defined in any one of the embodiments herein.

In certain embodiments of the present invention, $R^{10}$ is $R^{11}$ wherein $R^{11}$ is $C_1$-$C_6$ alkyl, wherein alkyl is optionally substituted with one to two $R^{13}$ groups and wherein each $R^{13}$ is independently halo, CN, $CF_3$, —$OCF_3$, oxo, —$(CR^{14}R^{15})_nC(O)OR^{16}$, —$(CR^{14}R^{15})_nC(O)NR^{16}R^{17}$, —$(CR^{14}R^{15})_nNR^{16}R^{17}$, —$(CR^{14}R^{15})_nOR^{16}$, —$(CR^{14}R^{15})_nNR^{16}C(O)R^{17}$, —$(CR^{14}R^{15})_nS(O)_2NR^{16}R^{17}$, or $R^{16}$; and all other variables are as defined in Formula (I), (I-a) or (I-b), or as defined in any one of the embodiments herein.

In certain embodiments of the present invention, $R^{10}$ is $R^{11}$ wherein $R^{11}$ is methyl, ethyl, i-butyl, t-butyl, $CH_2R^{27}$ wherein $R^{27}$ is $N(methyl)_2$, OH, $OCH_3$, $CH_2OH$, piperazinyl, piperidinyl, morpholinyl, pyrrolyl, azetidinyl, $C(CH_3)_2$-piperidinyl, wherein piperazinyl or piperidinyl is optionally substituted with one to two groups selected from methyl, ethyl, hydoxy or $(CH_2)_2OH$; and all other variables are as defined in Formula (I), (I-a) or (I-b), or as defined in any one of the embodiments herein.

In certain embodiments of the present invention, $R^{10}$ is $R^{11}$ wherein $R^{11}$ is 5-6 membered monocyclic or 8-10-membered bicyclic heterocyclyl having 1 to 2 heteroatoms selected from N and O, wherein said alkyl and heterocyclyl are optionally substituted with one to two $R^{13}$ groups and wherein each $R^{13}$ is independently halo, CN, $CF_3$, —$OCF_3$, oxo, —$(CR^{14}R^{15})_nC(O)OR^{16}$, —$(CR^{14}R^{15})_nC(O)NR^{16}R^{17}$, —$(CR^{14}R^{15})_nNR^{16}R^{17}$, —$(CR^{14}R^{15})_nOR^{16}$, —$(CR^{14}R^{15})_nNR^{16}C(O)R^{17}$, —$(CR^{14}R^{15})_nS(O)_2NR^{16}R^{17}$, or $R^{16}$; and all other variables are as defined in Formula (I), (I-a) or (I-b), or as defined in any one of the embodiments herein.

In certain embodiments of the present invention, $R^{10}$ is —$OR^{11}$; and all other variables are as defined in Formula (I), (I-a) or (I-b), or as defined in any one of the embodiments herein.

In certain embodiments of the present invention, $R^{10}$ is —$OR^{11}$ wherein $R^{11}$ is H, alkyl or heterocyclyl, wherein said alkyl or heterocyclyl is optionally substituted with one to four $R^{13}$ groups and all other variables are as defined in Formula (I), (I-a) or (I-b), or as defined in any one of the embodiments herein.

In certain embodiments of the present invention, $R^{10}$ is —$OR^{11}$ wherein $R^{11}$ is H, $C_1$-$C_4$ alkyl, or 4-6 membered (e.g., 5-6 membered) monocyclic or 8-10-membered bicyclic heterocyclyl having 1 to 2 nitrogen atoms, wherein said alkyl or heterocyclyl is optionally substituted with one to four $R^{13}$ groups; and all other variables are as defined in Formula (I), (I-a) or (I-b), or as defined in any one of the embodiments herein.

In certain embodiments of the present invention, $R^{10}$ is —$OR^{11}$ wherein $R^{11}$ is H, $C_1$-$C_4$ alkyl, or 4-6 membered (e.g., 5-6 membered) monocyclic or 8-membered bicyclic heterocyclyl having 1 to 2 nitrogen atoms, wherein said alkyl or heterocyclyl is optionally substituted with one to two $R^{13}$ groups, wherein each $R^{13}$ is independently halo, CN, $CF_3$, —$OCF_3$, oxo, —$(CR^{14}R^{15})_nC(O)OR^{16}$, —$(CR^{14}R^{15})_nC(O)NR^{16}R^{17}$, —$(CR^{14}R^{15})_nNR^{16}R^{17}$, —$(CR^{14}R^{15})_nOR^{16}$, —$(CR^{14}R^{15})_nNR^{16}C(O)R^{17}$, —$(CR^{14}R^{15})_nS(O)_2NR^{16}R^{17}$, or $R^{16}$; and all other variables are as defined in Formula (I), (I-a) or (I-b), or as defined in any one of the embodiments herein. In certain embodiments, $R^{10}$ is OH or $OCH_3$; and all other variables are as defined in Formula (I), (I-a) or (I-b), or as defined in any one of the embodiments herein.

In certain embodiments of the present invention, $R^3$ is selected from:

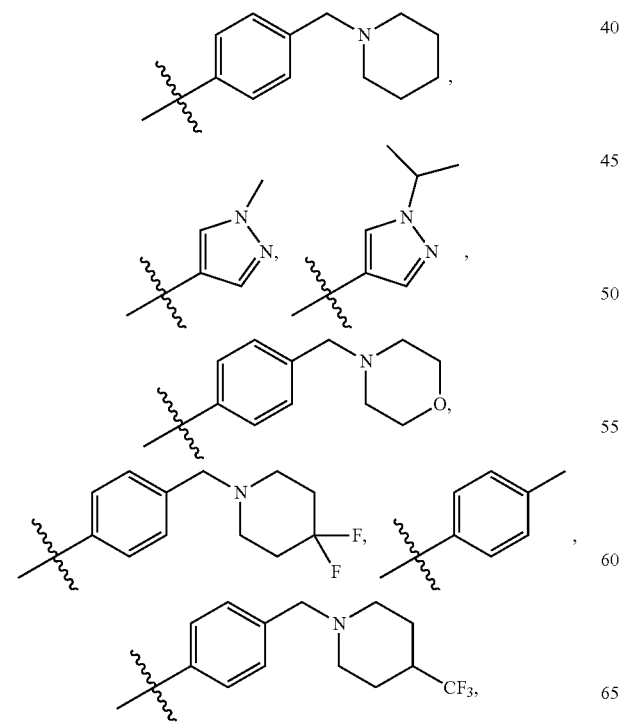

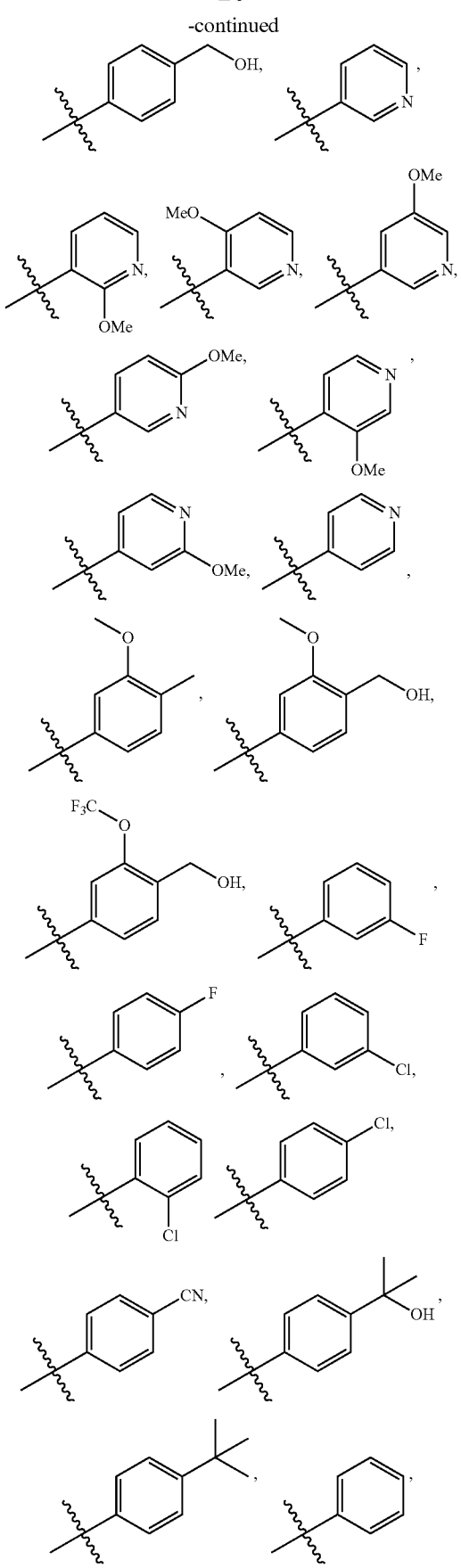

-continued

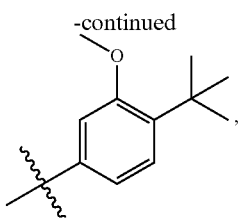

H, F, Cl, Br, iPr or $CO_2CH_3$; and all other variables are as defined in Formula (I), (I-a) or (I-b), or as defined in any one of the embodiments herein.

In certain embodiments of the present invention, $R^4$ is H; and all other variables are as defined in Formula (I), (I-a) or (I-b), or as defined in any one of the embodiments herein.

In certain embodiments of the present invention, $R^5$ is H, halo, $-(CR^{14}R^{15})_nC(O)NR^{11}R^{12}$, $-(CR^{14}R^{15})_nNR^{12}C(O)R^{11}$, $-(CR^{14}R^{15})_nNR^{11}R^{12}$, $-(CR^{14}R^{15})_nOR^{11}$, $-(CR^{14}R^{15})_nSR^{11}$, alkyl, heterocyclyl or heteroaryl, wherein the said alkyl, heterocyclyl or heteroaryl is optionally substituted with one to four $R^{13}$ groups; and all other variables are as defined in Formula (I), (I-a) or (I-b), or as defined in any one of the embodiments herein.

In certain embodiments of the present invention, $R^5$ is H, halo, $-(CR^{14}R^{15})_nC(O)NR^{11}R^{12}$, $-(CR^{14}R^{15})_nNR^{12}C(O)R^{11}$, $-(CR^{14}R^{15})_nNR^{11}R^{12}$, $-(CR^{14}R^{15})_nOR^{11}$, $-(CR^{14}R^{15})_nSR^{11}$, alkyl, or heterocyclyl, wherein the said alkyl or heterocyclyl is optionally substituted with one to four $R^{13}$ groups; and all other variables are as defined in Formula (I), (I-a) or (I-b), or as defined in any one of the embodiments herein.

In certain embodiments of the present invention, $R^5$ is halo or $C_2$-$C_6$ alkenyl; and all other variables are as defined in Formula (I), (I-a) or (I-b), or as defined in any one of the embodiments herein.

In certain embodiments of the present invention, $R^5$ is H; and all other variables are as defined in Formula (I), (I-a) or (I-b), or as defined in any one of the embodiments herein.

In certain embodiments of the present invention, $R^5$ is Cl, Br or F; and all other variables are as defined in Formula (I), (I-a) or (I-b), or as defined in any one of the embodiments herein.

In certain embodiments of the present invention, $R^5$ is $-(CR^{14}R^{15})_nC(O)NR^{11}R^{12}$, $-(CR^{14}R^{15})_nNR^{12}C(O)R^{11}$, $-(CR^{14}R^{15})_nNR^{11}R^{12}$, $-(CR^{14}R^{15})_nOR^{11}$, $-(CR^{14}R^{15})_nSR^{11}$, $C_1$-$C_6$ alkyl, or 4-6 membered (e.g., 5-6 membered) monocyclic or 7-10 membered bicyclic heterocyclyl having 1 to 2 nitrogen atoms, wherein said alkyl or heterocyclyl is optionally substituted with one to two $R^{13}$ groups; wherein $R^{14}$ and $R^{15}$ are H; n is 0-2; each $R^{11}$ is independently H, $C_1$-$C_4$ alkyl or 5-6 membered monocyclic heterocyclyl having 1 to 2 nitrogen atoms, wherein said alkyl or heterocyclyl is optionally substituted with one to two $R^{13}$ groups; and all other variables are as defined in Formula (I), (I-a) or (I-b), or as defined in any one of the embodiments herein.

In certain embodiments of the present invention, $R^5$ is $-(CR^{14}R^{15})_nC(O)NR^{11}R^{12}$, $-(CR^{14}R^{15})_nNR^{12}C(O)R^{11}$, $-(CR^{14}R^{15})_nNR^{11}R^{12}$, $-(CR^{14}R^{15})_nOR^{11}$, $-(CR^{14}R^{15})_nSR^{11}$, $C_1$-$C_6$ alkyl, or 4-6 membered (e.g., 5-6 membered) monocyclic or 7-10 membered bicyclic heterocyclyl having 1 to 2 nitrogen atoms, wherein said alkyl or heterocyclyl is optionally substituted with one to two $R^{13}$ groups; wherein $R^{14}$ and $R^{15}$ are H; n is 0-2; each $R^{11}$ is independently H, $C_1$-$C_4$ alkyl, or 5-6 membered monocyclic heterocyclyl having 1 to 2 nitrogen atoms, wherein said alkyl or heterocyclyl is optionally substituted with one to two $R^{13}$ groups; $R^{13}$ is OH, $O(C_1$-$C_3$ alkyl), or $C_1$-$C_3$ alkyl; and all other variables are as defined in Formula (I), (I-a) or (I-b), or as defined in any one of the embodiments herein.

In certain embodiments of the present invention, $R^5$ is $-(CR^{14}R^{15})_nOR^{11}$, $C_1$-$C_6$ alkyl, $C_2$-$C_6$ alkenyl, or halo; and all other variables are as defined in Formula (I), (I-a) or (I-b), or as defined in any one of the embodiments herein.

In certain embodiments of the present invention, $R^5$ is $-OR^{11}$; and all other variables are as defined in Formula (I), (I-a) or (I-b), or as defined in any one of the embodiments herein.

In certain embodiments of the present invention, $R^5$ is $-NR^{11}$; and all other variables are as defined in Formula (I), (I-a) or (I-b), or as defined in any one of the embodiments herein.

In certain embodiments of the present invention, $R^5$ is $C_1$-$C_6$ alkyl, or 4-6 membered (e.g., 5-6 membered) monocyclic or 7-10 membered bicyclic heterocyclyl having 1 to 2 nitrogen atoms wherein the point of attachment is via a carbon atom on said heterocyclyl, wherein said alkyl or heterocyclyl is optionally substituted with one to two $R^{13}$ groups; and all other variables are as defined in Formula (I), (I-a) or (I-b), or as defined in any one of the embodiments herein.

In certain embodiments of the present invention, $R^5$ is 5-6 membered heteroaryl; and all other variables are as defined in Formula (I), (I-a) or (I-b), or as defined in any one of the embodiments herein. In certain embodiments, $R^5$ is imidazolyl; and all other variables are as defined in Formula (I), (I-a) or (I-b), or as defined in any one of the embodiments herein.

In certain embodiments of the present invention, $R^5$ is F, ethyl, OH, OEt, $O(CH_2)_2OH$, O(pyrrolidinyl), Br, $-CH=CH_2$, or $O(CH_2)_2OCH_3$, and all other variables are as defined in Formula (I), (I-a) or (I-b), or as defined in any one of the embodiments herein.

In certain embodiments of the present invention, $R^5$ is tropinyl, quinuclideinyl, pyrrolidinyl, piperidinyl, piperazinyl, morpholinyl, or azetidine wherein said tropinyl, quinuclideinyl, pyrrolidinyl, piperidinyl, piperazinyl, morpholinyl, or azetidine is optionally substituted with one or more F; and all other variables are as defined in Formula (I), (I-a) or (I-b), or as defined in any one of the embodiments herein.

In certain embodiments of the present invention, $R^5$ is selected from the following; and all other variables are as defined in Formula (I), (I-a) or (I-b), or as defined in any one of the embodiments herein: ethyl, OH, ethoxy, $O(CH_2CH_2)OCH_3$,

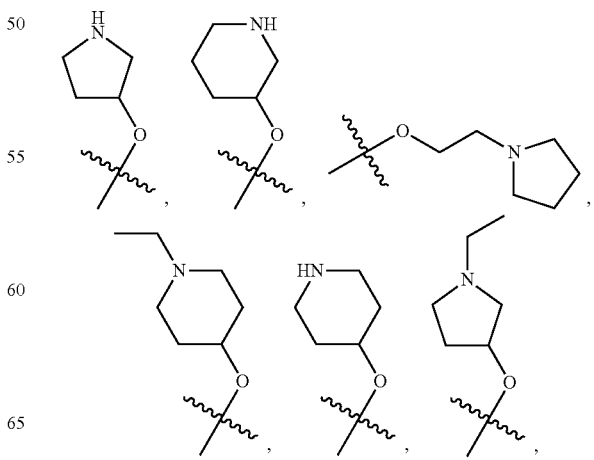

23
-continued
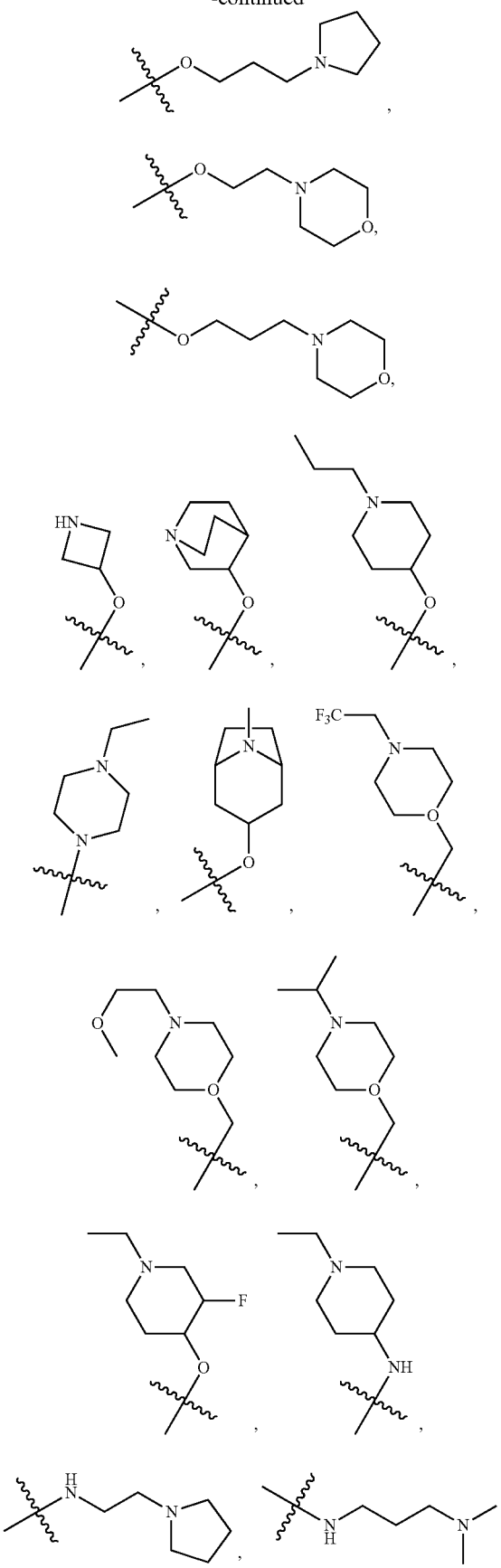
24
-continued
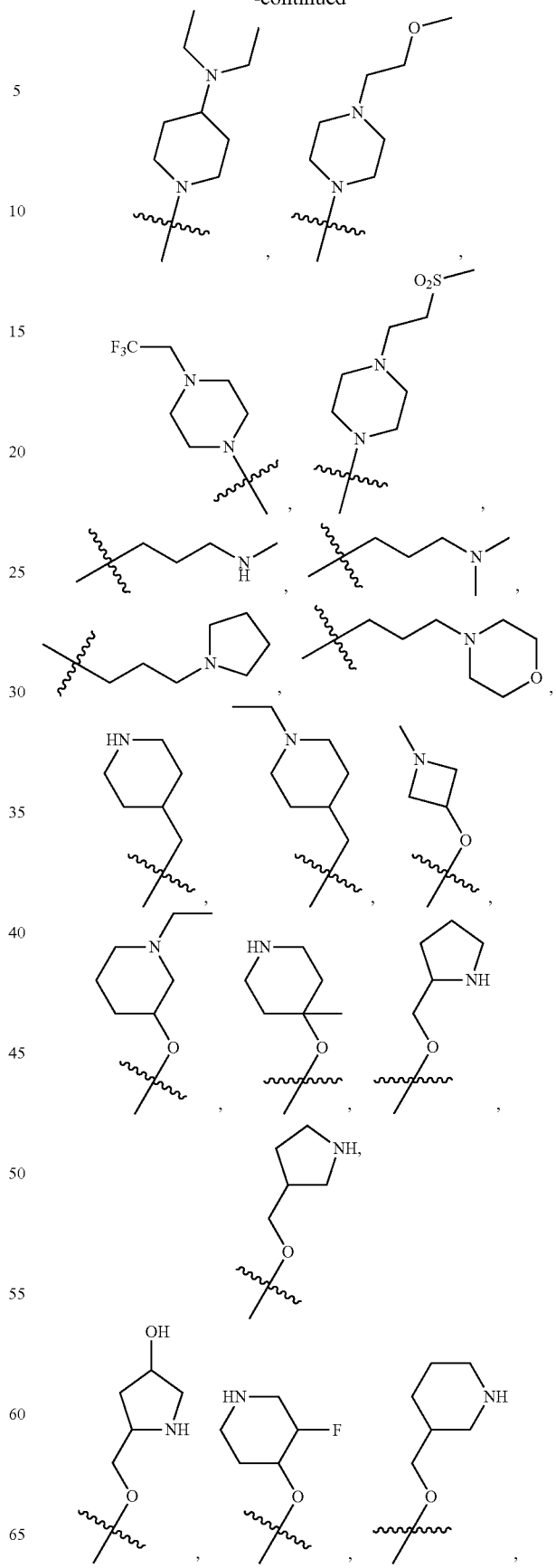

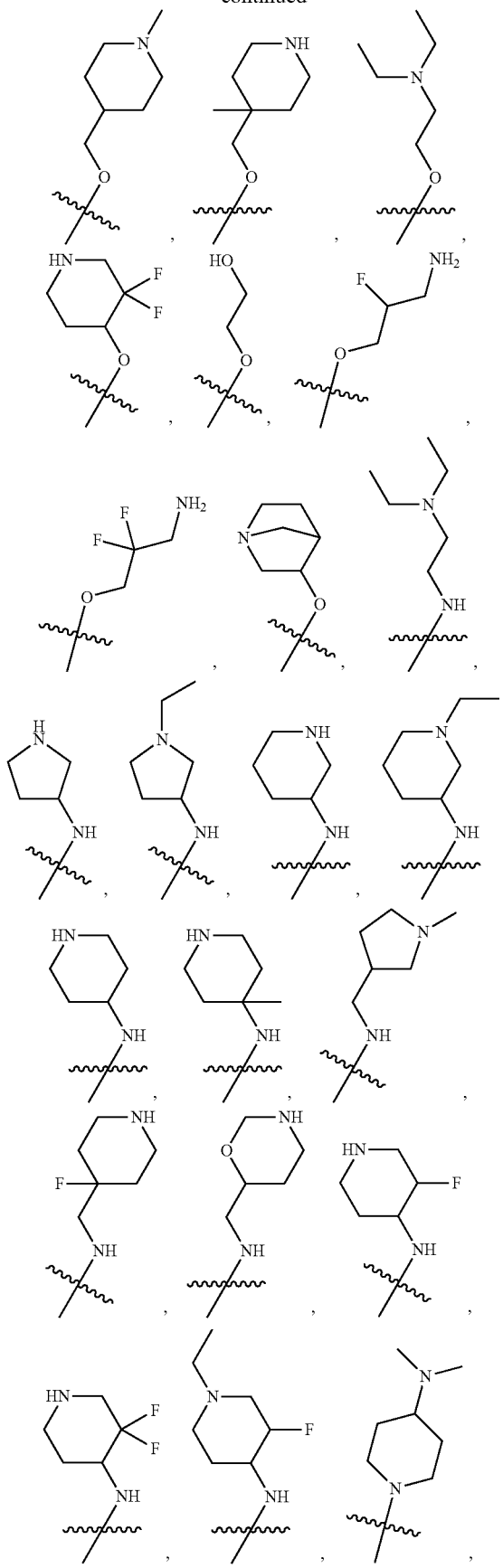
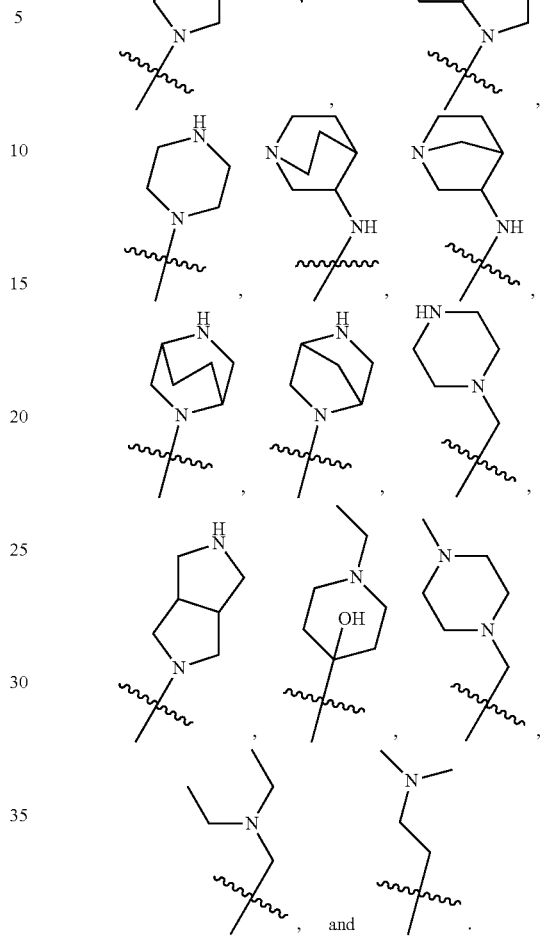

In certain embodiments of the present invention, $R^6$ is H; and all other variables are as defined in Formula (I), (I-a) or (I-b), or as defined in any one of the embodiments herein.

In certain embodiments of the present invention, $R^6$ is CN, —$CF_3$, —$OCF_3$, halo, —C(=Y')$OR^{11}$, —C(=Y')$NR^{11}R^{12}$, —$OR^{11}$, —OC(=Y')$R^{11}$, —$NR^{11}R^{12}$, —$NR^{12}$C(=Y')$R^{11}$, —$NR^{12}$C(=Y')$NR^{11}R^{12}$, —$NR^{12}S(O)_qR^{11}$, —$SR^{11}$, —S(O)$R^{11}$, —S(O)$_2R^{11}$, —OC(=Y')$NR^{11}R^{12}$, —S(O)$_2NR^{11}R^{12}$, alkyl, alkenyl, alkynyl, cycloalkyl, heterocyclyl, aryl, or heteroaryl wherein said alkyl, alkenyl, alkynyl, cycloalkyl, heterocyclyl, aryl and heteroaryl are optionally substituted by one to four $R^{13}$ groups; and all other variables are as defined in Formula (I), (I-a) or (I-b), or as defined in any one of the embodiments herein.

In certain embodiments of the present invention, $R^6$ is CN, $CF_3$, —$OCF_3$, halo, —C(O)$OR^{11}$, —C(O)$NR^{11}R^{12}$, —$OR^{11}$, —$NR^{11}R^{12}$, —$NR^{11}R^{12}$C(O)$R^{11}$, —$NR^{12}$C(=$NR^{12}$)$R^{11}$, —$NR^{12}S(O)_2R^{11}$, —$SR^{11}$, —S(O)$_2R^{11}$, alkyl, cycloalkyl, heterocyclyl, aryl, or heteroaryl wherein said alkyl is substituted with one to four $R^{13}$ groups except H and said heterocyclyl or heteroaryl is optionally substituted by one to four $R^{13}$ groups; and all other variables are as defined in Formula (I), (I-a) or (I-b), or as defined in any one of the embodiments herein.

In certain embodiments of the present invention, $R^6$ is CN, halo, —C(O)$NR^{11}R^{12}$, —$OR^{11}$, —$NR^{11}R^{12}$, —$NR^{12}$C(O)

$R^{11}$, alkyl, cycloalkyl, heterocyclyl, aryl, or heteroaryl, wherein said alkyl is substituted with one to two $R^{13}$ groups except H, and said heteroaryl is optionally substituted by one to two $R^{13}$ groups; and all other variables are as defined in Formula (I), (I-a) or (I-b), or as defined in any one of the embodiments herein.

In certain embodiments of the present invention, $R^6$ is CN, halo, —C(O)NR$^{11}$R$^{12}$, —OR$^{11}$, —NR$^{11}$R$^{12}$, —NR$^{12}$C(O)R$^{11}$, $C_1$-$C_3$ alkyl, $C_3$-$C_6$ cycloalkyl, 5-6 heterocyclyl having 1 to 2 heteroatoms, $C_6$ aryl, or 5-6 or 9-membered heteroaryl having 1 to 4 heteroatoms; wherein said alkyl is substituted with one to two $R^{13}$ groups except H; and said cycloalkyl, aryl, heterocyclyl or heteroaryl is optionally substituted by one to two $R^{13}$ groups; wherein heteroatoms are selected from N, O and S; wherein each $R^{12}$ is H or $C_1$-$C_3$ alkyl and each $R^{11}$ is independently H or $C_1$-$C_3$ alkyl optionally substituted by one to two $R^{13}$ groups; and all other variables are as defined in Formula (I), (I-a) or (I-b), or as defined in any one of the embodiments herein.

In certain embodiments of the present invention, $R^6$ is CN, halo, —C(O)NR$^{11}$R$^{12}$, —OR$^{11}$, —NR$^{11}$R$^{12}$, —NR$^{12}$C(O)R$^{11}$, $C_1$-$C_3$ alkyl, or 5-6 or 9-membered heteroaryl having 1 to 4 heteroatoms selected from N, O and S, wherein said alkyl is substituted with one to two $R^{13}$ groups (wherein $R^{13}$ is OR$^{16}$ where $R^{16}$ is H or alkyl), and said heteroaryl is optionally substituted by one to two $R^{13}$ groups (wherein $R^{13}$ is OR$^{16}$, NR$^{16}$R$^{17}$, or $C_1$-$C_2$ alkyl optionally substituted with $R^{18}$ where each of $R^{16}$ and $R^{17}$ is independently H or alkyl); wherein each $R^{12}$ is H or $C_1$-$C_3$ alkyl and each $R^{11}$ is independently H or $C_1$-$C_3$ alkyl optionally substituted by one to two $R^{13}$ groups (wherein $R^{13}$ is OR$^{16}$ where $R^{16}$ is H or alkyl); and all other variables are as defined in Formula (I), (I-a) or (I-b), or as defined in any one of the embodiments herein.

In certain embodiments of the present invention, $R^6$ is CN, F, Cl, Br, —C(O)OH, —C(O)NH$_2$, —C(O)NHCH$_2$CH$_2$OH, —C(O)N(CH$_3$)$_2$, —OCH$_3$, —CH$_2$OH, —C(CH$_3$)$_2$OH, pyridyl, pyrazolyl, pyrimidinyl, oxazolyl, isoxazolyl, thiazolyl, imidazolyl, pyrazinyl, imidazopyrimidinyl, pyridazinyl, triazolyl, tetrazolyl, thiadiazolyl, oxadiazolyl, —C(O)—N—pyrrolidinyl, —C(O)NHEt, or —C(O)NH(CH$_2$)$_2$NH$_2$, wherein said pyridyl, pyrazolyl, pyrimidinyl, oxazolyl, isoxazolyl, thiazolyl, imidazolyl, pyrazinyl, imidazopyrimidinyl, pyridazinyl, triazolyl, tetrazolyl, thiadiazolyl, and oxadiazolyl are optionally substituted with 1-2 groups selected from methyl, methoxy, NH$_2$, and benzyl; and all other variables are as defined in Formula (I), (I-a) or (I-b), or as defined in any one of the embodiments herein.

In certain embodiments of the present invention, $R^6$ is CN; and all other variables are as defined in Formula (I), (I-a) or (I-b), or as defined in any one of the embodiments herein.

In certain embodiments of the present invention, $R^6$ is pyridyl, or pyrazolyl optionally substituted with methyl; and all other variables are as defined in Formula (I), (I-a) or (I-b), or as defined in any one of the embodiments herein.

In certain embodiments of the present invention, $R^7$ is H, or $C_1$-$C_4$ alkyl optionally substituted with one to three halo groups or OH; and all other variables are as defined in Formula (I), (I-a) or (I-b), or as defined in any one of the embodiments herein.

In certain embodiments of the present invention, $R^7$ is H, methyl or ethyl; and all other variables are as defined in Formula (I), (I-a) or (I-b), or as defined in any one of the embodiments herein.

In certain embodiments, $R^{10}$ is methyl, ethyl or $R^{30}$ as defined in Formula (II) below.

In certain embodiments, compounds are of Formula (II):

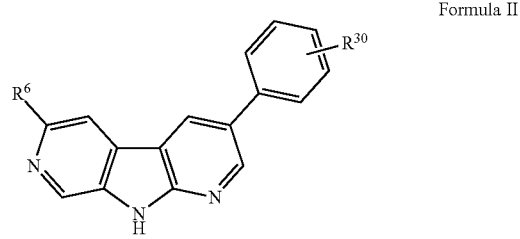

Formula II wherein $R^6$ is CN,

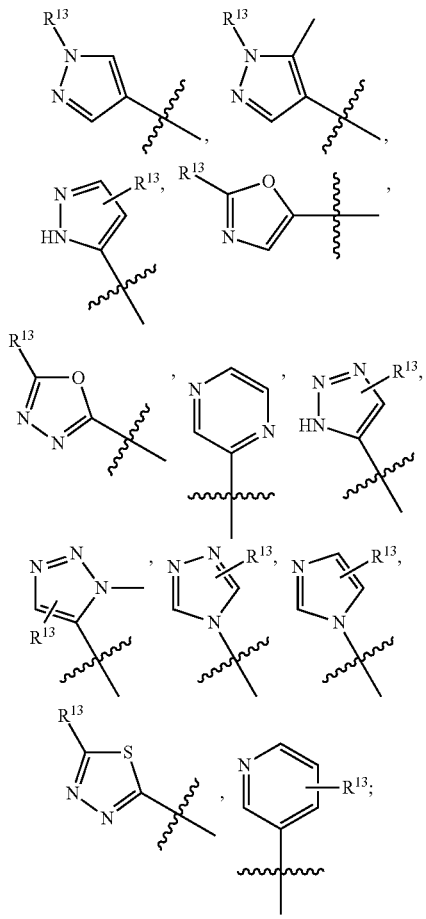

and $R^{30}$ is

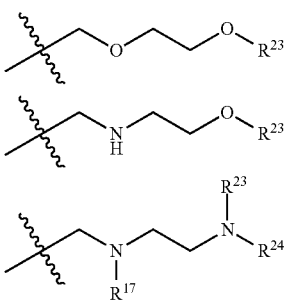

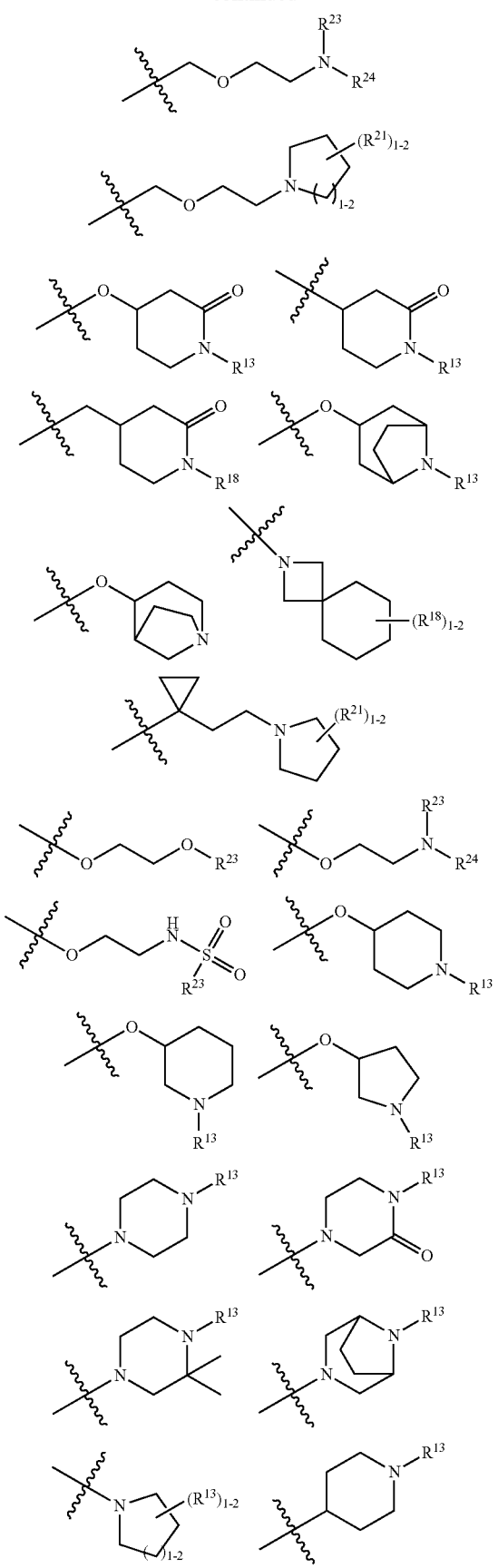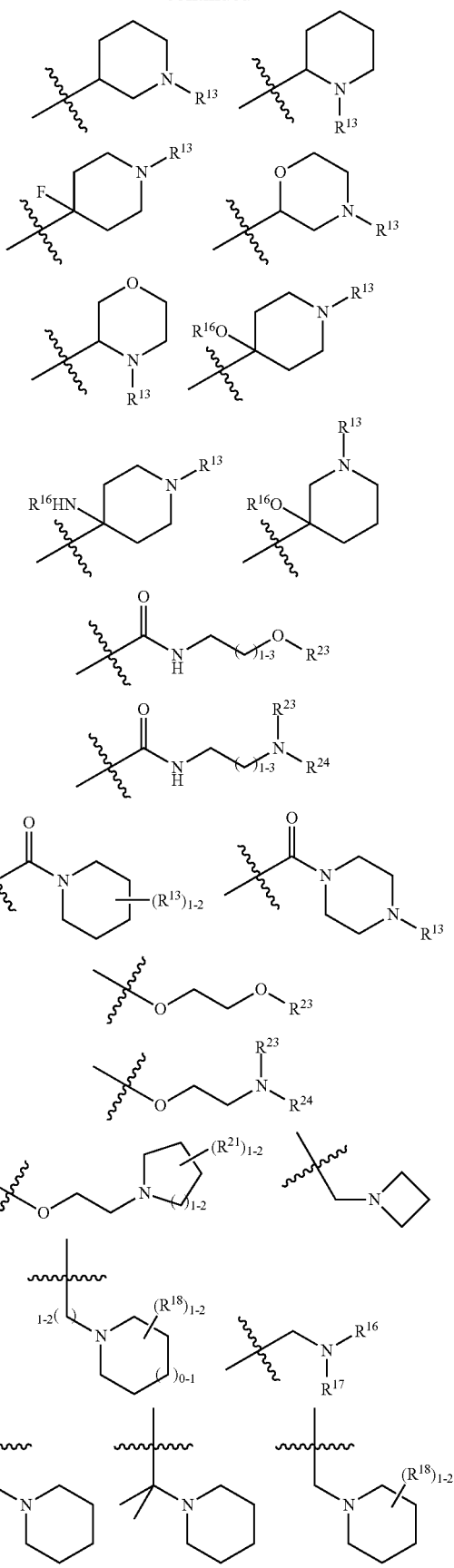

-continued
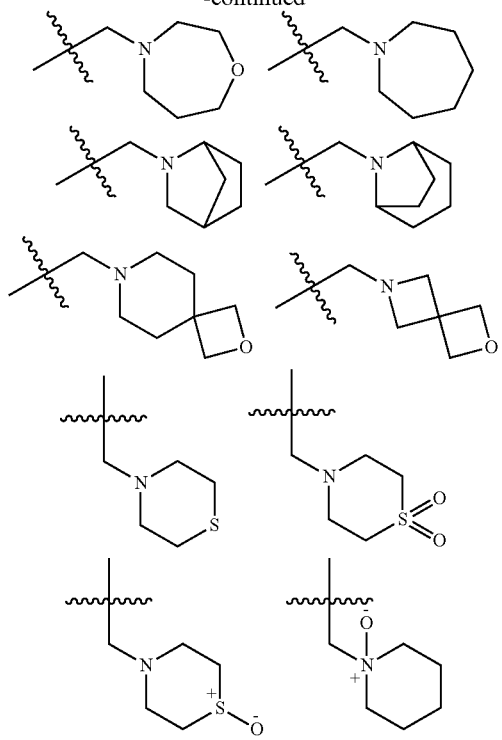
In certain embodiments, compounds are of Formula (II), wherein $R^6$ is
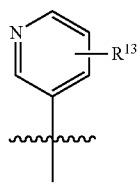
wherein $R^{13}$ is $OCH_3$, O-piperidinyl, O-(1-ethyl)piperidinyl or $O(CH_2)_2N(CH_3)_2$.
In certain embodiments, compounds are of Formula (II), wherein $R^{30}$ is
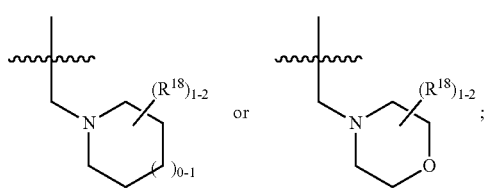
wherein
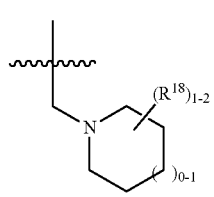
is
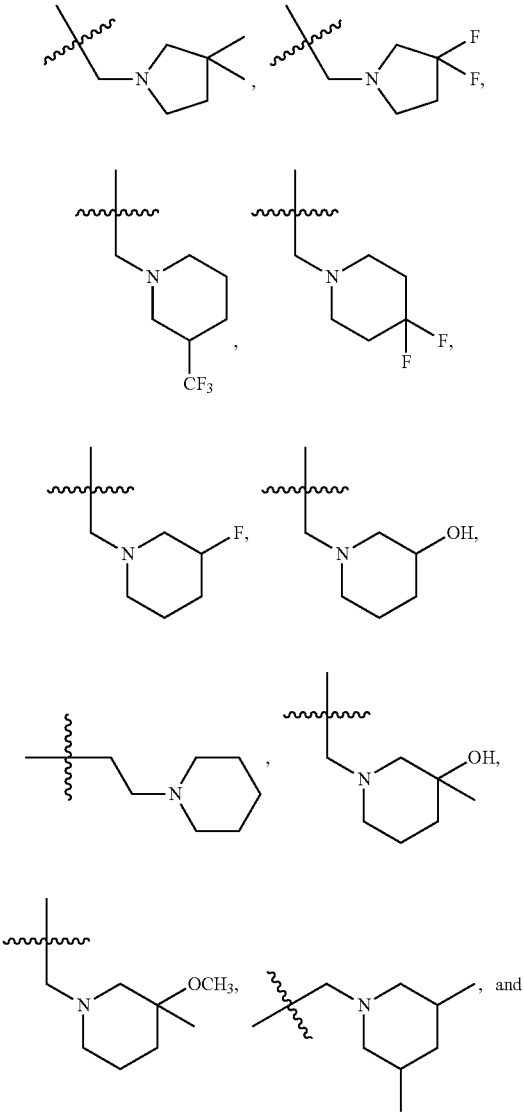
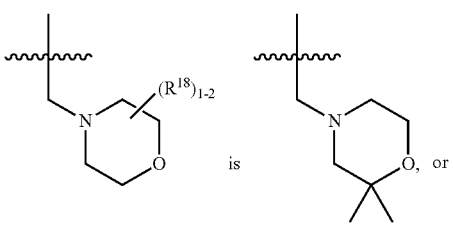
is
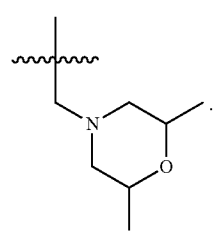

In certain embodiments, compounds are of Formula (III):
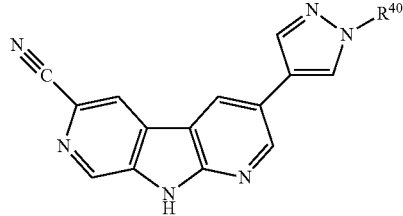
Formula III
wherein $R^{40}$ is
$CH_3$
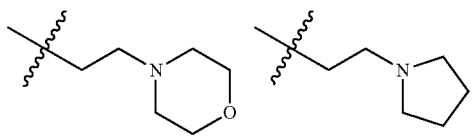
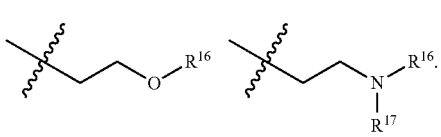
Another embodiment of the present invention includes title compounds described herein Examples 1-403 and compounds below.
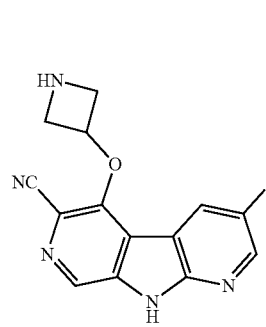
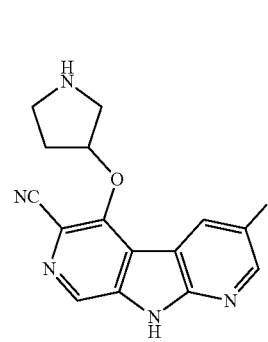
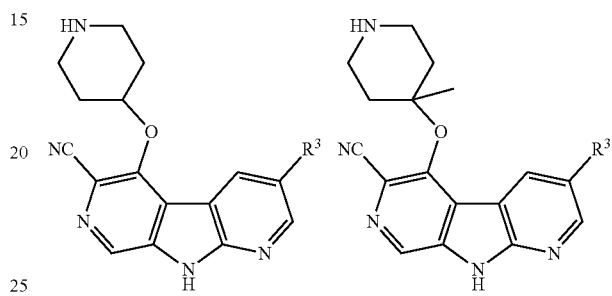
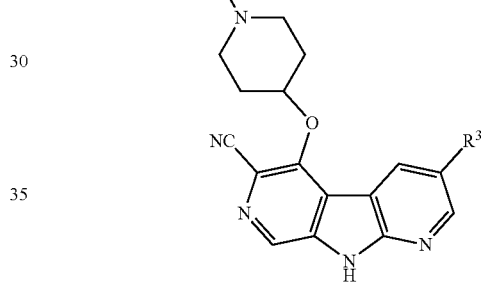
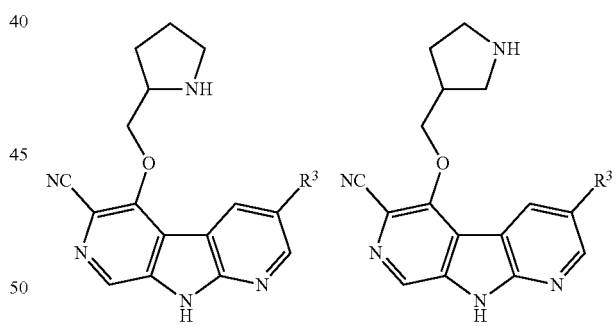
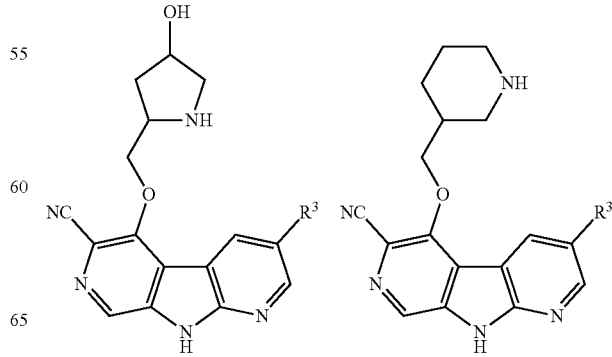

-continued
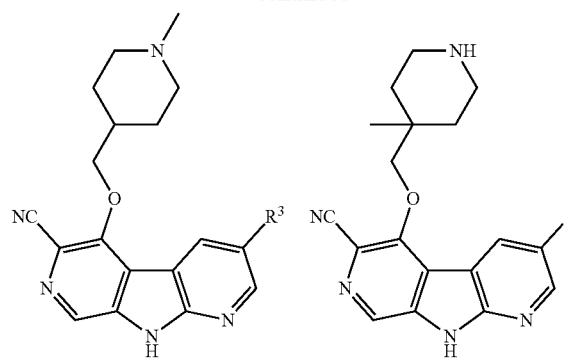
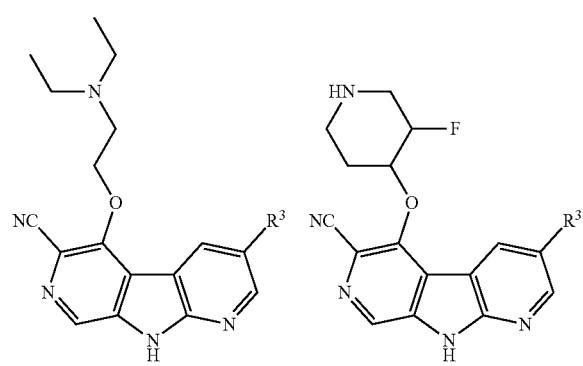
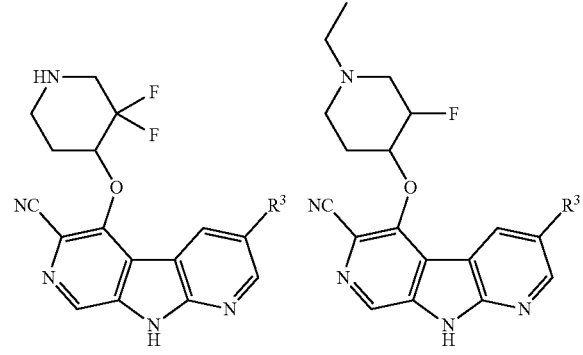
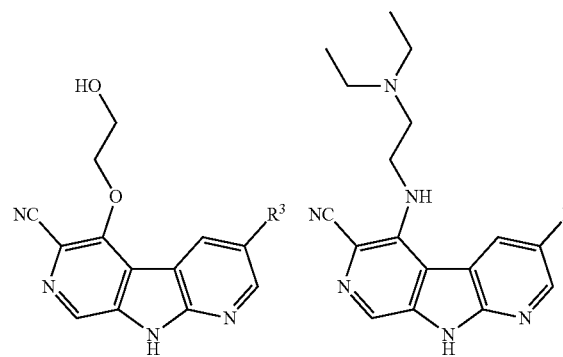
-continued
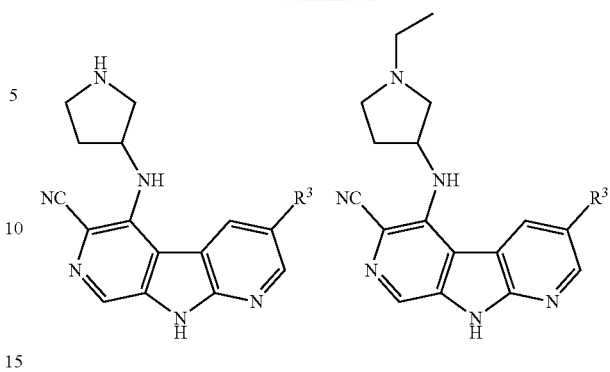
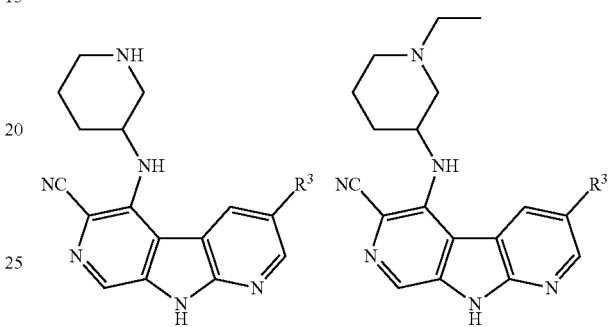
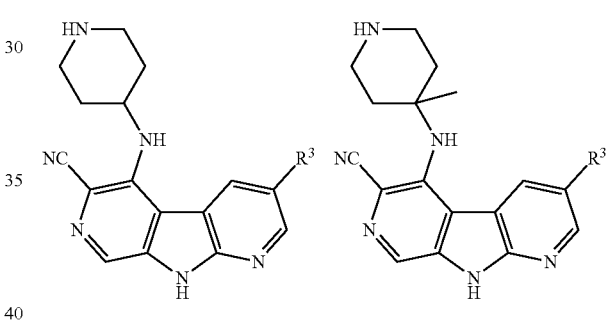
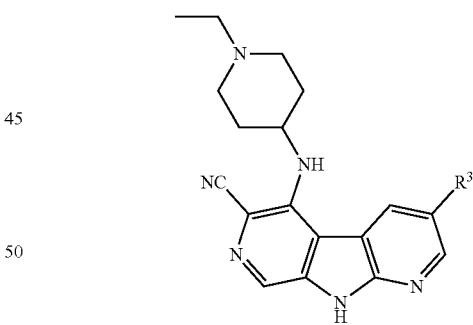
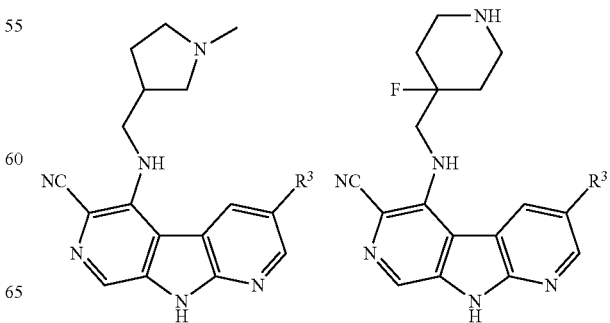

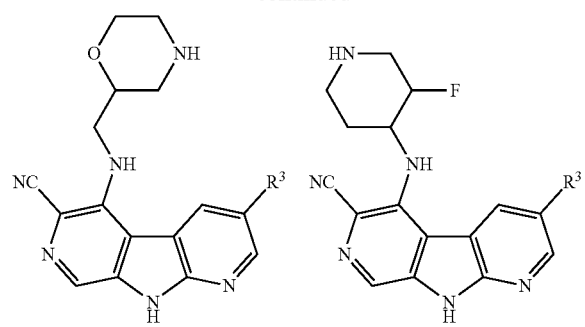
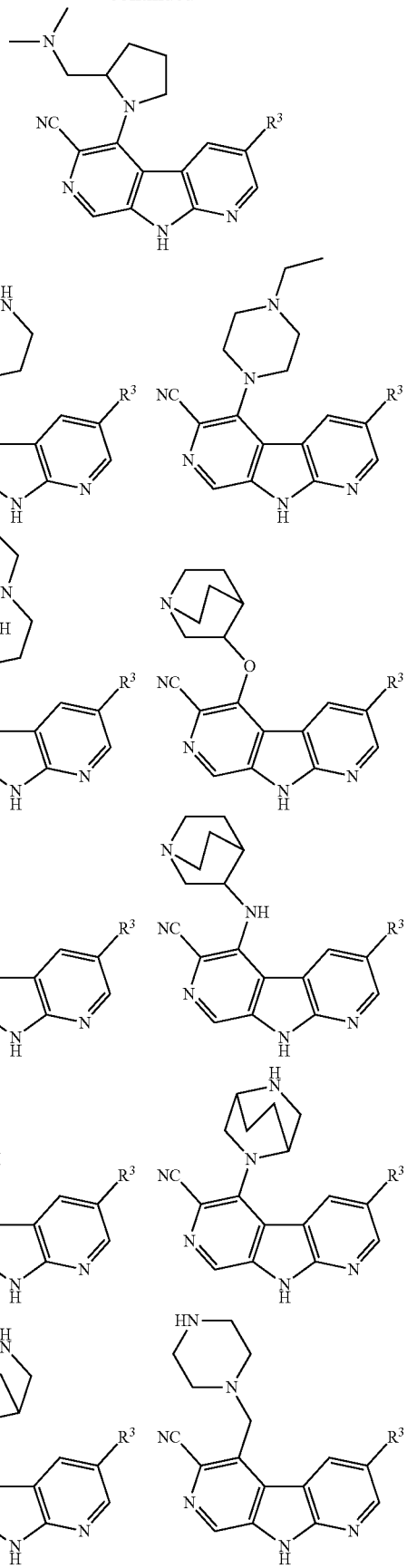

-continued

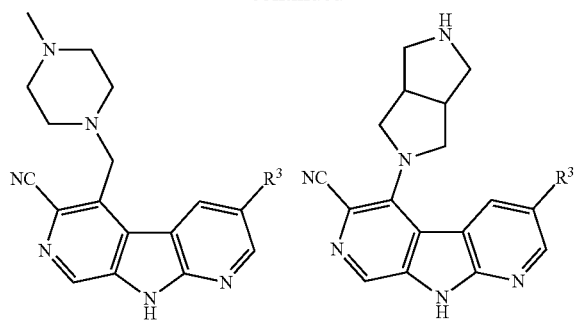

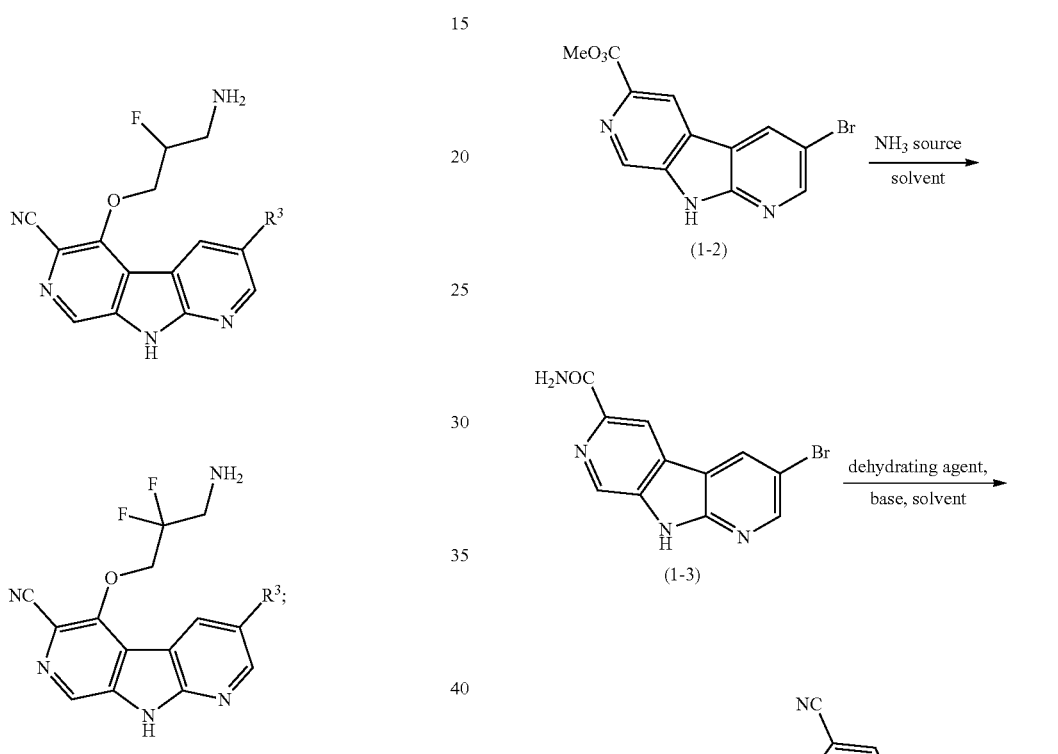

Scheme 1 wherein each R³ is independently H, hydrogen, fluoro, chloro, bromo, cyano, trifluoromethyl, methyl, (2-propyl), (2-hydroxy-2-propyl), (2-fluoro-2-propyl), cyclopropyl, methoxy, ethoxy, difluoromethoxy, trifluoromethoxy, (2-hydroxyethyl)oxy, (2,2,2-trifluoroethyl)oxy, methylsulfonyl, or aminosulfonyl.

The present compounds are prepared according to the procedures described below in the schemes and examples, or by methods known in the art. The starting materials and various intermediates may be obtained from commercial sources, prepared from commercially available compounds, or prepared using well known synthetic methods. Accordingly, methods for making the present compounds of Formula (I), (I-a) or (I-b) according to Scheme 1, 2, 3, 4, 5, 6, 7, 8, 9, 10, 11a, 11b, 11c, 11 d, 11c, 11d, 11e, 12, 13, 14, 15, 16, 17, 18, 19, 20, 21, 22, 23, 24, 25, 26, and/or 27 (27-1, 27-2, and 27-3) are within the scope of the present invention.

For example, 9H-dipyrido[2,3-b;4',3'-d]pyrrole (also referred to as diazacarbazole herein) compounds of formula (1-4) may be prepared using the synthetic route outlined in Scheme 1.

Compounds of formula (1-1) may be prepared using published methods described in the literature. Intermediates of formula (1-1) may then be brominated in the presence of a suitable brominating agent, such as bromine, in a suitable solvent such as acetic acid, at a temperature between 20° C. and 120° C., to obtain compounds of formula (1-2).

Compounds of formula (1-3) can be obtained by reaction of intermediate (1-2) with an appropriate source of ammonia, such as ammonia gas, in a suitable solvent such as methanol, at a temperature between 20° C. and 65° C.

Intermediates of formula (1-3) may then be dehydrated in the presence of a suitable dehydrating agent, such as trifluoroacetic anhydride, in a suitable solvent such as THF, at a temperature from 20° C. to the boiling point of the solvent, to obtain compounds of formula (1-4).

Scheme 2

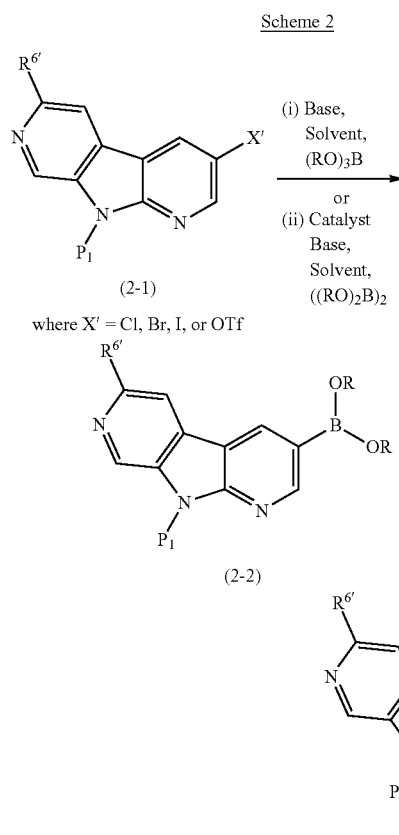

Compounds of formula (2-4) may also be prepared according to the procedure shown in Scheme 2 (wherein $R^{3'}$ is $R^3$ or intermediate moieties that may be manipulated to give $R^3$, and $R^{6'}$ is $R^6$ or intermediate moieties that may be manipulated to give $R^6$). The boronic acid of formula (2-2, where R=H) may be prepared from compounds of formula (2-1) by treatment with a base such as butyllithium in the presence of an alkyl borate such as trimethyl borate in a suitable solvent such as THF at a temperature between −78° C. and ambient temperature.

Alternatively, the boronate ester of formula (2-2, where R=alkyl) may be prepared from compounds of formula (2-1) with the appropriate alkylatodiboron in the presence of a catalyst such as bis(diphenylphosphino)ferrocene palladium (II) dichloride, using a suitable base such as potassium acetate in a solvent such as dioxane at a temperature from room temperature to the reflux temperature of the solvent, or under microwave irradiation at a temperature between 70° C. and 150° C.

Compounds of formula (2-4) may be prepared according to the procedure shown in Scheme 2 by reaction of compounds of formula (2-2) with appropriate halide of formula (2-3) (incorporating appropriate substituents $R^{3'}$), in the presence of a catalyst such as bis(triphenylphosphine) palladium(II) dichloride, with a base such as aqueous sodium carbonate in a suitable co-solvent such as acetonitrile at a temperature from room temperature to the reflux temperature of the solvent, or under microwave irradiation at a temperature between 70° C. and 150° C.

The protecting group ($P_1$) of compounds of formula (2-1), (2-2) and (2-4) may be manipulated at any stage of the synthesis. A protecting group such as SEM (trimethylsilyl ethoxymethyl), can be installed using an alkylating agent such as SEM-chloride, in a solvent such as DMF in the presence of a suitable base such as sodium hydride. Compounds of general formula (2-4) where $P_1$ is a protecting group such as SEM may be de-protected using a reagent such as tetrabutylammonium fluoride in a solvent such as THF at a temperature between −20° C. and 50° C. to provide compounds where $P_1$ is H.

Scheme 3

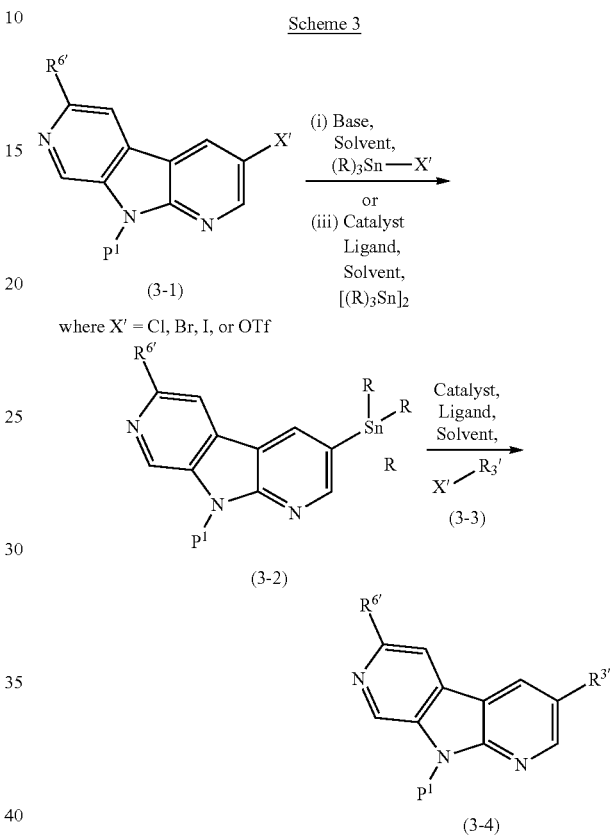

Compounds of general formula (3-4) may also be prepared according to the procedure shown in Scheme 3 (wherein $R^{3'}$ is $R^3$ or intermediate moieties that may be manipulated to give $R^3$, and $R^{6'}$ is $R^6$ or intermediate moieties that may be manipulated to give $R^6$). Stannanes of general formula (3-2) may be prepared from compounds of formula (3-1) with a base and the appropriate tin halide in a suitable solvent such as THF.

Alternatively, stannanes of general formula (3-2) may be prepared from compounds of formula (3-1) with the appropriate alkylditin (containing suitable R groups) in the presence of a catalyst such as tetrakis(triphenylphosphine) palladium(0) in a suitable solvent such as toluene at a temperature from room temperature to the reflux temperature of the solvent, or under microwave irradiation at a temperature between 70° C. and 150° C.

Compounds of general formula (3-4) may be prepared from compounds of general formula (3-2) with the appropriate halide or triflate of formula (3-3), in the presence of a catalyst such as tetrakis(triphenylphosphine) palladium(0) in a suitable solvent such as dioxane at a temperature from room temperature to the reflux temperature of the solvent, or under microwave irradiation at a temperature between 70° C. and 150° C.

Scheme 4

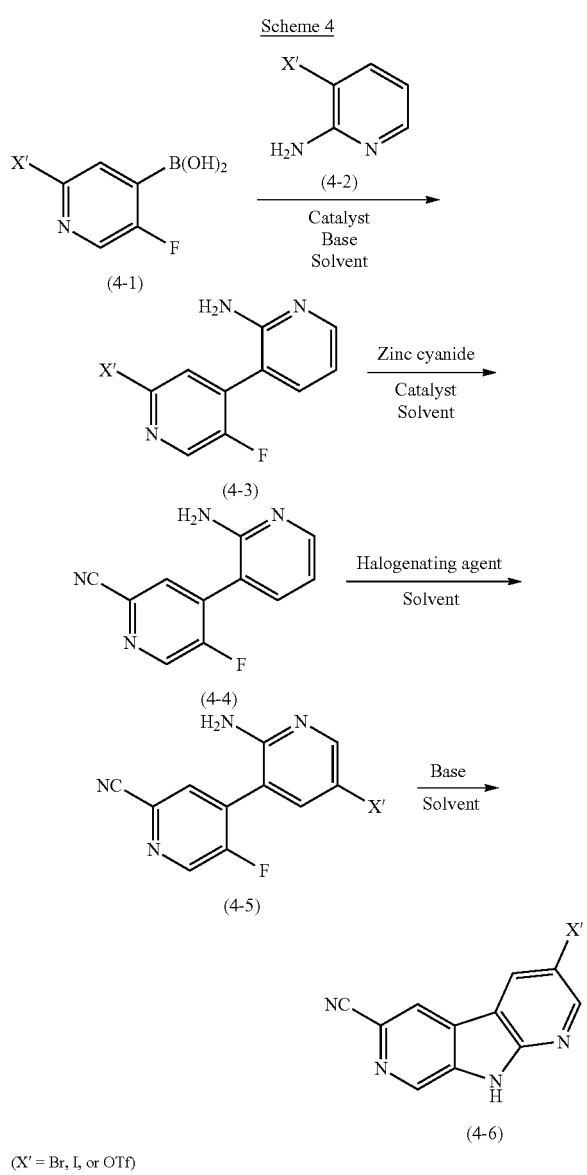

(X' = Br, I, or OTf)

Compounds of general formula (4-6) may be obtained from commercial sources or prepared using published methods described in the literature. Compounds of general formula (4-6) may also be prepared according to the procedure shown in Scheme 4.

Compounds of general formula (4-3) may be obtained from compounds of formula (4-1) by reaction with a halogenated pyridine or triflate of formula (4-2) in the presence of a transition metal catalyst such as bis(triphenylphosphine) palladium(II) dichloride, a base such as aqueous sodium carbonate in a suitable solvent such as acetonitrile at a temperature from room temperature to the reflux temperature of the solvent, or under microwave irradiation at a temperature between 70° C. and 150° C.

The 2-cyanopyridines of formula (4-4) may be prepared from 2-halopyridines of formula (4-3) by reaction with an inorganic cyanide such as zinc cyanide, in the presence of a transition metal catalyst such as tetrakis(triphenylphosphine) palladium(0), in a solvent such as DMF, at a temperature from 50° C. to reflux temperature of the solvent, or under microwave irradiation at a temperature between 70° C. and 200° C. The aminopyridine (4-4) may then be halogenated with a halogenating agent such as N-bromosuccinimide in a solvent such as DMF at a temperature between room temperature and 50° C. to give intermediates of formula (4-5).

Cyclisation of compounds with general formula (4-5) with a suitable base such as sodium hexamethyldisilazide in a suitable solvent such as THF at a temperature between 0° C. and 50° C. may give compounds of general formula (4-6).

Scheme 5

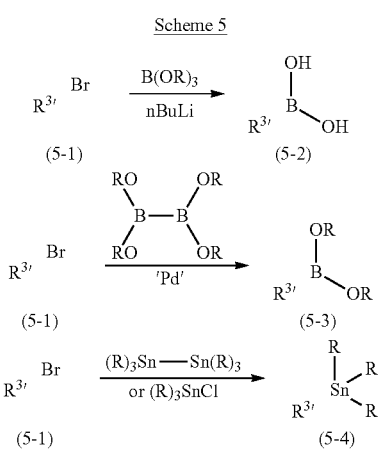

Compounds of general formulae (5-2), (5-3) and (5-4) may be prepared using published methods described in the literature. Compounds of formulae (5-2), (5-3) and (5-4) may also be prepared using the synthetic routes outlined in Scheme 5 (wherein $R^{3'}$ is $R^3$ or intermediate moieties that may be manipulated to give $R^3$).

Compounds of general formula (5-2) may be obtained from compounds of formula (5-1) by reaction with a reagent such as n-butyllithium in a polar aprotic solvent such as THF or diethylether at temperatures between −100° C. and 0° C. and quenched with a boronic ester such as trimethyl borate or triisopropyl borate.

Compounds of general formula (5-3) may be obtained from compounds of formula (5-1) by reaction with a reagent such as bis(pinacolato)diborane in the presence of a catalyst such as [1,1'-bis(diphenylphosphino)ferrocene]dichloropalladium(II), in the presence of a base such as potassium acetate in a suitable solvent such as dioxane, or a mixture of two or more appropriate solvents, at a temperature between room temperature to the reflux temperature of the solvent or solvents, or under microwave irradiation at a temperature between 70° C. and 160° C.

Compounds of general formula (5-4) may be obtained from compounds of formula (5-1) by reaction with a reagent such as hexamethylditin or triethyltin chloride in the presence of a catalyst such as tetrakis(triphenylphosphine)palladium (0), in the presence of a base such as potassium carbonate in a suitable solvent such as DMF, or a mixture of two or more appropriate solvents, at a temperature between room temperature to the reflux temperature of the solvent or solvents, or under microwave irradiation at a temperature between 70° C. and 160° C. Alternatively, these compounds of general formula (5-4) may be obtained from compounds of formula (5-1) by reaction with a reagent such as n-butyllithium in a suitable aprotic solvent such as THF at temperatures between −100° C. and 25° C. and then reacted with a reagent such as hexamethylditin or triethyltin chloride in a suitable aprotic solvent such as THF at temperatures between −100° C. and 50° C.

Scheme 6

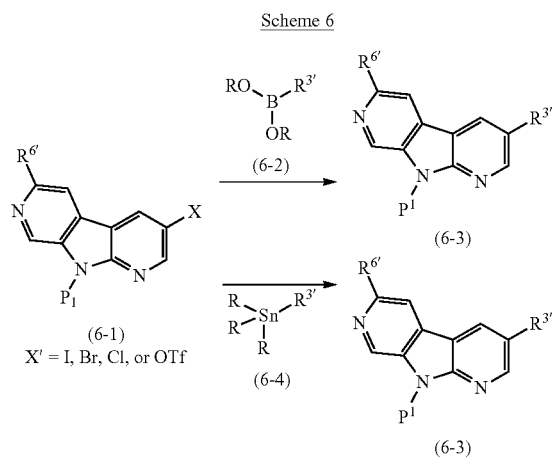

Compounds of general formula (6-3) may be prepared using published methods described in the literature. Compounds of formula (6-3) may also be prepared using the synthetic routes outlined in Scheme 6 (wherein $R^{3'}$ is $R^3$ or intermediate moieties that may be manipulated to give $R^3$, and $R^{6'}$ is $R^6$ or intermediate moieties that may be manipulated to give $R^6$). Compounds of general formula (6-3) may be obtained from compounds of formula (6-1) by reaction with a boronic acid or boronate ester of formula (6-2) (incorporating appropriate substituents $R^{3'}$), or by reaction with an aryl or alkyl tin compound of formula (6-4) (incorporating appropriate substituents $R^{3'}$), in the presence of a catalyst such as bis(triphenylphosphine)palladium(II)dichloride, [1,1′-bis(diphenylphosphino)ferrocene]dichloropalladium (II), an aqueous base such as sodium carbonate, in a suitable solvent such as acetonitrile or combination of solvents, at a temperature between room temperature to the reflux temperature of the solvent, or under microwave irradiation at a temperature between 70° C. and 150° C.

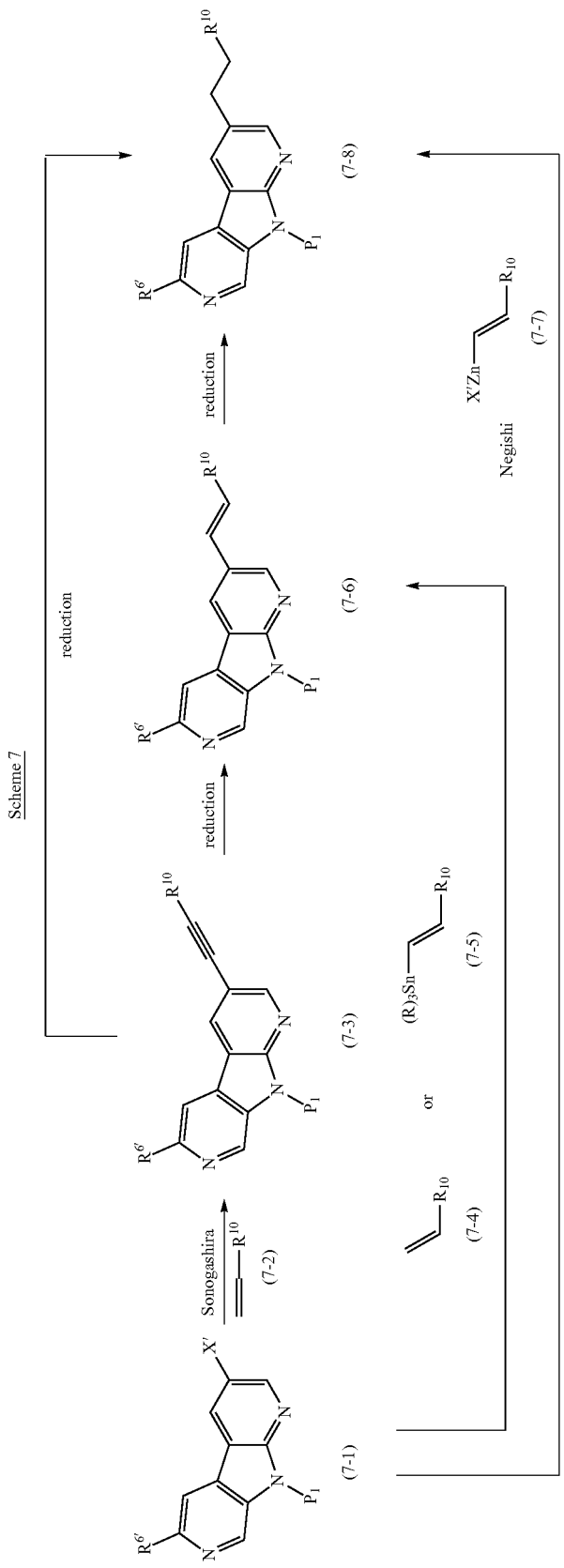

Compounds of general formula (7-8) may be prepared using published methods described in the literature. Compounds of formula (7-8) may also be prepared using the synthetic routes outlined in Scheme 7 (wherein $R^{6'}$ is $R^6$ or intermediate moieties that may be manipulated to give $R^6$). Compounds of general formula (7-3) may be obtained from compounds of general formula (7-1) and a suitable alkyne (7-2) (incorporating a group $R^{10}$ that could be either maintained without modification after coupling, or that could later be modified to give other groups)$R^{10}$ by reaction in the presence of a catalyst system such as tetrakis(triphenylphosphine)palladium(0) and copper (I) iodide in the presence of a base such as triethylamine and a suitable solvent such as N,N-dimethylformamide at a temperature between room temperature and the boiling point of the solvent. Such a coupling reaction could also be carried out in the presence of palladium on carbon, triphenylphosphine, copper (I) iodide and triethylamine in the presence of a suitable solvent such as acetonitrile at a temperature between room temperature and the reflux temperature of the solvent or solvents, or under microwave irradiation at a temperature between 70° C. and 160° C.

Compounds of general formula (7-6) may be obtained from compounds of general formula (7-3) and hydrogen in the presence of a suitable catalyst such as Lindlar catalyst or palladium on barium sulfate in the presence of quinoline and a suitable solvent such as methanol or ethanol. Compounds of general formula (7-6) may also be obtained by reaction of a compound of general formula (7-1) with a suitable alkene (7-4) (incorporating a group $R^{10}$ that could be either maintained without modification after coupling or that could later be modified to give other groups)$R^{10}$ in the presence of a base such as triethylamine or potassium carbonate, a phosphine such as triphenyl phosphine, a metal species such as palladium acetate and a solvent such as acetonitrile at a temperature between room temperature and the boiling point of the solvent. Compounds of general formula (7-6) may also obtained by the reaction of a compound of general formula (7-1) by reaction with a vinyl stannane (7-5) (incorporating a group $R^{10}$ that could be either maintained without modification after coupling or that could later be modified to give other groups $R^{10}$) in the presence of a metal species such as tetrakis(triphenylphosphine)palladium (0) in a suitable solvent such as toluene.

Compounds of general formula (7-8) may be obtained from compounds of general formula (7-3) or (7-6) by reaction with hydrogen in the presence of a catalyst such as palladium on carbon or platinum oxide monohydrate in a suitable solvent such as methanol or ethanol.

Compounds of general formula (7-8) may also be obtained by reaction of compounds of general formula (7-1) by reaction with a suitable alkyl zinc reagent (7-7) in the presence of a catalyst such as allyl palladium (II) chloride dimer or bis(tri-tert-butylphosphine)palladium (0) and a suitable solvent such as 1,4-dioxane at a temperature between room temperature and the boiling point of the solvent.

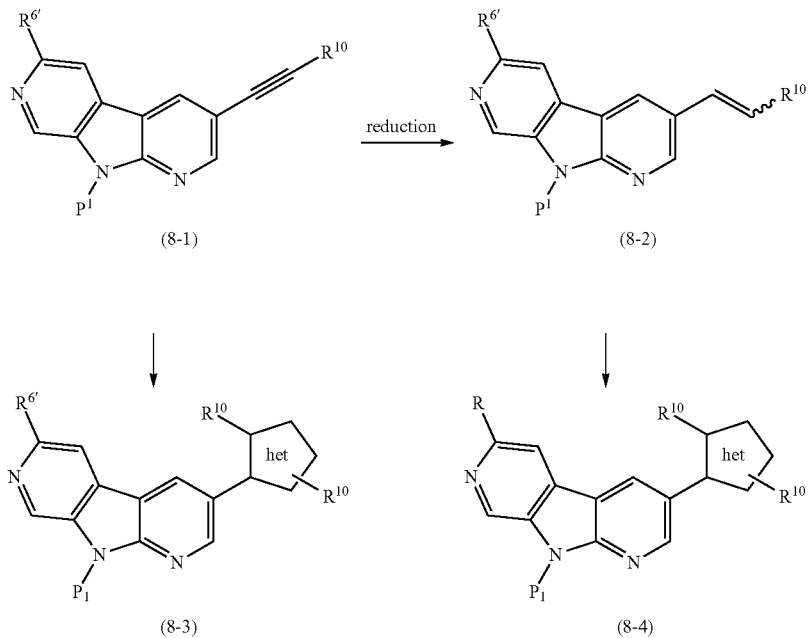

Scheme 8

Compounds of general formula (8-3) may be prepared from compounds of general formula (8-1) by reaction with a suitable 1,3-dipole such as trimethylsilylazide in a suitable solvent such as toluene at a temperature between room temperature and the boiling point of the solvent.

Compounds of general formula (8-2) may be obtained from compounds of general formula (8-1) and hydrogen in the presence of a suitable catalyst such as Lindlar catalyst or palladium on barium sulfate in the presence of quinoline and a suitable solvent such as methanol or ethanol.

Compounds of general formula (8-3) may be obtained by reaction of compounds of general formula (8-2) with a suitable 1,3-dipole (or its precursors, incorporating a group $R^{10}$ that could be either maintained without modification after coupling or that could later be modified to give other $R^{10}$ groups) such as N-methoxymethyl-N-(trimethylsilylmethyl)benzylamine and lithium fluoride in a solvent such as acetonitrile with ultrasonic treatment, or nitroethane and phenyl isocyanate in a suitable solvent such as toluene in the presence of a base such as triethylamine at a temperature between 0° C. and the boiling point of the solvent.

Scheme 9

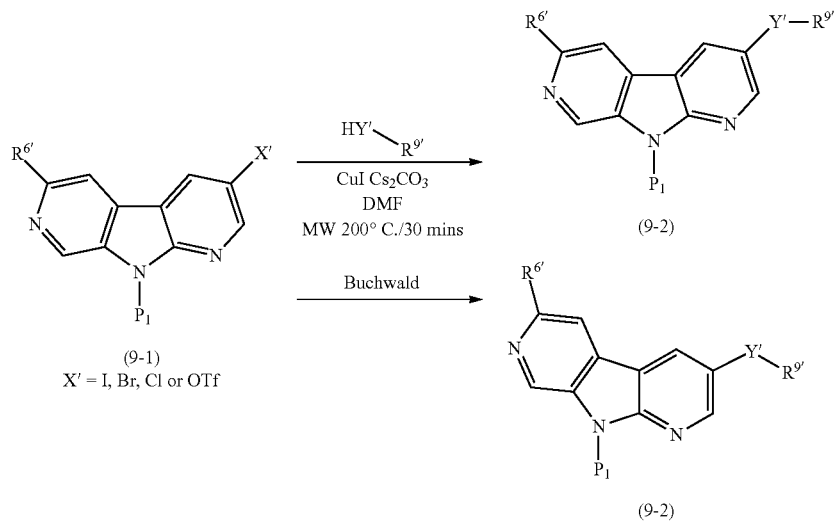

(9-1)
X' = I, Br, Cl or OTf

Compounds of general formula (9-2) may be prepared using published methods described in the literature. Compounds of formula (9-2) may be prepared using the synthetic routes outlined in Scheme 9 (wherein $R^{9'}$ is $R^9$ or intermediate moieties that may be manipulated to give $R^9$, and $R^{6'}$ is $R^6$ or intermediate moieties that may be manipulated to give $R^6$).

Compounds of general formula (9-2) may be obtained from compounds of formula (9-1) by reaction with compounds of general formula (HY'—$^{9'}$) in the presence of reagents such as copper(II) iodide or copper powder in the presence of a base such as cesium carbonate in a suitable solvent such as DMF at a temperature between room temperature and the reflux temperature of the solvent, or under microwave irradiation at a temperature between 70° C. and 240° C., which may be similar to conditions described in the literature by Ullmann.

Compounds of general formula (9-2) may be obtained from compounds of formula (9-1) by reaction with compounds of general formula (HY'—$R^{9'}$) in the presence of a catalyst such as [1,1'-bis(diphenylphosphino)ferrocene]dichloropalladium(II), in the presence of a base such as potassium tert-butoxide in a suitable solvent such as DME, or a mixture of two or more appropriate solvents, at a temperature between room temperature and the reflux temperature of the solvent or solvents, or under microwave irradiation at a temperature between 70° C. and 160° C., which may be similar to conditions described in the literature by Buchwald and Hartwig.

Scheme 10

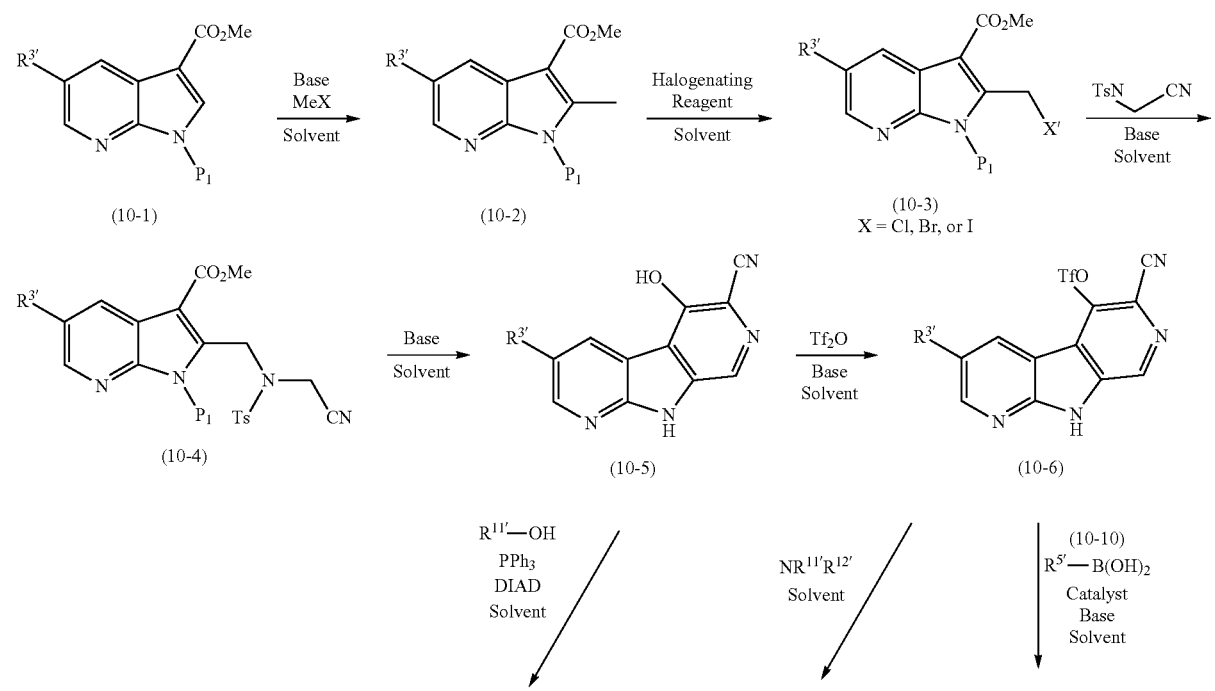

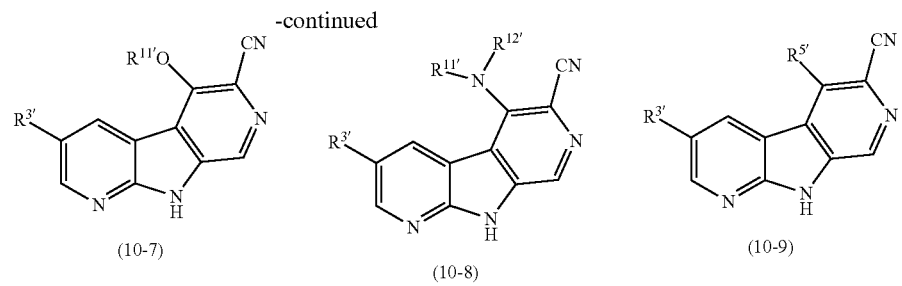

(10-7)　(10-8)　(10-9)

Compounds of general formula (10-7), (10-8) and (10-9) may be prepared using published methods described in the literature (WO2006001754). Compounds of formula (10-7), (10-8) and (10-9) may be prepared using the synthetic routes outlined in Scheme 10 (wherein $R^{3'}$ is $R^3$ or intermediate moieties that may be manipulated to give $R^3$, and $R^{5'}$ is $R^5$ or intermediate moieties that may be manipulated to give $R^5$). Compounds with a general formula (10-2) may be prepared from compounds of formula (10-1) by deprotonation using a suitable base such as lithium diisopropylamide in a suitable solvent such as THF at a temperature between −78° C. and room temperature followed by addition of a suitable methylating agent such as methyl iodide. The intermediate (10-2) may then be brominated with a brominating agent such as N-bromosuccinimide in a solvent such as carbon tetrachloride at a temperature between room temperature and the reflux temperature of the solvent to give compounds of formula (10-3).

Compounds of formula (10-3) may be converted to compounds of formula (10-4) by displacement with tosylaminoacetonitrile using a suitable base such as sodium hydride in a solvent such as DMF at a temperature between −20° C. and 50° C. Intermediates (10-4) may then be cyclised with a suitable base such as lithium hexamethylsilylamide in a solvent such as THF at a temperature between −20° C. and 50° C. to provide compounds of general formula (10-5). The phenol (10-5) may then be reacted with an appropriate alcohol ($R^{11'}$OH) using a phosphine and a coupling reagent such as diisopropylazodicarboxylate in an appropriate solvent such as THF to provide ethers of general formula (10-7).

Alternatively, the phenol intermediate (10-5) may be converted to the triflate using a reagent such as triflic anhydride in the presence of a base such as triethylamine in a suitable solvent such as dichloromethane at a temperature between −50° C. and 20° C. The triflate (10-6) may then be converted to compounds of general formula (10-9) by reaction with a boronic acid or boronate ester of formula (10-10) in the presence of a transition metal catalyst such as bis(triphenylphosphine) palladium(II)dichloride, a base such as aqueous sodium carbonate in a suitable solvent such as acetonitrile at a temperature from room temperature to the reflux temperature of the solvent, or under microwave irradiation at a temperature between 70° C. and 150° C. Alternatively, the triflate may be converted to compounds of general formula (10-8) by displacement with a suitable amine either (HNR$^{11'}$R$^{12'}$) as solvent or in a solvent such as 2-propanol at a temperature between ambient temperature and the reflux point of the solvent.

Compounds of general formula (10-8) may be obtained from compounds of formula (10-6) by reaction with compounds of general formula (HNR$^{11'}$R$^{12'}$) in the presence of a catalyst such as [1,1'-bis(diphenylphosphino)ferrocene] dichloropalladium(II), in the presence of a base such as potassium tert-butoxide in a suitable solvent such as DME, or a mixture of two or more appropriate solvents, at a temperature from room temperature to the reflux temperature of the solvent or solvents, or under microwave irradiation at a temperature between 70° C. and 160° C., which may be similar to conditions described in the literature by Buchwald and Hartwig.

Scheme 11a

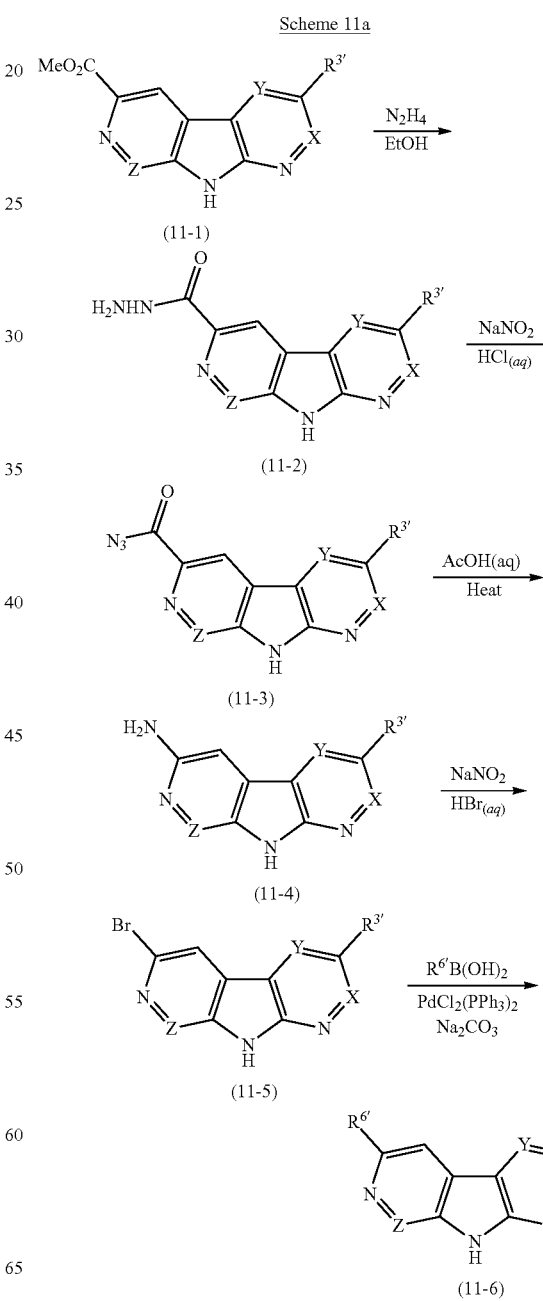

Compounds of general formula (11-6) may be prepared using published methods described in the literature. Compounds of formula (11-6) may be prepared using the synthetic routes outlined in Scheme 11a (wherein $R^{3'}$ is $R^3$ or intermediate moieties that may be manipulated to give $R^3$, and wherein $R^{6'}$ is $R^6$ or intermediate moieties that may be manipulated to give $R^6$). Compounds of the formula (11-1) may be converted via acyl hydrazide formation, diazotization and Curtius rearrangement to give compounds of the formula (11-4), which may be further converted by Sandmeyer reaction to compounds of the formula (11-5). Similarly, compounds of formula (11-4) may undergo Sandmeyer reaction to provide other 6-substituted derivatives such as 6-fluoro (11-7), 6-chloro (11-8), 6-iodo (11-9), 6-alkylthio (11-10), 6-hydroxy (11-11) and 6-cyano (11-12) as outlined in Scheme 11b.

Compounds of the formula (11-5) are useful for the introduction of group $R^6$ (or group $R^{6'}$ which may be converted into group $R^6$) in various ways, to generate compounds of the formula (11-6), for example, by coupling with organic boronic acid derivatives in the presence of a palladium catalyst. Similarly, organic stannanes (eg. $R^{6'}SnR_3$), organozinc ($R^{6'}ZnCl$) and other reagents can be used in the place of organic boronic acids. In particular compounds of the formula (11-6) where $R^{6'}$ represents such groups as alkyl, cycloalkyl, alkenyl, alkynyl, aryl, heterocyclyl and heteroaryl may be prepared in this manner. Compounds of the formula (11-5) may also be converted into organic boronic acid derivatives of the type (11-13), which may give compounds of the formula (11-6) by coupling with organic halide or triflate derivatives in the presence of a palladium catalyst, as outlined in Scheme 11c. Similarly, (11-5) may be converted to an organic stannane, organozinc and other derivatives to be used in the place of organic boronic acids in palladium catalyst-mediated couplings to give compounds of the formula (11-6).

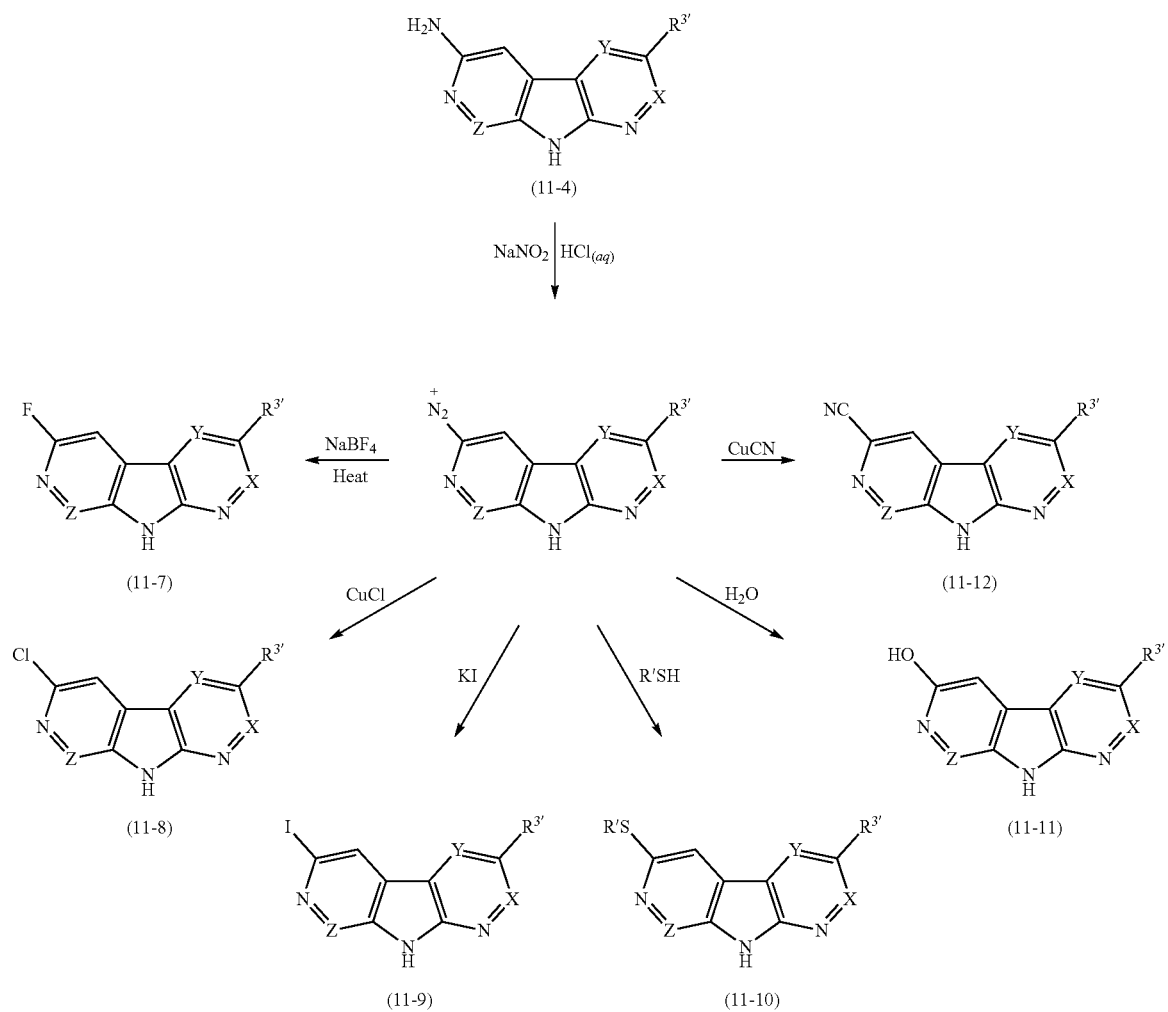

Scheme 11c

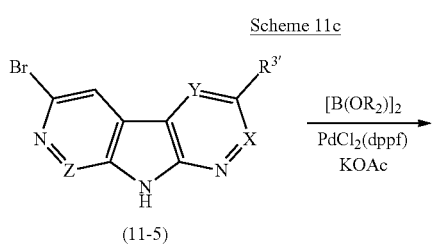

Compounds of general formula (11-5) are useful in the preparation of derivatives through nucleophilic aromatic displacement reactions utilizing nucleophilic reagents R-NuH, which may be facilitated in the presence of base, as outlined in Scheme 11d. Examples of such reagents and reactions are alcohols yielding compounds of the formula (11-14), thiols yielding compounds of the formula (11-15), primary and secondary amines yielding compounds of the formula (11-16), and heterocycles such as imidazole which yields compounds of the formula (11-17). Such displacement reactions may also be facilitated by the presence of a palladium, copper or other catalyst yielding compounds of the general formula (11-18), as outlined in Scheme 11d.

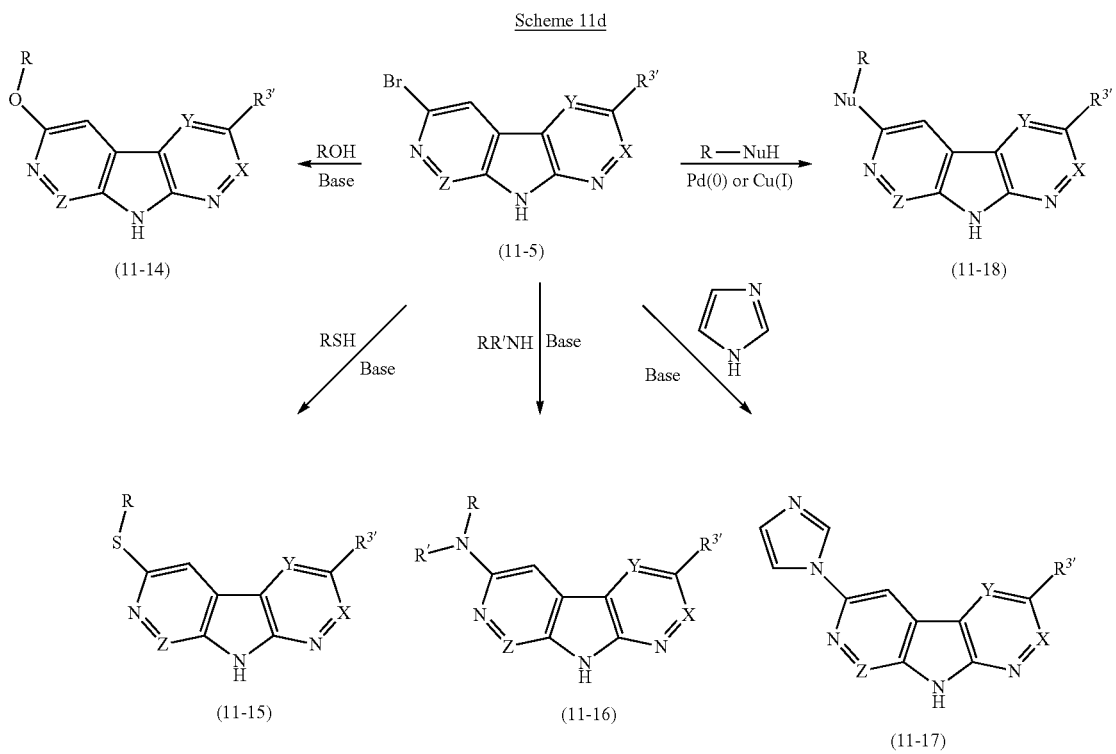

Scheme 11d

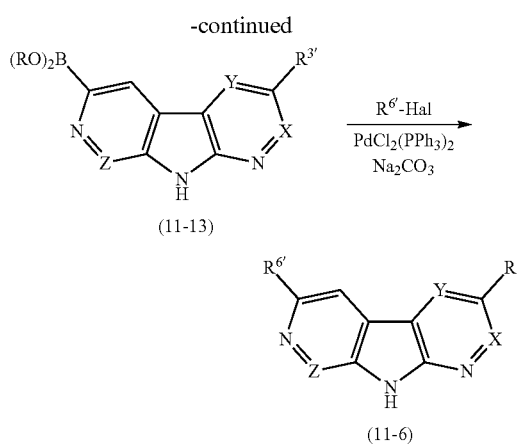

Compounds of general formula (11-5) are useful in the preparation of derivatives through nucleophilic aromatic displacement reactions utilizing nucleophilic reagents R-NuH, which may be facilitated in the presence of base, as outlined in. Scheme 11d. Examples of such reagents and reactions are alcohols yielding compounds of the formula (11-14), thiols yielding compounds of the formula (11-15), primary and secondary amines yielding compounds of the formula (11-16), and heterocycles such as imidazole which yields compounds of the formula (11-17). Such displacement reactions may also be facilitated by the presence of a palladium, copper or other catalyst yielding compounds of the general formula (11-18), for example reactions of alcohols and alkyl amines, as outlined in Scheme 11d.

Scheme 11e

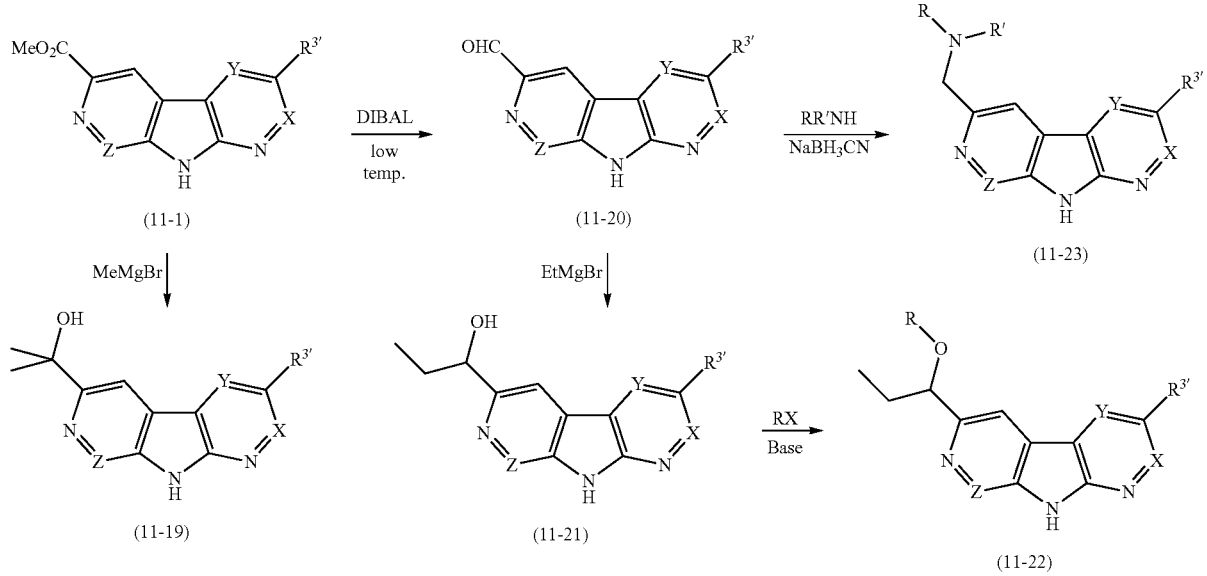

Compounds of the formula (11-1) are also of use as intermediates for the preparation of benzylic alcohols through nucleophilic addition of organometallic or hydride transfer reagents to the ester function, for example methylmagnesium bromide, to provide tertiary alcohols of the formula (11-19), as outlined in Scheme 11e. Compounds of the formula (11-1) may also be subject to partial reduction of the ester function to yield aldehydes of the formula (11-20), for example using hydride transfer reagents such as diisobutylaluminium hydride. Such intermediates as (11-20) may be transformed through nucleophilic addition of organometallic reagents to the aldehyde function, for example ethylmagnesium bromide, to provide secondary alcohols of the formula (11-21).

Such benzylic alcohols may further be transformed by O-alkylation, for example utilizing alkyl halide and base, such as transformation of compounds of the formula (11-21) to ether products of the formula (11-22). Aldheydes of the formula (11-20) may also be subject to reductive amination utilizing amines and hydride transfer reagents, for example sodium cyanoborohydride, yielding benzylic amines of the general formula (11-22), as outlined in Scheme 11e.

Reagents and conditions given in Schemes 11a, 11b, 11c, 11 d and 11e are examples of those that may be used, and comparable methods utilizing alternative reagents can be found in the literature.

Scheme 12

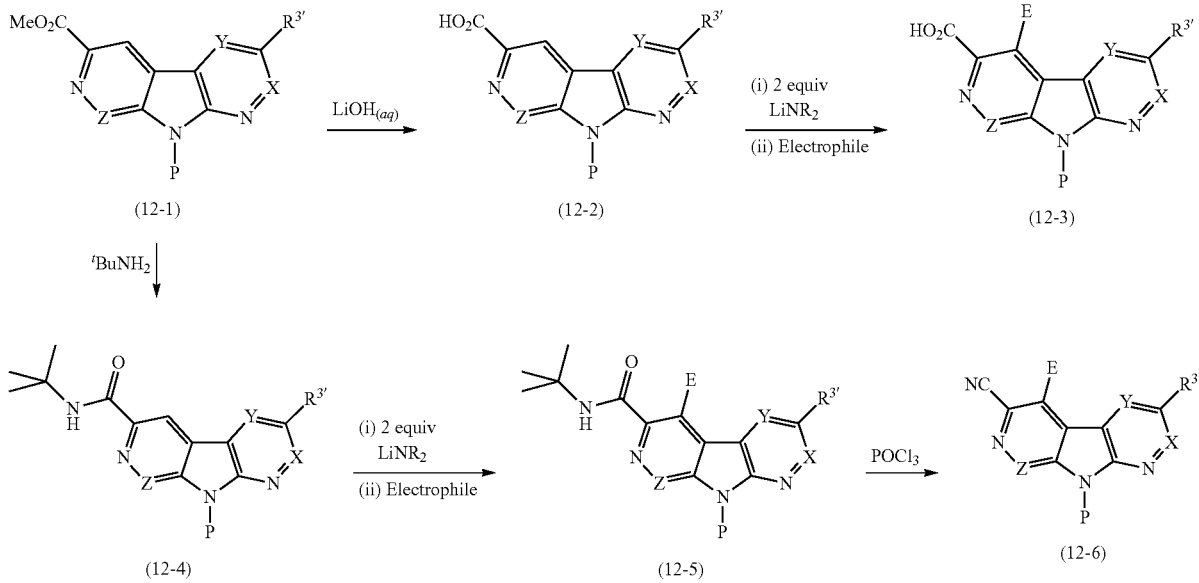

Compounds of general formula (12-1) may be prepared using methods described herein, and compounds of formula (12-6) may be prepared using the synthetic routes outlined in Scheme 12 (wherein $R^{3'}$ is $R^3$ or intermediate moieties that may be manipulated to give $R^3$, and wherein E is a generalized functional group derived from reaction with an electrophilic reagent following suitable work-up procedure, and P is a suitable protecting group). Carboxylic ester compounds of the formula (12-1) may be saponified to generate compounds of the formula (12-2), for example using aqueous lithium hydroxide. Alternatively, compounds of the formula (12-1) may be transformed into carboxamide compounds of the formula (12-4), by treatment for example with neat tert-butylamine. Compounds such as (12-2) may be treated two or more equivalents of with strong base, for example lithium tetramethylpiperidide, and quenched with a variety of electrophilic reagents, to generate derivatives of the general formula (12-3), in which the 5-position has become substituted with a functionality E derived form the electrophilic reagent. Such a transformation is exemplified by in the literature (WO 2003022849). For example, suitable electophilic reagents yielding derivatives with functional groups E include, respectively: ethyl iodide yielding 5-ethyl; formaldehyde yielding 5-hydroymethyl; dimethylformamide yielding 5-formyl; trimethylborate yielding 5-boronic acid ester, which may be further transformed to 5-hydroxy through oxidation using basic hydrogen peroxide. Similarly, carboxamide compounds of the formula (12-4) yield products of the formula (12-5) upon similar treatment, and these products may be further converted to the 6-cyano derivatives of formula (12-6) by treatment with acidic dehydrating agents, for example phosphorous oxychloride.

Reagents and conditions given in Scheme 12 are examples of those that may be used, and comparable methods utilizing alternative reagents can be found in the literature.

Scheme 13

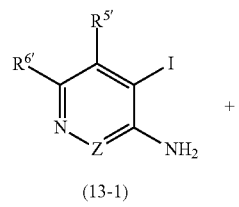

(13-1)

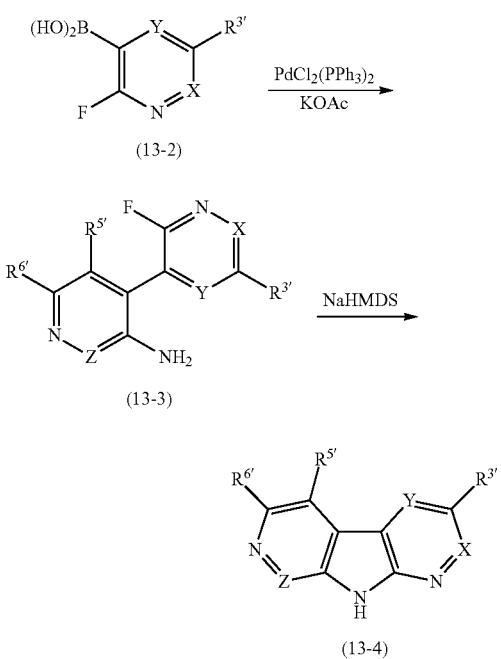

In a similar manner to that outlined in Scheme 14, compounds of the general formula (13-4) may be prepared using the synthetic routes outlined in Scheme 13 (wherein $R^{3'}$ is $R^3$ or intermediate moieties that may be manipulated to give $R^3$, $R^{5'}$ is $R^5$ or intermediate moieties that may be manipulated to give $R^5$, $R^{6'}$ is $R^6$ or intermediate moieties that may be manipulated to give $R^6$, and $R^{8'}$ is $R^8$ or intermediate moieties that may be manipulated to give $R^8$). For example, iodo-amino-heterocycle compounds of the formula (13-4) may be coupled with heterocycle-boronic acids of the formula (13-2) utilizing a suitable palladium catalyst and base, for example dichlorobis(triphenylphosphine)palladium(0) and potassium acetate in a suitable solvent, to yield biaryl compounds of the formula (13-3). Such compounds may be further transformed through treatment with base, for example sodium hexamethyldisilazide in a suitable solvent, to yield tricyclic compounds of the general formula (13-4). Thus further substitution of the tricycle, for example at the 3-, 5-, 6-, and 8-positions, may be achieved through utilizing compounds of the formula (13-1) and (13-2) in which one or more functionality $R^{3'}$, $R^{5'}$, $R^{6'}$ or $R^{8'}$ is already in place.

Compounds of formula (14-7) and (14-9) may be prepared using the synthetic routes outlined in Scheme 14.

Scheme 14

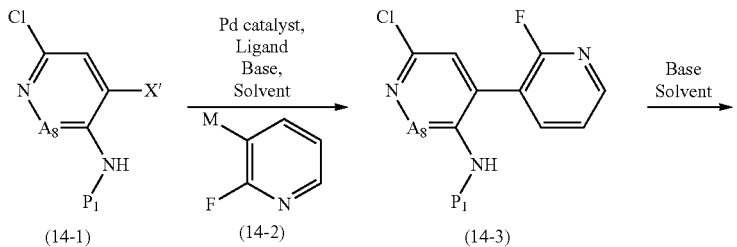

-continued

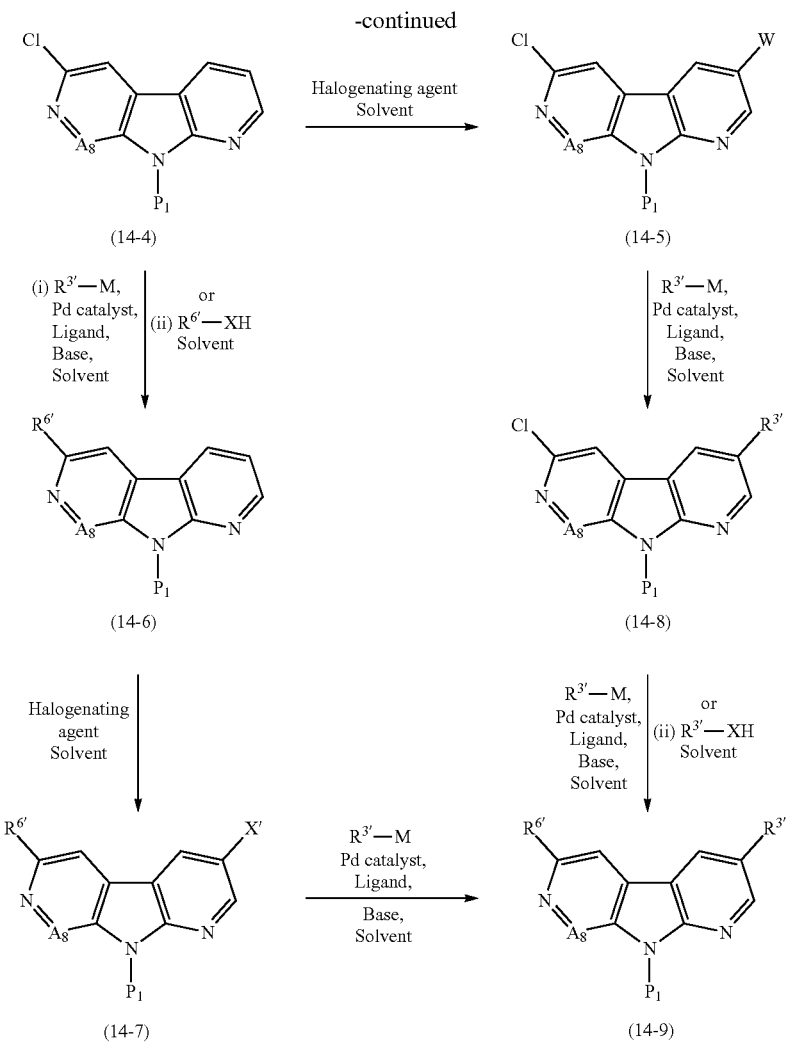

X' = Cl, Br, I or OTf
A₈ = CR⁸ or N
M = B(OR)₂, SnR₃, ZnX'
W = Br or I

Compounds of general formula (14-3) may be obtained from compounds of formula (14-1) by reaction with a boronic acid or boronate ester of formula (14-2), in the presence of a catalyst such as bis(triphenylphosphine)palladium(II) dichloride, a base such as aqueous sodium carbonate in a suitable solvent such as acetonitrile at a temperature between room temperature and the reflux temperature of the solvent, or under microwave irradiation at a temperature between 70° C. and 150° C. Compounds of general formula (14-3) may be cyclised to obtain compounds of formula (14-4) with a suitable base such as sodium hexamethyldisilazane in a suitable solvent such as THF at a temperature between 0° C. and 50° C.

Compounds of general formula (14-4) may then be converted to compounds of general formula (14-6) by reaction with a boronic acid or boronate ester (incorporating appropriate substituents $R^{6'}$), in the presence of a catalyst such as bis(triphenylphosphine) palladium(II) dichloride, a base such as aqueous sodium carbonate in a suitable solvent such as acetonitrile at a temperature between room temperature and the reflux temperature of the solvent, or under microwave irradiation at a temperature between 70° C. and 150° C.

Alternatively, Compounds of formula (14-4) may be coupled with an aryl or alkyl tin compound (incorporating appropriate substituents $R^{6'}$), in the presence of a catalyst such as bis (triphenylphosphine) palladium(II) dichloride or [1,1'-bis (diphenylphosphino)ferrocene]dichloropalladium (II), with or without an aqueous base such as sodium carbonate, in a suitable solvent such as acetonitrile at a temperature between room temperature and the reflux temperature of the solvent, or under microwave irradiation at a temperature between 70° C. and 150° C.

Compounds of general formula (14-6) may be obtained from compounds of formula (14-4) by reaction with compounds of general formula (HX—R₆') in the presence of a catalyst such as [1,1'-bis(diphenylphosphino)ferrocene] dichloropalladium(II), in the presence of a base such as potassium tert-butoxide in a suitable solvent such as DME, or a mixture of two or more appropriate solvents, at a temperature between room temperature and the reflux temperature of the solvent or solvents, or under microwave irradiation at a temperature between 70° C. to 160° C., as which may be similar to conditions described in the literature by Buchwald and Hartwig.

Intermediates of formula (14-6) may then be halogenated in the presence of a suitable halogenating agent, such as bromine, in a solvent such as acetic acid, at a temperature between 20° C. and 120° C., to obtain compounds of formula (14-7). Compounds of formula (14-7) may then be converted to compounds of formula (14-9) using methods described in Scheme 9.

Alternatively, compounds of formula (14-4) may be halogenated to give compounds of formula (14-5), then converted to compounds of formula (14-8) by reaction with a boronic acid, boronate ester or stannane then converted to compounds of formula (14-9) using similar conditions to those described for the introduction of $R^{3'}$.

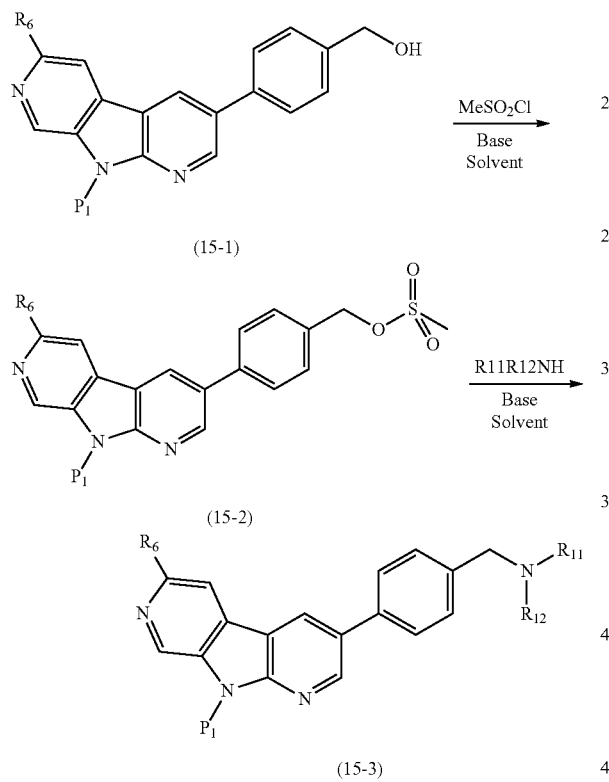

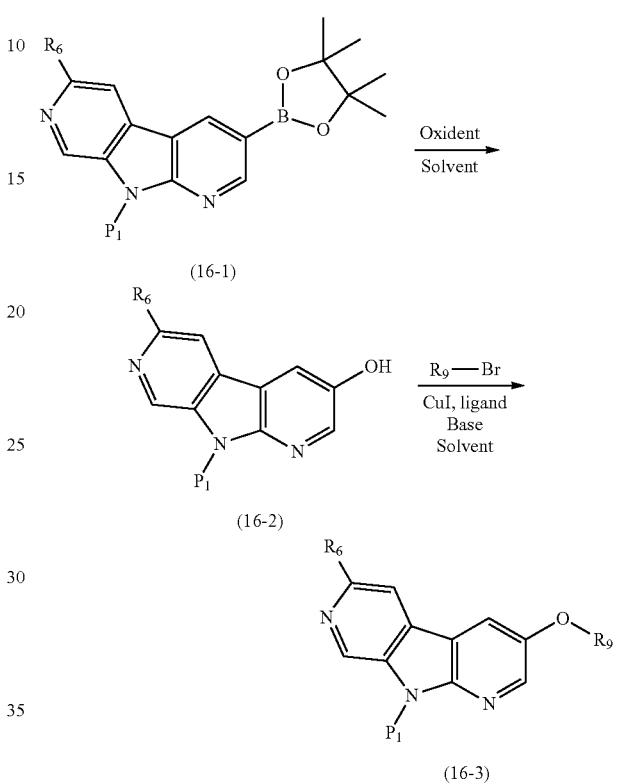

Compounds (15-1) may be prepared using the methods described herein. Subjecting compounds of the general formula (15-1) to reaction with methanesulfonyl chloride, in the presence of a base such as triethylamine, in a suitable solvent such as dichloromethane at a temperature between 0° C. and the reflux temperature of the solvent, yields compounds of formula (15-2).

Compounds of the general formula (15-3) may be obtained from compounds (15-2) by reaction with an amine, in the presence of a base such as triethylamine, in a suitable solvent such as acetonitrile at a temperature between ambient temperature and the reflux temperature of the solvent.

Compounds of general formula (16-3) may be prepared according to the procedure shown in Scheme 16.

Compounds (16-1) may be prepared using the methods described in Scheme 2. Subjecting compounds of the general formula (16-1) to reaction with an oxidant such as N-methylmorpholine-N-oxide, in a suitable solvent such as tetrahydrofuran, at a temperature between ambient temperature and the reflux temperature of the solvent, yields compound of formula (16-2).

Compounds of the general formula (16-3) may be obtained from compounds (16-2) by reaction with an alkyl halide, in the presence of a catalyst such as copper (I) iodide, a ligand such as N,N-dimethylglycine, a base such as cesium carbonate in a suitable solvent such as dioxane, at a temperature between ambient temperature and reflux temperature of the solvent, or under microwave irradiation at a temperature between 70° C. to 150° C.

Compounds of general formula (17-13) may be prepared according to the procedure shown in Scheme 17.

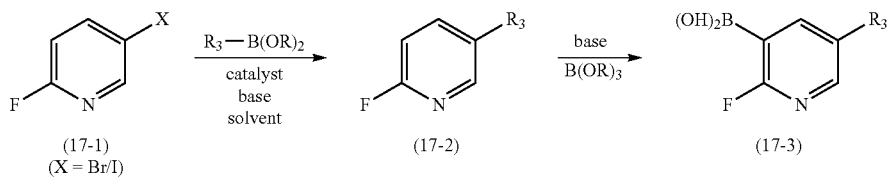

-continued

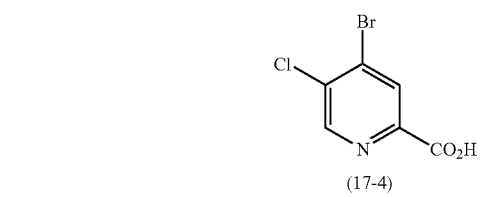 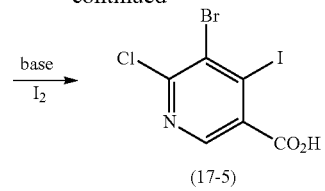

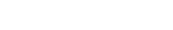

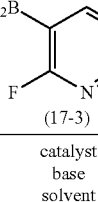

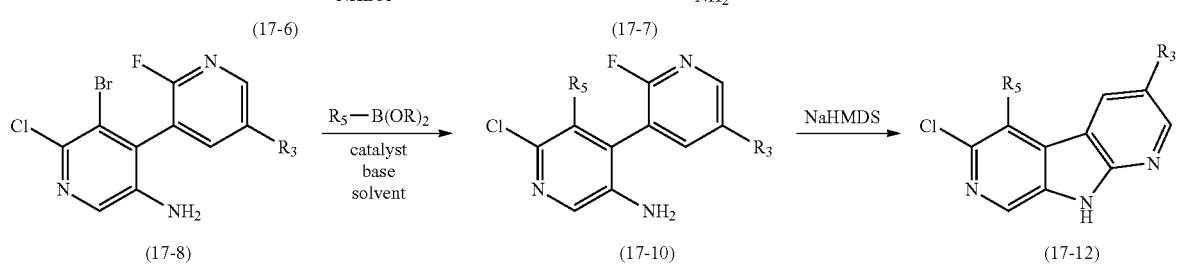

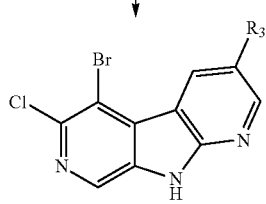 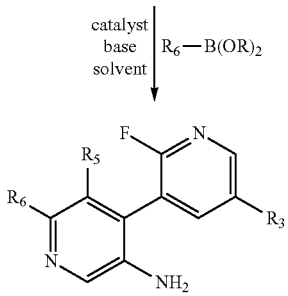 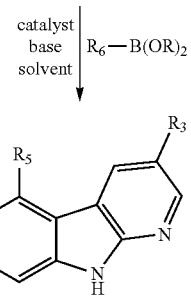

Compounds (17-1) and (17-4) may be obtained from commercial sources or prepared using published methods described in the literature. Compounds of general formula (17-2) may be obtained from compounds of formula (17-1) by reaction with an organometallic reagent such as a boronic acid or ester, in the presence of a transition metal catalyst such as [1,1'-bis(diphenylphosphino)ferrocene]dichloropalladium (II), a base such as aqueous potassium fluoride in a suitable solvent such as acetonitrile at a temperature between ambient temperature and the reflux temperature of the solvent, or under microwave irradiation at a temperature between 70° C. and 150° C.

Compounds of the general formula (17-3) may be obtained from compounds of formula (17-2) by reaction with a base such as lithium diisopropylamide and a boronate source such as triisopropylborate, in a suitable solvent such as THF, at a temperature between −78° C. and ambient temperature.

5-Bromo-6-chloro-4-iodo-nicotinic acid (17-5) may be obtained from 5-bromo-6-chloro-nicotinic acid (17-4) by reaction with a base, such as n-butyl lithium, an amine such as 2,2,6,6-tetramethylpiperidine and an iodine source, such as solid iodine, in a suitable solvent, such as THF at a temperature between −78° C. and ambient temperature. 5-Bromo-6-chloro-4-iodo-pyridin-3-yl)-carbamic acid tert-butyl ester (17-6) may be obtained from 5-bromo-6-chloro-4-iodo-nicotinic acid (17-5) by reaction with diphenylphosporyl azide in the presence of a base such as triethylamine and tert-butanol, in a suitable solvent such as toluene at a temperature between ambient temperature to reflux temperature of the solvent. 5-Bromo-6-chloro-4-iodo-pyridin-3-ylamine (17-7) may be obtained from 5-bromo-6-chloro-4-iodo-pyridin-3-yl)-carbamic acid tert-butyl ester (17-6) by reaction with trifluoroacetic acid in a suitable solvent such as DCM at a temperature between −10° C. and the reflux temperature of the solvent.

Compounds of general formula (17-8) may be obtained from compounds of formula (17-3) by reaction with 5-bromo-6-chloro-4-iodo-pyridin-3-ylamine (xiii) in the presence of a transition metal catalyst such as [1,1'-bis(diphenylphosphino)ferrocene]dichloropalladium(II), a base such as aqueous potassium fluoride in a suitable solvent such as acetonitrile at a temperature from ambient temperature to the reflux temperature of the solvent, or under microwave irradiation at a temperature between 70° C. and 150° C.

Cyclisation of compounds with general formula (17-8) with a suitable base such as sodium hexamethylsilazide in a suitable solvent such as THF at a temperature between 0° C. and 50° C. yields compounds of general formula (17-9).

Compounds of the general formula (17-10) may be obtained from compounds (17-8) by reaction with an organometallic reagent such as a boronic acid or ester, in the presence of a transition metal catalyst such as [1,1'-bis(diphenylphosphino)ferrocene]dichloropalladium(II), a base such as aqueous potassium fluoride in a suitable solvent such as acetonitrile at a temperature between ambient temperature and the reflux temperature of the solvent, or under microwave irradiation at a temperature between 70° C. and 150° C.

Cyclisation of compounds with general formula (17-10) with a suitable base such as sodium hexamethylsilazide in a suitable solvent such as THF at a temperature between 0° C. and 50° C. yields compounds of general formula (17-12).

Compounds of the general formula (17-13) may be obtained from compounds (17-12) by reaction with an organometallic reagent such as a boronic acid or ester, in the presence of a transition metal catalyst such as [1,1'-bis(diphenylphosphino)ferrocene]dichloropalladium(II), a base such as aqueous potassium fluoride in a suitable solvent such as acetonitrile at a temperature between ambient temperature and the reflux temperature of the solvent, or under microwave irradiation at a temperature between 70° C. and 150° C.

Compounds of the general formula (17-11) may be obtained from compound (17-10) by reaction with an organometallic reagent such as a boronic acid or ester, in the presence of a transition metal catalyst such as [1,1'-bis(diphenylphosphino)ferrocene]dichloropalladium(II), a base such as aqueous potassium fluoride in a suitable solvent such as acetonitrile at a temperature between ambient temperature and the reflux temperature of the solvent, or under microwave irradiation at a temperature between 70° C. and 150° C.

Cyclisation of compounds with general formula (17-11) with a suitable base such as sodium hexamethylsilazide in a suitable solvent such as THF at a temperature between 0° C. and 50° C. may give compounds of general formula (17-13).

Compounds of formula (18-8) may be prepared using the synthetic routes outlined in Scheme 18.

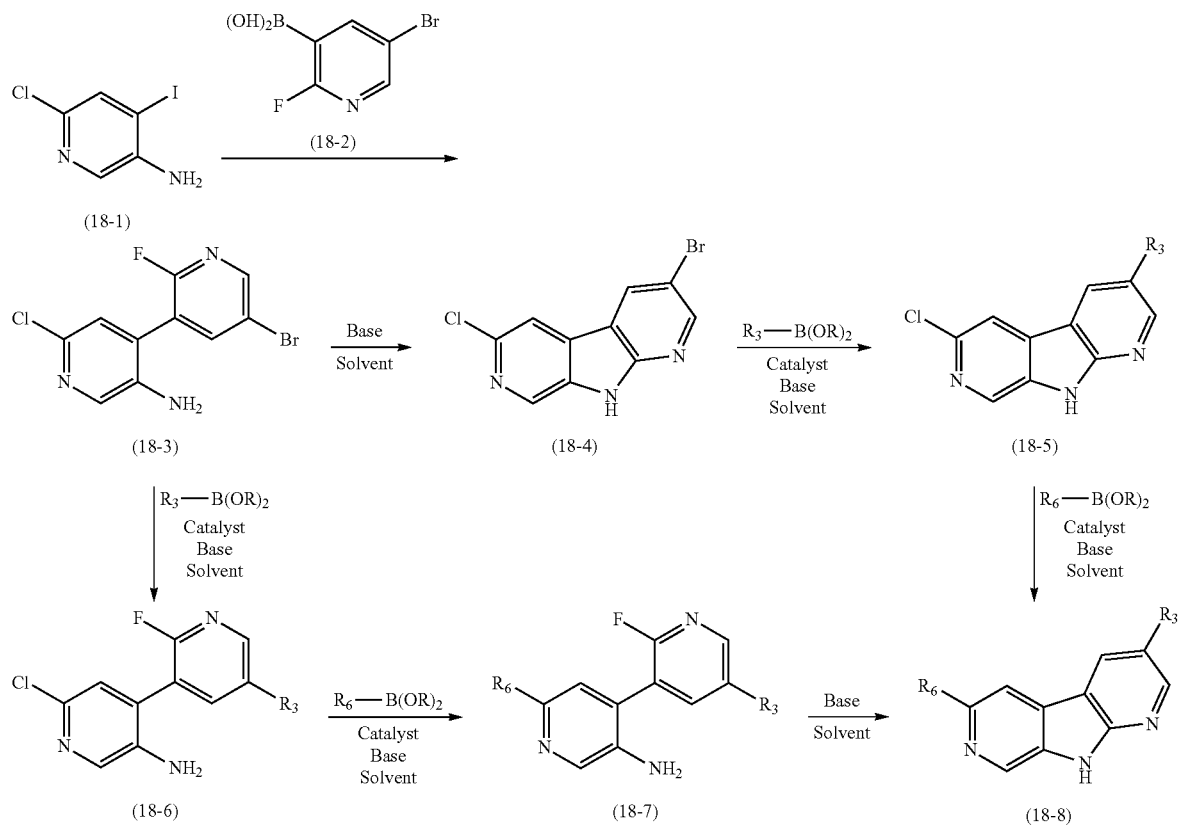

Scheme 18

Compounds (18-1) and (18-2) may be obtained from commercial sources, prepared using published methods described in the literature, or from methods described in Scheme 3. 5-Bromo-6'-chloro-2-fluoro-[3,4']bipyridinyl-3'-ylamine (18-3) may be obtained from 5-bromo-2-fluoropyridine-3-boronic acid (18-2) by reaction with 6-chloro-4-iodo-pyridin-3-ylamine (18-1) in the presence of a transition metal catalyst such as [1,1'-bis(diphenylphosphino)ferrocene]dichloropalladium(II), a base such as aqueous sodium carbonate in a suitable solvent such as acetonitrile at a temperature between ambient temperature and the reflux temperature of the solvent, or under microwave irradiation at a temperature between 70° C. to 150° C.

3-Bromo-6-chloro-1,7-diazacarbazole (18-4) may be obtained from 5-bromo-6'-chloro-2-fluoro-[3,4']bipyridinyl-3'-ylamine (18-3) by cyclisation with a suitable base such as sodium hexamethylsilazide in a suitable solvent such as THF at a temperature between 0° C. and 50° C.

Compounds of the general formula (18-5) may be obtained from compound (18-4) by reaction with an organometallic reagent such as a boronic acid or ester, in the presence of a transition metal catalyst such as [1,1'-bis(diphenylphosphino)ferrocene]dichloropalladium(II), a base such as aqueous sodium carbonate in a suitable solvent such as acetonitrile at a temperature between ambient temperature and the reflux temperature of the solvent, or under microwave irradiation at a temperature between 70° C. and 150° C.

Compounds of the general formula (18-8) may be obtained from compound (18-5) by reaction with an organometallic reagent such as a boronic acid or ester, in the presence of a transition metal catalyst such as [1,1'-bis(diphenylphosphino)ferrocene]dichloropalladium(II), a base such as aqueous sodium carbonate in a suitable solvent such as acetonitrile at a temperature from ambient temperature to the reflux temperature of the solvent, or under microwave irradiation at a temperature between 70° C. to 150° C.

Compounds of the general formula (18-6) may be obtained from compound (18-3) by reaction with an organometallic reagent such as a boronic acid or ester, in the presence of a transition metal catalyst such as [1,1'-bis(diphenylphosphino)ferrocene]dichloropalladium(II), a base such as aqueous sodium carbonate in a suitable solvent such as acetonitrile at a temperature between ambient temperature and the reflux temperature of the solvent, or under microwave irradiation at a temperature between 70° C. and 15.0° C.

Compounds of the general formula (18-7) may be obtained from compound (18-6) by reaction with an organometallic reagent such as a boronic acid or ester, in the presence of a transition metal catalyst such as [1,1'-bis(diphenylphosphino)ferrocene]dichloropalladium(II), a base such as aqueous sodium carbonate in a suitable solvent such as acetonitrile at a temperature between ambient temperature and the reflux temperature of the solvent, or under microwave irradiation at a temperature between 70° C. and 150° C.

Cyclisation of compounds with general formula (18-7) with a suitable base such as sodium hexamethylsilazide in a suitable solvent such as THF at a temperature between 0° C. and 50° C. may give compounds of general formula (18-8).

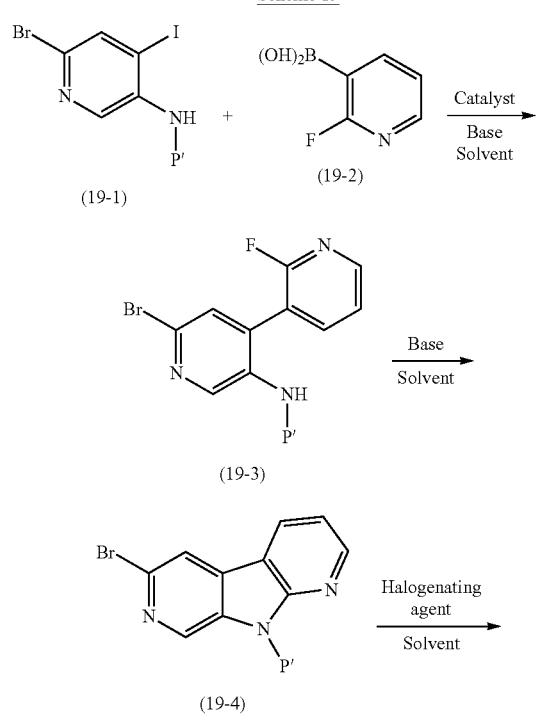

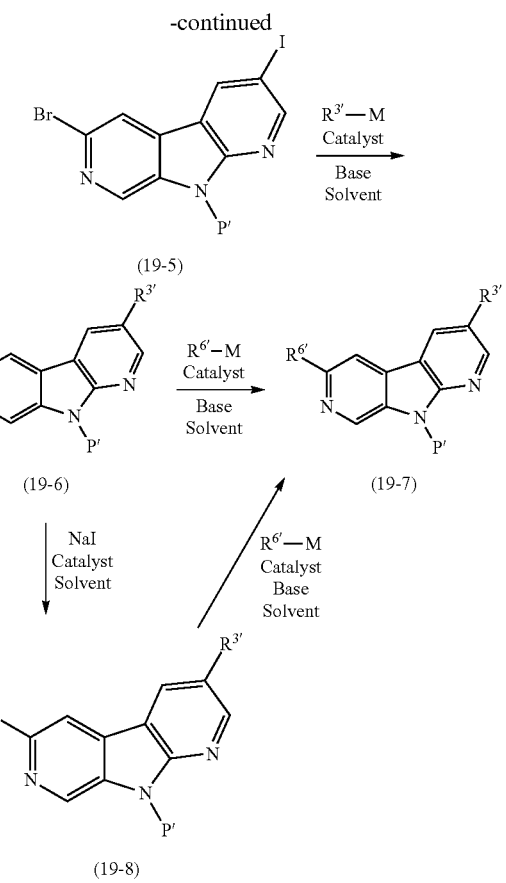

Compounds of formula (19-1) and (19-2) may be synthesized following procedures described in the literature or following the route outlined in scheme 17. Compounds of formula (19-3) may be obtained from compounds of formula (19-1) by reaction with a boronic acid or boronate ester of formula (19-2), in the presence of a catalyst such as bis(triphenylphosphine)palladium(II) dichloride, a base such as aqueous sodium carbonate in a suitable solvent such as acetonitrile at a temperature between room temperature and the reflux temperature of the solvent, or under microwave irradiation at a temperature between 70° C. and 150° C. Compounds of general formula (19-3) may be cyclised to obtain compounds of formula (19-4) with a base such as sodium hexamethyldisilazane in a suitable solvent such as THF at a temperature between 0° C. and 50° C. Intermediates of formula (19-4) may then be halogenated in the presence of a suitable halogenating agent, such as iodine monochloride, in a solvent such as acetic acid, at a temperature between 20° C. and the reflux point of the solvent, to obtain compounds of formula (19-5).

Compounds of formula (19-5) may then be converted to compounds of formula (19-6) by reaction with a boronic acid or boronate ester (incorporating appropriate substituents $R^{3'}$), in the presence of a catalyst such as bis(triphenylphosphine)palladium(II) dichloride, a base such as aqueous sodium carbonate in a suitable solvent such as acetonitrile at a temperature between room temperature and the reflux temperature of the solvent, or under microwave irradiation at a temperature between 70° C. and 150° C. Alternatively, compounds of formula (19-5) may be coupled with an aryl or alkyl tin compound (incorporating appropriate substituents $R^{3'}$), in the presence of a catalyst such as bis(triphenylphosphine) palladium(II) dichloride or [1,1'-bis(diphenylphosphino)ferrocene]dichloropalladium (II), with or without an aqueous base such as sodium carbonate, in a suitable solvent such as acetonitrile at a temperature between room temperature and the reflux temperature of the solvent, or under microwave irradiation at a temperature between 70° C. and 150° C.

Compounds of formula (19-6) may be converted to compounds of formula (19-8) by reaction with an iodine source such as sodium iodide using a copper catalyst such as a combination of copper (I) iodide and N,N'-dimethylethylenediamine in a solvent such as 1,4-dioxane at a temperature between room temperature and the reflux point of the solvent.

Compounds of formula (19-7) may be obtained from compounds of formula (19-6) and (19-8) by reaction with compounds of general formula ($R^{6'}$-M) by reaction with a boronic acid, boronate ester or stannane using similar conditions to those described previously for the introduction of $R^{3'}$.

outlined in schemes 1, 4, 10, 13, 14, 17 and 18. Compounds of formula (20-1) may be converted to compounds of formula (20-2) by reaction with an iodine source such as sodium iodide using a copper catalyst such as a combination of copper (I) iodide and N,N'-dimethylethylenediamine in a solvent such as 1,4-dioxane at a temperature between room temperature and the reflux point of the solvent.

Compounds of formula (20-1) may also be converted to compounds of general formula (20-3) using a catalyst such as

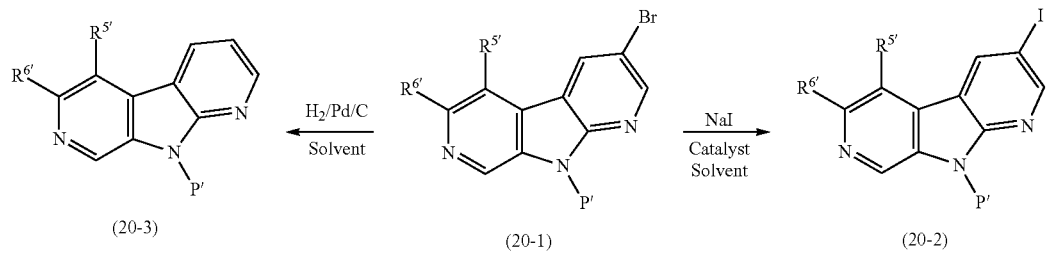

Scheme 20

Compounds of formula (20-1) may be synthesized following procedures described in the literature or following routes palladium in a solvent such as ethanol under an atmosphere of hydrogen at a temperature from room temperature to 50° C.

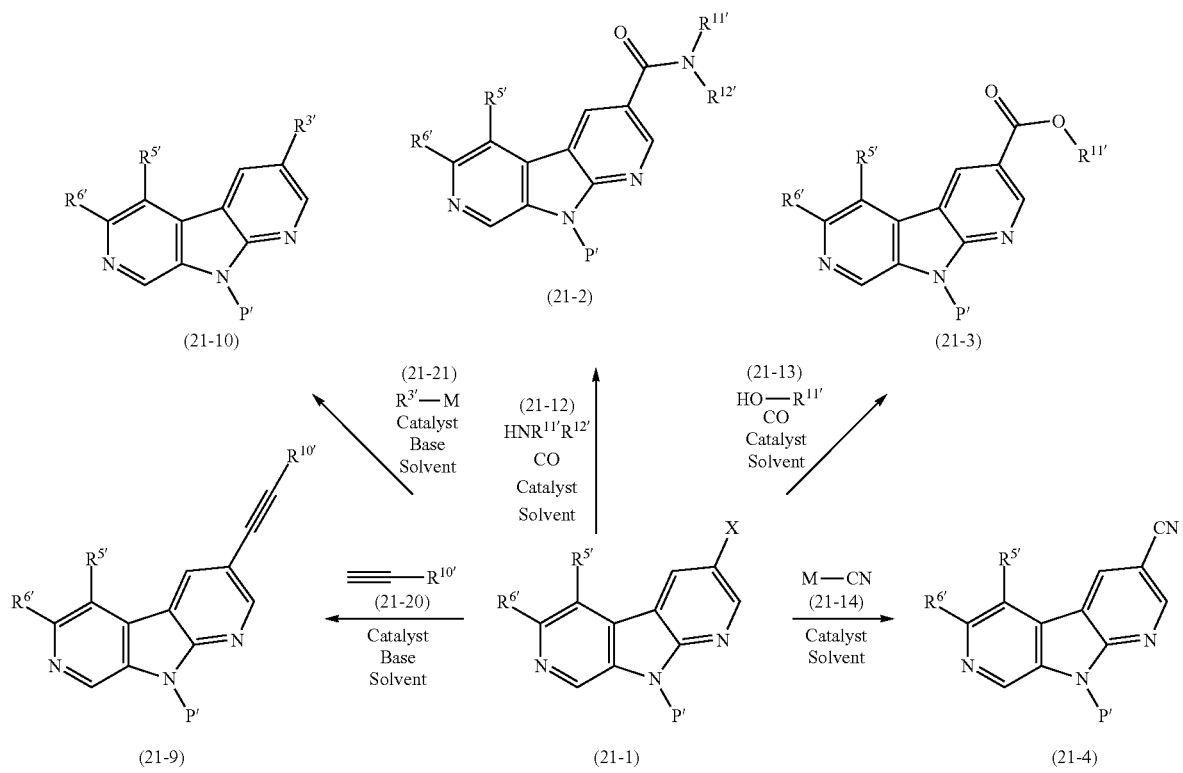

Scheme 21

-continued

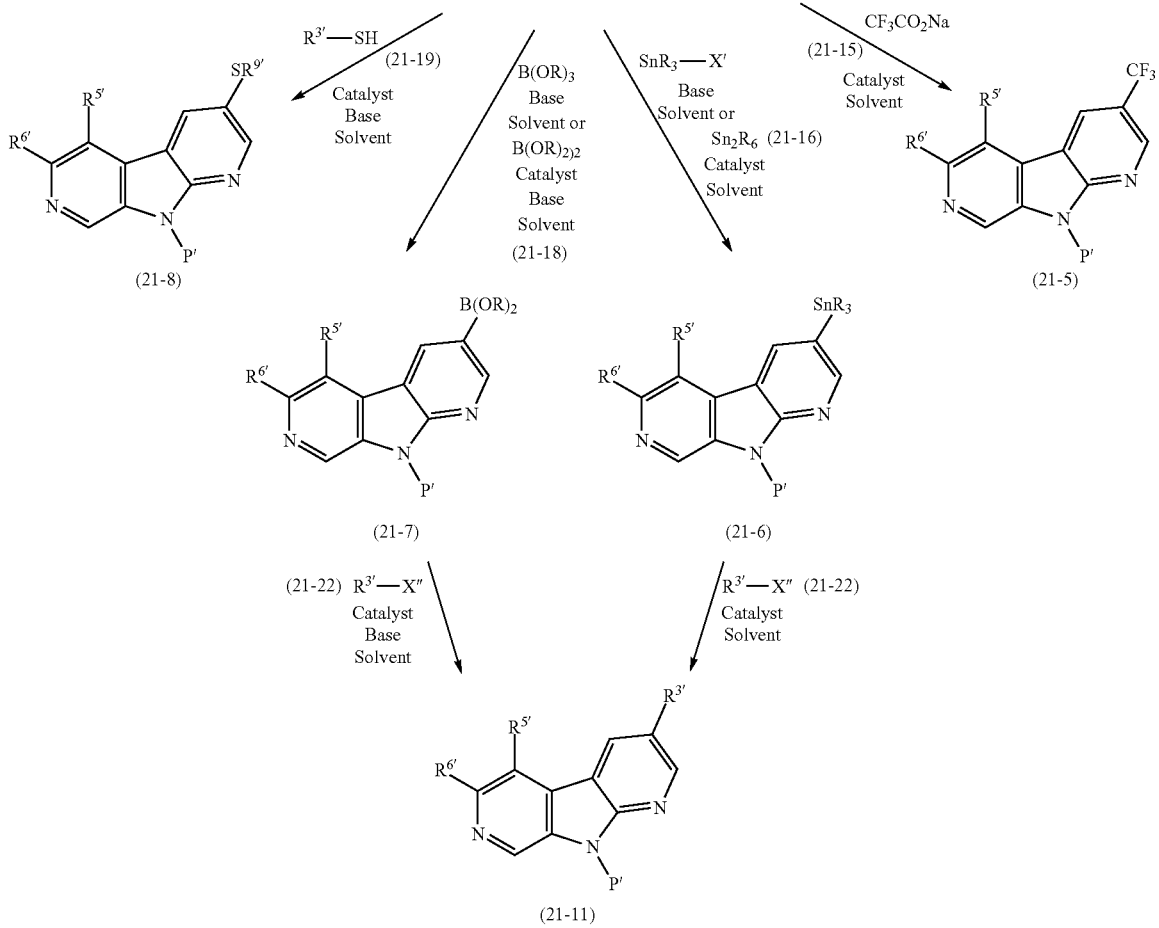

X = Br, I
X' = Cl, Br
X" = Cl, Br, I, OTf

Compounds of formula (21-1) may be synthesized following procedures described in the literature or following routes outlined in schemes 1, 4, 10, 13, 14, 17 and 18. Compounds of formula (21-1) (where X is a leaving group such as Br or I) may be converted to compounds of formula (21-2) using a source of carbon monoxide, such as molybdenum hexacarbonyl in the presence of a catalyst such as Herman's catalyst, containing the appropriate amine (21-12) (HNR$^{11'}$R$^{12'}$), a base such as 1,8-diazabicyclo[5,4,0]undec-7-ene in a solvent such as 1,4-dioxane at a temperature between room temperature and the reflux point of the solvent. Compounds of formula (21-1) may also be converted to compounds of formula (21-3) using a source of carbon monoxide, such as molybdenum hexacarbonyl in the presence of a catalyst such as Herman's catalyst, containing the appropriate alcohol (21-13) (HOR$^{11'}$), a base such as 1,8-diazabicyclo[5,4,0]undec-7-ene in a solvent such as 1,4-dioxane at a temperature between room temperature and the reflux point of the solvent. Compounds of formula (21-1) may be converted to compounds of formula (21-4) using a reagent (21-14) such as zinc (II) cyanide in the presence of a catalyst such as tetrakis(triphenylphosphine)palladium (0) in a solvent such as DMF at a temperature between room temperature and the reflux point of the solvent, or under microwave irradiation at a temperature between 70° C. and 150° C.

Compounds of formula (21-1) may be converted to compounds of formula (21-5) using a reagent such as sodium trifluoroacetate in the presence of a catalyst such as copper (I) iodide in a solvent such as DMF at a temperature between room temperature and the reflux point of the solvent.

Compounds of formula (21-6) may be prepared from compounds of formula (21-1) with a base such as n-butyllithium in a solvent such as THF with the appropriate tin halide (21-15) (where X' is a leaving group such as Cl or Br). Alternatively, compounds of formula (21-6) may be prepared from compounds of formula (21-1) with the appropriate alkylditin (21-16) (containing suitable R groups) in the presence of a catalyst such as tetrakis(triphenylphosphine) palladium (0) in a suitable solvent such as toluene at a temperature from room temperature to the reflux temperature of the solvent, or under microwave irradiation at a temperature between 70° C. and 150° C.

Compounds of formula (21-7) may be prepared from compounds of formula (21-1) by treatment with a base such as n-butyllithium in the presence of an alkyl borate (21-17) such as trimethyl borate in a suitable solvent such as THF at a temperature between −78° C. and ambient temperature. Alternatively, compounds of formula (21-7) may be prepared from compounds of formula (21-1) with the appropriate alkylatodiboron (21-18) in the presence of a catalyst such as bis(diphenylphosphino)ferrocene palladium(II) dichloride, using a suitable base such as potassium acetate in a solvent such as dioxane at a temperature from room temperature to the reflux temperature of the solvent, or under microwave irradiation at a temperature between 70° C. and 150° C.

Compounds of formula (21-8) may be obtained from compounds of formula (21-1) by reaction with compounds of formula (21-19) (HSR$^{9'}$) in the presence of a catalyst such as palladium (II) acetate/JOSIPHOS using a base such as potassium tert-butoxide in a suitable solvent such as DME at a temperature from room temperature to the reflux temperature of the solvent or solvents, or under microwave irradiation at a temperature between 70° C. and 160° C.

Compounds of formula (21-9) may be obtained from compounds of formula (21-1) with a suitable alkyne (21-20) (incorporating a R$^{10'}$ group that could be either maintained without modification after coupling, or that could later be modified to give other groups)R$^{10}$ by reaction in the presence of a catalyst system such as tetrakis(triphenylphosphine)palladium (0) and copper (I) iodide in the presence of a base such as triethylamine and a suitable solvent such as N,N-dimethylformamide at a temperature between room temperature and the boiling point of the solvent. Such a coupling reaction could also be carried out in the presence of palladium on carbon, triphenylphosphine, copper (I) iodide and triethylamine in the presence of a suitable solvent such as acetonitrile at a temperature between room temperature and the reflux temperature of the solvent or solvents, or under microwave irradiation at a temperature between 70° C. and 160° C.

Compounds of formula (21-1) may be converted to compounds of formula (21-10) by reaction with a boronic acid or boronate ester (21-21) (incorporating appropriate substituents R$^{3'}$), in the presence of a catalyst such as bis(triphenylphosphine)palladium(II) dichloride, a base such as aqueous sodium carbonate in a suitable solvent such as acetonitrile at a temperature between room temperature and the reflux temperature of the solvent, or under microwave irradiation at a temperature between 70° C. and 150° C. Alternatively, compounds of formula (21-1) may be coupled with an aryl or alkyl tin compound (21-21) (incorporating appropriate substituents R$^{3'}$), in the presence of a catalyst such as bis(triphenylphosphine)palladium(II) dichloride or [1,1'-bis(diphenylphosphino) ferrocene]dichloropalladium (II), with or without an aqueous base such as sodium carbonate, in a suitable solvent such as acetonitrile at a temperature between room temperature and the reflux temperature of the solvent, or under microwave irradiation at a temperature between 70° C. and 150° C.

Compounds of formula (21-11) may be prepared from compounds of formula (21-6) with the appropriate halide or triflate of formula (21-22) (R$^{3'}$—X"), in the presence of a catalyst such as tetrakis(triphenylphosphine)palladium(0) in a suitable solvent such as 1,4-dioxane at a temperature from room temperature to the reflux temperature of the solvent, or under microwave irradiation at a temperature between 70° C. and 150° C.

Compounds of formula (21-11) may also be prepared by reaction of compounds of formula (21-7) with appropriate halide of formula (21-22) (R$^{3'}$—X"), (incorporating appropriate substituents R$^{3'}$), in the presence of a catalyst such as bis(triphenylphosphine)palladium(II)dichloride, with a base such as aqueous sodium carbonate in a suitable co-solvent such as acetonitrile at a temperature from room temperature to the reflux temperature of the solvent, or under microwave irradiation at a temperature between 70° C. and 150° C.

Scheme 22

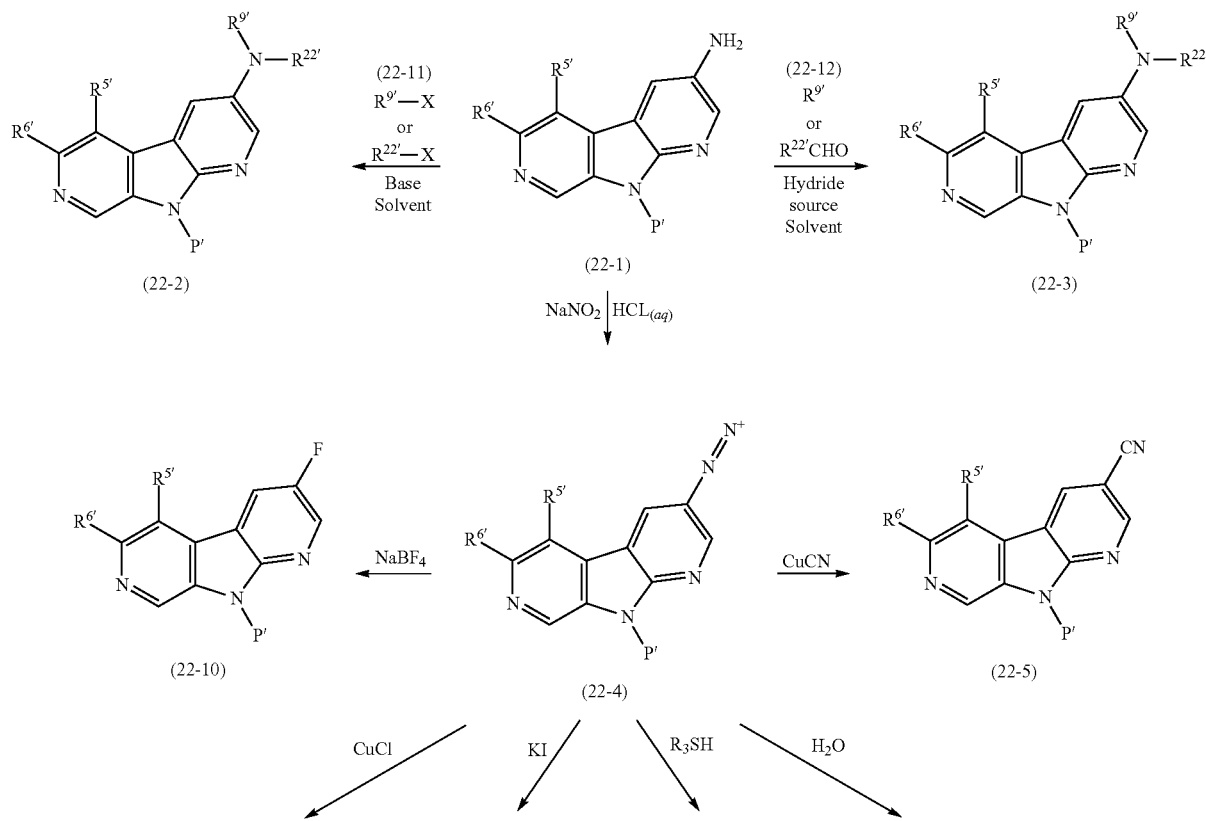

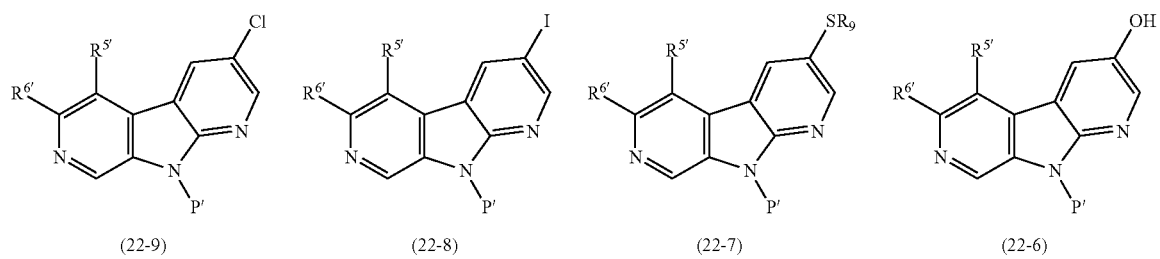

(22-9)　(22-8)　(22-7)　(22-6)

Compounds of formula (22-1) may be synthesized following procedures described in the literature or following routes outlined in scheme 9. Compounds of formula (22-1) may be converted to compounds of formula (22-2) by treatment with a suitable alkylating agent (22-11) $R^{9'}$—X or $R^{22'}$—X (where X is a suitable leaving group such as Cl, Br, I, OMs or OTf) using a suitable base such as cesium carbonate in a solvent such acetonitrile at a temperature between room temperature and the reflux point of the solvent. Alternatively, compounds of formula (22-1) may be converted to compounds of formula (22-3) by reaction with a suitable aldehyde (22-12) $R^{9'}$CHO or $R^{22'}$CHO and a suitable hydride source such as sodium triacetoxyborohydride in a solvent such as 1,2-dichloroethane at a temperature between 0° C. and 50° C.

Compounds of formula (22-1) may also be converted to compounds of formula (22-4) using a reagent such as sodium nitrite in an acidic solution such as aqueous hydrochloric acid, aqueous hydrobromic acid or aqueous sulfuric acid. Compounds of formula (22-4) may then be converted to the fluoro compounds of formula (22-10) with a reagent such as sodium tetrafluoroborate; to the chloro derivatives of formula (22-9) with a reagent such as copper (I) chloride; to the iodo compounds of formula (22-8) with a reagent such as potassium iodide; the alkylthio compounds of formula (22-7) with a reagent such as $NaSR^{9'}$ and the cyano derivatives (22-5) with reagents such as copper (I) cyanide and potassium cyanide all carried out at a temperature between 0° C. and the reflux point of the solvent.

Scheme 23

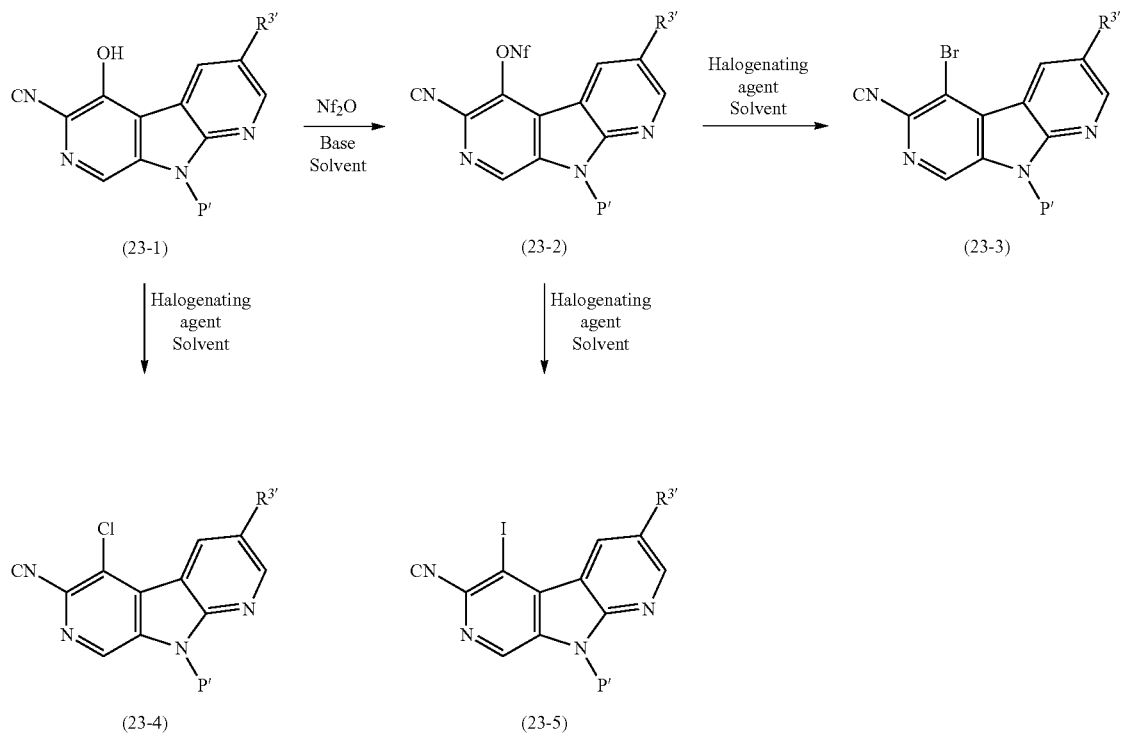

(23-1)　(23-2)　(23-3)

(23-4)　(23-5)

Compounds of formula (23-1) may be synthesized following procedures described in the literature or following the route outlined in scheme 10. Compounds of formula (23-3), (23-4) and (-5) may be prepared using the synthetic route outlined in Scheme 23. Compounds of formula (23-1) may be converted to the compounds of formula (23-4) by reaction with a suitable chloride source such as phosphorus pentachloride in a suitable solvent such as chlorobenzene at a temperature from room temperature to the reflux point of the solvent.

Compounds of formula (23-1) may also be converted to compounds of formula (23-2) using a reagent such as nonafluorobutanesulfonic anhydride in the presence of a base such as pyridine in a suitable solvent such as dichloromethane at a temperature between −50° C. and 20° C. Compounds of formula (23-2) may be converted to compounds of formula (23-3) by reaction with a suitable bromide source such as tetra-n-butylammonium bromide in a solvent such as 1,4-dioxane at a temperature from room temperature to the reflux temperature of the solvent, or under microwave irradiation at a temperature between 70° C. and 150° C.

Compounds of formula (23-2) may be converted to the compounds of formula (23-5) by reaction with a suitable iodide source such as tetra-n-butylammonium iodide in a solvent such as 1,4-dioxane at a temperature from room temperature to the reflux temperature of the solvent, or under microwave irradiation at a temperature between 70° C. and 150° C.

Scheme 24

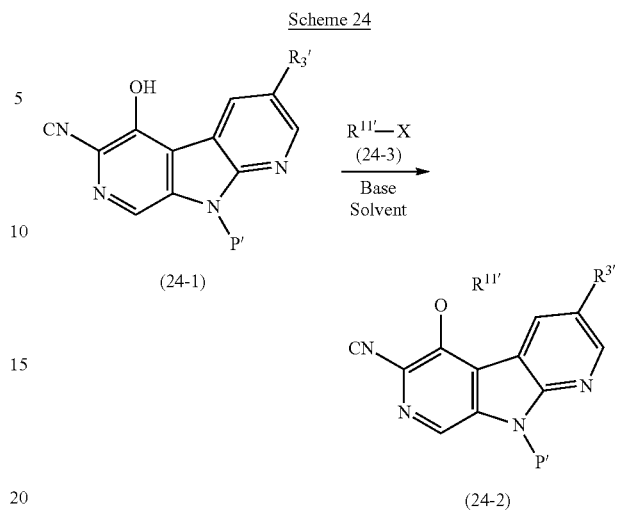

Compounds of formula (24-1) may be synthesized following procedures described in the literature or following the route outlined in scheme 10. Compounds of formula (24-2) may be obtained through alkylation of compounds of formula (24-1) with a suitable alkylating agent (24-3) $R^{11'}$—X (where X is a suitable leaving group such as Cl, Br, I, OMs or OTf) using a suitable base such as cesium carbonate in a solvent such as acetonitrile at a temperature between room temperature and the reflux point of the solvent.

Scheme 25

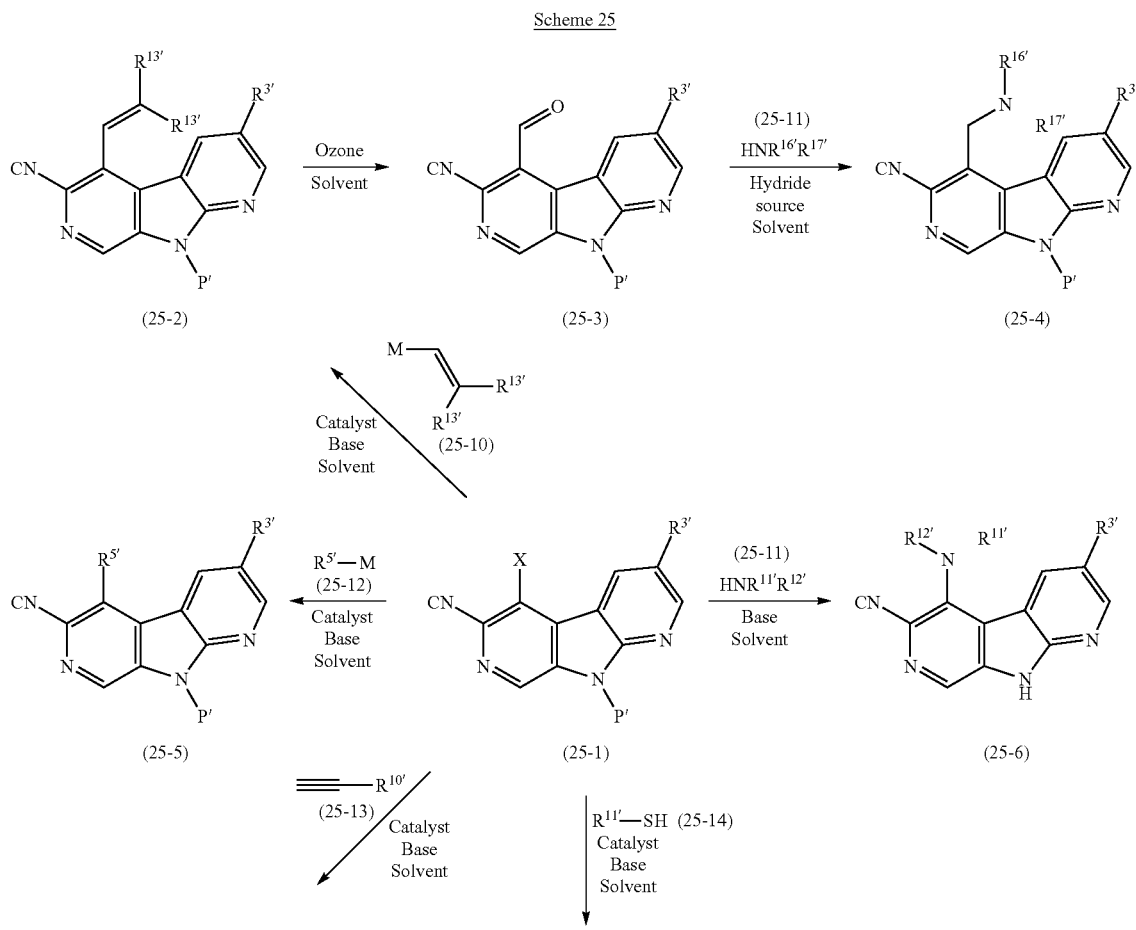

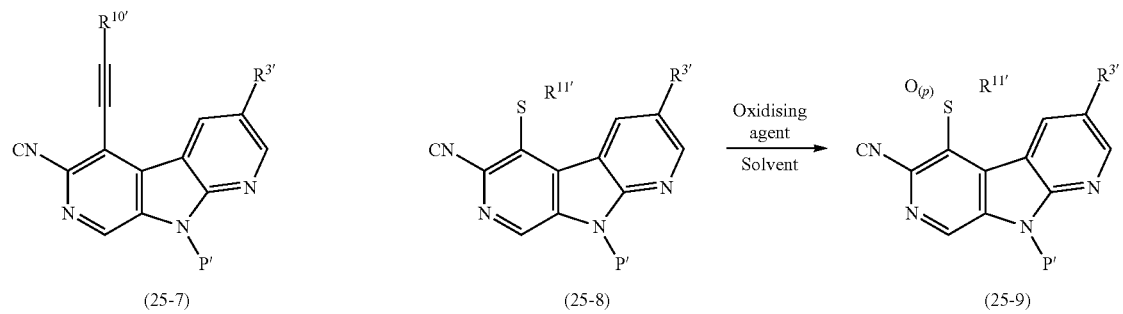

(25-7)  (25-8)  (25-9)

Compounds of formula (25-1) may be synthesized following procedures described in the literature or following the route outlined in scheme 23. Compounds of formula (25-1) (where X is a leaving group such as Br or I) may be converted to compounds of formula (25-2) by reaction with a suitable alkenyl tin reagent of formula (25-10) such as vinyltributyl tin in the presence of a transition metal catalyst such as tetrakis (triphenylphosphine)palladium(0) in a suitable solvent such as 1,4-dioxane at a temperature between room temperature and the reflux point of the solvent. Compounds of formula (25-2) may be converted to compounds of formula (25-3) by treatment with a reagent such as ozone in a suitable solvent such as methanol at a temperature between −78° C. and room temperature followed by decomposition of the ozonide with a reagent such as dimethylsufide. Compounds of formula (25-3) may be converted to compounds of formula (25-4) by reaction with a suitable amine of formula (25-11) (HNR$^{16'}$R$^{17'}$) and a suitable hydride source such as sodium triacetoxyborohydride in a solvent such as 1,2-dichloroethane at a temperature between 0° C. and 50° C.

Compounds of formula (25-1) (where X is a leaving group such as Br or I) may be converted to compounds of formula (25-5) by reaction with a potassium alkyl trifluoroborate or alkyl borate of formula (25-12) in the presence of a transition metal catalyst such as [1,1'-bis(diphenylphosphino)ferrocene]palladium (II) dichloride, a base such as aqueous potassium carbonate in a suitable solvent such as DMF at a temperature from room temperature to the reflux temperature of the solvent, or under microwave irradiation at a temperature between 70° C. and 150° C. Compounds of formula (25-5) may also be obtained from compounds of formula (25-1) by reaction with an aryl or alkyl tin compound of formula (25-12) (incorporating appropriate substituents R$^{5'}$) in the presence of a catalyst such as bis(triphenyl phosphine) palladium (II) dichloride or [1,1'-bis(diphenylphosphino)ferrocene]dichloropalladium (II), an aqueous base such as sodium carbonate, in a suitable solvent such as acetonitrile or combination of solvents, at a temperature between room temperature to the reflux temperature of the solvent, or under microwave irradiation at a temperature between 70° C. and 150° C.

Alternatively, compounds of formula (25-7) may be obtained from compounds of formula (25-1) (where X is a leaving group such as Br or I) and a suitable alkyne (25-13) (incorporating a R$^{10'}$ group that could be either maintained without modification after coupling, or that could later be modified to give other groups R$^{10}$) by reaction in the presence of a catalyst system such as tetrakis(triphenyl phosphine) palladium(0) and copper (I) iodide in the presence of a base such as triethylamine and a suitable solvent such as N,N-dimethylformamide at a temperature between room temperature and the boiling point of the solvent. Such a coupling reaction could also be carried out in the presence of palladium on carbon, triphenylphosphine, copper (I) iodide and triethylamine in the presence of a suitable solvent such as acetonitrile at a temperature between room temperature and the reflux temperature of the solvent or solvents, or under microwave irradiation at a temperature between 70° C. and 160° C.

Compounds of formula (25-1) (where X is a leaving group such as F, Cl, Br or I) may be converted to compounds of formula (25-6) by displacement with a suitable amine of formula (25-11) (HNR$^{11'}$R$^{12'}$) either as solvent or in a solvent such as NMP at a temperature between ambient temperature and the reflux point of the solvent. Compounds of formula (25-3) may also be obtained from compounds of formula (25-1) (where X is a leaving group such as Br or I) by reaction with compounds of formula (25-11) (HNR$^{11'}$R$^{12'}$) in the presence of a catalyst such as [1,1'-bis(diphenylphosphino) ferrocene]dichloropalladium(II), in the presence of a base such as potassium tert-butoxide in a suitable solvent such as DME, or a mixture of two or more appropriate solvents, at a temperature from room temperature to the reflux temperature of the solvent or solvents, or under microwave irradiation at a temperature between 70° C. and 160° C.

Compounds of formula (25-8) may be obtained from compounds of formula (25-1) (where X is a leaving group such as Br or I) by reaction with compounds of general formula (25-14) (HSR$^{11'}$) in the presence of a catalyst such as palladium(II) acetate/JOSIPHOS in the presence of a base such as potassium tert-butoxide in a suitable solvent such as DME, or a mixture of two or more appropriate solvents, at a temperature from room temperature to the reflux temperature of the solvent or solvents, or under microwave irradiation at a temperature between 70° C. and 160° C.

The sulfide intermediates of formula (25-8) may be converted to sulfoxides and sulfones of formula (25-9) by oxidation with a suitable oxidizing agent such as oxone in a solvent such as acetone at a temperature between 0° C. and 50° C.

Scheme 26

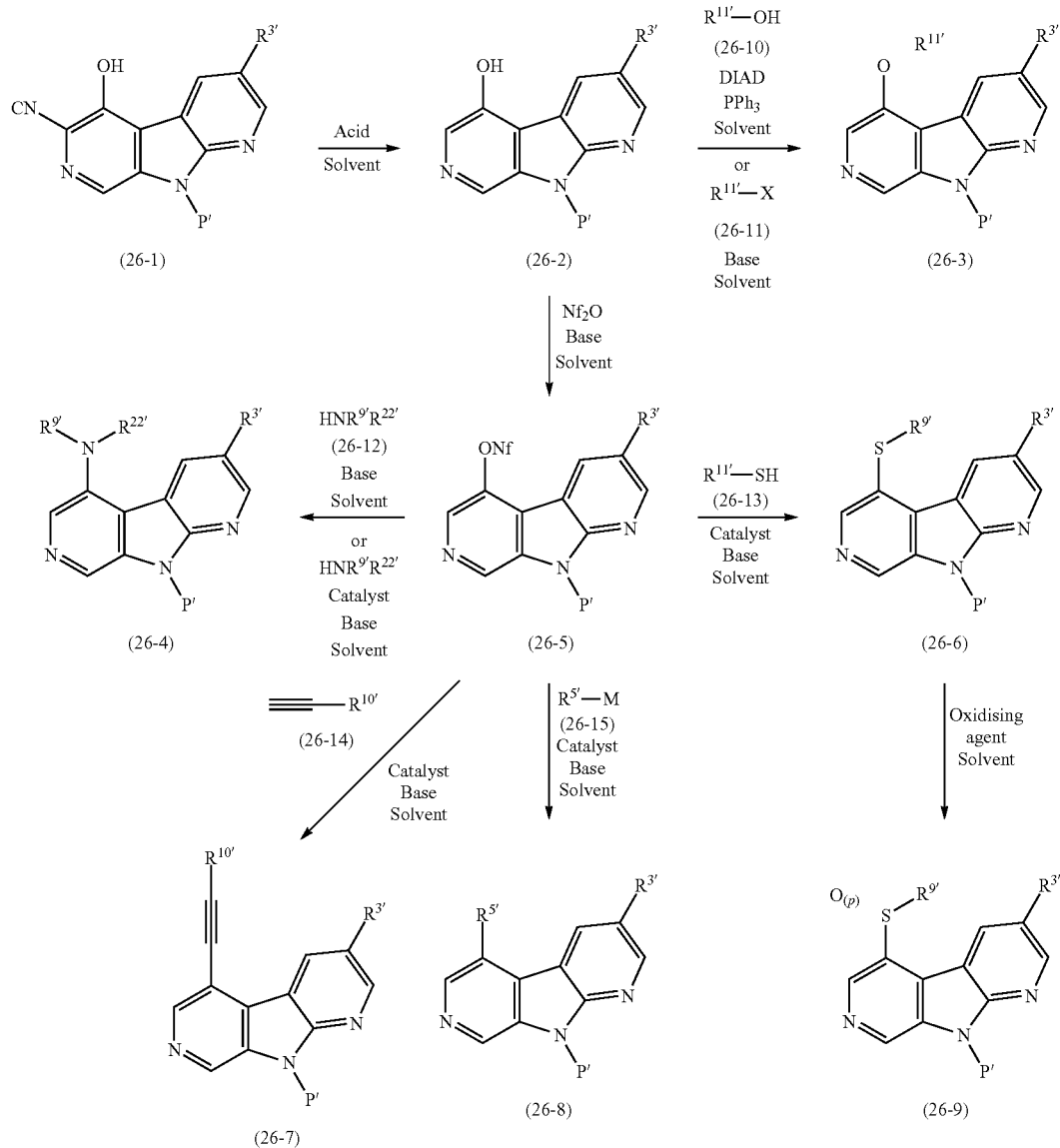

Compounds of formula (26-1) may be synthesized following procedures described in the literature or following the route outlined in scheme 10. Compounds of formula (26-1) may be converted to compounds of formula (26-2) by treatment with an acid such as hydrochloric acid in a solvent such as water at a temperature between room temperature and the reflux point of the solvent, or in a sealed vessel at a temperature between 70° C. and 140° C.

Compounds of formula (26-2) may then be reacted with an appropriate alcohol (26-10) ($R^{11'}$OH) using a phosphine and a coupling reagent such as diisopropylazodicarboxylate in an appropriate solvent such as THF to provide ethers of general formula (26-3). Alternatively, compounds of formula (26-3) may be obtained through alkylation of compounds of general formula (26-2) with a suitable alkylating agent (26-11) $R^{11'}$—X (where X is a suitable leaving group such as Cl, Br, I, OMs or OTf) using a suitable base such as cesium carbonate in a solvent such as acetonitrile at a temperature between room temperature and the reflux point of the solvent.

Compounds of formula (26-2) may also be converted to the nonaflates (26-5) using a reagent such as nonafluorobutanesulfonic anhydride in the presence of a base such as pyridine in a suitable solvent such as dichloromethane at a temperature between −50° C. and 20° C.

Compounds of formula (26-5) may be converted to compounds of formula (26-4) by displacement with a suitable amine of general formula (26-12) (HNR$^{11'}$R$^{12'}$) either as solvent or in a solvent such as NMP at a temperature between ambient temperature and the reflux point of the solvent. Compounds of formula (26-4) may also be obtained from compounds of formula (26-5) by reaction with compounds of general formula (26-12) (HNR$^{11'}$R$^{12'}$) in the presence of a catalyst such as [1,1'-bis(diphenylphosphino)ferrocene]dichloropalladium(II), in the presence of a base such as potassium tert-butoxide in a suitable solvent such as DME, or a mixture of two or more appropriate solvents, at a temperature from room temperature to the reflux temperature of the solvent or solvents, or under microwave irradiation at a temperature between 70° C. and 160° C.

Alternatively, compounds of formula (26-7) may be obtained from compounds of formula (26-5) with a suitable alkyne (26-14) (incorporating a $R^{10'}$ group that could be either maintained without modification after coupling, or that could later be modified to give other groups $R^{10}$) by reaction in the presence of a catalyst system such as tetrakis(triphenylphosphine)palladium (0) and copper (I) iodide in the presence of a base such as triethylamine and a suitable solvent such as N,N-dimethylformamide at a temperature between room temperature and the boiling point of the solvent. Such a coupling reaction could also be carried out in the presence of palladium on carbon, triphenylphosphine, copper (I) iodide and triethylamine in the presence of a suitable solvent such as acetonitrile at a temperature between room temperature and the reflux temperature of the solvent or solvents, or under microwave irradiation at a temperature between 70° C. and 160° C.

The nonaflate intermediates (26-5) may be converted to compounds of formula (26-8) by reaction with a potassium alkyl trifluoroborate or alkyl borate of formula (26-15) in the presence of a transition metal catalyst such as [1,1'-bis(diphenylphosphino)ferrocene]palladium (II) dichloride, a base such as aqueous potassium carbonate in a suitable solvent such as DMF at a temperature from room temperature to the reflux temperature of the solvent, or under microwave irradiation at a temperature between 70° C. and 150° C. Compounds of general formula (26-8) may also be obtained from compounds of formula (26-5) by reaction with an aryl or alkyl tin compound (incorporating appropriate substituents $R^{5'}$), in the presence of a catalyst such as bis(triphenylphosphine)palladium (II) dichloride or [1,1'-bis(diphenylphosphino)ferrocene]dichloropalladium (II), an aqueous base such as sodium carbonate, in a suitable solvent such as acetonitrile or combination of solvents, at a temperature between room temperature to the reflux temperature of the solvent, or under microwave irradiation at a temperature between 70° C. and 150° C.

Compounds of formula. (26-6) may be obtained from compounds of formula (26-5) (where X is a leaving group such as Br or I) by reaction with compounds of formula (26-13) ($HSR^{11'}$) in the presence of a catalyst such as palladium (II) acetate/JOSIPHOS in the presence of a base such as potassium tert-butoxide in a suitable solvent such as DME, or a mixture of two or more appropriate solvents, at a temperature from room temperature to the reflux temperature of the solvent or solvents, or under microwave irradiation at a temperature between 70° C. and 160° C.

The sulfide intermediates of formula (26-6) may be converted to sulfoxides and sulfones of formula (26-9) by oxidation with a suitable oxidizing agent such as oxone in a solvent such as acetone at a temperature between 0° C. and 50° C.

Scheme 27 scheme 27-1

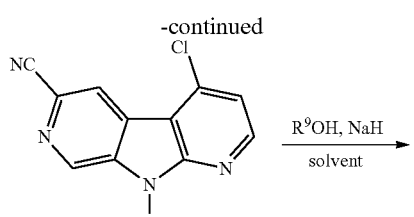

(27-8)

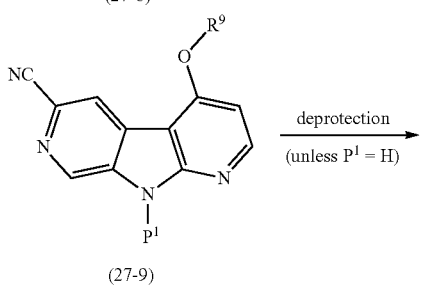

(27-9)

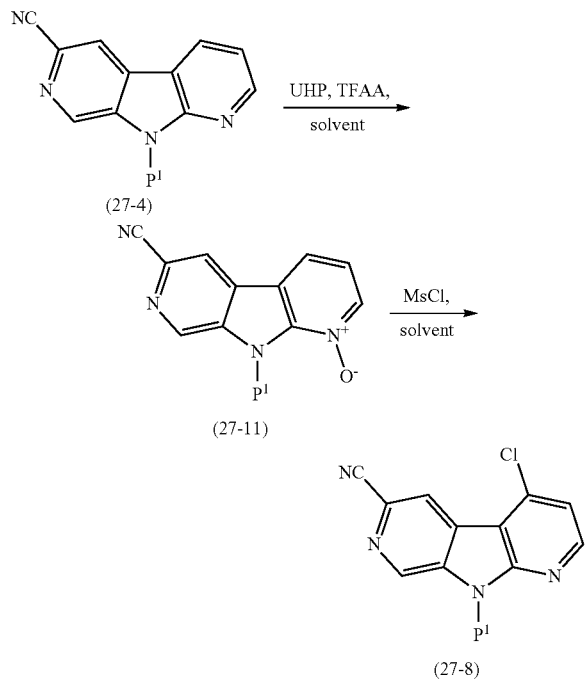

Compounds of formula (27-4) may be synthesized following procedures described in the literature or by the method outlined in Scheme 27-1. Compound (27-1) may be converted to compound (27-2) by treatment with ammonia in a suitable solvent such as methanol by heating in a sealed vessel at a temperature up to 150Error! Not a valid link.C. Compound (27-2) may be converted to compound (27-3) by treatment with a dehydrating agent in a suitable solvent at an appropriate temperature, such as trifluoroacetic acid anhydride in the presence of triethylamine at between 0Error! Not a valid link.C and ambient temperature. Compound (27-3) may be converted to protected compounds of formula (27-4) by literature methods wherein $P^1$ represents a suitable protecting group, such as the 2-trimethylsilanylethoxy methyl derivative by treatment with 2-trimethylsilanylethoxymethyl chloride and sodium hydride in tetrahydrofuran.

Compounds of formula (27-4) may also be synthesized from compounds of formula (27-5) as outlined in Scheme 27-2, by a literature or other reduction method, such as by hydrogenation in the presence of a carbon-supported palladium catalyst in a suitable solvent such as tetrahydrofuran, or by treatment with zinc powder and ammonium formate in tetrahydrofuran.

Compounds of formula (27-10) may be synthesized from compounds of formula (27-4) as outlined in Scheme 27-2. Compounds of the formula (27-4) may be converted to compounds of formula (27-6) by treatment with an oxidant in a suitable solvent, such as urea-hydrogen peroxide adduct andError! Not a valid link.in chloroform at ambient temperature. Compounds (27-6) may be converted to compounds (27-7) by treatment with an electrophilic agent and chloride source, such as methanesulfonyl chloride in N,N-dimethylformamide at ambient temperature. Compounds (27-7) may be deoxygenated to compounds (27-8) by treatment with a suitable reducing agent, such as triethylamine in the presence of [1,1'-bis(diphenyl phosphino)ferrocene]dichloropalladium(II) in acetonitrile under microwave irradiation.

Compounds of formula (27-8) may also be synthesized by the method outlined in scheme 27-3. Compounds (27-4) may also be converted to compounds of formula (27-11) by treatment with an oxidant in a suitable solvent, such as urea-hydrogen peroxide adduct andError! Not a valid link.in chloroform. Compounds (27-11) may be converted to compounds (27-8) by treatment with a suitable agent such as methanesulfonyl chloride in N,N-dimethylformamide at ambient temperature.

Compounds of formula (27-8) may be converted to compounds of formula (27-9) by treatment with an alcohol, represented by $R^9OH$, in the presence of a suitable base such as sodium hydride, in a suitable solvent such as tetrahydrofuran, at a temperature between ambient temperature and the boiling point of the solvent, or at a temperature in excess of the boiling point of the solvent in a sealed vessel. Compounds of formula (27-9) may be converted to compounds (27-10) by removal of the protecting group represented by $P^1$, such as the 2-trimethylsilanylethoxymethyl protecting group, for example by treatment with tetrabutylammonium fluoride in tetrahydrofuran, or as a further example by treatment with aqueous hydrobromic acid in dioxane followed by treatment with aqueous sodium hydroxide.

It will be appreciated that where appropriate functional groups exist, compounds described in the formulae of Schemes 1-27 or any intermediates used in their preparation may be further derivatised by one or more standard synthetic methods employing substitution, oxidation, reduction, or cleavage reactions. Particular substitution approaches include conventional alkylation, arylation, heteroarylation, acylation, sulfonylation, halogenation, nitration, formylation and coupling procedures.

In a further example primary amine (—$NH_2$) groups may be alkylated using a reductive alkylation process employing an aldehyde or a ketone and a borohydride, for example sodium triacetoxyborohydride or sodium cyanoborohydride, in a solvent such as a halogenated hydrocarbon, for example 1,2-dichloroethane, or an alcohol such as ethanol, where necessary in the presence of an acid such as acetic acid at around ambient temperature. Secondary amine (—NH—) groups may be similarly alkylated employing an aldehyde.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyluronium hexafluorophosphate) in a suitable solvent such as dichloromethane. Similarly, amine groups may be converted into sulphonamide groups (—NHSO$_2$R' or —NR"SO$_2$R') groups by reaction with an appropriate sulphonyl chloride in the presence of a suitable base, such as triethylamine, in a suitable solvent such as dichloromethane. Primary or secondary amine groups can be converted into urea groups (—NHCONR'R$^{11}$ or —NRCONR'R") by reaction with an appropriate isocyanate in the presence of a suitable base such as triethylamine, in a suitable solvent, such as dichloromethane.

An amine (—NH$_2$) may be obtained by reduction of a nitro (—NO$_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—CH$_2$NH$_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at a temperature from −78° C. to the reflux temperature of the solvent.

In a further example, amine (—NH$_2$) groups may be obtained from carboxylic acid groups (—CO$_2$H) by conversion to the corresponding acyl azide (—CON$_3$), Curtius rearrangement and hydrolysis of the resultant isocyanate (—N=C=O).

Aldehyde groups (—CHO) may be converted to amine groups (—CH$_2$NR'R")) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —CO$_2$Et) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—CO$_2$R') may be converted into the corresponding acid group (—CO$_2$H) by acid- or base-catalused hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—CO$_2$H) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e —CO$_2$H to —CH$_2$CO$_2$H) by conversion to the corresponding acid chloride (—COCl) followed by Arndt-Eistert synthesis.

In a further example, —OH groups may be generated from the corresponding ester (e.g. —CO$_2$R'), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—CO$_2$H), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

The compounds of the present invention are tested for their capacity to inhibit chk1 activity and activation (primary assays) and for their biological effects on growing cells (secondary assays) as described below. The compounds having IC$_{50}$ of less than 10 µM (more preferably less than 5 µM, even more preferably less than 1 µM, most preferably less than 0.5 µM) in the chk1 activity and activation assay of Example i, and EC$_{50}$ of less than 10 µM (more preferably less than 5 µM, most preferably less than 1 µM) in the cellular assay of Example ii, are useful as chk1 inhibitors.

The present invention includes a composition (e.g., a pharmaceutical composition) comprising a compound of Formula (I), (I-a) and/or (I-b), (and/or solvates, hydrates and/or salts thereof) and a carrier (a pharmaceutically acceptable carrier).

The present invention also includes a composition (e.g., a pharmaceutical composition) comprising a compound of Formula (I), (I-a) and/or (I-b) (and/or solvates, hydrates and/or salts thereof) and a carrier (a pharmaceutically acceptable carrier), further comprising a second chemotherapeutic agent such as those described herein. The present invention also includes a composition (e.g., a pharmaceutical composition) comprising a compound of Formula (I), (I-a) and/or (I-b) (and/or solvates, hydrates and/or salts thereof) and a carrier (a pharmaceutically acceptable carrier), further comprising a second chemotherapeutic agent such as a DNA damaging agent including those described herein. The present compositions are useful for inhibiting abnormal cell growth or treating a hyperproliferative disorder such as cancer in a mammal (e.g., human). For example, the present compounds and compositions are useful for treating breast cancer, colorectal cancer, ovarian cancer, non-small cell lung cancer, malignant brain tumors, sarcomas, melanoma, lymphoma, myelomas and/or leukemia in a mammal (e.g., human).

The present invention includes a method of inhibiting abnormal cell growth or treating a hyperproliferative disorder such as cancer in a mammal (e.g., human) comprising administering to said mammal a therapeutically effective amount of a compound of Formula (I), (I-a) and/or (I-b) (and/or solvates, hydrates and/or salts thereof) or a composition thereof. For example, the present invention includes a method of treating breast cancer, colorectal cancer, ovarian cancer, non-small cell lung cancer, malignant brain tumors, sarcomas, melanoma, lymphoma, myelomas and/or leukemia in a mammal (e.g., human), comprising administering to said mammal a therapeutically effective amount of a compound of Formula (I), (I-a) and/or (I-b) (and/or solvates, hydrates and/or salts thereof) or a composition thereof.

The present invention includes a method of inhibiting abnormal cell growth or treating a hyperproliferative disorder such as cancer in a mammal (e.g., human) comprising administering to said mammal a therapeutically effective amount of a compound of Formula (I), (I-a) and/or (I-b) (and/or solvates, hydrates and/or salts thereof) or a composition thereof, in combination with a second chemotherapeutic agent such as those described herein. The present invention also includes a method of inhibiting abnormal cell growth or treating a hyperproliferative disorder such as cancer in a mammal (e.g., human) comprising administering to said mammal a therapeutically effective amount of a compound of Formula (I), (I-a) and/or (I-b) (and/or solvates, hydrates and/or salts thereof) or a composition thereof, in combination with a second chemotherapeutic agent such as a DNA damaging agent including those described herein. For example, the present invention includes a method of treating breast cancer, colorectal cancer, ovarian cancer, non-small cell lung cancer, malignant brain tumors, sarcomas, melanoma, lymphoma, myelomas and/or leukemia in a mammal (e.g., human), comprising administering to said mammal a therapeutically effective amount of a compound of Formula (I), (I-a) and/or (I-b) (and/or solvates, hydrates and/or salts thereof) or a composition thereof, in combination with a second chemotherapeutic agent such as those described herein. The present invention also includes a method of treating breast cancer, colorectal cancer, ovarian cancer, non-small cell lung cancer, malignant brain tumors, sarcomas, melanoma, lymphoma, myelomas and/or leukemia in a mammal (e.g., human), comprising administering to said mammal a therapeutically effective amount of a compound of Formula (I), (I-a) and/or (I-b) (and/or solvates, hydrates and/or salts thereof) or a composition thereof, in combination with a second chemotherapeutic agent such as such as a DNA damaging agent including those described herein.

The present invention includes a method of using the present compounds for in vitro, in situ, and in vivo diagnosis or treatment of mammalian cells, organisms, or associated pathological conditions.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic.acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

EXAMPLES

Abbreviations

ACN Acetonitrile
AIBN 2,2'-Azobis(2-methylproprionitrile)
ATP Adenosine-5'-triphosphate
Biotage Pre-packed silica Biotage® SNAP Cartridge for flash chromatography
t-BME t-Butyl methyl ether
$CDCl_3$ Deuterated chloroform
DCM Dichloromethane
DIPEA Diisopropylethylamine
DMAP 4-Dimethylaminopyridine
DME 1,2-Dimethoxyethane
DMF Dimethylformamide
DMSO Dimethylsulfoxide
DMSO-$d_6$ Deuterated dimethylsulfoxide
EtOAc Ethyl acetate
EtOH Ethanol
h Hour
HCl Hydrochloric acid
HM-N Isolute® HM-N is a modified form of diatomaceous earth that can efficiently absorb aqueous samples
HOBt 1-Hydroxybenzotriazole
IMS Industrial methylated spirits
LDA Lithium diisopropylamide
HATU O-(7-Azabenzotriazol-1-yl)-N,N,N',N'-tetramethyluroniumhexafluorophosphate
LCMS Liquid Chromatography Mass Spectroscopy
LDA Lithium diisopropylamide
MeOH Methanol
mmol Millimoles
mol Moles
N Normal (concentration)
$NaHCO_3$ Sodium bicarbonate
NaOH Sodium hydroxide
NBS N-Bromosuccinimide
NMR Nuclear magnetic resonance
PyBOP (Benzotriazol-1-yloxy)tripyrrolidinophosphonium hexafluorophosphate
SCX-2 Strong cationic exchange resin
Si-SPE Pre-packed Isolute® silica flash chromatography cartridge
Si-ISCO Pre-packed ISCO® silica flash chromatography cartridge
THF Tetrahydrofuran
TFA Trifluoroacetic acid
TLC Thin layer chromatography
TMS Trimethylsilyl General Experimental Conditions $^1$H NMR spectra were recorded at ambient temperature using a Varian Unity Inova (400 MHz):spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography-Mass Spectrometry (LCMS) experiments to determine retention times ($R_T$) and associated mass ions were performed using one of the following Methods.

Method A: Experiments performed on a Waters Micromass ZQ quadrupole mass spectrometer linked to a Hewlett Packard HP 1100 LC system with diode array detector. This system uses a Higgins Clipeus 5 micron C18 100×3.0 mm column and a 1 ml/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method B: Experiments performed on a Waters Platform LC quadrupole mass spectrometer linked to a Hewlett Packard HP1100 LC system with diode array detector and 100 position autosampler using a Phenomenex Luna C18(2) 30×4.6 mm column and a 2 ml/minute flow rate. The solvent system was 95% water containing 0.1% formic acid (solvent A) and 5% acetonitrile containing 0.1% formic acid (solvent B) for the first 0.50 minutes followed by a gradient up to 5% solvent A and 95% solvent B over the next 4 minutes. The final solvent system was held constant for a further 0.50 minutes.

Method C: Experiments performed on a Shimadzu LCMS-2010EV liquid chromatography mass spectrometer linked to a Shimadzu LC-20AB LC system with diode array detector. Uses a Shim-pack XR-ODS 2.2 micron 30×3.0 mm column and a 1.2 ml/minute flow rate. The initial solvent system was 10% water containing 0.038% trifluoroacetic acid (solvent A) and 90% acetonitrile containing 0.019% trifluoroacetic acid (solvent B), followed by a gradient up to 80% solvent A and 90% solvent B over 2 minutes.

Method D: Experiments performed on an Agilent 1100 HPLC with Agilent MSD mass spectrometer using ESI as ionization source using an Agilent ZORBAX SB-C18 100×3.0 mm column and a 0.7 ml/minute flow rate. The solvent system was a gradient starting with 95% water with 0.05% TFA (solvent A) and 5% acetonitrile with 0.05% TFA (solvent B), ramping up to 5% solvent A and 95% solvent B over 25 minutes. The final solvent system was held constant for a further 5 minutes.

Method E: Experiments performed on an Agilent 1100 HPLC with Agilent MSD mass spectrometer using ESI as ionization source using an Agilent ZORBAX SB-C18 30×2.1 mm column and a 0.6 ml/minute flow rate. The solvent system was a gradient starting with 95% water with 0.05% TFA (solvent A) and 5% acetonitrile with 0.05% TFA (solvent B), ramping up to 5% solvent A and 95% solvent B over 9 minutes. The final solvent system was held constant for a further 1 minute.

Method F: Experiments performed on a Waters Micromass ZQ2000 quadrupole mass spectrometer using ESI as ionization source using a Higgins Clipeus 5 micron C18 100×3.0 mm column and a 1 ml/minute flow rate. The solvent system was a gradient starting with 85% water with 0.1% formic acid (solvent A) and 15% methanol with 0.1% formic acid (solvent B), ramping up to 5% solvent A and 95% solvent B over 12 minutes. The final solvent system was held constant for a further 1 minute.

Method G: Experiments performed on a Waters Platform LC quadrupole mass spectrometer linked to a Hewlett Packard HP1100 LC system with diode array detector and 100 position autosampler using a Phenomenex Luna C18(2) 30×4.6 mm column and a 2 ml/minute flow rate. The solvent system was 95% water containing 0.1% formic acid (solvent A) and 5% methanol containing 0.1% formic acid (solvent B) for the first 0.50 minutes followed by a gradient up to 5% solvent A and 95% solvent B over the next 4 minutes. The final solvent system was held constant for a further 0.50 minutes.

Method H: Experiments performed on a Waters Quattro Micro triple quadrupole mass spectrometer using ESI as ionization source using a Higgins Clipeus 5 micron C18 100×3.0 mm column and a 1 ml/minute flow rate. The solvent system was a gradient starting with 85% water with 0.1% formic acid (solvent A) and 15% methanol with 0.1% formic acid (solvent B), ramping up to 5% solvent A and 95% solvent B over 12 minutes. The final solvent system was held constant for a further 1 minute.

Microwave experiments were carried out using a Biotage Initiator 60™ which uses a single-mode resonator and dynamic field tuning. Temperature from 40-250° C. can be achieved, and pressures of up to 30 bar can be reached. Alternatively, a CEM Discover microwave was also used for some of the experiments.

Unless specified, typically preparative HPLC purification refers to the use of an Xbridge™ Prep C18 10 μm OBD™ 19×100 mm column or a similar C18 column unless stated otherwise. Methods are generally run on a gradient of 5-85% acetonitrile/water modified with either 0.1% formic acid or 0.1% ammonium hydroxide over 20 minutes at a flow rate of 35 mL/min.

General Methods

Boronic acids and boronate esters were prepared from the appropriate aryl halide intermediate by using the general coupling methods described below. All aryl halide intermediates were either commercially available, prepared using literature methods or could be readily prepared by those skilled in the art. In some cases the intermediate was not isolated, and the coupling reaction performed on the crude boronic acid/boronate ester. Suzuki reactions were performed using either commercially available boronic acids/boronate esters or from compounds prepared using the procedures detailed below. If necessary, any protecting groups were then removed using one of the deprotection conditions described below. Stille reactions were performed using either commercially available stannanes or from compounds prepared using the procedures detailed below. If necessary, any protecting groups were then removed using one of the deprotection conditions described below.

General Methylation of Piperidine Derivative Method

The appropriate BOC-protected/HCl salt/free amine piperidine derivative (1-2 eq.) was dissolved in a solution of aqueous formaldehyde in formic acid, and the mixture was heated with microwave irradiation (100-160° C.) for between 5 and 15 minutes. The resultant residue was loaded onto an Isolute® SCX-2 cartridge. The cartridge was then washed with acetonitrile before the desired product was eluted using 2M ammonia in MeOH.

General Mesylate Displacement Methods

Method A: A mixture of 6-cyano-3-(4-methanesulfonyloxymethyl-phenyl)-dipyrido[2,3-b;4',3'-d]pyrrole-9-carboxylic acid tert-butyl ester (1 eq.), amine (1.1-1.5 eq.) and triethylamine (1.1-1.5 eq.) in acetonitrile was stirred between ambient temperature and 50° C. until analysis (TLC/LCMS) showed complete consumption of starting material. The reaction mixture was allowed to cool to ambient temperature and was then partitioned between ethyl acetate and water. The organic layer was separated, dried over anhydrous sodium sulfate, filtered and evaporated in vacuo. The resultant residue was subjected to purification by one of the general methods described below.

Method B: A mixture of methanesulfonic acid 4-[6-cyano-9-(2-trimethylsilanyl-ethoxymethyl)-9H-dipyrido[2,3-b;4',3'-d]pyrrol-3-yl]-benzyl ester (1 eq.), amine (1.1-1.5 eq.) and triethylamine (1.1-1.5 eq.) in acetonitrile was stirred between ambient temperature and 50° C. until analysis (TLC/LCMS) showed complete consumption of starting material. The reaction mixture was allowed to cool to ambient temperature and was then partitioned between ethyl acetate and water. The organic layer was separated, dried over anhydrous sodium sulfate, filtered and evaporated in vacuo. The resultant residue was subjected first to deprotection, and then purification, by the general methods described below.

Method C: A mixture of methanesulfonic acid 4-[6-cyano-9-(2-trimethylsilanyl-ethoxymethyl)-9H-dipyrido[2,3-b;4',3'-d]pyrrol-3-yl]-benzyl ester (1 eq.), amine (1.1-1.5 eq.) and triethylamine (1.1-1.5 eq.) in acetonitrile was heated with microwave irradiation (100-150° C.) for between 1 and 30 minutes until analysis (TLC/LCMS) showed complete consumption of starting material. The reaction mixture was allowed to cool to ambient temperature and was then partitioned between ethyl acetate and water. The organic layer was separated, dried over anhydrous sodium sulfate, filtered and evaporated in vacuo. The resultant residue was subjected first to deprotection, and then purification, by the general methods described below.

Method D: 9-Benzenesulfonyl-5-(3-chloropropyl)-3-(1-methyl-1H-pyrazol-4-yl)-9H-dipyrido[2,3-b;4',3'-d]pyrrole-6-carbonitrile (1 eq.) was treated with a large excess of the amine (50-300 eq.) and the mixture was heated with microwave irradiation (between 90° C. and 140° C.) for between 1 and 30 minutes until analysis (TLC/LCMS) showed complete consumption of starting material. The reaction mixture was allowed to cool to ambient temperature and was then subjected to purification by the general methods described below.

Method E: Methanesulfonic acid 3-[9-benzenesulfonyl-6-cyano-3-(1-methyl-1H-pyrazol-4-yl)-9H-dipyrido[2,3-b;4',3'-d]pyrrol-5-yl]-propyl ester (1 eq.) was treated with a large excess of the amine (50-300 eq.) and the mixture was heated with microwave irradiation (between 90° C. and 140° C.) for between 1 and 30 minutes until reaction was deemed complete. The reaction mixture was allowed to cool to ambient temperature and was then subjected to purification by the general methods described below.

Method F: A mixture of 9-benzenesulfonyl-3-(1-methyl-1H-pyrazol-4-yl)-5-piperidin-4-ylmethyl-9H-dipyrido[2,3-b;4',3'-d]pyrrole-6-carbonitrile (1 eq.), alkyl halide (1.1-1.5 eq.) and triethylamine (1.1-1.5 eq.) in acetonitrile was heated at reflux for between 5 and 60 minutes until the reaction was deemed complete. The reaction mixture was allowed to cool to ambient temperature and was then subjected to purification by the general methods described below.

General Boronic Acid/Boronate Ester Preparation Method

Method A: The appropriate aryl halide (1-3 eq.) was suspended in a mixture of THF under an inert atmosphere then n-butyl lithium (1-3 eq.) was added at −78° C. After between 5 and 30 minutes at this temperature, trialkylborate (1-3 eq.) was added then the reaction mixture was warmed to ambient temperature and quenched by the addition of ammonium chloride. The resultant residue was purified by one of the general purification methods described below or used crude in the next step.

Method B: The appropriate aryl halide (1-3 eq.) was suspended in a mixture of dioxane and DMSO before bis(pinacolato)diboron (1-2 eq.), potassium acetate and 1,1'-bis (diphenylphosphino)-ferrocene]dichloropalladium(II) (5-10 mol %) were added and the reaction mixture was then heated with microwave irradiation (100-160° C.) for between 1 and 20 minutes. The resultant residue was purified by one of the general purification methods described below or used crude in the next step.

Method C: The appropriate (bromomethyl)phenyl boronic acid (1 eq.) was stirred with sodium iodide (0.05 eq.) and potassium carbonate (3.0 eq.) in acetonitrile and the appropriate amine (1.2 eq.) added. The mixture was heated to 50° C. for 2 h and then cooled to ambient temperature or stirred at room temperature until reaction complete, then the volatile components were removed in vacuo and the residue re-suspended in MeOH. The remaining solid was removed by filtration then the methanolic solution was collected and concentrated to dryness under reduced pressure. The resulting boronic acid was used with no further purification.

Method D: The appropriate electrophile (1-2 eq.) and potassium carbonate (3-5 eq.) were added to 4,4,5,5-tetramethyl-2(1H-pyrazol-4-yl)-1,3,2-dioxaborolane in acetonitrile and the mixture was stirred under reflux for between 1 and 7 days. The residue was purified by one of the general purification methods described below.

General Suzuki Coupling Method

Method A: The appropriate boronic acid/boronate ester/triflate (1-3 eq.) was suspended in acetonitrile before 3-bromo-9H-dipyrido[2,3-b;4',3'-d]pyrrole-6-carbonitrile or 3-bromo-9-(2-trimethylsilanylethoxymethyl)-9H-dipyrido[2,3-b;4',3'-d]pyrrole-6-carbonitrile (1 eq.), aqueous sodium carbonate solution and bis(triphenylphosphine)palladium(II) dichloride (5-10 mol %) were added and the reaction mixture was then heated with microwave irradiation (100-160° C.) for between 1 and 30 minutes. The resultant residue was purified by one of the general purification methods described below.

Method B: The appropriate boronic acid/boronate ester (1-3 eq.) was suspended in a mixture of dioxane and DMSO before 3-bromo-9H-dipyrido[2,3-b;4',3'-d]pyrrole-6-carbonitrile or 3-bromo-9-(2-trimethylsilanylethoxymethyl)-9H-dipyrido[2,3-b;4',3'-d]pyrrole-6-carbonitrile (1 eq.), aqueous potassium acetate solution and 1,1'-[bis(diphenylphosphino)ferrocene]dichloropalladium(II) (5-10 mol %) were added and the reaction mixture was then heated with microwave irradiation (100-160° C.) for between 1 and 20 minutes. The resultant residue was purified by one of the general purification methods described below.

Method C: The appropriate boronic acid/boronate ester (1-3 eq.) was suspended in DME before 3-bromo-9H-dipyrido[2,3-b;4',3'-d]pyrrole-6-carbonitrile or 3-bromo-9-(2-trimethylsilanylethoxymethyl)-9H-dipyrido[2,3-b;4',3'-d]pyrrole-6-carbonitrile (1 eq.), aqueous cesium carbonate solution and 1,1'-[bis(diphenylphosphino)ferrocene]dichloropalladium(II) (5-10 mol %) were added and the reaction mixture was then heated with microwave irradiation (100-160° C.) for between 1 and 20 minutes. The resultant residue was purified by one of the general purification methods described below.

Method D: The appropriate boronic acid/boronate ester (1-3 eq.) was suspended in acetonitrile before 3-bromo-9H-dipyrido[2,3-b;4',3'-d]pyrrole-6-carbonitrile or 3-bromo-9-(2-trimethylsilanyl-ethoxymethyl)-9H-dipyrido[2,3-b;4',3'-d]pyrrole-6-carbonitrile (1 eq.), aqueous sodium carbonate solution or potassium fluoride solution, and 1,1'-[bis(diphenylphosphino)ferrocene]dichloropalladium(II) (5-10 mol %) were added and the reaction mixture was then heated with microwave irradiation (100-160° C.) for between 1 and 30 minutes. The resultant residue was purified by one of the general purification methods described below.

Method E: The appropriate boronic acid/boronate ester (1-3 eq.) was suspended in DME/IMS before 3-bromo-9H-dipyrido[2,3-b;4',3'-d]pyrrole-6-carbonitrile or 3-bromo-9-(2-trimethylsilanyl-ethoxymethyl)-9H-dipyrido[2,3-b;4',3'-d]pyrrole-6-carbonitrile (1 eq.), aqueous cesium carbonate solution and tetrakis(triphenylphosphine)palladium(0) (5-10 mol %) were added, and the reaction mixture was heated with microwave irradiation (100-160° C.) for between 1 and 30 minutes. The resultant mixture was purified by one of the general purification methods described below.

Method F: 3-(4,4,5,5-Tetramethyl-[1,3,2]dioxaborolan-2-yl)-9-(2-trimethylsilanyl ethoxymethyl)-9H-dipyrido[2,3-b;4',3'-d]pyrrole-6-carbonitrile was suspended in acetonitrile before the appropriate aryl/heteroharyl bromide (1-3 eq.), aqueous sodium carbonate or potassium fluoride solution and 1,1'-[bis(diphenylphosphino)ferrocene]dichloropalladium (II) (5-10 mol %) were added and the reaction mixture was then heated with microwave irradiation (100-160° C.) for between 1 and 60 minutes. The resultant mixture was purified by one of the general purification methods described below.

Method G: The appropriate aryl halide (1-3 eq.) was suspended in DME/IMS before 3-(4,4,5,5-tetramethyl-[1,3,2]dioxaborolan-2-yl)-9-(2-trimethylsilanylethoxymethyl)-9H-dipyrido[2,3-b;4',3'-d]pyrrole-6-carbonitrile (1 eq.), aqueous cesium carbonate solution and tetrakis(triphenylphosphine)palladium(0) (5-10 mol %) were added and the reaction mixture was then heated with microwave irradiation (100-160° C.) for between 1 and 30 minutes. The resultant mixture was purified by one of the general purification methods described below.

Method H: The appropriate aryl halide (1-3 eq.) was suspended in acetonitrile before 3-(4,4,5,5-tetramethyl-[1,3,2]dioxaborolan-2-yl)-9-(2-trimethylsilanylethoxy methyl)-9H-dipyrido[2,3-b;4',3'-d]pyrrole-6-carbonitrile (1 eq.), aqueous sodium carbonate solution and bis(triphenylphosphine)palladium(II) dichloride (5-10 mol %) were added and the reaction mixture was then heated with microwave irradiation (100-160° C.) for between 1 and 30 minutes. The resultant mixture was purified by one of the general purification methods described below.

Method I: The appropriate boronic acid/boronate ester (1.5 eq.) was suspended in DMF before 6-chloro-3-(4-piperidin-1-ylmethyl-phenyl)-9H-dipyrido[2,3-b;4',3'-d]pyrrole (1.5 eq.), aqueous sodium carbonate solution and tetrakis(triphenylphosphine)palladium(0) (5 mol %) were added and the reaction mixture was then heated with microwave irradiation (140° C.) for 60-90 minutes. The resultant mixture was purified by one of the general purification methods described below.

Method J: The appropriate boronic acid/boronate ester (1.5 eq.) was suspended in acetonitrile before 6-chloro-3-(4-piperidin-1-ylmethyl-phenyl)-9H-dipyrido[2,3-b;4',3'-d]pyrrole (1.5 eq.), aqueous potassium carbonate solution and 1,1'-bis(diphenylphosphino)ferrocene]dichloropalladium(II) (10 mol %) were added and the reaction mixture was then heated with microwave irradiation (140° C.) for 60 minutes. The resultant mixture was purified by one of the general purification methods described below.

Method K: The appropriate aryl triflate (1-3 eq.) was suspended in DME/IMS before 3-(4,4,5,5-tetramethyl-[1,3,2]dioxaborolan-2-yl)-9-(2-trimethylsilanylethoxymethyl)-9H-dipyrido[2,3-b;4',3'-d]pyrrole-6-carbonitrile (1 eq.), aqueous cesium carbonate solution and 1,1'-[bis(diphenylphosphino)ferrocene]dichloropalladium(II) (5-10 mol %) were added and the reaction mixture was then heated with microwave irradiation (100-160° C.) for between 1 and 30 minutes.

Method L: 9-Benzenesulfonyl-5-bromo-3-(1-methyl-1H-pyrazol-4-yl)-9H-dipyrido[2,3-b;4',3'-d]pyrrole-6-carbonitrile (1 eq.) was suspended in tetrahydrofuran before the appropriate potassium alkylhalide trifluoroborate (2 eq.), aqueous sodium carbonate or potassium fluoride solution and 1,1'-[bis(diphenylphosphino)ferrocene]dichloropalladium (II) (5-10 mol %) were added and the reaction mixture was refluxed for 16 hours. The reaction mixture was allowed to cool to ambient temperature and was then partitioned between THF and brine. The organic layer was separated, dried over anhydrous sodium sulfate, filtered and evaporated in vacuo. The resultant residue was subjected to purification, by the general methods described below.

Method M: A mixture of 4-methylenepiperidine-1-carboxylic acid tert-butyl ester (1 eq.) and 9-borabicyclo[3.3.1]nonane (1 eq.) was heated to reflux for 1 hour before it was added to a degassed suspension of 9-benzenesulfonyl-5-bromo-3-(1-methyl-1H-pyrazol-4-yl)-9H-dipyrido[2,3-b;4',3'-d]pyrrole-6-carbonitrile (1-3 eq.), aqueous sodium carbonate or potassium fluoride solution and 1,1'-[bis(diphenylphosphino)ferrocene]dichloropalladium(II) (5-10 mol %) in DMF. The reaction mixture was then heated (60° C.) for between 5 and 75 minutes. The reaction mixture was allowed to cool to ambient temperature and was then partitioned between ethyl acetate and brine. The organic layer was separated, dried over anhydrous sodium sulfate, filtered and evaporated in vacuo. The resultant residue was subjected to purification, by the general methods described below.

Method N: The appropriate boronic acid/boronate ester (1-3 eq.) was suspended in anhydrous acetonitrile before the appropriate 5-substituted 9-benzenesulfonyl-3-bromo-5-hydroxy-9H-dipyrido[2,3-b;4',3'-d]pyrrole-6-carbonitrile (1 eq.), aqueous sodium carbonate solution or potassium fluoride solution, and 1,1'-[bis(diphenyl phosphino)ferrocene] dichloro palladium(II) (5-10 mol %) were added and the reaction mixture was then heated with microwave irradiation (100-160° C.) for between 1 and 30 minutes. The resultant residue was purified by one of the general purification methods described below. (Deviation: $^2$ Dioxane was used as a solvent instead of acetonitrile).

General Stille Coupling Methods

Method A: The appropriate stannane (1-3 eq.) was suspended in anhydrous dioxane before 3-bromo-9H-dipyrido[2,3-b;4',3'-d]pyrrole-6-carbonitrile or 3-bromo-9-(2-trimethylsilanylethoxymethyl)-9H-dipyrido[2,3-b;4',3'-d]pyrrole-6-carbonitrile (1 eq.) and tetrakis(triphenylphosphine)palladium(0) (5-10 mol %) were added and the reaction mixture was then irradiated in the microwave (100-160° C.) for between 15 and 75 minutes. The resultant mixture was purified by one of the general purification methods described below.

Method B: The appropriate stannane (1-3 eq.) was suspended in anhydrous dioxane before 3-bromo-9H-dipyrido[2,3-b;4',3'-d]pyrrole-6-carbonitrile or 3-bromo-9-(2-trimethylsilanylethoxymethyl)-9H-dipyrido[2,3-b;4',3'-d]pyrrole-6-carbonitrile (1 eq.) and tetrakis(triphenylphosphine)palladium(0) (5-10 mol %) and lithium chloride (1-3 eq.) were added and the reaction mixture was then irradiated in the microwave (100-160° C.) for between 15 and 30 minutes. The resultant mixture was purified by one of the general purification methods described below.

Method C: The appropriate stannane (1-3 eq.) was suspended in anhydrous dioxane before the appropriate 5-substituted 9-benzenesulfonyl-3-bromo-5-hydroxy-9H-dipyrido[2,3-b;4',3'-d]pyrrole-6-carbonitrile (1 eq.), tetrakis(triphenylphosphine)palladium(0) (5-10 mol %) and copper thiophene carboxylate (5-30 mol %) were added and the reaction mixture was then heated with microwave irradiation (100-160° C.) for between 1 and 30 minutes. The resultant residue was purified by one of the general purification methods described below.

General Sonagashira Coupling Methods

Method A: The appropriate acetylene (1.0 eq.) was added to a solution of 3-bromo-9-(2-trimethylsilanylethoxymethyl)-9H-dipyrido[2,3-b;4',3'-d]pyrrole-6-carbonitrile (1.0 eq.), tetrakis(triphenylphosphine)palladium(0) (10 mol %), and copper (I) iodide (25 mol %) in anhydrous DMF, under nitrogen. The reaction mixture was irradiated in the microwave (100° C.) for 10 minutes. The resulatant mixture was concentrated in vacuo and the resultant residue was purified by one of the general purification methods described below.

General Ullmann Coupling Methods

Method A: The appropriate phenol (1.5 eq.) was added to a suspension of 3-bromo-9-(2-trimethylsilanylethoxymethyl)-9H-dipyrido[2,3-b;4',3'-d]pyrrole-6-carbonitrile (1 eq.), N,N-dimethylglycine (50 mol %), copper (I) iodide (12.5 mol %), and cesium carbonate (2.0 eq.) in anhydrous dioxane, under argon. The reaction mixture was then heated (100-120° C.) in a sealed tube for between 1 and 3 days. The mixture was concentrated in vacuo and the resultant residue was purified by one of the general purification methods described below.

Method B: The appropriate aryl bromide (1-2 eq.) was added to a suspension of 3-hydroxy-9-(2-trimethylsilanylethoxymethyl)-9H-dipyrido[2,3-b;4',3'-d]pyrrole-6-carbonitrile (1 eq.), N,N-dimethylglycine (50 mol %), copper (I) iodide (15 mol %), and cesium carbonate (2.0 eq.) in anhydrous dioxane, under argon. The reaction mixture was then heated under microwave irradiation (150° C.) for between 1 and 2 hours. The mixture was concentrated in vacuo and the resultant residue was purified by one of the general purification methods described below.

General Buchwald Coupling Method

Method A: The appropriate amine (1-2 eq.) was added to a suspension of 3-(4,4,5,5-tetramethyl-[1,3,2]dioxaborolan-2-yl)-9-(2-trimethylsilanyl-ethoxymethyl)-9H-dipyrido[2,3-b;4',3'-d]pyrrole-6-carbonitrile (1 eq.) and copper (II) acetate (5 mol %) in methanol, under argon. The reaction mixture was then heated under microwave irradiation (85-130° C.) for 1-30 minutes. The mixture was concentrated in vacuo and the resultant residue was purified by one of the general purification methods described below.

General Mitsunobu Method

Method A: A solution of 9-benzenesulfonyl-3-bromo-5-hydroxy-9H-dipyrido[2,3-b;4',3'-d]pyrrole-6-carbonitrile (1 eq.), the appropriate hydroxypiperidine carboxylic acid tert-butyl ester (5 eq.) and triphenylphosphine (5 eq.) in anhydrous DMF or anhydrous THF was treated dropwise with diethyl azodicarboxylate (5 eq.) and the mixture stirred at a temperature between ambient and 50° C. for between 2 and 65 hours. The resultant reaction mixture was diluted with ethyl acetate and washed with brine, dried over anhydrous magnesium sulfate and concentrated in vacuo. The resultant residue was subjected to purification, by the general methods described below.

Method B: 3-Hydroxy-9-(2-trimethylsilanylethoxymethyl)-dipyrido[2,3-b;4',3'-d]pyrrole-6-carbonitrile (1 eq.), the appropriate hydroxyamine (2-4 eq.) and triphenylphosphine (2-4 eq.) in THF was treated dropwise with diethyl azodicarboxylate (2-4 eq.) and the mixture stirred at a temperature between ambient and 50° C. for between 2 and 65 hours. The resultant reaction mixture was diluted with DCM and washed with brine, dried over anhydrous sodium sulfate and concentrated in vacuo. The resultant residue was subjected to purification, by the general methods described below.

General Bromide Displacement Methods

Method A: 9-Benzenesulfonyl-5-bromo-3-(1-methyl-1H-pyrazol-4-yl)-9H-dipyrido[2,3-b;4',3'-d]pyrrole-6-carbonitrile (1 eq.) was heated in the appropriate amine (5 eq.) at 160° C. until the reaction deemed complete. The reaction mixture was cooled then diluted with water and extracted with an appropriate solvent. The resultant residue was purified by one of the general purification methods described below.

Method B: 9-Benzenesulfonyl-5-bromo-3-(1-methyl-1H-pyrazol-4-yl)-9H-dipyrido[2,3-b;4',3'-d]pyrrole-6-carbonitrile (1 eq.) was heated with the appropriate amine (2-3 eq.) and triethylamine (10-12 eq.) in 1-methyl-2-pyrrolidinone (3 mL) under microwave irradiation or thermally in a sealed tube at 160-180° C. until the reaction was deemed complete. The reaction mixture was allowed to cool then evaporated. The resultant residue was purified by one of the general purification methods described below.

Method C: 9-Benzenesulfonyl-3,5-dibromo-9H-dipyrido[2,3-b;4',3'-d]pyrrole-6-carbonitrile (1 eq.) or 3,5-dibromo-9H-dipyrido[2,3-b;4',3'-d]pyrrole-6-carbonitrile (1 eq.) was heated in the appropriate amine (5 eq.) at 160° C. until the reaction deemed complete. The reaction mixture was cooled then diluted with water and extracted with an appropriate solvent. The resultant residue was purified by one of the general purification methods described below.

Method D: 9-Benzenesulfonyl-3,5-dibromo-9H-dipyrido[2,3-b;4',3'-d]pyrrole-6-carbonitrile (1 eq.) or 3,5-dibromo-9H-dipyrido[2,3-b;4',3'-d]pyrrole-6-carbonitrile (1 eq.) was heated with the appropriate amine (2-3 eq.) and triethylamine (10-12 eq.) in 1-methyl-2-pyrrolidinone (3 mL) under microwave irradiation or thermally in a sealed tube at 160-180° C. until the reaction was deemed complete. The reaction mixture was allowed to cool then evaporated. The resultant residue was purified by one of the general purification methods described below.

Method E: 9-Benzenesulfonyl-5-hydroxy-3-(1-methyl-1H-pyrazol-4-yl)-9H-dipyrido[2,3-b;4',3'-d]pyrrole-6-carbonitrile (1 eq.) was treated with the appropriate amine (10-50 eq.) in tetrahydrofuran (3 mL) and then the reaction mixture was stirred at ambient temperature until the reaction was deemed complete. The reaction mixture was allowed to cool then evaporated. The resultant residue was purified by one of the general purification methods described below.

General Reduction Methods

Method A: A solution of the appropriately 5-substituted 9-benzenesulfonyl-3-bromo-9H-dipyrido[2,3-b;4',3'-d]pyrrole-6-carbonitrile or 5-substituted 3-bromo-9H-dipyrido[2,3-b;4',3'-d]pyrrole-6-carbonitrile (1 .eq) in a mixture of DMF and ethyl acetate (1:1 v/v) was treated with Pd/C (10% w/w) and triethylamine (1-5 eq.) then placed under an atmosphere of hydrogen and the reaction mixture was stirred at ambient temperature until the reaction was deemed complete. The reaction mixture was purged with argon then the Pd/C was removed by filtration then the filtrate evaporated. The resultant residue was purified by one of the general purification methods described below.

Method B: A solution of the appropriately 5-substituted 9-benzenesulfonyl-3-bromo-9H-dipyrido[2,3-b;4',3'-d]pyrrole-6-carbonitrile or 5-substituted 3-bromo-9H-dipyrido[2,3-b;4',3'-d]pyrrole-6-carbonitrile (1 .eq) in a mixture of ethanol and tetrahydrofuran (1:1 v/v) was treated with Pd/C (10% w/w) then placed under an atmosphere of hydrogen and the reaction mixture was stirred at ambient temperature until the reaction was deemed complete. The reaction mixture was purged with argon then the Pd/C was removed by filtration then the filtrate evaporated. The resultant residue was purified by one of the general purification methods described below.

General Alkylation Methods

Method A: A solution of the 9-benzenesulfonyl-5-hydroxy-3-(1-methyl-1H-pyrazol-4-yl)-9H-dipyrido[2,3-b;4', 3'-d]pyrrole-6-carbonitrile (1 eq), cesium carbonate (1-5 eq.), sodium iodide (0.5-2 eq.) and 1,3-dibromopropane in DMF was heated under microwave irradiation (85-150° C.) for between 1 and 30 minutes until the reaction was deemed complete. The reaction mixture was then concentrated in vacuo and subjected to purification by one of the general methods described below.

Method B: A solution of the 9-benzenesulfonyl-5-hydroxy-3-(1-methyl-1H-pyrazol-4-yl)-9H-dipyrido[2,3-b;4', 3'-d]pyrrole-6-carbonitrile (1 eq), cesium carbonate (1-5 eq.), sodium iodide (0.5-2 eq.) and 1,2-dibromoethane in DMF was heated under microwave irradiation (85-150° C.) for between 1 and 30 minutes until the reaction was deemed complete. The reaction mixture was then concentrated in vacuo and subjected to purification by one of the general methods described below.

Method C: To a solution of the appropriate amine (2 eq.) in tetrahydrofuran was added sodium hydride (60% dispersion in mineral oil, 2-4 eq.). The reaction mixture was stirred at ambient temperature for 5 minutes, then a mixture of 4-chloro-9-(2-trimethylsilanyl ethoxymethyl)-9H-dipyrido[2,3-b;4',3'-d]pyrrole-6-carbonitrile with 4-chloro-9-(2-trimethylsilanyl-ethoxymethyl)-9H-dipyrido[2,3-b;4',3'-d]pyrrole-6-carbonitrile (1 eq.) was added in one portion and the reaction mixture was stirred at this temperature for 10 minutes before being warmed to 40° C. for 5 h. The mixture was diluted with water and ethyl acetate then the organic layer was separated, dried over anhydrous sodium sulfate, filtered, concentrated in vacuo, and purified using one of the general methods described below.

General Deprotection Methods

Method A: 6N HCl (aqueous solution or in dioxane) was added to a mixture of the protected substrate in an appropriate solvent and the reaction mixture was stirred between ambient temperature and 75° C., until the reaction was deemed complete. The reaction mixture was concentrated in vacuo and subjected to purification by one of the general methods described below.

Method B: TFA was added to a mixture of the protected substrate in an appropriate solvent at ambient temperature. The mixture was stirred until the reaction was deemed complete. The reaction mixture was concentrated in vacuo and subjected to purification by one of the general methods described below.

Method C: The tertiary amine was dissolved or suspended in DCM and treated with an excess (at least 2 equivalents) of 1-chloroethyl chloroformate. DIPEA (at least 1 equivalent) was added and the resultant mixture was heated under reflux. When analysis by LCMS showed that starting material (or any 1-chloroethyl carbamate of starting material) had been consumed the solution was cooled and concentrated in vacuo. The residue was taken up in methanol and heated at reflux until analysis by LCMS showed complete consumption of the intermediates. The reaction mixture was then cooled and concentrated in vacuo. The residue was subjected to purification by one of the general methods described below.

Method D: 1N TBAF in THF was added to a mixture of the protected substrate in an appropriate solvent. The reaction mixture was stirred between ambient temperature and 55° C. until the reaction was deemed complete. The resultant solution was concentrated in vacuo before subjecting the crude material to purification by one of the general methods described below. Alternatively, the crude material was partitioned between water and ethyl acetate and the organic layer was dried, concentrated in vacuo, before subjecting the crude material to one of the general purification methods described below.

Method E: 2N ammonia in methanol was added to a mixture of the protected substrate. The reaction mixture was stirred at ambient temperature until the reaction was deemed complete. The resultant solution was concentrated in vacuo before subjecting the crude material to purification by one of the general methods described below. Alternatively, the crude material was partitioned between water and ethyl acetate and the organic layer was dried, concentrated in vacuo, before subjecting the crude material to one of the general purification methods described below.

Method F: 48% aqueous hydrobromic acid was added to a mixture of the protected substrate. The reaction mixture was stirred at 75° C. until the reaction was deemed complete. The cooled reaction mixture was basified to pH 12 with 6N sodium hydroxide solution and then adjusted to pH 7-9 with dropwise addition of 1N aqueous hydrochloric acid then the resultant solid was collected by filtration and purified using one of the general methods described below.

General Purification Methods

Method A: Si-SPE or Si-ISCO, ethyl acetate/DCM gradient.

Method B: Si-SPE or Si-ISCO or manual silica column, methanol/DCM gradient.

Method C: A solution of the substrate in methanol was loaded onto an Isolute® SCX-2 cartridge. The cartridge was then washed with methanol before the desired product was eluted using 2N ammonia in MeOH.

Method D: Reverse phase HPLC Phenomenex Gemini C18, 20 mM triethylamine in water/acetonitrile gradient.

Method E: Si-SPE or Si-ISCO, 2N ammonia in methanol/DCM gradient.

Method F: Ethyl acetate/methanol recrystallisation.

Method G: Solid filtered from reaction mixture and resultant solid washed thoroughly with water.

Method H: Reaction mixture was diluted with water, filtered and the resulting solid washed with THF.

Method I: Reverse phase HPLC Phenomenex Gemini C18, 0.1% formic acid in water/0.1% formic acid in acetonitrile gradient.

Method J: Si-SPE or Si-ISCO, isopropanol/DCM gradient.

Method K: Solid isolated from reaction mixture and washed with ethanol.

Method L: Si-SPE or Si-ISCO, cyclohexane/ethyl acetate gradient.

Method M: C18-ISCO, 10-100% methanol/water gradient

Method N: Redisep Basic Alumina-ISCO, ethyl acetate/cyclohexane gradient

Method O: Redisep, Basic Alumina-ISCO, methanol/DCM gradient

Method P: Biotage, Snap KP-NH, Amino Silica-ISCO, ethyl acetate/cyclohexane gradient Method Q: Biotage, Snap KP-NH, Amino Silica-ISCO, methanol/DCM gradient Method R: Si-SPE or Si-ISCO or Biotage Snap-Si, THF/pentane gradient Method S: Reverse phase HPLC Phenomenex Gemini C18, water/methanol gradient Method R: Solid isolated from reaction mixture and triturated with an appropriate solvent.

Method S: Solid isolated from reaction mixture and washed with methanol and diethyl ether.

Method T: Reverse phase HPLC Phenomenex Gemini C18, 0.1% ammonium hydroxide in water/methanol gradient.

Deviations from Purification General Methods:
[1] Triturated in hot methanol; [2] triturated in ethyl acetate; [3] triturated in acetonitrile; [4] recrystallised from DMSO-water; [5] triturated in diethyl ether; [6] triturated in DCM; [7] recrystallised from acetonitrile; [8] recrystallised from ethyl acetate; [9] recrystallised from methanol.

Synthesis of Intermediates

Preparation of 3-Bromo-9H-dipyrido[2,3-b;4',3'-d]pyrrole-6-carbonitrile

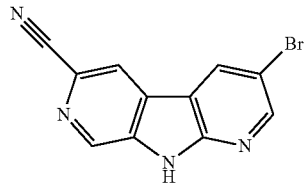

Step 1: 3-Bromo-9H-dipyrido[2,3-b;4',3'-d]pyrrole-6-carboxylic acid methyl ester

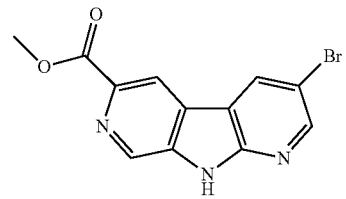 [SMILES: COC(=O)c1cc2c(cn1)[nH]c1ncc(Br)cc12]

Bromine (6.76 ml, 132.0 mmol) was added to a mixture of 9H-dipyrido[2,3-b;4',3'-d]pyrrole-6-carboxylic acid methyl ester (10.0 g, 44.0 mmol) and sodium acetate (11.2 g, 136.4 mmol) in acetic acid (360 mL) and then the reaction mixture was heated at 100° C. for 90 minutes. The reaction mixture was then cooled to ambient temperature and the solvent removed under reduced pressure then the residue was treated with saturated sodium thiosulfate solution (40 mL) followed by water (100 mL) and then the pH of the aqueous solution was adjusted to 7 by the addition of saturated sodium hydrogen carbonate solution. The resultant precipitate was collected by filtration and the solid was washed with water (20 mL) then dried at 60° C. until constant weight was achieved, to afford the desired material as an off-white solid (14.0 g, quantitative yield). $^1$H NMR (DMSO-D$_6$, 300 MHz): 9.13 (d, J=2.3 Hz, 1H), 9.00 (d, J=2.0 Hz, 2H), 8.70 (d, J=2.3 Hz, 1H), 3.92 (s, 3H). LCMS (Method B): R$_T$=2.92 min, M+H$^+$=306/308.

Step 2: 3-Bromo-9H-dipyrido[2,3-b;4',3'-d]pyrrole-6-carboxylic acid amide

In a steel bomb, a saturated solution of ammonia in methanol was prepared by passing gaseous ammonia through methanol (250 mL) then 3-bromo-9H-dipyrido[2,3-b;4',3'-d]pyrrole-6-carboxylic acid methyl ester (14.0 g, 38.3 mol) was added. The vessel was sealed, then the reaction mixture was heated at 140° C. (15 bar) for 18 h. After this time, the reaction vessel was allowed to cool to ambient temperature then the reaction mixture was transferred to a round-bottomed flask and the solvent was removed in vacuo to afford a solid residue. The resultant solid residue was collected by filtration, washed with methanol (50 mL) and then dried to yield the desired product as a grey solid (9.47 g, 85%). $^1$H NMR (DMSO-D$_6$, 400 MHz): 11.53 (s, 1H), 9.14 (d, J=2.3 Hz, 1H), 8.96 (d, J=1.1 Hz, 1H), 8.91 (d, J=1.1 Hz, 1H), 8.71 (d, J=2.3 Hz, 1H), 8.07 (s, 1H), 7.52 (s, 1H). LCMS (Method B): R$_T$=2.49 min, M+H$^+$=291/293.

Step 3: 3-Bromo-9H-dipyrido[2,3-b;4',3'-d]pyrrole-6-carbonitrile

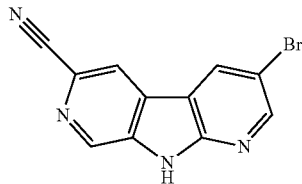 [SMILES: N#Cc1cc2c(cn1)[nH]c1ncc(Br)cc12]

To a cooled solution (0° C.) of a mixture of 3-bromo-9H-dipyrido[2,3-b;4',3'-d]pyrrole-6-carboxylic acid amide (5.0 g, 17.2 mmol) and triethylamine (24.0 mL, 172 mmol) in THF (200 mL) was slowly added trifluoroacetic anhydride (12.0 mL, 86 mmol). Upon complete addition, the reaction mixture was allowed to warm to ambient temperature and the stirring was continued for an additional 4 h. After this time, the solvent was removed in vacuo and the resultant residue was loaded onto H-MN. The residue was then purified by flash chromatography (silica, 330 g column, ISCO, 0-100% ethyl acetate in hexane) to afford the title compound as a pale brown solid (2.30 g, 49%). $^1$H NMR (DMSO-D$_6$, 300 MHz): 13.05 (s, 1H), 9.08-9.04 (m, 2H), 8.91 (d, J=1.1 Hz, 1H), 8.79 (d, J=2.3 Hz, 1H). LCMS (Method B): R$_T$=2.98 min, M+H$^+$= 271, 273.

Preparation of 3-Bromo-9-(2-trimethylsilanylethoxymethyl)-9H-dipyrido[2,3-b;4',3'-d]pyrrole-6-carbonitrile

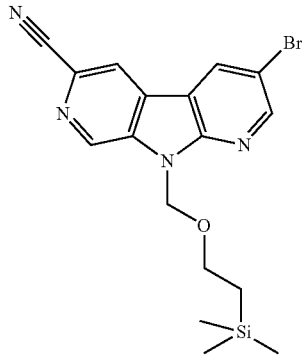 [SMILES: C[Si](C)(C)CCOCn1c2cnc(C#N)cc2c2cc(Br)cnc21]

To a suspension of 3-bromo-9H-dipyrido[2,3-b;4',3'-d]pyrrole-6-carbonitrile (300 mg, 1.1 mmol) in DMF (2.5 mL), under an inert atmosphere, was added sodium hydride (65 mg, 1.3 mmol) and the reaction mixture was allowed to stir at ambient temperature for 30 minutes. The reaction mixture was cooled to 0° C. and 2-(trimethylsilyl)ethoxymethyl chloride (0.25 mL, 1.3 mmol) was added dropwise and then the resultant suspension was allowed to warm to room temperature. Water (0.5 mL) was added to the resultant suspension to quench the reaction, the solvent was removed in vacuo and the resultant residue was purified by flash chromatography (silica, 12 g column, ISCO, 0-15% ethyl acetate in cyclohexane) to afford the title compound as an off-white crystalline solid (266 mg, 62%). $^1$H NMR (CDCl$_3$, 400 MHz): 9.18 (d, J=1.2 Hz, 1H), 8.74 (d, J=2.3 Hz, 1H), 8.58 (d, J=2.3 Hz, 1H), 8.34 (d, J=1.2 Hz, 1H), 5.98 (s, 1H), 3.56-3.60 (m, 2H), 0.94-0.98 (m, 2H), 0.08 (s, 9H). LCMS (Method B): R$_T$=4.55 min, M+H$^+$=(403, 405).

Preparation of 3-(4,4,5,5-Tetramethyl-[1,3,2]dioxaborolan-2-yl)-9-(2-trimethylsilanylethoxymethyl)-9H-dipyrido[2,3-b;4',3'-d]pyrrole-6-carbonitrile

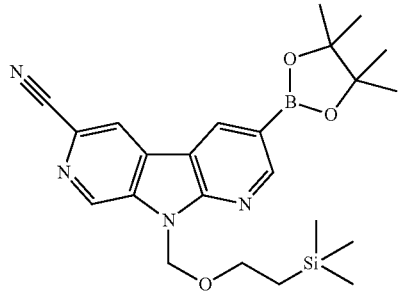 [SMILES: CC1(C)OB(c2cnc3c(c2)c2cc(C#N)ncc2n3COCC[Si](C)(C)C)OC1(C)C]

A mixture of 3-bromo-9-(2-trimethylsilanylethoxymethyl)-9H-dipyrido[2,3-b;4',3'-d]pyrrole-6-carbonitrile (1.41 g, 3.5 mmol), bis(pinacolato)diboron (980 mg, 3.85 mmol), potassium acetate (1.0 g, 10.5 mmol) and 1,1'-bis(diphenylphosphino)ferrocene]dichloropalladium(II) (140 mg, 0.175 mmol) in dioxane (18 mL) and DMSO (2 mL) was heated at 120° C., in a sealed vial and under argon, for 18 h. The reaction mixture was allowed to cool to ambient temperature then quenched by the addition of saturated aqueous sodium bicarbonate solution (200 mL) and extracted into ethyl acetate (200 mL). The organic layer was dried over sodium sulfate, filtered and evaporated in vacuo and the resultant residue was purified by flash chromatography (silica, 80 g column, ISCO, 0-50% ethyl acetate in cyclohexane) to afford the title compound as a white crystalline solid (1.32 g, 84%). $^1$H NMR (CDCl$_3$, 300 MHz): 9.16 (d, J=1.0 Hz, 1H), 9.05 (d, J=1.6 Hz, 1H), 8.86 (d, J=1.6 Hz, 1H), 8.37 (d, J=1.0 Hz, 1H), 6.03 (s, 2H), 3.61-3.54 (m, 2H), 1.41 (s, 12H), 0.94-0.87 (m, 2H), −0.10 (s, 9H). LCMS (Method B): R$_T$=5.0 min, M+H$^+$=451.

109

Preparation of 6-Cyano-3-(4-methanesulfonyloxymethylphenyl)-dipyrido[2,3-b;4',3'-d]pyrrole-9-carboxylic acid tert-butylester

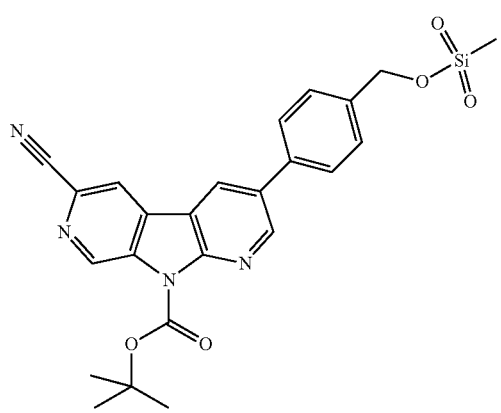

Step 1: 6-Cyano-3-(4-hydroxymethylphenyl)-dipyrido[2,3-b;4',3'-d]pyrrole-9-carboxylic acid tert-butyl ester

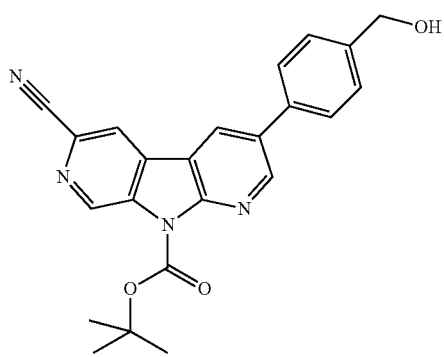 [SMILES: CC(C)(C)OC(=O)n1c2cnc(C#N)cc2c2cc(-c3ccc(CO)cc3)cnc21]

A mixture of 3-bromo-9H-dipyrido[2,3-b;4',3'-d]pyrrole-6-carbonitrile (1.00 g, 3.70 mmol), 4-bromomethylbenzeneboronic acid (1.18 g, 5.50 mmol) and 1,1'-[bis(diphenylphosphino)ferrocene]dichloropalladium(II) (152 mg, 0.19 mmol) in acetonitrile (40 mL) and 2N aqueous potassium fluoride solution (20 mL) was divided equally across four 25 mL microwave vials. Each vial was degassed with nitrogen for 10 minutes before the reaction mixtures were heated under microwave irradiation at 175° C. for 90 minutes. The reaction mixtures were then allowed to cool to ambient temperature, combined, diluted with water (100 mL), the resultant solid collected by filtration, washed with water (50 mL) and diethyl ether (40 mL) and left to air dry. The resultant grey solid was suspended in acetonitrile (250 mL), di-tert-butyl-dicarbonate (2.00 g, 9.17 mmol) was added and the resulting reaction mixture stirred at 50° C. for 1.5 h. The mixture was allowed to cool to ambient temperature, filtered to remove the solid and the filtrate was evaporated in vacuo. The resultant residue was purified by flash column chromatography (silica, 80 g column, ISCO, 0-70% ethyl acetate in DCM) to afford the title compound as a white solid (385 mg, 26%). $^1$H NMR (CDCl$_3$, 400 MHz): 9.67 (d, J=1.0 Hz, 1H), 9.08 (d, J=2.3 Hz, 1H), 8.56 (d, J=2.3 Hz, 1H), 8.38 (d, J=1.0 Hz, 1H), 7.68 (d, J=8.0 Hz, 2H), 7.56 (d, J=8.0 Hz, 2H), 4.81 (d, J=5.9 Hz, 2H), 1.82 (s, 9H), 1.75 (t, J=5.9 Hz, 1H). LCMS (Method B): R$_T$=2.70 min, M(-C$_5$H$_9$O$_2$)+H$^+$=301.

110

Step 2: 6-Cyano-3-(4-methanesulfonyloxymethylphenyl)-dipyrido[2,3-b;4',3'-d]pyrrole-9-carboxylic acid tert-butylester

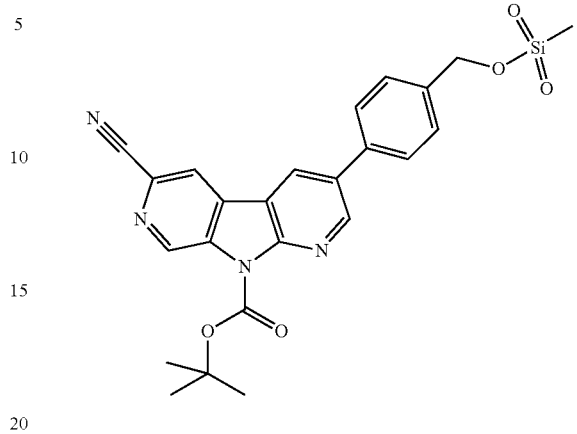

Methanesulfonyl chloride (60 μL, 0.70 mmol) was added to a solution of 6-cyano-3-(4-hydroxymethyl-phenyl)-dipyrido[2,3-b;4',3'-d]pyrrole-9-carboxylic acid tert-butyl ester (224 mg, 0.60 mmol) and triethylamine (110 μL, 0.80 mmol) in DCM (20 mL). The mixture was allowed to warm to ambient temperature and stirred for 2 h. The mixture was diluted with DCM (200 mL) and washed with water (100 mL). The organic phase was separated, dried over anhydrous sodium sulfate, filtered and evaporated in vacuo to afford the title compound as yellow oil (374 mg, 99%).

Preparation of Methanesulfonic acid 4-[6-cyano-9-(2-trimethyl silanylethoxymethyl)-9H-dipyrido[2,3-b;4',3'-d]pyrrol-3-yl]-benzyl ester

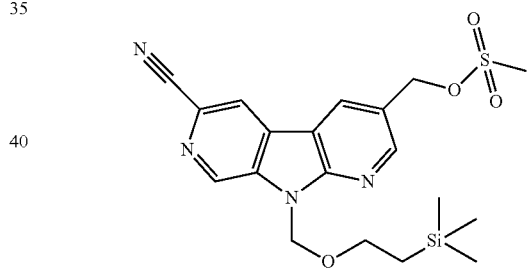

Step 1: (4-Hydroxymethyl-phenyl)-9-(2-trimethylsilanyl-ethoxymethyl)-9H-dipyrido[2,3-b;4',3'-d]pyrrole-6-carbonitrile

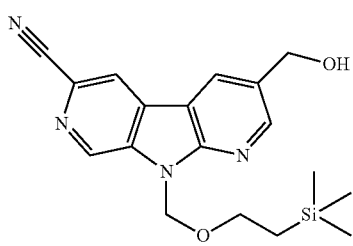 [SMILES: C[Si](C)(C)CCOCn1c2cnc(C#N)cc2c2cc(CO)cnc21]

A mixture of 3-bromo-9-(2-trimethylsilanyl-ethoxymethyl)-9H-dipyrido[2,3-b;4',3'-d]pyrrole-6-carbonitrile (700 mg, 0.87 mmol), 4-hydroxymethylbenzeneboronic acid (400 mg, 1.32 mmol) and 1,1'-[bis(diphenylphosphino)ferrocene]

dichloropalladium(II) (52.5 mg, 0.064 mmol) in acetonitrile (21 mL) and 2N aqueous potassium fluoride solution (21 mL) was divided equally across two 25 mL microwave vials. Each vial was degassed with nitrogen for 10 minutes before the mixtures were heated under microwave irradiation at 140° C. for 30 minutes. The reaction mixtures were allowed to cool to ambient temperature, combined and diluted with water (50 mL). The precipitate was collected by filtration, washed with water (50 mL) and left to air dry. The resultant grey solid was purified by flash column chromatography (silica, 40 g column, ISCO, 0-100% ethyl acetate in cyclohexane). The isolated solid was then triturated with hot t-BME to afford the title compound as a light grey solid (646 mg, 26%). LCMS (Method B): $R_T$=4.11 min, M+H$^+$=431.

Step 2: Methanesulfonic acid 4-[6-cyano-9-(2-trimethylsilanyl-ethoxymethyl)-9H-dipyrido[2,3-b;4',3'-d]pyrrol-3-yl]-benzyl ester

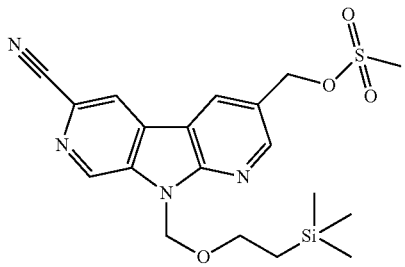 [SMILES: C[Si](C)(C)CCOCn1c2cnc(C#N)cc2c2cc(COS(C)(=O)=O)cnc21]

Methane sulfonyl chloride (366 mg, 0.25 ml, 3.20 mmol) was added to a suspension of (4-hydroxymethyl-phenyl)-9-(2-trimethylsilanyl-ethoxymethyl)-9H-dipyrido[2,3-b;4',3'-d]pyrrole-6-carbonitrile (646 mg, 1.56 mmol) and Silicycles' polymer supported diethylamine (2.5 g, 3.30 mmol) in acetonitrile (25 mL). The mixture was stirred at ambient temperature for 1 h. The resin was removed by filtration, washed with acetonitrile (50 mL) and the filtrate evaporated in vacuo to afford a pale yellow solid (737 mg, 96%). $^1$H NMR (CH$_3$CN-D$_3$, 400 MHz): 9.30 (d, J=1.1 Hz, 1H), 9.12 (d, J=2.2 Hz, 1H), 8.98 (d, J=2.2 Hz, 1H), 8.75 (d, J=1.1 Hz, 1H), 7.89-7.85 (m, 2H), 7.65-7.63 (m, 2H), 6.14 (s, 2H), 4.79 (s, 2H), 3.92 (s, 3H), 3.75 (t, J=8.1 Hz, 2H), 1.01 (t, J=8.1 Hz, 2H), 0.00 (s, 9H).

Step 3: 3-Hydroxy-9-(2-trimethylsilanyl-ethoxymethyl)-9H-dipyrido[2,3-b;4',3'-d]pyrrole-6-carbonitrile

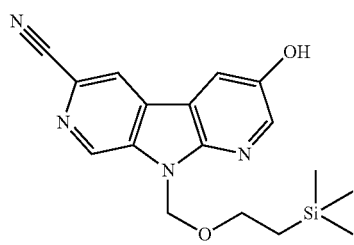 [SMILES: C[Si](C)(C)CCOCn1c2cnc(C#N)cc2c2cc(O)cnc21]

To a solution of 3-(4,4,5,5-tetramethyl-[1,3,2]dioxaborolan-2-yl)-9-(2-trimethylsilanylethoxymethyl)-9H-dipyrido [2,3-b;4',3'-d]pyrrole-6-carbonitrile (245 mg, 0.54 mmol) in THF (2.0 mL), under an inert atmosphere, was added N-methylmorpholine-N-oxide (191 mg, 1.63 mmol) and the reaction mixture was heated under reflux for 90 minutes. The reaction mixture was allowed to cool to ambient temperature and the solvent removed in vacuo. The residue was purified by flash chromatography (silica, 12 g column, ISCO 0-50% ethyl acetate in cyclohexane) to afford the title compound as a white solid (180 mg, 97%). $^1$H NMR (CD$_3$OD, 300 MHz): 9.10 (d, J=1.0 Hz, 1H), 8.64 (d, J=1.3 Hz, 1H), 8.35 (d, J=2.7 Hz, 1H), 8.04 (d, J=2.7 Hz, 1H), 5.99 (s, 2H), 3.59 (t, J=8.0 Hz, 2H), 0.86 (t, J=8.0 Hz, 2H), −0.14 (s, 9H). LCMS (Method B): $R_T$=3.75 min, M+H$^+$=341.

Preparation of 3-tert-Butyl-carbonylamino-9-(2-trimethylsilanylethoxymethyl)-dipyrido[2,3-b;4',3'-d]pyrrole-6-carbonitrile

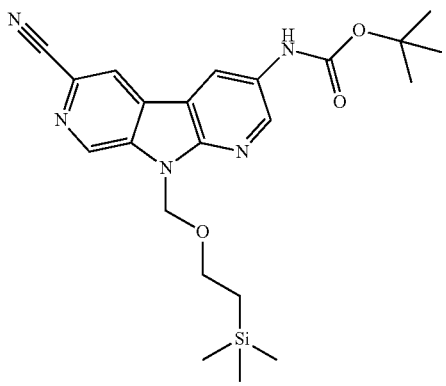 [SMILES: CC(C)(C)OC(=O)Nc1cnc2c(c1)c1cc(C#N)ncc1n2COCC[Si](C)(C)C]

A mixture of 3-bromo-9-(2-trimethylsilanylethoxymethyl)dipyrido[2,3-b;4',3'-d]pyrrole-6-carbonitrile (1.53 g, 3.79 mmol), tert-butyl carbamate (888 mg, 7.58 mmol), and cesium carbonate (2.47 g, 7.58 mmol) were suspended in 1,4-dioxane (30 mL) degassed and purged with nitrogen three times. 4,5-bis(Diphenylphosphino)-9,9-dimethylxanthene (219 mg, 0.379 mmol) and tris(dibenzylideneacetone)dipalladium(0) (173 mg, 0.189 mmol) were added and the reaction mixture heated at 90° C. for 25 h. The cooled reaction mixture was pre-absorbed onto silica gel and purified by flash chromatography on silica (silica, 120 g column, Biotage, 10-60% EtOAc in heptane) to afford the title compound as a white-yellow solid (1.3 g, 80%). $^1$H NMR (400 MHz, DMSO-D$_6$): 9.74 (s, 1H), 9.26 (s, 1H), 9.02 (s, 1H), 8.95 (s, 1H), 8.67 (d, J=2.4, 1H), 5.98 (s, 2H), 3.55 (t, J=7.9, 2H), 1.52 (s, 9H), 0.81 (t, J=7.9, 2H), −0.12--0.23 (m, 9H).

Preparation of 3-Amino-9-(2-trimethylsilanylethoxymethyl)-dipyrido[2,3-b;4',3'-d]pyrrole-6-carbonitrile

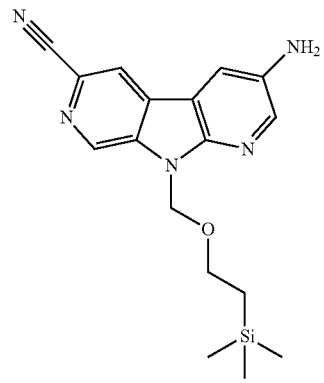 [SMILES: C[Si](C)(C)CCOCn1c2cnc(C#N)cc2c2cc(N)cnc21]

3-tert-Butyl-carbonylamino-9-(2-trimethylsilanylethoxymethyl)dipyrido[2,3-b;4',3'-d]pyrrole-6-carbonitrile (505 mg, 1.15 mmol) in DCM (30 mL) was treated with TFA (0.78 mL) and allowed to stir for 2.5 days at ambient temperature. The reaction mixture was treated with saturated sodium bicarbonate and diluted with DCM and water. The layers were separated, the aqueous phase was extracted further with DCM, and the combined organic phase was dried over sodium sulfate, filtered and concentrated in vacuo. The resultant residue was dissolved in ethyl acetate and pre-absorbed onto silica gel and purified by flash chromatography (silica, 24 g column, Biotage, 1-100% EtOAc in heptane) to afford the title compound as a yellow solid (152 mg, 39%). LCMS (Method D): $R_T$=2.40 min, M+H$^+$=340.

Preparation of 3-Chloro-9-(2-trimethylsilanylethoxymethyl)-dipyrido[2,3-b;4',3'-d]pyrrole-6-carbonitrile

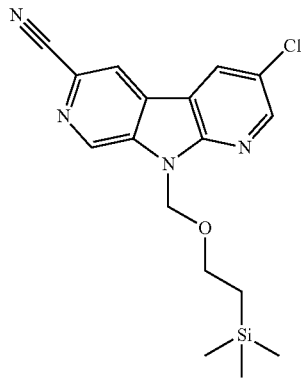 [SMILES: C[Si](C)(C)CCOCn1c2cnc(C#N)cc2c2cc(Cl)cnc21]

A solution of 3-amino-9-(2-trimethylsilanylethoxymethyl)-dipyrido[2,3-b;4',3'-d]pyrrole-6-carbonitrile (45.4 mg, 0.134 mmol) in 2M aqueous sulfuric acid (2.0 mL) and AcOH (1.0 mL) was cooled to 0° C. and treated with a solution of sodium nitrite (10.2 mg, 0.147 mmol) in water (0.30 mL). After 20 min, the solution of the diazonium salt was added slowly to a cooled (0° C.) solution of copper (I) chloride (29.1 mg, 0.294 mmol) in 1M hydrochloric acid (0.60 mL). The reaction mixture was allowed to warm to ambient temperature then diluted with DCM and water. The layers were separated, the aqueous phase extracted further with DCM, and the combined organic phases were dried over sodium sulfate and concentrated in vacuo. The resultant residue was dissolved in ethyl acetate and pre-absorbed onto silica gel and purified by flash chromatography (silica, 4 g column, Biotage, 1-50% EtOAc in heptane) to afford the title compound as a yellow-orange solid (20 mg, 43%). LCMS (Method D): $R_T$=3.61 min, M+H$^+$=359/361.

Preparation of 4-Chloro-9-(2-trimethylsilanylethoxymethyl)-9H-dipyrido[2,3-b;4',3'-d]pyrrole-6-carbonitrile

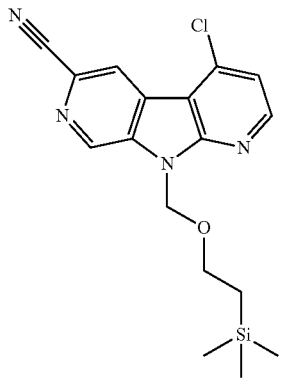 [SMILES: C[Si](C)(C)CCOCn1c2cnc(C#N)cc2c2c(Cl)ccnc21]

Step 1: 9-(2-Trimethylsilanylethoxymethyl)-9H-dipyrido[2,3-b;4'3'-d]pyrrole-6-carbonitrile

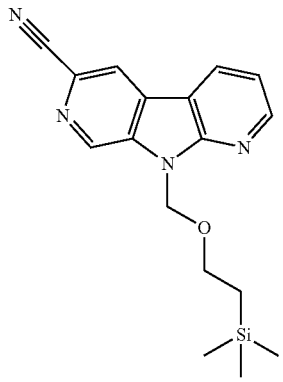 [SMILES: C[Si](C)(C)CCOCn1c2cnc(C#N)cc2c2cccnc21]

A mixture of 3-bromo-9-(2-trimethylsilanylethoxymethyl)-9H-dipyrido[2,3-b;4%3'-d]pyrrole-6-carbonitrile (5.6 g, 14 mmol), ammonium formate (8.8 g, 139 mmol), and zinc (9.1 g, 139 mmol) in tetrahydrofuran (85 mL) was heated at 75° C. for 10 h. The reaction was allowed to cool, filtered over a pad of celite, and washed with DCM (200 mL). The filtrate was concentrated in vacuo and then purified by flash chromatography (silica, 120 g, ISCO, 5-45% ethyl acetate in heptane) to afford the title compound as a white solid (3.6 g, 80%). $^1$H NMR (CDCl$_3$, 400 MHz): 9.17 (s, 1H), 8.73 (dd, 0.1=4.8 Hz, 1.5 Hz, 1H), 8.46 (dd, J=7.8 Hz, 1.5 Hz, 1H), 8.39 (s, 1H), 7.39 (dd, J=7.8 Hz, 4.8 Hz, 1H), 6.01 (s, 2H), 3.60 (t, J=8.0 Hz, 2H), 0.93 (t, J=8.0 Hz, 2H), −0.09 (s, 9H).

Step 2: 9-(2-Trimethylsilanylethoxymethyl)-9H-dipyrido[2,3-b;4',3'-d]pyrrole-6-carbonitrile-1,7-dioxide

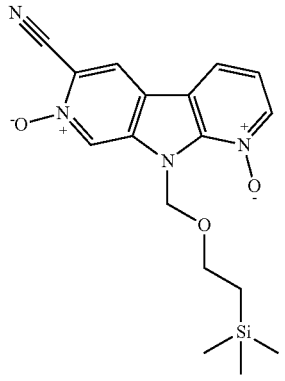

To a suspension of hydrogen peroxide-urea adduct (5.9 g, 62.2 mmol) in chloroform (40 mL) was added trifluoroacetic anhydride (8.7 mL, 61.6 mmol) dropwise over 10 minutes. The reaction mixture was stirred at room temperature for 5 minutes and then to this was added 9-(2-trimethylsilanylethoxymethyl)-9H-dipyrido[2,3-b;4',3'-d]pyrrole-6-carbonitrile (2.0 g, 6.0 mmol) as a solution in chloroform (30 mL). Note: an exotherm is observed upon addition of the substrate. The reaction mixture was stirred at room temperature for 10 minutes and then at 50° C. for 30 minutes. The reaction mixture was cooled to room temperature, treated with saturated sodium thiosulfate solution (20 mL), and diluted with water (50 mL) and methanol (10 mL). The layers were separated and the organic layer was washed with 0.5N hydrochloric acid (50 mL), dried over sodium sulfate, filtered, concentrated in vacuo, and purified by flash chromatography (silica, 80 g, ISCO, 0-10% methanol in dichloromethane) to afford the title compound as a pale yellow solid (930 mg, 40%). ¹H NMR (CDCl₃, 400 MHz): 8.86 (s, 1H), 8.39 (d, J=6.4 Hz, 1H), 8.27 (s, 1H), 7.94 (d, J=8.1 Hz, 1H), 7.32 (dd, J=7.9 Hz, 6.5 Hz, 1H), 6.55 (s, 2H), 3.73 (t, J=8.0, 2H), 0.93 (t, J=8.0, 2H), −0.04 (s, 9H).

Step 3: 4-Chloro-9-(2-trimethylsilanylethoxymethyl)-9H-dipyrido[2,3-b;4',3'-d]pyrrole-6-carbonitrile-7-oxide

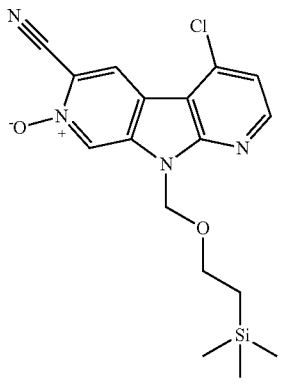

A mixture of 9-(2-trimethylsilanylethoxymethyl)-9H-dipyrido[2,3-b;4',3'-d]pyrrole-6-carbonitrile-1,7-dioxide (2.1 g, 5.9 mmol) in N,N-dimethylformamide (50 mL) was treated with methanesulfonyl chloride (0.78 mL, 10.0 mmol), and the reaction mixture was stirred at room temperature for 7 h. The reaction mixture was then diluted with ethyl acetate (150 mL) and water (200 mL). The layers were separated and the organic layer was dried over sodium sulfate, filtered, concentrated in vacuo, and purified by flash chromatography (silica, 40 g, ISCO, 5-85% ethyl acetate in heptane) to afford the title compound as a 6.5:1 mixture with 2-chloro-9-(2-trimethylsilanylethoxymethyl)-9H-dipyrido[2,3-b;4',3'-d]pyrrole-6-carbonitrile-7-oxide respectively as an off-white solid (1.7 g, 77%). The mixture was used in the next step without any further purification. ¹H NMR (CDCl₃, 400 MHz): 8.86 (s, 1H), 8.39 (d, J=6.4 Hz, 1H), 8.27 (s, 1H), 7.94 (d, J=8.1 Hz, 1H), 7.32 (dd, J=7.9 Hz, 6.5 Hz, 1H), 6.55 (s, 2H), 3.73 (t, J=8.0 Hz, 2H), 0.93 (t, J=8.0 Hz, 2H), −0.04 (s, 9H).

Step 4: 4-Chloro-9-(2-trimethylsilanylethoxymethyl)-9H-dipyrido[2,3-b;4',3'-d]pyrrole-6-carbonitrile

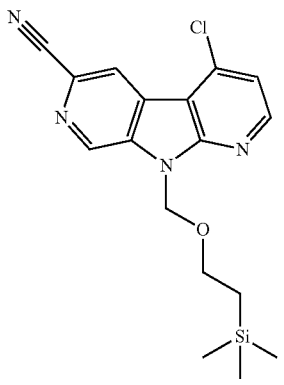 [SMILES: C[Si](C)(C)CCOCn1c2cnc(C#N)cc2c2c(Cl)ccnc21]

A solution of 4-chloro-9-(2-trimethylsilanylethoxymethyl)-9H-dipyrido[2,3-b;4',3'-d]pyrrole-6-carbonitrile-7-oxide with 2-chloro-9-(2-trimethylsilanyl-ethoxymethyl)-9H-dipyrido[2,3-b;4',3'-d]pyrrole-6-carbonitrile-7-oxide (6.5:1, 220 mg, 0.59 mmol), 1,1'-[bis(diphenylphosphino)ferrocene]dichloropalladium(II) (17 mg, 0.02 mmol), and triethylamine (0.24 mL, 1.8 mmol) in acetonitrile (3.1 mL) was heated under microwave irradiation at 130° C. for 20 minutes. The cooled reaction mixture was concentrated in vacuo and purified by flash chromatography (silica, 40 g, ISCO, 5-85% ethyl acetate in heptane) to afford the title compound as a 6.5:1 mixture of the title compound with 2-chloro-9-(2-trimethylsilanylethoxymethyl)-9H-dipyrido[2,3-b;4',3'-d]pyrrole-6-carbonitrile as an off-white solid (180 mg, 80%). The mixture was used in subsequent steps without any further purification. ¹H NMR (CDCl₃, 400 MHz): 9.20 (d, J=0.9 Hz, 1H), 8.74 (d, J=0.9 Hz, 1H), 8.60 (d, J=5.3 Hz, 1H), 7.39 (d, J=5.3 Hz, 1H), 6.02 (s, 2H), 3.60 (t, J=8.0 Hz, 2H), 0.94 (t, J=8.0 Hz, 2H), −0.08 (s, 9H).

2-Chloro-9-(2-trimethylsilanyl-ethoxymethyl)-9H-dipyrido[2,3-b;4',3'-d]pyrrole-6-carbonitrile

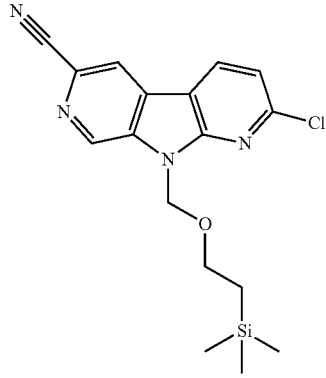 [SMILES: C[Si](C)(C)CCOCn1c2cnc(C#N)cc2c2ccc(Cl)nc21]

The title compound was prepared following the procedure from the previous step. ¹H NMR (CDCl₃, 400 MHz): 9.17 (s, 1H), 8.38 (d, J=8.2 Hz, 1H), 8.35 (s, 1H), 7.40 (d, J=8.2 Hz, 1H), 5.97 (s, 2H), 3.61 (t, J=8.0 Hz, 2H), 0.95 (t, J=8.0 Hz, 2H), −0.07 (s, 9H).

Preparation of 9-Benzenesulfonyl-5-hydroxy-9H-dipyrido[2,3-b;4',3'-d]pyrrole-6-carbonitrile

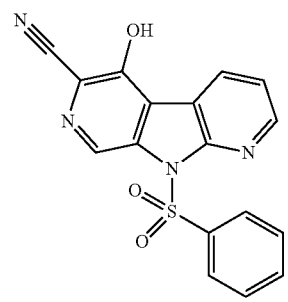 [SMILES: N#Cc1ncc2c(c1O)c1cccnc1n2S(=O)(=O)c1ccccc1]

Step 1: 1-Benzenesulfonyl-2-bromomethyl-1H-pyrrolo[2,3-b]pyridine-3-carboxylic acid methyl ester

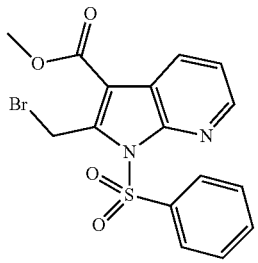 [SMILES: COC(=O)c1c(CBr)n(S(=O)(=O)c2ccccc2)c2ncccc12]

To 1-benzenesulfonyl-2-methyl-1H-pyrrolo[2,3-b]pyridine-3-carboxylic acid methyl ester (0.27 g, 0.88 mmol) in 1,2-dichloroethane (5.0 mL) was added NBS (0.178 g, 1.00 mmol) and AIBN (0.032 g, 0.20 mmol and the reaction mixture was heated under reflux for 1 h. After cooling to ambient temperature the solvent was removed by evaporation and the resultant residue was purified by flash chromatography (silica, 5 g column, ISCO, 0-65% DCM in pentane) to afford the title compound as a white solid (0.26 g, 72%). LCMS (Method B): $R_T$=3.95 min, M+H$^+$=409/411.

Step 2: 1-Benzenesulfonyl-2-{[cyanomethyl-(toluene-4-sulfonyl)amino]-methyl}-1H-pyrrolo[2,3-b]pyridine-3-carboxylic acid methyl ester

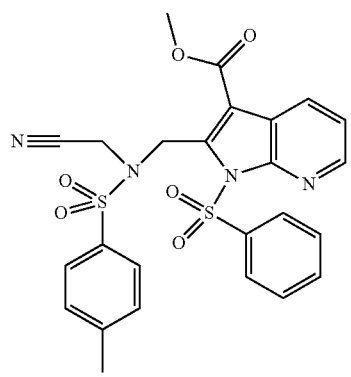 [SMILES: COC(=O)c1c(CN(CC#N)S(=O)(=O)c2ccc(C)cc2)n(S(=O)(=O)c2ccccc2)c2ncccc12]

To a cooled (0° C.) mixture of 1-benzenesulfonyl-2-bromomethyl-1H-pyrrolo[2,3-b]pyridine-3-carboxylic acid methyl ester (1.64 g, 4.00 mmol) and N-cyanomethyl-4-methyl-benzenesulfonamide (0.93 g, 4.40 mmol) in dry THF (10 mL) was added sodium hydride (0.176 g, 60% dispersion in mineral oil, 4.40 mmol) in two equal portions. The reaction mixture was stirred at 0° C. for 15 minutes then allowed to warm to room temperature. After 66 h the reaction mixture was diluted with DCM (60 mL) and saturated aqueous sodium carbonate solution (25 mL). The layers were separated and the aqueous phase was extracted with DCM (2×25 mL). The combined organic phase was dried over anhydrous magnesium sulfate and concentrated in vacuo. The residue was triturated with THF (5 mL) and the resultant solid dried in vacuo to afford the title compound as a beige solid (1.72 g, 80%). LCMS (Method B): $R_T$=3.91 min, M+H$^+$=539.

Step 3: 9-Benzenesulfonyl-5-hydroxy-9H-dipyrido[2,3-b;4',3'-d]pyrrole-6-carbonitrile

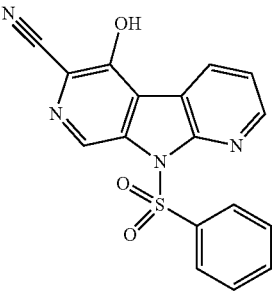 [SMILES: N#Cc1ncc2c(c1O)c1cccnc1n2S(=O)(=O)c1ccccc1]

Lithium bis(trimethylsilyl)amide (9.6 mL, 1N solution in THF, 9.60 mmol) was added dropwise to a cooled (−78° C.) suspension of 1-benzenesulfonyl-2-{[cyanomethyl(toluene-4-sulfonyl)amino]methyl}-1H-pyrrolo[2,3-b]pyridine-3-carboxylic acid methyl ester (1.72 g, 3.19 mmol) in dry THF (50 mL). The reaction mixture was allowed to warm to −30° C., stirred at −30° C. for 2 h, before warming to ambient temperature. The reaction mixture was quenched with saturated aqueous ammonium chloride solution (30 mL) and water (50 mL). The aqueous phase was extracted with DCM (2×20 mL) and the combined organic phase was washed with brine and concentrated in vacuo. The resultant solid was triturated with THF (2×4 mL) to afford the title compound. The filtrate was purified by flash chromatography (silica, 5 g column, Si-SPE, ethyl acetate then 10-20% MeOH in DCM) to afford the remaining title compound. The two batches of material were combined to afford a yellow solid (1.03 g, 90%). LCMS (Method B): $R_T$=3.26 min, M+H$^+$=351.

Preparation of 9-Benzenesulfonyl-3-bromo-5-hydroxy-9H-dipyrido[2,3-b;4',3'-d]pyrrole-6-carbonitrile

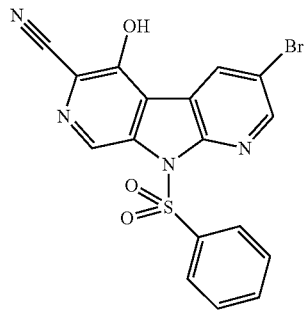 [SMILES: N#Cc1ncc2c(c1O)c1cc(Br)cnc1n2S(=O)(=O)c1ccccc1]

Step 1: 1-Benzenesulfonyl-5-bromo-1H-pyrrolo[2,3-b]pyridine-3-carboxylic acid methyl ester

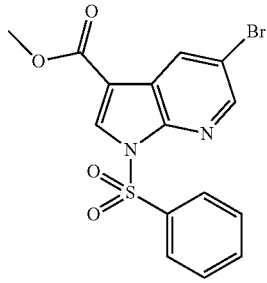 [SMILES: COC(=O)c1cn(S(=O)(=O)c2ccccc2)c2ncc(Br)cc12]

A mixture of 5-bromo-1H-pyrrolo[2,3-b]pyridine-3-carboxylic acid methyl ester (15.0 mmol), benzenesulfonyl chloride (11.9 g, 8.61 mL, 67.5 mmol) and triethylamine (9.61 g, 13.2 mmol) in dry THF (100 mL) was heated under reflux for 19 h. The resultant suspension was allowed to cool to ambient temperature and diluted with saturated aqueous sodium carbonate solution (50 mL) and extracted with DCM (2×50 mL) and THF (1×50 mL). The combined organic phase was dried over anhydrous magnesium sulfate and concentrated in vacuo. The resultant residue was purified by flash chromatography (silica, 50 g cartridge, Si-SPE, 0-100% DCM in pentane). The relevant fractions were concentrated in vacuo and the residue was triturated with pentane (10 mL) to afford the title compound as a white solid (5.25 g, 88%). LCMS (Method B): $R_T$=4.11 min, M+H$^+$=395/397.

Step 2: 1-Benzenesulfonyl-5-bromo-2-methyl-1H-pyrrolo[2,3-b]pyridine-3-carboxylic acid methyl ester

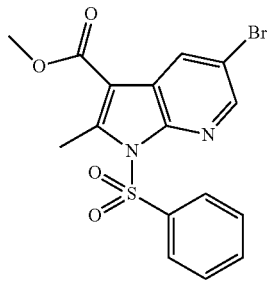 [SMILES: COC(=O)c1c(C)n(S(=O)(=O)c2ccccc2)c2ncc(Br)cc12]

A solution of 1-benzenesulfonyl-5-bromo-2-methyl-1H-pyrrolo[2,3-b]pyridine-3-carboxylic acid methyl ester (1.58 g, 4.0 mmol) in dry THF (14.0 mL) was added dropwise to a cold (−78° C.) solution of LDA [freshly prepared from diisopropylamine (0.67 mL, 4.8 mmol) and 2.5N n-butyllithium (1.92 mL, 4.8 mmol in hexanes) in THF (14 mL)]. The reaction mixture was stirred at −78° C. for 45 minutes before the addition of iodomethane (0.30 mL, 4.72 mmol), then the reaction mixture was warmed to 10° C. over 3.5 h. A solution of sodium dihydrogen phosphate (25 mL) was then added and the resultant mixture was allowed to warm to ambient temperature and the phases were separated. The aqueous phase was extracted with DCM (2×15 mL) and the combined organic phase was washed with brine, dried over anhydrous magnesium sulfate and concentrated in vacuo. The resultant residue was purified by chromatography (silica, 10 g cartridge, Si-SPE, DCM then ethyl acetate) and trituration with pentane to afford the title compound (0.42 g, 25%). $^1$H NMR (400 MHz, CDCl$_3$): 8.43 (d, J=2.3 Hz, 1H), 8.40 (d, J=2.3 Hz, 1H), 8.20-8.16 (m, 2H), 7.65-7.59 (m, 1H), 7.54-7.59 (m, 2H), 3.94 (s, 3H), 3.16 (s, 3H).

Step 3: 1-Benzenesulfonyl-5-bromo-2-bromomethyl-1H-pyrrolo[2,3-b]pyridine-3-carboxylic acid methyl ester

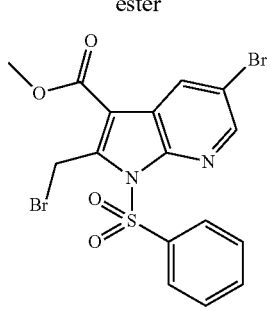

To a solution of 1-benzenesulfonyl-5-bromo-2-methyl-1H-pyrrolo[2,3-b]pyridine-3-carboxylic acid methyl ester (0.42 g, 1.0 mmol) in 1,2-dichloroethane (9 mL) were added NBS (0.20 g, 1.1 mmol) and AIBN (30 mg, 0.2 mmol) and the reaction mixture was heated under reflux for 45 minutes. The reaction mixture was allowed to cool to ambient temperature and was diluted with pentane (4.0 mL), the solid was removed by filtration and the liquors were then concentrated in vacuo. The resultant residue was purified by chromatography (silica, 5 g cartridge, Si-SPE, 30-100% DCM in pentane) to afford the title compound as a white solid (0.46 g, 90%). LCMS (Method B): $R_T$=4.55 min, M+H$^+$=489.

Step 4: 1-Benzenesulfonyl-5-bromo-2-{[cyanomethyl-(toluene-4-sulfonyl)amino]-methyl}-1H-pyrrolo[2,3-b]pyridine-3-carboxylic acid methyl ester

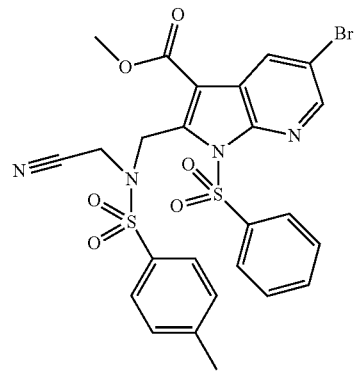 [SMILES: COC(=O)c1c(CN(CC#N)S(=O)(=O)c2ccc(C)cc2)n(S(=O)(=O)c2ccccc2)c2ncc(Br)cc12]

Sodium hydride (48 mg, 60% dispersion in mineral oil, 12.0 mmol) was added to a cooled (0° C.) mixture of 1-benzenesulfonyl-5-bromo-2-bromomethyl-1H-pyrrolo[2,3-b]pyridine-3-carboxylic acid methyl ester (0.56 g, 1.16 mmol) and N-cyanomethyl-4-methyl-benzenesulfonamide (0.25 g, 1.20 mmol) in dry THF (3.5 mL). The reaction mixture was stirred at 0° C. for 15 minutes, then allowed to warm to ambient temperature and stirred for 18 h. The reaction mixture was then diluted with DCM (40 mL), saturated aqueous sodium carbonate solution (20 mL) and water (20 mL). The organic phase was separated, washed with brine, dried over anhydrous magnesium sulfate and concentrated in vacuo. The resultant residue was purified by flash column chromatography (silica, 5 g cartridge, Si-SPE, DCM) to afford the title compound as a beige solid (0.59 g, 80%). LCMS (Method B): $R_T$=4.28 min, M+H$^+$=617/619.

Step 5: 9-Benzenesulfonyl-3-bromo-5-hydroxy-9H-dipyrido[2,3-b;4',3'-d]pyrrole-6-carbonitrile

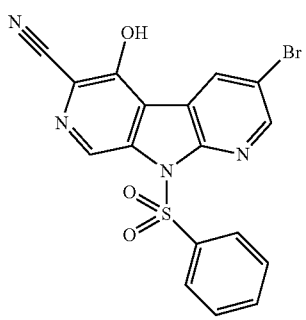 [SMILES: N#Cc1ncc2c(c1O)c1cc(Br)cnc1n2S(=O)(=O)c1ccccc1]

Lithium bis(trimethylsilyl)amide (2.34 mL of a 1N solution in THF, 2.34 mmol) was added dropwise to a cooled (−78° C.) suspension of 1-benzenesulfonyl-5-bromo-2-{[cyanomethyl-(toluene-4-sulfonyl)amino]methyl}-1H-pyrrolo[2,3-b]pyridine-3-carboxylic acid methyl ester (0.48 g, 0.78 mmol) in dry THF (12 mL). The reaction mixture was allowed to slowly warm to −10° C. and then quenched with saturated aqueous ammonium chloride solution (8 mL). The reaction mixture was diluted with water and washed with DCM (2×10 mL). The combined organic phase was dried over anhydrous magnesium sulfate and concentrated in vacuo. The resultant residue was purified by flash chromatography (silica, 5 g cartridge, Si-SPE, 10-100% THF in DCM) to afford the title compound as a brown solid (0.20 g, 60%). LCMS (Method B): $R_T$=3.83 min, M+H$^+$=429/431.

Preparation of 1,1,2,2,3,3,4,4,4-Nonafluoro-butane-1-sulfonic acid 9-benzenesulfonyl-3-bromo-6-cyano-9H-dipyrido[2,3-b;4',3'-d]pyrrol-5-yl ester

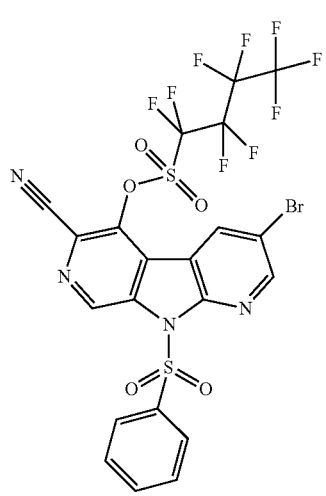 [SMILES: N#Cc1ncc2c(c1OS(=O)(=O)C(F)(F)C(F)(F)C(F)(F)C(F)(F)F)c1cc(Br)cnc1n2S(=O)(=O)c1ccccc1]

Pyridine (23.5 mL, 290 mmol) was added to a suspension of 9-benzenesulfonyl-3-bromo-5-hydroxy-9H-dipyrido[2,3-b;4',3'-d]pyrrole-6-carbonitrile (5.01 g, 11.7 mmol) in DCM (400 mL) at room temperature. The resultant solution was cooled to 0° C. then nonafluorobutanesulfonic anhydride (7.16 mL, 23.4 mmol) was added portionwise over 15 minutes maintaining the internal temperature below 5° C. The reaction mixture was stirred for 15 minutes at 0° C. then at room temperature for 3 h. The solution was cooled to 0° C. and 1M hydrochloric acid (290 mL) was added then the mixture was extracted with DCM (×3) and the combined organic phase was dried over sodium sulfate, filtered and evaporated. The residue was triturated with DCM and the resultant solid collected by filtration. The filtrate was purified by chromatography (silica, 50 g column, DCM) and the appropriate fractions were combined with the solid collected previously and dried to afford the title compound (6.63 g, 80%). $^1$H NMR (CDCl$_3$, 300 MHz): 9.93 (s, 1H); 8.86 (d, J=2.2 Hz, 1H); 8.75 (d, J=2.2 Hz, 1H); 8.30-8.24 (m, 2H); 7.73-7.65 (m, 1H); 7.61-7.52 (m, 2H).

Preparation of 9-Benzenesulfonyl-3,5-dibromo-9H-dipyrido[2,3-b;4',3'-d]pyrrole-6-carbonitrile

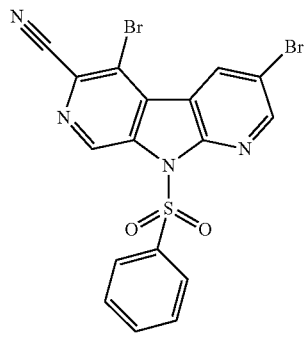 [SMILES: N#Cc1ncc2c(c1Br)c1cc(Br)cnc1n2S(=O)(=O)c1ccccc1]

A mixture of 1,1,2,2,3,3,4,4,4-nonafluorobutane-1-sulfonic acid 9-benzenesulfonyl-3-bromo-6-cyano-9H-dipyrido[2,3-b;4',3'-d]pyrrol-5-yl ester (6.63 g, 9.3 mmol) and tetra n-butylammonium bromide (11.3 g, 35 mmol) in 1,4-dioxane (400 mL) was heated under reflux for 2 h. The reaction mixture was evaporated to about a third of the original volume then left to stand overnight. The residue was taken up in DCM and purified twice by flash chromatography (silica, 70 g column, DCM) to afford the title compound (1.79 g, 39%). $^1$H NMR (DMSO-D$_6$, 300 MHz): 9.73 (d, J=0.6 Hz, 1H); 9.10 (d, J=2.3 Hz, 1H); 8.99 (d, J=2.3 Hz, 1H); 8.28-8.21 (m, 2H); 7.82-7.74 (m, 1H); 7.68-7.57 (m, 2H).

Preparation of 9-Benzenesulfonyl-5-hydroxy-3-(1-methyl-1H-pyrazol-4-yl)-9H-dipyrido[2,3-b;4',3'-d]pyrrole-6-carbonitrile

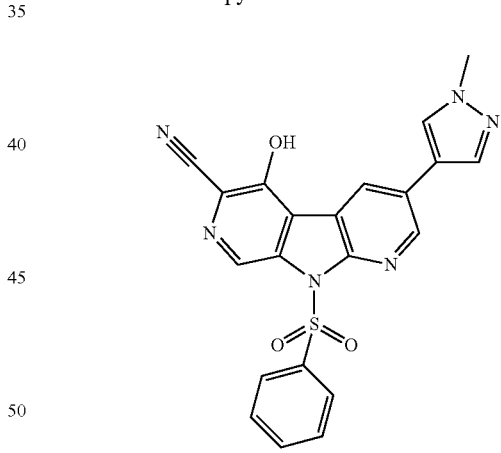

A mixture of 9-benzenesulfonyl-3-bromo-5-hydroxy-9H-dipyrido[2,3-b;4',3'-d]pyrrole-6-carbonitrile (500 mg, 1.16 mmol), 1-methyl-4-(4,4,5,5-tetramethyl-[1,3,2]dioxaborolan-2-yl)-1H-pyrazole (500 mg, 2.40 mmol) and [1,1'-bis(diphenylphosphino) ferrocene]dichloropalladium(II) (200 mg, 0.25 mmol) in 2N aqueous potassium acetate (3.6 mL) and acetonitrile (7.2 mL) was heated under microwave irradiation at 140° C., for 30 minutes. The reaction mixture was allowed to cool to ambient temperature, 1M hydrochloric acid (7.5 mL) was added and the mixture was stirred at room temperature for 1 h. The resulting precipitate was collected by filtration, washed with acetonitrile (5 mL) and left to air dry to afford the title compound as a crude brown solid (500 mg, 99%). LCMS (Method G): $R_T$=3.84 min, M+H$^+$=431.

Preparation of 1,1,2,2,3,3,4,4,4-Nonafluoro-butane-1-sulfonic acid 9-benzenesulfonyl-6-cyano-3-(1-methyl-1H-pyrazol-4-yl)-9H-dipyrido ester

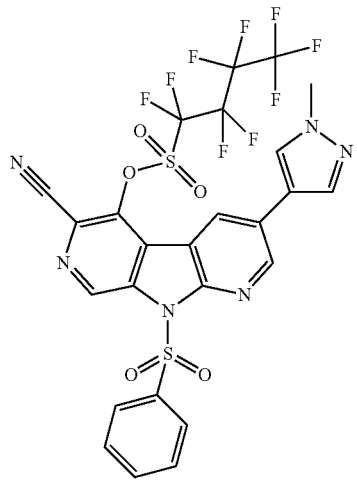 [SMILES: Cn1cc(-c2cnc3c(c2)c2c(OS(=O)(=O)C(F)(F)C(F)(F)C(F)(F)C(F)(F)F)c(C#N)ncc2n3S(=O)(=O)c2ccccc2)cn1]

1,1,2,2,3,3,4,4,4-Nonafluorobutanesulfonic anhydride (0.75 g, 0.40 mL, 1.3 mmol) was added dropwise to a suspension of 9-benzenesulfonyl-5-hydroxy-3-(1-methyl-1H-pyrazol-4-yl)-9H-dipyrido[2,3-b;4',3'-d]pyrrole-6-carbonitrile (106 mg, 0.25 mmol) in pyridine (0.7 mL, 8.0 mmol) and dry DCM (7 mL) at 0° C. The reaction mixture was then allowed to warm to ambient temperature and stirred for 4 h. The reaction mixture was treated with 1N hydrochloric acid (6 mL) and the phases were separated. The aqueous phase was extracted with DCM (2×10 mL), the combined organic phase was dried over anhydrous magnesium sulfate and concentrated in vacuo. The resultant residue was purified by chromatography (silica, 2 g column, Si-SPE, gradient of DCM/EtOAc) and further trituration with pentane (2 mL) to afford the title compound as a white solid (150 mg, 84%). $^1$H NMR (CDCl$_3$, 400 MHz): 9.95 (s, 1H), 8.99 (d, J=2.1 Hz, 1H), 8.74 (d, J=2.1 Hz, 1H), 8.35-8.32 (m, 2H), 7.86 (d, J=0.8 Hz, 1H), 7.74-7.68 (m, 2H), 7.61-7.56 (m, 2H), 4.04 (s, 3H). LCMS (Method G): R$_T$=4.80 min, M+H$^+$=713.

Preparation of 9-Benzenesulfonyl-5-bromo-3-(1-methyl-1H-pyrazol-4-yl)-9H-dipyrido[2,3-b;4',3'-d]pyrrole-6-carbonitrile

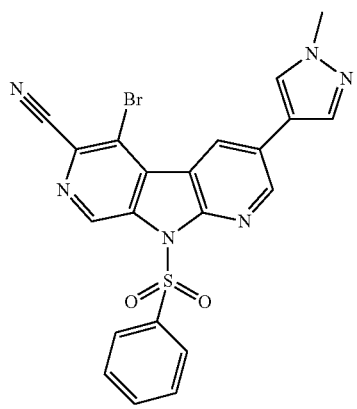 [SMILES: Cn1cc(-c2cnc3c(c2)c2c(Br)c(C#N)ncc2n3S(=O)(=O)c2ccccc2)cn1]

A mixture of 1,1,2,2,3,3,4,4-octafluoropentane-1-sulfonic acid 9-benzenesulfonyl-6-cyano-3-(1-methyl-1H-pyrazol-4-yl)-9H-dipyrido[2,3-b;4',3'-d]pyrrol-5-yl ester (150 mg, 0.2 mmol) and tetrabutylammonium bromide (240 mg, 0.75 mmol) in dry dioxane (10 mL) was heated at reflux for 1 h. The reaction mixture was allowed to cool to ambient temperature and was then concentrated in vacuo. The resultant residue was purified by chromatography (silica, 2 g column, Si-SPE, gradient of DCM/EtOAc) and further trituration with acetonitrile (2 mL) to afford the title compound as a white solid (60 mg, 60%). $^1$H NMR (CDCl$_3$, 400 MHz): 9.84 (s, 1H), 8.95-8.92 (m, 2H), 8.27-8.24 (m, 2H), 7.84 (d, J=0.9 Hz, 1H), 7.74 (s, 1H), 7.65-7.60 (m, 1H), 7.55-7.49 (m, 2H), 4.01 (s, 3H). LCMS (Method G): R$_T$=4.56 min, M+H$^+$=493.

Preparation of 9-Benzenesulfonyl-3-bromo-5-(1-ethyl-piperidin-4-yloxy)-9H-dipyrido[2,3-b;4',3'-d]pyrrole-6-carbonitrile

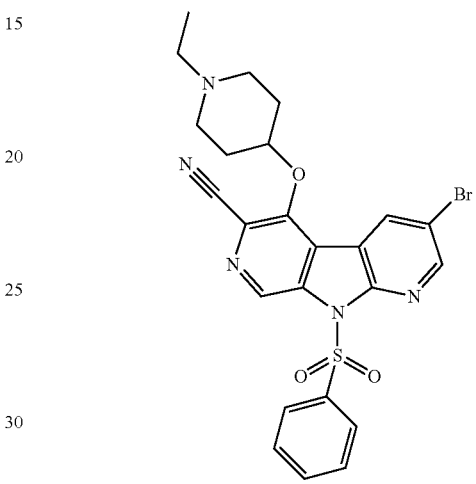

A solution of 9-benzenesulfonyl-3-bromo-5-(piperidin-4-yloxy)-9H-dipyrido[2,3-b;4',3'-d]pyrrole-6-carbonitrile (102 mg, 0.2 mmol) in acetonitrile (10 mL) was treated with ethyl iodide (34 mg, 17.4 µL, 0.2 mmol). The reaction mixture was heated for 24 h at 50° C., until analysis (TLC/LCMS) showed complete consumption of starting material. The reaction mixture was allowed to cool to ambient temperature and was then concentrated in vacuo. The resultant residue was partitioned between ethyl acetate (10 mL) and 1M sodium carbonate solution (5 mL). The organic layer was separated, dried over anhydrous sodium sulfate, filtered and evaporated in vacuo. The resultant residue was purified by chromatography (silica, Si-SPE, EtOAc) to afford the title compound as a white solid (72 mg, 60%). $^1$H NMR (CDCl$_3$, 400 MHz,): 9.56 (s, 1H), 8.76 (d, J=2.3 Hz, 1H), 8.65 (s, 1H), 8.25-8.22 (m, 2H), 7.67-7.62 (m, 1H), 7.54-7.49 (m, 2H), 5.15 (s, 1H), 2.96 (s, 2H), 2.48 (s, 2H), 2.23 (s, 4H), 2.02 (d, J=16.9 Hz, 2H), 1.18-1.04 (m, 3H). LCMS (Method G): R$_T$=3.5 min, M+H$^+$=541.

Preparation of 6-Bromo-3-iodo-9H-dipyrido[2,3-b;4',3'-d]pyrrole

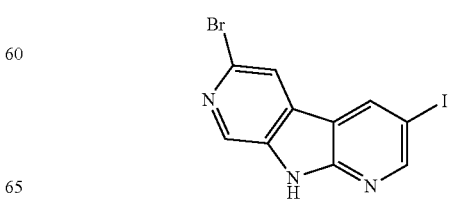

Step 1: 6-Bromo-4-iodo-nicotinic acid

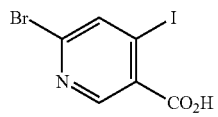

n-Butyllithium (2.5M in hexanes, 297 mL, 0.743 mol) was added over 1 h to a cooled (−25° C.) solution of 2,2,6,6,-tetramethylpiperidine (131 mL, 0.77 mol) in tetrahydrofuran (1 L). The mixture was left to stir for 16 h at −25° C. then cooled to −55° C. before addition of solid 6-bromonicotinic acid (50.0 g, 0.25 mmol). The mixture was allowed to warm to −20° C. and stirred for 2 h. The reaction mixture was cooled to −70° C. then poured onto a pre-cooled (−70° C.) solution of iodine (188.5 g, 0.74 mol) in tetrahydrofuran (500 mL). The mixture was then poured into the original reaction vessel and the contents allowed to warm to ambient temperature and stirred for 1 h. The solvent was evaporated and the resultant residue dissolved in water (500 mL) and washed with dichloromethane (3×300 mL). The aqueous phase was separated and the pH adjusted to 2 by the addition of concentrated hydrochloric acid. Aqueous sodium metabisulfite solution (20% w/w, 30 mL) was added and the solid which deposited was collected by filtration. The resultant solid was washed with water (75 mL) and pentane (75 mL) and dried at 75° C. under vacuum to furnish the title compound as a tan solid (53.1 g, 65%). $^1$H NMR (DMSO-D$_6$, 300 MHz): 8.62 (s, 1H), 8.35 (s, 1H). LCMS (Method B): R$_T$=2.16 min, M+H$^+$=328/330.

Step 2: (6-Bromo-4-iodo-pyridin-3-yl)-carbamic acid tert-butyl ester

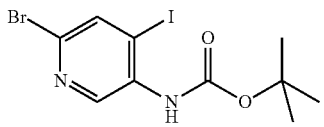 [SMILES: CC(C)(C)OC(=O)Nc1cnc(Br)cc1I]

A mixture of 6-bromo-4-iodo-nicotinic acid (18.3 g, 55.7 mmol), diphenylphosphorylazide (18 mL, 83.6 mmol) and triethylamine (23.5 mL, 167.2 mmol) in tert-butanol (110 mL) and toluene (120 mL) was heated at 110° C. for 3 h. The mixture was allowed to cool to ambient temperature then evaporated under reduced pressure. The resultant oil was treated with water (150 mL) and extracted with ethyl acetate (2×300 mL). The combined organic layer was dried over anhydrous sodium sulfate, filtered and evaporated to give a black solid. The resultant black solid was triturated with methanol (75 mL), collected by filtration, then washed with diethyl ether (30 mL) and left to air dry to afford the title compound as a brown solid (7.5 g, 34%). The remaining filtrate was evaporated and purified by flash chromatography on a pad of silica. The pad was washed with 20% ethyl acetate in cyclohexane. Collecting all fractions containing product followed by evaporation in vacuo and trituration with cyclohexane afforded further title compound (8.9 g, 40%) as a white solid (combined yield—16.4 g, 74%). $^1$H NMR (CDCl$_3$, 300 MHz): 8.95 (s, 1H), 7.87 (s, 1H), 6.64 (s, 1H), 1.54 (s, 9H). LCMS (Method B): R$_T$=3.83 min, M+H$^+$=399/401.

Step 3: 6-Bromo-4-iodo-pyridin-3-ylamine

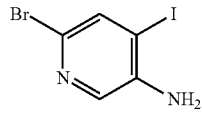

(6-Bromo-4-iodo-pyridin-3-yl)-carbamic acid tert-butyl ester (13.6 g, 34.1 mmol) was dissolved in dichloromethane (150 mL) and trifluoroacetic acid (50 mL) was then added. The resultant solution was stirred at ambient temperature for 2 h then evaporated under reduced pressure. The resultant residue was treated with a saturated solution of sodium hydrogen carbonate and the resultant solid was treated with water (50 mL) then extracted with ethyl acetate (2×200 mL). The combined organic layer was dried over anhydrous sodium sulfate, filtered and evaporated under reduced pressure to afford the title compound as an off-white solid (10.0 g, 98%). $^1$H NMR (CDCl$_3$, 300 MHz): 7.81 (s, 1H), 7.73 (s, 1H), 4.14 (s, 2H). LCMS (Method B): R$_T$=3.03 min, M+H$^+$=299/301.

Step 4: 6'-Bromo-2-fluoro-[3,4']bipyridinyl-3'-ylamine

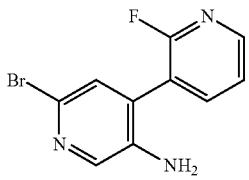

A mixture of 6-bromo-4-iodo-pyridin-3-ylamine (10.0 g, 33.4 mmol), 2-fluoropyridine-3-boronic acid (5.2 g, 36.8 mmol) and 1,1'-[bis(diphenylphosphino)ferrocene]dichloropalladium(II) dichloromethane complex (2.73 g, 3.34 mmol) in acetonitrile (150 mL) and 1N aqueous potassium fluoride solution (150 mL) was degassed with nitrogen for 20 minutes. The reaction mixture was heated at 70° C. for 2.5 h, allowed to cool to ambient temperature and then partitioned between ethyl acetate (400 mL) and water (150 mL). The organic layer was separated, dried over anhydrous sodium sulfate, filtered and evaporated in vacuo. The resultant solid residue was triturated with dichloromethane: methanol (1:1, 100 mL), collected by filtration and washed with diethyl ether (50 mL) to furnish the title compound as a brown solid (3.5 g, 39%). The filtrate was evaporated and purified by passing the resultant residue through a pad of silica eluting with ethyl acetate: cyclohexane (1:1). Collection of the appropriate fractions and evaporation to dryness afforded a solid that was then triturated with diethyl ether to afford the title compound as a brown solid (3.7 g, 42%) (combined yield—7.22 g, 81%). $^1$H NMR (CDCl$_3$, 300 MHz): 8.34 (ddd, J=4.9, 2.0, 1.2 Hz, 1H), 7.99 (s, 1H), 7.85 (ddd, J=9.4, 7.4, 2.0 Hz, 1H), 7.37 (ddd, J=7.4, 4.9, 2.0 Hz, 1H), 7.22 (s, 1H), 3.75 (s, 2H). LCMS (Method B): $R_T$=2.78 min, M+H$^+$=268/270.

Step 5: 6-Bromo-9H-dipyrido[2,3-b;4',3'-d]pyrrole

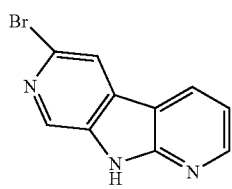 [SMILES: Brc1cc2c(cn1)[nH]c1ncccc12]

A solution of 6'-bromo-2-fluoro-[3,4']bipyridinyl-3'-ylamine (7.22 g, 26.9 mmol) in THF (75 mL) was added dropwise over 10 minutes to sodium bis-(trimethylsilyl) amide (1N solution in THF, 54 mL, 53.9 mmol). The reaction mixture was left to stir for 2.5 h then 1N aqueous potassium fluoride solution (7 mL) was added and the solvent evaporated in vacuo. The residue was diluted with water (100 mL) and the resultant solid was collected by filtration, washed with water (20 mL) and diethyl ether:pentane (1:1, 20 mL) and left to air dry. The resultant solid was triturated with methanol (50 mL), collected by filtration, washed with methanol (10 mL) and diethyl ether (20 mL) and pentane (20 mL) and left to air dry to afford the title compound as a brown solid (5.0 g, 75%). NMR (DMSO-D$_6$, 300 MHz): 8.73-8.69 (m, 2H), 8.63 (dd, J=4.8, 1.7 Hz, 1H), 8.48 (dd, J=1.0 Hz, 1H), 7.33 (dd, J=7.8, 4.8 Hz, 1H). LCMS (Method B): $R_T$=2.43 min, M+H$^+$=248/250.

Step 6: 6-Bromo-3-iodo-9H-dipyrido[2,3-b;4',3'-d]pyrrole

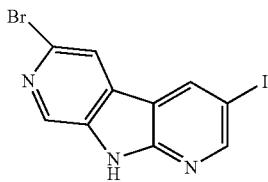 [SMILES: Brc1cc2c(cn1)[nH]c1ncc(I)cc12]

A solution of iodine monochloride (32.5 g, 200 mmol) in acetic acid (120 mL) was added portionwise over 2 h to a mixture of 6-bromo-9H-dipyrido[2,3-b;4',3'-d]pyrrole (5.0 g, 20 mmol) and sodium acetate (18.2 g, 221 mmol) in acetic acid (120 mL) at 100° C. The reaction mixture was cooled to ambient temperature and poured into saturated sodium metabisulfite solution (20% w/w, 400 mL). The resultant precipitate was collected by filtration and the solid was washed with water (50 mL) and diethyl ether (2×50 mL) then dried at 45° C. until constant weight was achieved, to afford the title compound as a grey solid (6.3 g, 83%). $^1$H NMR (DMSO-D$_6$, 300 MHz): 12.49 (s, 1H), 9.14 (d, J=2.1 Hz, 1H), 8.79 (d, J=2.1 Hz, 1H), 8.71 (s, 1H), 8.49 (s, 1H). LCMS (Method B): $R_T$=3.40 min, M+H$^+$=374/376.

Preparation of 3-Bromo-6-chloro-9H-dipyrido[2,3-b;4',3'-d]pyrrole

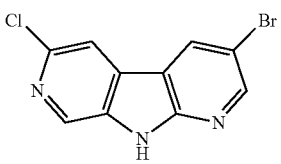

Step 1: 6-Chloro-4-iodo-pyridin-3-ylamine

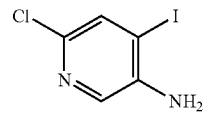

(6-Chloro-4-iodo-pyridin-3-yl)-carbamic acid tert-butyl ester (3.67 g, 10.3 mmol) was dissolved in DCM (32 mL) and TFA (8 mL) was added. The reaction mixture was stirred at ambient temperature for 2 h and then evaporated in vacuo. The resultant residue was treated with 5N aqueous sodium hydroxide solution (25 mL), diluted with water (100 mL) and extracted into ethyl acetate (2×100 mL). The combined organic layer was dried over anhydrous sodium sulfate, filtered and evaporated in vacuo to afford the title compound as yellow solid (2.37 g, 90%). $^1$H NMR (CD$_3$OD, 300 MHz): 7.80 (s, 1H), 7.60 (s, 1H), 4.14 (s, 2H). LCMS (Method B): $R_T$=3.00 min, M+H$^+$=255.

Step 2: 5-Bromo-6'-chloro-2-fluoro-[3,4']bipyridinyl-3'-ylamine

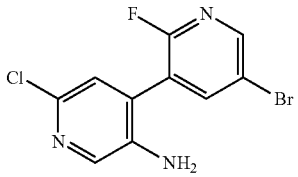 [SMILES: Nc1cnc(Cl)cc1-c1cc(Br)cnc1F]

A mixture of 6-chloro-4-iodo-pyridin-3-ylamine (2.37 g, 9.31 mmol), 2-fluoro-5-bromopyridine-3-boronic acid (2.64 g, 12.0 mmol) and 1,1'-[bis(diphenylphosphino)ferrocene] dichloropalladium(II) (0.76 g, 0.93 mmol) in acetonitrile (35 mL) and 1N aqueous potassium fluoride solution (35 mL) was degassed with nitrogen for 20 minutes. The reaction mixture was heated at 80° C. for 3 h, allowed to cool to ambient temperature then partitioned between ethyl acetate (100 mL) and water (75 mL). The organic layer was separated, dried over anhydrous sodium sulfate, filtered and evaporated in vacuo. The resultant solid residue was triturated using 1:1 DCM/methanol, collected by filtration, washed with diethyl ether and ethyl acetate to afford the title compound as a tan solid (1.37 g, 49%). The filtrate was concentrated under reduced pressure and the residue was purified by flash chromatography (silica, 80 g column, ISCO, 0-40% ethyl acetate in pentane) to afford further title compound as a brown solid (0.73 g, 26%). $^1$H NMR (DMSO-D$_6$, 300 MHz): 8.46 (dd, J=2.5, 1.3 Hz, 1H), 8.24 (dd, J=8.3, 2.5 Hz, 1H), 7.88 (s, 1H), 7.19 (s, 1H), 5.57 (s, 2H). LCMS (Method B): R$_T$=3.21 min, M+H$^+$=304.

Step 3: 3-Bromo-6-chloro-9H-dipyrido[2,3-b;4′,3′-d] pyrrole

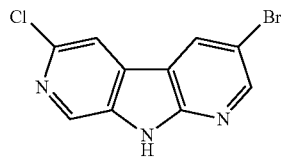 [SMILES: Clc1cc2c(cn1)[nH]c1ncc(Br)cc12]

A solution of 5-bromo-6′-chloro-2-fluoro-[3,4]bipyridinyl-3′-ylamine (2.21 g, 7.32 mmol) in THF (124 mL) was added dropwise over 10 minutes to sodium bis-(trimethylsilyl)amide (1N solution in THF, 14.6 mL, 14.6 mmol). The reaction mixture was stirred for 1 h at ambient temperature and then quenched by the addition of water (2 mL). The resultant brown solution was partitioned between ethyl acetate (75 mL) and brine (50 mL). An off-white solid precipitated and was collected by filtration to afford the title compound as a grey solid (1.01 g, 49%). $^1$H NMR (DMSO-D$_5$, 300 MHz): 9.01 (d, J=2.3 Hz, 1H), 8.73 (s, 1H), 8.70 (d, J=2.3 Hz, 1H), 8.35 (s, 1H). LCMS (Method B): R$_T$=3.33 min, M+H$^+$=284.

Preparation of
4-(4-Bromobenzyl)-1-methylpiperidine

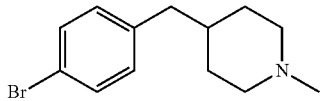

A mixture of 4-(4-bromobenzyl)-piperidine (290 mg, 1.14 mmol), formic acid (12 mL) and 37% aqueous formaldehyde (0.30 mL, 3.75 mmol) was divided into three portions. Each portion was heated at 150° C. for 5 minutes in a microwave reactor. The combined cold mixture was loaded onto a 5 g SCX-2 cartridge which was then washed with methanol (30 mL) then 2 N ammonia in methanol (50 mL). Concentration of the combined basic fractions in vacuo gave the title compound (300 mg, 98%) as a colourless oil. LCMS (Method B): R$_T$=2.18 min, M+H$^+$=268, 270.

Preparation of
4-(3-Bromo-5-methoxyphenoxy)-1-methylpiperidine

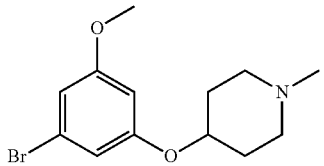 [SMILES: COc1cc(Br)cc(OC2CCN(C)CC2)c1]

To a suspension of sodium hydride (60% in mineral oil, 600 mg, 15.0 mmol) in DMF (20 mL) at 65° C. was slowly added a solution of 4-hydroxy-1-methylpiperidine (1.15 g, 10 mmol) in DMF (7.0 mL). After stirring for 30 minutes, a solution of 3-bromo-5-fluoroanisole (2.05 g, 10 mmol) in DMF (7.0 mL) was added and the reaction mixture was stirred at 65° C. for 24 h. The reaction mixture was allowed to cool to ambient temperature then was poured into water (200 mL) and extracted with ethyl acetate (2×100 mL). The combined organic layers were loaded onto a SCX-2 cartridge, which was then washed with acetonitrile then eluted with 2N ammonia in methanol. Concentration of the basic methanolic fractions in vacuo gave the title compound (1.5 g, 50%). $^1$H NMR (CDCl$_3$, 400 MHz): 6.65 (dd, J=2.2, 1.6 Hz, 1H), 6.63 (dd, J=2.3, 1.6 Hz, 1H), 6.37 (dd, J=2.3, 2.1 Hz, 1H), 4.29-4.21 (m, 1H), 3.75 (s, 3H), 2.70-2.61 (m, 2H), 2.31-2.21 (m, 5H), 2.01-1.93 (m, 2H), 1.86-1.75 (m, 2H). LCMS (Method B): R$_T$=2.1 min, M+H$^+$=300.

Preparation of
4-(3,5-Dibromophenoxy)-1-methylpiperidine

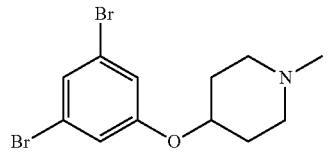 [SMILES: CN1CCC(Oc2cc(Br)cc(Br)c2)CC1]

To a suspension of sodium hydride (60% in mineral oil, 600 mg, 15.0 mmol) in DMF (20 mL), at 65° C., was slowly added a solution of 4-hydroxy-1-methylpiperidine (1.15 g, 10 mmol) in DMF (7.0 mL). After stirring for 1 h, a solution of 1,3-dibromo-5-fluorobenzene (1.26 mL, 10.0 mmol) in DMF (7.0 mL) was added and the reaction mixture was stirred at 65° C. for 3 days. The mixture was allowed to cool to ambient temperature then poured into water (100 mL) and extracted with ethyl acetate (150 mL). The organic layer was washed with water (100 mL) and loaded onto an SCX-2 cartridge, which was then washed with acetonitrile and eluted with 2N ammonia in methanol. Concentration of the basic methanolic fraction in vacuo gave the title compound (1.88 g, 54%). $^1$H NMR (CDCl$_3$, 400 MHz): 7.22 (t, J=1.6 Hz, 1H), 6.98 (d, J=1.7 Hz, 2H), 4.31-4.23 (m, 1H), 2.69-2.59 (m, 2H), 2.37-2.18 (m, 5H), 2.01-1.92 (m, 2H), 1.86-1.75 (m, 2H). LCMS (Method B): R$_T$=2.3 min, M+H$^+$=350.

Preparation of
1-(4-Bromo-2,6-difluorobenzyl)-piperidine

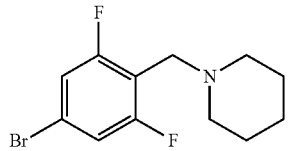 [SMILES: Fc1cc(Br)cc(F)c1CN1CCCCC1]

Methane sulfonyl chloride (0.38 mL, 4.93 mmol) was added dropwise to a cooled (0° C.) solution of (4-bromo-2,6-difluorophenyl)-methanol (1.00 g, 4.48 mmol) and triethylamine (0.75 mL, 5.38 mmol) in DCM (50 mL). The reaction mixture was allowed to warm to ambient temperature and stirred for 2 h. The mixture was diluted with DCM (30 mL)

and washed with water (20 mL). The organic phase was separated, dried over anhydrous sodium sulfate, filtered and evaporated in vacuo to afford a colourless oil. The oil was dissolved in acetonitrile (30 mL), piperidine (0.53 mL, 5.38 mmol) and potassium carbonate (0.93 g, 6.72 mmol) were added and the reaction mixture was heated at 50° C. for 90 minutes. The reaction mixture was allowed to cool to ambient temperature and the solid removed by filtration. The filtrate was evaporated in vacuo and the resultant residue purified by flash column chromatography (silica, 12 g column, ISCO, 0-40% ethyl acetate in cyclohexane) to afford the title compound as a colourless oil (1.23 g, 99%). $^1$H NMR (CDCl$_3$, 300 MHz): 7.07 (d, J=6.6 Hz, 2H), 3.62 (t, J=1.7 Hz, 2H), 2.41 (t, J=5.1 Hz, 4H), 1.59-1.50 (m, 4H), 1.42-1.33 (m, 2H). LCMS (Method B): R$_T$=1.67 min, M+H$^+$=290/292.

Preparation of
1-[1-(4-Bromophenyl)-1-methyl-ethyl]-piperidine

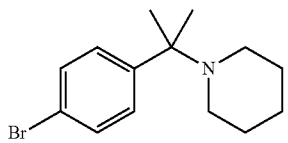 [SMILES: CC(C)(c1ccc(Br)cc1)N1CCCCC1]

In a three necked round bottom flask fitted with a condenser and nitrogen stream, was placed a small quantity of ground glass and magnesium turnings (190 mg, 7.40 mmol). The mixture was stirred for 30 minutes under vacuum then placed under nitrogen and iodine added (one small crystal), followed by the rapid addition of 1,4-dibromobenzene (2.43 g, 10.3 mmol) in 15 ml of anhydrous diethyl ether. The reaction mixture was then heated under reflux for 5 minutes. After this time, a solution of 1-(1-cyano-1-methylethyl)-piperidine (1.0 g, 6.60 mmol) in anhydrous THF was added dropwise resulting in the formation of a white precipitate. The reaction mixture was heated under reflux for 1.5 h, before cooling to ambient temperature. The resultant mixture was treated with saturated aqueous potassium carbonate solution and extracted with DCM. The organic extract was dried over magnesium sulfate and concentrated in vacuo. The crude residue was purified by column chromatography (silica, 12 g column, ISCO, 0-40% ethyl acetate in cyclohexane) to afford the title compound (200 mg, 95%) as a colourless oil. LCMS (Method B): R$_T$=1.99 min, M+H$^+$=282, 284.

Preparation of 1-(4-Bromobenzyl)-azetidine

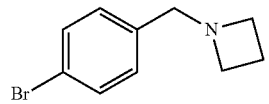 [SMILES: Brc1ccc(CN2CCC2)cc1]

A solution of 4-bromobenzyl bromide (1.00 g, 4.0 mmol) and triethylamine (0.84 ml, 6.0 mmol) in THF (20 mL) was stirred at ambient temperature for 10 minutes. Azetidine (0.54 ml, 8.0 mmol) was then added and a white precipitate resulted. The slurry was stirred at ambient temperature for 18 h then evaporated in vacuo. The resultant residue was partitioned between DCM and saturated aqueous sodium hydrogen carbonate, the organic phase was separated, dried over magnesium sulfate and concentrated in vacuo to afford the title compound (0.76 g, 3.40 mmol) as a colourless oil. $^1$H NMR (CDCl$_3$, 400 MHz): 7.42 (d, J=8.3 Hz, 2H), 7.15 (d, J=8.2 Hz, 2H), 3.50 (s, 2H), 3.19 (t, J=7.0 Hz, 4H), 2.08 (p, J=7.0 Hz, 2H).

Preparation of
1-(4-Bromobenzyl)-cis-2,6-dimethylpiperidine

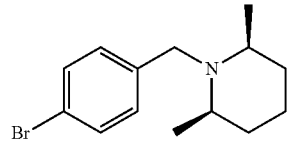 [SMILES: C[C@@H]1CCC[C@H](C)N1Cc1ccc(Br)cc1]

A mixture of 1-bromo-4-bromomethylbenzene (500 mg, 2.0 mmol), cis-2,6-dimethylpiperidine (0.30 mL, 2.2 mmol) and potassium carbonate (332 mg, 2.4 mmol) in acetonitrile (20 mL) was heated under reflux for 2 h. The reaction mixture was allowed to cool to ambient temperature, the solid removed by filtration and the filtrate evaporated in vacuo. The resultant residue was partitioned between ethyl acetate (100 mL) and water (25 mL). The organic phase was dried over anhydrous sodium sulfate, filtered and evaporated in vacuo to give the title compound as a pale brown oil (464 mg, 82%). $^1$H NMR (CDCl$_3$, 300 MHz): 7.40 (d, J=8.3 Hz, 2H), 7.27 (d, J=7.0 Hz, 2H), 3.71 (s, 2H), 2.56-2.36 (m, 2H), 1.68-1.61 (m, 1H), 1.61-1.47 (m, 2H), 1.33-1.24 (m, 3H), 1.01 (d, J=6.2 Hz, 6H). LCMS (Method B): R$_T$=0.8 min, M+H$^+$=282/284.

Preparation of
4-(4-Bromophenyl)-4-hydroxypiperidine-1-carboxylic acid tert-butyl ester

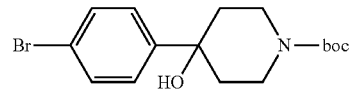

Triethylamine (3.69 mL, 26.3 mmol) was added to a solution of 4-(4-bromo-phenyl)-piperidin-4-ol (5.18 g, 20.2 mmol) and di-tert-butyl dicarbonate (5.30 g, 20.2 mmol) in DCM (60 mL). The resultant reaction mixture was stirred at ambient temperature for 18 h, then diluted with water (100 mL) and extracted into DCM (3×50 mL). The combined organic phase was concentrated in vacuo and the residue purified by flash chromatography (silica, 40 g column, ISCO, 0-100% ethyl acetate in cyclohexane) to afford the title compound as a white solid (7.03 g, 98%). $^1$H NMR (CDCl$_3$, 300 MHz): 7.49 (d, J=8.5 Hz, 2H), 7.35 (d, J=8.5 Hz, 2H), 4.04 (d, J=13.0 Hz, 2H), 3.29-3.15 (m, 2H), 1.96 (td, J=13.0, 5.0 Hz, 2H), 1.69 (dd, J=14.0, 2.5 Hz, 2H), 1.48 (s, 9H). LCMS (Method B): R$_T$=3.88 min.

Preparation of
4-(4-Bromophenyl)-4-methoxypiperidine-1-carboxylic acid tert-butyl ester

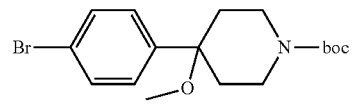

Sodium hydride (76 mg, 1.90 mmol) was added portionwise to a solution of 4-(4-bromophenyl)-4-hydroxypiperidine-1-carboxylic acid tert-butyl ester (519 mg, 1.46 mmol) in anhydrous THF (10 mL) at 0° C. After 1 h, methyl iodide (136 μL, 2.19 mmol) was added and the reaction mixture was allowed to warm to ambient temperature and stirred for 18 h. The reaction was quenched by the addition of water (10 mL), the organic layer was separated and the aqueous layer back-extracted with DCM (3×10 mL). The combined organic phase was concentrated in vacuo to afford the title compound (607 mg, quantitative). $^1$H NMR (CDCl$_3$, 400 MHz): 7.49 (d, J=8.5 Hz, 2H), 7.25 (d, J=8.5 Hz, 2H), 3.97 (d, J=13.0 Hz, 2H), 3.15 (t, J=13.0 Hz, 2H), 2.97 (s, 3H), 1.97 (d, J=13.5 Hz, 2H), 1.83-1.74 (m, 2H), 1.47 (s, 9H). LCMS (Method B): $R_T$=4.61 min.

Preparation of
4-(4-Bromophenyl)-4-fluoropiperidine-1-carboxylic
acid tert-butyl ester

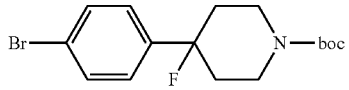

[Bis(2-Methoxyethyl)amino]sulfur trifluoride (2.1 mL, 11.4 mmol) was added to a stirred solution of 4-(4-bromophenyl)-4-hydroxypiperidine-1-carboxylic acid tert-butyl ester (810 mg, 2.28 mmol) in anhydrous DCM (25 mL), at −78° C. The reaction mixture was allowed to warm to ambient temperature and stirred for 72 h. The reaction mixture was quenched by the addition of saturated aqueous potassium carbonate (10 mL) and extracted into DCM (3×10 mL). The combined organic phase was concentrated in vacuo and the residue purified by flash chromatography (silica, 40 g column, ISCO, 0-100% ethyl acetate in cyclohexane) to afford the title compound as a colourless oil (738 mg, 91%). $^1$H NMR (CDCl$_3$, 300 MHz): 7.50 (d, J=8.5 Hz, 2H), 7.24 (d, J=8.5 Hz, 2H), 4.19-4.05 (m, 2H), 3.29-3.05 (m, 2H), 2.04-1.84 (m, 4H), 1.49 (s, 9H). LCMS (Method B): $R_T$=4.55 min.

Preparation of
1-(5-Bromothiophen-3-ylmethyl)-piperidine

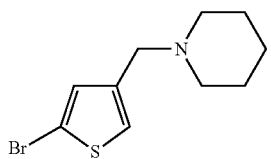 [SMILES: Brc1cc(CN2CCCCC2)cs1]

Step 1: 5-Bromothiophene-3-carboxylic acid

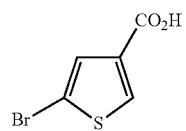

To a solution of thiophene-3-carboxylic acid (5.00 g, 39.0 mmol) in acetic acid (140 mL), was added dropwise, a solution of bromine (6.60 g, 40.0 mmol) in acetic acid (40 mL). The reaction mixture was stirred for 30 minutes and then poured into water. The resultant solid was collected by filtration to afford the title compound as a grey solid (2.07 g, 26%). LCMS (Method B): $R_T$=2.9 min, M+H$^+$=208.

Step 2:
(5-Bromothiophen-3-yl)-piperidin-1-yl-methanone

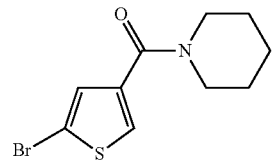 [SMILES: O=C(c1csc(Br)c1)N1CCCCC1]

To a solution of 5-bromothiophene-3-carboxylic acid (1.03 g, 5.00 mmol) in acetonitrile (10 mL), were added HATU (2.09 g, 5.50 mmol), DIPEA (2.6 mL, 15.0 mmol) and piperidine (1.0 mL, 10.0 mmol) and the reaction mixture was stirred at room temperature for 24 h. The reaction mixture was diluted with ethyl acetate (75 mL) and was washed with saturated aqueous citric acid (2×50 mL). The organic layer was concentrated in vacuo and the resultant residue was loaded onto an SCX-2 cartridge. Eluting with acetonitrile and evaporation of the organic fraction in vacuo afforded the title compound as an off-white solid (1.00 g, 73%). LCMS (Method B): $R_T$=3.3 min, M+H$^+$=274.

Step 3: 1-(5-Bromothiophen-3-ylmethyl)-piperidine

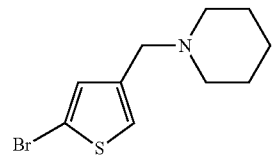

To a solution of (5-bromothiophen-3-yl)-piperidin-1-yl-methanone (907 mg, 3.30 mmol) in DCM (33 mL) was added tetrabutylammonium borohydride (2.54 g, 9.90 mmol) portionwise over 10 minutes. The reaction mixture was heated under reflux for 19 h then further tetrabutylammonium borohydride (2.54 mg, 9.90 mmol) was added to the reaction mixture, in four portions over 6 h. and then the reaction mixture was heated under reflux for 18 h. After this time the reaction mixture was partitioned between DCM (100 mL) and saturated aqueous sodium bicarbonate solution (100 mL). The organic layer was dried over sodium sulfate, the solvent was removed in vacuo and the residue was purified by flash chromatography (silica, 40 g column, ISCO, 0-50% ethyl acetate in cyclohexane) to afford an oil which solidified on standing to afford the title compound as a white solid (301 mg, 35%). $^1$H NMR (CDCl$_3$, 300 MHz):7.23 (d, J=1.7 Hz, 1H), 7.15 (d, J=1.7 Hz, 1H), 3.91 (s, 2H), 2.97-2.87 (m, 2H), 2.72-2.62 (m, 2H), 2.15-2.06 (m, 2H), 1.70-1.52 (m, 2H), 1.41-1.25 (m, 2H); LCMS (Method B): $R_T$=4.0 min, M+H$^+$=260.

Preparation of 1-(2-Bromothiazol-4-ylmethyl)-piperidine

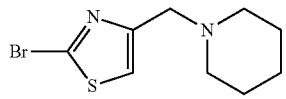

The title compound was prepared from (2-bromothiazol-4-yl)-methanol, following the procedure outlined above for 1-(4-bromo-2,6-difluoro-benzyl)-piperidine, to afford the title compound as a yellow oil. $^1$H NMR (CDCl$_3$, 300 MHz): 7.09 (s, 1H), 3.61 (d, J=0.9 Hz, 2H), 3.19 (t, J=5.4 Hz, 1H), 2.45 (t, J=5.1 Hz, 4H), 1.69-1.62 (m, 4H), 1.48-1.41 (m, 2H). LCMS (Method B): R$_T$=0.8 min, M+H$^+$=261/263.

Preparation of Trifluoromethanesulfonic acid 3,5-dimethoxy-4-piperidin-1-ylmethyl-phenyl ester

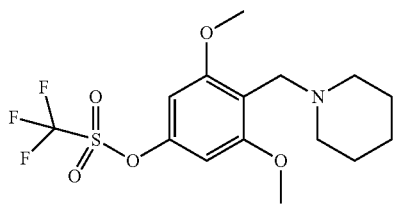 [SMILES: COc1cc(OS(=O)(=O)C(F)(F)F)cc(OC)c1CN1CCCCC1]

Step 1: 3,5-Dimethoxy-4-piperidin-1-ylmethyl-phenol

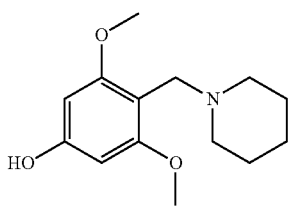 [SMILES: COc1cc(O)cc(OC)c1CN1CCCCC1]

A solution of 4-hydroxy-2,6-dimethoxybenzaldehyde (0.30 g, 1.65 mmol), piperidine (0.20 mL, 1.98 mmol) and acetic acid (0.47 mL, 8.25 mmol) in methanol (20 mL) was stirred for 20 minutes before addition of sodium cyanoborohydride (0.27 g, 4.30 mmol). The reaction mixture was allowed to stir at ambient temperature for 4 h then loaded onto a 10 g SCX-2 cartridge which was then washed with methanol (30 mL) and then eluted with 2N ammonia in methanol (50 mL). Concentration of the combined basic fractions in vacuo afforded the title compound (220 mg, 53%) as a white solid. $^1$H NMR (DMSO-D$_6$, 300 MHz): 9.39 (s, 1H), 6.03 (s, 2H), 3.66 (s, 6H), 3.30 (s, 2H), 2.32-2.24 (m, 4H), 1.42-1.35 (m, 4H), 1.34-1.26 (m, 2H). LCMS (Method B): R$_T$=1.90 min, M+H$^+$=252.

Step 2: Trifluoromethanesulfonic acid 3,5-dimethoxy-4-piperidin-1-ylmethyl-phenyl ester

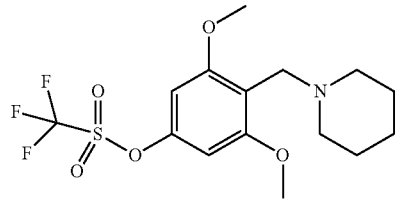 [SMILES: COc1cc(OS(=O)(=O)C(F)(F)F)cc(OC)c1CN1CCCCC1]

To a cooled solution (−20° C.) of 3,5-dimethoxy-4-piperidin-1-ylmethyl-phenol (0.22 g, 0.88 mmol) and pyridine (1.0 mL) in DCM (5 mL) was added trifluoromethanesulfonic anhydride (0.18 mL, 1.05 mmol) over 5 minutes. After complete addition, the reaction mixture was allowed to warm to ambient temperature and stirring was continued for 2 h. The resultant mixture was diluted with DCM (50 mL) and washed with water (20 mL). The organic phase was separated, dried over anhydrous sodium sulfate, filtered and evaporated in vacuo. The resultant residue was purified by flash column chromatography (silica, 5 g, SPE column, 0-50% ethyl acetate in cyclohexane) to afford an orange oil which crystallized on standing to yield the title compound (93 mg, 28%). $^1$H NMR (CDCl$_3$, 300 MHz): 6.44 (s, 2H), 3.81 (s, 6H), 3.60 (s, 2H), 2.46 (t, J=5.0 Hz, 4H), 1.56 (p, J=5.8 Hz, 4H), 1.43-1.36 (in, 2H). LCMS (Method B): R$_T$=2.77 min, M+H$^+$=384.

Preparation of 1-(4-Bromo-2-methoxybenzyl)-piperidine

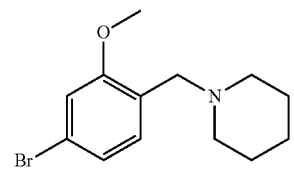

To a stirred solution of 4-bromo-1-chloromethyl-2-methoxybenzene (1.50 g, 6.36 mmol) in acetonitrile (64 mL) was added potassium carbonate (1.05 g, 6.36 mmol) and piperidine (0.63 mL, 6.36 mmol) then the reaction mixture was heated under reflux for 15 h. The reaction mixture was cooled to ambient temperature and then filtered, the filtrate was then concentrated under reduced pressure to afford a residue that was then loaded onto an SCX-2 cartridge (10 g) and eluted with 2N ammonia in methanol to afford the title compound (1.73 g, 96%). $^1$H NMR (CDCl$_3$, 300 MHz): 7.23 (d, J=8.1 Hz, 1H), 7.05 (dd, J=8.1, 1.9 Hz, 1H), 6.97 (d, J=1.9 Hz, 1H), 3.80 (s, 3H), 3.45 (s, 2H), 2.39 (t, J=5.0 Hz, 4H), 1.62-1.51 (m, 4H), 1.47-1.39 (m, 2H).

Preparation of 1-[2-Methoxy-4-(4,4,5,5-tetramethyl-[1,3,2]dioxaborolan-2-yl)-benzyl]-piperidine

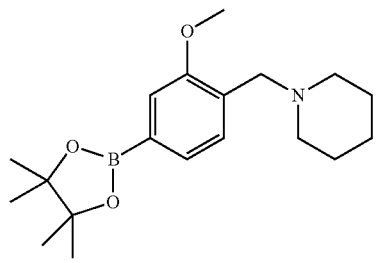 [SMILES: COc1cc(B2OC(C)(C)C(C)(C)O2)ccc1CN1CCCCC1]

A degassed mixture of 1-(4-bromo-2-methoxybenzyl)-piperidine (1.73 g, 6.1 mmol), bis(pinacolato)diborane (1.86 g, 7.3 mmol), 1,1'-[bis(diphenylphosphino)ferrocene]dichloropalladium(II) (249 mg, 0.31 mmol) and potassium acetate (1.79 mg, 18.3 mmol) in dioxane (31 mL) and DMSO (5 mL) was heated under microwave irradiation at 150° C. for 30 minutes. The cooled reaction mixture was diluted with ethyl acetate (100 mL) then filtered and the filtrate was washed with water (100 mL). The organic phase was dried over anhydrous sodium sulfate, filtered and evaporated in vacuo to afford the title compound as a beige solid (2.2 g, quantitative yield) that was used in the next step without further purification. $^1$H NMR (CDCl$_3$, 300 MHz): 7.42 (d, J=0.7 Hz, 2H), 7.29 (s, 1H), 3.87 (s, 3H), 3.85 (s, 2H), 2.72-2.64 (m, 4H), 1.74-1.65 (m, 4H), 1.50-1.39 (m, 2H), 1.35 (s, 12H).

Preparation of 2-Bromo-5-ethyl-4,5,6,7-tetrahydrothieno[3,2-c]pyridine

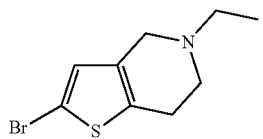

To a suspension of 2-bromo-4,5,6,7-tetrahydrothieno[3,2-c]pyridine (1.86 g, 8.50 mmol) in THF (30.6 mL) was added acetic acid (17 mL) then the reaction temperature was reduced to 0° C. and sodium borohydride (2.55 g, 42.5 mmol) was added in portions. After the addition was complete, the reaction mixture was heated at 60° C. for 1 h then the reaction mixture was cooled to ambient temperature and quenched by the addition of water. The resultant solution was partitioned between ethyl acetate (75 mL) and 1N sodium hydroxide solution (50 mL) and the layers separated. The organic phase was collected then dried over anhydrous sodium sulfate, filtered and evaporated in vacuo to give the title compound (1.87 g, 89%). $^1$H NMR (MeOD, 300 MHz): 6.78 (s, 1H), 3.50 (s, 2H), 2.81 (s, 4H), 2.62 (q, J=7.2 Hz, 2H), 1.17 (t, J=7.2 Hz, 3H).

Preparation of 4,4-Dimethyl-1-[4-(4,4,5,5-tetramethyl-[1,3,2]dioxaborolan-2-yl)-benzyl]-piperidine

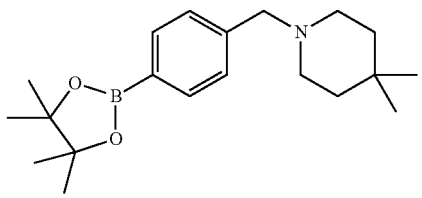

Step 1: 1-(4-Bromobenzyl)-4,4-dimethylpiperidine

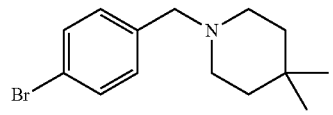 [SMILES: CC1(C)CCN(Cc2ccc(Br)cc2)CC1]

A mixture of 4-bromobenzyl bromide (500 mg, 2.0 mmol) and 4,4-dimethylpiperidine (249 mg, 2.2 mmol) and potassium carbonate (331 mg, 2.4 mmol) in acetonitrile (20 mL) was heated under reflux for 2 h. The reaction mixture was then cooled to ambient temperature and the reaction mixture concentrated under reduced pressure. The resultant oil was loaded onto an SCX-2 cartridge (10 g) and eluted with 2N ammonia in methanol to afford the title compound (323 mg, 57%). $^1$H NMR (CDCl$_3$, 300 MHz): 7.42 (d, J=8.31 Hz, 2H), 7.19 (d, J=8.24 Hz, 2H), 3.44 (s, 2H), 2.35 (t, J=5.44 Hz, 4H), 1.37 (t, J=5.60 Hz, 4H), 0.90 (s, 6H).

Step 2: 4,4-Dimethyl-1-[4-(4,4,5,5-tetramethyl-[1,3,2]dioxaborolan-2-yl)-benzyl]-piperidine

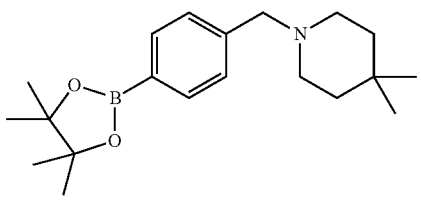

A degassed mixture of 1-(4-bromobenzyl)-4,4-dimethylpiperidine (320 mg, 1.1 mmol), bis(pinacolato)diborane (346 mg, 1.4 mmol), 1,1'-[bis(diphenylphosphino)ferrocene]dichloropalladium(II) (46.4 mg, 0.06 mmol) and potassium acetate (334 mg, 3.4 mmol) in dioxane (5.8 mL) and DMSO (0.6 mL) was heated under microwave irradiation at 150° C. for 30 minutes. The cooled reaction mixture was diluted with ethyl acetate (50 mL) then filtered and the filtrate was washed with water (75 mL). The organic phase was dried over anhydrous sodium sulfate, filtered and evaporated in vacuo to afford the title compound as a brown oil (264 mg, 71%) that was used in the next step without further purification. $^1$H NMR (CDCl$_3$, 300 MHz): 7.77 (d, J=7.8 Hz, 2H), 7.34 (d, J=7.7 Hz, 2H), 3.63 (s, 2H), 2.47 (t, J=5.3 Hz, 4H), 1.43 (t, J=5.6 Hz, 4H), 1.38-1.31 (m, 12H), 0.91 (s, 6H).

Preparation of (2S,6R)-2,6-Dimethyl-1-[4-(4,4,5,5-tetramethyl[1,3,2]dioxaborolan-2-yl)-benzyl]-piperidine

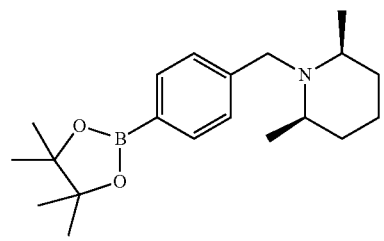 [SMILES: C[C@@H]1CCC[C@H](C)N1Cc1ccc(B2OC(C)(C)C(C)(C)O2)cc1]

A degassed mixture of (2S,6R)-1-(4-bromobenzyl)-2,6-dimethylpiperidine (1.70 g, 6.0 mmol), bis(pinacolato)diborane (1.83 g, 7.2 mmol), 1,1'-[bis(diphenylphosphino) ferrocene]dichloropalladium(II) (245 mg, 0.3 mmol) and potassium acetate (1.76 mg, 18.0 mmol) in dioxane (31 mL) and DMSO (4 mL) was heated under microwave irradiation at 150° C. for 30 minutes. The cooled reaction mixture was diluted with ethyl acetate (100 mL) then filtered and the filtrate was washed with water (100 mL). The organic phase was dried over anhydrous sodium sulfate, filtered and evaporated in vacuo to afford the title compound as a beige solid (1.54 g, 78%) that was used in the next step without further purification. $^1$H NMR (CDCl$_3$, 300 MHz): 7.75 (d, J=7.7 Hz, 2H), 7.39 (d, J=7.6 Hz, 2H), 3.88 (s, 2H), 2.58-2.25 (m, 2H), 1.51-1.70 (m, 4H), 1.43-1.21 (m, 14H), 1.10 (d, J=6.2 Hz, 6H).

Preparation of Trifluoromethanesulfonic acid 3-methoxy-4-piperidin-1-ylmethyl-phenylester

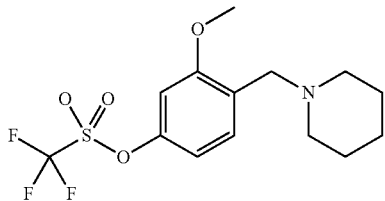

Step 1: 3-Methoxy-4-piperidin-1-ylmethylphenol

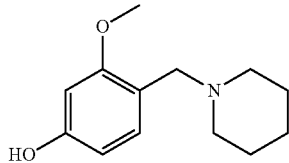 [SMILES: COc1cc(O)ccc1CN1CCCCC1]

To a pre-stirred solution of 4-hydroxy-2-methoxybenzaldehyde (1.02 g, 6.7 mmol), titanium isopropoxide (2.14 mL, 7.0 mmol) and piperidine (0.70 mL, 7.0 mmol) in DCM (20 mL) was added sodium triacetoxyborohydride (2.84 g, 13.4 mmol) in portions. After 3 h the reaction mixture was quenched by the addition of methanol (1.0 mL) and then the solvents were removed under reduced pressure to afford a residue. The resultant residue was then loaded onto an SCX-2 cartridge (10 g) and eluted with 2N ammonia in methanol to afford the title compound (456 mg, 30%). $^1$H NMR (CD$_3$OD, 300 MHz): 7.17 (d, J=8.3 Hz, 1H), 6.51 (d, J=2.3 Hz, 1H), 6.43 (dd, J=8.2, 2.2 Hz, 1H), 4.07 (s, 2H), 3.84 (s, 3H), 3.16-2.99 (m, 4H), 1.84-1.73 (m, 4H), 1.67-1.56 (m, 2H).

Step 2: Trifluoromethanesulfonic acid 3-methoxy-4-piperidin-1-ylmethyl-phenylester

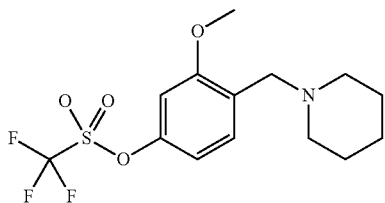

To a stirred solution of 3-methoxy-4-piperidin-1-ylmethylphenol (456 mg, 2.06 mmol) and diisopropylamine (0.77 mL, 4.54 mmol) in DCM (10 mL) at 0° C. was added N-phenyltriflamide (958 mg, 2.68 mmol). After the addition was complete the reaction mixture was allowed to warm to ambient temperature and then stirred overnight. The reaction mixture was concentrated under reduced pressure and then purified by flash chromatography (silica, 40 g column, ISCO, 0-10% methanol in DCM) to afford the title compound as a colourless oil (408 mg, 56%). NMR (CDCl$_3$, 300 MHz): 7.60 (d, J=8.4 Hz, 1H), 6.93 (dd, J=8.4, 2.4 Hz, 1H), 6.80 (d, J=2.4 Hz, 1H), 3.93 (s, 2H), 3.89 (s, 3H), 2.87-2.74 (m, 4H), 1.82-1.75 (m, 4H), 1.57-1.50 (m, 2H).

Preparation of 1-(4-Bromo-2,6-diethylbenzyl)-piperidine

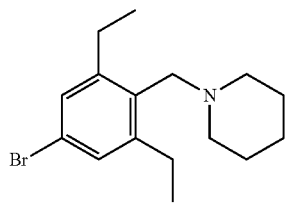 [SMILES: CCc1cc(Br)cc(CC)c1CN1CCCCC1]

Step 1: 4-Bromo-2,6-diethylbenzonitrile

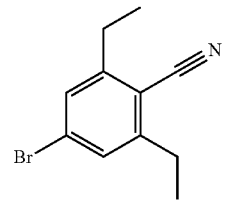

4-Bromo-2,6-diethylaniline (4.80 g, 21.0 mmol) was suspended in a mixture of water (25 mL) and concentrated hydrochloric acid (8.0 mL) then sonicated for 10 minutes. The resultant suspension was cooled to 0° C. and a solution of sodium nitrite (1.60 g, 23.1 mmol) in water (5 mL) was slowly added, maintaining the reaction temperature below 5° C. After 30 minutes, the reaction mixture was neutralised by the careful addition of sodium bicarbonate, then the resultant suspension was added in aliquots to a solution of copper (I) cyanide (2.26 g, 25.2 mmol) and potassium cyanide (3.43 g, 52.6 mmol) in water (25 mL) at 70° C. After complete addition, heating at 70° C. was continued for 1 h then the reaction mixture was cooled to ambient temperature. Water and DCM were added then the organic phase was collected, dried over anhydrous sodium sulfate and concentrated in vacuo to afford a brown residue that was purified by flash chromatography (silica, 80 g column, ISCO, 0-10% ethyl acetate in cyclohexane) to afford the title compound as an off-white solid (4.43 g, 88%). $^1$H NMR (DMSO-D$_6$, 300 MHz): 7.58 (s, 2H), 2.78 (q, J=7.6 Hz, 4H), 1.21 (t, J=7.6 Hz, 6H).

Step 2: 4-Bromo-2,6-diethylbenzylamine

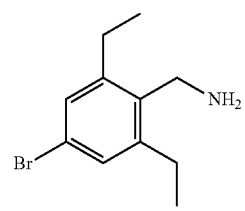

Under an inert atmosphere, lithium aluminum hydride (359 mg, 9.4 mmol) was suspended in anhydrous THF (9 mL) was cooled to 0° C. and then a solution of 4-bromo-2,6- diethylbenzonitrile (1.73 g, 7.36 mmol) in anhydrous THF (3 mL) was added dropwise. The reaction mixture was then allowed to warm to ambient temperature and stirring was continued for 20 h. Sodium sulfate decahydrate (6 g) was then added to quench the reaction and the resultant reaction mixture was filtered then the filtrate was then evaporated under reduced pressure. The resultant oil was purified by flash chromatography (silica, 50 g column, ISCO, 0-10% methanol in DCM) to afford the title compound as an orange oil (96 mg, 5%). $^1$H NMR (DMSO-D$_6$, 400 MHz): 7.18 (s, 2H), 3.68 (s, 2H), 2.73-2.64 (m, 4H), 2.52-2.48 (m, 2H), 1.19-1.11 (m, 6H).

Step 3: 1-(4-Bromo-2,6-diethylbenzyl)-piperidine

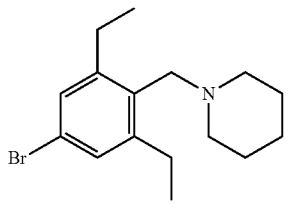 [SMILES: CCc1cc(Br)cc(CC)c1CN1CCCCC1]

4-Bromo-2,6-diethylbenzylamine (90 mg, 0.37 mmol), 1,5-dibromopentane (56 μL, 0.41 mmol) and potassium carbonate (206 mg, 1.5 mmol) were suspended in dioxane (5 mL) and heated at 100° C. overnight. The reaction mixture was then cooled to ambient temperature, the solid removed by filtration and the filtrate concentrated in vacuo to afford an orange oil. The resultant oil was purified by flash chromatography (silica, 12 g column, ISCO, 0-10% methanol in DCM) to afford the title compound as yellow oil (66 mg, 58%). NMR (CDCl$_3$, 300 MHz): 7.16 (s, 2H), 3.38 (s, 2H), 2.80-2.62 (m, 4H), 2.35 (s, 4H), 1.54-1.34 (m, 6H), 1.27-1.13 (m, 6H).

Preparation of Trifluoromethanesulfonic acid 3,5-dichloro-4-piperidin-1-yl methylphenyl ester

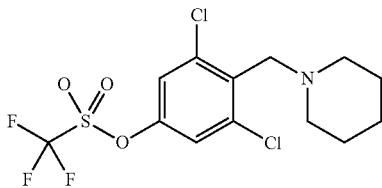

Step 1: 3,5-Dichloro-4-piperidin-1-ylmethylphenol

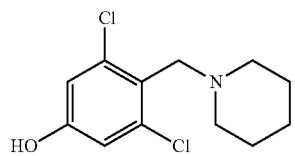 [SMILES: Oc1cc(Cl)c(CN2CCCCC2)c(Cl)c1]

To a pre-stirred solution of 2,6-dichloro-4-hydroxybenzaldehyde (1.88, 9.8 mmol) and piperidine (1.07 mL, 10.8 mmol) in DCM (40 mL) was added sodium triacetoxyborohydride (3.13 g, 14.8 mmol) in portions. After 14 h the reaction mixture was quenched by the addition of water (50 mL), the pH of the solution adjusted to 2 by the addition of hydrochloric acid and the solution washed with DCM (50 mL). The pH of the aqueous phase was then adjusted to 9 by the addition of saturated aqueous sodium carbonate and then the organic component was extracted with DCM (50 mL), dried over anhydrous sodium sulfate and evaporated under reduced pressure to afford the title compound as a beige solid (2.03 g, 80%) that was used without further purification. $^1$H NMR (CD$_3$OD, 300 MHz): 6.81-6.77 (m, 2H), 3.72 (s, 2H), 2.67-2.57 (m, 4H), 1.64-1.54 (m, 4H), 1.51-1.44 (m, 2H).

Step 2: Trifluoromethanesulfonic acid 3,5-dichloro-4-piperidin-1-ylmethylphenyl ester

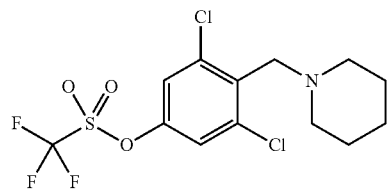

To a stirred solution of 3,5-dichloro-4-piperidin-1-ylmethylphenol (290 mg, 1.1 mmol) and pyridine (0.36 mL, 4.5 mmol) in DCM (10 mL) at −20° C. was added trifluoromethanesulfonyl chloride (0.38 mL, 2.2 mmol). After the addition was complete the reaction was allowed to warm to ambient temperature and stirred for 10 minutes. The mixture was diluted with DCM (20 mL), washed with water (10 mL). The organic phase was separated, dried over anhydrous sodium sulfate, filtered and evaporated in vacuo to afford a residue that was purified by flash chromatography (silica, 12 g column, ISCO, 0-100% ethyl acetate in cyclohexane) to afford the title compound as a colourless oil (334 mg, 76%). $^1$H NMR (CDCl$_3$, 300 MHz): 7.26 (s, 2H), 3.66 (s, 2H), 2.53-2.44 (m, 4H), 1.58-1.48 (m, 4H), 1.50-1.34 (m, 2H).

Preparation of Trifluoromethanesulfonic acid 3-chloro-5-methoxy-4-piperidin-1-ylmethyl-phenyl ester

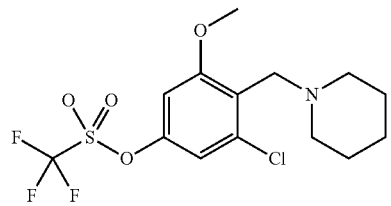

Step 1: 1-(2-Chloro-4,6-dimethoxybenzyl)-piperidine

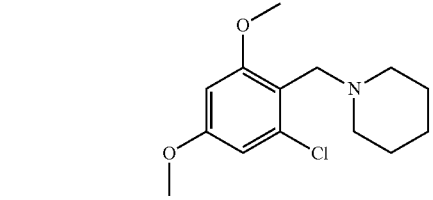 [SMILES: COc1cc(Cl)c(CN2CCCCC2)c(OC)c1]

To a pre-stirred solution of 2-chloro-4,6-dimethoxybenzaldehyde (2.7 g, 13.5 mmol) and piperidine (1.46 mL, 14.9 mmol) in DCM (50 mL) at 0° C. was added sodium triacetoxyborohydride (4.29 g, 20.0 mmol) in portions. The reaction mixture was then allowed to warm to ambient and stirred for an additional 3 h before the addition of water (50 mL). The pH of the aqueous phase was adjusted to 2 by the addition of hydrochloric acid and then washed with DCM (50 mL). The pH of the aqueous phase was then adjusted to 9 by the addition of saturated aqueous sodium carbonate and then the organic component was extracted into DCM (50 mL), dried over sodium sulfate and evaporated under reduced pressure to afford the title compound as a beige solid (3.3 g, 91%) that was used without further purification. $^1$H NMR (CDCl$_3$, 300 MHz): 6.60 (d, J=2.4 Hz, 1H), 6.43 (d, J=2.4 Hz, 1H), 4.35 (s, 2H), 3.90 (s, 3H), 3.83 (s, 3H), 3.6-2.57 (v br m, 4H), 2.29-1.88 (br m, 4H), 1.71-1.40 (br m, 2H).

Step 2:
3-Chloro-5-methoxy-4-piperidin-1-ylmethylphenol

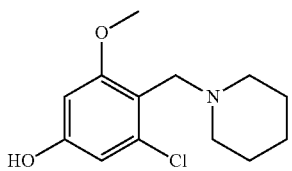

Hydroiodic acid (57% solution, 5 mL) was added to 1-(2-chloro-4,6-dimethoxybenzyl)-piperidine (360 mg, 1.3 mol) and the mixture heated at 60° C. for 2 h. The reaction mixture was cooled to ambient temperature, diluted with saturated aqueous sodium carbonate solution (20 mL) and extracted with DCM (3×30 mL). The combined organic layer was dried over anhydrous sodium sulfate, filtered and evaporated in vacuo to afford an beige solid that was then purified by flash chromatography (silica, 12 g column, ISCO, 0-15% (2N ammonia in methanol) in DCM) to afford the title compound as a white solid (277 mg, 88%). $^1$H NMR (CDCl$_3$, 400 MHz): 6.08 (d, J=2.2 Hz, 1H), 5.96 (d, J=2.2 Hz, 1H), 3.61 (s, 3H), 3.59 (s, 2H), 3.31 (br s, 1H), 2.74-2.64 (m, 4H), 1.70-1.62 (m, 4H), 1.60-1.43 (m, 2H).

Step 3: Trifluoromethanesulfonic acid 3-chloro-5-methoxy-4-piperidin-1-ylmethylphenyl ester

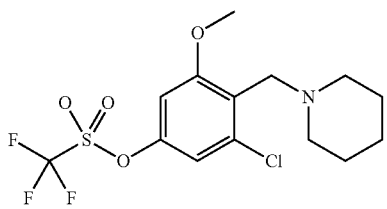

To a stirred solution of 3-chloro-5-methoxy-4-piperidin-1-ylmethylphenol (223 mg, 0.87 mmol) and pyridine (0.28 mL, 3.5 mmol) in DCM (10 mL) at −20° C. was added trifluoromethanesulfonyl chloride (0.29 mL, 1.7 mmol). After the addition was complete the reaction mixture was allowed to warm to ambient temperature then diluted with DCM (20 mL) then washed with water (10 mL). The organic phase was separated, dried over anhydrous sodium sulfate, filtered and evaporated in vacuo to afford an oil that was purified by flash chromatography (silica, 12 g column, ISCO, 0-100% ethyl acetate in cyclohexane) to afford the title compound as a red oil (341 mg, 73%). $^1$H NMR (CDCl$_3$, 300 MHz): 7.06 (d, J=2.3 Hz, 1H), 6.85 (d, J=2.3 Hz, 1H), 4.40 (s, 2H), 4.05 (s, 3H), 3.72-3.42 (m, 1H), 3.06-2.72 (m, 1H), 2.23-1.75 (m, 4H), 1.73-1.36 (m, 4H).

Preparation of Trifluoromethanesulfonic acid 3-methoxy-5-methyl-4-piperidin-1-ylmethylphenyl ester

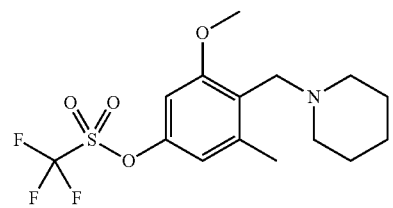 [SMILES: COc1cc(OS(=O)(=O)C(F)(F)F)cc(C)c1CN1CCCCC1]

Step 1: 1-[2-Methoxy-6-methyl-4-(tetrahydropyran-2-yloxy)-benzyl]-piperidine

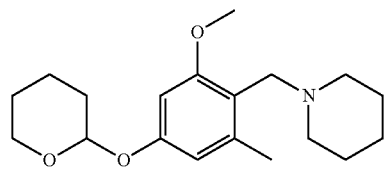 [SMILES: COc1cc(OC2CCCCO2)cc(C)c1CN1CCCCC1]

To a pre-stirred solution of 2-methoxy-6-methyl-4-(tetrahydropyran-2-yloxy)-benzaldehyde (2.14 g, 8.6 mmol) and piperidine (0.93 mL, 9.4 mmol) in DCM (35 mL) at 0° C. was added sodium triacetoxyborohydride (2.72 g, 12.8 mmol) in portions. The reaction mixture was allowed to warm to ambient temperature and then partitioned between water (30 mL) and ethyl acetate (75 mL). The organic phase was dried over anhydrous sodium sulfate, filtered and evaporated in vacuo to afford the title compound as a colourless oil (2.78 g, quantitative yield) that was used in the next step without further purification. $^1$H NMR (CDCl$_3$, 400 MHz): 6.51 (d, J=2.4 Hz, 1H), 6.45 (d, J=2.4 Hz, 1H), 5.40 (t, J=3.3 Hz, 1H), 3.98-3.88 (m, 1H), 3.76 (s, 3H), 3.64-3.55 (m, 1H), 3.39 (s, 2H), 2.42-2.27 (m, 7H), 2.07-1.93 (m, 1H), 1.90-1.77 (m, 2H), 1.75-1.52 (m, 3H), 1.54-1.44 (m, 4H), 1.43-1.34 (m, 2H).

Step 2:
3-Methoxy-5-methyl-4-piperidin-1-ylmethylphenol

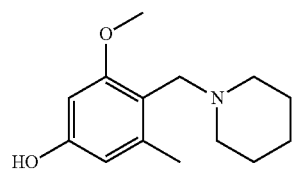 [SMILES: COc1cc(O)cc(C)c1CN1CCCCC1]

1N Hydrochloric acid (10 mL) was added to 1-[2-methoxy-6-methyl-4-(tetrahydropyran-2-yloxy)-benzyl]-piperidine (2.33 g, 7.3 mmol) in methanol (30 mL) and the reaction mixture was stirred at ambient temperature for 2 h. The pH of the solution was adjusted to 9 by the addition of saturated aqueous sodium carbonate solution (20 mL) and the aqueous phase was extracted with DCM (3×30 mL). The combined organic layer was dried over anhydrous sodium sulfate, filtered and evaporated in vacuo to afford a colourless oil. The resultant oil was purified by flash chromatography (silica, 12 g column, ISCO, 0-15% (2N ammonia in MeOH) in DCM) to afford the title compound as a white solid (570 mg, 33%). NMR (CDCl$_3$, 400 MHz): 6.14 (d, J=2.4 Hz, 1H), 5.99 (s, 1H), 3.68 (s, 3H), 3.49 (s, 2H), 2.56-2.46 (m, 4H), 2.25 (s, 3H), 1.65-1.51 (m, 4H), 1.48-1.36 (s, 2H).

Step 3: Trifluoromethanesulfonic acid 3-methoxy-5-methyl-4-piperidin-1-ylmethylphenyl ester

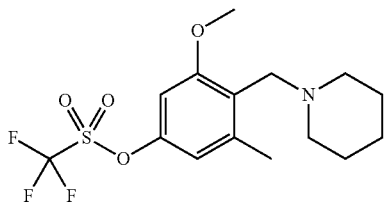 [SMILES: COc1cc(OS(=O)(=O)C(F)(F)F)cc(C)c1CN1CCCCC1]

To a stirred solution 3-methoxy-5-methyl-4-piperidin-1-ylmethylphenol (563 mg, 2.4 mmol) and pyridine (0.77 mL, 10.0 mmol) in DCM (20 mL) at 0° C. was added trifluoromethanesulfonyl chloride (0.81 mL, 4.8 mmol). After the addition was complete the reaction was allowed to warm to ambient temperature. The mixture was diluted with DCM (20 mL) and washed with water (10 mL). The organic phase was separated, dried over anhydrous sodium sulfate, filtered and evaporated in vacuo to afford an oil that was purified by flash chromatography (silica, 40 g column, ISCO, 0-100% ethyl acetate in cyclohexane) to afford the title compound as a red oil (698 mg, 58%). NMR (CDCl$_3$, 300 MHz): 6.82 (d, J=2.4 Hz, 1H), 6.73 (d, J=2.4 Hz, 1H), 4.28 (s, 2H), 3.96 (s, 3H), 3.67-3.35 (m, 1H), 2.99-2.66 (m, 1H), 2.47 (s, 3H), 2.21-1.75 (m, 4H), 1.73-1.35 (m, 4H).

Preparation of 1-(4-Bromo-2-fluorobenzyl)-piperidine

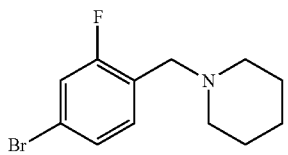 [SMILES: Fc1cc(Br)ccc1CN1CCCCC1]

To a pre-stirred solution of 4-bromo-2-fluorobenzaldehyde (1.82 g, 9.0 mmol) and piperidine (0.97 mL, 9.9 mmol) in DCM (40 mL) at 0° C. was added sodium triacetoxyborohydride (2.85 g, 13.4 mmol) in portions. The reaction mixture was allowed to warm to ambient temperature and stirred for an additional 14 h. The reaction was quenched by the addition of water (30 mL) and extracted with ethyl acetate (75 mL). The organic phase was separated, dried over anhydrous sodium sulfate, filtered and evaporated in vacuo to afford the title compound as a colourless oil (2.6 g, 84%) that was used in the next step without further purification. NMR (CDCl$_3$, 400 MHz): 7.33-7.17 (m, 3H), 3.49 (d, J=1.6 Hz, 2H), 2.43-2.33 (m, 4H), 1.61-1.53 (m, 4H), 1.46-1.38 (m, 2H).

Preparation of 1-(4-Bromo-2-ethoxybenzyl)-piperidine

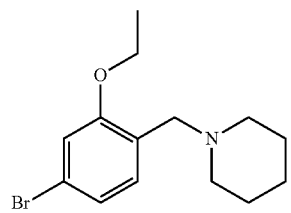 [SMILES: CCOc1cc(Br)ccc1CN1CCCCC1]

Sodium hydride (306 mg, 60%, 7.6 mmol) was added in portions to a solution of 1-(4-bromo-2-fluorobenzyl)-piperidine (520 mg, 1.9 mmol) and ethyl urethane (0.91 mL, 7.6 mmol) in dioxane (10 mL) under an atmosphere of nitrogen. The reaction mixture was then sonicated for 30 minutes until gas evolution ceased then heated at 140° C. overnight in a sealed tube. The reaction mixture was diluted with water and extracted with DCM (3×30 mL). The combined organic layer was dried over anhydrous sodium sulfate, filtered and evaporated in vacuo to afford a colourless oil that was then purified by flash chromatography (silica, 12 g column, ISCO, 0-10% methanol in DCM) to afford the title compound as a white solid (416 mg, 74%). $^1$H NMR (CDCl$_3$, 400 MHz): 7.23 (d, J=8.1 Hz, 1H), 7.03 (dd, J=8.1, 1.9 Hz, 1H), 6.95 (d, J=1.9 Hz, 1H), 3.99 (q, J=7.0 Hz, 2H), 3.47 (s, 2H), 2.46-2.35 (m, 4H), 1.61-1.53 (m, 4H), 1.45-1.36 (m, 5H).

Preparation of 1-(4-Bromo-2-trifluoromethoxybenzyl)-piperidine

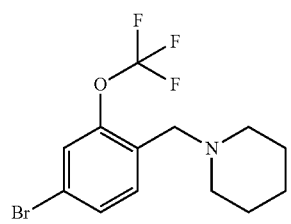 [SMILES: FC(F)(F)Oc1cc(Br)ccc1CN1CCCCC1]

To a pre-stirred solution of 4-bromo-2-trifluoromethoxybenzaldehyde (1.82 g, 9.0 mmol) and piperidine (0.97 mL, 9.9 mmol) in DCM (40 mL) at 0° C. was added sodium triacetoxyborohydride (2.85 g, 13.4 mmol) in portions. The reaction mixture was then allowed to warm to ambient temperature and stirred for an additional 14 h. The reaction was quenched by the addition of water (30 mL) and extracted into ethyl acetate (75 mL). The organic phase was separated, dried over anhydrous sodium sulfate, filtered and evaporated in vacuo to afford the title compound as a colourless oil (2.6 g, 84%) that was used in the next step without further purification. $^1$H NMR (CDCl$_3$, 300 MHz): 7.47 (d, J=8.2 Hz, 1H), 7.41 (d, J=1.9 Hz, 1H), 7.39-7.35 (m, 1H), 3.46 (s, 2H), 2.42-2.32 (m, 4H), 1.64-1.51 (m, 4H), 1.48-1.37 (m, 2H).

Preparation of 1-(3-Bromo-5-methoxybenzyl)-piperidine

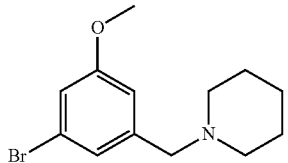 [SMILES: COc1cc(Br)cc(CN2CCCCC2)c1]

To a pre-stirred solution of 3-bromo-5-methoxybenzaldehyde (0.56 g, 2.61 mmol) and piperidine (0.29 mL, 3.93 mmol) in DCM (10 mL) at 0° C. was added sodium borohydride (197 mg, 5.22 mmol) in portions. The reaction mixture was allowed to warm to ambient temperature and stirred for an additional 2 h. The reaction was quenched by the addition of water (30 mL) and extracted into ethyl acetate (75 mL) then washed with water (50 mL) then the organic phase was dried over anhydrous sodium sulfate, filtered and evaporated in vacuo to afford the title compound as a colourless oil (510 mg, 69%) that was used in the next step without further purification. $^1$H NMR (CDCl$_3$, 400 MHz): 7.08-7.06 (m, 1H), 6.94-6.91 (m, 1H), 6.83-6.80 (s, 1H), 3.79 (s, 3H), 3.39 (s, 2H), 2.40-2.30 (s, 4H), 1.61-1.51 (m, 4H), 1.47-1.38 (m, 2H).

Preparation of 4-[1-(4-Bromobenzyl)-piperidin-4-yl]-morpholine

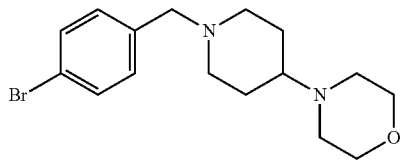 [SMILES: Brc1ccc(CN2CCC(N3CCOCC3)CC2)cc1]

4-Bromobenzyl bromide (0.5 g, 2.0 mmol) was stirred with 4-piperidin-4-yl-morpholine (0.67 g, 4.0 mmol) and triethylamine (0.42 mL, 3.0 mmol) in THF (20 mL) at ambient temperature for 28 h then a further 1.5 eq of triethylamine was added and stirring continued for 16 h. The mixture was diluted with water (50 mL) and extracted with ethyl acetate (50 mL). The organic phase was separated, dried over anhydrous sodium sulfate, filtered and evaporated in vacuo. The resultant residue was purified by flash chromatography (silica, 12 g column, ISCO, 0-100% ethyl acetate in cyclohexane then 0-10% (2N ammonia in methanol) in DCM) to afford the title compound as an off-white solid (0.62 g, 92%). $^1$H NMR (CDCl$_3$, 400 MHz): 7.44-7.40 (m, 2H), 7.21-7.15 (m, 2H), 3.74-3.69 (m, 4H), 3.42 (s, 2H), 2.93-2.85 (m, 2H), 2.56-2.50 (m, 4H), 2.22-2.13 (m, 1H), 2.00-1.91 (m, 2H), 1.82-1.74 (m, 2H), 1.59-1.47 (m, 2H).

Preparation of [1-(4-Bromobenzyl)-piperidin-4-yl]-dimethylamine

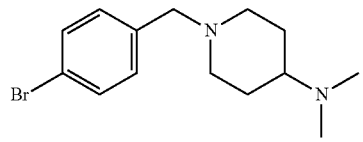 [SMILES: CN(C)C1CCN(Cc2ccc(Br)cc2)CC1]

4-Bromobenzyl bromide (0.5 g, 2.0 mmol) was stirred with 4-dimethylaminopiperidine (0.51 g, 4.0 mmol) and triethylamine (0.42 mL, 3.0 mmol) in THF (20 mL) at ambient temperature for 96 h. The mixture was diluted with water (50 mL) and extracted with ethyl acetate (50 mL). The organic phase was separated, dried over anhydrous sodium sulfate, filtered and evaporated in vacuo to afford the title compound (0.51 g, 86%). $^1$H NMR (CDCl$_3$, 400 MHz): 7.44-7.40 (m, 2H), 7.21-7.16 (m, 2H), 3.43 (s, 2H), 2.91-2.85 (m, 2H), 2.27 (s, 6H), 2.17-2.07 (m, 1H), 2.00-1.91 (m, 2H), 1.80-1.72 (m, 2H), 1.58-1.45 (m, 2H).

Preparation of 4-(4-Bromobenzyl)-2,2-dimethylmorpholine

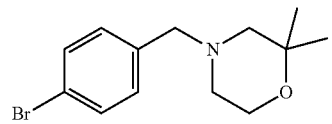 [SMILES: CC1(C)CN(Cc2ccc(Br)cc2)CCO1]

A mixture of 4-bromobenzyl bromide (1.5 g, 6.0 mmol), 2,2-dimethylmorpholine (0.69 g, 6.0 mmol) and potassium carbonate (0.99 g, 7.2 mmol) in acetonitrile (60 mL) was heated at 85° C. for 20 h. The mixture was allowed to cool to ambient temperature and the solid was removed by filtration and the filtrate evaporated. The resultant residue was dissolved in DCM/methanol and loaded onto a 20 g SCX-2 cartridge which was washed with methanol then 2N ammonia in methanol. Concentration of the combined basic fractions afforded the title compound (1.65 g, 97%) as an orange oil. $^1$H NMR (CDCl$_3$, 300 MHz): 7.44 (d, J=8.0 Hz, 2H), 7.22 (d, J=8.0 Hz, 2H), 3.75 (t, J=4.8 Hz, 2H), 3.39 (s, 2H), 2.37 (t, J=4.6 Hz, 2H), 2.16 (s, 2H), 1.23 (s, 6H).

Preparation of cis-4-(4-Bromo-2-ethoxybenzyl)-2,6-dimethylmorpholine

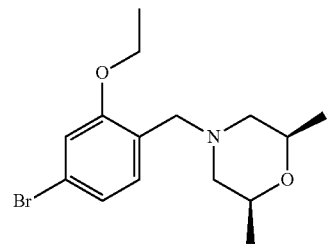

Step 1: cis-4-(4-Bromo-2-fluorobenzyl)-2,6-dimethylmorpholine

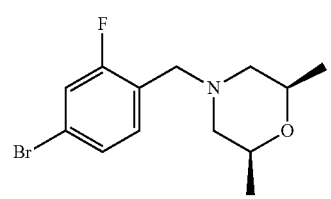 [SMILES: C[C@@H]1CN(Cc2ccc(Br)cc2F)C[C@H](C)O1]

To a suspension of 4-bromo-2-fluorobenzyl bromide (1.0 g, 3.7 mmol) and potassium carbonate (0.61 g, 4.4 mmol) in THF (37 mL) was added cis-2,6-dimethylmorpholine (0.43 g, 3.7 mmol). The reaction mixture was heated under reflux for 6 h and then cooled, the solid removed by filtration and the filtrate was evaporated. The resultant residue was loaded onto a 10 g SCX-2 cartridge which was washed with methanol then 2N ammonia in methanol. Concentration of the combined basic fractions in vacuo afforded the title compound (76 mg, 7%). $^1$H NMR (CDCl$_3$, 300 MHz): 7.28-7.19 (m, 3H), 3.73-3.59 (m, 2H), 3.49 (d, J=1.5 Hz, 2H), 2.71-2.64 (m, 2H), 1.86-1.73 (m, 2H), 1.14 (d, J=6.3 Hz, 6H). LCMS (Method G): $R_T$=2.84 min, M+H$^+$=302.

Step 2: cis-4-(4-Bromo-2-ethoxybenzyl)-2,6-dimethylmorpholine

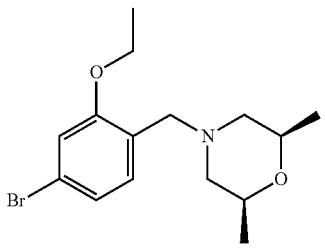 [SMILES: CCOc1cc(Br)ccc1CN1C[C@@H](C)O[C@@H](C)C1]

To a solution of cis 4-(4-bromo-2-fluorobenzyl)-2,6-dimethylmorpholine (0.76 g, 2.5 mmol) in 1,4-dioxane (7.5 mL) under nitrogen was added ethyl urethane (1.2 mL, 10.0 mmol) followed by portionwise addition of sodium hydride (60% dispersion in mineral oil, 0.40 g, 10.0 mmol). The reaction mixture was heated at 100° C. for 24 h then partitioned between DCM and water and the phases were separated. The aqueous phase was further extracted with DCM and the combined organic layers were dried over sodium sulfate, filtered and evaporated. The residue was purified by flash chromatography (silica, 80 g column, ISCO, 0-100% ethyl acetate in pentane) to afford the title compound (0.114 g, 14%). $^1$H NMR (CD$_3$OD and CDCl$_3$, 300 MHz): 7.22 (d, J=8.0 Hz, 1H), 7.05 (dd, J=8.1, 1.9 Hz, 1H), 6.97 (d, J=1.9 Hz, 1H), 4.01 (q, J=7.0 Hz, 2H), 3.75-3.62 (m, 2H), 3.47 (s, 2H), 2.75-2.66 (m, 2H), 1.86-1.76 (m, 2H), 1.41 (t, J=7.0 Hz, 3H), 1.14 (d, J=6.3 Hz, 6H). LCMS (Method G): $R_T$=3.24 min, M+H$^+$=328.

Preparation of 2-Bromo-4,5,6,7-tetrahydrobenzo[b]thiophene

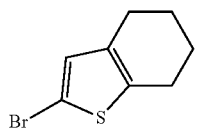

Step 1: 4,5,6,7-Tetrahydrobenzo[b]thiophene

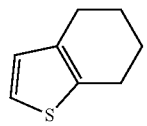

Aluminium trichloride (0.61 g, 4.60 mmol) in anhydrous diethyl ether (5 mL) was placed under an atmosphere of argon and lithium aluminium hydride (1M in diethyl ether, 4.6 mL, 4.60 mmol) was added dropwise. The resultant solution was stirred for 2 minutes and then a solution of 6,7-dihydro-4-benzo[b]thiophen-4-one (0.59 g, 3.83 mmol) in diethyl ether (10 mL) was added dropwise. The reaction mixture was stirred at ambient temperature for 4.5 h then was quenched with water (5 mL) followed by 6M sulfuric acid (10 mL) before being extracted into diethyl ether (4×15 mL). The combined organic phase was washed with water (20 mL) and brine, dried over sodium sulfate, filtered and evaporated to afford the title compound (0.49 g, 91%). $^1$H NMR (CDCl$_3$, 300 MHz): 7.04 (d, J=5.2 Hz, 1H), 6.75 (d, J=5.1 Hz, 1H), 2.83-2.72 (m, 2H), 2.67-2.59 (m, 2H), 1.89-1.74 (m, 4H).

Step 2: 2-Bromo-4,5,6,7-tetrahydrobenzo[b]thiophene

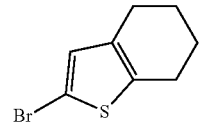

4,5,6,7-Tetrahydrobenzo[b]thiophene (0.252 g, 1.79 mmol) was dissolved in chloroform (10 mL), cooled to 0° C. and N-bromosuccinimide (0.334 g, 1.88 mmol) was added. The reaction mixture was stirred at 0° C. for 1 h then at ambient temperature for 1.75 h and then heated at 40° C. for a further 4 h. The reaction mixture was cooled to room temperature, concentrated in vacuo and the residue diluted with water and extracted with diethyl ether (4×10 mL). The combined organic phase was washed with water and brine, dried over sodium sulfate, filtered and evaporated to afford the title compound (0.35 g, 88%) as a brown oil. NMR (CDCl$_3$, 300 MHz): 6.69 (s, 1H), 2.73-2.59 (m, 2H), 2.58-2.49 (m, 2H), 1.88-1.70 (m, 4H).

Preparation of 6-(4-Bromobenzyl)-2-oxa-6-aza-spiro[3.3]heptane

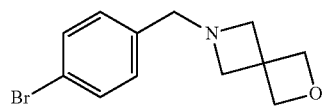

A mixture of 2-oxa-6-aza-spiro[3.3]heptane (~3.72 mmol), 4-bromobenzyl bromide (0.39 g, 1.54 mmol), potassium carbonate (0.64, 4.63 mmol) and sodium iodide (11 mg, 0.08 mmol) in THF (10 mL) was stirred at ambient temperature for 16 h. The solid was removed by filtration, washed with THF and the combined filtrate was evaporated. The resultant residue was purified by flash chromatography (silica, 12 g column, ISCO, 0-100% ethyl acetate in pentane then 10% methanol in DCM) to afford the title compound (0.28 g, 68%) as a viscous oil which crystallised on standing to a pale yellow solid. $^1$H NMR (CDCl$_3$, 300 MHz): 7.46-7.40 (m, 2H), 7.15-7.09 (m, 2H), 4.73 (s, 4H), 3.48 (s, 2H), 3.35 (s, 4H).

Preparation of
1-[2-(4-Bromophenyl)-ethyl]-piperidine

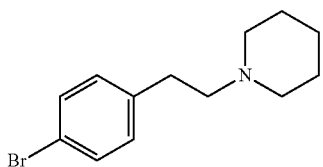 [SMILES: Brc1ccc(CCN2CCCCC2)cc1]

Methanesulfonyl chloride (0.43 mL, 5.47 mmol) was added to a solution of 2-(4-bromophenyl)-ethanol (1.0 g, 4.97 mmol) and triethylamine (0.84 mL, 5.96 mmol) in DCM (20 mL) at 0° C. The reaction mixture was stirred at 0° C. for 15 minutes then at ambient temperature for 2 h. The reaction mixture was partitioned between water and DCM and the organic phase was dried over sodium sulfate, filtered and evaporated to give a colourless oil. The resultant residue was dissolved in acetonitrile (10 mL), piperidine (0.491 mL, 4.97 mmol) and potassium carbonate (0.823 g, 5.96 mmol) were added and the reaction mixture was heated at 70° C. for 2.5 h. The reaction mixture was allowed to cool to ambient temperature then partitioned between ethyl acetate and water. The organic phase was dried over sodium sulfate, filtered and evaporated and the resultant residue dissolved in methanol and loaded onto a 10 g SCX-2 cartridge. The column was washed with methanol then eluted with 2N ammonia in methanol and the basic fractions were evaporated to afford the title compound (1.27 g, 95%) as a colourless oil. $^1$H NMR (CDCl$_3$, 300 MHz): 7.41-7.36 (m, 2H), 7.10-7.04 (m, 2H), 2.79-2.71 (m, 2H), 2.54-2.40 (m, 6H), 1.66-1.56 (m, 4H), 1.50-1.40 (m, 2H).

Preparation of
1-(4-Bromobenzyl)-3-methyl-piperidin-3-ol

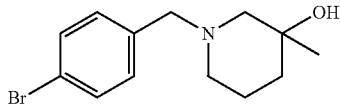 [SMILES: CC1(O)CCCN(Cc2ccc(Br)cc2)C1]

A mixture of 4-bromobenzyl bromide (0.50 g, 2.0 mmol), triethylamine (0.42 mL, 3.0 mmol) and 3-methyl-piperidin-3-ol (0.46 g, 4.0 mmol) in THF (20 mL) was stirred at ambient temperature for 16 h. The reaction mixture was evaporated and the resultant residue diluted with saturated aqueous sodium bicarbonate solution and extracted with ethyl acetate (2×50 mL). The combined organic layer was dried over sodium sulfate, filtered and evaporated to afford the title compound (0.50 g, 88%). $^1$H NMR (CDCl$_3$, 300 MHz): 7.49-7.43 (m, 2H), 7.23-7.15 (m, 2H), 3.78 (s, 2H), 3.69-3.59 (m, 2H), 2.63-2.51 (m, 2H), 2.14 (br s, 1H), 1.77-1.49 (m, 4H), 1.15 (s, 3H).

Preparation of
1-(4-Bromobenzyl)-4-methoxy-4-methylpiperidine

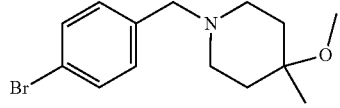 [SMILES: COC1(C)CCN(Cc2ccc(Br)cc2)CC1]

Step 1: 4-Hydroxy-4-methylpiperidine-1-carboxylic acid tert-butyl ester

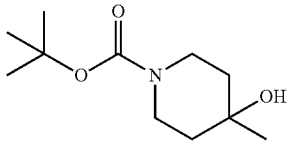

To a solution of 4-oxo-piperidine-1-carboxylic acid tert-butyl ester (2.0 g, 10.05 mmol) in diethyl ether (20 mL) at −25 to −30° C. was added methyl magnesium bromide (3M in diethyl ether, 3.35 mL, 10.05 mmol) dropwise under argon. The reaction mixture was allowed to warm to room temperature and stirred for 2 h. Water (20 mL) was then added dropwise, followed by saturated ammonium chloride (20 mL) and the ether layer was separated. The aqueous phase was further extracted with ether (50 mL) and the combined organic layer was dried over sodium sulfate, filtered and evaporated to afford the title compound (2.09 g, 97%). $^1$H NMR (CDCl$_3$, 300 MHz): 3.76-3.62 (m, 2H), 3.30-3.13 (m, 2H), 2.48-2.39 (m, 1H), 1.57-1.51 (m, 4H), 1.46 (s, 9H), 1.27 (s, 3H).

Step 2: 4-Methoxy-4-methylpiperidine

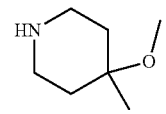

A suspension of sodium hydride (60% dispersion in mineral oil, 0.44 g, 11.66 mmol) in DMF (20 mL) was cooled to 0° C. then 4-hydroxy-4-methylpiperidine-1-carboxylic acid tert-butyl ester (2.09 g, 9.72 mmol) in DMF (5 mL) was added. The reaction mixture was stirred at room temperature for 1 h then sodium iodide (3.03 mL, 48.6 mmol) was added and stirring continued at room temperature for 16 h then heated at 70° C. for 16 h. The reaction mixture was allowed to cool to room temperature and ice-cold brine was added before the mixture was extracted with ethyl acetate (2×100 mL). The combined organic phase was dried over sodium sulfate, filtered and evaporated and the resultant residue was purified by flash chromatography (silica, Biotage 50 g column, 0-20% ethyl acetate in cyclohexane) to afford a colourless oil (0.94 g). The resultant oil was dissolved in DCM (5 mL) and TFA (5 mL) and stirred at ambient temperature for 2 h. The reaction mixture was loaded onto an SCX-2 cartridge which was washed with acetonitrile and methanol then eluted with 2N ammonia in methanol. The basic methanol fractions were evaporated to afford the title compound (0.50 g, 40%) $^1$H NMR (CDCl$_3$, 300 MHz): 3.19 (s, 3H), 2.96-2.85 (m, 2H), 2.81-2.70 (m, 2H), 1.79-1.66 (m, 2H), 1.51-1.38 (m, 2H), 1.15 (s, 3H) plus 1 exchangeable not observed.

Step 3:
1-(4-Bromobenzyl)-4-methoxy-4-methylpiperidine

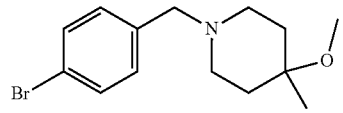

A mixture of 4-bromobenzyl bromide (0.44 g, 1.74 mmol), triethylamine (0.37 mL, 2.61 mmol) and 4-methoxy-4-methylpiperidine (0.45 g, 3.49 mmol) in THF (10 mL) was stirred at ambient temperature for 16 h. The solvent was evaporated and the resultant residue was diluted with saturated aqueous sodium bicarbonate solution and extracted with ethyl acetate (2×50 mL). The combined organic layer was dried over sodium sulfate, filtered and evaporated to afford the title compound as a yellow oil (0.50 g, 96%). $^1$H NMR (CDCl$_3$, 300 MHz): 7.45-7.39 (m, 2H), 7.22-7.17 (m, 2H), 3.44 (s, 2H), 3.17 (s, 3H), 2.52-2.42 (m, 2H), 2.36-2.25 (m, 2H), 1.79-1.70 (m, 2H), 1.59-1.47 (m, 2H), 1.13 (s, 3H).

Preparation of 4-(4-Bromobenzyl)-thiomorpholine

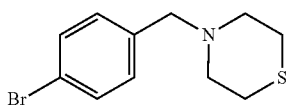 [SMILES: Brc1ccc(CN2CCSCC2)cc1]

A mixture of 4-bromobenzyl bromide (1.0 g, 4.0 mmol), triethylamine (0.84 mL, 6.0 mmol) and thiomorpholine (0.82 mL, 8.0 mmol) in THF (10 mL) was stirred at ambient temperature for 16 h. The solvent was evaporated and the resultant residue diluted with saturated aqueous sodium bicarbonate solution and extracted with ethyl acetate (2×50 mL). The combined organic layer was dried over sodium sulfate, filtered and evaporated to afford the title compound as an off-white solid (1.13 g, quantitative yield). $^1$H NMR (CDCl$_3$, 300 MHz): 7.46-7.40 (m, 2H), 7.21-7.16 (m, 2H), 3.45 (s, 2H), 3.15-3.09 (m, 1H), 2.76-2.60 (m, 6H), 2.62-2.57 (m, 1H).

Preparation of 4-(4-Bromobenzyl)-thiomorpholine 1,1-dioxide

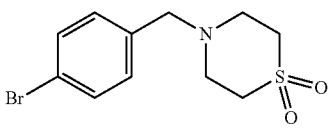 [SMILES: O=S1(=O)CCN(Cc2ccc(Br)cc2)CC1]

A mixture of 4-bromobenzyl bromide (1.0 g, 4.0 mmol), triethylamine (0.84 mL, 6.0 mmol) and thiomorpholine 1,1-dioxide (1.09 g, 8.0 mmol) in THF (10 mL) was stirred at ambient temperature for 16 h. The solvent was evaporated and the resultant residue diluted with saturated aqueous sodium bicarbonate solution and extracted with ethyl acetate (2×50 mL). The combined organic layer was dried over sodium sulfate, filtered and evaporated to afford the title compound (0.90 g, 74%). $^1$H NMR (CDCl$_3$, 300 MHz): 7.50-7.44 (m, 2H), 7.22-7.16 (m, 2H), 3.60 (s, 2H), 3.09-3.02 (m, 4H), 3.00-2.94 (m, 4H).

Preparation of 4-(4-Bromobenzyl)-thiomorpholine 1-oxide

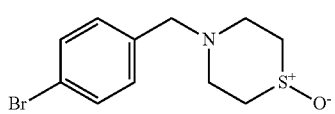 [SMILES: [O-][S+]1CCN(Cc2ccc(Br)cc2)CC1]

A mixture of 4-(4-bromobenzyl)-thiomorpholine (0.20 g, 0.735 mmol) was dissolved in DCM (10 mL) under a nitrogen atmosphere and m-chloroperbenzoic acid (0.13 g, 0.74 mmol) was added portionwise. The reaction mixture was stirred at room temperature for 1 h then purified by flash chromatography (silica, Biotage 50 g column, 0-75% (10% methanol in DCM)) to afford the title compound (0.125 g, 59%). $^1$H NMR (DMSO-D$_6$, 400 MHz): 7.55-7.49 (m, 2H), 7.31-7.25 (m, 2H), 3.53 (s, 2H), 2.92-2.80 (m, 4H), 2.78-2.65 (m, 2H), 2.64-2.54 (m, 2H). LCMS (Method G): R$_T$=2.66 min, M+H$^+$=289.

Preparation of 4-(4-Bromobenzyl)-piperazin-2-one

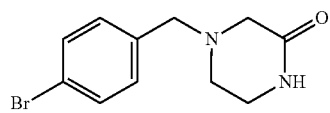 [SMILES: O=C1CN(Cc2ccc(Br)cc2)CCN1]

A mixture of 4-bromobenzyl bromide (1.0 g, 4.0 mmol), triethylamine (0.84 mL, 6.0 mmol) and piperazin-2-one (0.81 g, 8.0 mmol) in THF (20 mL) was stirred at ambient temperature for 16 h. The solvent was evaporated and the resultant residue diluted with saturated aqueous sodium bicarbonate solution and extracted with ethyl acetate (2×50 mL). The combined organic layer was dried over sodium sulfate, filtered and evaporated to afford the title compound (1.0 g, 93%). $^1$H NMR (CDCl$_3$, 300 MHz): δ 7.49-7.43 (m, 2H); 7.24-7.16 (m, 2H); 6.20 (s, 1H); 3.53 (s, 2H); 3.38-3.32 (m, 2H); 3.15 (s, 2H); 2.66-2.59 (m, 2H).). LCMS (Method G): R$_T$=2.54 min, M−H$^+$=268.

Preparation of (4-Bromobenzyl)-diethylamine

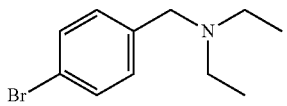

A mixture of 4-bromobenzyl bromide (1.0 g, 4.0 mmol), triethylamine (0.84 mL, 6.0 mmol) and diethylamine (0.84 mL, 8.0 mmol) in THF (20 mL) was stirred at ambient temperature for 16 h. The solvent was evaporated and the resultant residue diluted with saturated aqueous sodium bicarbonate solution and extracted with ethyl acetate (2×50 mL). The combined organic layer was dried over sodium sulfate, filtered and evaporated to afford the title compound (0.85 g, 88%). $^1$H NMR (CDCl$_3$, 300 MHz): 7.45-7.38 (m, 2H), 7.27-7.18 (m, 2H), 3.50 (s, 2H), 2.50 (q, J=7.1 Hz, 4H), 1.03 (t, J=7.1 Hz, 6H). LCMS (Method G): R$_T$=1.98 min, M−H$^+$=242.

Preparation of (S)-1-(4-Bromobenzyl)-piperidin-3-ol

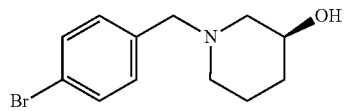 [SMILES: O[C@H]1CCCN(Cc2ccc(Br)cc2)C1]

A mixture of 4-bromobenzyl bromide (1.0 g, 4.0 mmol), triethylamine (0.84 mL, 6.0 mmol) and (S)-3-methyl-piperidin-3-ol (1.11 g, 8.0 mmol) in THF (20 mL) was stirred at ambient temperature for 16 h. The solvent was evaporated and the resultant residue diluted with saturated aqueous sodium bicarbonate solution and extracted with ethyl acetate (2×50 mL). The combined organic layer was dried over sodium sulfate, filtered and evaporated. The resultant residue was purified by flash chromatography (silica, Biotage 50 g column, 50-100% ethyl acetate in cyclohexane) to afford the title compound (0.8 g, 74%). $^1$H NMR (CDCl$_3$, 300 MHz): 7.46-7.40 (m, 2H), 7.21-7.14 (m, 2H), 3.85-3.76 (m, 1H), 3.45 (s, 2H), 2.45 (s, 3H), 2.29-2.16 (m, 1H), 1.86-1.70 (m, 1H), 1.67-1.45 (m, 3H) plus 1 exchangeable not observed. LCMS (Method G): R$_T$=1.42 min, M+H$^+$=270.

Preparation of (R)-1(4-Bromobenzyl)-piperidin-3-ol

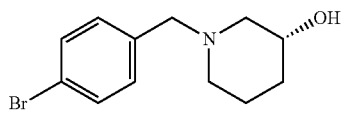 [SMILES: O[C@@H]1CCCN(Cc2ccc(Br)cc2)C1]

A mixture of 4-bromobenzyl bromide (1.0 g, 4.0 mmol), triethylamine (0.84 mL, 6.0 mmol) and (R)-3-methyl-piperidin-3-ol (1.11 g, 8.0 mmol) in THF (20 mL) was stirred at ambient temperature for 16 h. The solvent was evaporated and the resultant residue diluted with saturated aqueous sodium bicarbonate solution and extracted with ethyl acetate (2×50 mL). The combined organic layer was dried over sodium sulfate, filtered and evaporated. The material was purified by flash chromatography (silica, Biotage 50 g column, 50-100% ethyl acetate in cyclohexane) to afford the title compound (0.75 g, 69%). $^1$H NMR (CDCl$_3$, 300 MHz): 7.46-7.40 (m, 2H), 7.21-7.14 (m, 2,H), 3.85-3.76 (m, 1H), 3.45 (s, 2H), 2.45 (s, 3H), 2.29-2.16 (m, 1H), 1.86-1.70 (m, 1H) 1.67-1.45 (m, 3H) plus 1 exchangeable not observed. LCMS (Method G): R$_T$=2.00 min, M+H$^+$=270.

Preparation of 4-(3-Bromophenyl)-1-methyl-piperidine

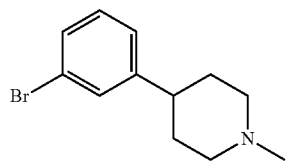

A mixture of 4-(3-bromophenyl)-1-N-Boc piperidine (430 mg, 1.26 mmol), formic acid (5 mL) and formaldehyde (0.5 mL) was heated under microwave irradiation at 150° C. for 10 minutes. The cooled reaction mixture was loaded onto a 70 g SCX-2 cartridge which was washed with methanol (200 mL) and then eluted with 2N ammonia in methanol (200 mL). Concentration of the combined basic fractions in vacuo afforded the title compound (318 mg, 99%) as a brown oil. $^1$H NMR (CDCl$_3$, 300 MHz): 7.38-7.36 (m, 1H); 7.35-7.29 (m, 1H); 7.17-7.14 (m, 2H); 3.03-2.92 (m, 2H); 2.52-2.37 (m, 1H); 2.32 (s, 3H); 2.10-1.99 (m, 2H); 1.87-1.69 (m, 4H).

Preparation of 3-(4-Bromophenyl)-3-hydroxypiperidine-1-carboxylic acid tert-butyl ester

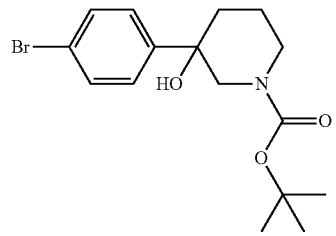 [SMILES: CC(C)(C)OC(=O)N1CCCC(O)(c2ccc(Br)cc2)C1]

n-Butyllithium (2.5 M in hexanes, 8.2 mL, 20.5 mmol) was added over 10 min to a solution of 1-bromo-4-iodobenzene (5.79 g, 20.5 mmol) in THF (100 mL) at −78° C. After 15 min, a solution of 1-boc-3-piperidone (3.71 g, 18.6 mmol) in THF (10 mL) was added and the resultant reaction mixture was left to stir at −78° C. for 1 h, then warmed to 0° C. and quenched by the addition of saturated aqueous ammonium chloride (50 mL). The mixture was allowed to warm to ambient temperature and partitioned between ethyl acetate (400 mL) and water (150 mL). The organic layer was separated, dried over anhydrous magnesium sulfate, filtered and evaporated in vacuo. The resultant residue was purified by flash chromatography (silica, 80 g column, ISCO, 0-100% ethyl acetate in cyclohexane) to afford the title compound as a colourless gum (3.69 g, 56%). $^1$H NMR (CDCl$_3$, 300 MHz): 7.52-7.46 (m, 2H); 7.42-7.36 (m, 2H); 4.16-3.87 (m, 2H); 3.13 (d, J=13.7 Hz, 1H); 2.92-2.77 (m, 1H); 2.03-1.53 (m, 4H); 1.47 (s, 9H).

Preparation of 3-(4-Bromo-phenyl)-1-methyl-piperidin-3-ol

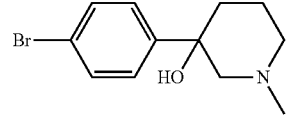

A mixture of 3-(4-bromo-phenyl)-3-hydroxypiperidine-1-carboxylic acid tert-butyl ester (1.39 g, 3.9 mmol), formic acid (18.4 mL) and formaldehyde (1.6 mL) was heated under microwave irradiation at 150° C. for 5 minutes. The cooled reaction mixture was loaded onto a 70 g SCX-2 cartridge which was washed with methanol (200 mL) and then eluted with 2N ammonia in methanol (200 mL). Concentration of the combined basic fractions in vacuo afforded the title compound (978 mg, 93%) as a brown oil. LCMS (Method B): R$_T$=1.84 min, M+H$^+$=270.

Preparation of 3-(3-Bromophenyl)-3-hydroxypiperidine-1-carboxylic acid tert-butyl ester

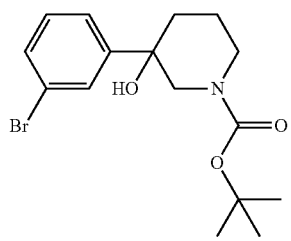 [SMILES: CC(C)(C)OC(=O)N1CCCC(O)(c2cccc(Br)c2)C1]

n-Butyllithium (2.5 M in hexanes, 7.6 mL, 19.0 mmol) was added over 10 min to a solution of 1-bromo-3-iodobenzene (5.37 g, 19.0 mmol) in THF (100 mL) at −78° C. After 15 min, a solution of 1-boc-3-piperidone (3.44 g, 17.3 mmol) in THF (10 mL) was added and the resultant reaction mixture was left to stir at −78° C. for 1 h, then warmed to 0° C. and quenched by the addition of saturated aqueous ammonium chloride (50 mL). The mixture was allowed to warm to ambient temperature and partitioned between ethyl acetate (400 mL) and water (150 mL). The organic layer was separated, dried over anhydrous magnesium sulfate, filtered and evaporated in vacuo. The resultant residue was purified by flash chromatography (silica, 80 g column, ISCO, 0-100% ethyl acetate in cyclohexane) to afford the title compound as a colourless gum (1.99 g, 33%). $^1$H NMR (CDCl$_3$, 300 MHz): 7.70-7.67 (m, 1H); 7.46-7.40 (m, 2H); 7.24-7.20 (m, 1H); 4.15-3.88 (m, 2H); 3.21-3.08 (m, 1H); 2.93-239 (m, 1H); 2.03-1.82 (m, 2H); 1.75-1.51 (m, 2H); 1.48 (s, 9H). LCMS (Method B): $R_T$=3.88 min, M-[Boc-18]$^+$238.

Preparation of
4-[(3,3-Dimethylpyrrolidine)-methyl]phenyl boronic acid

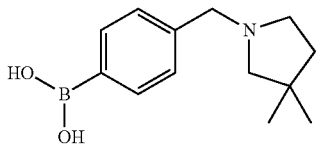

A mixture of 4-(bromomethyl)benzene boronic acid (565 mg, 2.63 mmol), 3,3-dimethylpyrrolidine (390 mg, 3.94 mmol), potassium carbonate (1.09 g, 7.88 mmol) and sodium iodide (20 mg, 0.13 mmol) in acetonitrile (30 mL) were stirred at ambient temperature for 18 h. The resultant reaction mixture was evaporated in vacuo to afford the crude title compound as a yellow solid (quantitative yield), which was used without further purification. LCMS (Method B): $R_T$=1.69 min, M+H$^+$=234

Preparation of
4-[(3,3-Difluoropyrrolidine)-methyl]phenyl boronic acid

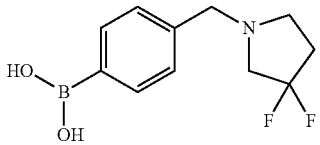 [SMILES: OB(O)c1ccc(CN2CCC(F)(F)C2)cc1]

A mixture of 4-(bromomethyl)benzene boronic acid (517 mg, 2.40 mmol), 3,3-difluoropyrrolidine hydrochloride (415 mg, 2.89 mmol), potassium carbonate (1.33 g, 9.62 mmol) and sodium iodide (18 mg, 0.12 mmol) in acetonitrile (30 mL) were stirred at ambient temperature for 18 h. The resultant reaction mixture was evaporated in vacuo to afford the crude title compound as a white solid (quantitative yield), which was used without further purification. $^1$H NMR (MeOD, 300 MHz): 7.48 (d, J=7.7 Hz, 2H); 7.11 (d, J=7.7 Hz, 2H); 3.58 (s, 2H); 2.89-2.70 (m, 4H); 2.32-2.14 (m, 2H). LCMS (Method B): $R_T$=1.46 min, M+H$^+$=242.

Preparation of
4-[(3-Trifluoromethylpiperidine)-methyl]phenyl boronic acid

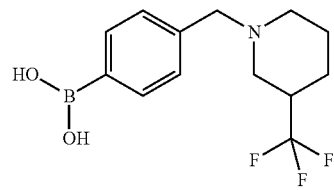 [SMILES: OB(O)c1ccc(CN2CCCC(C(F)(F)F)C2)cc1]

A mixture of 4-(bromomethyl)benzene boronic acid (473 mg, 2.20 mmol), 3-trifluoromethylpiperidine (403 mg, 2.63 mmol) and potassium carbonate (910 mg, 6.60 mmol) in acetonitrile (30 mL) were stirred at ambient temperature for 18 h. The reaction mixture was evaporated in vacuo and the resultant residue suspended in MeOH and the solid removed by filtration. The filtrate was evaporated to afford the title compound as a yellow solid (quantitative yield), which was used without further purification. $^1$H NMR (MeOD, 300 MHz): 7.49 (d, J 7.6 Hz, 2H); 7.11 (d, J=7.7 Hz, 2H); 3.56-3.43 (m, 2H); 3.10-3.01 (m, 1H); 2.98-2.88 (m, 1H); 2.46-2.24 (m, 1H); 2.00-1.85 (m, 3H); 1.81-1.70 (m, 1H); 1.67-1.43 (m, 1H); 1.34-1.14 (m, 1H). LCMS (Method G): $R_T$=1.85 min, M+H$^+$=288.

Preparation of 4[(3-Fluoropiperidine)-methyl]phenyl boronic acid

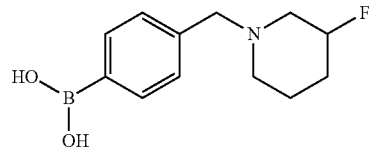 [SMILES: OB(O)c1ccc(CN2CCCC(F)C2)cc1]

A mixture of 4-(bromomethyl)benzene boronic acid (419 mg, 1.95 mmol), 3-fluoropiperidine (326 mg, 2.34 mmol) and potassium carbonate (1.08 g, 7.71 mmol) in acetonitrile (30 mL) were stirred at ambient temperature for 18 h. The reaction mixture was evaporated in vacuo and the resultant residue suspended in MeOH and the solid removed by filtration. The filtrate was evaporated to afford the title compound as a yellow solid (quantitative yield), which was used without further purification. $^1$H NMR (MeOD, 300 MHz): 7.48 (d, J=7.6 Hz, 2H); 7.11 (d, J=7.7 Hz, 2H); 4.72-4.44 (m, 1H); 3.50 (s, 2H); 2.77-2.60 (m, 1H); 2.54-2.27 (m, 3H); 1.90-1.73 (m, 2H); 1.67-1.44 (m, 2H). LCMS (Method G): $R_T$=1.35 min, M+H$^+$=238.

Preparation of
1-(4-Bromobenzyl)-piperidine-4-carbonitrile

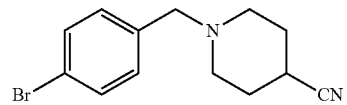 [SMILES: N#CC1CCN(Cc2ccc(Br)cc2)CC1]

A mixture of 4-bromobenzyl bromide (1.0 g, 4.0 mmol), triethylamine (0.84 mL, 6.0 mmol) and piperidine-4-carbonitrile (880 mg, 8.0 mmol) in THF (20 mL) was stirred at ambient temperature for 18 h. The reaction mixture was evaporated in vacuo and the residue partitioned between saturated sodium bicarbonate solution (100 mL) and dichloromethane (100 mL). The organic phase was separated, dried over sodium sulfate, filtered and evaporated in vacuo. The resultant residue was purified by flash chromatography (silica, Biotage 50 g column, 0-100% ethyl acetate in cyclohexane) to afford the title compound (1.10 g, 99%). $^1$H NMR (CDCl$_3$, 300 MHz): 7.46-7.41 (m, 2H); 7.21-7.15 (m, 2H); 3.44 (s, 2H); 2.70-2.57 (m, 3H); 2.38-2.22 (m, 2H); 1.99-1.74 (m, 4H). LCMS (Method B): R$_T$=1.82 min, M+H$^+$=280.

Preparation of (4-Bromo-2-methoxy-benzyloxy)-tert-butyldimethylsilane

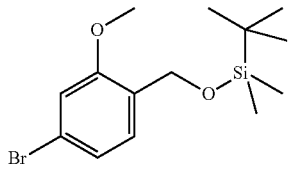 [SMILES: COc1cc(Br)ccc1CO[Si](C)(C)C(C)(C)C]

tert-Butyldimethylsilyl chloride (1.04 g, 6.9 mmol) was added to a mixture of (4-bromo-2-methoxyphenyl)methanol (1.0 g, 4.6 mol) and imidazole (470 mg, 7.0 mmol) in DMF (15 mL) and the resultant mixture was stirred at ambient temperature for 66 h. The mixture was concentrated to about a third of the original volume then diluted with water and extracted with diethyl ether (×3). The combined organic layer was dried over magnesium sulfate, filtered and evaporated. The resultant residue was purified by chromatography (silica, 50 g column, Si-SPE, 5% diethyl ether in pentane) to afford the title compound as a colourless oil (1.51 g, 98%). $^1$H NMR (CDCl$_3$, 400 MHz): 7.34 (dt, J=8.1, 1.05 Hz, 1H); 7.11 (dd, J=8.1, 1.8 Hz, 1H); 6.95 (d, J=1.8 Hz, 1H); 4.69 (d, J=1.0 Hz, 2H); 3.81 (s, 3H); 0.97-0.94 (m, 9H); 0.13-0.08 (m, 6H).

Preparation of cis-1-(4-Bromobenzyl)-3,5-dimethylpiperidine and trans-1-(4-Bromobenzyl)-3,5-dimethylpiperidine

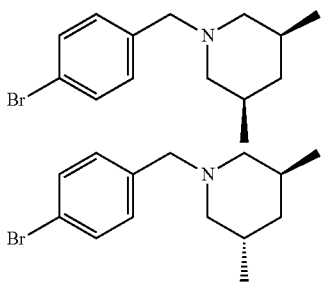

A suspension of 4-bromobenzyl bromide (4.0 g, 16.0 mmol), cis, trans-(3,5-dimethylpiperidine) (1.81 g, 16.0 mmol) and potassium carbonate (2.65 g, 19.2 mmol) in THF (160 mL) was heated under reflux for 24 h. The reaction mixture was allowed to cool to ambient temperature, the solid removed by filtration and the filtrate evaporated in vacuo. The resultant residue was loaded onto a 50 g SCX-2 cartridge which was washed with methanol then eluted with 2N ammonia in methanol. Concentration of the combined basic fractions in vacuo followed by flash chromatography of the resultant residue (silica, 330 g column, ISCO, 0-25% ethyl acetate in pentane) afforded cis-1-(4-bromobenzyl)-3,5-dimethylpiperidine (1.60 g, 35%) as a colourless oil. $^1$H NMR (CDCl$_3$, 300 MHz): 7.47-7.39 (m, 2H); 7.20 (d, J=8.0 Hz, 2H); 3.42 (s, 2H); 2.82-2.71 (m, 2H); 1.76-1.61 (m, 4H); 1.51-1.37 (m, 2H); 0.82 (d, J=6.4 Hz, 6H).

Further elution furnished trans-1-(4-bromobenzyl)-3,5-dimethylpiperidine (956 mg, 21%) as a colourless oil. $^1$H NMR (CDCl$_3$, 300 MHz): 7.42 (d, J=8.2 Hz, 2H); 7.21 (d, J=8.1 Hz, 2H); 3.46-3.26 (m, 2H); 2.40-2.28 (m, 2H); 2.08-1.96 (m, 2H); 1.95-1.80 (m, 2H); 1.32-1.23 (m, 2H); 0.94 (d, J=6.7 Hz, 6H).

Preparation of 1-(4-Bromo-2-chloro-benzyl)-piperidine

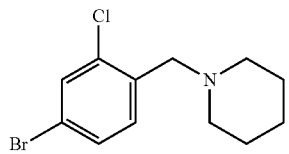 [SMILES: Clc1cc(Br)ccc1CN1CCCCC1]

To a pre-stirred solution of 4-bromo-2-chlorobenzaldehyde (1.01 g, 4.6 mmol) and piperidine (500 µL, 5.0 mmol) in DCM (20 mL) at 0° C. was added sodium triacetoxyborohydride (1.46 g, 6.9 mmol) in portions. The reaction mixture was allowed to warm to ambient temperature and then partitioned between water (50 mL) and dichloromethane (50 mL). The organic phase was separated, washed with saturated aqueous sodium carbonate (50 mL), dried over anhydrous sodium sulfate, filtered and evaporated in vacuo. The resultant residue was loaded onto a 20 g SCX-2 cartridge which was washed with methanol then 2N ammonia in methanol. Concentration of the combined basic fractions in vacuo afforded the title compound as a colourless oil (1.15 g, 87%). NMR (CDCl$_3$, 400 MHz): 7.50-7.48 (m, 1H); 7.40-7.33 (m, 2H); 3.50 (s, 2H); 2.46-2.38 (m, 4H); 1.62-1.53 (m, 4H); 1.49-1.40 (m, 2H). LCMS (Method B): R$_T$=2.03 min, M+H$^+$=288.

Preparation of (4-Bromobenzyloxy)-tert-butyldimethylsilane

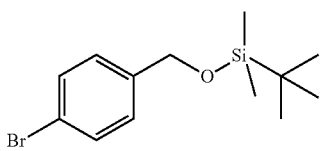 [SMILES: CC(C)(C)[Si](C)(C)OCc1ccc(Br)cc1]

tert-Butyldimethylsilyl chloride (2.42 g, 16 mmol) was added to a mixture of (4-bromophenyl)methanol (2.0 g, 107 mmol) and imidazole (1.09 g, 16 mmol) in DMF (30 mL) and the resultant mixture was stirred at ambient temperature for 72 h. The mixture was concentrated to one third of the original volume then diluted with water (50 mL) and extracted with diethyl ether (3×50 mL). The combined organic layer was dried over anhydrous sodium sulfate, filtered and evaporated in vacuo. The resultant residue was purified by chromatography (silica, 50 g column, Si-SPE, 0-5% diethyl ether in pentane) to afford the title compound as a colourless oil (3.21 g, 100%). NMR (CDCl₃, 400 MHz): 7.45-7.42 (m, 2H); 7.21-7.17 (m, 2H); 4.68 (s, 2H); 0.93 (s, 9H); 0.09 (s, 6H).

Preparation of [1-(4-Bromophenyl)-1-methylethoxy]-tert-butyldimethylsilane

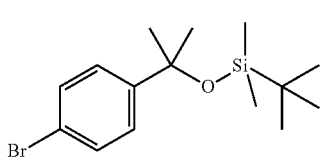 [SMILES: CC(C)(O[Si](C)(C)C(C)(C)C)c1ccc(Br)cc1]

tert-Butyldimethylsilyl chloride (2.10 g, 14 mmol) was added to a mixture of 2-(4-bromophenyl)-propan-2-ol (2.0 g, 9.3 mmol) and imidazole (0.95 g 14 mmol) in DMF (30 mL) and the resultant mixture was stirred at 80° C. for 24 h. The mixture was concentrated to one third of the original volume then diluted with water (50 mL) and extracted with diethyl ether (3×50 mL). The combined organic layer was dried over anhydrous sodium sulfate, filtered and evaporated in vacuo. The resultant residue was purified by chromatography (silica, 50 g column, Si-SPE, 0-5% diethyl ether in pentane) to afford the title compound as a colourless oil (1.39 g, 46%). ¹H NMR (MeOD, 400 MHz): 7.46-7.37 (m, 4H); 1.56 (s, 6H); 0.95-0.91 (m, 9H); 0.06 (s, 6H).

Preparation of 1-(5-Tributylstannanylisothiazol-3-ylmethyl)-piperidine

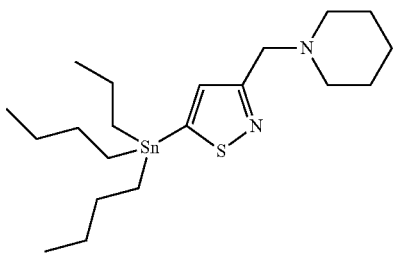 [SMILES: CCC[CH2][Sn]([CH2]CC)([CH2]CCC)[c]1cc(CN2CCCCC2)ns1]

Step 1: 1-(5-Bromoisothiazol-3-ylmethyl)-piperidine

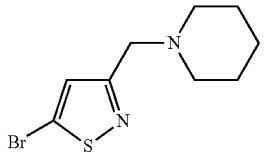 [SMILES: Brc1cc(CN2CCCCC2)ns1]

5-Bromo-3-bromomethylisothiazole (1.92 g, 7.5 mmol), triethylamine (1.57 mL, 11.2 mmol) and piperidine (1.5 mL, 15.0 mmol) in DCM (10 mL) were stirred for 16 h at ambient temperature. The reaction mixture was partitioned between water (50 mL) and ethyl acetate (75 mL). The organic phase was separated, dried over anhydrous sodium sulfate, filtered and evaporated in vacuo to afford the title compound as a colourless oil (1.49 g, 97%) that was used in the next step without further purification. ¹H NMR (CDCl₃, 400 MHz): 7.25 (s, 1H), 3.59 (s, 2H), 2.46-2.33 (m, 4H), 1.62-1.53 (m, 4H), 1.48-1.38 (m, 2H).

Step 2: 1-(5-Tributylstannanylisothiazol-3-ylmethyl)-piperidine

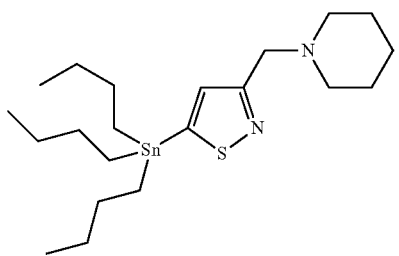 [SMILES: CCC[CH2][Sn]([CH2]CCC)([CH2]CCC)[c]1cc(CN2CCCCC2)ns1]

To a cold (−78° C.) solution of nBuLi (2.5M in hexanes, 0.88 mL, 0.35 mmol) in anhydrous THF (20 mL) was added diisopropylamine (0.32 mL, 2.2 mmol). The solution was allowed to warm to −20° C. for 30 minutes then cooled to −78° C. before addition of a solution of (1-(5-bromoisothiazol-3-ylmethyl)-piperidine (600 mg, 1.2 mmol) in anhydrous THF (5 mL). After 30 minutes, the reaction mixture was allowed to warm to ambient temperature and saturated aqueous sodium hydrogen carbonate was added. The aqueous phase was extracted with DCM (3×50 mL), the combined organic phase was dried over anhydrous sodium sulfate, filtered and evaporated in vacuo to afford a colourless oil that was purified by flash chromatography (silica, 12 g column, ISCO, 0-40% acetone in DCM) to afford the title compound as a colourless oil (110 mg, 73%). ¹H NMR (CDCl₃, 400 MHz): 7.23 (s, 1H), 3.74 (s, 2H), 2.49-2.36 (m, 4H), 1.69-1.50 (m, 10H), 1.48-1.40 (m, 2H), 1.39-1.19 (m, 6H), 1.18-1.12 (m, 6H), 0.95-0.86 (m, 9H).

Preparation of 1-(5-Tributylstannanylthiazol-2-ylmethyl)-piperidine

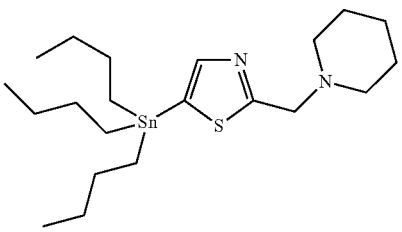 [SMILES: CCC[CH2][Sn]([CH2]CCC)([CH2]CCC)[c]1cnc(CN2CCCCC2)s1]

To a cold (−78° C.) solution of 1-thiazol-2-ylmethylpiperidine (2.73 g, 15.0 mmol) anhydrous THF (100 mL) was added n-butyllithium (8.95 mL, 16.5 mmol). After 30 minutes, a solution of tributyltin chloride (4.93 mL, 18.2 mmol) in anhydrous THF (40 mL) was to the reaction mixture. After 10 minutes, the solution was allowed to warm to ambient temperature and saturated aqueous sodium hydrogen carbonate was added. The aqueous phase was extracted with tert-butylmethyl ether (3×50 mL). The combined organic phase was dried over anhydrous sodium sulfate, filtered and evaporated in vacuo to afford a colourless oil that was then purified by flash chromatography (silica, 12 g column, ISCO, 0-40% ethyl acetate in cyclohexane) to afford the title compound as a colourless oil (5.1 g, 72%). $^1$H NMR (CDCl$_3$, 400 MHz): 7.62 (t, J=6.4 Hz, 1H), 3.88 (s, 2H), 2.54-2.47 (m, 4H), 1.69-1.49 (m, 10H), 1.50-1.40 (m, 2H), 1.40-1.26 (m, 6H), 1.15-1.08 (m, 6H), 0.95-0.85 (m, 9H).

Preparation of 5-Ethyl-2-tributylstannanyl-4,5,6,7-tetrahydro-thiazolo[4,5c]pyridine

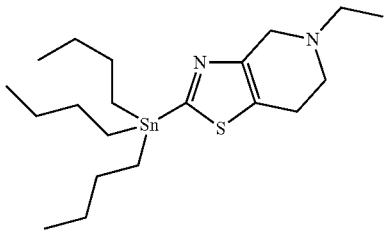 [SMILES: CCC[CH2][Sn]([CH2]CCC)([CH2]CCC)[c]1nc2c(s1)CCN(CC)C2]

To a cold (−78° C.) solution of 5-ethyl-4,5,6,7-tetrahydrothiazolo-[4,5-c]pyridine (262 g, 1.56 mmol) anhydrous THF (10 mL) was added n-butyllithium (2.5M in hexanes, 0.68 mL, 1.72 mmol). After 30 minutes, a solution of tributyltin chloride (0.51 mL, 1.87 mmol) in anhydrous THF (5 mL) was to the reaction mixture. After 10 minutes, the solution was allowed to warm to ambient temperature and saturated aqueous sodium hydrogen carbonate was added. The aqueous phase was extracted with ethyl acetate (50 mL), dried over anhydrous sodium sulfate, filtered and evaporated in vacuo to afford a colourless oil (450 mg, quantitative yield) that was used in the next step without purification. NMR (CDCl$_3$, 300 MHz): 3.78 (m, 1H), 2.96-2.88 (m, 2H), 2.78 (t, J=5.6 Hz, 2H), 2.64 (q, J=7.2 Hz, 2H), 1.62-1.49 (m, 6H), 1.36-1.12 (m, 12H), 0.94-0.82 (m, 12H).

Preparation of 1-Methyl-5-(trimethylstannyl)-1H-1,2,3-triazole

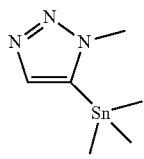

To a stirred solution of 1-methyl-1H-1,2,3-triazole (0.5 g, 6.0 mmol) in anhydrous tetrahydrofuran (50 mL) at −78° C. under an atmosphere of nitrogen was added n-butyllithium (2.5M solution in hexanes, 2.6 mL, 6.6 mmol) dropwise over ten minutes. On complete addition the reaction was allowed to warm to −30° C. and stirred for 2 h. A solution of chlorotrimethylstannane (1.3 g, 6.6 mmol) in tetrahydrofuran (2 mL) was added dropwise over 10 minutes then the reaction mixture was allowed to warm to room temperature over 2 h. The reaction was quenched by the addition of saturated ammonium chloride solution (5 mL) then diluted with water (20 mL). The solvent was evaporated in vacuo and the aqueous phase extracted with ethyl acetate (2×30 mL). The combined organic layer was dried over sodium sulfate, filtered and concentrated to afford a pale yellow oil (1.4 g, 90%). $^1$H NMR (DMSO-D$_6$, 400 MHz): 7.61 (s, 1H), 4.04 (s, 3H), 0.40 (s, 9H).

Preparation of 1-Benzyl-4-((tert-butyldimethylsilyloxy)methyl)-5-(trimethylstannyl)-1H-1,2,3-triazole

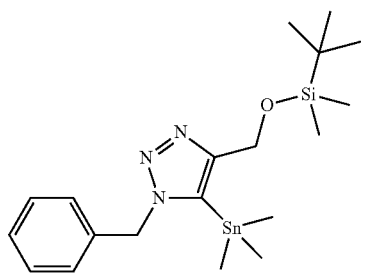 [SMILES: CC(C)(C)[Si](C)(C)OCc1nnn(Cc2ccccc2)[c]1[Sn]([CH3])([CH3])[CH3]]

Step 1: 1-Benzyl-4-((tert-butyldimethylsilyloxy)methyl)-5-iodo-1H-1,2,3-triazole

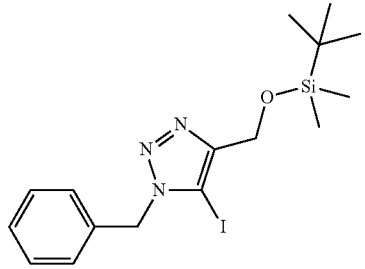 [SMILES: CC(C)(C)[Si](C)(C)OCc1nnn(Cc2ccccc2)c1I]

A mixture of tert-butyldimethyl(prop-2-ynyloxy)silane (1.2 mL, 5.9 mmol), (azidomethyl)benzene (0.81 mL, 6.5 mmol), N-bromosuccinimide (1.25 g, 7.0 mmol), copper (I) iodide (1.23 g, 6.5 mmol) and N,N-diisopropylethylamine (1.0 mL, 5.9 mmol) in tetrahydrofuran (48 mL) was stirred at room temperature for 3 h. The mixture was concentrated in vacuo and the resultant residue was dissolved in ethyl acetate (75 mL) and washed with water (50 mL). The layers were separated, the organic layer was dried over anhydrous sodium sulfate, filtered and evaporated to afford a residue that was purified by flash chromotagraphy (silica, 40 g column, ISCO, 0-25% ethyl acetate in heptane) to afford the title compound as a white solid (970 mg, 40%). $^1$H NMR (DMSO-D$_6$, 400 MHz,) δ 7.34 (m, 3H), 7.18 (m, 2H), 5.63 (s, 2H), 4.65 (s, 2H), 0.85 (s, 9H), 0.07 (s, 6H).

Step 2: 1-Benzyl-4-((tert-butyldimethylsilyloxy)methyl)-5-(trimethylstannyl)-1H-1,2,3-triazole

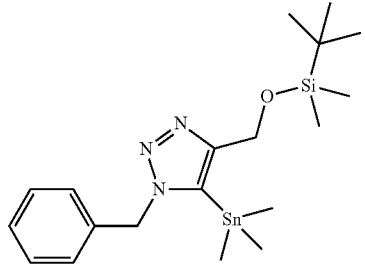 [SMILES: CC(C)(C)[Si](C)(C)OCc1nnn(Cc2ccccc2)[c]1[Sn]([CH3])([CH3])[CH3]]

A degassed mixture of 1-benzyl-4-((tert-butyldimethylsilyloxy)methyl)-5-iodo-1H-1,2,3-triazole (450 mg, 1.0 mmol), bis(triphenylphosphine) palladium(II) dichloride (37 mg, 0.05 mmol), hexamethylditin (0.65 mL, 3.1 mmol) and N,N-diisopropylethylamine (0.36 mL, 2.1 mmol) in 1,4-dioxane (8 mL) was heated at 105° C. for 2 h. The reaction mixture was quenched with water (1 mL) and concentrated to afford a residue that was purified by flash chromatagraphy (silica, 40 g column, ISCO, 0-25% ethyl acetate in heptane) to afford the title compound as a yellow oil (270 mg, 55%). $^1$H NMR (DMSO-D$_6$, 400 MHz,): 7.31 (m, 3H), 6.94 (m, 2H), 5.62 (s, 2H), 4.72 (s, 2H), 0.83 (s, 9H), 0.20 (s, 9H), 0.03 (s, 6H).

Preparation of
1-Isopropyl-4-tributylstannanyl-1H-pyrazole

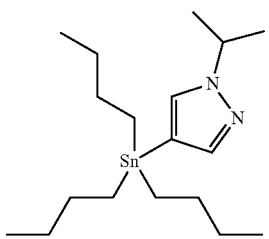 [SMILES: CCC[CH2][Sn]([CH2]CCC)([CH2]CCC)[c]1cnn(C(C)C)c1]

n-Butyllithium (2.5M in hexanes, 1.38 mL, 3.45 mmol) was added over 15 min to a solution of 4-bromo-1-isopropyl-1H-pyrazole (500 mg, 2.65 mmol) in diethyl ether (10 mL) at −78° C. After 30 min, a solution of tri-n-butylstannane chloride (920 μL, 3.45 mmol) in diethyl ether (1 mL) was added and the resultant reaction mixture was left to stir at −78° C. for 1 h, then allowed to warm to ambient temperature. The reaction mixture was diluted with diethyl ether (40 mL) and washed with water (20 mL), then brine (20 mL). The organic layer was separated, dried over sodium sulfate, filtered and evaporated in vacuo to afford the title product as a colourless oil (98 mg, 94%) which was used without further purification. $^1$H NMR (CDCl$_3$, 400 MHz): 7.46-7.42 (m, 1H); 7.28 (t, J=4.2 Hz, 1H); 4.59-4.43 (m, 1H); 1.58-1.42 (m, 12H); 1.39-1.24 (m, 6H); 1.02-0.77 (m, 15H).

Preparation of
7-(4-Bromobenzyl)-2-oxa-7-aza-spiro[3.5]nonane

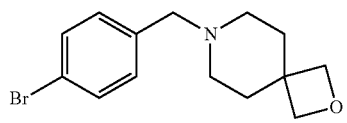 [SMILES: Brc1ccc(CN2CCC3(CC2)COC3)cc1]

A mixture of 4-bromobenzyl bromide (0.26 g, 1.04 mmol), triethylamine (0.21 mL, 2.07 mmol) and 2-oxa-7-azaspiro[3.5]nonane (0.50 g, 2.07 mmol) in THF (20 mL) was heated under reflux for 5 h. The reaction mixture was cooled to ambient temperature, the solid removed by filtration and the filtrate was concentrated under reduced pressure. The resultant residue was loaded onto an SCX-2 cartridge (10 g) and eluted with 2N ammonia in MeOH to afford the title compound (0.30 g, 97%). $^1$H NMR (CDCl$_3$, 300 MHz): 7.47-7.41 (m, 2H), 7.19 (d, J=8.1 Hz, 2H), 4.40 (s, 4H), 3.45-3.40 (m, 2H), 2.38-2.28 (s, 2H), 1.92-1.86 (s, 4H). LCMS (Method B): R$_T$=1.89 min, M+H$^+$=296/298.

Preparation of
2-(4-Bromobenzyl)-2-aza-bicyclo[2.2.1]heptane

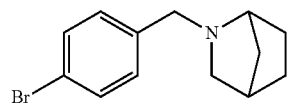

A stirred solution of 4-bromobenzyl bromide (66 mg, 0.26 mmol), triethylamine (0.22 mL, 1.56 mmol) and 2-azabicyclo[2.2.1]heptane (71 mg, 0.52 mmol) in THF (10 mL) was heated under reflux for 5 h. The reaction mixture was cooled to ambient temperature, the solid removed by filtration and the filtrate concentrated under reduced pressure to afford the title compound (70 mg, quantitative yield) that was used in the next step without further purification. LCMS (Method B): R$_T$=2.04 min, M+H$^+$=266/268.

Preparation of 2-Bromo-6-ethyl-4,5,6,7-tetrahydrothieno[2,3-c]pyridine

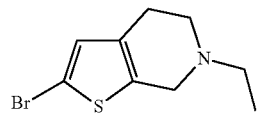

Step 1:
2-Bromo-4,5,6,7-tetrahydrothieno[2,3-c]pyridine hydrobromide

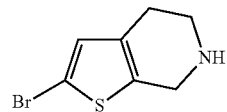

A solution of bromine (139 mg, 0.87 mmol) in acetic acid (0.5 mL) was added to a solution of 4,5,6,7-tetrahydrothieno[2,3-c]pyridine hydrochloride (150 mg, 0.85 mmol) in acetic acid (3 mL) and the mixture left to stir at ambient temperature for 1.5 h. The resultant precipitate was collected by filtration, washed with diethyl ether and left to air dry to afford the title compound as an off-white solid (230 mg, 90%). NMR (DMSO-D$_6$, 300 MHz): 9.19 (s, 2H), 7.09 (s, 1H), 4.29-4.26 (m, 2H), 2.86-2.78 (m, 2H), 2.52-2.48 (m, 2H). LCMS (Method B): R$_T$=1.65 min, M+H$^+$=218/220.

Step 2: 2-Bromo-6-ethyl-4,5,6,7-tetrahydrothieno[2,3-c]pyridine

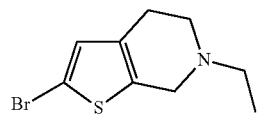

Sodium borohydride (146 mg, 3.85 mmol) was added to cooled (0° C.) a suspension of 2-bromo-4,5,6,7-tetrahydrothieno[2,3-c]pyridine hydrobromide (230 mg, 0.77 mmol) in acetic acid (1.5 mL) and tetrahydrofuran (2.8 mL). On complete addition the mixture was heated to 60° C. for 3 h. The mixture was allowed to cool to ambient temperature then partitioned between ethyl acetate and water. The pH of the aqueous phase was adjusted to 10 by the addition of 3N sodium hydroxide solution and the layers separated. The organic layer was washed with brine, dried over anhydrous sodium sulfate and evaporated to give the title compound as a yellow oil (181 mg, 96%). $^1$H NMR (DMSO-D$_6$, 300 MHz): 6.93 (s, 1H), 3.50-3.47 (m, 2H), 3.66-2.46 (m, 6H), 1.05 (t, J=7.2 Hz, 3H). LCMS (Method B): R$_T$=1.79 min, M+H$^+$=246/248.

Preparation of Trifluoromethanesulfonic acid 2-ethyl-8-methoxy-1,2,3,4-tetrahydroisoquinolin-6-yl ester

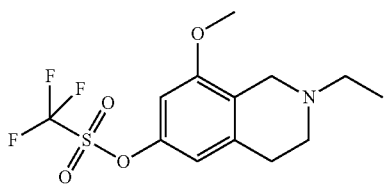 [SMILES: CCN1CCc2cc(OS(=O)(=O)C(F)(F)F)cc(OC)c2C1]

Step 1:
2-Ethyl-6,8-dimethoxy-3,4-dihydroisoquinolinium iodide

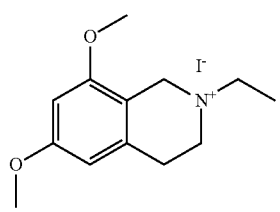 [SMILES: CC[NH+]1CCc2cc(OC)cc(OC)c2C1 ; [I-]]

Ethyl iodide (0.6 mL, 7.32 mmol) was added to a solution of 6,8-dimethoxy-3,4-dihydroisoquinoline (700 mg, 3.66 mmol) in acetonitrile (15 mL) and the mixture was left to stir in the dark for 20 h. The resultant precipitate was collected by filtration, washed with acetonitrile and left to air dry to afford the title compound as a yellow solid (750 mg, 95%). $^1$H NMR (CD$_3$OD, 300 MHz): 8.96 (s, 1H), 6.63 (d, J=2.2 Hz, 1H), 6.61 (d, J=2.2 Hz, 1H), 4.02-3.88 (m, 7H), 3.18 (t, J=7.9 Hz, 2H), 2.03 (s, 5H), 1.47 (t, J=7.3 Hz, 3H).

Step 2: 2-Ethyl-6-8-dimethoxy-1,2,3,4-tetrahydroisoquinoline

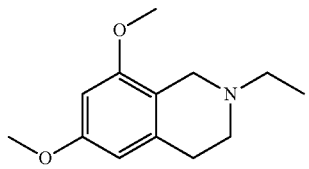 [SMILES: CCN1CCc2cc(OC)cc(OC)c2C1]

Sodium borohydride (260 mg, 6.86 mmol) was added to a cooled (0° C.) solution of 2-ethyl-6,8-dimethoxy-3,4-dihydroisoquinolinium iodide (1.19 g, 3.43 mmol) in methanol (15 mL). On complete addition the mixture was allowed to warm to ambient temperature and stirred for 1.5 h. The mixture was evaporated in vacuo and the resultant residue was partitioned between diethyl ether and water. The organic phase was dried over sodium sulfate, filtered and evaporated to afford the title compound as a yellow oil (741 mg, 98%). $^1$H NMR (CDCl$_3$, 300 MHz): 6.27 (d, J=2.3 Hz, 1H), 6.24 (d, J=2.3 Hz, 1H), 3.78 (s, 3H), 3.76 (s, 3H), 3.51-3.47 (m, 2H), 2.89-2.83 (m, 2H), 2.71-2.64 (m, 2H), 2.60 (q, J=7.2 Hz, 2H), 1.19 (t, J=7.2 Hz, 3H). LCMS (Method B): R$_T$=1.62 min, M+H$^+$=222.

Step 3: 2-Ethyl-8-methoxy-1,2,3,4-tetrahydroisoquinolin-6-ol

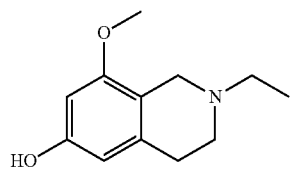

A mixture of 2-ethyl-6,8-dimethoxy-1,2,3,4-tetrahydroisoquinoline (280 mg, 1.27 mmol) in 48% aqueous hydrobromic acid (3 mL) was heated at 65° C. for 24 h. The mixture was added to saturated sodium hydrogen carbonate solution and extracted with ethyl acetate (3×50 mL). The combined organic phase was washed with water, dried over anhydrous sodium sulfate, filtered and evaporated in vacuo. The resultant solid was purified by flash chromatography (silica, 12 g column, ISCO, 0-20% (2N ammonia in MeOH) in DCM) to afford the title compound as an off white solid (153 mg, 58%). $^1$H NMR (CDCl$_3$, 300 MHz): 6.11 (d, J=2.2 Hz, 1H), 5.93 (d, J=2.2 Hz, 1H), 3.67 (s, 3H), 3.55-3.49 (m, 2H), 2.72-2.58 (m, 6H), 1.21 (t, J=7.2 Hz, 3H). LCMS (Method B): R$_T$=1.58 min, M+H$^+$=208.

Step 4: Trifluoromethanesulfonic acid 2-ethyl-8-methoxy-1,2,3,4-tetrahydroisoquinolin-6-yl ester

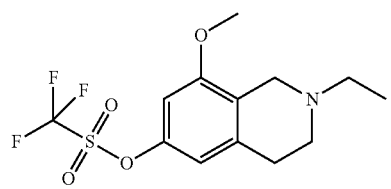

Triflic anhydride (0.54 mL, 3.2 mmol) was added dropwise over 15 minutes to a suspension of 2-ethyl-8-methoxy-1,2,3,4-tetrahydroisoquinolin-6-ol (328 mg, 1.6 mmol) in pyridine (0.52 mL, 6.4 mmol) and DCM (15 mL). The reaction mixture was allowed to warm to ambient temperature and stirred for 2 h. The mixture was diluted with DCM (60 mL), washed with water (100 mL), dried over sodium sulfate, filtered and evaporated in vacuo. The resultant solid was purified by flash chromatography (silica, 12 g column, ISCO, 0-100% ethyl acetate in pentane) to afford the title compound as a yellow solid (341 mg, 63%). $^1$H NMR (CDCl$_3$, 300 MHz): 6.76 (d, J=2.3 Hz, 1H), 6.68 (d, J=2.3 Hz, 1H), 4.30-4.10 (m, 2H), 3.87 (s, 3H), 3.50-3.37 (m, 2H), 3.36-3.10 (s, 4H), 1.51 (t, J=7.2 Hz, 3H). LCMS (Method B): R$_T$=2.39 min, M+H$^+$=340.

Preparation of 5-(4,4,5,5-Tetramethyl-1,3,2-dioxaborolan-2-yl)thiazole

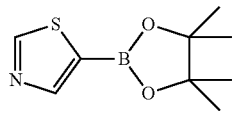

A mixture of 5-bromothiazole (0.54 mL, 6.1 mmol), bis(pinacolato)diboron (1.56 g, 6.1 mmol), 1,1'-[bis(diphenylphosphino)ferrocene]dichloropalladium(II) (250 mg, 0.3 mmol), and potassium acetate (1.8 g, 18.3 mmol) in 1,4-dioxane (20 mL) was heated at 100° C. for 12 h. The cooled reaction mixture was diluted with DCM (50 mL) and washed with water (15 mL). The organic phase was separated, dried over sodium sulfate, filtered and evaporated in vacuo. The resultant residue was purified by flash chromatography through a thin pad of silica eluting with DCM to afford the title compound as a brown solid which was used without further purification.

Preparation of 2-Methyl-5-(trimethylstannyl)thiazole

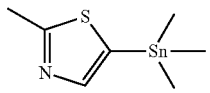

To a cooled (−78° C.) solution of 2-methylthiazole (1.0 g, 10 mmol) in anhydrous diethyl ether (20 mL) under an atmosphere of nitrogen was added n-butyllithium (2.5M solution in hexanes, 5.2 mL, 13 mmol) dropwise over 10 minutes. The reaction mixture was stirred for 1 h and then allowed to warm to 0° C. and stirred for 1 h. The reaction mixture was then cooled to −78° C. and a solution of chlorotrimethytstannane (1.8 g, 9.0 mmol) in anhydrous diethyl ether (10 mL) was added dropwise over 10 minutes. The reaction mixture was stirred for 30 minutes and then allowed to warm to room temperature and stirred for 16 h. The reaction was quenched with water (20 mL) and extracted with ethyl acetate (2×50 mL). The combined organic layer was dried over sodium sulfate, filtered, and evaporated in vacuo to afford the title compound as a yellow oil which was used without any further purification.

Preparation of 1,2-Dimethyl-5-(tributylstannyl)-1H-imidazole

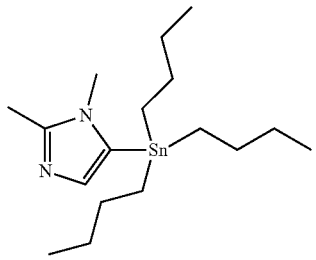 [SMILES: CCC[CH2][Sn]([CH2]CCC)([CH2]CCC)[c]1cnc(C)n1C]

The title compound was prepared following a similar procedure to previous example using 5-bromo-1,2-dimethyl-1H-imidazole and tributylchlorostannane.

Preparation of 3-(Trimethylstannyl)imidazo[1,2-a]pyrimidine

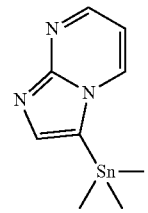

To a cooled (−78° C.) solution of 3-bromoimidazo[1,2-a]pyrimidine (1.0 g, 5.1 mmol) in anhydrous tetrahydrofuran (40 mL) under an atmosphere of nitrogen was added isopropylmagnesium chloride (2.0M solution in tetrahydrofuran, 2.8 mL, 5.6 mmol) dropwise over 10 minutes. The reaction was stirred for 2 h then a solution of chlorotrimethylstannane (1.1 g, 5.6 mmol) in tetrahydrofuran (10 mL) was added dropwise over 10 minutes. The reaction mixture was stirred for 30 minutes then allowed to warm to room temperature. The reaction was quenched with water (20 mL) and extracted with DCM (2×50 mL). The combined organic layer was dried over sodium sulfate, filtered, and evaporated in vacuo to afford the title compound as an orange oil which was used without any further purification.

Compounds of the Examples in Table 1 were made via procedures described above using appropriate starting materials, reagents and general Suzuki conditions.

TABLE 1

| Example | Structure/Name | Boronic acid/ester preparation general Method | Coupling Method | Final purification Method(s) | LCMS $R_T$, $M + H^+$, Method | $^1$H NMR (ppm) |
|---|---|---|---|---|---|---|
| 1 | 3-[4-(1-Methyl-piperidin-4-yl)-phenyl]-9H-dipyrido[2,3-b;4',3'-d]pyrrole-6-carbonitrile | B | A | E$^2$ | 5.8, 368, A | (DMSO-D$_6$, 300 MHz): 12.87 (br s, 1H), 9.05-9.02 (m, 2H), 8.99 (d, J = 2.3 Hz, 1H), 8.93 (d, J = 1.0 Hz, 1H), 7.73 (d, J = 8.1 Hz, 2H), 7.41 (d, J = 8.1 Hz, 2H), 2.94-2.84 (m, 2H), 2.54-2.47 (m, 1H), 2.21 (s, 3H), 2.04-1.94 (m, 2H), 1.82-1.66 (m, 4H). |

TABLE 1-continued

| Example | Structure/Name | Boronic acid/ester preparation general Method | Coupling Method | Final purification Method(s) | LCMS $R_T$, M + H+, Method | ¹H NMR (ppm) |
|---|---|---|---|---|---|---|
| 2 | 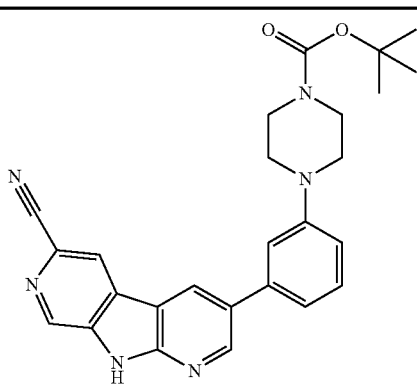<br>4-[3-(6-Cyano-9H-dipyrido[2,3-b;4',3'-d]pyrrol-3-yl)-phenyl]-piperazine-1-carboxylic acid tert-butyl ester | A | A | G | 11.6, 455, A | (DMSO-$D_6$, 300 MHz): 9.02-8.95 (m, 3H), 8.85 (s, 1H), 7.41-7.32 (m, 2H), 7.24 (d, J = 7.6 Hz, 1H), 7.00 (d, J = 8.3 Hz, 1H), 3.51 (m, 4H), 3.24 (m, 4H), 1.44 (s, 9H). |
| 3 | 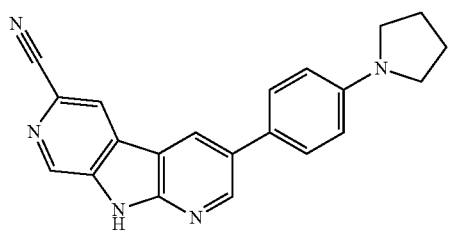 [SMILES: N#Cc1cc2c(cn1)[nH]c1ncc(-c3ccc(N4CCCC4)cc3)cc12]<br>3-(4-Pyrrolidin-1-yl-phenyl)-9H-dipyrido[2,3-b;4',3'-d]pyrrole-6-carbonitrile | A | A | none | 11.7, 340, A | (DMSO-$D_6$, 400 MHz): 12.78 (br. s, 1H), 9.01 (d, J = 1.0 Hz, 1H), 8.95-8.91 (m, 3H), 7.63 (d, J = 8.5 Hz, 2H), 6.69 (d, J = 8.5 Hz, 2H), 3.33-3.25 (m, 4H), 2.01-1.95 (m, 4H). |
| 4 | 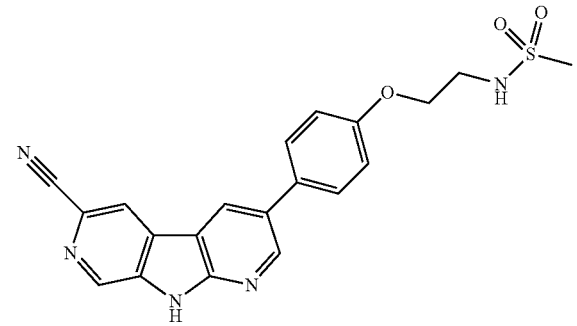 [SMILES: CS(=O)(=O)NCCOc1ccc(-c2cnc3[nH]c4cnc(C#N)cc4c3c2)cc1]<br>N-{2-[4-(6-Cyano-9H-dipyrido[2,3-b;4',3'-d]pyrrol-3-yl)-phenoxy]-ethyl}-methanesulfonamide | A | A | B | 8.4, 408, A | (DMSO-$D_6$, 400 MHz): 12.85 (s, 1H), 9.05-9.00 (m, 2H), 8.98 (d, J = 2.3 Hz, 1H), 8.94-8.91 (m, 1H), 7.75 (d, J = 8.3 Hz, 2H), 7.31 (t, J = 5.9 Hz, 1H), 7.14 (d, J = 8.3 Hz, 2H), 4.12 (t, J = 5.6 Hz, 2H), 3.41-3.35 (m, 2H), 2.98 (s, 3H). |
| 5 | 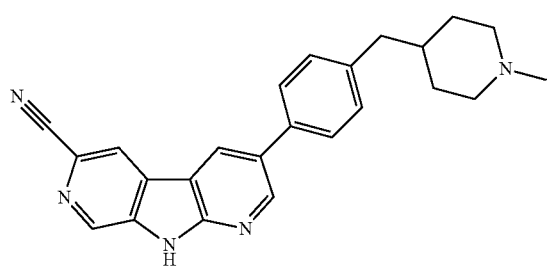 [SMILES: CN1CCC(Cc2ccc(-c3cnc4[nH]c5cnc(C#N)cc5c4c3)cc2)CC1]<br>3-[4-(1-Methyl-piperidin-4-ylmethyl)-phenyl]-9H-dipyrido[2,3-b;4',3'-d]pyrrole-6-carbonitrile | A | A | E[3] | 6.24, 382, A | (DMSO-$D_6$, 300 MHz): 9.06 (d, J = 2.3 Hz, 1H), 9.04 (d, J = 1.0 Hz, 1H), 9.01 (d, J = 2.3 Hz, 1H), 8.94 (d, J = 1.0 Hz, 1H), 7.72 (d, J = 7.9 Hz, 2H), 7.34 (d, J = 7.9 Hz, 2H), 2.73 (d, J = 10.7 Hz, 2H), 2.57 (d, J = 6.6 Hz, 2H), 2.12 (s, 3H), 1.80 (t, J = 5.8 Hz, 2H), 1.60-1.40 (m, 3H), 1.30-1.10 (m, 2H). |

TABLE 1-continued

| Example | Structure/Name | Boronic acid/ester preparation general Method | Coupling Method | Final purification Method(s) | LCMS $R_T$, $M + H^+$, Method | $^1$H NMR (ppm) |
|---|---|---|---|---|---|---|
| 6 | 3-(4-Piperidin-1-ylmethyl-phenyl)-9H-dipyrido[2,3-b;4',3'-d]pyrrole-6-carbonitrile | C | A | B | 5.83, 368, A | (DMSO-$D_6$, 300 MHz): 9.09-9.01 (m, 3H), 8.95 (d, J = 1.0 Hz, 1H), 7.76 (d, J = 8.0 Hz, 2H), 7.46 (d, J = 8.0 Hz, 2H), 3.50 (s, 2H), 2.37 (m, 4H), 1.55-1.48 (m, 4H), 1.41 (m, 2H). |
| 7 | 3-(4-Morpholin-4-ylmethyl-phenyl)-9H-dipyrido[2,3-b;4',3'-d]pyrrole-6-carbonitrile | C | A | H[1] | 5.43, 370, A | (DMSO-$D_6$, 300 MHz): 9.09-9.01 (m, 3H), 8.94 (d, J = 1.1 Hz, 1H), 7.78 (d, J = 7.9 Hz, 2H), 7.49 (d, J = 7.9 Hz, 2H), 3.60 (m, 4H), 3.54 (s, 2H), 2.40 (m, 4H). |
| 8 | 3-[4-(4-Benzyl-morpholin-2-yl)-phenyl]-9H-dipyrido[2,3-b;4',3'-d]pyrrole-6-carbonitrile | A | A | A[3] | 6.77, 446, A | (DMSO-$D_6$, 400 MHz): 12.90 (br. s, 1H), 9.10 (d, J = 2.3 Hz, 1H), 9.07 (d, J = 1.1 Hz, 1H), 9.00 (d, J = 2.3 Hz, 1H), 8.94 (d, J = 1.1 Hz, 1H), 7.77 (d, J = 8.2 Hz, 2H), 7.50 (d, J = 8.2 Hz, 2H), 7.35-7.30 (m, 4H), 7.29-7.24 (m, 1H), 4.59 (dd, J = 10.1, 2.3 Hz, 1H), 3.98-3.93 (m, 1H), 3.72 (td, J = 11.4, 2.4 Hz, 1H), 3.56 (d, J = 13.0 Hz, 1H), 3.53 (d, J = 13.0 Hz, 1H), 2.91 (d, J = 11.5 Hz, 1H), 2.72 (d, J = 11.5 Hz, 1H), 2.20 (td, J = 11.5, 3.3 Hz, 1H), 2.08-2.01 (m, 1H). |

TABLE 1-continued

| Example | Structure/Name | Boronic acid/ester preparation general Method | Coupling Method | Final purification Method(s) | LCMS R$_T$, M + H$^+$, Method | $^1$H NMR (ppm) |
|---|---|---|---|---|---|---|
| 9 | 3-(3-Piperidin-1-ylmethyl-phenyl)-9H-dipyrido[2,3-b;4',3'-d]pyrrole-6-carbonitrile | C | A | B$^1$ | 5.94, 368, A | (CDCl$_3$, 300 MHz): 9.02 (d, J = 1.0 Hz, 1H), 8.91 (d, J = 2.2 Hz, 1H), 8.70 (d, J = 2.2 Hz, 1H), 8.48 (d, J = 1.0 Hz, 1H) 7.66 (s, 1 H), 7.57 (d, J = 7.1 Hz, 1H), 7.49 (t, J = 7.5 Hz, 1H), 7.39 (d, J = 7.1 Hz, 1H), 3.60 (s, 2H), 2.47 (m, 4H), 1.63 (m, 4H), 1.48 (m, 2H). |
| 10 | 3-(3-Morpholin-4-ylmethyl-phenyl)-9H-dipyrido[2,3-b;4',3'-d]pyrrole-6-carbonitrile | C | A | B$^1$ | 5.59, 370, A | (CDCl$_3$, 300 MHz): 9.03 (s, 1H), 8.90 (s, 1H), 8.69 (s, 1H), 8.48 (s, 1H), 7.66 (s, 1H), 7.58 (m, 1H), 7.52 (br. t, J = 7.8 Hz, 1H), 7.43 (m, 1H), 3.76 (m, 4H), 3.63 (s, 2H), 2.54 (m, 4H). |
| 11 | 4-[4-(6-Cyano-9H-dipyrido[2,3-b;4',3'-d]pyrrol-3-yl)-benzyl]-piperazine-1-carboxylic acid tert-butyl ester | A | A | B$^1$ | 6.75, 469, A | (CDCl$_3$, 300 MHz): 9.02 (d, J = 1.1 Hz, 1H), 8.89 (d, J = 2.2 Hz, 1H); 8.68 (d, J = 2.2 Hz, 1H); 8.48 (d, J = 1.1 Hz, 1H); 7.65 (br d, J = 7.9 Hz, 2H); 7.50 (br d, J = 7.9 Hz, 2H); 3.62 (s, 2H); 3.55-3.44 (m, 4H); 2.47 (m, 4H); 1.46 (s, 9H) |
| 12 | 3-[4-(4-Ethyl-piperazin-1-yl)-phenyl]-9H-dipyrido[2,3-b;4',3'-d]pyrrole-6-carbonitrile | A | A | B$^1$ | 5.83, 383, A | (DMSO-D$_6$, 400 MHz): 12.76 (s, 1H); 9.00-8.86 (m, 4H); 7.62 (d, J = 8.4 Hz, 2H); 7.05 (d, J = 8.4 Hz, 2H); 3.18 (m, 4H); 2.48 (m, 4H); 2.34 (q, J = 7.2 Hz, 2H); 1.00 (t, J = 7.2 Hz, 3H). |

TABLE 1-continued

| Example | Structure/Name | Boronic acid/ester preparation general Method | Coupling Method | Final purification Method(s) | LCMS $R_T$, M + H$^+$, Method | $^1$H NMR (ppm) |
|---|---|---|---|---|---|---|
| 13 | 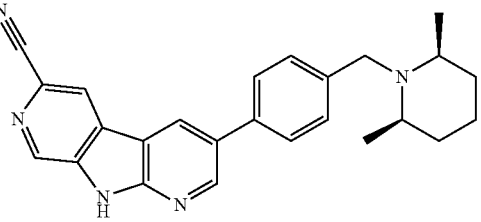 3-[4-((2S,6R)-2,6-Dimethyl-piperidin-1-ylmethyl)-phenyl]-9H-dipyrido[2,3-b;4',3'-d]pyrrole-6-carbonitrile | B | A | B | 6.26, 396, A | (DMSO-D$_6$, 300 MHz): 9.05 (d, J = 2.3 Hz, 1H), 9.04 (d, J = 1.1 Hz, 1H), 9.00 (d, J = 2.3 Hz, 1H), 8.93 (d, J = 1.1 Hz, 1H), 7.72 (d, J = 8.1 Hz, 2H), 7.54 (d, J = 8.0 Hz, 2H), 3.78 (s, 2H), 2.55-2.42 (m, 2H), 1.66-1.52 (m, 3H), 1.37-1.20 (m, 3H), 1.00 (d, J = 6.2 Hz, 6H). |

Compounds of the Examples in Table 2 were prepared via procedures described above using appropriate starting materials, reagents and general Suzuki conditions.

TABLE 2

| Example | Structure/Name | Boronic acid/ester general Method | Coupling Method | Deprotection Method | Final purification Method(s) | LCMS $R_T$, M + H$^+$, Method | $^1$H NMR (ppm) |
|---|---|---|---|---|---|---|---|
| 14 | 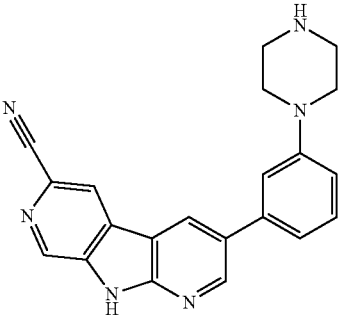 [SMILES: N#Cc1cc2c(cn1)[nH]c1ncc(-c3cccc(N4CCNCC4)c3)cc12] 3-(3-Piperazin-1-yl-phenyl)-9H-dipyrido[2,3-b;4',3'-d]pyrrole-6-carbonitrile | From Example 1 | N/A | A | G$^1$ | 5.81, 355, A | (DMSO-D$_6$, 300 MHz): 12.99 (s, 1H), 9.30 (s, 2H), 9.11 (d, J = 2.2 Hz, 1H), 9.06-9.01 (m, 2H), 8.95 (s, 1H), 7.47-7.39 (m, 2H), 7.30 (d, J = 7.6 Hz, 1H), 7.09-7.03 (m, 1H), 3.53 (m, 4H), 3.26 (s, 4H). |
| 15 | 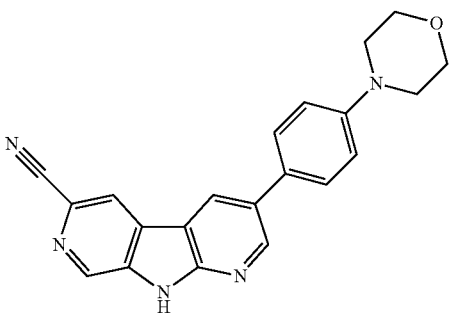 [SMILES: N#Cc1cc2c(cn1)[nH]c1ncc(-c3ccc(N4CCOCC4)cc3)cc12] 3-(4-Morpholin-4-yl-phenyl)-9H-dipyrido[2,3-b;4',3'-d]pyrrole-6-carbonitrile | NA | D | A | G$^1$ | 9.1, 356, A | (DMSO-D$_6$, 400 MHz): 12.88 (s, 1H), 9.04-9.02 (m, 2H), 8.98 (d, J = 2.3 Hz, 1H), 8.94 (d, J = 1.0 Hz, 1H), 7.72 (d, J = 8.6 Hz, 2H), 7.19 (d, J = 8.4 Hz, 2H), 3.81 (t, J = 4.6 Hz, 4H), 3.24 (t, J = 4.6 Hz, 4H). |

TABLE 2-continued

| Example | Structure/Name | Boronic acid/ ester general Method | Coupling Method | Deprotection Method | Final purification Method(s) | LCMS R$_T$, M + H+, Method | 1H NMR (ppm) |
|---|---|---|---|---|---|---|---|
| 16 | 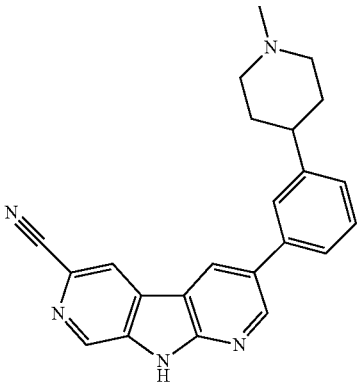 [SMILES: CN1CCC(c2cccc(-c3cnc4[nH]c5cnc(C#N)cc5c4c3)c2)CC1]<br>3-[3-(1-Methyl-piperidin-4-yl)-phenyl]-9H-dipyrido[2,3-b;4',3'-d]pyrrole-6-carbonitrile | B | D | A | F | 6.1, 368, A | (DMSO-D$_6$, 400 MHz): 12.96 (s, 1H), 10.35 (s, 1H), 9.09 (d, J = 2.2 Hz, 1H), 9.06 (d, J = 1.0 Hz, 1H), 9.02 (d, J = 2.2 Hz, 1H), 8.95 (s, 1H), 7.72-7.65 (m, 2H), 7.53 (t, J = 7.6 Hz, 1H), 7.32 (d, J = 7.6 Hz, 1H), 3.53 (d, J = 12.0 Hz, 2H), 3.16-3.06 (m, 2H), 2.95-2.90 (m, 1H), 2.80 (d, J = 4.6 Hz, 3H), 2.13-2.04 (m, 4H). |
| 17 | 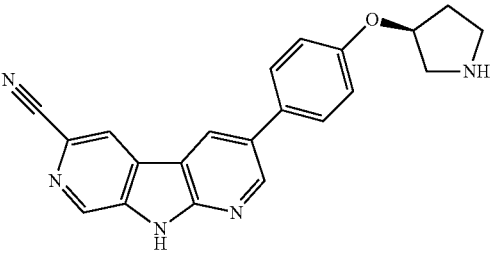 [SMILES: N#Cc1cc2c(cn1)[nH]c1ncc(-c3ccc(O[C@H]4CCNC4)cc3)cc12]<br>3-[4-((S)-Pyrrolidin-3-yloxy)-phenyl]-9H-dipyrido[2,3-b;4',3'-d]pyrrole-6-carbonitrile | A | D | B | C, E | 5.64, 356, A | (DMSO-D$_6$, 400 MHz): 8.99-8.93 (m, 2H), 8.92 (d, J = 2.3 Hz, 1H), 8.87 (d, J = 1.1 Hz, 1H), 7.67 (d, J = 8.3 Hz, 2H), 7.03 (d, J = 8.3 Hz, 2H), 4.92-4.85 (m, 1H), 3.14-2.99 (m, 1H), 2.94-2.71 (m, 3H), 2.06-1.95 (m, 1H), 1.80-1.72 (m, 1H). |
| 18 | 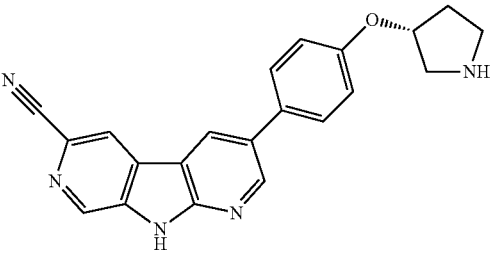 [SMILES: N#Cc1cc2c(cn1)[nH]c1ncc(-c3ccc(O[C@@H]4CCNC4)cc3)cc12]<br>3-[4-((R)-Pyrrolidin-3-yloxy)-phenyl]-9H-dipyrido[2,3-b;4',3'-d]pyrrole-6-carbonitrile | A | D | B | C, E | 5.64, 356, A | (DMSO-D$_6$, 300 MHz): 9.03 (d, J = 1.0 Hz, 1H), 9.01 (d, J = 2.3 Hz, 1H), 8.97 (d, J = 2.3 Hz, 1H), 8.92 (d, J = 1.1 Hz, 1H), 7.73 (d, J = 8.4 Hz, 2H), 7.08 (d, J = 8.5 Hz, 2H), 4.98-4.90 (m, 1H), 3.15-3.08 (m, 1H), 2.97-2.81 (m, 3H), 2.08-2.02 (m, 1H), 1.85-1.75 (m, 1H). |

TABLE 2-continued

| Example | Structure/Name | Boronic acid/ ester general Method | Coupling Method | Deprotection Method | Final purification Method(s) | LCMS $R_T$, M + H$^+$, Method | $^1$H NMR (ppm) |
|---|---|---|---|---|---|---|---|
| 19 | 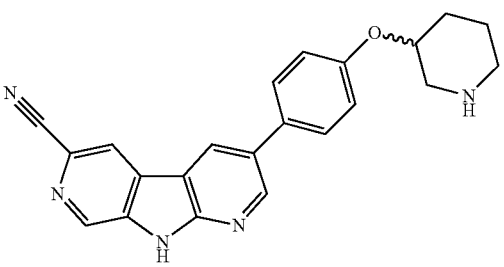 [SMILES: N#Cc1cc2c(cn1)[nH]c1ncc(-c3ccc(OC4CCCNC4)cc3)cc12]<br>3-[4-(Piperidin-3-yloxy)-phenyl]-9H-dipyrido[2,3-b;4',3'-d]pyrrole-6-carbonitrile | A | D | B | C, E | 5.85, 370, A | (DMSO-D$_6$, 300 MHz): 9.02 (d, J = 1.1 Hz, 1H), 9.00 (d, J = 2.3 Hz, 1H), 8.96 (d, J = 2.3 Hz, 1H), 8.92 (d, J = 1.1 Hz, 1H), 7.71 (d, J = 8.5 Hz, 2H), 7.11 (d, J = 8.5 Hz, 2H), 4.37-4.29 (m, 1H), 3.19-3.09 (m, 1H), 2.84-2.73 (m, 1H), 2.59-2.44 (m, 2H), 2.12-2.02 (m, 1H), 1.75-1.63 (m, 1H), 1.57-1.43 (m, 2H). |
| 20 | 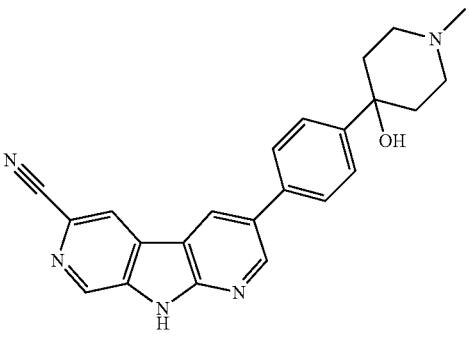 [SMILES: CN1CCC(O)(c2ccc(-c3cnc4[nH]c5cnc(C#N)cc5c4c3)cc2)CC1]<br>3-[4-(4-Hydroxy-1-methyl-piperidin-4-yl)-phenyl]-9H-dipyrido[2,3-b;4',3'-d]pyrrole-6-carbonitrile | B | D | A | A | 5.3, 384, A | (DMSO-D$_6$, 300 MHz): 12.80 (br. s, 1H), 9.08 (d, J = 2.3 Hz, 1H), 9.05 (d, J = 1.1 Hz, 1H), 9.03 (d, J = 2.3 Hz, 1H), 8.95 (d, J = 1.1 Hz, 1H), 7.78 (d, J = 8.3 Hz, 2H), 7.65 (d, J = 8.3 Hz, 2H), 4.99 (s, 1H), 2.71 (d, J = 10.4 Hz, 2H), 2.57-2.46 (m, 2H), 2.32 (s, 3H), 2.13-2.01 (m, 2H), 1.67 (d, J = 13.0 Hz, 2H). |
| 21 | 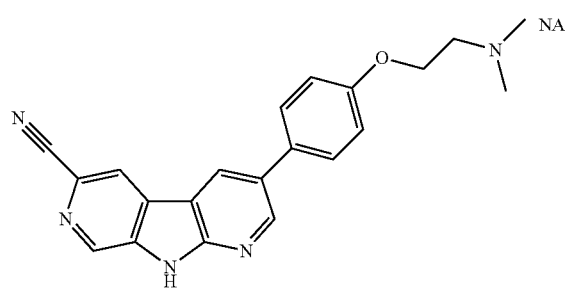<br>3-[4-(2-Dimethylamino-ethoxy)-phenyl]-9H-dipyrido[2,3-b;4',3'-d]pyrrole-6-carbonitrile | NA | D | A | A | 5.6, 358, A | (DMSO-D$_6$, 300 MHz): 12.75 (br. s, 1H), 9.05-9.02 (m, 2H), 8.99 (d, J = 2.3 Hz, 1H), 8.95 (d, J = 1.1 Hz, 1H), 7.75 (d, J = 8.6 Hz, 2H), 7.13 (d, J = 8.7 Hz, 2H), 4.14 (t, J = 5.8 Hz, 2H), 2.68 (t, J = 5.8 Hz, 2H), 2.26 (s, 6H). |

TABLE 2-continued

| Example | Structure/Name | Boronic acid/ ester general Method | Coupling Method | Deprotection Method | Final purification Method(s) | LCMS $R_T$, M + H$^+$, Method | $^1$H NMR (ppm) |
|---|---|---|---|---|---|---|---|
| 22 | 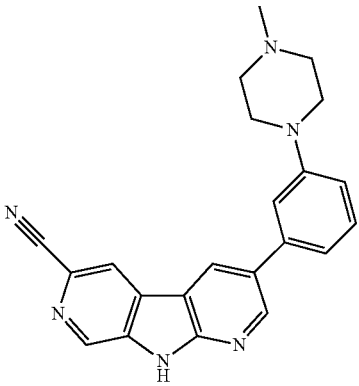 [SMILES: CN1CCN(c2cccc(-c3cnc4[nH]c5cnc(C#N)cc5c4c3)c2)CC1]<br>3-[3-(4-Methyl-piperazin-1-yl)-phenyl]-9H-dipyrido[2,3-b;4',3'-d]pyrrole-6-carbonitrile | A | A | A | B | 5.86, 368, A | (DMSO-D$_6$, 300 MHz): 9.09-8.98 (m, 3H), 8.95 (s, 1H), 7.42-7.30 (m, 2H), 7.20 (d, J = 7.6 Hz, 1H), 7.00 (d, J = 8.3 Hz, 1H), 3.33 (s, 4H), 2.50 (s, 4H), 2.25 (s, 3H). |
| 23 | 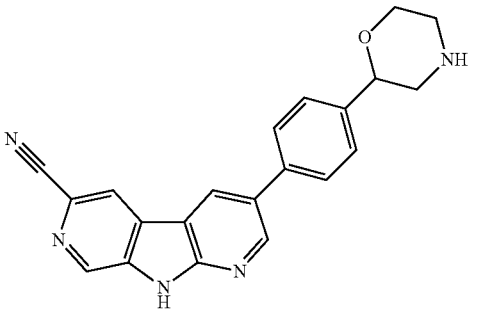 [SMILES: N#Cc1cc2c(cn1)[nH]c1ncc(-c3ccc(C4CNCCO4)cc3)cc12]<br>3-(4-Morpholin-2-yl-phenyl)-9H-dipyrido[2,3-b;4',3'-d]pyrrole-6-carbonitrile | From Example 8 | NA | C | C$^2$ | 5.57, 356, A | (DMSO-D$_6$, 300 MHz): 9.08 (d, J = 2.3 Hz, 1H), 9.04 (d, J = 1.1 Hz, 1H), 9.02 (d, J = 2.3 Hz, 1H), 8.95 (d, J = 1.1 Hz, 1H), 7.78 (d, J = 8.2 Hz, 2H), 7.50 (d, J = 8.2 Hz, 2H), 4.47 (dd, J = 10.2, 2.4 Hz, 1H), 3.92 (dt, J = 10.9, 2.2 Hz, 1H), 3.58-3.69 (m, 1H), 2.99 (dd, J = 12.3, 2.5 Hz, 1H), 2.80-2.74 (m, 2H), 2.59-2.54 (m, 1H). |
| 24 | 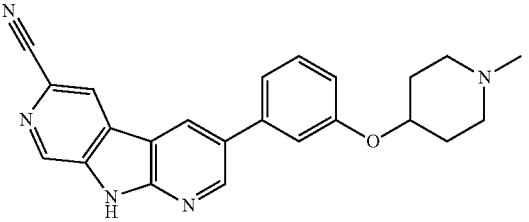 [SMILES: CN1CCC(Oc2cccc(-c3cnc4[nH]c5cnc(C#N)cc5c4c3)c2)CC1]<br>3-[3-(1-Methyl-piperidin-4-yloxy)-phenyl]-9H-dipyrido[2,3-b;4',3'-d]pyrrole-6-carbonitrile | B | D | A | G, E | 6.15, 384, A | (DMSO-D$_6$, 300 MHz): 12.90 (s, 1H), 9.09 (d, J = 2.3 Hz, 1H), 9.04 (s, 1H), 9.02 (d, J = 2.3 Hz, 1H), 8.95 (s, 1H), 7.44 (t, J = 8.0 Hz, 1H), 7.40-7.32 (m, 2H), 7.02 (d, J = 8.1 Hz, 1H), 4.63-4.43 (m, 1H), 2.69-2.59 (m, 2H), 2.30-2.13 (m, 5H), 2.05-1.93 (m, 2H), 1.75-1.64 (m, 2H). |

TABLE 2-continued

| Example | Structure/Name | Boronic acid/ester general Method | Coupling Method | Deprotection Method | Final purification Method(s) | LCMS $R_T$, M + H⁺, Method | ¹H NMR (ppm) |
|---|---|---|---|---|---|---|---|
| 25 | 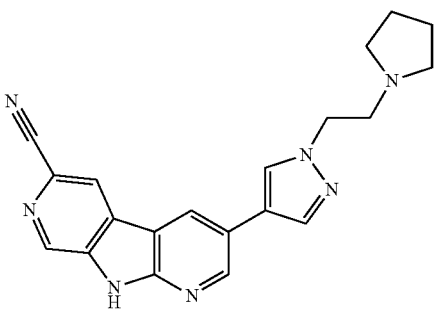 [SMILES: N#Cc1cc2c(cn1)[nH]c1ncc(-c3cnn(CCN4CCCC4)c3)cc12]<br>3-[1-(2-Pyrrolidin-1-yl-ethyl)-1H-pyrazol-4-yl]-9H-dipyrido[2,3-b;4',3'-d]pyrrole-6-carbonitrile | D | D | A | E, K | 5.07, 358, A | (DMSO-D₆, 400 MHz): 12.88 (s, 1H), 10.93 (s, 1H), 9.02 (d, J = 1.0 Hz, 1H), 8.98 (d, J = 2.2 Hz, 1H), 8.97 (d, J = 2.2 Hz, 1H), 8.85 (d, J = 1.0 Hz, 1H), 8.42 (s, 1H), 8.12 (s, 1H), 4.65 (t, J = 6.3 Hz, 2H), 3.70 (q, J = 6.0 Hz, 2H), 3.57-3.46 (m, 2H), 3.02-2.94 (m, 2H), 2.04-1.93 (m, 2H), 1.91-1.82 (m, 2H). |
| 26 | 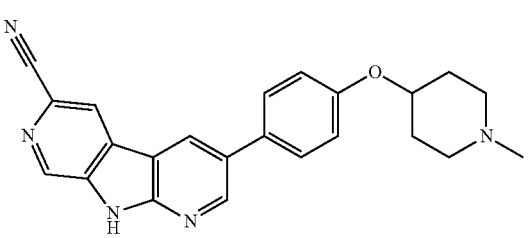 [SMILES: CN1CCC(Oc2ccc(-c3cnc4[nH]c5cnc(C#N)cc5c4c3)cc2)CC1]<br>3-[4-(1-Methyl-piperidin-4-yloxy)-phenyl]-9H-dipyrido[2,3-b;4',3'-d]pyrrole-6-carbonitrile | B | D | A | G, E | 6.05, 384, A | (DMSO-D₆, 400 MHz): 12.82 (s, 1H), 9.03 (d, J = 1.1 Hz, 1H), 9.01 (d, J = 2.3 Hz, 1H), 8.97 (d, J = 2.3 Hz, 1H), 8.94 (d, J = 1.1 Hz, 1H), 7.72 (d, J = 8.5 Hz, 2H), 7.12 (d, J = 8.5 Hz, 2H), 4.49-4.42 (m, 1H), 2.68-2.60 (m, 2H), 2.27-2.15 (m, 5H), 2.02-1.93 (m, 2H), 1.73-1.63 (m, 2H). |
| 27 | 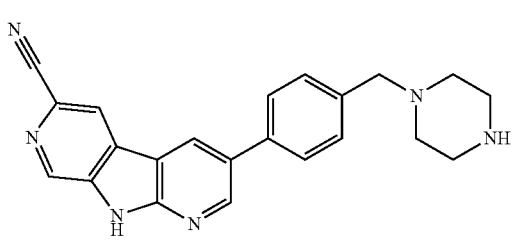 [SMILES: N#Cc1cc2c(cn1)[nH]c1ncc(-c3ccc(CN4CCNCC4)cc3)cc12]<br>3-(4-Piperazin-1-ylmethyl-phenyl)-9H-dipyrido[2,3-b;4',3'-d]pyrrole-6-carbonitrile | C | A | B | B¹, F¹,²,⁵ | 4.92, 369, A | (DMSO-D₆, 400 MHz): 12.54 (br. s, 1H), 9.03 (m, 1H), 8.99 (d, J = 2.2 Hz, 1H), 8.97 (d, J = 2.2 Hz, 1H), 8.83 (m, 1H), 7.77 (d, J = 8.1 Hz, 2H), 7.48 (d, J = 8.1 Hz, 2H), 3.68 (s, 2H), 3.14 (t, J = 5.1 Hz, 4H), 2.69 (t, J = 5.1 Hz, 4H). |
| 28 | 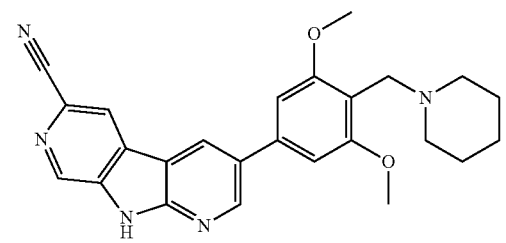 [SMILES: COc1cc(-c2cnc3[nH]c4cnc(C#N)cc4c3c2)cc(OC)c1CN1CCCCC1]<br>3-(3,5-Dimethoxy-4-piperidin-1-ylmethyl-phenyl)-9H-dipyrido[2,3-b;4',3'-d]pyrrole-6-carbonitrile | NA | A | A | E | 6.42, 428, A | (DMSO-D₆, 300 MHz): 9.13 (d, J = 2.3 Hz, 1H), 9.11 (d, J = 2.3 Hz, 1H), 9.04 (d, J = 1.0 Hz, 1H), 8.94 (d, J = 1.0 Hz, 1H), 7.05 (s, 2H), 3.90 (s, 6H), 3.50 (s, 2H), 2.41-2.36 (m, 4H), 1.49-1.40 (m, 4H), 1.29-1.38 (m, 2H). |

| Example | Structure/Name | Boronic acid/ester general Method | Coupling Method | Deprotection Method | Final purification Method(s) | LCMS $R_T$, M + H+, Method | 1H NMR (ppm) |
|---|---|---|---|---|---|---|---|
| 29 | 3-[4-(4-Methoxy-piperidin-4-yl)-phenyl]-9H-dipyrido[2,3-b;4',3'-d]pyrrole-6-carbonitrile | B | D | B | D | 5.99, 384, A | (DMSO-D$_6$, 400 MHz): 9.12 (d, J = 2.0 Hz, 1H), 9.07-9.05 (m, 2H), 8.95 (d, J = 1.0 Hz, 1H), 7.88 (d, J = 8.0 Hz, 2H), 7.57 (d, J = 8.0 Hz, 2H), 3.30-3.23 (m, 2H), 3.20-3.07 (m, 2H), 2.97 (s, 3H), 2.30-2.20 (m, 2H), 2.15-2.05 (m, 2H). |
| 30 | 3-[4-(3-Hydroxy-piperidin-3-yl)-phenyl]-9H-dipyrido[2,3-b;4',3'-d]pyrrole-6-carbonitrile | B | D | B | D | 5.51, 370, A | (DMSO-D$_6$, 400 MHz): 9.06 (d, J = 2.5 Hz, 1H), 9.04 (d, J = 1.0 Hz, 1H), 9.01 (d, J = 2.5 Hz, 1H), 8.93 (d, J = 1.0 Hz, 1H), 7.76 (d, J = 8.0 Hz, 2H), 7.67 (d, J = 8.0 Hz, 2H), 2.98-2.88 (m, 1H), 2.88-2.81 (m, 1H), 2.70-2.64 (m, 1H), 2.61-2.52 (m, 1H), 2.02-1.95 (m, 1H), 1.86-1.80 (m, 1H), 1.78-1.70 (m, 1H), 1.49-1.41 (m, 1H). |
| 31 | 3-[3-(3-Hydroxy-piperidin-3-yl)-phenyl]-9H-dipyrido[2,3-b;4',3'-d]pyrrole-6-carbonitrile | B | D | B | D | 5.77, 370, A | (DMSO-D$_6$, 400 MHz): 9.09 (d, J = 2.0 Hz, 1H), 9.05 (d, J = 1.0 Hz, 1H), 9.02 (d, J = 2.0 Hz, 1H), 8.99 (d, J = 1.0 Hz, 1H), 7.92 (s, 1H), 7.66 (d, J = 8.0 Hz, 1H), 7.58 (d, J = 8.0 Hz, 1H), 7.50 (t, J = 8.0 Hz, 1H), 2.98-2.91 (m, 2H), 2.76-2.68 (m, 1H), 2.67-2.53 (m, 1H), 2.07 (td, J = 8.5, 4.0 Hz, 1H), 1.90-1.85 (m, 1H), 1.81-1.73 (m, 1H), 1.51-1.44 (m, 1H). |

TABLE 2-continued

| Example | Structure/Name | Boronic acid/ ester general Method | Coupling Method | Deprotection Method | Final purification Method(s) | LCMS $R_T$, M + H+, Method | 1H NMR (ppm) |
|---|---|---|---|---|---|---|---|
| 32 | 3-[4-(3-Hydroxy-1-methyl-piperidin-3-yl)-phenyl]-9H-dipyrido[2,3-b;4',3'-d]pyrrole-6-carbonitrile | B | D | B | B | 5.58, 384, A | (DMSO-D6, 400 MHz): 9.11 (d, J = 2.0 Hz, 1H), 9.06 (d, J = 1.0 Hz, 1H), 9.05 (d, J = 2.0 Hz, 1H), 8.95 (d, J = 1.0 Hz, 1H), 7.88 (d, J = 8.0 Hz, 2H), 7.70 (d, J = 8.0 Hz, 2H), 3.27-3.22 (m, 2H), 3.17-3.16 (m, 1H), 3.09-2.97 (m, 1H), 2.75 (s, 3H), 2.20-1.99 (m, 2H), 1.88-1.81 (m, 2H). |
| 33 | 3-[4-(4-Fluoro-piperidin-4-yl)-phenyl]-9H-dipyrido[2,3-b;4',3'-d]pyrrole-6-carbonitrile | B | D | B | B | 6.15, 372, A | (DMSO-D6, 400 MHz): 9.11 (d, J = 2.0 Hz, 1H), 9.06 (d, J = 1.0 Hz, 1H), 9.04 (d, J = 2.0 Hz, 1H), 8.95 (d, J = 1.0 Hz, 1H), 7.87 (d, J = 8.0 Hz, 2H), 7.58 (d, J = 8.0 Hz, 2H), 3.14-2.95 (m, 2H), 3.03-2.95 (m, 2H), 2.26-2.13 (m, 2H), 2.10-1.95 (m, 2H). |
| 34 | 3-[4-(3,3-Dimethyl-pyrrolidin-1-ylmethyl)-phenyl]-9H-dipyrido[2,3-b;4',3'-d]pyrrole-6-carbonitrile | C | A | — | B | 6.32, 382, A | (DMSO-D6, 400 MHz): 12.89 (br s, 1H), 9.08 (d, J = 2.3 Hz, 1H), 9.04 (d, J = 1.1 Hz, 1H), 9.02 (d, J = 2.3 Hz, 1H), 8.94 (d, J = 1.1 Hz, 1H), 7.76 (d, J = 8.0 Hz, 2H), 7.47 (d, J = 8.0 Hz, 2H), 3.63 (s, 2H), 2.60 (t, J = 7.0 Hz, 2H), 2.29 (s, 2H), 1.55 (t, J = 7.0 Hz, 2H), 1.07 (s, 6H). |
| 35 | 3-[4-(3,3-Difluoro-pyrrolidin-1-ylmethyl)-phenyl]-9H-dipyrido[2,3-b;4',3'-d]pyrrole-6-carbonitrile | C | D | — | B, S | 6.44, 390, A | (DMSO-D6, 300 MHz): 12.89 (s, 1H), 9.09 (d, J = 2.3 Hz, 1H), 9.05 (d, J = 1.0 Hz, 1H), 9.03 (d, J = 2.2 Hz, 1H), 8.95 (d, J = 1.0 Hz, 1H), 7.79 (d, J = 8.0 Hz, 2H), 7.49 (d, J = 7.99 Hz, 2H), 3.70 (s, 2H), 2.91 (t, J = 13.3 Hz, 2H), 2.77-2.70 (m, 2H), 2.34-2.21 (m, 2H). |

TABLE 2-continued

| Example | Structure/Name | Boronic acid/ester general Method | Coupling Method | Deprotection Method | Final purification Method(s) | LCMS $R_T$, M + H$^+$, Method | $^1$H NMR (ppm) |
|---|---|---|---|---|---|---|---|
| 36 | 3-[4-(3-Trifluoromethyl-piperidin-1-ylmethyl)-phenyl]-9H-dipydrido[2,3-b;4',3'-d]pyrrole-6-carbonitrile | C* | D | — | B$^8$ | 6.67, 436 A | (DMSO-D$_6$, 400 MHz): 12.91 (s, 1H), 9.09 (d, J = 2.3 Hz, 1H), 9.04 (d, J = 1.1 Hz, 1H), 9.03 (d, J = 2.3 Hz, 1H), 8.94 (d, J = 1.1 Hz, 1H), 7.78 (d, J = 8.0 Hz, 2H), 7.48 (d, J = 8.0 Hz, 2H), 3.61 (s, 2H), 3.03-2.95 (m, 1H), 2.87-2.79 (m, 1H), 2.03-1.93 (m, 2H), 1.92-1.83 (m, 1H), 1.76-1.67 (m, 1H), 1.60-1.47 (m, 1H), 1.32-1.18 (m, 1H). |
| 37 | 3-[4-(3-Fluoro-piperidin-1-ylmethyl)-phenyl]-9H-dipyrido[2,3-b;4',3'-d]pyrrole-6-carbonitrile | C* | D | — | B | 5.76, 386, A | (DMSO-D$_6$, 400 MHz): 12.91 (s, 1H), 9.09 (d, J = 2.3 Hz, 1H), 9.05 (d, J = 1.1 Hz, 1H), 9.03 (d, J = 2.3 Hz, 1H), 8.94 (d, J = 1.1 Hz, 1H), 7.78 (d, J = 8.0 Hz, 2H), 7.47 (d, J = 8.0 Hz, 2H), 4.74-4.57 (m, 1H), 3.59 (s, 2H), 2.78-2.64 (m, 1H), 2.49-2.36 (m, 2H), 2.35-2.24 (m, 1H), 1.91-1.65 (m, 2H), 1.62-1.41 (m, 2H). |
| 38 | 3-(3-Piperidin-1-ylmethyl-isothiazol-5-yl)-9H-dipyrido[2,3-b;4',3'-d]pyrrole-6-carbonitrile monoformate | Stille B | — | D | | 5.70, 375, A | (CDCl$_3$ plus CD$_3$OD, 400 MHz): 9.03 (d, J = 1.0 Hz, 1H), 8.97 (d, J = 2.2 Hz, 1H), 8.92 (d, J = 2.2 Hz, 1H), 8.68 (d, J = 1.1 Hz, 1H), 8.42 (s, 1H), 4.12 (s, 2H), 2.99-2.86 (m, 4H), 1.85-1.74 (m, 4H), 1.66-1.55 (m, 2H). |

TABLE 2-continued

| Example | Structure/Name | Boronic acid/ester general Method | Coupling Method | Deprotection Method | Final purification Method(s) | LCMS R_T, M + H+, Method | 1H NMR (ppm) |
|---|---|---|---|---|---|---|---|
| 39 | 3-(2-Piperidin-1-ylmethyl-thiazol-5-yl)-9H-dipyrido[2,3-b;4',3'-d]pyrrole-6-carbonitrile | | Stille B | — | 5 | 5.55, 375, A | (DMSO-D_6, 400 MHz): 9.06-9.02 (m, 3H), 8.94 (d, J = 1.0 Hz, 1H), 8.18 (s, 1H), 3.81 (s, 2H), 2.56-2.49 (m, 4H), 1.62-1.52 (m, 4H), 1.49-1.38 (m, 2H). |
| 40 | 3-(5-Ethyl-4,5,6,7-tetrahydro-thiazolo[4,5-c]pyridin-2-yl)-9H-dipyrido[2,3-b;4',3'-d]pyrrole-6-carbonitrile | | Stille B | — | B[4] | 5.62, 360, A | (DMSO-D_6, 400 MHz): 12.90 (s, 1H), 9.02 (d, J = 1.1 Hz, 1H), 8.96 (d, J = 2.3 Hz, 1H), 8.95 (d, J = 1.1 Hz, 1H), 8.93 (d, J = 2.3 Hz, 1H), 7.32 (s, 1H), 3.63 (s, 2H), 2.77-2.65 (m, 4H), 2.57 (q, J = 7.2 Hz, 2H), 1.11 (t, J = 7.2 Hz, 3H). |

*no sodium iodide used in this reaction

The compounds of the Examples in Table 3 were prepared via general Suzuki procedures described above, employing commercially available boronic acids.

TABLE 3

| Example | Structure/Name | Coupling Method | Deprotection Method | Purification Method(s) | LCMS R_T, M + H+, Method | 1H NMR (ppm) |
|---|---|---|---|---|---|---|
| 41 | 3-(1,2,3,6-Tetrahydro-pyridin-4-yl)-9H-dipyrido[2,3-b;4',3'-d]pyrrole-6-carbonitrile | E | A | E, H | 4.38, 276, A | (DMSO-D_6, 400 MHz): 12.96 (s, 1H), 9.35 (s, 2H), 9.04 (d, J = 1.0 Hz, 1H), 8.93 (d, J = 1.0 Hz, 1H), 8.91 (d, J = 2.3 Hz, 1H), 8.88 (d, J = 2.3 Hz, 1H), 6.36 (s, 1H), 3.82 (s, 2H), 3.42-3.35 (m, 2H), 2.89-2.81 (s, 2H). |

TABLE 3-continued

| Example | Structure/Name | Coupling Method | Deprotection Method | Purification Method(s) | LCMS R_T, M + H+, Method | 1H NMR (ppm) |
|---|---|---|---|---|---|---|
| 42 | 3-(3,5-Dimethoxy-phenyl)-9H-dipyrido[2,3-b;4',3'-d]pyrrole-6-carbonitrile | D | A | G², J | 10.0, 331, A | (DMSO-D₆, 400 MHz): 12.91 (s, 1H), 9.11 (d, J = 2.3 Hz, 1H), 9.05-9.03 (m, 2H), 8.93 (d, J = 1.0 Hz, 1H), 6.96 (d, J = 2.2 Hz, 2H), 6.57 (t, J = 2.2 Hz, 1H), 3.85 (s, 6H). |
| 43 | 3-(4-Pyrrolidin-1-ylmethyl-phenyl)-9H-dipyrido[2,3-b;4',3'-d]pyrrole-6-carbonitrile | B | NA | B | 5.69, 354, A | (CD₃OD, 400 MHz): 9.02 (d, J = 1.0 Hz, 1H), 8.95 (d, J = 2.2 Hz, 1H), 8.93 (d, J = 2.2 Hz, 1H), 8.72 (d, J = 1.1 Hz, 1H), 7.82 (d, J = 8.0 Hz, 2H), 7.61 (d, J = 8.0 Hz, 2H), 4.16 (s, 2H), 3.12-3.05 (m, 4H), 2.06-2.01 (m, 4H). |
| 44 | 3-[4-(1-Piperidin-1-yl-ethyl)-phenyl]-9H-dipyrido[2,3-b;4',3'-d]pyrrole-6-carbonitrile | B | NA | B | 2.28, 382, A | (CDCl₃, 400 MHz): 9.02 (t, J = 1.0 Hz, 1H), 8.91 (dd, J = 2.1, 0.9 Hz, 1H), 8.73 (dd, J = 2.3, 1.3 Hz, 1H), 8.53 (t, J = 1.1 Hz, 1H), 7.68 (d, J = 7.9 Hz, 2H), 7.51 (d, J = 7.9 Hz, 2H), 3.67 (q, J = 6.7 Hz, 1H), 2.68-2.50 (m, 4H), 1.73-1.63 (m, 4H), 1.56 (d, J = 6.8 Hz, 3H), 1.50-1.44 (m, 2H). |

Compounds of the Examples in Table 4 were made via procedures described above using appropriate starting materials, reagents and general Suzuki Methods.

TABLE 4

| Example | Structure/Name | Coupling Method | Deprotection Method | Purification Method(s) | LCMS R$_T$, M + H$^+$, Method | $^1$H NMR (ppm) |
|---|---|---|---|---|---|---|
| 45 | 3-[3-Methoxy-5-(1-methyl-piperidin-4-yloxy)-phenyl]-9H-dipyrido[2,3-b;4',3'-d]pyrrole-6-carbonitrile | F | A | E$^5$ | 6.4, 414, A | (DMSO-D$_6$, 400 MHz): 12.85 (s, 1H), 9.10 (d, J = 2.3 Hz, 1H), 9.04-9.02 (m, 2H), 8.94 (d, J = 1.1 Hz, 1H), 6.95 (dt, J = 9.8, 1.8 Hz, 2H), 6.57 (t, J = 2.2 Hz, 1H), 4.56-4.49 (m, 1H), 3.85 (s, 3H), 2.68-2.60 (m, 2H), 2.29-2.16 (m, 5H), 2.03-1.92 (m, 2H), 1.74-1.63 (m, 2H). |
| 46 | 3-(3,5-Difluoro-4-piperidin-1-ylmethyl-phenyl)-9H-dipyrido[2,3-b;4',3'-d]pyrrole-6-carbonitrile | F | D | B | 5.87, 404, A | (DMSO-D$_6$, 300 MHz): 9.19 (d, J = 2.3 Hz, 1H), 9.10 (d, J = 2.3 Hz, 1H), 9.05 (d, J = 1.1 Hz, 1H), 8.87 (d, J = 1.1 Hz, 1H), 7.61 (d, J = 8.6 Hz, 2H), 3.58 (s, 2H), 2.43-2.37 (m, 4H), 1.51-1.44 (m, 4H), 1.39-1.32 (m, 2H). |
| 47 | 3-[3-Bromo-5-(1-methyl-piperidin-4-yloxy)-phenyl]-9H-dipyrido[2,3-b;4',3'-d]pyrrole-6-carbonitrile | F | A | G$^3$, E | 7.1, 462, A | (DMSO-D$_6$, 400 MHz): 12.85 (s, 1H), 9.14 (d, J = 2.3 Hz, 1H), 9.06-9.04 (m, 2H), 8.93 (d, J = 1.1 Hz, 1H), 7.58 (dd, J = 1.6, 1.5 Hz, 1H), 7.40 (dd, J = 2.1, 1.7 Hz, 1H), 7.23 (dd, J = 2.2, 1.7 Hz, 1H), 4.63-4.56 (m, 1H), 2.67-2.59 (m, 2H), 2.28-2.15 (m, 5H), 2.02-1.91 (m, 2H), 1.74-1.64 (m, 2H). |
| 48 | 3-(4,5,6,7-Tetrahydrothieno[3,2-c]pyridin-2-yl)-9H-dipyrido[2,3-b;4',3'-d]pyrrole-6-carbonitrile | G | A | H, B | 5.33, 332, A | (DMSO-D$_6$, 400 MHz): 12.96 (s, 1H), 9.44 (br. s, 1H), 9.00 (d, J = 1.1 Hz, 1H), 8.94-8.93 (m, 2H), 8.94 (d, J = 1.0 Hz, 1H), 7.39 (s, 1H), 4.20 (s, 2H), 3.41 (m, 2H), 3.08 (t, J = 6.0 Hz, 2H). |

TABLE 4-continued

| Example | Structure/Name | Coupling Method | Deprotection Method | Purification Method(s) | LCMS $R_T$, M + H+, Method | 1H NMR (ppm) |
|---|---|---|---|---|---|---|
| 49 | 3-(5-Ethyl-4,5,6,7-tetrahydro-thieno[3,2-c]pyridin-2-yl)-9H-dipyrido[2,3-b;4',3'-d]pyrrole-6-carbonitrile | G | A | H, B | 2.17, 360, A | (DMSO-D$_6$, 400 MHz): 13.02 (s, 1H), 10.68 (s, 1H), 9.05 (d, J = 1.0 Hz, 1H), 9.00 (s, 2H), 8.99 (s, 1H), 7.42 (s, 1H), 4.51 (d, J = 15.0 Hz, 1H), 4.27-4.16 (m, 1H), 3.85-3.73 (m, 1H), 3.40-3.14 (m, 5H), 1.36 (t, J = 7.2 Hz, 3H). |
| 50 | 3-(4-Piperidin-1-ylmethyl-thiophen-2-yl)-9H-dipyrido[2,3-b;4',3'-d]pyrrole-6-carbonitrile | F | D | J$^{3,5}$ | 5.8, 374, A | (DMSO-D$_6$, 400 MHz): 12.90 (br. s, 1H), 9.05 (d, J = 2.3 Hz, 1H), 9.02 (d, J = 1.1 Hz, 1H), 9.00 (d, J = 2.3 Hz, 1H), 8.96 (d, J = 1.1 Hz, 1H), 7.53 (d, J = 1.4 Hz, 1H), 7.34 (d, J = 1.3 Hz, 1H), 3.45 (s, 2H), 2.40-2.33 (m, 4H), 1.56-1.48 (m, 4H), 1.42-1.37 (m, 2H). |
| 51 | 3-(4-Piperidin-1-ylmethyl-thiazol-2-yl)-9H-dipyrido[2,3-b;4',3'-d]pyrrole-6-carbonitrile | F | D | E | 5.45, 375, A | (CDCl$_3$, 300 MHz): 9.21 (d, J = 2.1 Hz, 1H), 9.05 (d, J = 2.1 Hz, 1H), 9.02 (d, J = 1.1 Hz, 1H), 8.50 (d, J = 1.1 Hz, 1H), 3.79 (s, 2H), 2.63-2.55 (m, 4H), 1.71-1.62 (m, 4H), 1.54-1.46 (m, 2H). |
| 52 | 3-(4,5,6,7-Tetrahydro-thiazolo[5,4-c]pyridin-2-yl)-9H-dipyrido[2,3-b;4',3'-d]pyrrole-6-carbonitrile | F | D | E | 4.66, 333, A | (DMSO-D$_6$, 300 MHz): 9.29 (s, 1H), 9.19 (s, 1H), 9.07 (s, 1H), 9.05 (s, 1H), 4.05 (s, 2H), 3.14-3.07 (m, 2H), 2.85-2.79 (m, 2H). |

TABLE 4-continued

| Example | Structure/Name | Coupling Method | Deprotection Method | Purification Method (s) | LCMS $R_T$, M + H$^+$, Method | $^1$H NMR (ppm) |
|---|---|---|---|---|---|---|
| 53 | 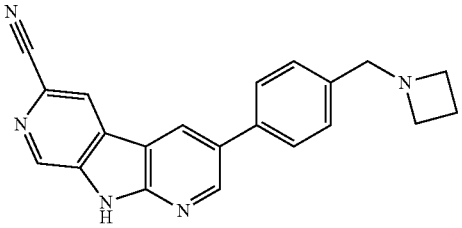 [SMILES: N#Cc1cc2c(cn1)[nH]c1ncc(-c3ccc(CN4CCC4)cc3)cc12]<br>3-(4-Azetidin-1-ylmethyl-phenyl)-9H-dipyrido[2,3-b;4',3'-d]pyrrole-6-carbonitrile | G | D | B | 5.48, 340, A | (DMSO-D$_6$, 400 MHz): 9.07 (d, J = 2.3 Hz, 1H), 9.04 (d, J = 1.1 Hz, 1H), 9.01 (d, J = 2.3 Hz, 1H), 8.94 (d, J = 1.1 Hz, 1H), 7.75 (d, J = 8.1 Hz, 2H), 7.44 (d, J = 8.0 Hz, 2H), 3.62 (s, 2H), 3.19 (t, J = 6.9 Hz, 4H), 2.02 (p, J = 7.0 Hz, 2H). |
| 54 | 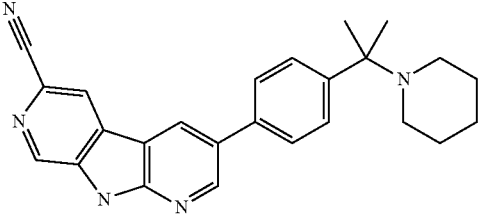 [SMILES: CC(C)(c1ccc(-c2cnc3[nH]c4cnc(C#N)cc4c3c2)cc1)N1CCCCC1]<br>3-[4-(1-Methyl-1-piperidin-1-yl-ethyl)-phenyl]-9H-dipyrido[2,3-b;4',3'-d]pyrrole-6-carbonitrile | G | D | B | 6.24, 396, A | (DMSO-D$_6$, 400 MHz): 9.07 (d, J = 2.3 Hz, 1H), 9.04 (d, J = 1.1 Hz, 1H), 9.01 (d, J = 2.3 Hz, 1H), 8.94 (d, J = 1.1 Hz, 1H), 7.75 (d, J = 8.1 Hz, 2H), 7.44 (d, J = 8.0 Hz, 2H), 3.62 (s, 2H), 3.19 (t, J = 6.9 Hz, 4H), 2.02 (p, J =7.0 Hz, 2H). |
| 55 | 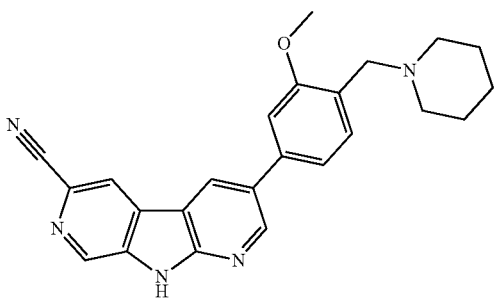 [SMILES: COc1cc(-c2cnc3[nH]c4cnc(C#N)cc4c3c2)ccc1CN1CCCCC1]<br>3-(3-Methoxy-4-piperidin-1-ylmethyl-phenyl)-9H-dipyrido[2,3-b;4',3'-d]pyrrole-6-carbonitrile | K | D | B, G$^4$ | 6.29, 398, A | (CDCl$_3$ plus CD$_3$OD, 300 MHz): 9.02 (s, 1H), 8.90 (d, J = 2.2 Hz, 1H), 8.69 (d, J = 2.1 Hz, 1H), 8.51 (s, 1H), 7.47 (d, J = 7.7 Hz, 1H), 7.23 (d, J = 7.8 Hz, 1H), 7.14 (s, 1H), 3.95 (s, 3H), 3.64 (s, 2H), 2.58-2.45 (s, 4H), 1.65-1.56 (m, 4H), 1.52-1.39 (m, 2H) |
| 56 | 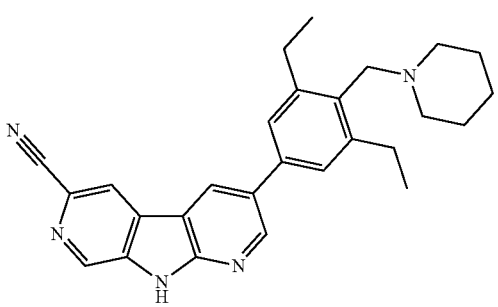 [SMILES: CCc1cc(-c2cnc3[nH]c4cnc(C#N)cc4c3c2)cc(CC)c1CN1CCCCC1]<br>3-(3,5-Diethyl-4-piperidin-1-ylmethyl-phenyl)-9H-dipyrido[2,3-b;4',3'-d]pyrrole-6-carbonitrile | G | D | B$^4$ | 2.53, 424, B | (CDCl$_3$, 300 MHz): 9.02 (s, 1H), 8.90 (d, J = 2.1 Hz, 1H), 8.68 (d, J = 2.1 Hz, 1H), 8.49 (d, J = 1.0 Hz, 1H), 7.33 (s, 2H), 3.54 (s, 2H), 2.89 (q, J = 7.5 Hz, 4H), 2.51-2.38 (m, 4H), 1.60-1.39 (m, 6H), 1.36-1.22 (m, 6H). |

TABLE 4-continued

| Example | Structure/Name | Coupling Method | Deprotection Method | Purification Method (s) | LCMS $R_T$, M + H$^+$, Method | $^1$H NMR (ppm) |
|---|---|---|---|---|---|---|
| 57 | 3-(3,5-Dichloro-4-piperidin-1-ylmethyl-phenyl)-9H-dipyrido[2,3-b;4',3'-d]pyrrole-6-carbonitrile | K | D | B$^4$ | 6.55, 436, A | (CDCl$_3$ plus CD$_3$OD, 300 MHz): 9.03 (s, 1H), 8.85 (s, 1H), 8.65 (d, J = 2.1 Hz, 1H), 8.48 (d, J = 0.9 Hz, 1H), 7.62 (s, 2H), 3.79 (s, 2H), 2.64-2.52 (s, 4H), 1.64-1.53 (m, 4H), 1.51-1.38 (m, 2H). |
| 58 | 3-(3-Chloro-5-methoxy-4-piperidin-1-ylmethyl-phenyl)-9H-dipyrido[2,3-b;4',3'-d]pyrrole-6-carbonitrile | K | D | B$^4$ | 6.80, 432, A | (CDCl$_3$ plus CD$_3$OD, 300 MHz): 8.97 (s, 1H), 8.83 (d, J = 2.2 Hz, 1H), 8.60 (d, J = 2.2 Hz, 1H), 8.46 (d, J = 1.0 Hz, 1H), 7.26 (d, J = 1.7 Hz, 1H), 6.98 (d, J = 1.7 Hz, 1H), 3.90 (s, 3H), 3.77 (s, 2H), 2.70-2.55 (m, 4H), 1.68-1.55 (m, 4H), 1.51-1.37 (m, 2H). |
| 59 | 3-(3-Methoxy-5-methyl-4-piperidin-1-ylmethyl-phenyl)-9H-dipyrido[2,3-b;4',3'-d]pyrrole-6-carbonitrile | K | D | B$^4$ | 6.68, 412, A | (CDCl$_3$, 300 MHz): 8.93 (s, 1H), 8.82-8.80 (m, 1H), 8.59 (d, J = 2.1 Hz, 1H), 8.42 (s, 1H), 7.02 (s, 1H), 6.91 (s, 1H), 3.84 (s, 3H), 3.50 (s, 2H), 2.48-2.34 (m, 7H), 1.55-1.43 (m, 4H), 1.43-1.31 (m, 2H). |
| 60 | 3-(3-Ethoxy-4-piperidin-1-ylmethyl-phenyl)-9H-dipyrido[2,3-b;4',3'-d]pyrrole-6-carbonitrile | G | D | B$^4$ | 6.78, 412, A | (DMSO-D$_6$, 400 MHz): 12.94 (s, 1H), 9.12 (s, 1H), 9.07 (s, 1H), 9.05 (d, J = 1.1 Hz, 1H), 8.94 (d, J = 1.0 Hz, 1H), 7.52 (s, 1H), 7.41 (m, 2H), 4.23 (d, J = 7.8 Hz, 2H), 1.72-1.50 (m, 4H), 1.49-1.33 (m, 5H). |

TABLE 4-continued

| Example | Structure/Name | Coupling Method | Deprotection Method | Purification Method (s) | LCMS R_T, M + H+, Method | 1H NMR (ppm) |
|---|---|---|---|---|---|---|
| 61 | 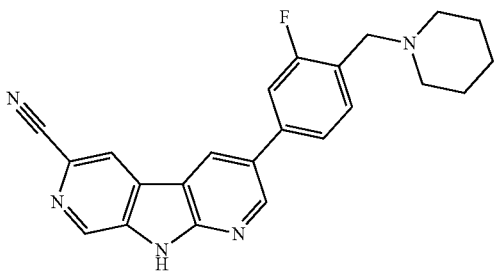 [SMILES: N#Cc1cc2c(cn1)[nH]c1ncc(-c3ccc(CN4CCCCC4)c(F)c3)cc12]<br>3-(3-Fluoro-4-piperidin-1-ylmethyl-phenyl)-9H-dipyrido[2,3-b;4',3'-d]pyrrole-6-carbonitrile | G | D | B$^4$ | 6.13, 386, A | (DMSO-D$_6$ plus TFA-D, 400 MHz): 9.22 (d, J = 2.3 Hz, 1H), 9.14 (d, J = 2.3 Hz, 1H), 9.09 (d, J = 1.0 Hz, 1H), 8.92 (d, J = 1.0 Hz, 1H), 7.82-7.91 (m, 2H), 7.78 (t, J = 7.8 Hz, 1H), 4.44 (s, 2H), 3.40-3.52 (m, 2H), 2.96-3.09 (m, 2H), 1.81-1.94 (m, 2H), 1.62-1.78 (m, 2H), 1.36-1.50 (m, 1H), 1.20-1.34 (m, 1H). |
| 62 | 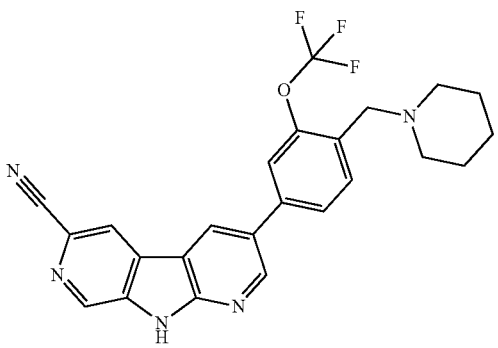 [SMILES: N#Cc1cc2c(cn1)[nH]c1ncc(-c3ccc(CN4CCCCC4)c(OC(F)(F)F)c3)cc12]<br>3-(4-Piperidin-1-ylmethyl-3-trifluoromethoxy-phenyl)-9H-dipyrido[2,3-b;4',3'-d]pyrrole-6-carbonitrile | G | D | B$^4$ | 6.91, 452, A | (DMSO-D$_6$, 400 MHz): 12.96 (br s, 1H), 9.14 (d, J = 2.3 Hz, 1H), 9.06-9.04 (m, 2H), 8.95 (d, J = 1.1 Hz, 1H), 7.86 (dd, J = 8.0, 1.8 Hz, 1H), 7.76-7.74 (m, 1H), 7.72 (d, J = 8.1 Hz, 1H), 3.55 (s, 2H), 2.43-2.35 (m, 4H), 1.57-1.48 (m, 4H), 1.46-1.36 (m, 2H). |
| 63 | 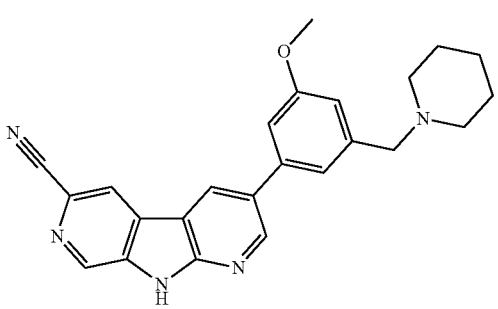 [SMILES: COc1cc(CN2CCCCC2)cc(-c2cnc3[nH]c4cnc(C#N)cc4c3c2)c1]<br>3-(3-Methoxy-5-piperidin-1-ylmethyl-phenyl)-9H-dipyrido[2,3-b;4',3'-d]pyrrole-6-carbonitrile | G | D | B$^4$ | 6.37, 398, A | (CDCl$_3$ plus DMSO-D$_6$, 400 MHz): 9.02 (s, 1H), 8.91-8.87 (m, 1H), 8.70-8.66 (m, 1H), 8.48 (s, 1H), 7.24 (s, 1H), 7.09 (s, 1H), 6.99 (s, 1H), 3.92 (s, 3H), 3.57 (s, 2H), 2.53-2.39 (s, 4H), 1.69-1.58 (m, 4H), 1.54-1.42 (m, 2H). |
| 64 | 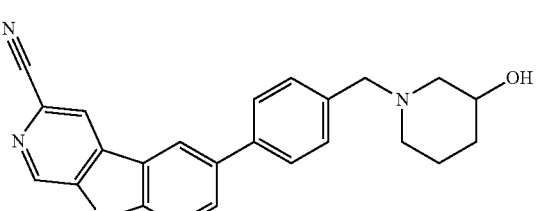<br>3-[4-(3-Hydroxy-piperidin-1-ylmethyl)-phenyl]-9H-dipyrido[2,3-b;4',3'-d]pyrrole-6-carbonitrile | G | D | B$^4$ | 5.39, 384, A | (DMSO-D$_6$, 400 MHz): 12.91 (s, 1H), 9.08 (d, J = 2.3 Hz, 1H), 9.04 (d, J = 1.1 Hz, 1H), 9.02 (d, J = 2.3 Hz, 1H), 8.94 (d, J = 1.1 Hz, 1H), 7.77 (d, J = 8.1 Hz, 2H), 7.46 (d, J = 8.0 Hz, 2H), 4.58 (d, J = 4.8 Hz, 1H), 3.58 (d, J = 13.3 Hz, 1H), 3.53-3.43 (m, 2H), 2.83 (dd, J = 10.4, 3.9 Hz, 1H), 2.72-2.65 (m, 1H), 1.94-1.86 (m, 1H), 1.85-1.78 (m, 1H), 1.77-1.70 (m, 1H), 1.67-1.59 (m, 1H), 1.51-1.38 (m, 1H), 1.13-1.02 (m, 1H). |

TABLE 4-continued

| Example | Structure/Name | Coupling Method | Deprotection Method | Purification Method (s) | LCMS R$_T$, M + H$^+$, Method | $^1$H NMR (ppm) |
|---|---|---|---|---|---|---|
| 65 | 3-[4-(4-Fluoro-piperidin-1-ylmethyl)-phenyl]-9H-dipyrido[2,3-b;4',3'-d]pyrrole-6-carbonitrile | G | D | B$^4$ | 5.95, 386, A | (DMSO-D$_6$, 400 MHz): 12.91 (s, 1H), 9.08 (d, J = 2.3 Hz, 1H), 9.05 (d, J = 1.1 Hz, 1H), 9.02 (d, J = 2.3 Hz, 1H), 8.94 (d, J = 1.0 Hz, 1H), 7.78 (d, J = 7.8 Hz, 2H), 7.47 (d, J = 7.8 Hz, 2H), 4.81-4.60 (m, 1H), 3.55 (s, 2H), 2.62-2.49 (m, 2H), 2.39-2.28 (m, 2H), 1.96-1.80 (m, 2H), 1.80-1.67 (s, 2H). |
| 66 | 3-(2-Ethyl-1,2,3,4-tetrahydro-isoquinolin-7-yl)-9H-dipyrido[2,3-b;4',3'-d]pyrrole-6-carbonitrile | G | D | B | 5.53, 354, A | (DMSO-D$_6$, 400 MHz): 12.86 (s, 1H), 9.05 (d, J = 2.3 Hz, 1H), 9.03 (d, J = 1.1 Hz, 1H), 8.98 (d, J = 2.3 Hz, 1H), 8.93 (d, J = 1.1 Hz, 1H), 7.56 (dd, J = 7.9, 1.9 Hz, 1H), 7.51 (d, J = 1.9 Hz, 1H), 7.27 (d, J = 7.9 Hz, 1H), 3.65 (s, 2H), 2.90-2.83 (m, 2H), 2.73-2.66 (m, 2H), 2.57-2.51 (m, 2H), 1.13 (t, J = 7.2 Hz, 3H). |
| 67 | 3-(2-Ethyl-1,2,3,4-tetrahydro-isoquinolin-6-yl)-9H-dipyrido[2,3-b;4',3'-d]pyrrole-6-carbonitrile | G | D | B | 5.68, 354, A | (CDCl$_3$ plus CD$_3$OD, 400 MHz): 9.01 (d, J = 1.0 Hz, 1H), 8.87 (d, J = 2.2 Hz, 1H), 8.66 (d, J = 2.2 Hz, 1H), 8.48 (d, J = 1.0 Hz, 1H), 7.47-7.42 (m, 2H), 7.22 (d, J = 7.8 Hz, 1H), 3.78 (s, 2H), 3.13-3.02 (m, 2H), 2.94-2.83 (m, 2H), 2.76-2.65 (m, 2H), 1.26 (t, J = 7.2 Hz, 3H) |
| 68 | 3-[4-(4-Trifluoromethyl-piperidin-1-ylmethyl)-phenyl]-9H-dipyrido[2,3-b;4',3'-d]pyrrole-6-carbonitrile | G | D | B | 6.58, 436, A | (CDCl$_3$ plus CD$_3$OD, 400 MHz): 9.02 (d, J = 1.0 Hz, 1H), 8.89 (d, J = 2.2 Hz, 1H), 8.67 (d, J = 2.2 Hz, 1H), 8.47 (d, J = 1.0 Hz, 1H), 7.64 (d, J = 7.9 Hz, 2H), 7.49 (d, J = 7.9Hz, 2H), 3.61 (s, 2H), 3.08-3.01 (m, 2H), 2.11-1.99 (m, 3H), 1.91-1.83 (m, 2H), 1.75-1.61 (m, 2H). |
| 69 | 3-(4-[1,4]Oxazepan-4-ylmethyl-phenyl)-9H-dipyrido[2,3-b;4',3'-d]pyrrole-6-carbonitrile | G | D | B | 5.68, 384, A | (CDCl$_3$ plus CD$_3$OD, 400 MHz): 9.02 (s, 1 H), 8.90 (d, J = 2.2 Hz, 1H), 8.68 (d, J = 2.2 Hz, 1H), 8.48 (s, 1H), 7.65 (d, J = 7.8 Hz, 2H), 7.53 (d, J = 7.7 Hz, 2H), 3.87 (t, J = 6.1 Hz, 2H), 3.81-3.74 (m, 4H), 2.84-2.69 (m, 4H), 2.02-1.90 (s, 2H). |

TABLE 4-continued

| Example | Structure/Name | Coupling Method | Deprotection Method | Purification Method (s) | LCMS R_T, M + H+, Method | ¹H NMR (ppm) |
|---|---|---|---|---|---|---|
| 70 | 3-[4-(2-Aza-bicyclo[2.2.1]hept-2-ylmethyl)-phenyl]-9H-dipyrido[2,3-b;4',3'-d]pyrrole-6-carbonitrile | G | D | B | 6.11, 380, A | (CDCl₃ plus CD₃OD, 400 MHz): 9.03-9.00 (m, 1H), 8.91-8.88 (m, 1H), 8.70-8.67 (m, 1H), 8.50-8.48 (m, 1H), 7.64 (d, J = 7.8 Hz, 2H), 7.52 (d, J = 7.9 Hz, 2H), 3.80-3.68 (m, 2H), 3.18 (s, 1H), 2.86-2.80 (m, 1H), 2.41 (s, 1H), 2.34 (d, J = 9.3 Hz, 1H), 1.93-1.83 (m, 1H), 1.79-1.72 (m, 1H), 1.68-1.56 (m, 1H), 1.53-1.43 (m, 1H), 1.42-1.39 (m, 2H). |
| 71 | 3-(4-Azepan-1-ylmethyl-phenyl)-9H-dipyrido[2,3-b;4',3'-d]pyrrole-6-carbonitrile | G | D | B | 6.36, 382, A | (CDCl₃ plus CD₃OD, 400 MHz): 9.02-9.00 (m, 1H), 8.91-8.89 (m, 1H), 8.71-8.68 m, 1H), 8.50-8.48 (m, 1H), 7.66-7.62 (m, 2H), 7.53-7.49 (m, 2H), 3.74 (s, 2H), 3.42-3.35 (m, 4H), 2.74-2.67 (m, 5H), 1.74-1.62 (m, 3H). |
| 72 | 3-[4-(8-Aza-bicyclo[3.2.1]oct-8-ylmethyl)-phenyl]-9H-dipyrido[2,3-b;4',3'-d]pyrrole-6-carbonitrile | G | D | B | 6.31, 394, A | (CDCl₃ plus CD₃OD, 400 MHz): 9.02 (d, J = 1.0 Hz, 1H), 8.90 (d, J = 2.2 Hz, 1H), 8.69 (d, J = 2.2 Hz, 1H), 8.49 (d, J = 1.0 Hz, 1H), 7.66-7.62 (m, 2H), 7.58-7.53 (m, 2H), 3.64-3.59 (m, 2H), 3.26-3.21 (m, 2H), 2.14-1.99 (m, 2H), 1.86-1.75 (m, 2H), 1.71-1.64 (m, 2H), 1.63-1.46 (m, 2H), 1.44-1.36 (m, 2H). |
| 73 | 3-[4-(4-Methoxy-piperidin-1-ylmethyl)-phenyl]-9H-dipyrido[2,3-b;4',3'-d]pyrrole-6-carbonitrile | G | D | B | 5.89, 398, A | (CDCl₃ plus CD₃OD, 400 MHz): 9.02 (d, J = 1.0 Hz, 1H), 8.90 (d, J = 2.2 Hz, 1H), 8.69 (d, J = 2.2 Hz, 1H), 8.50 (d, J = 1.0 Hz, 1H), 7.67-7.60 (m, 2H), 7.49 (d, J = 8.0 Hz, 2H), 3.60 (s, 2H), 3.36 (s, 3H), 3.33-3.24 (m, 2H), 2.30-2.21 (m, 2H), 1.99-1.89 (m, 2H), 1.71-1.60 (m, 2H). |
| 74 | 3-[4-(4-Hydroxy-4-methyl-piperidin-1-ylmethyl)-phenyl]-9H-dipyrido[2,3-b;4',3'-d]pyrrole-6-carbonitrile | G | D | B | 5.69, 398, A | (CDCl₃ plus CD₃OD, 400 MHz): 9.02-9.01 (m, 1H), 8.90 (d, J = 2.2 Hz, 1H), 8.69 (d, J = 2.2 Hz, 1H), 8.49 (d, J = 1.0 Hz, 1H), 7.66-7.62 (m, 2H), 7.50 (d, J = 8.0 Hz, 2H), 3.63 (s, 2H), 3.16 (s, 1H), 2.64-2.56 (m, 2H), 2.55-2.46 (m, 2H), 1.75-1.60 (m, 4H), 1.26 (s, 3H). |

TABLE 4-continued

| Example | Structure/Name | Coupling Method | Deprotection Method | Purification Method (s) | LCMS $R_T$, M + H+, Method | 1H NMR (ppm) |
|---|---|---|---|---|---|---|
| 75 | 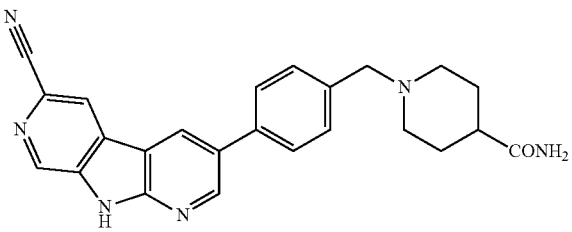 [SMILES: N#Cc1cc2c(cn1)[nH]c1ncc(-c3ccc(CN4CCC(C(N)=O)CC4)cc3)cc12]<br>1-[4-(6-Cyano-9H-dipyrido[2,3-b;4',3'-d]pyrrol-3-yl-)-benzyl]-piperidine-4-carboxylic acid amide | G | D | B | 5.58, 411, A | (DMSO-D$_6$, 400 MHz): 12.89 (s, 1H), 9.08 (d, J = 2.2 Hz, 1H), 9.04 (d, J = 1.1 Hz, 1H), 9.02 (d, J = 2.3 Hz, 1H), 8.94 (d, J = 1.1 Hz, 1H), 7.77 (d, J = 7.8 Hz, 2H), 7.46 (d, J = 7.9 Hz, 2H), 7.20 (s, 1H), 6.70 (s, 1H), 3.52 (s, 2H), 2.89-2.82 (m, 2H), 2.11-2.01 (m, 1H), 2.00-1.89 (m, 2H), 1.72-1.64 (m, 2H), 1.63-1.50 (m, 2H). |
| 76 | 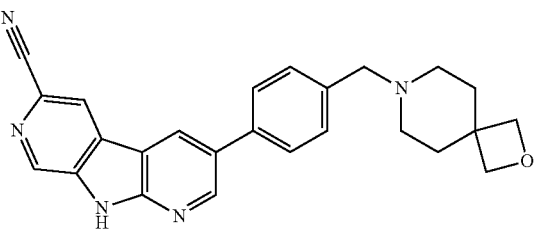 [SMILES: N#Cc1cc2c(cn1)[nH]c1ncc(-c3ccc(CN4CCC5(CC4)COC5)cc3)cc12]<br>3-[4-(4-Cyano-piperidin-1-ylmethyl)-phenyl]-9H-dipyrido[2,3-b;4',3'-d]pyrrole-6-carbonitrile | G | D | B | 5.77, 410, A | (CDCl$_3$ plus CD$_3$OD, 400 MHz): 9.02 (d, J = 1.0 Hz, 1H), 8.90 (d, J = 2.2 Hz, 1H), 8.69 (d, J = 2.2 Hz, 1H), 8.49 (d, J = 1.0 Hz, 1H), 7.67-7.62 (m, 2H), 7.48 (d, J = 8.0 Hz, 2H), 4.45 (s, 4H), 3.56 (s, 2H), 2.48-2.31 (m, 4H), 1.97-1.87 (m, 4H). |
| 77 | 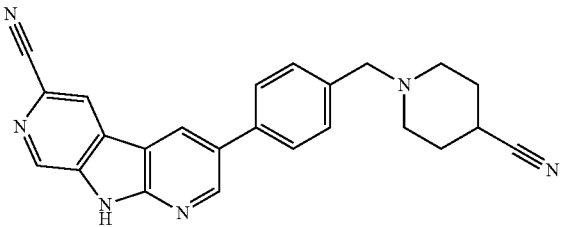 [SMILES: N#Cc1cc2c(cn1)[nH]c1ncc(-c3ccc(CN4CCC(C#N)CC4)cc3)cc12]<br>3-[4-(4-Cyano-piperidin-1-ylmethyl)-phenyl]-9H-dipyrido[2,3-b;4',3'-d]pyrrole-6-carbonitrile | G | D | B | 5.86, 393, A | (CDCl$_3$ plus CD$_3$OD, 400 MHz): 9.02 (d, J = 1.1 Hz, 1H), 8.89 (d, J = 2.2 Hz, 1H), 8.68 (d, J = 2.2 Hz, 1H), 8.48 (d, J = 1.1 Hz, 1H), 7.67-7.61 (m, 2H), 7.48 (d, J = 8.0 Hz, 2H), 3.61 (s, 2H), 2.77-2.66 (m, 3H), 2.49-2.36 (s, 2H), 2.03-1.86 (m, 4H). |
| 78 | 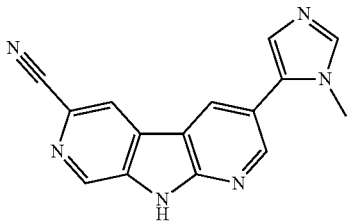 [SMILES: Cn1cncc1-c1cnc2[nH]c3cnc(C#N)cc3c2c1]<br>3-(3-Methyl-3H-imidazol-4-yl)-9H-dipyrido[2,3-b;4',3'-d]pyrrole-6-carbonitrile | F | D | L, G | 4.33, 275, A | (DMSO-D$_6$, 300 MHz): 12.98 (br s, 1H), 9.06 (s, 1H), 8.96 (s, 1H), 8.92 (s, 1H), 8.83 (s, 1H), 7.81 (s, 1H), 7.20 (s, 1H), 3.76 (s, 3H). |
| 79 | 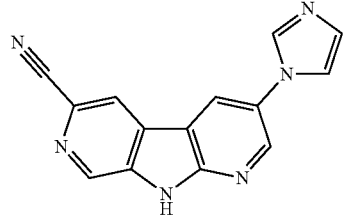 [SMILES: N#Cc1cc2c(cn1)[nH]c1ncc(-n3ccnc3)cc12]<br>3-Imidazol-1-yl-9H-dipyrido[2,3-b;4',3'-d]pyrrole-6-carbonitrile | Buchwald A | D | L[4] | 4.16, 261, A | (DMSO-D$_6$, 300 MHz): 13.35 (s, 1H), 9.70 (s, 1H), 9.21 (d, J = 2.6 Hz, 1H), 9.15 (s, 1H), 9.12 (d, J = 2.6 Hz, 1H), 8.92 (s, 1H), 8.32 (s, 1H), 7.99 (s, 1H). |

TABLE 4-continued

| Example | Structure/Name | Coupling Method | Deprotection Method | Purification Method(s) | LCMS $R_T$, M + H+, Method | $^1$H NMR (ppm) |
|---|---|---|---|---|---|---|
| 80 | 3-(1-Methyl-1H-pyrazol-3-yl)-9H-dipyrido[2,3-b;4',3'-d]pyrrole-6-carbonitrile | F | D | L$^4$ | 7.44, 275, A | (DMSO-D$_6$, 300 MHz): 12.88 (br s, 1H), 9.14 (s, 2H), 9.02 (s, 1H), 8.98 (s, 1H), 7.82 (s, 1H), 6.84 (s, 1H), 3.94 (s, 3H). |
| 81 | 3-(2-Methyl-2H-[1,2,4]triazol-3-yl)-9H-dipyrido[2,3-b;4',3'-d]pyrrole-6-carbonitrile | F | D | L$^4$ | 6.05, 276, A | (DMSO-D$_6$, 300 MHz): 13.16 (br s, 1H), 9.24-9.19 (m, 1H), 9.13-9.06 (m, 2H), 9.03 (s, 1H), 8.10 (s, 1H), 4.09 (s, 3H). |
| 82 | 3-(2,3-Dihydro-benzo[1,4]dioxin-6-yl)-9H-dipyrido[2,3-b;4',3'-d]pyrrole-6-carbonitrile | F | D | A$^4$ | 9.72, 329, A | (DMSO-D$_6$, 300 MHz): 12.86 (br s, 1H), 8.87-9.07 (m, 4H), 7.28 (d, J = 2.2 Hz, 1H), 7.23 (dd, J = 8.4, 2.3 Hz, 1H), 7.02 (d, J = 8.3 Hz, 1H), 4.27 (s, 4H). |
| 83 | 3-(1H-Imidazol-2-yl)-9H-dipyrido[2,3-b;4',3'-d]pyrrole-6-carbonitrile | A | D | L, B | 4.32, 261, A | (DMSO-D$_6$, 400 MHz): 12.93 (s, 1H), 12.74 (s, 1H), 9.26 (m, 2H), 9.05 (d, J = 1.1 Hz, 1H), 8.96 (d, J = 1.1 Hz, 1H), 7.34 (s, 1H), 7.12 (s, 1H). |
| 84 | 3-(2-Ethyl-8-methoxy-1,2,3,4-tetrahydro-isoquinolin-6-yl)-9H-dipyrido[2,3-b;4',3'-d]pyrrole-6-carbonitrile | A | D | L, B | 6.04, 384, A | (CDCl$_3$ plus CD$_3$OD, 400 MHz): 9.01 (d, J = 1.0 Hz, 1H), 8.87 (d, J = 2.2 Hz, 1H), 8.65 (d, J = 2.2 Hz, 1H), 8.50 (d, J = 1.0 Hz, 1H), 7.03 (d, J = 1.3 Hz, 1H), 6.92 (d, J = 1.6 Hz, 1H), 3.94 (s, 3H), 3.67 (s, 2H), 3.03 (t, J = 5.9 Hz, 2H), 2.81 (t, J = 5.9 Hz, 2H), 2.70 (q, J = 7.2 Hz, 2H), 1.26 (t, J = 7.2 Hz, 3H). |

TABLE 4-continued

| Example | Structure/Name | Coupling Method | Deprotection Method | Purification Method(s) | LCMS $R_T$, M + H+, Method | $^1$H NMR (ppm) |
|---|---|---|---|---|---|---|
| 85 | 3-[4-((3S,5R)-3,5-Dimethyl-piperidin-1-ylmethyl)-phenyl]-9H-dipyrido[2,3-b;4',3'-d]pyrrole-6-carbonitrile | A | D | L, B | 6.68, 396, A | (DMSO-D$_6$ plus TFA-D, 400 MHz): 13.00 (s, 1H), 9.15 (d, J = 2.3 Hz, 1H), 9.09 (d, J = 2.3 Hz, 1H), 9.07 (d, J = 1.1 Hz, 1H), 8.94 (d, J = 1.1 Hz, 1H), 7.94 (d, J = 7.9 Hz, 2H), 7.75 (d, J = 8.0 Hz, 2H), 4.39-4.32 (m, 2H), 3.34-3.26 (m, 2H), 2.05-1.91 (m, 2H), 1.80-1.72 (m, 1H), 0.90 (s, 3H), 0.89 (s, 3H). |
| 86 | 3-[4-(4-Morpholin-4-yl-piperidin-1-ylmethyl)-phenyl]-9H-dipyrido[2,3-b;4',3'-d]pyrrole-6-carbonitrile | F | D | E$^5$ | 4.7, 453, A | (CDCl$_3$, 400 MHz): 10.17 (s, 1H), 9.09 (s, 1H), 8.97-8.96 (m, 1H), 8.65 (dd, J = 2.2, 0.9 Hz, 1H), 8.45 (s, 1H), 7.63 (d, J = 7.9 Hz, 2H), 7.50 (d, J = 7.9 Hz, 2H), 3.73 (t, J = 4.4 Hz, 4H), 3.59 (s, 2H), 3.04-2.97 (m, 2H), 2.57 (t, J = 4.4 Hz, 4H), 2.28-2.18 (m, 1H), 2.09-1.99 (m, 2H), 1.88-1.80 (m, 2H), 1.67-1.53 (m, 2H). |
| 87 | 3-[4-(4-Dimethylamino-piperidin-1-ylmethyl)-phenyl]-9H-dipyrido[2,3-b;4',3'-d]pyrrole-6-carbonitrile | F | D | E$^3$ | 4.6, 411, A | (DMSO-D$_6$, 400 MHz): 12.84 (br s, 1H), 9.08 (d, J = 2.3 Hz, 1H), 9.04 (d, J = 1.1 Hz, 1H), 9.02 (d, J = 2.3 Hz, 1H), 8.95 (d, J = 1.0 Hz, 1H), 7.76 (d, J = 8.0 Hz, 2H), 7.46 (d, J = 8.0 Hz, 2H), 3.51 (s, 2H), 2.90-2.83 (m, 2H), 2.17 (s, 6H), 2.10-2.01 (m, 1H), 2.00-1.90 (m, 2H), 1.76-1.67 (m, 2H), 1.45-1.31 (m, 2H). |
| 88 | 3-[4-(2,2-Dimethyl-morpholin-4-ylmethyl)-phenyl]-9H-dipyrido[2,3-b;4',3'-d]pyrrole-6-carbonitrile | G$^a$ | D | R, B$^3$ | 5.95, 398, A | (CDCl$_3$ plus CD$_3$OD, 300 MHz): 9.02 (d, J = 1.0 Hz, 1H), 8.93 (d, J = 2.2 Hz, 1H), 8.83 (d, J = 2.2 Hz, 1H), 8.64 (d, J = 1.1 Hz, 1H), 7.69 (d, J = 8.0 Hz, 2H), 7.52 (d, J = 8.0 Hz, 2H), 3.83-3.78 (m, 2H), 3.57 (s, 2H), 2.53-2.45 (m, 2H), 2.28 (s, 2H), 1.29 (s, 6H). |

TABLE 4-continued

| Example | Structure/Name | Coupling Method | Deprotection Method | Purification Method (s) | LCMS R_T, M + H+, Method | ¹H NMR (ppm) |
|---|---|---|---|---|---|---|
| 89 | 3-[4-((2R,6S)-2,6-Dimethyl-morpholin-4-ylmethyl)-phenyl]-9H-dipyrido[2,3-b;4',3'-d]pyrrole-6-carbonitrile | G$^a$ | D | B$^3$ | 5.98, 398, A | (CDCl₃ plus CD₃OD, 300 MHz): 9.02 (d, J = 1.0 Hz, 1H), 8.93 (d, J = 2.2 Hz, 1H), 8.80 (d, J = 2.2 Hz, 1H), 8.61 (d, J = 1.1 Hz, 1H), 7.70 (d, J = 8.0 Hz, 2H), 7.51 (d, J = 8.0 Hz, 2H), 3.83-3.69 (m, 2H), 3.61 (s, 2H), 2.85-2.76 (m, 2H), 1.92-1.80 (m, 2H), 1.18 (d, J = 6.3 Hz, 6H). |
| 90 | 3-[4-((2R,6S)-2,6-Dimethyl-morpholin-4-ylmethyl)-3-ethoxy-phenyl]-9H-dipyrido[2,3-b;4',3'-d]pyrrole-6-carbonitrile | G$^a$ | D | R, B | 7.51, 442, F | (CDCl₃ plus CD₃OD, 300 MHz): 9.02 (d, J = 1. Hz, 1H), 8.92 (d, J = 2.2 Hz, 1H), 8.81 (d, J = 2.2 Hz, 1H), 8.64 (d, J = 1.1 Hz, 1H), 7.47 (d, J = 7.8 Hz, 1H), 7.28 (dd, J = 7.7, 1.7 Hz, 1H), 7.21 (d, J = 1.7 Hz, 1H), 4.22 (q, J = 7.0 Hz, 2H), 3.82-3.69 (m, 2H), 3.68 (s, 2H), 2.89-2.80 (m, 2H), 1.99-1.88 (m, 2H), 1.51 (t, J = 7.0 Hz, 3H), 1.18 (d, J = 6.3 Hz, 6H). |
| 91 | 3-(4,5,6,7-Tetrahydro-benzo[b]thiophen-2-yl)-9H-dipyrido[2,3-b;4',3'-d]pyrrole-6-carbonitrile | F | D | A, H$^7$ | 12.5, 331, A | (DMSO-D₆, 300 MHz): 12.90 (s, 1H), 9.02 (d, J = 1.1 Hz, 1H), 8.95 (d, J = 2.3 Hz, 2H), 8.93 (d, J = 2.3 Hz, 1H), 7.29 (s, 1H), 2.81-2.74 (m, 2H), 2.66-2.60 (m, 2H), 1.88-1.73 (m, 4H). |
| 92 | 4-(6-Cyano-9H-dipyrido[2,3-b;4',3'-d]pyrrol-6-carbonitrile | F$^b$ | D | B$^9$, H$^9$ | 7.93, 315, A | (DMSO-D₆, 300 MHz): 13.00 (s, 1H), 9.20 (d, J = 2.2 Hz, 1H), 9.10 (d, J = 2.2 Hz, 1H), 9.06 (s, 1H), 8.96 (s, 1H), 8.11 (d, J = 8.3 Hz, 2H), 7.96 (d, J = 8.3 Hz, 2H). |
| 93 | 3-[4-(2-Oxa-6-aza-spiro[3.3]hept-6-ylmethyl)-phenyl]-9H-dipyrido[2,3-b;4',3'-d]pyrrole-6-carbonitrile | F$^c$ | D | H$^3$ | 5.57, 382, A | (DMSO-D₆, 400 MHz): 12.90 (s, 1H), 9.07 (d, J = 2.3 Hz, 1H), 9.04 (d, J = 1.1 Hz, 1H), 9.01 (d, J = 2.3 Hz, 1H), 8.94 (d, J = 1.1 Hz, 1H), 7.75 (d, J = 8.0 Hz, 2H), 7.41 (d, J = 8.0 Hz, 2H), 4.63 (s, 4H), 3.56 (s, 2H). |

TABLE 4-continued

| Example | Structure/Name | Coupling Method | Deprotection Method | Purification Method (s) | LCMS R$_T$, M + H$^+$, Method | $^1$H NMR (ppm) |
|---|---|---|---|---|---|---|
| 94 | 3-[4-(2-Piperidin-1-yl-ethyl)-phenyl]-9H-dipyrido[2,3-b;4',3'-d]pyrrole-6-carbonitrile | G | D | B,$^3$ | 6.23, 382, A | (CDCl$_3$ plus CD$_3$OD, 400 MHz): 9.01 (d, J = 1.0 Hz, 1 H), 8.88 (d, J = 2.2 Hz, 1H), 8.67 (d, J = 2.2 Hz, 1 H), 8.49 (d, J = 1.0 Hz, 1H), 7.62-7.57 (m, 2H), 7.41-7.36 (m, 2H), 2.95-2.87 (m, 2H), 2.68-2.61 (m, 2H), 2.54 (s, 4H), 1.71-1.62 (m, 4H), 1.56-1.46 (m, 2H). |
| 95 | (Z)-3-(5-[4-(3-Hydroxy-3-methyl-piperidin-1-ylmethyl)-phenyl]-2-methyl-1H-pyrrolo-[2,3-b]pyridin-3-yl)-2-methyleneamino-acrylonitrile | G | D | E | 5.48, 416, (M + 18), A | (DMSO-D$_6$, 400 MHz): 9.08 (d, J = 2.3 Hz, 1H), 9.04 (d, J = 1.1 Hz, 1H), 9.02 (d, J = 2.3 Hz, 1H), 8.94 (d, J = 1.1 Hz, 1 H), 7.76 (d, J = 8.0 Hz, 2H), 7.51 (d, J = 8.0 Hz, 2H), 4.36 (s, 1H), 3.81 (s, 2H), 3.40-3.34 (m, 2H), 2.42 (s, 2H), 1.46-1.38 (m, 4H), 1.08 (s, 3H). |
| 96 | 3-[4-(4-Methoxy-4-methyl-piperidin-1-ylmethyl)-phenyl]-9H-dipyrido[2,3-b;4',3'-d]pyrrole-6-carbonitrile | G | D | B | 6.27, 412, (M + 18), A | (CDCl$_3$ plus CD$_3$OD, 400 MHz): 9.01 (d, J = 1.0 Hz, 1H), 8.89 (d, J = 2.2 Hz, 1H), 8.68 (d, J = 2.2 Hz, 1H), 8.48 (d, J = 1.1 Hz, 1H), 7.66-7.62 (m, 2H), 7.52-7.48 (m, 2H), 3.60 (s, 2H), 3.20 (s, 3H), 2.63-2.55 (m, 2H), 2.46-2.36 (m, 2H), 1.85-1.76 (m, 2H), 1.65-1.55 (m, 2H), 1.18 (s, 3H). |
| 97 | 3-(4-Thiomorpholin-4-ylmethyl-phenyl)-9H-dipyrido[2,3-b;4',3'-d]pyrrole-6-carbonitrile | G | D | B | 5.98, 386, A | (CDCl$_3$ plus CD$_3$OD, 400 MHz): 9.02 (d, J = 1.0 Hz, 1H), 8.89 (d, J = 2.2 Hz, 1H), 8.67 (d, J = 2.2 Hz, 1H), 8.47 (d, J = 1.1 Hz, 1H), 7.66-7.61 (m, 2H), 7.51-7.46 (m, 2 H), 3.62 (s, 2H), 2.81-2.76 (m, 4H), 2.75-2.69 (m, 4H). |

TABLE 4-continued

| Example | Structure/Name | Coupling Method | Deprotection Method | Purification Method (s) | LCMS R$_T$, M + H$^+$, Method | $^1$H NMR (ppm) |
|---|---|---|---|---|---|---|
| 98 | 3-[4-(1,1-Dioxo-1lambda*6*-thiomorpholin-4-ylmethyl)-phenyl]-9H-dipyrido[2,3-b;4',3'-d]pyrrole-6-carbonitrile | G | D | L, B$^{3,1}$ | 7.43, 418, A | (DMSO-D$_6$, 400 MHz): 12.91 (s, 1H), 9.09 (d, J = 2.3 Hz, 1H), 9.05 (d, J = 1.1 Hz, 1H), 9.03 (d, J = 2.3 Hz, 1H), 8.94 (d, J = 1.1 Hz, 1H), 7.82-7.77 (m, 2H), 7.54-7.49 (m, 2H), 3.76 (s, 2H), 3.18-3.10 (m, 4H), 2.97-2.89 (m, 4H). |
| 99 | 3-[4-(1-Oxo-thiomorpholin-4-ylmethyl)-phenyl]-9H-dipyrido[2,3-b;4',3'-d]pyrrole-6-carbonitrile | G | D | B | 5.34, 402, A | (DMSO-D$_6$, 400 MHz): 12.91 (s, 1H), 9.09 (d, J = 2.3 Hz, 1H), 9.05 (d, J = 1.1 Hz, 1H), 9.03 (d, J = 2.3 Hz, 1H), 8.94 (d, J = 1.1 Hz, 1H), 7.81-7.76 (m, 2H), 7.53-7.48 (m, 2H), 3.66 (s, 2H), 2.97-2.84 (m, 4H), 2.82-2.62 (m, 4H). |
| 100 | 3-[4-(3-Oxo-piperazin-1-ylmethyl)-phenyl]-9H-dipyrido[2,3-b;4',3'-d]pyrrole-6-carbonitrile | G | D | B | 5.50, 383, A | (CDCl$_3$ plus CD$_3$OD, 400 MHz): 9.02 (s, 1H), 8.90 (d, J = 2.2 Hz, 1H), 8.72 (d, J = 2.2 Hz, 1H), 8.53 (s, 1H), 7.67 (d, J = 7.9 Hz, 2H), 7.51 (d, J = 7.9 Hz, 2H), 3.70 (s, 2H), 3.42-3.36 (m, 2H), 3.20 (s, 2H), 2.76-2.71 (m, 2H). |
| 101 | 3-(4-Diethylaminomethyl-phenyl)-9H-dipyrido[2,3-b;4',3'-d]pyrrole-6-carbonitrile | G | D | B, B$^3$ | 5.90, 356, A | (CDCl$_3$, 400 MHz): 10.27 (s, 1H), 9.09 (s, 1H), 8.98 (d, J = 2.2 Hz, 1H), 8.66 (d, J = 2.2 Hz, 1H), 8.45 (s, 1H), 7.63 (d, J = 7.9 Hz, 2H), 7.54 (d, J = 7.8 Hz, 2H), 3.68 (s, 2H), 2.66-2.54 (m, 4H), 1.11 (t, J = 7.1 Hz, 6H). |
| 102 | 3-[4-((S)-3-Hydroxy-piperidin-1-ylmethyl)-phenyl]-9H-dipyrido[2,3-b;4',3'-d]pyrrole-6-carbonitrile | G | D | B, B$^3$ | 5.45, 384, A | (CDCl$_3$ plus CD$_3$OD, 400 MHz): 9.02-9.00 (m, 1H), 8.90 (d, J = 2.2 Hz, 1H), 8.70 (d, J = 2.2 Hz, 1H), 8.51 (d, J = 1.0 Hz, 1H), 7.64 (d, J = 7.9 Hz, 2H), 7.48 (d, J = 7.9 Hz, 2H), 3.85-3.73 (m, 1H), 3.62 (s, 2H), 2.84-2.72 (m, 1H), 2.64-2.52 (m, 1H), 2.37-2.18 (m, 2H), 1.89-1.74 (m, 2H), 1.67-1.52 (m, 1H), 1.48-1.34 (m, 1H). |

TABLE 4-continued

| Example | Structure/Name | Coupling Method | Deprotection Method | Purification Method (s) | LCMS $R_T$, M + H+, Method | $^1$H NMR (ppm) |
|---|---|---|---|---|---|---|
| 103 | 3-[4-((R)-3-Hydroxy-piperidin-1-ylmethyl)-phenyl]-9H-dipyrido[2,3-b;4',3'-d]pyrrole-6-carbonitrile | G | D | B, B$^3$ | 5.54, 384, A | (CDCl$_3$ plus CD$_3$OD, 400 MHz): 9.02-9.00 (m, 1H), 8.90-8.87 (m, 1H), 8.70-8.66 (m, 1H), 8.50-8.48 (m, 1H), 7.66-7.61 (m, 2H), 7.50-7.45 (m, 2H), 3.84-3.75 (m, 1H), 3.61 (s, 2H), 2.79-2.70 (m, 1H), 2.59-2.50 (m, 1H), 2.37-2.22 (s, 2H), 1.85-1.75 (m, 2H), 1.64-1.52 (m, 1H), 1.48-1.37 (m, 1H). |
| 104 | 3-[4-((3S,5S)-3,5-Dimethyl-piperidin-1-ylmethyl)-phenyl]-9H-dipyrido[2,3-b;4',3'-d]pyrrole-6-carbonitrile | G | D | B, B$^3$ | 7.17, 396, F | (DMSO-D$_6$, 400 MHz): 12.89 (s, 1H), 9.08 (d, J = 2.3 Hz, 1H), 9.04 (d, J = 1.1 Hz, 1H), 9.02 (d, J = 2.3 Hz, 1H), 8.93 (d, J = 1.1 Hz, 1H), 7.77 (d, J = 8.1 Hz, 2H), 7.46 (d, J = 8.0 Hz, 2H), 3.54-3.40 (m, 2H), 2.44-2.35 (m, 2H), 2.12-1.98 (m, 2H), 1.94-1.82 (m, 2H), 1.31-1.24 (m, 2H), 0.94 (d, J = 6.8 Hz, 6H). |
| 105 | 3-(6-Piperidin-1-ylmethyl-pyridin-3-yl)-9H-dipyrido[2,3-b;4',3'-d]pyrrole-6-carbonitrile | F | B | R$^3$ | 5.51, 369, A | (DMSO-D$_6$, 400 MHz): 12.99 (s, 1H), 9.16 (dd, J = 5.4, 2.3 Hz, 1H), 9.09-9.07 (m, 2H), 8.95-8.93 (m, 2H), 8.21 (dd, J = 8.1, 2.5 Hz, 1H), 7.61 (d, J = 8.1 Hz, 1H), 3.64 (s, 2H), 2.44 (s, 4H), 1.56 (p, J = 5.5 Hz, 4H), 1.47-1.41 (m, 2H). |
| 106 | 3-(5-Piperidin-1-ylmethyl-pyridin-2-yl)-9H-dipyrido[2,3-b;4',3'-d]pyrrole-6-carbonitrile | F | B | R$^6$ | 5.46, 369, A | (DMSO-D$_6$, 400 MHz): 12.99 (s, 1H), 9.48 (d, J = 2.2 Hz, 1H), 9.43 (d, J = 2.2 Hz, 1H), 9.07 (d, J = 1.1 Hz, 1H), 9.04 (s, 1H), 8.65 (d, J = 2.1 Hz, 1H), 8.11 (d, J = 8.1 Hz, 1H), 7.89 (dd, J = 8.2, 2.2 Hz, 1H), 3.55 (s, 2H), 2.36 (s, 4H), 1.58-1.50 (m, 4H), 1.43 (d, J = 7.0 Hz, 2H). |
| 107 | 3-(3-Chloro-4-piperidin-1-ylmethyl-phenyl)-9H-dipyrido[2,3-b;4',3'-d]pyrrole-6-carbonitrile | G | D | R$^{3/7}$ | 6.38, 402, A | (CD$_3$OD, 400 MHz): 8.83 (d, J = 2.1 Hz, 1H), 8.70 (s, 1H), 8.62 (d, J = 2.1 Hz, 1H), 8.08 (s, 1H), 7.92 (s, 1H), 4.71 (t, J = 6.1 Hz, 2H), 4.02 (s, 3H), 2.89 (t, J = 7.8 Hz, 2H), 2.66 (s, 4H), 2.33-2.23 (m, 2H), 1.88-1.83 (m, 4H). |

TABLE 4-continued

| Example | Structure/Name | Coupling Method | Deprotection Method | Purification Method (s) | LCMS R_T, M + H+, Method | $^1$H NMR (ppm) |
|---|---|---|---|---|---|---|
| 108 | 3-(6-Ethyl-4,5,6,7-tetrahydro-thieno[2,3-c]pyridin-2-yl)-9H-dipyrido[2,3-b;4',3'-d]pyrrole-6-carbonitrile | H | D | B | 5.62, 360, A | (DMSO-D$_6$, 400 MHz): 12.90 (br s, 1H); 9.02 (d, J = 1.1 Hz, 1H); 8.96 (d, J = 2.3 Hz, 1H); 8.95 (d, J = 1.1 Hz, 1H); 8.93 (d, J = 2.3 Hz, 1H); 7.33 (s, 1H); 3.64 (s, 2H); 2.76-2.66 (m, 4H); 2.57 (q, J = 7.2 Hz, 2H); 1.11 (t, J = 7.15 Hz, 3H). |

$^a$1,1'-[bis(diphenylphosphino)ferrocene] dichloropalladium(II) used as catalyst
$^b$Aryl iodide used in coupling
$^c$THF used as solvent The compounds of the Examples in Table 5 were prepared from commercially available amines using the general Mesylate Displacement Methods described above.

TABLE 5

| Example | Structure/Name | Mesylate displacement Method | Deprotection Method | Purification Method (s) | LCMS R_T, M + H+, Method | $^1$H NMR (ppm) |
|---|---|---|---|---|---|---|
| 109 | 3-[4-((3S,5R)-3,5-Dimethyl-piperidin-1-ylmethyl)-phenyl]-9H-dipyrido[2,3-b;4',3'-d]pyrrole-6-carbonitrile | A | NA | B | 6.10, 396, A | (CDCl$_3$, 400 MHz): 9.00 (dd, J = 1.1, 0.5 Hz, 1H), 8.91 (d, J = 2.2 Hz, 1H), 8.71 (d, J = 2.2 Hz, 1H), 8.51 (dd, J = 1.1, 0.5 Hz, 1H), 7.65 (d, J = 8.0 Hz, 2H), 7.49 (d, J = 8.0 Hz, 2H), 3.60 (s, 2H), 2.91-2.88 (m, 1H), 2.90-2.84 (m, 1H), 1.79-1.68 (m, 4H), 1.55 (t, J = 11 Hz, 2H), 0.86 (d, J = 6.4 Hz, 6H). |
| 110 | 3-[4-(4,4-Dimethyl-piperidin-1-ylmethyl)-phenyl]-9H-dipyrido[2,3-b;4',3'-d]pyrrole-6-carbonitrile | A | NA | B | 6.60, 396, A | (CDCl$_3$, 400 MHz): 9.01 (s, 1H), 8.91 (d, J = 2.2 Hz, 1H), 8.72 (d, J = 2.2 Hz, 1H), 8.52 (s, 1H), 7.66 (d, J = 8.0 Hz, 2H), 7.51 (d, J = 8.0 Hz, 2H), 3.65 (s, 2H), 2.56-2.48 (m, 4H), 1.47 (t, J = 5.6 Hz, 4H), 0.96 (s, 6H). |
| 111 | 3-[4-(3,3-Dimethyl-piperidin-1-ylmethyl)-phenyl]-9H-dipyrido[2,3-b;4',3'-d]pyrrole-6-carbonitrile | A | NA | L | 6.34, 396, A | (CDCl$_3$, 300 MHz): 10.69 (s, 1H), 9.12 (d, J = 1.1 Hz, 1H), 9.00 (d, J = 2.1 Hz, 1H), 8.68 (d, J = 2.1 Hz, 1H), 8.46 (d, J = 1.0 Hz, 1H), 7.63 (d, J = 8.1 Hz, 2H), 7.52 (d, J = 8.0 Hz, 2H), 3.53 (s, 2H), 2.43-2.35 (m, 2H), 2.09-2.05 (m, 2H), 1.68-1.57 (m, 2H), 1.26 (t, J = 6.8 Hz, 2H), 0.97 (s, 6H). |

TABLE 5-continued

| Example | Structure/Name | Mesylate displacement Method | Deprotection Method | Purification Method(s) | LCMS $R_T$, M + H⁺, Method | ¹H NMR (ppm) |
|---|---|---|---|---|---|---|
| 112 | 3-[4-(2,2-Dimethyl-piperidin-1-ylmethyl)-phenyl]-9H-dipyrido[2,3-b;4',3'-d]pyrrole-6-carbonitrile | B | D | B | 2.31, 396, A | (CDCl₃, 400 MHz): 10.07 br. s, 1H), 9.09 (d, J = 1.0 Hz, 1H), 8.96 (d, J = 2.1 Hz, 1H), 8.64 (d, J = 2.1 Hz, 1H), 8.45 (d, J = 1.0 Hz, 1H), 7.61 (d, J = 7.7 Hz, 2H), 7.54 (d, J = 7.8 Hz, 2H), 3.59 (s, 2H), 2.44-2.39 (m, 2H), 1.52 (m, 2H), 1.38-1.30 (m, 2H), 1.16 (s, 6H), 0.94 (t, J = 7.3 Hz, 2H). |
| 113 | 3-[4-(4-Hydroxy-piperidin-1-ylmethyl)-phenyl]-9H-dipyrido[2,3-b;4',3'-d]pyrrole-6-carbonitrile | A | NA | B | 5.41, 384, A | (CDCl₃, 400 MHz): 9.02 (s, 1H), 8.90 (d, J = 2.2 Hz, 1H), 8.71 (d, J = 2.2 Hz, 1H), 8.52 (m, 1H), 7.66 (d, J = 7.9 Hz, 2H), 7.50 (d, J = 7.9 Hz, 2H), 3.72-3.63 (m, 1H), 3.63 (s, 2H), 2.90-2.83 (m, 2H), 2.30-2.20 (m, 2H), 1.95-1.86 (m, 2H), 1.68-1.57 (m, 2H). |
| 114 | 3-[4-(3-Hydroxy-pyrrolidin-1-ylmethyl)-phenyl]-9H-dipyrido[2,3-b;4',3'-d]pyrrole-6-carbonitrile | A | NA | B | 5.41, 370, A | (CDCl₃, 400 MHz): 9.02 (s, 1H), 8.90 (d, J = 2.2 Hz, 1H), 8.71 (d, J = 2.2 Hz, 1H), 8.52 (s, 1H), 7.67 (d, J = 8.0 Hz, 2H), 7.53 (d, J = 7.9 Hz, 2H), 4.44-4.38 (m, 1H), 3.81 (s, 2H), 3.74-3.54 (br. m, 1H), 2.94 (q, J = 8.0 Hz, 1H), 2.89-2.81 (m, 1H), 2.77-2.69 (m, 1H), 2.66-2.55 (m, 1H), 2.25 (dt, J = 14.1, 7.0 Hz, 1H), 1.85-1.76 (m, 1H). |
| 115 | 3-{4-[4-(2-Hydroxy-ethyl)-piperidin-1-ylmethyl]-phenyl}-9H-dipyrido[2,3-b;4',3'-d]pyrrole-6-carbonitrile | A | NA | B[6] | 5.62, 412, A | (CD₃OD, 400 MHz): 9.01 (d, J = 1.0 Hz, 1H), 8.97 (d, J = 2.2 Hz, 1H), 8.95 (d, J = 2.2 Hz, 1H), 8.75 (d, J = 1.0 Hz, 1H), 7.82 (d, J = 8.2 Hz, 2H), 7.59 (d, J = 7.8 Hz, 2H), 4.53 (s, 1H), 3.99 (s, 2H), 3.62 (t, J = 6.4 Hz, 2H), 3.28-3.19 (m, 2H), 2.72 (s, 1H), 2.68-2.49 (m, 2H), 1.94-1.82 (m, 2H), 1.70-1.60 (m, 2H), 1.52 (q, J = 6.5 Hz, 2H), 1.47-1.34 (m, 2H). |
| 116 | 3-[4-(4,4-Difluoro-piperidin-1-ylmethyl)-phenyl]-9H-dipyrido[2,3-b;4',3'-d]pyrrole-6-carbonitrile | C | D | L | 5.93, 404, A | (DMSO-D₆, 400 MHz): 12.91 (s, 1H), 9.08 (d, J = 2.3 Hz, 1H), 9.05 (d, J = 1.1 Hz, 1H), 9.02 (d, J = 2.3 Hz, 1H), 8.94 (d, J = 1.1 Hz, 1H), 7.78 (d, J = 8.0 Hz, 2H), 7.49 (d, J = 8.0 Hz, 2H), 3.63 (s, 2H), 2.58-2.51 (m, 4H), 2.05-1.92 (m, 4H). |

The compounds of the Examples in Table 6 were prepared from alkynes using the general Sonagashira Method described above.

TABLE 6

| Example | Structure/Name | Sonagashira coupling Method | Deprotection Method | Purification Method(s) | LCMS $R_T$, M + H+, Method | $^1$H NMR (ppm) |
|---|---|---|---|---|---|---|
| 117 | 3-(3-Dimethylamino-prop-1-ynyl)-9H-dipyrido[2,3-b;4',3'-d]pyrrole-6-carbonitrile | A | NA | M | 4.60, 276 A | (CDCl$_3$, 400 MHz): 9.18 (d, J = 1.2 Hz, 1H), 8.58 (d, J = 2.3 Hz, 1H), 8.34 (d, J = 1Hz, 1H), 5.98 (s, 1H), 3.56-3.60 (m, 2H), 0.94-0.98 (m, 2H), 0.08 (s, 9H). |
| 118 | 3-Piperidin-4-ylethynyl-9H-dipyrido[2,3-b;4',3'-d]pyrrole-6-carbonitrile | A | A | I | 5.22, 302, A | (DMSO-D$_6$, 400 MHz): 9.02 (d, J = 1.1 Hz, 1H), 8.87 (d, J = 1.0 Hz, 1H), 8.82 (d, J = 2.1 Hz, 1H), 8.68 (d, J = 2.1 Hz, 1H), 3.00-2.93 (m, 2H), 2.83-2.74 (m, 1H), 2.65-2.57 (m, 2H), 1.88-1.82 (m, 2H), 1.61-1.50 (m, 2H). |
| 119 | 3-Piperidin-3-ylethynyl-9H-dipyrido[2,3-b;4',3'-d]pyrrole-6-carbonitrile | A | A | I | 5.25, 302, A | (DMSO-D$_6$, 400 MHz): 9.02 (d, J = 1.1 Hz, 1H), 8.88 (d, J = 1.1 Hz, 1H), 8.82 (d, J = 2.1 Hz, 1H), 8.68 (d, J = 2.1 Hz, 1H), 3.10 (d, J = 10.6 Hz, 1H), 2.84-2.77 (m, 1H), 2.71-2.52 (m, 3H), 2.09-1.99 (m, 1H), 1.69-1.55 (m, 2H), 1.46-1.36 (m, 1H). |

The compounds of the Examples in Table 7 were prepared from commercially available phenols or aryl bromides using the general Ullmann Methods described above.

TABLE 7

| Example | Structure/Name | Ullmann Coupling Method | Deprotection Method | Purification Method (s) | LCMS $R_T$, M + H$^+$, Method | $^1$H NMR (ppm) |
|---|---|---|---|---|---|---|
| 120 | 3-(3,5-Dimethoxy-phenoxy)-9H-dipyrido[2,3-b;4',3'-d]pyrrole-6-carbonitrile | A | D | I | 10.1, 347, A | (DMSO-D$_6$, 400 MHz): 13.09 (s, 1H), 9.03 (d, J = 1.1 Hz, 1H), 8.91 (d, J = 1.1 Hz, 1H), 8.58 (d, J = 2.7 Hz, 1H), 8.55 (d, J = 2.7 Hz, 1H), 6.31 (t, J = 2.2 Hz, 1H), 6.20 (d, J = 2.2 Hz, 2H), 3.71 (s, 6H). |
| 121 | 3-(3-Piperazin-1-yl-phenoxy)-9H-dipyrido[2,3-b;4',3'-d]pyrrole-6-carbonitrile | A | A | B | 6.1, 371, A | (DMSO-D$_6$, 400 MHz): 8.98 (d, J = 1.1 Hz, 1H), 8.88 (s, 1H), 8.84 (d, J = 1.1 Hz, 1H), 8.52 (d, J = 2.7 Hz, 1H), 8.46 (d, J = 2.7 Hz, 1H), 7.20 (t, J = 8.2 Hz, 1H), 6.73 (dd, J = 8.3, 2.3 Hz, 1H), 6.69 (t, J = 2.3 Hz, 1H), 6.43 (dd, J = 8.1, 2.2 Hz, 1H), 3.33-3.28 (m, 4H), 3.18-3.12 (m, 4H). |
| 122 | 3-(4-Morpholin-4-ylmethyl-phenoxy)-9H-dipyrido[2,3-b;4',3'-d]pyrrole-6-carbonitrile | B | A | B | 5.7, 386, A | (DMSO-D$_6$, 300 MHz): 9.03 (d, J = 1.0 Hz, 1H), 8.90 (d, J = 1.0 Hz, 1H), 8.59 (d, J = 2.7 Hz, 1H), 8.54 (d, J = 2.7 Hz, 1H), 7.33 (d, J = 8.3 Hz, 2H), 7.02 (d, J = 8.3 Hz, 2H), 3.57 (t, J = 4.5 Hz, 4H), 3.44 (s, 2H), 2.35 (t, J = 4.2 Hz, 4H). |
| 123 | 3-(4-Piperidin-1-ylmethyl-phenoxy)-9H-dipyrido[2,3-b;4',3'-d]pyrrole-6-carbonitrile | B | D | B | 6.0, 384, A | (DMSO-D$_6$, 300 MHz): 9.03 (d, J = 1.0 Hz, 1H), 8.90 (d, J = 1.0 Hz, 1H), 8.59 (d, J = 2.7 Hz, 1H), 8.54 (d, J = 2.7 Hz, 1H), 7.30 (d, J = 8.4 Hz, 2H), 7.02 (t, J = 8.4 Hz, 2H), 3.40 (s, 2H), 2.35-2.27 (m, 4H), 1.54-1.43 (m, 4H), 1.43-1.33 (d, J = 7.2 Hz, 2H). |

The compounds of the Examples in Table 8 were prepared from commercially available boronic acids.

TABLE 8

| Example | Structure/Name | Coupling Method | Purification Method(s) | LCMS $R_T$/M + H$^+$/ Method | $^1$H NMR (ppm) |
|---|---|---|---|---|---|
| 124 | 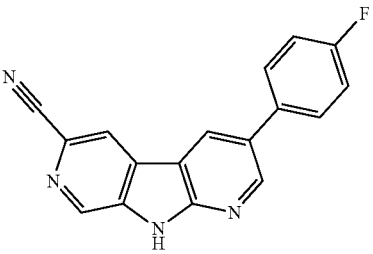 [SMILES: N#Cc1cc2c(cn1)[nH]c1ncc(-c3ccc(F)cc3)cc12]<br>3-(4-Fluoro-phenyl)-9H-dipyrido[2,3-b;4',3'-d]pyrrole-6-carbonitrile | A | B, H | 9.94, 289, A | (DMSO-D$_6$, 300 MHz): 12.96 (s, 1H), 9.09-9.00 (m, 3H), 8.95-8.90 (m, 1H), 7.86 (dd, J = 8.7, 5.5 Hz, 2H), 7.46-7.33 (m, 2H). |
| 125 | 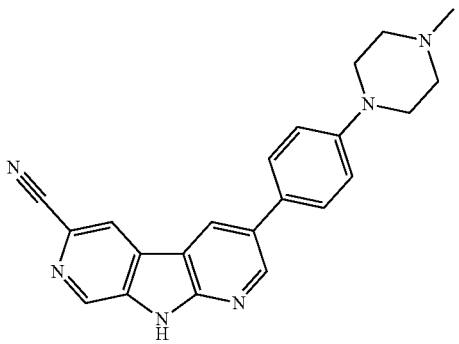 [SMILES: CN1CCN(c2ccc(-c3cnc4[nH]c5cnc(C#N)cc5c4c3)cc2)CC1]<br>3-[4-(4-Methyl-piperazin-1-yl)-phenyl]-9H-dipyrido[2,3-b;4',3'-d]pyrrole-6-carbonitrile | A | B | 5.66, 369, A | (DMSO-D$_6$, 300 MHz): 12.84 (s, 1H), 9.03-8.93 (m, 4H), 7.67 (d, J = 8.7 Hz, 2H), 7.10 (d, J = 8.7 Hz, 2H), 3.22 (m, 4H), 2.54-2.46 (m, 4H), 2.24 (s, 3H). |
| 126 | 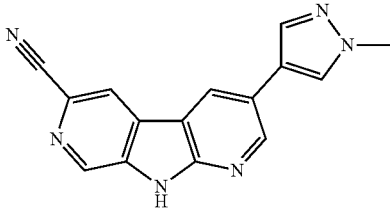 [SMILES: Cn1cc(-c2cnc3[nH]c4cnc(C#N)cc4c3c2)cn1]<br>3-(1-Methyl-1H-pyrazol-4-yl)-9H-dipyrido[2,3-b;4',3'-d]pyrrole-6-carbonitrile | A | G$^4$ | 6.90, 275, A | (DMSO-D$_6$, 300 MHz): 12.79 (s, 1H), 9.01 (d, J = 1.1 Hz, 1H), 8.96 (d, J = 2.2 Hz, 1H), 8.92 (d, J = 2.2 Hz, 1H), 8.84 (d, J = 1.1 Hz, 1H), 8.24 (s, 1H), 7.97 (s, 1H), 3.92 (s, 3H). |
| 127 | 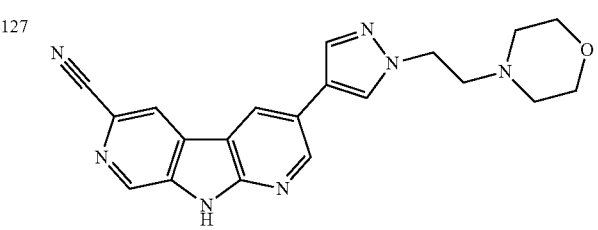<br>3-[1-(2-Morpholin-4-yl-ethyl)-1H-pyrazol-4-yl]-9H-dipyrido[2,3-b;4',3'-d]pyrrole-6-carbonitrile | D | D | 5.0, 374, A | (DMSO-D$_6$, 400 MHz): 12.98 (s, 1H), 9.04-9.02 (m, 1H), 8.98 (d, J = 2.2 Hz, 1H), 8.96-8.94 (m, 1H), 8.87 (d, J = 1.1 Hz, 1H), 8.32 (d, J = 0.8 Hz, 1H), 8.01 (d, J = 0.8 Hz, 1H), 4.32 (t, J = 6.6 Hz, 2H), 3.59 (t, J = 4.5 Hz, 4H), 2.79 (t, J = 6.6 Hz, 2H), 2.46 (m, 4H). |

TABLE 8-continued

| Example | Structure/Name | Coupling Method | Purification Method (s) | LCMS R$_T$/M + H$^+$/ Method | $^1$H NMR (ppm) |
|---|---|---|---|---|---|
| 128 | 3-(1-Methyl-1H-imidazol-2-yl)-9H-dipyrido[2,3-b;4',3'-d]pyrrole-6-carbonitrile | Stille A | D | 4.1, 275, A | (DMSO-D$_6$, 400MHz): 12.52 (br s, 1H), 9.04 (d, J = 1.1 Hz, 1H), 8.94 (d, J = 1.1 Hz, 1H), 8.90 (d, J = 2.2 Hz, 1H), 8.81 (d, J = 2.2 Hz, 1H), 7.79-7.76 (m, 1H), 7.18 (d, J = 1.1 Hz, 1H), 3.75 (s, 3H). |
| 129 | 3-(2-Methoxy-phenyl)-9H-dipyrido[2,3-b;4',3'-d]pyrrole-6-carbonitrile | C | Preparative HPLC | 1.17, 301, C | (DMSO-D$_6$, 400 MHz): 12.96 (s, 1H), 9.01 (s, 1H), 8.92 (s, 1H), 8.82 (s, 1H), 8.74 (s, 1H), 7.41-7.37 (m, 2H), 7.16-7.14 (m, 1H), 7.09-7.07 (m, 1H), 3.77 (s, 3H) |
| 130 | 3-Phenyl-9H-dipyrido[2,3-b;4',3'-d]pyrrole-6-carbonitrile | C | Preparative HPLC | 1.18, 271, C | (DMSO-D$_6$, 400 MHz): 12.89 (s, 1H), 9.06-9.01 (m, 3H), 8.99-8.91 (m, 1H), 7.79-7.77 (m, 2H), 7.54-7.50 (m, 2H), 7.38-7.42 (m, 1H) |
| 131 | 3-(4-Methoxy-phenyl)-9H-dipyrido[2,3-b;4',3'-d]pyrrole-6-carbonitrile | C | Preparative HPLC | 1.42, 301, C | (DMSO-D$_6$, 400 MHz): 12.96 (s, 1H), 9.15-8.89 (m, 4H), 7.70 (br, 2H), 7.12 (br, 2H), 3.75 (s, 3H) |
| 132 | 4-(6-Cyano-9H-dipyrido[2,3-b;4',3'-d]pyrrol-3-yl)-N,N-diethyl-benzamide | C | Preparative HPLC | 1.20, 370, C | (DMSO-D$_6$, 400 MHz): 12.96 (s, 1H), 9.11 (s, 1H), 9.10 (s, 2H), 8.91 (s, 1H), 7.85-7.83 (d, J = 8.0 Hz, 2H), 7.49-7.47 (d, J = 8.4 Hz, 2H), 3.30-3.10 (m, 4H), 1.20-1.08 (m, 6H) |

TABLE 8-continued

| Example | Structure/Name | Coupling Method | Purification Method (s) | LCMS R$_T$/M + H$^+$/ Method | $^1$H NMR (ppm) |
|---|---|---|---|---|---|
| 133 | 3-m-Tolyl-9H-dipyrido[2,3-b;4',3'-d]pyrrole-6-carbonitrile | C | Preparative HPLC | 1.25, 285, C | (DMSO-D$_6$, 400 MHz): 12.90 (s, 1H), 9.04 -8.97 (m, 3H), 8.92 (s, 1H), 7.06-7.56 (m, 2H), 7.42-7.38 (m, 1H), 7.23-7.21 (m, 1H), 2.40 (s, 3H) |
| 134 | 3-(4-tert-Butyl-phenyl)-9H-dipyrido[2,3-b;4',3'-d]pyrrole-6-carbonitrile | C | Preparative HPLC | 1.40, 327, C | (DMSO-D$_6$, 400 MHz): 12.89 (s, 1H), 9.03-9.02 (m, 2H), 8.98 (s, 1H), 8.93 (s, 1H), 7.73-7.71 (d, J = 8.4 Hz, 2H), 7.55-7.53 (d, J = 8.4 Hz, 2H), 1.32 (s, 9H) |
| 135 | 3-(4-Isopropoxy-phenyl)-9H-dipyrido[2,3-b;4',3'-d]pyrrole-6-carbonitrile | C | Preparative HPLC | 1.28, 329, C | (DMSO-D$_6$, 400 MHz): 12.96 (s, 1H), 9.01-8.91 (m, 4H), 7.70-7.68 (d, J = 8.4 Hz, 2H), 7.07-7.05 (d, J = 8.8 Hz, 2H), 4.71- 4.65 (m, 1H), 1.29-1.28 (d, J = 6.0 Hz, 6H) |
| 136 | 3-(3-Hydroxymethyl-phenyl)-9H-dipyrido[2,3-b;4',3'-d]pyrrole-6-carbonitrile | C | Preparative HPLC | 1.26, 301, C | (DMSO-D$_6$, 400 MHz): 12.96 (s, 1H), 9.28 (m, 4H), 7.75 (s, 1H), 7.68-7.66 (m , 1H), 7.51-7.48 (m, 1H), 7.38-7.36 (m, 1H), 5.50 (br, 1H), 4.61 (s, 2H) |

TABLE 8-continued

| Example | Structure/Name | Coupling Method | Purification Method (s) | LCMS R$_T$/M + H$^+$/ Method | $^1$H NMR (ppm) |
|---|---|---|---|---|---|
| 137 | 3-p-Tolyl-9H-dipyrido[2,3-b;4',3'-d]pyrrole-6-carbonitrile | C | Preparative HPLC | 1.24, 285, C | (DMSO-D$_6$, 400 MHz): 12.96 (s, 1H), 9.04-8.93 (m, 4H), 7.70-7.68 (d, J = 8.0 Hz, 2H), 7.35-7.33 (d, J = 8.0 Hz, 2H), 2.36 (s, 3H) |
| 138 | N-[3-(6-Cyano-9H-dipyrido[2,3-b;4',3'-d]pyrrol-3-yl)-phenyl]-acetamide | C | Preparative HPLC | 1.27, 328, C | (DMSO-D$_6$, 400 MHz): 12.96 (s, 1H), 10.11 (s, 1H), 9.04-8.98 (m, 3H), 8.92 (s, 1H), 8.02 (s, 1H), 7.59-7.56 (m, 1H), 7.48-7.43 (m, 2H), 2.07 (s, 3H) |
| 139 | 3-(4-Methanesulfonyl-phenyl)-9H-dipyrido[2,3-b;4',3'-d]pyrrole-6-carbonitrile | C | Preparative HPLC | 1.26, 349, C | (DMSO-D$_6$, 400 MHz): 13.01 (s, 1H), 9.21 (s, 1H), 9.11 (s, 1H), 9.06 (s, 1H), 8.95 (s, 1H), 8.12-8.04 (m, 4H), 3.28 (s, 3H) |
| 140 | 3-(2-Hydroxy-phenyl)-9H-dipyrido[2,3-b;4',3'-d]pyrrole-6-carbonitrile | C | Preparative HPLC | 1.05, 287, C | (DMSO-D$_6$, 400 MHz): 12.96 (s, 1H), 9.85 (s, 1H), 9.09 (s, 1H), 9.02 (s, 1H), 8.96 (s, 1H), 8.91 (s, 1H), 7.47-7.45 (m, 1H), 7.33-7.28 (m, 1H), 7.09-7.00 (m, 2H) |
| 141 | 3-(2-Hydroxymethyl-phenyl)-9H-dipyrido[2,3-b;4',3'-d]pyrrole-6-carbonitrile | C | Preparative HPLC | 1.02, 301, C | (DMSO-D$_6$, 400 MHz): 13.02 (s, 1H), 9.13 (s, 1H), 9.00 (s, 1H), 8.87 (s, 1H), 8.79 (s, 1H), 7.66 (m, 1H), 7.69-7.44 (m, 3H), 5.32-5.29 (m, 1H), 4.53-4.52 (d, J = 5.2 Hz, 2H) |

TABLE 8-continued

| Example | Structure/Name | Coupling Method | Purification Method(s) | LCMS $R_T$/M + H$^+$/ Method | $^1$H NMR (ppm) |
|---|---|---|---|---|---|
| 142 | 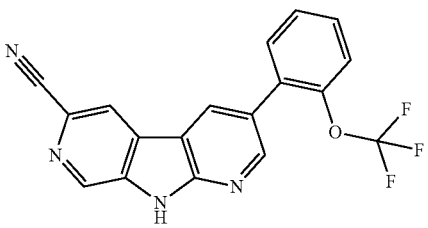 [SMILES: N#Cc1cc2c(cn1)[nH]c1ncc(-c3ccccc3OC(F)(F)F)cc12]<br>3-(2-Trifluoromethoxy-phenyl)-9H-dipyrido[2,3-b;4',3'-d]pyrrole-6-carbonitrile | C | Preparative HPLC | 1.25, 355, C | (DMSO-D$_6$, 400 MHz): 13.05 (s, 1H), 9.05 (s, 1H), 8.94 (s, 1H), 8.91 (s, 1H), 8.78 (s, 1H), 7.70-7.67 (m, 1H), 7.63-7.53 (m, 3H) |
| 143 | 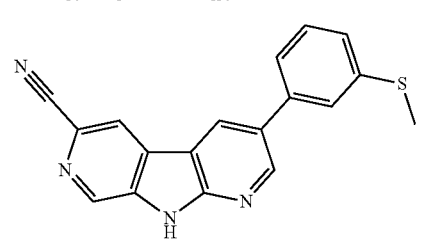 [SMILES: CSc1cccc(-c2cnc3[nH]c4cnc(C#N)cc4c3c2)c1]<br>3-(3-Methylsulfanyl-phenyl)-9H-dipyrido[2,3-b;4',3'-d]pyrrole-6-carbonitrile | C | Preparative HPLC | 1.24, 317, C | (DMSO-D$_6$, 400 MHz): 12.96 (s, 1H), 9.11 (s, 1H), 9.03 (s, 2H), 8.94 (s, 1H), 7.65 (s, 1H), 7.58-7.56 (m, 1H), 7.45-7.49 (m, 1H), 7.32-7.30 (m, 1H), 2.57 (s, 3H) |
| 144 | 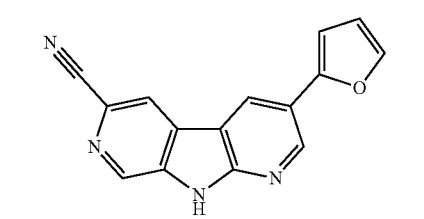 [SMILES: N#Cc1cc2c(cn1)[nH]c1ncc(-c3ccco3)cc12]<br>3-Furan-2-yl-9H-dipyrido[2,3-b;4',3'-d]pyrrole-6-carbonitrile | C | Preparative HPLC | 1.10, 261, C | (DMSO-D$_6$, 400 MHz): 12.96 (s, 1H), 9.06 (s, 1H), 9.00-8.99 (m, 2H), 8.92 (s, 1H), 7.83 (s, 1H), 7.06-7.05 (d, J = 3.2 Hz, 1H), 6.65-6.55 (m, 1H) |
| 144 | 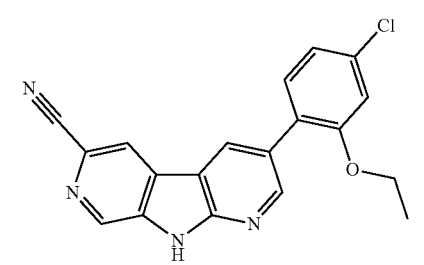 [SMILES: CCOc1cc(Cl)ccc1-c1cnc2[nH]c3cnc(C#N)cc3c2c1]<br>3-(4-Chloro-2-ethoxy-phenyl)-9H-dipyrido[2,3-b;4',3'-d]pyrrole-6-carbonitrile | C | Preparative HPLC | 1.30, 349, C | (DMSO-D$_6$, 400 MHz): 12.96 (s, 1H), 9.04 (s, 1H), 8.93-8.90 (m, 2H), 8.83 (s, 1H), 7.50 (s, 1H), 7.42-7.39 (m, 1H), 7.18-7.16 (d, J = 8.8 Hz, 1H), 4.10-4.05 (m, 2H), 1.28-1.24 (m, 3H) |
| 145 | 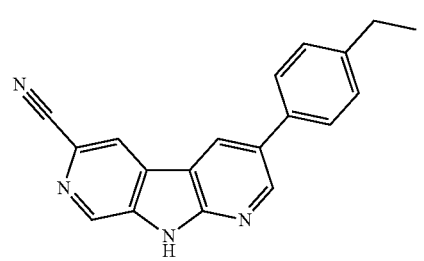 [SMILES: CCc1ccc(-c2cnc3[nH]c4cnc(C#N)cc4c3c2)cc1]<br>3-(4-Ethyl-phenyl)-9H-dipyrido[2,3-b;4',3'-d]pyrrole-6-carbonitrile | C | Preparative HPLC | 1.56, 299, C | (DMSO-D$_6$, 400 MHz): 12.89 (s, 1H), 9.04-9.02 (m, 2H), 8.98 (s, 1H), 8.92 (s, 1H), 7.72-7.70 (d, J = 8.0 Hz, 2H), 7.38-7.36 (d, J = 8.4 Hz, 2H), 2.69-2.64 (m, 2H), 1.20-1.24 (m, 3H) |

TABLE 8-continued

| Example | Structure/Name | Coupling Method | Purification Method (s) | LCMS R$_T$/M + H$^+$/ Method | $^1$H NMR (ppm) |
|---|---|---|---|---|---|
| 146 | 3-(3,4-Difluoro-phenyl)-9H-dipyrido[2,3-b;4',3'-d]pyrrole-6-carbonitrile | C | Preparative HPLC | 1.48, 307, C | (DMSO-D$_6$, 400 MHz): 12.96 (s, 1H), 9.11 (s, 1H), 9.04-9.03 (m, 2H), 8.89 (s, 1H), 7.97-7.9 (m, 1H), 7.70-7.58 (m, 2H) |
| 147 | 3-(2-Ethyl-phenyl)-9H-dipyrido[2,3-b;4',3'-d]pyrrole-6-carbonitrile | C | Preparative HPLC | 1.27, 299, C | (DMSO-D$_6$, 400 MHz): 12.96 (s, 1H), 9.04 (s, 1H), 8.93 (s, 1H), 8.74 (s, 1H), 8.83 (s, 1H), 7.40-7.36 (m, 2H), 7.33-7.27 (m, 2H), 2.61-2.55 (m, 2H), 1.04-1.01 (m, 3H) |
| 148 | 3-(2-Fluoro-phenyl)-9H-dipyrido[2,3-b;4',3'-d]pyrrole-6-carbonitrile | C | Preparative HPLC | 1.29, 289, C | (DMSO-D$_6$, 400 MHz): 12.96 (s, 1H), 9.02 (s, 1H), 8.96-8.94 (m, 2H), 8.84 (s, 1H), 7.71-7.69 (m, 1H), 7.40-7.36 (m, 1H), 7.37-7.35 (m, 2H) |
| 149 | 3-o-Tolyl-9H-dipyrido[2,3-b;4',3'-d]pyrrole-6-carbonitrile | C | Preparative HPLC | 1.22, 285, C | (DMSO-D$_6$, 400 MHz): 12.96 (s, 1H), 9.04 (s, 1H), 8.93 (s, 1H), 8.78 (s, 1H), 8.67 (s, 1H), 7.37-7.33 (m, 4H), 2.29 (s, 3H) |
| 150 | 3-(4-Trifluoromethoxy-phenyl)-9H-dipyrido[2,3-b;4',3'-d]pyrrole-6-carbonitrile | C | Preparative HPLC | 1.56, 355, C | (DMSO-D$_6$, 400 MHz): 13.01 (s, 1H), 9.11 (s, 1H), 9.05-9.02 (m, 2H), 8.92 (s, 1H), 7.94-7.92 (d, J = 8.4 Hz, 2H), 7.55-7.53 (d, J = 8.4 Hz, 2H) |

TABLE 8-continued

| Example | Structure/Name | Coupling Method | Purification Method (s) | LCMS $R_T$/M + H$^+$/ Method | $^1$H NMR (ppm) |
|---|---|---|---|---|---|
| 151 | 3-(4-Trifluoromethyl-phenyl)-9H-dipyrido[2,3-b;4',3'-d]pyrrole-6-carbonitrile | C | Preparative HPLC | 1.54, 339, C | (DMSO-D$_6$, 400 MHz): 9.25 (s, 1H), 9.16-9.12 (m, 2H), 9.00 (s, 1H), 8.13-8.11 (d, J = 8.4 Hz, 1H), 7.98-7.96 (d, J = 8.4 Hz, 1H) |
| 152 | 3-(4-Ethoxy-phenyl)-9H-dipyrido[2,3-b;4',3'-d]pyrrole-6-carbonitrile | C | Preparative HPLC | 1.23, 315, C | (DMSO-D$_6$, 400 MHz): 12.89 (s, 1H), 9.02-9.00 (m, 2H), 8.96 (s, 1H), 8.92 (s, 1H), 7.73-7.71 (d, J = 8.8 Hz, 2H), 7.08-7.07 (d, J = 8.8 Hz, 2H), 4.11-4.06 (m, 2H), 1.37-1.34 (m, 3H) |
| 153 | 3-(4-Methylsulfanyl-phenyl)-9H-dipyrido[2,3-b;4',3'-d]pyrrole-6-carbonitrile | C | Washing with THF and methanol | 1.24, 317, C | (DMSO-D$_6$, 400 MHz): 12.89 (s, 1H), 9.07 (s, 1H), 9.03 (s, 1H), 9.00 (s, 1H), 8.94 (s, 1H), 7.77-7.75 (d, J = 8.4 Hz, 2H), 7.43-7.41 (d, J = 8.4 Hz, 2H), 2.53 (s, 3H) |
| 154 | 3-(3-Chloro-4-ethoxy-phenyl)-9H-dipyrido[2,3-b;4',3'-d]pyrrole-6-carbonitrile | C | Preparative HPLC | 1.27, 323, C | (DMSO-D$_6$, 400 MHz): 12.73 (s, 1H), 8.89-8.82 (m, 3H), 8.72 (s, 1H), 7.71 (s, 1H), 7.58-7.55 (d, J = 8.4 Hz, 1H), 7.13-7.11 (d, J = 8.4 Hz, 1H), 4.04-3.99 (m, 2H), 1.25-1.14 (m, 3H) |

TABLE 8-continued

| Example | Structure/Name | Coupling Method | Purification Method(s) | LCMS R_T/M+H+/ Method | $^1$H NMR (ppm) |
|---|---|---|---|---|---|
| 155 | 3-(4-Fluoro-2-methoxy-phenyl)-9H-dipyrido[2,3-b;4',3'-d]pyrrole-6-carbonitrile | C | Preparative HPLC | 1.48, 319, C | (DMSO-D_6, 400 MHz): 12.89 (s, 1H), 9.03 (s, 1H), 8.94 (s, 1H), 8.83 (s, 1H), 8.74 (s, 1H), 7.48-7.44 (m, 1H), 7.12-7.09 (m, 1H), 6.94-6.93 (m, 1H), 3.82 (s, 3H) |
| 156 | 3-(3-Methoxy-phenyl)-9H-dipyrido[2,3-b;4',3'-d]pyrrole-6-carbonitrile | C | Preparative HPLC | 1.44, 301, C | (DMSO-D_6, 400 MHz): 12.96 (s, 1H), 9.04 (s, 1H), 8.99-8.96 (m, 2H), 8.88 (s, 1H), 7.42-7.39 (m, 1H), 7.32-7.28 (m, 2H), 6.98-6.89 (m, 1H), 3.81 (s, 3H) |
| 157 | 3-(4-Hydroxymethyl-phenyl)-9H-dipyrido[2,3-b;4',3'-d]pyrrole-6-carbonitrile | C | Preparative HPLC | 1.24, 301, C | (DMSO-D_6, 400 MHz): 12.96 (s, 1H), 9.15 (s, 1H), 9.11-9.08 (m, 2H), 9.02 (s, 1H), 7.86-7.84 (d, J = 8.4 Hz, 2H), 7.57-7.55 (d, J = 8.4 Hz, 2H), 5.35-5.20 (s, 1H), 4.65 (s, 2H) |
| 158 | 3-(3-Chloro-4-fluoro-phenyl)-9H-dipyrido[2,3-b;4',3'-d]pyrrole-6-carbonitrile | C | Preparative HPLC | 1.24, 317, C | (DMSO-D_6, 400 MHz): 12.96 (s, 1H), 9.11 (s, 1H), 9.03-9.02 (m, 2H), 8.88 (s, 1H), 8.06-8.03 (m, 1H), 7.84-7.81 (m, 1H), 7.61-7.56 (m, 1H) |
| 159 | N-[2-(6-Cyano-9H-dipyrido[2,3-b;4',3'-d]pyrrol-3-yl)-phenyl]-acetamide | C | Preparative HPLC | 1.22, 328, C | (DMSO-D_6, 400 MHz): 13.01 (s, 1H), 9.46 (s, 1H), 9.12 (s, 1H), 9.05 (s, 1H), 8.85 (s, 1H), 8.71 (s, 1H), 7.70-7.65 (m, 1H), 7.53-7.45 (m, 2H), 7.42-7.39 (m, 1H), 1.93 (s, 3H) |

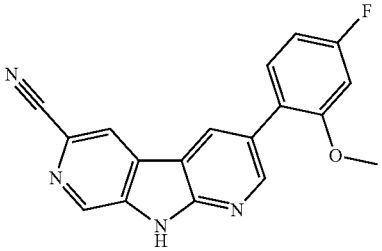 [SMILES: COc1cc(F)ccc1-c1cnc2[nH]c3cnc(C#N)cc3c2c1]

TABLE 8-continued

| Example | Structure/Name | Coupling Method | Purification Method (s) | LCMS R$_T$/M + H$^+$/ Method | $^1$H NMR (ppm) |
|---|---|---|---|---|---|
| 160 | 3-Thiophen-2-yl-9H-dipyrido[2,3-b;4',3'-d]pyrrole-6-carbonitrile | C | Washing with THF and methanol | 1.46, 277, C | (DMSO-D$_6$, 400 MHz): 13.13 (s, 1H), 9.23-9.21 (m, 3H), 9.19-9.15 (m, 1H), 7.81-7.80 (m, 2H), 7.39-7.37 (m, 1H) |
| 161 | 3-(2-Chloro-phenyl)-9H-dipyrido[2,3-b;4',3'-d]pyrrole-6-carbonitrile | C | Washing with THF and methanol | 1.33, 305, C | (DMSO-D$_6$, 400 MHz): 12.96 (s, 1H), 9.03 (s, 1H), 8.92 (s, 1H), 8.85 (s, 1H), 8.72 (s, 1H), 7.63-7.16 (m, 1H), 7.54-7.61 (m, 1H), 7.48-7.45 (m, 2H) |
| 162 | 3-(3-Chloro-phenyl)-9H-dipyrido[2,3-b;4',3'-d]pyrrole-6-carbonitrile | C | Washing with THF and methanol | 1.28, 305, C | (DMSO-D$_6$, 400 MHz): 12.96 (s, 1H), 9.12 (s, 1H), 9.02-9.01 (m, 2H), 8.88 (s, 1H), 7.87 (s, 1H), 7.78-7.76 (m 1H), 7.56-7.52 (m, 1H), 7.47-7.45 (m, 1H) |
| 163 | 3-(3-Fluoro-phenyl)-9H-dipyrido[2,3-b;4',3'-d]pyrrole-6-carbonitrile | C | Washing with methanol | 1.31, 289, C | (DMSO-D$_6$, 400 MHz): 13.09 (s, 1H), 9.02 (s, 1H), 8.95-8.94 (m, 2H), 8.84 (s, 1H), 7.82-7.81 (m, 2H), 7.69-7.60 (m, 1H), 7.42-7.39 (m, 1H) |
| 164 | 3-(3-Trifluoromethoxy-phenyl)-9H-dipyrido[2,3-b;4',3'-d]pyrrole-6-carbonitrile | C | Preparative HPLC | 1.57, 355, C | (DMSO-D$_6$, 400 MHz): 12.96 (s, 1H), 9.14 (s, 1H), 9.04-9.02 (m, 2H), 8.90 (s, 1H), 7.79 (s, 1H), 7.68-7.67 (m, 1H), 7.65-7.63 (m, 1H), 7.73-7.41 (m, 1H) |

TABLE 8-continued

| Example | Structure/Name | Coupling Method | Purification Method (s) | LCMS $R_T$/M + H$^+$/ Method | $^1$H NMR (ppm) |
|---|---|---|---|---|---|
| 165 | 3-(4-Chloro-phenyl)-9H-dipyrido[2,3-b;4',3'-d]pyrrole-6-carbonitrile | C | Washing with THF and methanol | 1.57, 305, C | (DMSO-D$_6$, 400 MHz): 12.96 (s, 1H), 9.07 (s, 1H), 9.01-8.99 (m, 2H), 8.90 (s, 1H), 7.82-7.80 (d, J = 8.4 Hz, 2H), 7.59-7.57 (d, J = 8.4 Hz, 2H) |
| 166 | 3-(3-Amino-phenyl)-9H-dipyrido[2,3-b;4',3'-d]pyrrole-6-carbonitrile | C | Washing with methanol | 0.83, 286, C | (DMSO-D$_6$, 400 MHz): 13.01 (s, 1H), 9.07-9.03 (m, 2H), 8.95-8.94 (m, 2H), 7.82-7.80 (m, 1H), 7.75 (s, 1H), 7.66-7.62 (s, 1H), 7.40-7.44 (m, 1H) |
| 167 | 3-(4-Cyano-phenyl)-9H-dipyrido[2,3-b;4',3'-d]pyrrole-6-carbonitrile | C | Washing with methanol and DMF | 1.12, 296, C | (DMSO-D$_6$, 400 MHz): 13.18 (s, 1H), 9.34 (s, 1H), 9.24 (s, 1H), 9.19 (s, 1H), 9.06 (s, 1H), 8.20-8.15 (m, 4H) |
| 168 | 3-(4-Hydroxy-phenyl)-9H-dipyrido[2,3-b;4',3'-d]pyrrole-6-carbonitrile | C | Washing with methanol | 1.13, 287, C | (DMSO-D$_6$, 400 MHz): 12.80 (s, 1H), 8.99 (s, 1H), 8.94 (s, 1H), 8.89 (s, 2H), 7.60-7.57 (d, J = 8.4 Hz, 2H), 6.90-6.88 (d, J = 8.8 Hz, 2H) |

TABLE 8-continued

| Example | Structure/Name | Coupling Method | Purification Method (s) | LCMS R_T/M + H+/ Method | 1H NMR (ppm) |
|---|---|---|---|---|---|
| 169 | 3-(3-Cyano-phenyl)-9H-dipyrido[2,3-b;4',3'-d]pyrrole-6-carbonitrile | C | Washing with methanol and DMF | none | (DMSO-D_6, 400 MHz): 13.10 (s, 1H), 9.32 (s, 1H), 9.26-9.22 (m, 2H), 9.03 (s, 1H), 8.47 (s, 1H ), 8.33-8.31 (m, 1H), 8.06-8.03 (m, 1H), 7.98-7.88 (m, 1H) |
| 170 | 3-(3-Trifluoromethyl-phenyl)-9H-dipyrido[2,3-b;4',3'-d]pyrrole-6-carbonitrile | C | Precipitate from DMF | 1.39, 339, C | (DMSO-D_6, 400 MHz): 12.96 (s, 1H), 9.21 (s, 1H), 9.10 (s, 1H), 9.04 (s, 1H), 8.94 (s, 1H), 8.15 (s, 2H), 7.79 (s, 2H) |
| 171 | 3-(2-Fluoro-5-hydroxymethyl-phenyl)-9H-dipyrido[2,3-b;4',3'-d]pyrrole-6-carbonitrile | C | Preparative HPLC | 1.30, 319, C | (DMSO-D_6, 400 MHz): 12.96 (s, 1H), 9.02 (s, 1H), 8.96 (s, 2H), 8.83 (s, 1H), 7.61-7.51 (m, 1H), 7.40-7.32 (m, 2H), 5.31-5.28 (m, 1H), 4.55-4.54 (d, J = 5.6 Hz, 2H) |
| 172 | 3-(2-Methylsulfanyl-phenyl)-9H-dipyrido[2,3-b;4',3'-d]pyrrole-6-carbonitrile | D | Washing with methanol | 1.34, 317, C | (DMSO-D_6, 400 MHz): 12.96 (s, 1H), 9.04 (s, 1H), 8.93 (s, 1H), 8.91 (s, 1H), 8.78 (s, 1H), 8.64 (s, 1H), 7.49-7.38 (m, 2H), 7.35-7.25 (m, 2H), 2.38 (s, 3H) |
| 173 | 3-(3-Fluoro-4-methoxy-phenyl)-9H-dipyrido[2,3-b;4',3'-d]pyrrole-6-carbonitrile | D | Washing with methanol and DMF | 1.50, 319, C | (DMSO-D_6, 400 MHz): 12.89 (s, 1H), 9.05 (s, 1H), 9.02-8.99 (m, 2H), 8.89 (s, 1H), 7.73-7.69 (m, 1H), 7.61-7.59 (d, J = 8.4 Hz, 1H), 7.35-7.30 (m, 1H), 3.90 (s, 3H) |

TABLE 8-continued

| Example | Structure/Name | Coupling Method | Purification Method (s) | LCMS $R_T$/M + H$^+$/ Method | $^1$H NMR (ppm) |
| --- | --- | --- | --- | --- | --- |
| 174 | 3-(2,4-Difluoro-phenyl)-9H-dipyrido[2,3-b;4',3'-d]pyrrole-6-carbonitrile | D | Washing with methanol then further purified by preparative HPLC | 1.32, 307, C | (DMSO-D$_6$, 400 MHz): 12.96 (s, 1H), 9.02 (s, 1H), 8.93 (s, 2H), 8.81 (s, 1H), 7.74-7.68 (m, 1H), 7.47-7.41 (m, 1H), 7.28-7.24 (m, 1H) |
| 175 | 3-(4-Chloro-3-fluoro-phenyl)-9H-dipyrido[2,3-b;4',3'-d]pyrrole-6-carbonitrile | D | Washing with methanol and DMF | 1.41, 323/325, C | (DMSO-D$_6$, 400 MHz): 12.96 (s, 1H), 9.13 (s, 1H), 9.04-9.01 (m, 2H), 8.87 (s, 1H), 7.91-7.81 (m, 1H), 7.73-7.68 (m, 2H) |
| 176 | 9H-dipyrido[2,3-b;4',3'-d]pyrrole-6-carbonitrile | D | Washing with methanol and DMF | 1.11, 331, C | (DMSO-D$_6$, 400 MHz): 12.96 (s, 1H), 9.02-8.97 (m, 3H), 8.88 (s, 1H), 7.36-7.32 (m, 1H), 7.30-7.27 (m, 1H), 7.08-7.06 (d, J = 8.4 Hz, 1H), 3.87 (s, 3H), 3.78 (s, 3H) |
| 177 | 9H-dipyrido[2,3-b;4',3'-d]pyrrole-6-carbonitrile | D | Washing with methanol | 1.35, 307, C | (DMSO-D$_6$ 400 MHz): 13.16 (s, 1H), 9.34 (s, 1H), 9.25 (s, 1H), 9.21 (s, 1H), 9.03 (s, 1H), 7.78-7.76 (d, J = 6.8 Hz, 2H), 7.47-7.42 (m, 1H) |

TABLE 8-continued

| Example | Structure/Name | Coupling Method | Purification Method (s) | LCMS R$_T$/M + H$^+$/ Method | $^1$H NMR (ppm) |
|---|---|---|---|---|---|
| 178 | 9H-dipyrido[2,3-b;4',3'-d]pyrrole-6-carbonitrile | D | Washing with methanol | 1.20, 307, C | (DMSO-D$_6$, 400 MHz): 12.96 (s, 1H), 9.03 (s, 1H), 9.03 (s, 1H), 8.99 (s, 1H), 8.86 (s, 1H), 7.60-7.56 (m, 1H), 7.47-7.41 (m, 1H), 7.33-7.31 (m, 1H) |
| 179 | 9H-dipyrido[2,3-b;4',3'-d]pyrrole-6-carbonitrile | D | Washing with methanol | 1.29, 331, C | (DMSO-D$_6$, 400 MHz): 12.87 (s, 1H), 9.02 (s, 1H), 8.93 (s, 1H), 8.86 (s, 1H), 8.79 (s, 1H), 7.11-7.09 (d, J = 9.2 Hz, 1H), 7.02-7.01 (m, 1H), 6.98-6.96 (m, 1H), 3.76 (s, 3H), 3.73 (s, 3H) |
| 181 | 3-(2,3-Dimethoxy-phenyl)-9H-dipyrido[2,3-b;4',3'-d]pyrrole-6-carbonitrile | D | Washing with methanol | 1.28, 331, C | (DMSO-D$_6$, 400 MHz): 12.89 (s, 1H), 9.01 (s, 1H), 8.94 (s, 1H), 8.93 (s, 1H), 8.82 (s, 1H), 8.75 (s, 1H), 7.18-7.16 (m, 1H), 7.13-7.12 (m, 1H), 7.04-7.01 (m, 1H), 3.84 (s, 3H), 3.54 (s, 3H) |
| 182 | 3-(2,3-Difluoro-phenyl)-9H-dipyrido[2,3-b;4',3'-d]pyrrole-6-carbonitrile | D | Washing with methanol | 1.32, 307, C | (DMSO-D$_6$, 400 MHz): 13.23 (s, 1H), 9.22 (s, 1H), 9.18 (s, 1H), 9.12 (s, 1H), 9.05 (s, 1H), 7.69-7.67 (m, 2H), 7.55-7.54 (m, 1H) |

TABLE 8-continued

| Example | Structure/Name | Coupling Method | Purification Method (s) | LCMS R$_T$/M + H$^+$/ Method | $^1$H NMR (ppm) |
|---|---|---|---|---|---|
| 183 | 3-(2-Chloro-5-methoxy-phenyl)-9H-dipyrido[2,3-b;4',3'-d]pyrrole-6-carbonitrile | D | Washing with methanol and DMF | 1.24, 335, C | (DMSO-D$_6$, 400 MHz): 13.19 (s, 1H), 9.20 (s, 1H), 9.10 (s, 1H), 9.03 (s, 1H), 8.90 (s, 1H), 7.70-7.68 (d, J = 8.8 Hz, 1H), 7.29 (s, 1H), 7.22-7.19 (m, 1H), 3.97 (s, 3H) |
| 184 | 3-(3-Fluoro-5-methyl-phenyl)-9H-dipyrido[2,3-b;4',3'-d]pyrrole-6-carbonitrile | D | Washing with methanol and DMF | 1.27, 303, C | (DMSO-D$_6$, 400 MHz): 12.96 (s, 1H), 9.13 (s, 1H), 9.05 (s, 2H), 8.92 (s, 1H), 7.52 (s, 1H), 7.50-7.47 (d, J = 10.4 Hz, 1H), 7.11-7.09 (d, J = 9.6 Hz, 1H), 2.44 (s, 3H) |
| 185 | 3-(3-Chloro-5-methoxy-phenyl)-9H-dipyrido[2,3-b;4',3'-d]pyrrole-6-carbonitrile | D | Washing with methanol and DMF | 1.40, 335, C | (DMSO-D$_6$, 400 MHz): 13.11 (s, 1H), 9.32 (s, 1H), 9.22-9.19 (m, 2H), 9.02 (s, 1H), 7.63 (s, 1H), 7.51 (s, 1H), 7.24 (s, 1H), 4.04 (s, 3H) |
| 186 | N-[4-(6-Cyano-9H-dipyrido[2,3-b;4',3'-d]pyrrol-3-yl)-phenyl]-acetamide | D | Preparative HPLC | 0.98, 328, C | (DMSO-D$_6$, 400 MHz): 12.92 (s, 1H), 10.10 (s, 1H), 9.02 (s, 2H), 8.98 (s, 1H), 8.92 (s, 1H), 7.74 (s, 4H), 2.07 (s, 3H) |

TABLE 8-continued

| Example | Structure/Name | Coupling Method | Purification Method(s) | LCMS $R_T$/M + H$^+$/ Method | $^1$H NMR (ppm) |
|---|---|---|---|---|---|
| 187 | N-[4-(6-Cyano-9H-dipyrido[2,3-b;4',3'-d]pyrrol-3-yl)-phenyl]-methanesulfonamide | D | Washing with THF and water then MeCN | 1.15, 364, C | (DMSO-D$_6$, 400 Hz): 12.89 (s, 1H), 9.88 (s, 1H), 9.01-9.00 (m, 2H), 8.96 (s, 1H), 8.90 (s, 1H), 7.77-7.75 (d, J = 8.8 Hz, 2H), 7.36-7.33 (d, J = 8.4 Hz, 2H), 3.02 (s, 3H) |
| 188 | 3-(3-Methanesulfonyl-phenyl)-9H-dipyrido[2,3-b;4',3'-d]pyrrole-6-carbonitrile | D | Washing with methanol | 1.15, 349, C | (DMSO-D$_6$, 400 MHz): 13.01 (s, 1H), 9.23 (s, 1H), 9.13 (s, 1H), 9.06 (s, 1H), 8.97 (s, 1H), 8.33 (s, 1H), 8.20-8.19 (d, J = 7.6 Hz, 1H), 7.98-7.96 (d, J = 8.0 Hz, 1H), 7.85-7.81 (m, 1H), 3.33 (s, 3H) |
| 189 | 4-(6-Cyano-9H-dipyrido[2,3-b;4',3'-d]pyrrol-3-yl)-N,N-dimethyl-benzenesulfonamide | C | Preparative HPLC | 1.11, 378, C | (DMSO-D$_6$, 400 MHz): 13.01 (s, 1H), 9.20 (s, 1H), 9.11 (s, 1H), 9.05 (s, 1H), 8.94 (s, 1H), 8.10-8.08 (d, J = 8.4 Hz, 2H), 7.91-7.89 (d, J = 8.4 Hz, 2H), 2.66 (s, 6H) |
| 190 | 3-(6-Cyano-9H-dipyrido[2,3-b;4',3'-d]pyrrol-3-yl)-N,N-dimethyl-benzenesulfonamide | C | Preparative HPLC | 1.22, 378, C | (DMSO-D$_6$, 400 MHz): 13.01 (s, 1H), 9.19 (s, 1H), 9.09 (s, 1H), 9.04 (s, 1H), 8.99 (s, 1H), 8.19-8.17 (m, 1H), 8.09 (s, 1H), 7.80-7.84 (m, 2H), 2.68 (s, 6H) |

TABLE 8-continued

| Example | Structure/Name | Coupling Method | Purification Method (s) | LCMS R$_T$/M + H$^+$/Method | $^1$H NMR (ppm) |
|---|---|---|---|---|---|
| 191 | 3-(3-Fluoro-5-hydroxy-phenyl)-9H-dipyrido[2,3-b;4',3'-d]pyrrole-6-carbonitrile | D | Washing with methanol | 1.21, 305, C | (DMSO-D$_6$, 400 MHz): 12.92 (s, 1H), 9.04-9.00 (m, 1H), 9.12 (s, 1H), 8.94 (s, 1H), 8.90 (s, 1H), 7.06-7.00 (m, 2H), 6.62-6.59 (m, 1H) |
| 192 | 3-(5-Fluoro-2-hydroxy-phenyl)-9H-dipyrido[2,3-b;4',3'-d]pyrrole-6-carbonitrile | D | Washing with methanol | 1.21, 305, C | (DMSO-D$_6$, 400 MHz): 12.86 (s, 1H), 9.74 (s, 1H), 9.00 (s, 1H), 8.94-8.92 (m, 2H), 8.85 (s, 1H), 7.27-7.23 (m, 1H), 7.07-6.95 (m, 2H) |
| 193 | 3-(3-Fluoro-pyridin-4-yl)-9H-dipyrido[2,3-b;4',3'-d]pyrrole-6-carbonitrile | D | Washing with methanol | 1.06, 290, C | (DMSO-D$_6$, 400 MHz): 13.15 (s, 1H), 9.14 (s, 1H), 9.07 (s, 1H), 9.00-8.99 (m, 2H), 8.78 (s, 1H), 8.60 (s, 1H), 7.86-7.83 (m, 1H) |
| 194 | 3-(4-Hydroxy-phenyl)-9H-dipyrido[2,3-b;4',3'-d]pyrrole-6-carboxylic acid amide | C | Preparative HPLC | 0.85, 305, C | (DMSO-D$_6$, 400 MHz): 13.15 (s, 1H), 9.61 (s, 1H), 9.05 (s, 1H), 8.97 (s, 1H), 8.87-8.86 (m, 2H), 8.09 (s, 1H), 7.65-7.63 (d, J = 8.8 Hz, 2H), 7.52 (s, 1H), 6.91-6.89 (d, J = 8.8 Hz, 2H) |

TABLE 8-continued

| Example | Structure/Name | Coupling Method | Purification Method (s) | LCMS $R_T$/M + H$^+$/Method | $^1$H NMR (ppm) |
|---|---|---|---|---|---|
| 195 | 3-(3-Isopropyl-phenyl)-9H-dipyrido[2,3-b;4',3'-d]pyrrole-6-carbonitrile | D | Preparative HPLC | 0.98, 313, C | (DMSO-D$_6$, 400 MHz): 12.96 (s, 1H), 9.07 (s, 1H), 9.02-8.99 (m, 2H), 8.94 (s, 1H), 7.65 (s, 1H), 7.60-7.58 (d, J = 6.8 Hz, 1H), 7.46-7.42 (m, 1H), 7.30-7.28 (d, J = 7.2 Hz, 1H), 3.00-2.97 (m, 1H), 1.28-1.27 (d, J = 6.8 Hz, 6H) |

Preparative HPLC condition used in Table 8:
Autopurification system equipped with a YMC s-5μ. RP column (12 μm, 250×20 mm; flowrate, 15 mL/min; solvent A:0.1% TFA/water; solvent B: 0.1% TFA/CH$_3$CN; gradient: 30-60% B over 13 min; UV detector fraction collection.

| Time(min) | Flowrate(mL/min) | solvent A % | solvent B % |
|---|---|---|---|
| 0 | 15 | 30 | 70 |
| 12 | 15 | 60 | 40 |
| 12.2 | 18 | 100 | 0 |
| 15.2 | 18 | 100 | 0 |
| 17 | 15 | 30 | 70 |

The compounds of the Examples in Table 9 were prepared via the general Mitsunobu methods followed by the general deprotection methods described above.

TABLE 9

| Example | Structure/Name | Mitunobu Method | Deprotection Mehod | Final purification Method(s) | LCMS $R_T$, M + H$^+$, Method | $^1$H NMR (ppm) |
|---|---|---|---|---|---|---|
| 196 | 3-[2-(dimethylamino)ethoxy]-9H-dipyrido[2,3-b;4',3'-d]pyrrole-6 carbonitrile | B | F | I | 2.70, 282, E | (400 MHz, DMSO-D$_6$): 12.66 (s, 1H), 8.98 (s, 1H), 8.85 (s, 1H), 8.47 (d, J = 2.8 Hz, 1H), 8.44 (d, J = 2.8 Hz, 1H), 4.22 (t, J = 5.8 Hz, 2H), 2.71 (t, J = 5.8 Hz, 2H), 2.26 (s, 6H). |
| 197 | 3-[3-(dimethylamino)propoxy]-9H-dipyrido[2,3-b;4',3'-d]pyrrole-6-carbonitrile | B | F | I | 2.79, 296, E | (400 MHz, DMSO-D$_6$): 12.65 (s, 1H), 8.98 (s, 1H), 8.87 (s, 1H), 8.45 (d, J = 2.8 Hz, 1H), 8.42 (d, J = 2.8 Hz, 1H), 4.16 (t, J = 6.5 Hz, 2H), 2.41 (t, J = 7.0 Hz, 2H), 2.17 (s, 6H), 1.94 (p, J = 6.8 Hz, 2H). |

TABLE 9-continued

| Example | Structure/Name | Mitunobu Method | Deprotection Mehod | Final purification Method(s) | LCMS $R_T$, M + H+, Method | ¹H NMR (ppm) |
|---|---|---|---|---|---|---|
| 198 | 3-(piperidin-4-yloxy)-9H-dipyrido[2,3-b;4',3'-d]pyrrole-6-carbonitrile | B | F | I | 6.46, 294, D | 400 MHz, DMSO-D₆): 8.93 (d, J = 0.9 Hz, 1H), 8.77 (s, 1H), 8.43-8.35 (m, 2H), 4.47-4.35 (m, 1H), 4.03 (m, 1H), 2.99 (dt, J = 12.9, 4.1 Hz, 2H), 2.62-2.53 (m, 1H), 1.99 (m, 2H), 1.59-1.42 (m, 2H), 1.18 (m, 1H). |
| 199 | 3-(2-(ethylamino)ethoxy)-9H-dipyrido[2,3-b;4',3'-d]pyrrole-6-carbonitrile | B | F | I | 6.04, 282, D | (400 MHz, DMSO-D₆): 8.99 (s, 1H), 8.87 (s, 1H), 8.48 (d, J = 2.8 Hz, 1H), 8.45-8.41 (m, 1H), 4.18 (t, J = 5.6 Hz, 2H), 2.97 (t, J = 5.6 Hz, 2H), 2.64 (q, J = 7.1 Hz, 2H), 1.05 (t, J = 7.1 Hz, 3H) |
| 200 | 3-(pyrrolidin-2-ylmethoxy)-9H-dipyrido[2,3-b;4',3'-d]pyrrole-6-carbonitrile | B | F | I | 2.77, 294, E | (500 MHz, DMSO-D₆): 8.99 (d, J = 1.0 Hz, 1H), 8.85 (d, J = 0.9 Hz, 1H), 8.48 (d, J = 2.8 Hz, 1H), 8.43 (d, J = 2.8 Hz, 1H), 8.30 (s, 1H), 4.12-4.01 (m, 2H), 3.64-3.56 (m, 2H), 3.00-2.89 (m, 2H), 2.01-1.93 (m, 1H), 1.77 (m, 2H), 1.58 (m, 1H). |
| 201 | 3-((S)-Pyrrolidin-3-yloxy)-9H-dipyrido[2,3-b;4',3'-d]pyrrole-6-carbonitrile | B | F | I | 2.65, 280, E | (400 MHz, DMSO-D₆): 8.99 (s, 1H), 8.90 (s, 1H), 8.43 (d, J = 2.8 Hz, 1H), 8.41 (d, J = 2.8 Hz, 1H), 5.00 (t, J = 5.6 Hz, 1H), 3.19 (dd, J = 12.4, 5.2 Hz, 2H), 3.05-2.95 (m, 2H), 2.94-2.85 (m, 1H), 2.13 (m, 1H), 1.96-1.85 (m, 1H). |
| 202 | 3-((1-methylpiperidin-4-yl)methoxy)-9H-dipyrido[2,3-b;4',3'-d]pyrrole-6-carbonitrile | B | F | I | 7.06, 322, D | (400 MHz, DMSO-D₆): 12.65 (s, 1H), 8.98 (d, J = 0.9 Hz, 1H), 8.86 (d, J = 0.9 Hz, 1H), 8.46 (d, J = 2.8 Hz, 1H), 8.43 (d, J = 2.9 Hz, 1H), 4.10-3.93 (m, 2H), 2.84 (d, J = 10.1 Hz, 1H), 2.71-2.56 (m, 1H), 2.15 (s, 3H), 2.13-2.01 (m, 1H), 1.91 (m, 1H), 1.81-1.71 (m, 1H), 1.66 (m, 1H), 1.60-1.43 (m, 1H), 1.24 (s, 1H), 1.21-1.06 (m, 1H). |

| Example | Structure/Name | Mitunobu Method | Deprotection Method | Final purification Method(s) | LCMS $R_T$, M + H⁺, Method | ¹H NMR (ppm) |
|---|---|---|---|---|---|---|
| 203 | 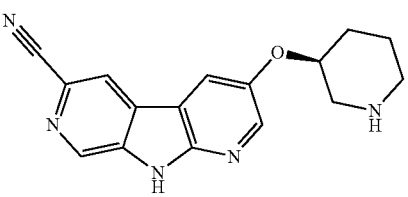 [SMILES: N#Cc1cc2c(cn1)[nH]c1ncc(O[C@H]3CCCNC3)cc12]<br>3-(piperidin-3-yloxy)-9H-dipyrido[2,3-b;4',3'-d]pyrrole-6-carbonitrile | B | F | I | 6.48, 294, D | (400 MHz, DMSO-D₆): 8.96 (d, J = 0.8 Hz, 1H), 8.83 (s, 1H), 8.43 (m, 2H), 4.29 (m, 1H), 3.16 (m, 1H), 2.84-2.75 (m, 1H), 2.64-2.51 (m, 2H), 2.11 (s, 1H), 1.76-1.67 (m, 1H), 1.51 (m, 2H). |
| 204 | 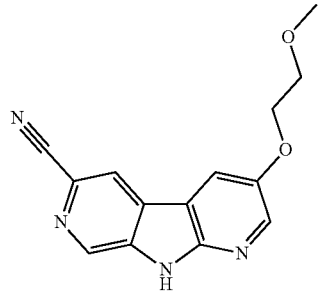 [SMILES: COCCOc1cnc2[nH]c3cnc(C#N)cc3c2c1]<br>3-(2-methoxyethoxy)-9H-dipyrido[2,3-b;4',3'-d]pyrrole-6-carbonitrile | B | F | I | 9.04, 269, D | (400 MHz, DMSO-D₆): 12.66 (s, 1H), 8.98 (d, J = 0.9 Hz, 1H), 8.84 (d, J = 0.9 Hz, 1H), 8.48 (d, J = 2.9 Hz, 1H), 8.42 (d, J = 2.9 Hz, 1H), 4.29-4.23 (m, 2H), 3.75 (m, 2H), 3.35 (s, 3H). |
| 205 | 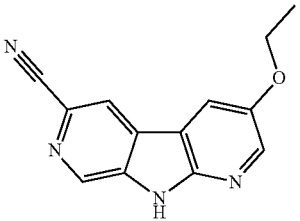 [SMILES: CCOc1cnc2[nH]c3cnc(C#N)cc3c2c1]<br>3-ethoxy-9H-dipyrido[2,3-b;4',3'-d]pyrrole-6-carbonitrile | B | F | I | 10.53, 239, D | (400 MHz, DMSO-D₆): 8.96 (d, J = 0.9 Hz, 1H), 8.82 (d, J = 0.9 Hz, 1H), 8.44 (d, J = 2.9 Hz, 1H), 8.37 (d, J = 2.9 Hz, 1H), 4.19 (q, J = 7.0 Hz, 2H), 1.42 (t, J = 7.0 Hz, 3H). |

Example 206

3-(2,3-Dihydroindol-1-yl)-9H-dipyrido[2,3-b;4',3'-d]pyrrole-6-carbonitrile

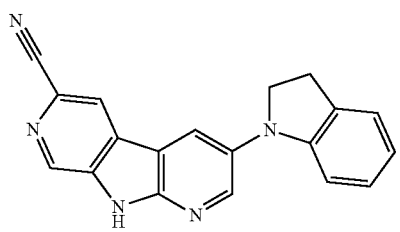 [SMILES: N#Cc1cc2c(cn1)[nH]c1ncc(N3CCc4ccccc43)cc12]

Step 1: 3-(2,3-Dihydro-indol-1-yl)-9-(2-trimethylsilanyl-ethoxymethyl)-9H-dipyrido[2,3-b;4',3'-d]pyrrole-6-carbonitrile

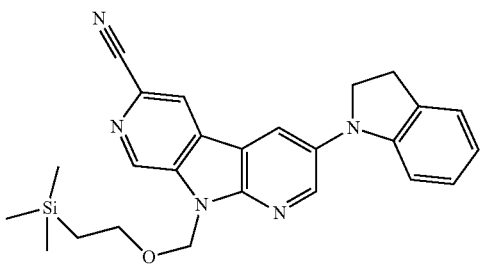 [SMILES: C[Si](C)(C)CCOCn1c2cnc(C#N)cc2c2cc(N3CCc4ccccc43)cnc21]

Indoline (67 mg, 0.56 mmol) was added to a solution of 3-bromo-9-(2-trimethylsilanyl-ethoxymethyl)-9H-dipyrido[2,3-b;4',3'-d]pyrrole-6-carbonitrile (210 mg, 0.52 mmol), tribasic potassium phosphate (164 mg, 0.77 mmol) and dicyclohexyl-(2',6'-diisopropoxy-biphenyl-2-yl)-phosphane (88 mg, 0.19 mmol) in anhydrous toluene (5.0 mL). The reaction mixture was degassed with nitrogen for 10 minutes, heated at 110° C. for 18 h and then allowed to cool to ambient temperature. The resultant mixture was poured into water (40 mL) and extracted with DCM (2×40 mL). The combined organic phase was separated, dried over anhydrous sodium sulfate, filtered and evaporated in vacuo. The resultant residue was purified by flash chromatography (silica, 12 g column, ISCO, 0-40% ethyl acetate in cyclohexane) and the isolated solid triturated with diethylether/pentane and air dried to afford the title compound as a yellow powder (124 mg, 54%). LCMS (Method B): $R_T$=4.83 min, M±H$^+$=442.

Step 2: 3-(2,3-Dihydroindol-1-yl)-9H-dipyrido[2,3-b;4',3'-d]pyrrole-6-carbonitrile

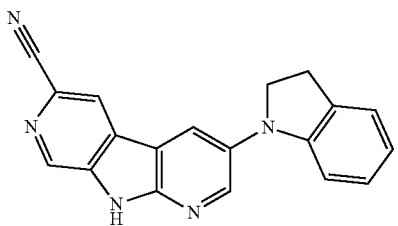 [SMILES: N#Cc1cc2c(cn1)[nH]c1ncc(N3CCc4ccccc43)cc12]

3-(2,3-Dihydroindol-1-yl)-9-(2-trimethylsilanyl-ethoxymethyl)-9H-dipyrido[2,3-b;4',3'-d]pyrrole-6-carbonitrile (124 mg) was subjected to general deprotection Method A. The resultant residue was purified by flash chromatography (silica, 40 g column, ISCO, 0-20% MeOH in DCM), then HPLC (20-90% MeCN over 30 min, 15 mL/min) to afford the title compound as an orange solid (10.5 mg). $^1$H NMR (DMSO-D$_6$, 400 MHz): 12.70 (s, 1H), 9.00 (d, J=1.1 Hz, 1H), 8.96 (d, J=1.1 Hz, 1H), 8.72 (d, J=2.7 Hz, 1H), 8.70 (d, J=2.7 Hz, 1H), 7.22 (d, J=7.3 Hz, 1H), 7.11-7.01 (m, 2H), 6.76 (td, J=7.1, 1.4 Hz, 1H), 4.05 (t, J=8.4 Hz, 2H), 3.17 (t, J=8.4 Hz, 2H). LCMS (Method A): $R_T$=10.52 min, M+H$^+$=311.

Example 207

3-[4-(8-Aza-bicyclo[3.2.1]oct-8-ylmethyl)-phenyl]-9H-dipyrido[2,3-b;4',3'-d]pyrrole-6-carbonitrile

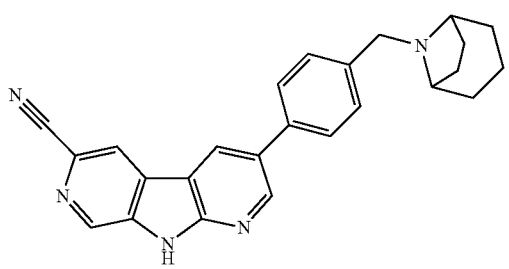 [SMILES: N#Cc1cc2c(cn1)[nH]c1ncc(-c3ccc(CN4C5CCCC4CC5)cc3)cc12]

Step 1: 8-(4-Bromobenzyl)-8-aza-bicyclo[3.2.1]octan-3-one

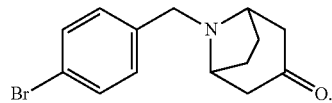 [SMILES: O=C1CC2CCC(C1)N2Cc1ccc(Br)cc1]

A stirred solution of 1-bromo-4-bromomethylbenzene (0.39 g, 1.56 mmol), triethylamine (0.45 mL, 3.20 mmol) and 8-azabicyclo[3.2.1]octan-3-one (0.33 mL, 2.32 mmol) in THF (10 mL) was heated under reflux for 5 h. The reaction mixture was allowed to cool to ambient temperature and the solid removed by filtration. The filtrate was concentrated under reduced pressure to afford a residue that was purified by flash chromatography (silica, 50 g column, Biotage, 0-100% DCM in ethyl acetate) to afford the title compound as an off-white solid (400 mg, 90%). $^1$H NMR (CDCl$_3$, 300 MHz): 7.48-7.43 (m, 2H), 7.32-7.28 (m, 2H), 3.69 (s, 2H), 3.49-3.43 (m, 2H), 2.66 (dd, J=16.0, 4.3 Hz, 2H), 2.26-2.17 (m, 2H), 2.14-2.06 (m, 2H), 1.66-1.56 (s, 2H). LCMS (Method B): $R_T$=1.86 min, M+H$^+$=294/296.

Step 2: 8-(4-Bromobenzyl)-8-aza-bicyclo[3.2.1]octan-3-ol

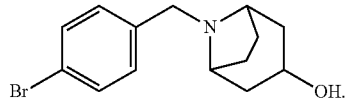 [SMILES: OC1CC2CCC(C1)N2Cc1ccc(Br)cc1]

Sodium borohydride (95 mg, 1.50 mmol) was added to a solution of 8-(4-bromobenzyl)-8-azabicyclo-[3.2.1]octan-3-one (0.22 g, 0.75 mmol) in methanol (10 mL) and the reaction mixture was stirred for 30 minutes. The reaction was diluted with water (10 mL) and extracted into DCM (3×20 mL). The combined organic layer was washed with saturated aqueous sodium bicarbonate solution (10 mL), dried over anhydrous sodium sulfate, filtered and evaporated in vacuo to afford the title compound as an off-white solid (200 mg, 90%). $^1$H NMR (CDCl$_3$, 300 MHz): 7.43 (dd, J=8.3, 2.0 Hz, 3H), 7.29-7.23 (m, 2H), 3.60-3.45 (m, 2H), 3.23-3.10 (m, 2H), 2.16-1.40 (m, 8H). LCMS (Method B): $R_T$=1.90 min, M+H$^+$=296/298.

Step 3: 3-[4-(3-Hydroxy-8-aza-bicyclo[3.2.1]oct-8-ylmethyl)-phenyl]-9-(2-trimethylsilanyl-ethoxymethyl)-9H-dipyrido[2,3-b;4',3'-d]pyrrole-6-carbonitrile

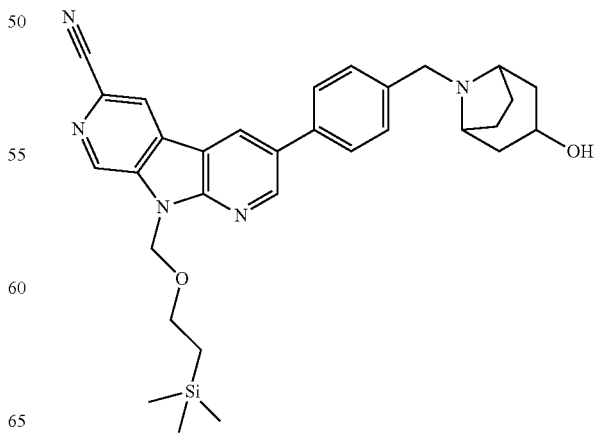

A degassed mixture of 3-(4,4,5,5-tetramethyl-[1,3,2]dioxaborolan-2-yl)-9-(2-trimethylsilanylethoxymethyl)-9H-dipyrido[2,3-b;4',3'-d]pyrrole-6-carbonitrile (217 mg, 0.48 mmol), 8-(4-bromobenzyl)-8-aza-bicyclo[3.2.1]octan-3-ol (157 mg, 0.53 mmol), tetrakis(triphenylphosphine)palladium (0) (33 mg, 5 mol %) and cesium carbonate (157 mg, 0.48 mmol) in a mixture of DME (5 mL), IMS (2 mL) and water (1.3 mL) was heated under microwave irradiation at 100° C. for 30 minutes. The cooled reaction mixture was purified by flash chromatography (silica, 50 g column, Biotage, 0-5% (2N ammonia in MeOH) in DCM) to afford the title compound as an off-white solid (155 mg, 60%). $^1$H NMR (CDCl$_3$, 300 MHz): 9.21-9.17 (m, 1H), 8.95 (d, J=2.1 Hz, 1H), 8.61 (d, J=2.1 Hz, 1H), 8.43 (s, 1H), 7.67-7.53 (m, 4H), 6.04 (s, 2H), 3.70-3.58 (m, 4H), 3.35-3.15 (m, 2H), 2.20-1.60 (m, 10H), 0.95 (t, J=8.2 Hz, 2H), 0.00 (s, 9H). LCMS (Method B): R$_T$=2.92 min, M+H$^+$=540.

Step 4: Imidazole-1-carbothioic acid O-(8-{4-[6-cyano-9-(2-trimethylsilanylethoxymethyl)-9H-dipyrido[2,3-b;4',3'-d]pyrrol-3-yl]-benzyl}-8-aza-bicyclo[3.2.1]oct-3-yl) ester

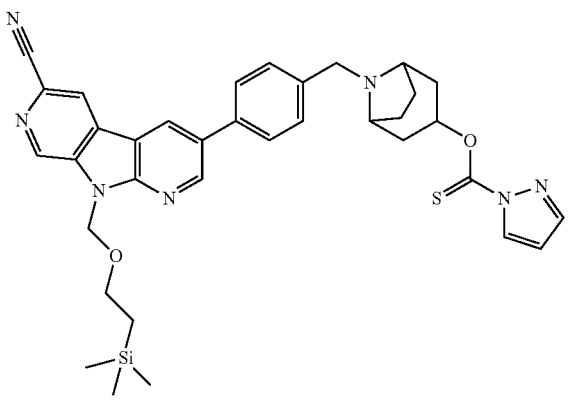 [SMILES: C[Si](C)(C)CCOCn1c2cnc(C#N)cc2c2cc(-c3ccc(CN4C5CCC4CC(OC(=S)n4cccn4)C5)cc3)cnc21]

A solution of 3-[4-(3-hydroxy-8-aza-bicyclo[3.2.1]oct-8-ylmethyl)-phenyl]-9-(2-trimethylsilanylethoxymethyl)-9H-dipyrido[2,3-b;4',3'-d]pyrrole-6-carbonitrile (155 mg, 0.29 mmol), DMAP (5 mg, catalytic) and N,N'-thiocarbonyldiimidazole (455 mg, 8.76 mmol) in DCM (10 mL) was heated under reflux for 12 h. The cooled reaction mixture was purified by flash chromatography (silica, 50 g column, Biotage, 0-5% MeOH in DCM) to afford the title compound as a white solid (182 mg, 97%). $^1$H NMR (CDCl$_3$, 300 MHz): 9.28-9.25 (m, 1H), 9.04 (dd, J=7.0, 2.2 Hz, 1H), 8.69-8.66 (m, 1H), 8.51 (d, J=1.0 Hz, 1H), 8.47-8.39 (m, 1H), 7.81-7.61 (m, 5H), 7.15-7.10 (m, 1H), 6.12 (s, 2H), 4.35 (s, 2H), 3.76-3.61 (m, 4H), 2.32-2.17 (m, 4H), 2.13-1.93 (m, 5H), 1.08-0.96 (m, 2H), 0.00 (s, 9H). LCMS (Method B): R$_T$=3.13 min, M+H$^+$=650.

Step 5: 3-[4-(8-Aza-bicyclo[3.2.1]oct-8-ylmethyl)-phenyl]-9-(2-trimethylsilanyl-ethoxymethyl)-9H-dipyrido[2,3-b;4',3'-d]pyrrole-6-carbonitrile

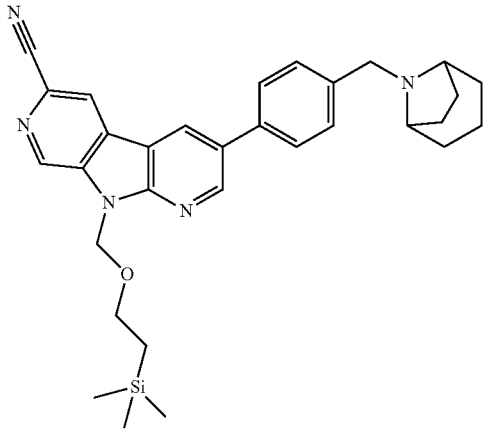 [SMILES: C[Si](C)(C)CCOCn1c2cnc(C#N)cc2c2cc(-c3ccc(CN4C5CCCC4CC5)cc3)cnc21]

To a solution of imidazole-1-carbothioic acid O-(8-{4-[6-cyano-9-(2-trimethylsilanylethoxymethyl)-9H-dipyrido[2,3-b;4',3'-d]pyrrol-3-yl]-benzyl}-8-aza-bicyclo[3.2.1]oct-3-yl) ester (182 mg, 0.28 mmol) and AIBN (60 mg, 0.36 mmol) in toluene (10 mL) under an argon atmosphere was added tributyltin hydride (0.58 mL, 1.85 mmol). On complete addition, the reaction was heated at 110° C. for 15 minutes then allowed to cool to ambient temperature. The mixture was concentrated in vacuo and the resultant residue was purified by flash chromatography (silica, 50 g column, Biotage, 0-5% MeOH in DCM) to afford the title compound as a white solid (123 mg, 84%). $^1$H NMR (CDCl$_3$, 300 MHz): 9.26 (d, J=1.0 Hz, 1H), 9.03 (d, J=2.2 Hz, 1H), 8.69 (d, J=2.2 Hz, 1H), 8.51 (d, J=1.0 Hz, 1H), 7.72-7.60 (m, 4H), 6.12 (s, 2H), 3.74-3.65 (m, 4H), 3.37-3.22 (m, 2H), 2.16-1.40 (m, 10H), 1.06-0.97 (m, 2H), 0.00 (s, 9H). LCMS (Method B): R$_T$=2.96 min, M+H$^+$=524.

Step 6: 3-[4-(3-Hydroxy-8-aza-bicyclo[3.2.1]oct-8-ylmethyl)-phenyl]-9H-dipyrido[2,3-b;4',3'-d]pyrrole-6-carbonitrile

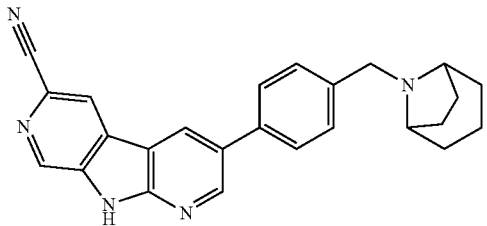 [SMILES: N#Cc1cc2c(cn1)[nH]c1ncc(-c3ccc(CN4C5CCCC4CC5)cc3)cc12]

A solution of 3-[4-(8-aza-bicyclo[3.2.1]oct-8-ylmethyl)-phenyl]-9-(2-trimethylsilanyl-ethoxymethyl)-9H-dipyrido[2,3-b;4',3'-d]pyrrole-6-carbonitrile (120 mg, 0.23 mmol) in TBAF (1N in THF, 3 mL) and the reaction mixture was heated at 55° C. for 16 h. The mixture was then concentrated in vacuo and the resultant residue purified by flash column chromatography (silica, 50 g column, Biotage, 0-20% MeOH in DCM) to afford the title compound as an off-white solid (85 mg, 94%). $^1$H NMR (CDCl$_3$, 300 MHz): 9.01 (d, J=1.0 Hz, 1H), 8.90 (d, J=2.2 Hz, 1H), 8.69 (d, J=2.2 Hz, 1H), 8.49 (d, J=1.0 Hz, 1H), 7.64 (d, J=8.0 Hz, 2H), 7.58-7.51 (m, 2H), 3.64-3.57

(m, 2H), 3.39-3.37 (m, 2H), 2.11-2.04 (m, 2H), 1.90-1.72 (m, 2H), 1.68-1.33 (m, 6H). LCMS (Method A): $R_T$=6.31 min, M+H$^+$=394.

Example 208

6-Cyano-3-(4-piperidin-1-ylmethyl-phenyl)-9H-dipyrido[2,3-b;4',3'-d]pyrrole-N-oxide

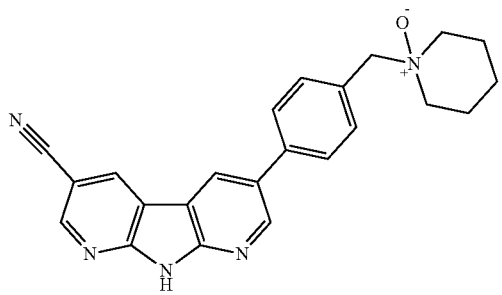

A mixture of 6-cyano-3-(4-piperidin-1-ylmethyl-phenyl)-9H-dipyrido[2,3-b;4',3'-d]pyrrole (110 mg, 0.30 mmol) and 3-phenyl-2-(phenylsulfonyl)oxaziridine (102 mg, 0.39 mmol) in DCM (5.8 mL) was stirred at room temperature for 2 h. The solid was collected by filtration and washed with DCM (3×20 mL) to afford a bright yellow solid (100 mg, 90%). NMR (400 MHz, DMSO-D$_6$): 8.98 (s, 1H), 8.91 (s, 1H), 8.90 (s, 1H), 8.83 (s, 1H), 7.66 (m, 4H), 4.43 (s, 2H), 3.13 (m, 2H), 2.14 (m, 2H), 1.59 (m, 4H), 1.34 (m, 2H). LCMS (method D): $R_T$=8.82 min, M+H$^+$=384.

Example 209

3-[4-(1-Ethyl-piperidin-2-yl)-phenyl]-9H-dipyrido[2,3-b;4',3'-d]pyrrole-6-carbonitrile

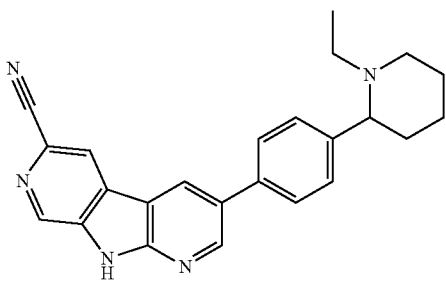 [SMILES: CCN1CCCCC1c1ccc(-c2cnc3[nH]c4cnc(C#N)cc4c3c2)cc1]

Step 1: 2-(4-Bromophenyl)pyridine

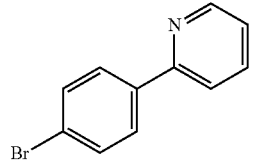 [SMILES: Brc1ccc(-c2ccccn2)cc1]

1,4-Dibromobenzene (5.90 g, 25.0 mmol) was dissolved in anhydrous diethyl ether (40 mL) and flushed with argon before the solution was cooled to −78° C. and n-butyl lithium (2.5M in hexanes, 10.2 mL, 25.6 mmol) was added dropwise at a rate that maintained the temperature below −70° C. The reaction mixture was stirred at this temperature for 30 minutes then 2-fluoropyridine (1.72 mL, 20.0 mmol) was added dropwise and stirring continued at −78° C. for 1 h then the reaction mixture was allowed to warm to room temperature and stirred for 1 h. The reaction mixture was poured onto water (50 mL) and extracted with diethyl ether (3×50 mL). The combined organic layers were washed with 5% HCl (3×200 mL) then the pH of the aqueous phase was adjusted to 10 by the addition of potassium hydroxide and the aqueous phase was extracted with diethyl ether (3×200 mL). The combined organic phase was dried over sodium sulfate, filtered and evaporated to afford the title compound (2.7 g, 58%). $^1$H NMR (CDCl$_3$, 300 MHz): 8.71-8.66 (m, 1H), 7.91-7.85 (m, 2H), 7.79-7.67 (m, 2H), 7.64-7.57 (m, 2H), 7.28-7.22 (m, 1H).

Step 2: 2-(4-Bromophenyl)-1-ethyl-1,2,3,6-tetrahydropyridine

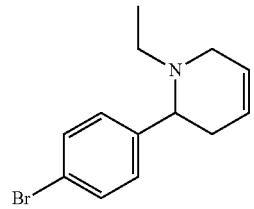

To a solution of 2-(4-bromophenyl)pyridine (2.7 g, 11.5 mmol) in DMF (50 mL) was added ethyl iodide (1.9 mL, 23.1 mmol) and the reaction mixture was heated to 80° C. for 16 h. The mixture was cooled then evaporated and the resultant residue dissolved in methanol (100 mL) before addition of sodium borohydride (1.5 g, 39.2 mmol) portionwise. The reaction mixture was stirred at ambient temperature for 1 h then evaporated and saturated aqueous sodium carbonate solution was added. The mixture was extracted with ethyl acetate (2×100 mL). The combined organic layer was dried over sodium sulfate, filtered and evaporated then the residue was purified by flash chromatography (silica, Biotage 100 g column, 50% ethyl acetate in cyclohexane) to afford the title compound (0.9 g, 29%), which was used without further purification. $^1$H NMR (CDCl$_3$, 300 MHz): 7.47-7.42 (m, 2H), 7.24-7.19 (m, 2H), 5.86-5.74 (m, 2H), 3.47-3.35 (m, 2H), 2.98-2.87 (m, 1H), 2.64-2.46 (m, 1H), 2.33-2.26 (m, 2H), 2.13-2.00 (m, 1H), 0.99 (t, J=7.2 Hz, 3H).

Step 3: 3-[4-(1-Ethylpiperidin-2-yl)-phenyl]-9-(2-trimethylsilanylethoxymethyl)-9H-dipyrido[2,3-b;4',3'-d]pyrrole-6-carbonitrile

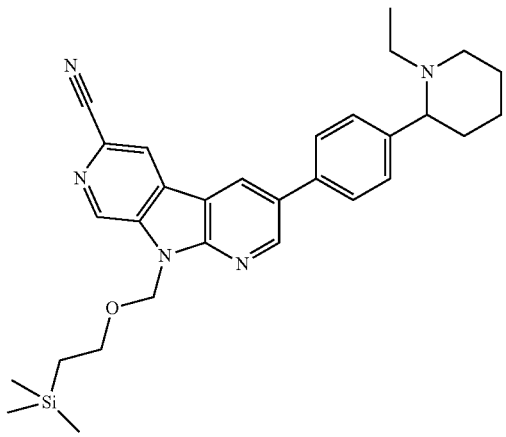 [SMILES: CCN1CCCCC1c1ccc(-c2cnc3c(c2)c2cc(C#N)ncc2n3COCC[Si](C)(C)C)cc1]

A degassed mixture of 2-(4-bromophenyl)-1-ethyl-1,2,3,6-tetrahydropyridine (0.13 g, 0.49 mmol), 3-(4,4,5,5-tetramethyl-[1,3,2]dioxaborolan-2-yl)-9-(2-trimethyl silanylethoxymethyl)-9H-dipyrido[2,3-b;4',3'-d]pyrrole-6-carbonitrile (0.20 g, 0.44 mmol), cesium carbonate (0.15 g) and tetrakis(triphenylphosphine)palladium(0) (30 mg) in DME (5 mL), IMS (2 mL) and water (1.3 mL) was heated under microwave irradiation at 140° C. for 30 minutes. The reaction mixture was allowed to cool to ambient temperature then purified by flash chromatography (silica, Biotage 50 g column, 0-100% (5% methanol in DCM)) to afford a colorless residue (95 mg). The resultant residue was dissolved in IMS (10 mL) and the flask degassed with nitrogen. Palladium on carbon (10% by wt., 11 mg) was added and the reaction mixture placed under an atmosphere of hydrogen and stirred for 16 h. The solid was removed by filtration and the filtrate evaporated to afford the title compound (85 mg) which was used without further purification. $^1$H NMR (CHCl$_3$, 400 MHz,): 9.18 (d, J=1.0 Hz, 1H), 8.95 (d, J=2.2 Hz, 1H), 8.61 (d, J=2.2 Hz, 1H), 8.42 (d, J=1.0 Hz, 1H), 7.68-7.61 (m, 2H), 7.60-7.53 (m, 2H), 6.04 (s, 2H), 3.67-3.59 (m, 2H), 3.40-3.20 (m, 2H), 2.79-2.67 (m, 1H), 2.37-2.16 (m, 2H), 1.93-1.73 (m, 4H), 1.46-1.35 (m, 2H), 1.34-1.20 (m, 2H), 1.05-0.78 (m, 3H), −0.07 (s, 9H).

Step 4: 3-[4-(1-Ethylpiperidin-2-yl)-phenyl]-9H-dipyrido[2,3-b;4',3'-d]pyrrole-6-carbonitrile

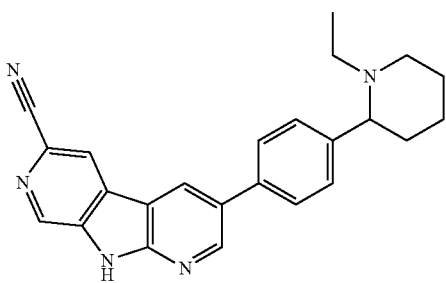 [SMILES: CCN1CCCCC1c1ccc(-c2cnc3[nH]c4cnc(C#N)cc4c3c2)cc1]

A solution of 3-[4-(1-ethyl-piperidin-2-yl)-phenyl]-9-(2-trimethylsilanylethoxy methyl)-9H-dipyrido[2,3-b;4',3'-d]pyrrole-6-carbonitrile (75 mg, 0.147 mmol) in TBAF (1M in THF, 1.5 mL, 1.47 mmol) was heated at 55° C. for 16 h. The reaction mixture was concentrated in vacuo and the resultant residue was partitioned between water and ethyl acetate. The organic layer was separated, dried over sodium sulfate, filtered and evaporated to give a yellow solid. The resultant solid was purified by flash chromatography (silica, Biotage 50 g column, 0-100% (10% methanol in DCM)) to afford the title compound (11 mg, 20%). $^1$H NMR (DMSO-D$_6$, 400 MHz): 12.89 (s, 1H), 9.08 (d, J=2.3 Hz, 1H), 9.04 (d, J=1.1 Hz, 1H), 9.02 (d, J=2.3 Hz, 1H), 8.93 (d, J=1.1 Hz, 1H), 7.75 (d, J=8.0 Hz, 2H), 7.49 (d, J=8.0 Hz, 2H), 3.16-3.07 (m, 2H), 2.54-2.42 (m, 1H), 2.11-1.93 (m, 2H), 1.79-1.64 (m, 3H), 1.63-1.20 (m, 3H), 0.89 (t, J=7.1 Hz, 3H). LCMS (Method A): R$_T$=6.23 min; M+H$^+$=382

Example 210

3-(Oxazol-2-yl)-9H-dipyrido[2,3-b;4',3'-d]pyrrole-6-carbonitrile

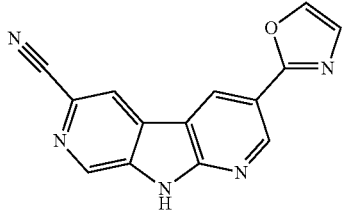 [SMILES: N#Cc1cc2c(cn1)[nH]c1ncc(-c3ncco3)cc12]

A solution of 3-bromo-9H-dipyrido[2,3-b;4',3'-d]pyrrole-6-carbonitrile (101 mg, 0.369 mmol) and lithium chloride (46.9 mg, 1.11 mmol) in DMF (0.63 mL) was treated with DIPEA (161 µL, 0.922 mmol) and 2-(tri-n-butylstannyl)oxazole (232 µL, 1.11 mmol), and then degassed by the bubbling of nitrogen for 5 minutes. Tetrakis(triphenylphosphine)palladium(0) (21.3 mg, 18.4 µmol, 5.0 mol %) was added and the mixture heated at 165° C. for 15 hours. The mixture was allowed to cool and treated with saturated aqueous potassium fluoride solution at ambient temperature. The resulting solids were removed by filtration and washed with 20% methanol in DCM and water. The filtrate was filtered through a pad of celite, washing with 20% methanol in DCM. The layers were separated, the aqueous phase extracted into 20% methanol in DCM, and the combined organic phases concentrated in vacuo. The residue was dissolved in AcOH with sonication and heating, filtered hot, and allowed to cool. The resulting suspension was treated with water and then filtered to collect the tan-gray solid, which was redissolved in DMF and purified by preparative HPLC [2-60% MeCN/water modified with 0.1% ammonium hydroxide] to afford a tan solid (43.5 mg, 45%). $^1$H NMR (400 MHz, DMSO-D$_6$): 9.29 (d, J=2.2 Hz, 1H), 9.26 (d, J=2.2 Hz, 1H), 9.03 (m, 1H), 8.97 (m, 1H), 8.28 (m, 1H), 7.43 (m, 1H). LCMS (Method D): R$_T$=8.29 min, M+H$^+$=262.

Example 211

3-(Thiazol-2-yl)-9H-dipyrido[2,3-b;4',3'-d]pyrrole-6-carbonitrile

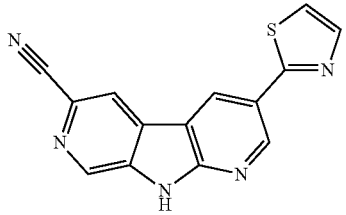 [SMILES: N#Cc1cc2c(cn1)[nH]c1ncc(-c3nccs3)cc12]

A solution of 3-bromo-9H-dipyrido[2,3-b;4',3'-d]pyrrole-6-carbonitrile (100 mg, 0.366 mmol) and lithium chloride (46.6 mg, 1.10 mmol) in DMF (0.63 mL) was treated with DIPEA (159 uL, 0.915 mmol) and 2-(tri-n-butylstannyl)thiazole (345 uL, 1.10 mmol), and then degassed by the bubbling of nitrogen for 5 minutes. Tetrakis(triphenylphosphine)palladium(0) (21.2 mg, 18.3 umol, 5.0 mol %) was added and the mixture heated at 165° C. for 15 hours. The mixture was allowed to cool and treated with saturated aqueous potassium fluoride solution at ambient temperature. The resulting solids were removed by filtration and washed with 20% methanol in DCM and water. The filtrate was filtered through a pad of celite, washing with 20% methanol in DCM. The layers were separated, the aqueous phase extracted into 20% methanol in DCM, and the combined organic phases concentrated in vacuo. The residue was dissolved in AcOH with sonication and heating, filtered hot and allowed to cool. The resulting suspension was treated with water and then filtered to collect the off-white solid. This solid was purified by preparative HPLC [0-30% MeCN/water modified with 0.1% formic acid] to afford an off-white solid powder (5.0 mg, 18%). $^1$H NMR (400 MHz, DMSO-D$_6$): 9.26 (s, 1H), 9.24 (s, 1H), 9.01 (s, 1H), 8.94 (s, 1H), 7.96 (d, J=3.2 Hz, 1H), 7.80 (d, J=3.2 Hz, 1H). LCMS (Method D): R$_T$=9.31 min, M+H$^+$=278.

Example 212

3-Ethylamino-9H-dipyrido[2,3-b;4',3'-d]pyrrole-6-carbonitrile

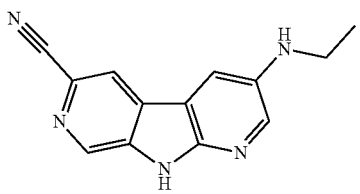 [SMILES: CCNc1cnc2[nH]c3cnc(C#N)cc3c2c1]

Step 1: 3-(tert-Butylcarbonyl)ethylamino-9-(2-trimethylsilanylethoxymethyl)-dipyrido[2,3-b;4',3'-d]pyrrole-6-carbonitrile

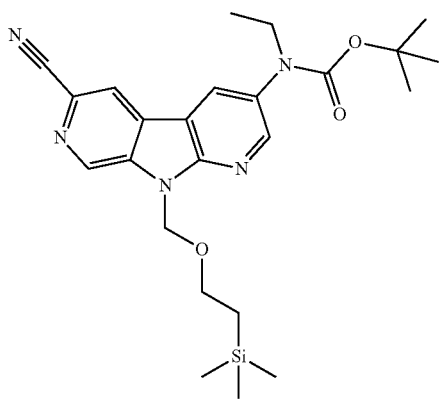 [SMILES: CCN(C(=O)OC(C)(C)C)c1cnc2c(c1)c1cc(C#N)ncc1n2COCC[Si](C)(C)C]

To a solution of 3-tert-butyl-carbonylamino-9-(2-trimethylsilanylethoxymethyl)-dipyrido[2,3-b;4',3'-d]pyrrole-6-carbonitrile (108 mg, 0.25 mmol) in THF (2.0 mL) was added sodium hydride (14.2 mg, 0.59 mmol). After the bubbling had ceased, iodoethane (47.3 µL, 0.592 mmol) was added and the reaction mixture heated at 55° C. overnight. The cooled reaction mixture was diluted with water and EtOAc, the layers separated, and the aqueous phase extracted into EtOAc. The combined organic phase was dried over sodium sulfate, filtered, and concentrated in vacuo. The resultant residue was dissolved in EtOAc and absorbed onto silica gel for purification by flash chromatography (silica, 12 g column, Biotage, 1-50% EtOAc in heptane) to afford the title compound as a viscous yellow oil (96 mg, 83%).

Step 2: 3-ethylamino-9H-dipyrido[2,3-b;4',3'-d]pyrrole-6-carbonitrile

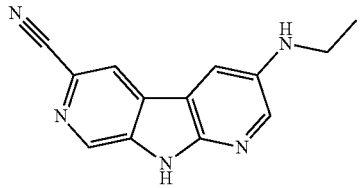 [SMILES: CCNc1cnc2[nH]c3cnc(C#N)cc3c2c1]

A solution of 3-(tert-butylcarbonyl)ethylamino-9-(2-trimethylsilanyl-ethoxymethyl)-dipyrido[2,3-b;4',3'-d]pyrrole-6-carbonitrile (161 mg, 0.345 mmol) in 1,4-dioxane (500 µL) was treated with 48% aqueous hydrobromic acid (500 µL) and heated at 75° C. for 10 min. The cooled reaction mixture was basified to pH 12 with 6N aqueous sodium hydroxide solution and then adjusted to pH 7-9 with dropwise addition of 1N hydrochloric acid. The solid was collected via centrifugation, the aqueous supernate discarded, and the solid dissolved in 1-2 mL of DMSO and purified by preparative HPLC (5-85% MeCN in water (0.1% NH$_4$OH) over 30 min, 35 mL/min) to afford the title compound as a yellow solid (22 mg, 26%). $^1$H NMR (DMSO-D$_6$, 500 MHz): 8.89 (d, J=1.0 Hz, 1H), 8.78 (d, J=0.9 Hz, 1H), 8.22 (d, J=2.7 Hz, 1H), 7.78 (d, J=2.7 Hz, 1H), 5.76 (t, J=5.5 Hz, 1H), 3.20-3.07 (m, 2H), 1.25 (t, J=7.1 Hz, 3H). LCMS (Method E): R$_T$=2.69 min, M+H$^+$=238.1.

Example 213

3-(1-Pyrrolidinylcarbonylamino)-9H-dipyrido[2,3-b;4',3'-d]pyrrole-6-carbonitrile

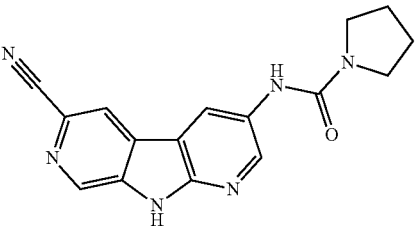 [SMILES: N#Cc1cc2c(cn1)[nH]c1ncc(NC(=O)N3CCCC3)cc12]

Step 1: 3-Amino-9H-dipyrido[2,3-b;4',3'-d]pyrrole-6-carbonitrile

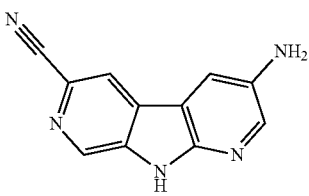 [SMILES: N#Cc1cc2c(cn1)[nH]c1ncc(N)cc12]

A solution of 3-tert-butyl-carbonylamino-9-(2-trimethylsilanylethoxymethyl)-dipyrido[2,3-b;4',3'-d]pyrrole-6-carbonitrile (101 mg, 0.229 mmol) in 1,4-dioxane (1.0 mL) was treated with a solution of 4M HCl in 1,4-dioxane (6 mL). After 1 h, an additional portion of 4.0M HCl in 1,4-dioxane (1.5 mL) was added to the reaction mixture. After 4.5 h at ambient temperature, the solvent was evaporated to afford an orange solid (70 mg, quantitative yield). The solid was used without purification.

Step 2: 3-(1-Pyrrolidinylcarbonylamino)-9H-dipyrido[2,3-b;4',3'-d]pyrrole-6-carbonitrile

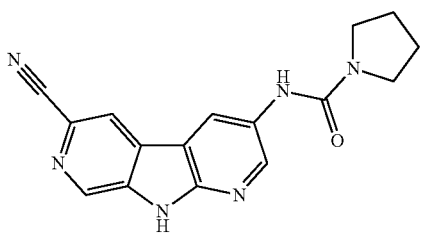 [SMILES: N#Cc1cc2c(cn1)[nH]c1ncc(NC(=O)N3CCCC3)cc12]

A solution of 3-amino-9H-dipyrido[2,3-b;4',3'-d]pyrrole-6-carbonitrile (47.9 mg, 0.229 mmol) in pyridine (6.1 mL) was treated with pyrrolidine-1-carbonyl chloride (83.4 µL, 0.755 mmol) and heated at 60° C. for 4 h. The cooled reaction mixture was treated with saturated aqueous sodium bicarbonate solution then diluted with 20% MeOH in DCM and water. The layers were separated, the aqueous phase extracted with 20% MeOH in DCM, and the combined organic phase was dried over sodium sulfate and concentrated in vacuo. The resultant residue was dissolved in DCM/methanol, absorbed onto silica gel, and purified by flash chromatography (silica, 4 g column, Biotage, 1-20% methanol in DCM containing 0 1% 7N ammonia in MeOH). Collecting appropriate fractions afforded a yellow solid which was further purified by preparative HPLC (5-85% MeCN in water (0.1% NH$_4$OH) over 30 min, 35 mL/min) to afford the title compound as an off-white solid (8.0 mg, 11%). $^1$H NMR (400 MHz, DMSO-D$_6$): 12.92 (s, 1H), 8.78 (s, 1H), 8.70 (dd, J=4.7, 1.4 Hz, 1H), 8.60 (dd, J=7.9, 1.4 Hz, 1H), 7.47 (dd, J=7.9, 4.8 Hz, 1H), 4.71 (dd, J=8.7, 4.6 Hz, 1H), 2.85 (m, 2H), 2.07 (m, 4H), 1.92 (m, 2H). LCMS (Method E): R$_T$=3.36 min, M+H$^+$=307.

Example 214

3-Chloro-9H-dipyrido[2,3-b;4',3'-d]pyrrole-6-carbonitrile

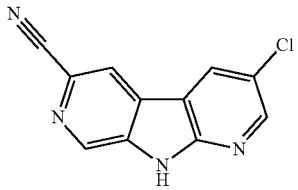 [SMILES: N#Cc1cc2c(cn1)[nH]c1ncc(Cl)cc12]

A solution of 3-chloro-9-(2-trimethylsilanylethoxymethyl)-dipyrido[2,3-b;4',3'-d]pyrrole-6-carbonitrile (24.2 mg, 67.4 µmol) in THF (1.3 mL) was treated with TBAF (398 µL, 1.35 mmol) and heated to 60° C. for 2 h. The reaction mixture was cooled to ambient temperature and the solvent removed in vacuo. The resultant residue was dissolved in DCM/EtOAc, absorbed onto silica gel, and purified by flash chromatography (silica, 4 g column, Biotage, 1-20% methanol in DCM containing 0 1% 7N ammonia in MeOH). Collecting appropriate fractions afforded a solid which was further purified by preparative HPLC (5-85% MeCN in water (0.1% NH$_4$OH) over 30 min, 35 mL/min) to afford the title compound as an off-white solid (10 mg, 66%). $^1$H NMR (400 MHz, DMSO-D$_6$): 13.07 (s, 1H), 9.05 (d, J=0.9 Hz, 1H), 8.95 (d, J 2.4 Hz, 1H), 8.92 (d, J=0.9 Hz, 1H), 8.73 (d, J=2.4 Hz, 1H). LCMS (Method E): R$_T$=3.98 min, M+H$^+$=229.

Example 215

3-(3-Hydroxy-3-methylbut-1-ynyl)-9H-dipyrido[2,3-b;4',3'-d]pyrrole-6-carbonitrile

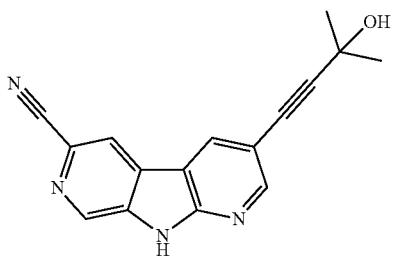 [SMILES: CC(C)(O)C#Cc1cnc2[nH]c3cnc(C#N)cc3c2c1]

Step 1: 3-(3-Hydroxy-3-methylbut-1-ynyl)-9-(2-trimethylsilanylethoxymethyl)-dipyrido[2,3-b;4',3'-d]pyrrole-6-carbonitrile

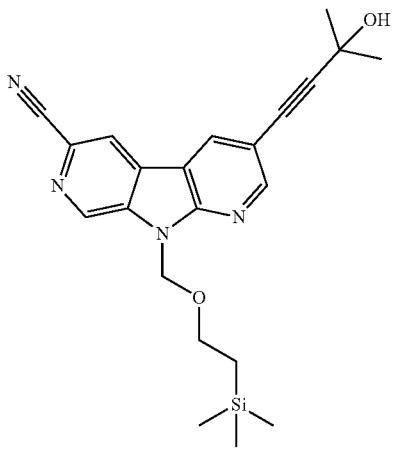 [SMILES: CC(C)(O)C#Cc1cnc2c(c1)c1cc(C#N)ncc1n2COCC[Si](C)(C)C]

In a flame dried flask, a mixture of 3-bromo-9-(2-trimethylsilanylethoxymethyl)-dipyrido[2,3-b;4',3'-d]pyrrole-6-carbonitrile (203 mg, 0.503 mmol) and copper (I) iodide (9.58 mg, 50.3 µmol) in 1,4-dioxane (5.3 mL) was degassed and flushed with nitrogen. Tetrakis(triphenylphosphine)palladium(0) (58.1 mg, 50.3 µmol) and 2-methyl-3-butyn-2-ol (244 µL, 2.52 mmol) were added and the reaction mixture was degassed, purged with nitrogen, and heated at 105° C. for 70 min. The cooled reaction mixture was diluted with DCM and water, the layers separated, and the aqueous phase extracted into DCM. The combined organic phase was dried over sodium sulfate and concentrated in vacuo. The resultant residue was dissolved in EtOAc and absorbed onto silica gel for purification by flash chromatography (silica, 25 g column, Biotage, 1-100% EtOAc in heptane) to afford further title compound as a white-yellow solid (254 mg, 124%). The solid was used without further purification. $^1$H NMR (DMSO-D$_6$, 400 MHz,): 9.33 (s, 1H), 8.98 (s, 1H), 8.91 (d, J=1.9 Hz, 1H), 8.76 (d, J=1.9 Hz, 1H), 6.03 (s, 2H), 5.55 (s, 1H), 3.57 (t, J=7.9 Hz, 2H), 1.51 (s, 6H), 0.82 (t, J=8.0 Hz, 2H), −0.16 (s, 9H).

Step 2: 3-(3-Hydroxy-3-methylbut-1-ynyl)-9H-dipyrido[2,3-b;4',3'-d]pyrrole-6-carbonitrile

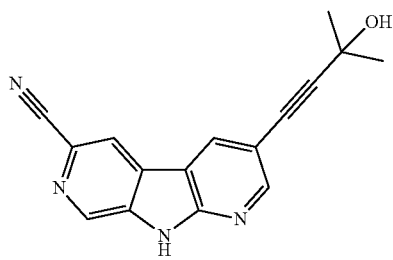 [SMILES: CC(C)(O)C#Cc1cnc2[nH]c3cnc(C#N)cc3c2c1]

A solution of 3-(3-hydroxy-3-methylbut-1-ynyl)-9-(2-trimethylsilanyl-ethoxymethyl)dipyrido[2,3-b;4',3'-d]pyrrole-6-carbonitrile (254 mg, 0.624 mmol) in THF (12 mL) was treated with TBAF (3.7 mL, 12.5 mmol) and heated to 60° C. for 24 h. The reaction mixture was allowed to cool to ambient temperature and the solvent removed in vacuo. The resultant residue was dissolved in DCM, absorbed onto silica gel, and purified by flash chromatography (Biotage, 25 g, 1-100% EtOAc in heptane). The light orange solid was further purified by preparative HPLC (5-85% MeCN in water (0.1% NH$_4$OH) over 30 min, 35 mL/min) to afford the title compound as an off-white solid (21 mg, 12%). $^1$H NMR (DMSO-D$_6$, 400 MHz,): 12.99 (s, 1H), 9.04 (s, 1H), 8.93 (s, 1H), 8.86 (d, J=2.0 Hz, 1H), 8.69 (d, J=2.0 Hz, 1H), 5.53 (s, 1H), 1.55 (s, 6H). LCMS (Method D): R$_T$=9.66 min, M+H$^+$=277.

Example 216

3-Hydroxy-9H-dipyrido[2,3-b;4',3'-d]pyrrole-6-carbonitrile

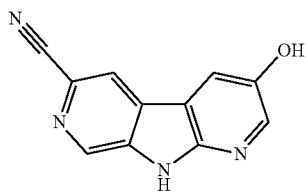 [SMILES: N#Cc1cc2c(cn1)[nH]c1ncc(O)cc12]

A solution of 3-hydroxy-9-(2-trimethylsilanylethoxymethyl)-dipyrido[2,3-b;4',3'-d]pyrrole-6-carbonitrile (90.9 mg, 0.267 mmol) in 1,4-dioxane (500 µL) was treated with 48% aqueous hydrobromic acid (500 µL) and heated at 75° C. for 10 min. The cooled reaction mixture was basified to pH 12 with 6N aqueous sodium hydroxide solution and then adjusted to pH 7-9 with dropwise addition of 1N hydrochloric acid. The solid was collected via centrifugation, the aqueous supernate discarded, and the solid dissolved in 1-2 mL of DMSO and purified by preparative HPLC (0-30% MeCN in water (0.1% formic acid) over 30 min, 35 mL/min) to afford the title compound as an off-white solid (19 mg, 33%). $^1$H NMR (DMSO-D$_6$, 400 MHz,): 12.51 (s, 1H), 9.94 (s, 1H), 8.94 (s, 1H), 8.87 (s, 1H), 8.32 (d, J=2.7 Hz, 1H), 8.08 (d, J=2.7 Hz, 1H). LCMS (Method E): R$_T$=2.90 min, M+H$^+$=211.

Example 217

3-(Pyridin-2-yl)-9H-dipyrido[2,3-b;4',3'-d]pyrrole-6-carbonitrile

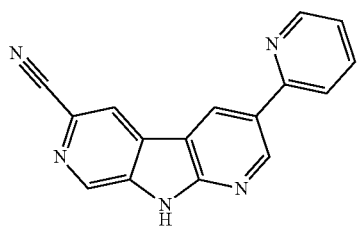 [SMILES: N#Cc1cc2c(cn1)[nH]c1ncc(-c3ccccn3)cc12]

A solution of 3-bromo-9H-dipyrido[2,3-b;4',3'-d]pyrrole-6-carbonitrile (150 mg, 0.549 mmol) and lithium chloride (69.9 mg, 1.65 mmol) in DMF (0.94 mL) was treated with DIPEA (239 µL, 1.37 mmol) and 2-(tributylstannyl)pyridine (607 µL, 1.65 mmol), and then degassed by the bubbling of nitrogen for 5 minutes. Tetrakis(triphenylphosphine)palladium(0) (31.7 mg, 27.5 µmol, 5.0 mol %) was added and the mixture heated at 165° C. for 15 h. The mixture was allowed to cool and treated with saturated aqueous potassium fluoride at ambient temperature. The resulting solids were removed by filtration and washed with 20% methanol in DCM and water. The filtrate was filtered through a pad of celite, washing with 20% methanol in DCM. The layers were separated, the aqueous phase extracted into 20% methanol in DCM, and the combined organic phases concentrated in vacuo to afford a solid residue. This solid was purified by preparative HPLC (0-30% MeCN/water modified with 0.1% formic acid) to afford an off-white solid powder (8.9 mg, 6.0%). $^1$H NMR (DMSO-D$_6$, 400 MHz,): 13.01 (s, 1H), 9.49 (d, J=2.2 Hz, 1H), 9.43 (d, J=2.2 Hz, 1H), 9.04 (dd, J=11.6, 0.8 Hz, 2H), 8.75 (d, J=4.0 Hz, 1H), 8.15 (d, J=8.0 Hz, 1H), 7.98 (td, J=7.8, 1.8 Hz, 1H), 7.43 (dd, J=6.7, 4.9 Hz, 1H). LCMS (Method D): R$_T$=7.26 min, M+H$^+$=272.

Compounds of the Examples in Table 10 were made via procedures described above using appropriate starting materials, reagents and following the procedures outlined in the general methods.

TABLE 10

| Example | Structure/Name | General Alkylation Method | General Deprotection Mehod | Final purification Method(s) | LCMS $R_T$, M + H+, Method | $^1$H NMR (ppm) |
|---|---|---|---|---|---|---|
| 218 | 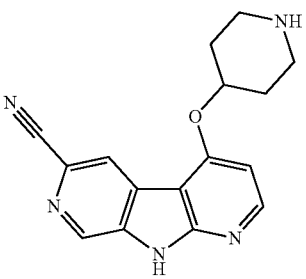 [SMILES: N#Cc1cc2c(cn1)[nH]c1nccc(OC3CCNCC3)c12]<br>4-(Piperidin-4-yloxy)-9H-dipyrido[2,3-b;4',3'-d]pyrrole-6-carbonitrile | C | F | T | 5.67, 294, D | (DMSO-D$_6$, 400 MHz): 8.97 (s, 1H), 8.52 (d, J = 5.8 Hz, 1H), 8.47 (s, 1H), 7.10 (d, J = 5.9 Hz, 1H), 4.95 (m, 1H), 3.11-3.03 (m, 2H), 2.76 (m, 2H), 2.08 (m, 2H), 1.88-1.67 (m, 2H). |
| 219 | 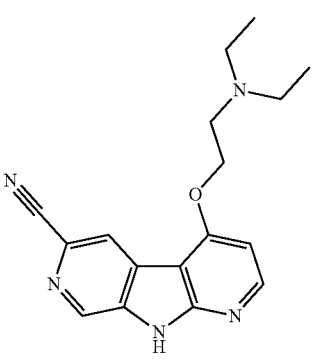 [SMILES: CCN(CC)CCOc1ccnc2[nH]c3cnc(C#N)cc3c12]<br>4-[2-(diethylamino)ethoxy]-9H-dipyrido[2,3-b;4',3'-d]pyrrole-6-carbonitrile | C | F | T | 6.00, 310, D | (DMSO-D$_6$, 400 MHz): 12.76 (s, 1H), 8.97 (s, 1H), 8.55 (d, J = 5.7 Hz, 1H), 8.50 (s, 1H), 7.06 (d, J = 5.8 Hz, 1H), 4.41 (t, J = 5.5 Hz, 2H), 3.02 (s, 2H), 2.65 (d, J = 6.8 Hz, 4H), 1.04 (t, J = 7.1 Hz, 6H). |
| 220 | 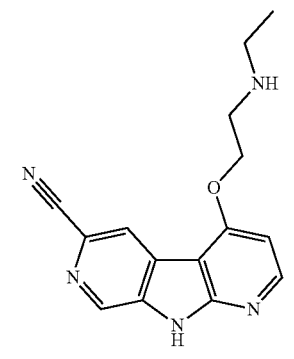 [SMILES: CCNCCOc1ccnc2[nH]c3cnc(C#N)cc3c12]<br>4-[2-(ethylamino)ethoxy]-9H-dipyrido[2,3-b;4',3'-d]pyrrole-6-carbonitrile | C | F | T | 5.68, 282, D | (DMSO-D$_6$, 400 MHz): 8.97 (s, 1H), 8.57 (s, 1H), 8.54 (d, J = 5.7 Hz, 1H), 8.28 (s, 1H), 7.05 (d, J = 5.8 Hz, 1H), 4.41 (t, J = 5.5 Hz, 2H), 3.13 (t, J = 5.6 Hz, 2H), 2.72 (q, J = 7.1 Hz, 2H), 1.08 (t, J = 7.1 Hz, 3H). |

TABLE 10-continued

| Example | Structure/Name | General Alkylation Method | General Deprotection Mehod | Final purification Method(s) | LCMS R_T, M + H+, Method | ¹H NMR (ppm) |
|---|---|---|---|---|---|---|
| 221 | (R)-4-(Pyrrolidin-2-ylmethoxy)-9H-dipyrido[2,3-b;4',3'-d]pyrrole-6-carbonitrile | C | F | T | 5.94, 294, D | (DMSO-D₆, 400MHz): 8.98 (s, 1H), 8.63 (s, 1H), 8.56 (d, J = 5.7 Hz, 1H), 7.06 (d, J = 5.8 Hz, 1H), 4.41 (m, 4.4 Hz, 1H), 4.27 (m, 1H), 3.86 (m, 1H), 3.07 (m, 2H), 2.08 (m, 1H), 1.84 (m, 2H), 1.65 (m, 1H). |
| 222 | (S)-4-(Pyrrolidin-2-ylmethoxy)-9H-dipyrido[2,3-b;4',3'-d]pyrrole-6-carbonitrile | C | F | T | 5.87, 294, D | (DMSO-D₆, 400 MHz): 8.97 (s, 1H), 8.55 (s, 1H), 8.53 (d, J = 5.7 Hz, 1H), 7.03 (d, J = 5.8 Hz, 1H), 4.23 (m, 1H), 4.15 (m, 1H), 3.70-3.55 (m, 1H), 2.90 (t, J = 6.5 Hz, 2H), 1.98 (m, 1H), 1.85-1.64 (m, 2H), 1.65-1.45 (m, 1H). |
| 223 | 4-(Azetidin-3-yloxy)-9H-dipyrido[2,3-b;4',3'-d]pyrrole-6-carbonitrile | C | F | T | 5.27, 266, D | (DMSO-D₆, 400 MHz): 8.98 (d, J = 0.8 Hz, 1H), 8.63 (s, 1H), 8.51 (d, J = 5.7 Hz, 1H), 6.75 (d, J = 5.7 Hz, 1H), 5.46-5.30 (m, 1H), 4.01-3.86 (m, 2H), 3.86-3.72 (m, 2H). |
| 224 | (R)-4-(Pyrrolidin-3-yloxy)-9H-dipyrido[2,3-b;4',3'-d]pyrrole-6-carbonitrile | C | F | T | 5.56, 280, D | (DMSO-D₆, 500 MHz): 8.95 (s, 1H), 8.60 (s, 1H), 8.53 (d, J = 5.7 Hz, 1H), 7.01 (d, J = 5.8 Hz, 1H), 5.27 (s, 1H), 3.13 (m, 2H), 3.10-3.05 (m, 1H), 2.85 (d, J = 8.0 Hz, 1H), 2.19 (m, 1H), 2.01 (m, 1H). |

TABLE 10-continued

| Example | Structure/Name | General Alkylation Method | General Deprotection Mehod | Final purification Method(s) | LCMS R$_T$, M + H⁺, Method | ¹H NMR (ppm) |
|---|---|---|---|---|---|---|
| 225 | (S)-4-(Pyrrolidin-3-ylmethoxy)-9H-dipyrido[2,3-b;4',3'-d]pyrrole-6-carbonitrile | C | F | T | 5.53, 280, D | (DMSO-D$_6$, 500 MHz): 8.95 (s, 1H), 8.60 (s, 1H), 8.53 (d, J = 5.7 Hz, 1H), 7.01 (d, J = 5.8 Hz, 1H), 5.28 (m, 1H), 3.18 (m, 1H), 3.16-3.13 (m, 1H), 3.13-3.08 (m, 1H), 2.88 (m, 1H), 2.21 (m, 1H), 2.07-1.99 (m, 1H). |
| 226 | (R)-4-(Piperidin-3-yloxy)-9H-dipyrido[2,3-b;4',3'-d]pyrrole-6-carbonitrile | C | F | T | 6.10, 294, D | (DMSO-D$_6$, 500 MHz): 8.96 (d, J = 1.0 Hz, 1H), 8.53 (d, J = 0.9 Hz, 1H), 8.51 (d, J = 5.8 Hz, 1H), 7.07 (d, J = 5.9 Hz, 1H), 4.72 (m, 1H), 3.19 (m, 1H), 2.85 (m, 1H), 2.82-2.76 (m, 1H), 2.68-2.61 (m, 1H), 2.13 (s, 1H), 1.85 (m, 1H), 1.76 (m, 1H), 1.53 (m, 1H). |
| 227 | (R)-4-(Piperidin-3-ylmethoxy)-9H-dipyrido[2,3-b;4',3'-d]pyrrole-6-carbonitrile | C | F | T | 6.26, 308, D | (DMSO-D$_6$, 400 MHz): 8.97 (s, 1H), 8.53 (d, J = 5.7 Hz, 1H), 8.41 (s, 1H), 7.02 (d, J = 5.8 Hz, 1H), 4.23 (d, J = 6.4 Hz, 2H), δ 3.16 (m, 1H), 2.89 (m, 1H), 2.15 (m, 2H), 1.91 (d, J = 9.6 Hz, 1H), 1.64 (m, 1H), 1.57-1.19 (m, 3H). |
| 228 | (S)-4-(Piperidin-3-ylmethoxy)-9H-dipyrido[2,3-b;4',3'-d]pyrrole-6-carbonitrile | C | F | T | 6.31, 308, D | (DMSO-D$_6$, 400 MHz): 8.97 (s, 1H), 8.53 (d, J = 5.7 Hz, 1H), 8.41 (s, 1H), 7.03 (d, J = 5.8 Hz, 1H), 4.23 (d, J = 6.5 Hz, 2H), 3.17 (m, 1H), 2.89 (m, 1H), 2.15 (m, 2H), 1.90 (m, 1H), 1.65 (m, 1H), 1.54-1.20 (m, 3H). |

| Example | Structure/Name | General Alkylation Method | General Deprotection Method | Final purification Method(s) | LCMS $R_T$, M + H+, Method | $^1$H NMR (ppm) |
|---|---|---|---|---|---|---|
| 229 | 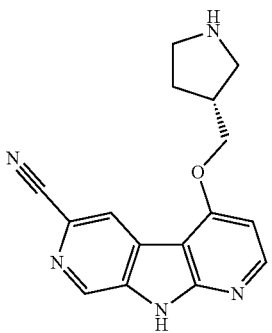 [SMILES: N#Cc1cc2c(cn1)[nH]c1nccc(OC[C@@H]3CCNC3)c12]<br>(R)-4-(Pyrrolidin-3-ylmethoxy)-9H-dipyrido[2,3-b;4',3'-d]pyrrole-6-carbonitrile | C | F | T | 2.61, 294, E | (DMSO-D$_6$, 400 MHz): 8.98 (s, 1H), 8.55 (d, J = 5.7 Hz, 1H), 8.45 (s, 1H), 7.04 (d, J = 5.8 Hz, 1H), 4.32 (m, 2H), 3.21 (m, 1H), 3.05 (m, 1H), 3.00-2.92 (m, 1H), 2.92-2.85 (m, 1H), 2.79 (m, 1H), 2.06 (m, 1H), 1.65 (m, 1H). |
| 230 | 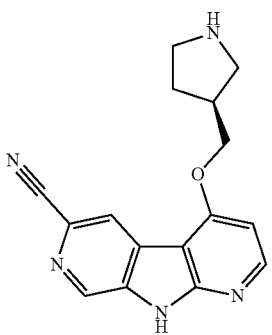 [SMILES: N#Cc1cc2c(cn1)[nH]c1nccc(OC[C@H]3CCNC3)c12]<br>(S)-4-(Pyrrolidin-3-ylmethoxy)-9H-dipyrido[2,3-b;4',3'-d]pyrrole-6-carbonitrile | C | F | T | 2.66, 294, E | (DMSO-D$_6$, 400 MHz): 8.96 (d, J = 0.9 Hz, 1H), 8.53 (d, J = 5.7 Hz, 1H), 8.42 (s, 1H), 7.01 (d, J = 5.7 Hz, 1H), 4.28 (m, 2H), 3.06 (m, 1H), 2.91 (m, 9.1, 1H), 2.88-2.64 (m, 3H), 1.98 (m, 7.9, 1H), 1.56 (m, 1H). |
| 231 | 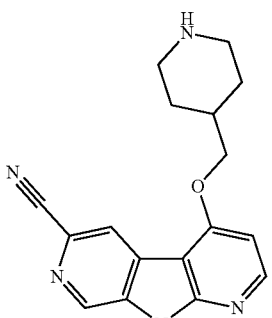<br>4-(Piperidin-4-ylmethoxy)-9H-dipyrido[2,3-b;4',3'-d]pyrrole-6-carbonitrile | C | F | T | 2.67, 308, E | (DMSO-D$_6$, 400 MHz): 8.97 (d, J = 0.8 Hz, 1H), 8.54 (d, J = 5.7 Hz, 1H), 8.41 (s, 1H), 7.05 (d, J = 5.8 Hz, 1H), 4.22 (d, J = 6.3 Hz, 2H), 3.05 (d, J = 11.8 Hz, 2H), 2.60 (m, 2H), 2.10 (m, 1H), 1.83 (d, J = 10.9 Hz, 2H), 1.41-1.26 (m, 2H). |

Example 232

4-(Piperidin-4-ylamino)-9H-dipyrido[2,3-b;4',3'-d]pyrrole-6-carbonitrile

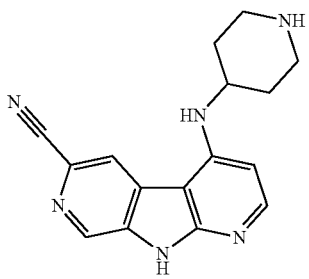 [SMILES: N#Cc1cc2c(cn1)[nH]c1nccc(NC3CCNCC3)c12]

Step 1: tert-Butyl 4-{6-cyano-9-(2-trimethylsilanylethoxymethyl)-dipyrido[2,3-b;4',3'-d]pyrrol-4-ylamino}piperdine-1-carboxylate

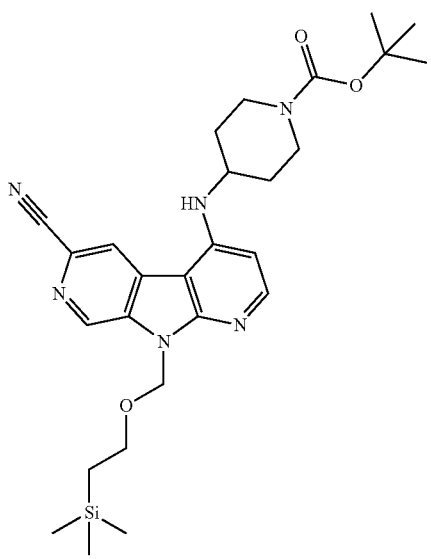 [SMILES: CC(C)(C)OC(=O)N1CCC(Nc2ccnc3c2c2cc(C#N)ncc2n3COCC[Si](C)(C)C)CC1]

A mixture of 4-chloro-9-(2-trimethylsilanylethoxymethyl)-9H-dipyrido[2,3-b;4',3'-d]pyrrole-6-carbonitrile with 4-chloro-9-(2-trimethylsilanylethoxymethyl)-9H-dipyrido[2,3-b;4',3'-d]pyrrole-6-carbonitrile (6.5:1, 85 mg, 0.24 mmol), tert-butyl 4-aminopiperidine-1-carboxylate (240 mg, 1.2 mmol), 4,5-bis(diphenylphosphino)-9,9-dimethylxanthene (20 mg, 0.04 mmol), tris(dibenzylideneacetone)dipalladium(0) (16 mg, 0.02 mmol), and cesium carbonate (150 mg, 0.47 mmol) in 1,4-dioxane (2 mL) was sealed and heated at 110° C. for 2 h. The mixture was diluted with water (20 mL) and ethyl acetate (50 mL). The organic layer was separated, dried over sodium sulfate, filtered, concentrated in vacuo, and purified flash chromatography (silica, 40 g, ISCO, 5-75% ethyl acetate in heptane) to afford the title compound as a yellow solid (80 mg, 60%).

Step 2: 4-(Piperidin-4-ylamino)-9H-dipyrido[2,3-b;4',3'-d]pyrrole-6-carbonitrile

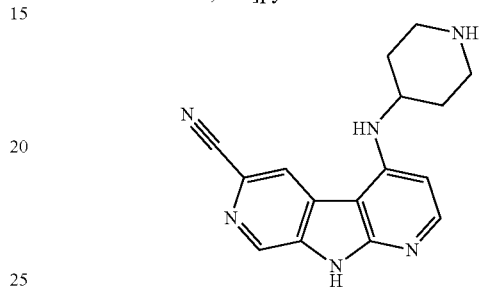

tert-Butyl 4-{6-cyano-9-(2-trimethylsilanylethoxymethyl)-dipyrido[2,3-b;4',3'-d]pyrrol-4-ylamino}piperdine-1-carboxylate (80 mg, 0.14 mmol) was dissolved in 1,4-dioxane (0.4 mL) and then treated with 48% $HBr_{(aq)}$ (0.5 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC (5-85% methanol in water (0.1% formic acid) over 30 min, 35 mL/min) to afford the title compound as a pale yellow solid (20 mg, 30% over two steps). $^1$H NMR (DMSO-D$_6$, 400 MHz): 9.08 (s, 1H), 8.83 (s, 1H), 8.20 (d, J=5.9 Hz, 1H), 6.63 (d, J=6.0 Hz, 1H), 6.46 (d, J=8.0 Hz, 1H), 3.74 (m, 1H), 3.11 (m, 2H), 2.71 (m, 2H), 1.97 (m, 2H), 1.70 (m, 2H). LCMS (Method E): R$_T$=2.28 min, M+H$^+$ =293.

The compounds of the Examples in Table 11 were prepared via general Suzuki procedures described above.

TABLE 11

| Example | Structure/Name | Coupling Method | Halide or Mesylate displacement | Deprotection Method | Purification Method(s) | LCMS R$_T$, M + H$^+$, Method | $^1$H NMR (ppm) |
|---|---|---|---|---|---|---|---|
| 233 | ![structure] 5-(3-Methylamino-propyl)-3-(1-methyl-1H-pyrazol-4-yl)-9H-dipyrido[2,3-b;4',3'-d]pyrrole-6-carbonitrile | L | D/E | — | B | 5.21, 346, A | (DMSO-D$_6$, (400 MHz): 8.99 (d, J = 2.0 Hz, 1H), 8.92 (s, 1H), 8.73 (d, J = 2.1 Hz, 1H), 8.42 (s, 1H), 8.14 (d, J = 0.8 Hz, 1H), 3.92 (s, 3H), 3.53 (t, J = 7.7 Hz, 2H), 3.10 (t, J = 7.8 Hz, 2H), 2.54 (s, 3H), 2.16-2.06 (m, 2H). |

TABLE 11-continued

| Example | Structure/Name | Coupling Method | Halide or Mesylate displacement | Deprotection Method | Purification Method(s) | LCMS R_T, M + H+, Method | ¹H NMR (ppm) |
|---|---|---|---|---|---|---|---|
| 234 | 3-(1-Methyl-1H-pyrazol-4-yl)-5-(3-pyrrolidin-1-yl-propyl)-9H-dipyrido[2,3-b;4',3'-d]pyrrole-6-carbonitrile | L | D | — | B | 5.35, 346, A | (CD$_3$OD, 400 MHz): 8.84 (d, J = 2.1 Hz, 1H), 8.82-8.79 (m, 1H), 8.68 (d, J = 2.1 Hz, 1H), 8.13-8.10 (m, 1H), 7.97 (d, J = 0.8 Hz, 1H), 3.96 (s, 3H), 3.53 (t, J = 7.8 Hz, 2H), 2.75 (t, J = 7.6 Hz, 2H), 2.57 (m, 4H), 2.09 (m, J = 7.7 Hz, 2H), 1.78-1.71 (m, 4H). |
| 235 | 3-(1-Methyl-1H-pyrazol-4-yl)-5-(3-morpholin-4-yl-propyl)-9H-dipyrido[2,3-b;4',3'-d]pyrrole-6-carbonitrile | L | D/E | — | B | 5.50, 402, F | (DMSO-D$_6$, 400 MHz): 12.83 (s, 1H), 8.96 (t, J = 2.1 Hz, 1H), 8.88 (s, 1H), 8.70 (d, J = 2.1 Hz, 1H), 8.36 (s, 1H), 8.07 (d, J = 0.8 Hz, 1H), 3.97-3.90 (m, 3H), 3.52 (t, J = 7.4 Hz, 2H), 3.43 (t, J = 4.4 Hz, 4H), 2.47 (t, J = 6.7 Hz, 2H), 2.27 (s, 4H), 2.03-1.93 (m, 2H). |
| 236 | 3-(1-Methyl-1H-pyrazol-4-yl)-5-piperidin-4-ylmethyl-9H-dipyrido[2,3-b;4',3'-d]pyrrole-6-carbonitrile | M | NA | E | B | 6.08, 372, F | (DMSO-D$_6$, 400 MHz): 12.99 (s, 1H), 12.66 (s, 1H), 9.01 (d, J = 2.0 Hz, 1H), 8.96 (s, 1H), 8.70 (d, J = 2.1 Hz, 1H), 8.38 (s, 1H), 8.12 (s, 1H), 3.97 (s, 3H), 3.50 (d, J = 7.2 Hz, 2H), 3.30 (d, J = 12.5 Hz, 2H), 2.86 (t, J = 12.4 Hz, 2H), 2.20 (s, 1H), 1.90 (d, J = 13.9 Hz, 2H), 1.71 (t, J = 13.0 Hz, 2H). |

TABLE 11-continued

| Example | Structure/Name | Coupling Method | Halide or Mesylate displacement | Deprotection Method | Purification Method(s) | LCMS $R_T$, $M+H^+$, Method | $^1$H NMR (ppm) |
|---|---|---|---|---|---|---|---|
| 237 | 5-(1-Ethyl-piperidin-4-ylmethyl)-3-(1-methyl-1H-pyrazol-4-yl)-9H-dipyrido[2,3-b;4',3'-d]pyrrole-6-carbonitrile | M | F | D | C | 5.96, 400, F | (DMSO-D$_6$, 400 MHz): 12.82 (s, 1H), 8.95 (d, J = 2.0 Hz, 1H), 8.87 (s, 1H), 8.62 (d, J = 2.1 Hz, 1H), 8.32 (s, 1H), 8.04 (d, J = 0.8 Hz, 1H), 3.92 (s, 3H), 3.40 (d, J = 7.0 Hz, 2H), 2.82 (d, J = 10.9 Hz, 2H), 2.23 (q, J = 7.2 Hz, 2H), 1.82-1.61 (m, 5H), 1.55-1.41 (m, 2H), 0.93 (t, J = 7.1 Hz, 3H). |
| 238 | 5-(1-Ethyl-piperidin-4-ylmethyl)-3-pyridin-4-yl-9H-dipyrido[2,3-b;4',3'-d]pyrrole-6-carbonitrile | M† | F | D | C | 3.73, 397, F | (DMSO-D$_6$, 400 MHz): 13.03 (s, 1H), 9.14 (d, J = 2.1 Hz, 1H), 8.94 (s, 1H), 8.89 (d, J = 2.2 Hz, 1H), 8.75-8.70 (m, 2), 7.94-7.89 (m, 2H), 3.46 (d, J = 7.1 Hz, 2H), 2.87-2.79 (m, 2H), 2.24 (q, J = 7.2 Hz, 2H), 1.90-1.59 (m, 5H), 1.57-1.42 (m, 2H), 0.94 (t, J = 7.1 Hz, 3). |

†Deviation from method: 9-Benzenesulfonyl 5-bromo-3-pyridin-4-yl-9H-dipyrido[2,3-b;4',3'-d]pyrrole-6-carbonitrile was used in place of 9-benzenesulfonyl-5-bromo-3-(1-methyl-1H- pyrazol-4-yl)-9H-dipyrido[2,3-b;4',3'-d]pyrrole-6-carbonitrile.

The compounds of the Examples in Table 12 were prepared via general Mitsunobu procedures followed by general Suzuki coupling described above.

TABLE 12

| Example | Structure/Name | Amino alcohol | Mitsunobu Method | Coupling Method | Deprotection Method | Purification Method(s) | LCMS R$_T$, M + H$^+$, Method | $^1$H NMR (ppm) |
|---|---|---|---|---|---|---|---|---|
| 239 | 3-(1-Methyl-1H-pyrazol-4-yl)-5-(piperidin-4-yloxy)-9H-dipyrido[2,3-b;4',3'-d]pyrrole-6-carbonitrile | 4-Hydroxypiperidine carboxylic acid tert-butyl ester | A | N | F | R$^3$ | 5.38, 374, A | (DMSO-D$_6$, 400 MHz): 13.07 (s, 1H), 9.00 (d, J = 2.1 Hz, 1H), 8.95 (s, 2H), 8.85 (s, 1H), 8.53 (d, J = 2.1 Hz, 1H), 8.43 (s, 1H), 8.07 (d, J = 0.8 Hz, 1H), 5.01-4.94 (m, 1H), 3.95 (s, 3H), 3.42 (d, J = 12.0 Hz, 2H), 3.12 (s, 2H), 2.34-2.18 (m, 4H). |
| 240 | 3-(1-Methyl-1H-pyrazol-4-yl)-5-((S)-(piperidin-3-yloxy)-9H-dipyrido[2,3-b;4',3'-d]pyrrole-6-carbonitrile | 3-(S)-Hydroxy-piperidine carboxylic acid teru-butyl ester | A | N | F | R$^3$ | 5.37, 374, A | (DMSO-D$_6$, 400 MHz): 13.14 (s, 1H), 9.42 (s, 2H), 9.00 (d, J = 2.0 Hz, 1H), 8.86 (s, 1H), 8.62 (d, J = 2.1 Hz, 1H), 8.45 (s, 1H), 8.12 (s, 1H), 5.01 (m, 1H), 3.95 (s, 3H), 3.72 (d, J = 11.5 Hz, 1H), 3.51 (d, J = 10.1 Hz, 1H), 3.24-3.11 (m, 1H), 3.09 (d, J = 9.9 Hz, 1H), 2.18 (s, 1H), 2.13-1.93 (m, 2H), 1.75 (d, J = 12.3 Hz, 1H). |
| 241 | 5-(1-Ethyl-piperidin-4-yloxy)-3-(1-methyl-1H-pyrazol-4-yl)-9H-dipyrido[2,3-b;4',3'-d]pyrrole-6-carbonitrile | N-Ethyl 4-hydroxy-piperidine | A | N | NA | E$^2$ | 5.44, 402, A | (DMSO-D$_6$, 400 MHz): 12.92 (s, 1H), 8.97 (d, J = 2.1 Hz, 1H), 8.78 (s, 1H), 8.57 (d, J = 2.2 Hz, 1H), 8.32 (s, 1H), 8.01 (d, J = 0.8 Hz, 1H), 4.81-4.74 (m, 1H), 3.94 (s, 3H), 2.91-2.83 (m, 2H), 2.35 (q, J = 7.2 Hz, 2H), 2.12 (d, J = 11.7 Hz, 4H), 2.05-1.94 (m, 2H), 1.01 (t, J = 7.1 Hz, 3H). |

TABLE 12-continued

| Example | Structure/Name | Amino alcohol | Mitsunobu Method | Coupling Method | Deprotection Method | Purification Method(s) | LCMS R_T, M + H+, Method | 1H NMR (ppm) |
|---|---|---|---|---|---|---|---|---|
| 242 | 3-(4-Morpholin-4-ylmethyl-phenyl)-5-(piperidin-4-yloxy)-9H-dipyrido[2,3-b;4',3'-d]pyrrole-6-carbonitrile | 4-Hydroxypiperidine carboxylic acid tert-butyl ester | A | N | A | S | 4.55, 469, A | (DMSO-D_6, 400 MHz): 13.23 (s, 1H), 11.52 (s, 1H), 9.07 (d, J = 2.4 Hz, 2H), 8.88 (s, 1H), 8.67 (d, J = 2.2 Hz, 1H), 7.98 (d, J = 7.8 Hz, 2H), 7.82 (d, J = 7.8 Hz, 2H), 5.07-4.99 (m, 1H), 4.42 (d, J = 5.3 Hz, 2H), 3.97 (d, J = 12.7 Hz, 2H), 3.85 (t, J = 12.1 Hz, 2H), 3.43-3.35 (m, 2H), 3.28 (d, J = 12.6 Hz, 2H), 3.12 (s, 4H), 2.33-2.16 (m, 4H). |
| 243 | 3-[4-(4,4-Difluoro-piperidin-1-ylmethyl)-phenyl]-5-(piperidin-4-yloxy)-9H-dipyrido[2,3-b;4',3'-d]pyrrole-6-carbonitrile | 4-Hydroxypiperidine carboxylic acid tert-butyl ester | A | N | A | S | 4.93, 503, A | (DMSO-D_6, 400 MHz): 13.21 (s, 1H), 11.75 (s, 1H), 9.10-8.96 (m, 3H), 8.86-8.82 (m, 1H), 8.66 (d, J = 2.2 Hz, 1H), 7.96 (d, J = 7.8 Hz, 2H), 7.80 (d, J = 7.8 Hz, 2H), 5.06-4.97 (m, 1H), 4.45 (s, 2H), 3.52-3.30 (m, 4H), 3.21-3.15 (m, 2H), 3.10 (d, J = 12.4 Hz, 2H), 2.36 (s, 3H), 2.33-2.17 (m, 5H). |
| 244 | 5-(Piperidin-4-yloxy)-3-[4-(4-trifluoromethyl-piperidin-1-ylmethyl)-phenyl]-9H-dipyrido[2,3-b;4',3'-d]pyrrole-6-carbonitrile | 4-Hydroxypiperidine carboxylic acid tert-butyl ester | A | N | A | S | 5.14, 535, A | (DMSO-D_6, 400 MHz): 13.25 (s, 1H), 11.25 (s, 1H), 9.10 (d, J = 2.4 Hz, 3H), 8.89 (s, 1H), 8.69 (d, J = 2.2 Hz, 1H), 8.00 (d, J = 7.9 Hz, 2H), 7.83 (d, J = 7.9 Hz, 2H), 5.09-5.02 (m, 1H), 4.39 (d, J = 5.0 Hz, 2H), 3.50 (d, J = 12.2 Hz, 2H), 3.46-3.36 (m, 2H), 3.19-2.96 (m, 4H), 2.69 (s, 1H), 2.35-2.19 (m, 4H), 2.10-1.91 (m, 4H). |

TABLE 12-continued

| Example | Structure/Name | Amino alcohol | Mitsunobu Method | Coupling Method | Deprotection Method | Purification Method(s) | LCMS R$_T$, M + H$^+$, Method | $^1$H NMR (ppm) |
|---|---|---|---|---|---|---|---|---|
| 245 | 3-(4-Hydroxymethyl-phenyl)-5-(piperidin-4-yloxy)-9H-dipyrido[2,3-b;4',3'-d]pyrrole-6-carbonitrile | 4-Hydroxypiperidine carboxylic acid tert-butyl ester | A | N | A | S | 5.62, 400, A | (DMSO-D$_6$, 400 MHz): 13.17 (s, 1H) 9.07 (d, J = 10.0 Hz, 1H), 9.02 (t, J = 2.2 Hz, 1H), 8.95-8.84 (m, 1H), 8.91-8.82 (m, 1H), 8.61 (d, J = 2.2 Hz, 1H), 7.81 (d, J = 8.1 Hz, 2H), 7.50 (d, J = 8.0 Hz, 2H), 5.06-4.98 (m, 1H), 4.59 (s, 2H), 3.39 (m, 2H), 3.10 (d, J = 11.3 Hz, 2H) 2.31-2.12 (m, 4H). |
| 246 | 5-(Piperidin-4-yloxy)-3-pyridin-4-yl-9H-dipyrido[2,3-b;4',3'-d]pyrrole-6-carbonitrile | 4-Hydroxypiperidine carboxylic acid tert-butyl ester | A | N | A | R$^7$ | 4.16, 371, A | (DMSO-D$_6$, 400 MHz): 13.52 (s, 1H), 9.33 (d, J = 2.2 Hz, 1H), 9.30 (s, 1H); 9.19 (s, 1H), 8.96 (d, J = 6.2 Hz, 2H), 8.94-8.90 (m, 2H), 8.53 (d, J = 6.0 Hz, 2H), 5.12-5.03 (m, 1H), 3.39 (s, 2H), 3.11 (t, J = 8.8 Hz, 2H) 2.34-2.28 (m, 4H). |
| 247 | 5-(Piperidin-4-yloxy)-3-pyridin-3-yl-9H-dipyrido[2,3-b;4',3'-d]pyrrole-6-carbonitrile | 4-Hydroxypiperidine carboxylic acid tert-butyl ester | A | N | A | R$^7$ | 4.58, 371, A | (DMSO-D$_6$, 400 MHz): 13.36 (s, 1H), 9.36 (s, 1H), 9.16 (d, J = 2.3 Hz, 2H), 8.90 (s, 1H), 8.84-8.77 (m, 3H), 7.95 (dd, J = 8.1, 5.3 Hz, 1H), 5.09-5.01 (m, 1H), 3.38 (d, J = 11.8 Hz, 2H), 3.10 (d, J = 10.4 Hz, 2H), 2.31-2.22 (m, 4H). |
| 248 | 3-(4-Methoxy-pyridin-3-yl)-5-(piperidin-4-yloxy)-9H-dipyrido[2,3-b;4',3'-d]pyrrole-6-carbonitrile | 4-Hydroxypiperidine carboxylic acid tert-butyl ester | A | N | A | R$^7$ | 4.11, 401, A | (DMSO-D$_6$, 400 MHz): 13.35 (s, 1H), 9.19 (s, 2H), 9.04 (s, 1H), 8.95-8.93 (m, 1H), 8.91-8.82 (m, 2H), 8.73 (d, J = 2.1 Hz, 1H), 7.78 (d, J = 6.8 Hz, 1 H), 5.04-4.97 (m, 1H), 4.16 (s, 3H), 3.38 (m, 2H), 3.09 (d, J = 10.8 Hz, 2H), 2.32-2.16 (m, 4H). |

TABLE 12-continued

| Example | Structure/Name | Amino alcohol | Mitsunobu Method | Coupling Method | Deprotection Method | Purification Method(s) | LCMS $R_T$, M + H+, Method | $^1$H NMR (ppm) |
|---|---|---|---|---|---|---|---|---|
| 249 | 3-(5-Methoxy-pyridin-3-yl)-5-(piperidin-4-yloxy)-9H-dipyrido[2,3-b;4',3'-d]pyrrole-6-carbonitrile | 4-Hydroxypiperidine carboxylic acid tert-butyl ester | A | N | A | R$^7$ | 5.23, 401, A | (DMSO-D$_6$, 400 MHz): 13.35 (s, 1H), 9.16 (d, J = 2.2 Hz, 2H), 8.99 (s, 1H), 8.90-8.86 (m, 2H), 8.76 (d, J = 2.2 Hz, 1H), 8.53 (d, J = 2.6 Hz, 1H), 8.22 (s, 1H), 5.10-5.02 (m, 1H), 4.04 (s, 3H), 3.38 (m, 2H), 3.11 (d, J = 11.0 Hz, 2H), 2.34-2.17 (m, 4H). |
| 250 | 3-(2-Methoxy-pyridin-3-yl)-5-(piperidin-4-yloxy)-9H-dipyrido[2,3-b;4',3'-d]pyrrole-6-carbonitrile | 4-Hydroxypiperidine carboxylic acid tert-butyl ester | A | N | B | C$^2$ | 5.78, 401, A | (DMSO-D$_6$, 400 MHz): 8.86 (t, J = 2.2 Hz, 1H), 8.81 (s, 1H), 8.78 (d, J = 2.2 Hz, 1H), 8.26 (dd, J = 5.0, 1.8 Hz, 1H), 7.99-7.94 (m, 1H), 7.20 (dd, J = 7.3, 5.0 Hz, 1H), 4.83-4.75 (m, 1H), 3.99-3.92 (m, 3H), 3.08-3.01 (m, 2H), 2.59-2.52 (m, 2H), 2.06 (d, J = 11.9 Hz, 2H), 1.85-1.74 (m, 2H). |
| 251 | 3-(6-Methoxy-pyridin-3-yl)-5-(piperidin-4-yloxy)-9H-dipyrido[2,3-b;4',3'-d]pyrrole-6-carbonitrile | 4-Hydroxypiperidine carboxylic acid tert-butyl ester | A | N | B | C$^2$ | 7.36, 401, F | (DMSO-D$_6$, 400 MHz): 8.99 (d, J = 2.2 Hz, 1H), 8.80 (s, 1H), 8.63 (d, J = 2.3 Hz, 1H), 8.60 (dd, J = 2.6, 0.8 Hz, 1H), 8.15 (dd, J = 8.6, 2.6 Hz, 1H), 7.01 (dd, J = 8.6, 0.7 Hz, 1H), 4.86-4.77 (m, 1H), 3.94 (s, 3H), 3.10-3.01 (m, 2H), 2.62-2.52 (m, 2H), 2.07 (d, J = 11.9 Hz, 2H), 1.87-1.76 (m, 2H). |

TABLE 12-continued

| Example | Structure/Name | Amino alcohol | Mitsunobu Method | Coupling Method | Deprotection Method | Purification Method(s) | LCMS R$_T$, M + H$^+$, Method | $^1$H NMR (ppm) |
|---|---|---|---|---|---|---|---|---|
| 252 | 3-(3-Methoxy-pyridin-4-yl)-5-(piperidin-4-yloxy)-9H-dipyrido[2,3-b;4',3'-d]pyrrole-6-carbonitrile | 4-Hydroxypiperidine carboxylic acid tert-butyl ester | A | N | A | R$^1$ | 5.10, 401, F | (DMSO-D$_6$, 400 MHz): 13.38 (s, 1H), 9.14 (s, 2H), 9.02 (d, J = 2.1 Hz, 1H), 8.89 (s, 1H), 8.81 (d, J = 2.1 Hz, 1H), 8.75 (s, 1H), 8.59 (d, J = 5.4 Hz, 1H), 8.10 (d, J = 5.4 Hz, 1H) 5.03-4.96 (m, 1H), 4.07 (s, 3H), 3.37 (m, 2H), 3.08 (d, J = 10.6 Hz, 2H), 2.32-2.14 (m, 4H). |
| 253 | 3-(2-Methoxy-pyridin-4-yl)-5-(piperidin-4-yloxy)-9H-dipyrido[2,3-b;4',3'-d]pyrrole-6-carbonitrile | 4-Hydroxypiperidine carboxylic acid tert-butyl ester | A | N | B | E$^5$ | 7.33, 401, F | (DMSO-D$_6$, 400 MHz): 9.09 (d, J = 2.2 Hz, 1H), 8.81 (s, 1H), 8.72 (d, J = 2.3 Hz, 1H), 8.31 (d, J = 5.4 Hz, 1H), 7.44 (dd, J = 5.4, 1.6 Hz, 1H), 7.24 (d, J = 1.5 Hz, 1H), 4.87-4.78 (m, 1H), 3.94 (s, 3H), 3.12-3.01 (m, 2H), 2.62-2.52 (m, 2H), 2.08 (d, J = 11.9 Hz, 2H), 1.88-1.77 (m, 2H). |
| 254 | 5-(1-Ethyl-piperidin-4-yloxy)-3-(4-hydroxymethyl-phenyl)-9H-dipyrido[2,3-b;4',3'-d]pyrrole-6-carbonitrile | N-Ethyl 4-hydroxy-piperidine | A | N$^2$ | D | B$^8$ | 6.89, 428, F | (CDCl$_3$ and CD$_3$OD, 400 MHz): 8.90 (d, J = 2.2 Hz, 1 H), 8.79 (d, J = 2.2 Hz, 1H), 8.75 (s, 1H), 7.73-7.69 (m, 2H), 7.57-7.52 (m, 2H), 5.04-4.94 (m, 1H), 4.72 (s, 2H), 3.04-2.95 (m, 2H), 2.49 (q, J = 7.2 Hz, 2H), 2.38-2.19 (m, 4H), 2.18-2.07 (m, 2H), 1.12 (t, J = 7.2 Hz, 3H). |

TABLE 12-continued

| Example | Structure/Name | Amino alcohol | Mitsunobu Method | Coupling Method | Deprotection Method | Purification Method(s) | LCMS $R_T$, M + H$^+$, Method | $^1$H NMR (ppm) |
|---|---|---|---|---|---|---|---|---|
| 255 | 5-(1-Ethyl-piperidin-4-yloxy)-3-p-tolyl-9H-dipyrido[2,3-b;4',3'-d]pyrrole-6-carbonitrile | N-Ethyl 4-hydroxy-piperidine | A | N$^2$ | D | B$^5$ | 8.41, 412, F | (CDCl$_3$ and CD$_3$OD, 400 MHz): 8.85 (d, J = 2.2 Hz, 1H), 8.76 (d, J = 2.1 Hz, 1H), 8.73 (s, 1H), 7.57 (d, J = 7.9 Hz, 2H), 7.36 (d, J = 7.9 Hz, 2H), 5.06-4.96 (m, 1H), 3.04-2.92 (m, 2H), 2.54-2.43 (m, 5H), 2.38-2.20 (m, 4H), 2.18-2.07 (m, 2H), 1.12 (t, J = 7.2 Hz, 3H). |
| 256 | 5-(1-Ethyl-piperidin-4-yloxy)-3-[4-(1-hydroxy-1-methyl-ethyl)-phenyl]-9H-dipyrido[2,3-b;4',3'-d]pyrrole-6-carbonitrile | N-Ethyl 4-hydroxy-piperidine | A | N$^2$ | D | B$^5$ | 7.87, 456, F | CDCl$_3$ and CD$_3$OD, 400 MHz): 8.90 (d, J = 2.2 Hz, 1 H), 8.79 (d, J = 2.2 Hz, 1H), 8.76 (s, 1H), 7.68-7.67 (s, 4H), 5.06-4.95 (m, 1H), 3.05-2.96 (m, 2H), 2.50 (q, J = 7.2 Hz, 2H), 2.38-2.20 (m, 4H), 2.19-2.08 (m, 2H), 1.63 (s, 6H), 1.13 (t, J = 7.2 Hz, 3H). |
| 257 | 5-(1-Ethyl-piperidin-4-yloxy)-3-(4-hydroxymethyl-3-methoxy-phenyl)-9H-dipyrido[2,3-b;4',3'-d]pyrrole-6-carbonitrile | N-Ethyl 4-hydroxy-piperidine | A | N$^2$ | D | B$^5$ | 7.29, 458, F | CDCl$_3$ and CD$_3$OD, 400 MHz): 8.91 (d, J = 2.2 Hz, 1 H), 8.78 (d, J = 2.2 Hz, 1H), 8.76 (s, 1H), 7.55 (d, J = 7.7 Hz, 1H), 7.29 (dd, J = 7.7, 1.7 Hz, 1H), 7.22 (d, J = 1.6 Hz, 1H), 5.05-4.95 (m, 1H), 4.74 (s, 2H), 3.98 (s, 3H), 3.03-2.94 (m, 2H), 2.49 (q, J = 7.2 Hz, 2H), 2.40-2.29 (m, 2H), 2.28-2.20 (m, 2H), 2.19-2.08 (m, 2H), 1.12 (t, J = 7.2 Hz, 3H). |

TABLE 12-continued

| Example | Structure/Name | Amino alcohol | Mitsunobu Method | Coupling Method | Deprotection Method | Purification Method(s) | LCMS $R_T$, M + H+, Method | 1H NMR (ppm) |
|---|---|---|---|---|---|---|---|---|
| 258 | 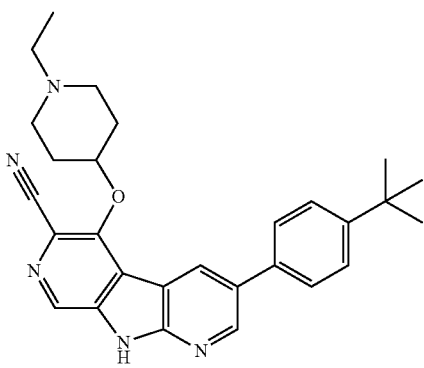 [SMILES: CCN1CCC(Oc2c(C#N)ncc3[nH]c4ncc(-c5ccc(C(C)(C)C)cc5)cc4c23)CC1]<br>3-(4-tert-Butyl-phenyl)-5-(1-ethyl-piperidin-4-yloxy)-9H-dipyrido[2,3-b;4',3'-d]pyrrole-6-carbonitrile | N-Ethyl 4-hydroxy-piperidine | A | $N^2$ | D | $B^5$ | 9.86, 454, F | (DMSO-$D_6$, 400 MHz): 13.03 (s, 1H), 9.00 (d, J = 2.2 Hz, 1H), 8.80 (s, 1H), 8.68 (d, J = 2.3 z, 1H), 7.75-7.70 (m, 2H), 7.61-7.55 (m, 2H), 4.88 (m, 1H), 2.92-2.80 (m, 2H), 2.40-2.29 (m, 2H), 2.21-2.04 (m, 4H), 2.02-1.89 (m, 2H), 1.35 (s, 9H), 0.99 (t, J = 7.1 Hz, 3H). |
| 259 | 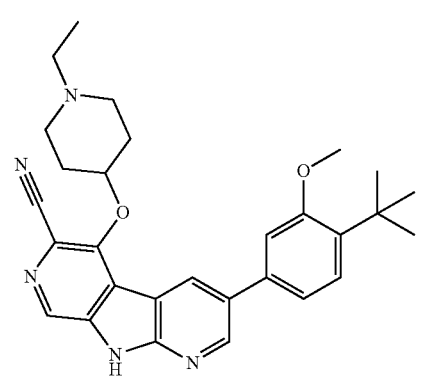 [SMILES: CCN1CCC(Oc2c(C#N)ncc3[nH]c4ncc(-c5ccc(C(C)(C)C)c(OC)c5)cc4c23)CC1]<br>3-(4-tert-Butyl-3-methoxy-phenyl)-5-(1-ethyl-piperidin-4-yloxy)-9H-dipyrido[2,3-b;4',3'-d]pyrrole-6-carbonitrile | N-Ethyl 4-hydroxy-piperidine | A | $N^2$ | D | $B^5$ | 10.17, 484, F | (DMSO-$D_6$, 400 MHz): 13.05 (s, 1H), 9.05 (d, J = 2.2 Hz, 1H), 8.80 (s, 1H), 8.70 (d, J = 2.2 Hz, 1H), 7.39 (d, J = 8.0 Hz, 1H), 7.35 (d, J = 1.8 Hz, 1H), 7.29 (dd, J = 8.0, 1.8 Hz, 1H), 4.87-4.77 (m, 1H), 3.96 (s, 3H), 2.87-2.79 (m, 2H), 2.33 (q, J = 7.1 Hz, 2H), 2.21-2.05 (m, 4H), 2.03-1.90 (m, 2H), 1.39 (s, 9H), 0.98 (t, J = 7.2 Hz, 3 H). |
| 260 | 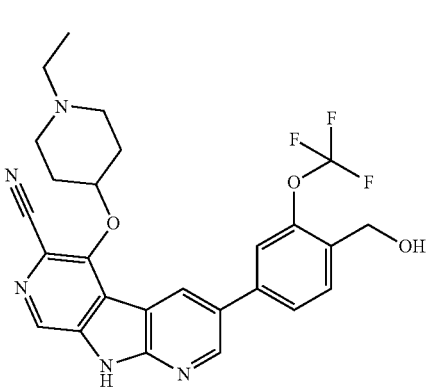 [SMILES: CCN1CCC(Oc2c(C#N)ncc3[nH]c4ncc(-c5ccc(CO)c(OC(F)(F)F)c5)cc4c23)CC1]<br>5-(1-Ethyl-piperidin-4-yloxy)-3-(4-hydroxymethyl-3-trifluoromethoxy-phenyl)-9H-dipyrido[2,3-b;4',3'-d]pyrrole-6-carbonitrile | N-Ethyl 4-hydroxy-piperidine | A | $N^2$ | D | $B^1$ | 8.49, 512, F | (DMSO-$D_6$, 400 MHz): 13.10 (s, 1H), 9.06 (d, J = 2.2 Hz, 1H), 8.82 (s, 1H), 8.69 (d, J = 2.3 Hz, 1H), 7.88 (dd, J = 8.1, 1.7 Hz, 1H), 7.77 (d, J = 8.0 Hz, 1H), 7.72 (s, 1H), 5.46 (t, J = 5.7 Hz, 1H), 4.90-4.81 (m, 1H), 4.65 (d, J = 5.6 Hz, 2H), 2.86-2.76 (m, 2,H), 2.34 (q, J = 7.1 Hz, 2H), 2.23-2.04 (m, 4H), 2.03-1.90 (m, 2H), 0.99 (t, J = 7.1 Hz, 3H) |

TABLE 12-continued

| Example | Structure/Name | Amino alcohol | Mitsunobu Method | Coupling Method | Deprotection Method | Purification Method(s) | LCMS $R_T$, M + H+, Method | 1H NMR (ppm) |
|---|---|---|---|---|---|---|---|---|
| 261 | 5-(1-Ethyl-piperidin-4-yloxy)-3-pyridin-4-yl-9H-dipyrido[2,3-b;4',3'-d]pyrrole-6-carbonitrile | N-Ethyl 4-hydroxy-piperidine | A | N | NA | B/C[2] | 4.42, 399, F | (DMSO-D6, 400 MHz): 13.07 (s, 1H), 9.14 (d, J = 2.2 Hz, 1H), 8.84-8.79 (m, 2H), 8.72 (d, J = 5.3 Hz, 2H), 7.87 (dd, J = 4.8, 1.6 Hz, 2H), 4.89-4.80 (m, 1H), 2.92-2.81 (m, 2H), 2.36 (q, J = 7.2 Hz, 2H), 2.23-2.06 (m, 4H), 2.04-1.93 (m, 2H), 1.00 (t, J = 7.1 Hz, 3H). |
| 262 | 5-(1-Ethyl-piperidin-4-yloxy)-3-(6-methoxy-pyridin-3-yl)-9H-dipyrido[2,3-b;4',3'-d]pyrrole-6-carbonitrile | N-Ethyl 4-hydroxy-piperidine | A | N | NA | B[2] | 7.45, 429, F | (DMSO-D6, 400 MHz): 13.02 (s, 1H), 8.99 (d, J = 2.2 Hz, 1H), 8.80 (s, 1H), 8.66 (d, J = 2.3 Hz, 1H), 8.60 (d, J = 2.6 Hz, 1H), 8.15 (dd, J = 8.6, 2.6 Hz, 1H), 7.01 (d, J = 8.6 Hz, 1H), 4.86-4.75 (m, 1H), 3.94 (s, 3H), 2.92-2.79 (m, 2H), 2.35 (q, J = 7.2 Hz, 2H), 2.21-2.04 (m, 4H), 2.03-1.90 (m, 2H), 0.99 (t, J = 7.2 Hz, 3H). |
| 263 | 5-(1-Ethyl-piperidin-4-yloxy)-3-pyridin-3-yl-9H-dipyrido[2,3-b;4',3'-d]pyrrole-6-carbonitrile | N-Ethyl 4-hydroxy-piperidine | A | N | NA | B[2/6] | 5.53, 399, F | (DMSO-D6, 400 MHz): 13.21 (s, 1H), 9.09 (d, J = 2.2 Hz, 1H), 9.06 (d, J = 2.4 Hz, 1H), 8.86 (s, 1H), 8.73 (d, J = 2.2 Hz, 1H) 8.66 (dd, J = 4.8, 1.6 Hz, 1H), 8.29 (d, J = 8.0 Hz, 1H), 7.61-7.56 (m, 1H), 4.95 (s, 1 H), 3.22-2.63 (m, 4H), 2.38-2.03 (m, 4H), 1.27-1.06 (m, 3H). |

TABLE 12-continued

| Example | Structure/Name | Amino alcohol | Mitsunobu Method | Coupling Method | Deprotection Method | Purification Method(s) | LCMS $R_T$, M + H$^+$, Method | $^1$H NMR (ppm) |
|---|---|---|---|---|---|---|---|---|
| 264 | 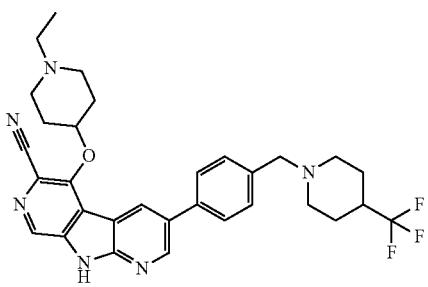 [SMILES: CCN1CCC(Oc2c(C#N)ncc3[nH]c4ncc(-c5ccc(CN6CCC(C(F)(F)F)CC6)cc5)cc4c23)CC1] 5-(1-Ethyl-piperidin-4-yloxy)-3-[4-(4-trifluoromethyl-piperidin-1-ylmethyl)-phenyl]-9H-dipyrido[2,3-b;4',3'-d]pyrrole-6-carbonitrile | N-Ethyl 4-hydroxypiperidine | A | N$^2$ | NA | B$^8$ | 5.68, 563, F | (CDCl$_3$ and CD$_3$OD, 400 MHz): 8.85 (s, 1H), 8.78 (s, 1H), 8.73 (s, 1H), 7.63 (d, J = 7.7 Hz, 2H), 7.49 (d, J = 7.9 Hz, 2H), 5.02 (s, 1H), 3.61 (s, 2H), 3.09-3.01 (m, 2H), 3.01-2.93 (m, 2H), 2.53-2.42 (m, 2H), 2.33-2.19 (m, 4H), 2.16-1.98 (m, 5H), 1.92-1.83 (m, 2H), 1.76-1.62 (m, 2H), 1.17-1.06 (m, 3H). |
| 265 | 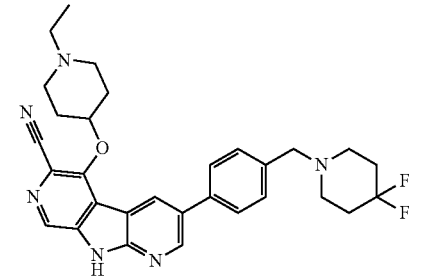 [SMILES: CCN1CCC(Oc2c(C#N)ncc3[nH]c4ncc(-c5ccc(CN6CCC(F)(F)CC6)cc5)cc4c23)CC1] 3-[4-(4,4-Difluoro-piperidin-1-ylmethyl)-phenyl]-5-(1-ethyl-piperidin-4-yloxy)-9H-dipyrido[2,3-b;4',3'-d]pyrrole-6-carbonitrile | N-Ethyl 4-hydroxypiperidine | A | N$^2$ | NA | B | 5.46, 531, F | (CDCl$_3$, 400 MHz): 10.67 (s, 1H), 8.92 (d, J = 2.1 Hz, 1 H), 8.81 (s, 1H) 8.78 (s, 1,H), 7.62 (d, J = 7.9 Hz, 2H), 7.51 (d, J = 7.9 Hz, 2H), 5.11-5.01 (m, 1H), 3.66 (s, 2H), 3.09-2.94 (m, 2H), 2.68-2.59 (m, 4H), 2.56-2.42 (m, 2H), 2.37-2.18 (m, 4H), 2.17-1.98 (s, 6H), 1.18-1.05 (m, 3H). |
| 266 | 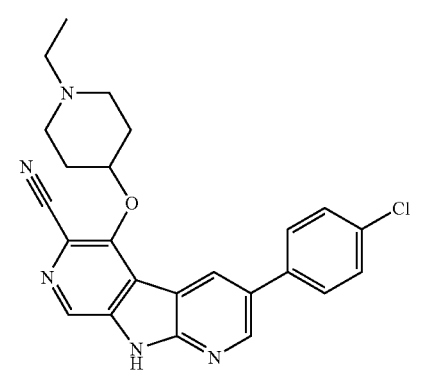 [SMILES: CCN1CCC(Oc2c(C#N)ncc3[nH]c4ncc(-c5ccc(Cl)cc5)cc4c23)CC1] 3-(4-Chloro-phenyl)-5-(1-ethyl-piperidin-4-yloxy)-9H-dipyrido[2,3-b;4',3'-d]pyrrole-6-carbonitrile | N-Ethyl 4-hydroxypiperidine | A | N$^2$ | NA | B | 8.58, 432, F | (CDCl$_3$ and CD$_3$OD, 400 MHz): 8.82 (d, J = 2.2 Hz, 1H), 8.76 (s, 1H), 8.74 (s, 1H), 7.65-7.58 (m, 2H), 7.55-7.50 (m, 2H), 5.08-4.97 (m, 1H), 3.02-2.91 (m, 2H), 2.52-2.42 (m, 2H), 2.34-2.19 (m, 4H), 2.17-2.03 (m, 2H), 1.16-1.07 (m, 3H). |

TABLE 12-continued

| Example | Structure/Name | Amino alcohol | Mitsunobu Method | Coupling Method | Deprotection Method | Purification Method(s) | LCMS $R_T$, M + H+, Method | $^1$H NMR (ppm) |
|---|---|---|---|---|---|---|---|---|
| 267 | 5-(1-Ethyl-piperidin-4-yloxy)-3-(4-fluoro-phenyl)-9H-dipyrido[2,3-b;4',3'-d]pyrrole-6-carbonitrile | N-Ethyl 4-hydroxy-piperidine | A | $N^2$ | NA | $B^3$ | 8.04, 416, F | (CDCl$_3$ and DMSO-D6, 400 MHz): 12.39 (s, 1H), 8.84 (d, J = 2.2 Hz, 1H), 8.77 (s, 1H), 8.67 (s, 1H), 7.66-7.58 (m, 2H), 7.27-7.20 (m, 2H), 4.96 (s, 1H), 3.06-2.91 (m, 2H), 2.53-2.39 (m, 2H), 2.30-1.99 (m, 6H), 1.16-1.04 (m, 3H). |
| 268 | 5-(1-Ethyl-piperidin-4-yloxy)-3-(3-fluoro-phenyl)-9H-dipyrido[2,3-b;4',3'-d]pyrrole-6-carbonitrile | N-Ethyl 4-hydroxy-piperidine | A | $N^2$ | NA | B | 8.23, 416, F | (CDCl$_3$, 400 MHz): 10.20 (s, 1H), 8.89 (d, J = 2.2 Hz, 1H), 8.80 (s, 1H), 8.78 (s, 1H), 7.56-7.48 (m, 1H), 7.46-7.42 (m, 1H), 7.36 (dt, J = 9.8, 2.0 Hz, 1H), 7.19-7.13 (m, 1H), 5.14-5.04 (m, 1H), 3.03-2.90 (m, 2H), 2.53-2.41 (m, 2H), 2.33-2.19 (m, 4H), 2.16-2.03 (m, 2H), 1.11 (t, J = 7.2 Hz, 3H). |
| 269 | 3-(4-Cyano-phenyl)-5-(1-ethyl-piperidin-4-yloxy)-9H-dipyrido[2,3-b;4',3'-d]pyrrole-6-carbonitrile | N-Ethyl 4-hydroxy-piperidine | A | $N^2$ | NA | $B^3$ | 7.51, 423, F | (CDCl$_3$ and DMSO-D$_6$, 400 MHz): 12.54 (s, 1H) 8.89 (d, J = 2.2 Hz, 1H), 8.79 (s, 1H), 8.77-8.68 (m, 1H), 7.87-7.74 (m, 4H), 5.05-4.92 (m, 1H), 3.10-2.87 (m, 2H), 2.57-2.37 (m, 2H), 2.35-1.97 (m, 6H), 1.22-1.02 (m, 3H). |

TABLE 12-continued

| Example | Structure/Name | Amino alcohol | Mitsunobu Method | Coupling Method | Deprotection Method | Purification Method(s) | LCMS $R_T$, M + H+, Method | $^1$H NMR (ppm) |
|---|---|---|---|---|---|---|---|---|
| 270 | 5-(1-Ethyl-piperidin-4-yloxy)-3-phenyl-9H-dipyrido[2,3-b;4',3'-d]pyrrole-6-carbonitrile | N-Ethyl 4-hydroxy-piperidine | A | N$^2$ | NA | B$^3$ | 7.92, 398, F | (CDCl$_3$ and DMSO-D6, 400 MHz): 12.37 (s, 1H), 8.89 (d, J = 2.2 Hz, 1H), 8.78 (s, 1H), 8.75-8.65 (m, 1H), 7.69-7.62 (m, 2H), 7.57-7.50 (m, 2H), 7.47-7.40 (m, 1H), 4.97 (s, 1H), 3.10-2.87 (m, 2H), 2.55-2.37 (m, 2H), 2.34-2.05 (m, 6H), 1.21-1.03 (m, 3H). |
| 271 | 3-(2-Chloro-phenyl)-5-(1-ethyl-piperidin-4-yloxy)-9H-dipyrido[2,3-b;4',3'-d]pyrrole-6-carbonitrile | N-Ethyl 4-hydroxy-piperidine | A | N$^2$ | NA | B$^3$ | 8.08, 432, F | (CDCl$_3$, 400 MHz): 10.64 (s, 1H), 8.82 (s, 1H), 8.78 (d, J = 2.1 Hz, 1H), 8.73 (s, 1H), 7.61-7.56 (m, 1H), 7.48-7.39 (m, 3H), 5.08-4.96 (m, 1H), 3.06-2.88 (m, 2H), 2.53-2.38 (m, 2H), 2.32-2.00 (m, 6H), 1.16-1.01 (m, 3H). |
| 272 | 3-(3-Chloro-phenyl)-5-(1-ethyl-piperidin-4-yloxy)-9H-dipyrido[2,3-b;4',3'-d]pyrrole-6-carbonitrile | N-Ethyl 4-hydroxy-piperidine | A | N$^2$ | NA | B$^3$ | 8.66, 432, F | (CDCl$_3$, 400 MHz): 10.34 (s, 1H), 8.88 (d, J = 2.2 Hz, 1H), 8.82 (s, 1H), 8.77 (s, 1H), 7.64 (s, 1H), 7.56-7.41 (m, 3H), 5.17-5.05 (m, 1H), 3.06-2.88 (m, 2H), 2.56-2.40 (m, 2H), 2.38-2.20 (m, 4H), 2.19-2.05 (m, 2H), 1.17-1.05 (m, 3H). |

TABLE 12-continued

| Example | Structure/Name | Amino alcohol | Mitsunobu Method | Coupling Method | Deprotection Method | Purification Method(s) | LCMS $R_T$, M + H+, Method | $^1$H NMR (ppm) |
|---|---|---|---|---|---|---|---|---|
| 273 | 3-Bromo-5-(1-ethyl-piperidin-4-yloxy)-9H-dipyrido[2,3-b;4',3'-d]pyrrole-6-carbonitrile | N-Ethyl 4-hydroxy-piperidine | A | NA | D | B | 6.43, 400/402, F | (400 MHz, CD$_3$OD): 8.71 (s, 1H), 8.70 (d, J = 2.2 Hz, 1H), 8.66 (d, J = 2.3 Hz, 1H), 5.00-4.91 (m, 1H), 3.03-2.95 (m, 2H), 2.51 (q, J = 7.3 Hz, 2H), 2.36-2.25 (m, 2H), 2.24-2.15 (m, 2H), 2.12-2.00 (m, 2H), 1.14 (t, J = 7.2 Hz, 3H). |
| 274 | 3-(1-Isopropyl-1H-pyrazol-4-yl)-5-(piperidin-4-yloxy)-9H-dipyrido[2,3-b;4',3'-d]pyrrole-6-carbonitrile | 4-Hydroxy-piperidine carboxylic acid tert-butyl ester | A | Still C | B | $^1$C | 7.27, 402, F | (DMSO-D$_6$, 400 MHz): 13.03 (s, 1H), 9.01 (d, J = 2.1 Hz, 1H), 8.83 (s, 1H), 8.55 (br s, 1H), 8.53 (d, J = 2.2 Hz, 1H), 8.41 (s, 1H), 8.05 (s, 1H), 5.02-4.93 (m, 1H), 4.63-4.51 (m, 1H), 3.47-3.38 (m, 2H), 3.18-3.06 (m, 2H), 2.35-2.24 (m, 2H), 2.22-2.10 (m, 2H), 1.49 (d, J = 6.7 Hz, 6H). |
| 275 | 3-(3-Methoxy-4-methyl-phenyl)-5-(piperidin-4-yloxy)-9H-dipyrido[2,3-b;4',3'-d]pyrrole-6-carbonitrile | 4-Hydroxy-piperidine carboxylic acid tert-butyl ester | A | N | B | C$^2$ | 8.66, 414, F | (CD$_3$OD and CDCl$_3$, 400 MHz): 8.84 (d, J = 2.0 Hz, 1H), 8.73 (d, J = 8.7 Hz, 2H), 7.34-7.27 (m, 1H), 7.14 (d, J = 7.7 Hz, 1H), 7.08 (s, 1H), 5.06-4.96 (m, 1H), 3.95 (s, 3H), 3.27-3.17 (m, 2H), 2.79-2.68 (m, 2H), 2.31 (s, 3H), 2.29-2.19 (m, 2H), 2.01-1.89 (m, 2H). |

TABLE 12-continued

| Example | Structure/Name | Amino alcohol | Mitsunobu Method | Coupling Method | Deprotection Method | Purification Method(s) | LCMS $R_T$, M + H+, Method | 1H NMR (ppm) |
|---|---|---|---|---|---|---|---|---|
| 276 | 5-(1-Ethyl-piperidin-4-yloxy)-3-(3-methoxy-4-methyl-phenyl)-9H-dipyrido[2,3-b;4',3'-d]pyrrole-6-carbonitrile | N-Ethyl 4-hydroxy-piperidine | A | N | NA | B | 8.79, 442, F | (CDCl$_3$, 400 MHz): 10.81 (s, 1H), 8.91 (d, J = 2.1 Hz, 1H), 8.81 (s, 1H), 8.75 (s, 1H), 7.30 (d, J = 7.6 Hz, 1H), 7.14 (dd, J = 7.6, 1.7 Hz, 1H), 7.08 (d, J = 1.6 Hz, 1H), 5.11-5.02 (m, 1H), 3.96 (s, 3H), 3.09-2.88 (m, 2H), 2.57-2.40 (m, 3H), 2.38-2.05 (m, 8H), 1.20-1.02 (m, 3H). |
| 277 | 3-(4-Hydroxymethyl-3-methoxy-phenyl-)-5-(piperidin-4-yloxy)-9H-dipyrido[2,3-b;4',3'-d]pyrrole-6-carbonitrile | 4-Hydroxy-piperidine carboxylic acid tert-butyl ester | A | N | B | C | 5.86, 430, A | (DMSO-D$_6$, 400 MHz): 9.05 (d, J = 2.2 Hz, 1H), 8.80 (s, 1H), 8.66 (d, J = 2.2 Hz, 1H), 7.53 (d, J = 7.7 Hz, 1H), 7.36 (dd, J = 7.8, 1.6 Hz, 1H), 7.32 (d, J = 1.6 Hz, 1H), 4.88-4.78 (m, 1H), 4.57 (s, 2H), 3.92 (s, 3H), 3.10-3.01 (m, 2H), 2.60-2.51 (m, 2H), 2.13-2.04 (m, 2H), 1.88-1.75 (m, 2H). |
| 278 | 5-(1-Aza-bicyclo[2.2.2]oct-3-yloxy)-3-(1-methyl-1H-pyrazol-4-yl)-9H-dipyrido[2,3-b;4',3'-d]pyrrole-6-carbonitrile | 3-Quinuclininol | A | N | NA | C[8] | 6.25, 400, F | (DMSO-D$_6$, 300 MHz): 12.90 (s, 1H); 8.95 (d, J = 2.1 Hz, 1H), 8.75 (s, 1H), 8.50 (d, J = 2.2 Hz, 1H), 8.25 (s, 1H), 7.95 (s, 1H), 5.06-4.98 (m, 1H), 3.93 (s, 3H), 3.45-3.26 (m, 1H), 3.17-2.95 (m, 2H), 2.92-2.78 (m, 1H), 2.77-2.56 (m, 2H), 2.29-2.10 (m, 1H), 1.77-1.63 (m, 1H), 1.56-1.42 (m, 2H). |

TABLE 12-continued

| Example | Structure/Name | Amino alcohol | Mitsunobu Method | Coupling Method | Deprotection Method | Purification Method(s) | LCMS $R_T$, M + H$^+$, Method | $^1$H NMR (ppm) |
|---|---|---|---|---|---|---|---|---|
| 279 | 5-(1-Ethyl-piperidin-4-yloxy)-3-(4-morpholin-4-ylmethyl-phenyl)-9H-dipyrido[2,3-b;4',3'-d]pyrrole-6-carbonitrile | N-Ethyl 4-hydroxy-piperidine | A | N | NA | B$^5$ | 4.72, 497, F | (CDCl$_3$, 400 MHz): 10.01 (s, 1H), 8.91 (s, 1H), 8.84-8.71 (m, 2H), 7.65-7.56 (m, 2H), 7.55-7.49 (m, 2H), 5.12-5.01 (m, 1H), 3.77 (t, J = 4.5 Hz, 4H), 3.61 (s, 2H), 2.99 (s, 2H), 2.57-2.41 (m, 5H), 2.37-2.00 (m, 4H), 1.73-1.50 (br s, 4H), 1.20-1.04 (br s, 2H). |
| 280 | 3-(1-Methyl-1H-pyrazol-4-yl)-5-(1-propyl-piperidin-4-yloxy)-9H-dipyrido[2,3-b;4',3'-d]pyrrole-6-carbonitrile | N-Propyl 4-hydroxy-piperidine | A | N | NA | Q | 6.75, 416, F | (DMSO-D$_6$, 300 MHz): 12.91 (br s, 1H), 8.96 (d, J = 2.1 Hz, 1H), 8.76 (d, J = 0.5 Hz, 1H), 8.56 (d, J = 2.2 Hz, 1H), 8.30 (s, 1 H), 7.99 (s, 1H), 4.83-4.71 (m, 1H), 3.92 (s, 3H), 2.89-2.77 (m, 2H), 2.24 (t, J = 7.4 Hz, 2H), 2.18-1.88 (m, 6H), 1.51-1.35 (m, 2H), 0.84 (t, J = 7.4 Hz, 3H). |
| 281 | 5-((S)-1-Ethyl-pyrrolidin-3-yloxy)-3-pyridin-4-yl-9H-dipyrido[2,3-b;4',3'-d]pyrrole-6-carbonitrile | (R)-1-Ethyl-pyrrolidin-3-ol | A | N | NA | B | 3.40, 385, F | (DMSO-D$_6$, 400 MHz): 13.11 (s, 1H), 9.15 (d, J = 2.3 Hz, 1H), 9.06 (d, J = 2.3 Hz, 1H), 8.82 (s, 1H), 8.71 (dd, J = 4.7, 1.6 Hz, 2H), 7.85 (dd, J = 4.6, 1.7 Hz, 2H), 5.49-5.44 (m, 1H), 3.20-3.13 (m, 1H), 3.10-3.03 (m, 1H), 2.55-2.22 (m, 5H), 2.21-2.11 (m, 1H), 0.94 (t, J = 7.2 Hz, 3H). |

| Example | Structure/Name | Amino alcohol | Mitsunobu Method | Coupling Method | Deprotection Method | Purification Method(s) | LCMS R$_T$, M + H$^+$, Method | $^1$H NMR (ppm) |
|---|---|---|---|---|---|---|---|---|
| 282 | trans-3-[4-(4,4-Difluoro-piperidin-1-ylmethyl)-phenyl]-5-(-1-ethyl-3-fluoro-piperidin-4-yloxy)-9H-dipyrido[2,3-b;4',3'-d]pyrrole-6-carbonitrile | cis-1-Ethyl-3-fluoro-piperidin-4-ol | A | N | NA | B$^4$ | 4.73, 340, F | (CDCl$_3$ 400 MHz): 10.70 (s, 1H), 8.92 (d, J = 1.9 Hz, 1H), 8.85 (s, 1H), 8.83 (s, 1H), 7.64 (d, J = 8.0 Hz, 2H), 7.53 (d, J = 7.5 Hz, 2H), 5.14-4.79 (m, 2H), 3.74-3.60 (m, 2H), 3.38-3.23 (m, 1H), 3.07-2.93 (m, 1H), 2.74-2.41 (m, 6H), 2.26-1.96 (m, 6H), 1.69-1.48 (m, 2H), 1.18-1.03 (m, 3H). |
| 283 | 3-Pyridin-4-yl-5-[1-(2,2,2-trifluoro-ethyl)-piperidin-4-yloxy]-9H-dipyrido[2,3-b;4',3'-d]pyrrole-6-carbonitrile | 1-(2,2,2-Trifluoroethyl)piperidin-4-ol | A | N | NA | B, Q$^1$ | 9.41, 453, F | (CDCl$_3$ and CD$_3$OD, 300 MHz): 9.00 (d, J = 2.2 Hz, 1H), 8.87 (d, J = 2.3 Hz, 1H), 8.78 (s, 1H), 8.74-8.67 (m, 2H), 7.80-7.74 (m, 2H), 5.09-4.96 (m, 1H), 3.18-3.02 (m, 4H), 2.72-2.57 (m, 2H), 2.32-2.07 (m, 4H). |
| 284 | 5-(8-Methyl-8-aza-bicyclo[3.2.1]oct-3-yloxy)-3-pyridin-4-yl-9H-dipyrido[2,3-b;4',3'-d]pyrrole-6-carbonitrile | 8-Methyl-8-azabicyclo[3.2.1]octan-3-ol | A | N | NA | E$^1$ | 4.40, 411, F | (DMSO-D$_6$, 300 MHz): 13.03 (br s, 1H), 9.14 (d, J = 2.2 Hz, 1H), 8.81-8.78 (m, 2H), 8.75-8.71 (m, 2H), 7.88-7.83 (m, 2H), 5.15-4.99 (m, 1H), 3.25-3.17 (m, 2H), 2.25 (s, 3H), 2.06 (dd, J = 8.4, 2.9 Hz, 4H), 1.94-1.86 (m, 2H), 1.54-1.43 (m, 2H). |

TABLE 12-continued

| Example | Structure/Name | Amino alcohol | Mitsunobu Method | Coupling Method | Deprotection Method | Purification Method(s) | LCMS $R_T$, M + H$^+$, Method | $^1$H NMR (ppm) |
|---|---|---|---|---|---|---|---|---|
| 285 | 5-(1-Isopropyl-piperidin-4-yloxy)-3-pyridin-4-yl-9H-dipyrido[2,3-b;4',3'-d]pyrrole-6-carbonitrile | 1-Isopropyl-piperidin-4-ol | A | N | NA | E | 4.93, 413, F | (CDCl$_3$ and CD$_3$OD, 300 MHz): 8.99 (d, J = 2.3 Hz, 1H), 8.91 (d, J = 2.3 Hz, 1H), 8.78 (s, 1H), 8.73-8.66 (m, 2H), 7.81-7.75 (m, 2H), 5.09-4.93 (m, 1H), 3.05-2.90 (m, 2H), 2.88-2.71 (m, 1H), 2.53-2.35 (m, 2H), 2.33-2.00 (m, 4H), 1.09 (d, J = 6.5 Hz, 6H). |
| 286 | 5-[1-(2-Methoxy-ethyl)-piperidin-4-yloxy]-3-pyridin-4-yl-9H-dipyrido[2,3-b;4',3'-d]pyrrole-6-carbonitrile | 1-(2-Methoxyethyl)-4-piperidinol | A | N | NA | E$^2$ | 4.76, 429, F | (CDCl$_3$ and CD$_3$OD, 300 MHz): 9.01 (d, J = 2.2 Hz, 1 H), 8.91 (d, J = 2.3 Hz, 1H), 8.78 (s, 1H), 8.73-8.66 (m, 2H), 7.84-7.78 (m, 2H), 5.08-4.95 (m, 1H), 3.56 (t, J = 5.5 Hz, 2H), 3.10-2.97 (m, 2H), 2.65 (t, J = 5.5 Hz, 2H), 2.45-2.32 (m, 2H), 2.31-2.07 (m, 4H). |

The compounds of the Examples in Table 13 were prepared via the general alkylation procedure followed by the general bromide displacement procedures described above.

TABLE 13

| Example | Structure/Name | Alkylation Method | Bromide Displacement Method | Purification Method (s) | LCMS $R_T$, M + H⁺, Method | ¹H NMR (ppm) |
|---|---|---|---|---|---|---|
| 287 | 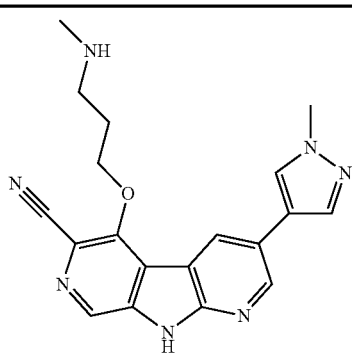<br>5-(3-Methylamino-propoxy)-3-(1-methyl-1H-pyrazol-4-yl)-9H-dipyrido[2,3-b,4',3'-d]pyrrole-6-carbonitrile | A | E | Q | 5.29, 362, A | (CD₃OD, 400 MHz): 8.84 (d, J = 2.2 Hz, 1H), 8.73-8.69 (m, 1H), 8.62 (d, J = 2.2 Hz, 1H), 8.06 (s, 1H), 7.92 (s, 1H), 4.70 (t, J = 6.1 Hz, 2H), 4.05-3.96 (m, 3H), 3.00 (t, J = 7.2 Hz, 2H), 2.51 (s, 3H) 2.32-2.22 (m, 2H). |
| 288 | 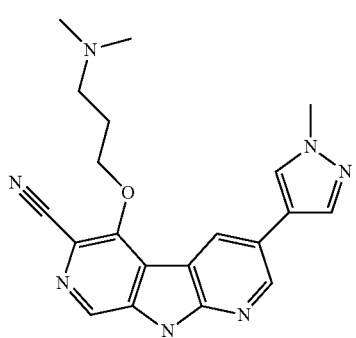<br>5-(3-Dimethylamino-propoxy)-3-(1-methyl-1H-pyrazol-4-yl)-9H-dipyrido[2,3-b;4',3'-d]pyrrole-6-carbonitrile | A | E | Q | 4.96, 362, A | (CD₃OD, 400 MHz): 8.83 (s, 2H), 8.71 (s, 1H), 8.08 (s, 1H), 7.94-7.92 (m, 1H), 4.70 (t, J = 5.4 Hz, 2H), 4.02-3.97 (m, 3H), 3.00 (t, J = 5.4 Hz, 2H), 2.44 (s, 6H). |
| 289 | 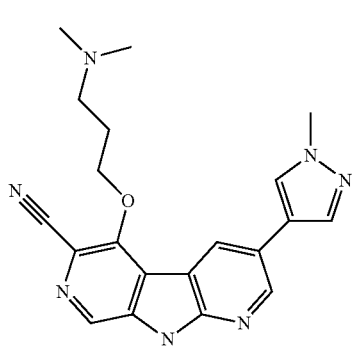<br>5-(3-Dimethylamino-propoxy)-3-(1-methyl-1H-pyrazol-4-yl)-9H-dipyrido[2,3-b;4',3'-d]pyrrole-6-carbonitrile | A | E | Q | 5.20, 388, A | (DMSO-D₆, 400 MHz, DMSO-d₆): 12.89 (s, 1H), 8.95 (d, J = 2.2 Hz, 1H), 8.80 (d, J = 2.2 Hz, 1H), 8.79-8.75 (m, 1H), 8.28 (s, 1H), 7.99 (d, J = 0.8 Hz, 1H), 4.66 (t, J = 5.4 Hz, 2H), 3.93 (s, 3H), 3.00 (t, J = 5.3 Hz, 2H), 2.54 (s, 4H), 1.66-1.50 (m, 4H). |

The compounds of the Examples in Table 14 were prepared via the general bromide displacement procedures described above.

TABLE 14

| Example | Structure/Name | Bromide Displacement Method | Purification Method (s) | LCMS $R_T$, M + H[+], Method | $^1$H NMR (ppm) |
|---|---|---|---|---|---|
| 290 | 5-(1-Ethyl-piperidin-4-ylamino)-3-(1-methyl-1H-pyrazol-4-yl)-9H-dipyrido[2,3-b;4',3'-d]pyrrole-6-carbonitrile | B | C, Q, B | 5.85, 4.01, F | (CDCl$_3$ and MeOD, 400 MHz): 8.73 (d, J = 2.0 Hz, 1 H); 8.62 (d, J = 2.0 Hz, 1 H); 8.40 (s, 1 H); 8.03 (s, 1 H); 7.95 (d, J = 0.8 Hz, 1 H); 4.17-4.07 (m, 1 H); 4.02 (s, 3 H); 3.11-3.01 (m, 2 H); 2.51 (q, J = 7.2 Hz, 2 H); 2.29-2.12 (m, 4 H); 1.92-1.78 (m, 2 H); 1.16 (t, J = 7.2 Hz, 3 H). |
| 291 | 3-(1-Methyl-1H-pyrazol-4-yl)-5-(2-pyrrolidin-1-yl-ethylamino)-9H-dipyrido[2,3-b;4',3'-d]pyrrole-6-carbonitrile | B | C, B[1] | 5.84, 3.87, F | (CDCl$_3$ and MeOD, 400 MHz): 8.75 (d, J = 2.0 Hz, 1 H); 8.72 (d, J = 2.0 Hz, 1 H); 8.37 (s, 1 H); 8.03 (s, 1 H); 7.91 (s, 1 H); 4.02-3.97 (m, 5 H); 2.98 (t, J = 6.1 Hz, 2 H); 2.76-2.68 (m, 4 H); 1.86-1.77 (m, 4 H). |
| 292 | 5-(3-Dimethylamino-propylamino)-3-(1-methyl-1H-pyrazol-4-yl)-9H-dipyrido[2,3-b;4',3'-d]pyrrole-6-carbonitrile | B | C, B[2] | 6.09, 375, F | (CDCl$_3$ and MeOD, 400 MHz): 8.87 (d, J = 2.0 Hz, 1 H); 8.73 (d, J = 2.0 Hz, 1 H); 8.38 (s, 1 H); 8.07 (s, 1 H); 7.96 (d, J = 0.8 Hz, 1 H); 4.02 (s, 3 H); 3.99 (t, J = 6.9 Hz, 2H); 2.72 (t, J = 7.1 Hz, 2 H); 2.44 (s, 6 H); 2.16-2.06 (m, 2 H). |

TABLE 14-continued

| Example | Structure/Name | Bromide Displacement Method | Purification Method (s) | LCMS $R_T$, M + H$^+$, Method | $^1$H NMR (ppm) |
|---|---|---|---|---|---|
| 293 | 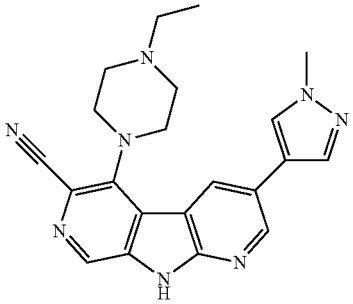<br>5-(4-Ethyl-piperazin-1-yl)-3-(1-methyl-1H-pyrazol-4-yl)-9H-dipyrido[2,3-b;4',3'-d]pyrrole-6-carbonitrile | A | Q$^1$ | 5.15, 387, F | (CDCl$_3$ and MeOD, 400 MHz): 8.82 (d, J = 2.1 Hz, 1 H); 8.74-8.71 (m, 2H); 8.05 (s, 1 H); 7.90 (d, J = 0.8 Hz, 1 H); 4.02 (s, 3 H); 3.71-3.64 (m, 4 H); 2.94-2.84 (m, 4 H); 2.67 (q, J = 7.2 Hz, 2 H); 1.25 (t, J = 7.2 Hz, 3 H). |
| 294 | 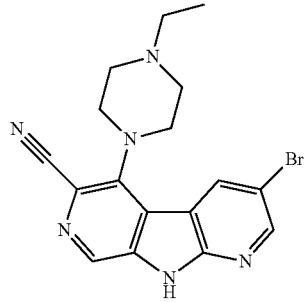<br>3-Bromo-5-(4-ethyl-piperazin-1-yl)-9H-dipyrido[2,3-b;4',3'-d]pyrrole-6-carbonitrile | C | B$^1$ | 4.62, 385, F | (CDCl$_3$ and MeOD, 400 MHz): 8.78 (d, J = 2.2 Hz, 1 H); 8.75 (s, 1 H); 8.70 (d, J = 2.2 Hz, 1 H); 3.68-3.61 (m, 4 H); 2.90-2.81 (m, 4H); 2.65 (q, J = 7.25 Hz, 2H); 1.24 (t, J = 7.2 Hz, 3 H). |
| 295 | 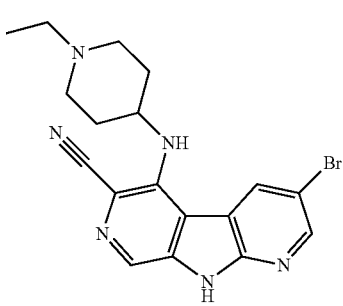<br>3-Bromo-5-(1-ethyl-piperidin-4-ylamino)-9H-dipyrido[2,3-b;4',3'-d]pyrrole-6-carbonitrile | C | C, Q | 2.84, 399, G | (CDCl$_3$ and MeOD, 400 MHz): 8.70 (d, J = 2.1 Hz, 1 H); 8.62 (d, J = 2.1 Hz, 1 H); 8.43 (s, 1 H); 4.22-4.08 (m, 1 H); 3.12-3.01 (m, 2H); 2.52 (q, J = 7.2 Hz, 2H); 2.31-2.14 (m, 4 H); 1.93-1.74 (m, 2 H); 1.16 (t, J = 7.2 Hz, 3 H). |

TABLE 14-continued

| Example | Structure/Name | Bromide Displacement Method | Purification Method (s) | LCMS R$_T$, M + H$^+$, Method | $^1$H NMR (ppm) |
|---|---|---|---|---|---|
| 296 | 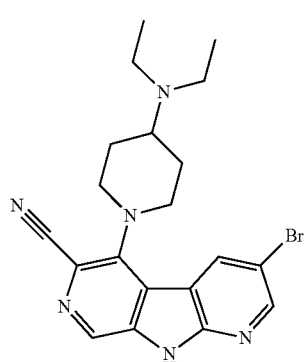<br>3-Bromo-5-(4-diethylamino-piperidin-1-yl)-9H-dipyrido[2,3-b;4',3'-d]pyrrole-6-carbonitrile | D | C, B | 2.57, 427, G | (CDCl$_3$ and MeOD, 400 MHz): 8.73-8.71 (m, 2 H); 8.69 (d, J = 2.2 Hz, 1 H); 3.68-3.54 (m, 4 H); 2.96-2.86 (m, 1 H); 2.80 (q, J = 7.2 Hz, 4 H); 2.19-2.11 (m, 2 H); 1.99-1.86 (m, 2 H); 1.17 (t, J = 7.2 Hz, 6 H). |
| 297 | 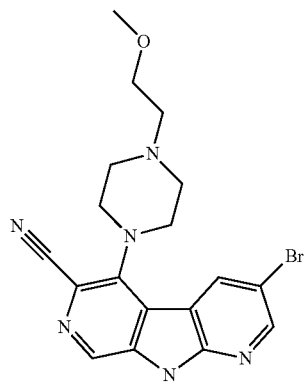<br>3-Bromo-5-[4-(2-methoxy-ethyl)-piperazin-1-yl]-9H-dipyrido[2,3-b;4',3'-d]pyrrole-6-carbonitrile | D | C, B$^1$ | 5.42, 415, F | (CDCl$_3$ and MeOD, 400 MHz): 8.80 (d, J = 2.2 Hz, 1 H); 8.74 (s, 1 H); 8.70 (d, J = 2.2 Hz, 1 H); 3.69-3.60 (m, 6 H); 3.42 (s, 3 H); 2.94-2.87 (m, 4 H); 2.79 (t, J = 5.45 Hz, 2 H). |
| 298 | 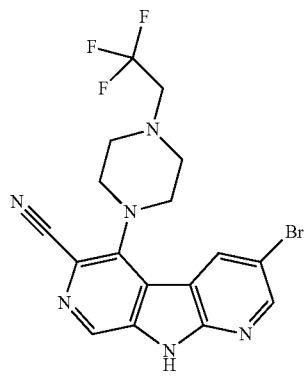<br>3-Bromo-5-[4-(2,2,2-trifluoro-ethyl)-piperazin-1-yl]-9H-dipyrido[2,3-b;4',3'-d]pyrrole-6-carbonitrile | D | C, B$^1$ | 4.60, 439, G | (CDCl$_3$ and MeOD, 300 MHz): 8.76 (d, J = 2.2 Hz, 1 H); 8.75 (s, 1 H); 8.69 (d, J = 2.2 Hz, 1 H); 3.66-3.60 (m, 4 H); 3.25 (q, J = 9.6 Hz, 2 H); 3.10-3.04 (m, 4 H). |

TABLE 14-continued

| Example | Structure/Name | Bromide Displacement Method | Purification Method (s) | LCMS $R_T$, M + H+, Method | ¹H NMR (ppm) |
|---|---|---|---|---|---|
| 299 | 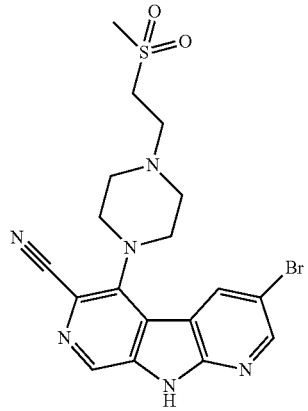<br>3-Bromo-5-[4-(2-methanesulfonyl-ethyl)-piperazin-1-yl]-9H-dipyrido[2,3-b;4′,3′-d]pyrrole-6-carbonitrile | D | | 2.45, 463, G | |

The compounds of the Examples in Table 15 were prepared via the general Mitsunobu or the general Bromide Displacement Methods followed by the general reduction procedure described above.

TABLE 15

| Example | Structure/Name | Mitsunobu Method | Bromide Displacement Method | Reduction Method | Deprotection Method | Purification Method | LCMS $R_T$, M + H+, Method | ¹H NMR (ppm) |
|---|---|---|---|---|---|---|---|---|
| 300 | 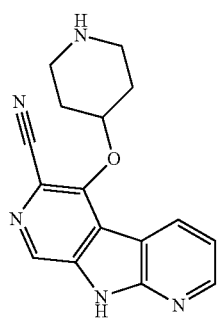<br>5-(Piperidin-4-yloxy)-9H-dipyrido[2,3-b;4′,3′-d]pyrrole-6-carbonitrile | A | NA | A | B | C² | 4.74, 294, F | (MeOD and CDCl₃, 300 MHz): 8.73 (s, 1 H); 8.66 (s, 1 H); 8.65-8.63 (m, 1 H); 7.46-7.41 (m, 1 H); 4.96-4.87 (m, 1 H); 3.21-3.13 (m, 2 H); 2.72-2.62 (m, 2 H); 2.23-2.13 (m, 2 H); 1.99-1.88 (m, 2 H). |
| 301 | 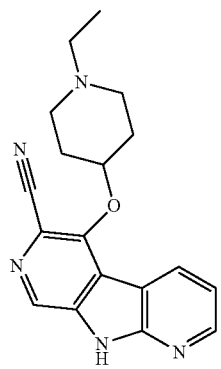<br>5-(1-Ethyl-piperidin-4-yloxy)-9H-dipyrido[2,3-b;4′,3′-d]pyrrole-6-carbonitrile | A | NA | A | E | B⁴ | 5.10, 322, F | (DMSO-D₆, 400 MHz): 12.94 (s, 1H); 8.79 (s, 1 H); 8.71 (dd, J = 6.0, 1.7 Hz, 1 H); 8.60 (dd, J = 9.4, 1.7 Hz, 1 H); 7.47 (dd, J = 12.5, 4.7 Hz, 1 H); 4.78-4.66 (m, 1 H); 2.90-2.78 (m, 2 H); 2.34 (q, J = 7.2 Hz, 2 H); 2.13-2.00 (m, 4 H); 1.99-1.86 (m, 2 H); 1.00 (t, J = 7.2 Hz, 3 H). |

TABLE 15-continued

| Example | Structure/Name | Mitsunobu Method | Bromide Displacement Method | Reduction Method | Deprotection Method | Purification Method | LCMS $R_T$, M + H+, Method | $^1$H NMR (ppm) |
|---|---|---|---|---|---|---|---|---|
| 302 | 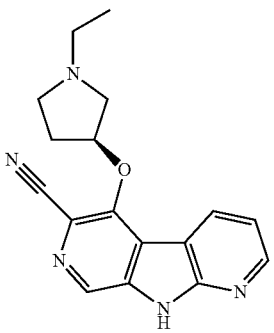<br>5-((S)-1-Ethyl-pyrrolidin-3-yloxy)-9H-dipyrido[2,3-b;4′,3′-d]pyrrole-6-carbonitrile | A | NA | B | E | B² | 4.28, 308, F | (DMSO-D$_6$, 400 MHz): 12.92 (s, 1 H); 8.78 (s, 1 H); 8.74-8.68 (m, 2 H); 7.45 (dd, J = 7.9, 4.8 Hz, 1 H); 5.43-5.36 (m, 1 H); 3.05-2.94 (m, 2 H); 2.71-2.62 (m, 1 H); 2.57-2.42 (m, 2 H); 2.41-2.26 (m, 2 H); 2.21-2.09 (m, 1 H); 1.06 (t, J = 7.2 Hz, 3 H). |
| 303 | 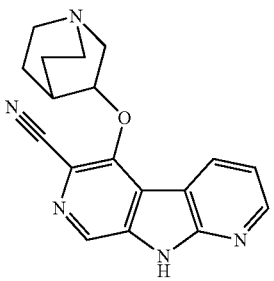<br>5-(1-Aza-bicyclo[2.2.2]oct-3-yloxy)-9H-dipyrido[2,3-b;4′,3′-d]pyrrole-6-carbonitrile | A | NA | B | E | C, Q² | 4.88, 320, F | (DMSO-D$_6$, 300 MHz): 13.27-12.47 (brs, 1 H); 8.76 (s, 1 H); 8.70 (dd, J = 4.8, 1.6 Hz, 1 H); 8.53 (dd, J = 7.9, 1.7 Hz, 1 H); 7.48 (dd, J = 7.9, 4.8 Hz, 1 H); 5.09-4.98 (m, 1 H); 3.11-2.97 (m, 2 H); 2.89-2.54 (s, 4 H); 2.26-2.18 (m, 1 H); 2.17-2.03 (m, 1 H); 1.76 (m, 1 H); 1.56-1.39 (m, 2 H). |
| 304 | 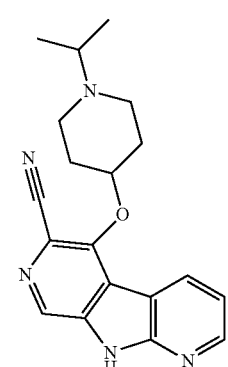<br>5-(1-Isopropyl-piperidin-4-yloxy)-9H-dipyrido[2,3-b;4′,3′-d]pyrrole-6-carbonitrile | A | NA | B | E | C, Q² | 2.25, 336, H | (CDCl$_3$ and MeOD, 300 MHz): 8.74 (s, 1 H); 8.68-8.66 (m, 1 H); 8.65 (s, 1 H); 7.46-7.40 (m, 1 H); 4.99-4.86 (m, 1 H); 3.05-2.94 (m, 2 H); 2.87-2.74 (m, 1 H); 2.50-2.38 (m, 2 H); 2.29-2.02 (m, 4 H); 1.11 (d, J = 6.6 Hz, 6 H). |

TABLE 15-continued

| Example | Structure/Name | Mitsunobu Method | Bromide Displacement Method | Reduction Method | Deprotection Method | Purification Method | LCMS $R_T$, M + H+, Method | $^1$H NMR (ppm) |
|---|---|---|---|---|---|---|---|---|
| 305 | 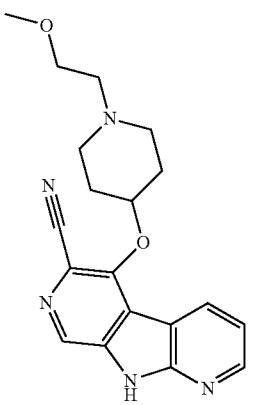<br>5-[1-(2-Methoxy-ethyl)-piperidin-4-yloxy]-9H-dipyrido[2,3-b;4′,3′-d]pyrrole-6-carbonitrile | A | NA | B | E | C, Q$^2$ | 5.46, 352, F | (CDCl$_3$ and MeOD, 300 MHz): 8.74 (s, 1 H); 8.68-8.63 (m, 2 H); 7.45-7.40 (m, 1 H); 5.00-4.86 (m, 1 H); 3.57 (t, J = 5.5 Hz, 2 H); 3.37 (s, 3 H); 3.07-2.97 (m, 2 H); 2.66 (t, J = 5.55 Hz, 2 H); 2.44-2.31 (m, 2 H); 2.28-2.04 (m, 4 H). |
| 306 | 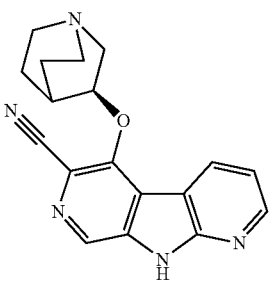<br>5-[(S)-(1-Aza-bicyclo[2.2.2]oct-3-yl)oxy]-9H-dipyrido[2,3-b;4′,3′-d]pyrrole-6-carbonitrile | A | NA | B | E | B$^1$ | 5.02, 320, F | (DMSO-D$_6$, 300 MHz): 13.01 (br s, 1 H); 8.82 (d, J = 0.5 Hz, 1 H); 8.73 (dd, J = 4.8, 1.6 Hz, 1 H); 8.56 (dd, J = 7.9, 1.6 Hz, 1 H); 7.49 (dd, J = 7.9, 4.8 Hz, 1 H); 5.27-5.17 (m, 1 H); 4.14-3.99 (m, 1 H); 3.83-3.69 (m, 1 H); 3.55-2.92 (m, 5 H); 2.42-2.23 (m, 1 H); 1.97-1.62 (m, 3 H). |
| 307 | 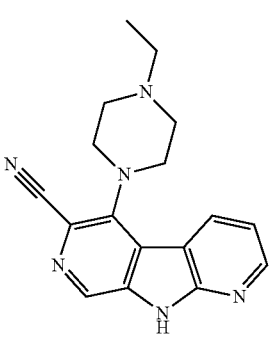<br>5-(4-Ethyl-piperazin-1-yl)-9H-dipyrido[2,3-b;4′,3′-d]pyrrole-6-carbonitrile | NA | C | A | NA | R$^7$ | 3.29, 307, F | (CDCl$_3$ and CD$_3$OD, 400 MHz): 8.86 (s, 1 H); 8.84 (dd, J = 8.0, 1.6 Hz, 1 H); 8.69 (dd, J = 4.8, 1.6 Hz, 1 H); 7.50 (dd, J = 8.0, 4.8 Hz, 1 H); 4.01-3.76 (m, 4 H); 3.74-3.57 (m, 4 H); 3.42 (q, J = 7.3 Hz, 2 H); 1.49 (t, J = 7.3 Hz, 3 H). |

TABLE 15-continued

| Example | Structure/Name | Mitsunobu Method | Bromide Displacement Method | Reduction Method | Deprotection Method | Purification Method | LCMS $R_T$, M + H⁺, Method | ¹H NMR (ppm) |
|---|---|---|---|---|---|---|---|---|
| 308 | 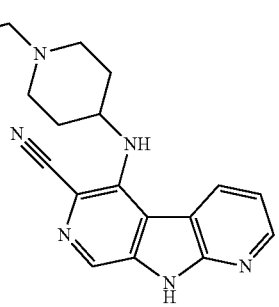<br>5-(1-Ethyl-piperidin-4-ylamino)-9H-dipyrido[2,3-b;4',3'-d]pyrrole-6-carbonitrile | NA | C | A | NA | R⁷ | 4.27, 321, F | (CDCl₃ and CD₃OD, 400 MHz): 8.71 (d, J = 8.0 Hz, 1 H); 8.62 (dd, J = 4.9, 1.5 Hz, 1 H); 8.53 (s, 1 H); 7.43 (dd, J = 8.0, 4.9 Hz, 1 H); 4.44-4.32 (m, 1 H); 3.74-3.61 (m, 2 H); 3.27-3.03 (m, 4 H); 2.56-2.41 (m, 2 H); 2.30-2.14 (m, 2 H); 1.42 (t, J = 7.3 Hz, 3 H). |
| 309 | 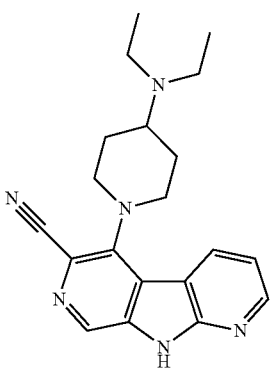<br>5-(4-Diethylamino-piperidin-1-yl)-9H-dipyrido[2,3-b;4',3'-d]pyrrole-6-carbonitrile | NA | D | A | NA | R⁷ | 5.05, 349, F | (CDCl₃ plus CD₃OD, 400 MHz): 8.78 (s, 1H), 8.72 (dd, J = 8.0, 1.5 Hz, 1H), 8.66 (dd, J = 4.9, 1.8 Hz, 1H), 7.48 (dd, J = 8.0, 4.9 Hz, 1H), 3.75-3.61 (m, 5H), 3.46-3.35 (m, 4H), 2.37-2.29 (m, 2H), 2.28-2.15 (m, 2H), 1.44 (t, J = 7.3 Hz, 6H). |
| 310 | 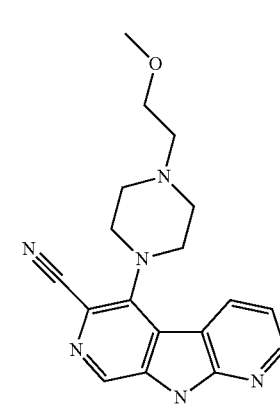<br>5-[4-(2-Methoxy-ethyl)-piperazin-1-yl]-9H-dipyrido[2,3-b;4',3'-d]pyrrole-6-carbonitrile | NA | D | A | NA | R⁷ | 4.17, 337, F | (CDCl₃ plus CD₃OD, 400 MHz): 8.84 (s, 1H), 8.80 (dd, J = 8.0, 1.6 Hz, 1H), 8.68 (dd, J = 4.9, 1.6 Hz, 1H), 7.49 (dd, J = 8.0, 4.9 Hz, 1H), 3.87-3.76 (m, 6H), 3.66-3.50 (m, 4H), 3.47 (s, 3H), 3.45-3.36 (m, 2H). |

TABLE 15-continued

| Example | Structure/Name | Mitsunobu Method | Bromide Displacement Method | Reduction Method | Deprotection Method | Purification Method | LCMS $R_T$, M + H$^+$, Method | $^1$H NMR (ppm) |
|---|---|---|---|---|---|---|---|---|
| 311 | 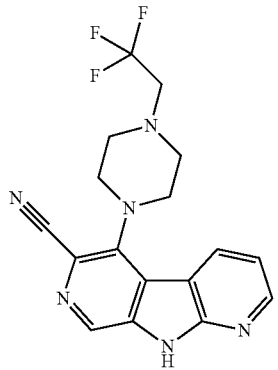<br>5-[4-(2,2,2-Trifluoro-ethyl)-piperazin-1-yl]-9H-dipyrido[2,3-b;4',3'-d]pyrrole-6-carbonitrile | NA | D | A | NA | R$^7$ | 10.56, 361, F | (CDCl$_3$ plus CD$_3$OD, 400 MHz): 8.75 (s, 1H), 8.72 (dd, J = 8.0, 1.6 Hz, 1H), 8.65 (dd, J = 6.3, 1.6 Hz, 1H), 7.45 (dd, J = 8.0, 4.9 Hz, 1H), 3.66-3.60 (m, 4H), 3.24 (q, J = 9.7 Hz, 2H), 3.10-3.05 (m, 4H). |
| 312 | 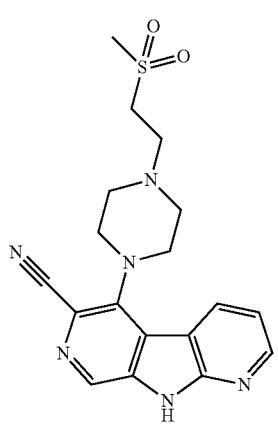<br>5-[4-(2-Methanesulfonyl-ethyl)-piperazin-1-yl]-9H-dipyrido[2,3-b;4',3'-d]pyrrole-6-carbonitrile | NA | D | A | NA | R$^7$ | 4.53, 385, F | (CDCl$_3$ plus CD$_3$OD, 400 MHz): 8.77 (s, 1H), 8.74 (dd, J = 8.0, 1.6 Hz, 1H), 8.65 (dd, J = 6.2, 1.6 Hz, 1H), 7.46 (dd, J = 8.0, 4.9 Hz, 1H), 3.73-3.62 (m, 4H), 3.51-3.39 (m, 2H), 3.24-3.12 (m, 4H), 3.10-2.94 (m, 5H). |
| 313 | 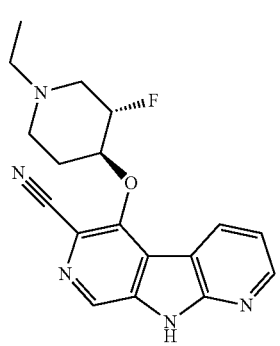<br>trans-5-(-1-Ethyl-3-fluoro-piperidin-4-yloxy)-9H-dipyrido[2,3-b;4',3'-d]pyrrole-6-carbonitrile | A | NA | A | E | R$^5$ | 4.73, 340, F | (CDCl$_3$ plus CD$_3$OD, 300 MHz): 8.75 (s, 1H), 8.69 (dd, J = 7.9, 1.6 Hz, 1H), 8.63 (dd, J = 4.9, 1.6 Hz, 1H), 7.38 (dd, J = 7.9, 4.9 Hz, 1H), 5.15-4.74 (m, 2H), 3.36-3.23 (m, 1H), 3.04-2.94 (m, 1H), 2.62-2.35 (m, 3H), 2.28-2.04 (m, 3H), 1.13 (t, J = 7.2 Hz, 3H). |

Example 314

5-Bromo-6-chloro-3-(4-piperidin-1-ylmethyl-phenyl)-9H-dipyrido[2,3-b;4',3'-d]pyrrole

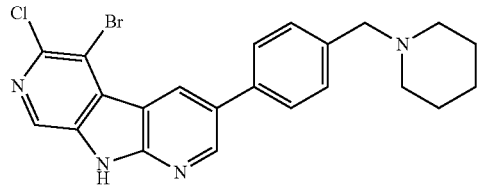 [SMILES: Clc1ncc2[nH]c3ncc(-c4ccc(CN5CCCCC5)cc4)cc3c2c1Br]

Step 1: 5-Bromo-6-chloro-4-iodonicotinic acid

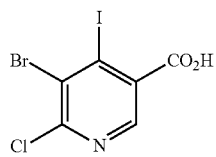

n-Butyllithium (1.6M in hexanes, 172 mL, 276 mmol) was added to a solution of 2,2,6,6-tetramethylpiperidine (48.5 mL, 285 mmol) in anhydrous THF (200 mL) at −50° C. After 20 min, solid 5-bromo-6-chloronicotinic acid (21.6 g, 92 mmol) was added portionwise and the resultant slurry was allowed to warm to −20° C. over 1 h and stirred at that temperature for 1 h. After this time, the reaction mixture was cooled to −60° C. and transferred via cannula to a solution of iodine (70 g, 276 mmol) in anhydrous THF (100 mL) at −60° C. at such a rate that the internal temperature of the solution remained below −40° C. On complete addition, the reaction mixture was allowed to warm slowly to ambient temperature and stirred for 18 h. The reaction mixture was concentrated in vacuo and the resultant dark red slurry was dissolved in water (500 mL) and washed with diethyl ether (3×200 mL). The pH of aqueous layer was adjusted to 2 by the addition of 1M aqueous hydrochloric acid and the resulting beige precipitate was collected by filtration and dried under vacuum to afford the title compound (17.7 g, 53%). $^1$H NMR (DMSO-D$_6$, 400 MHz): 8.30 (s, 1H).

Step 2: (5-Bromo-6-chloro-4-iodo-pyridin-3-yl)-carbamic acid tert-butyl ester

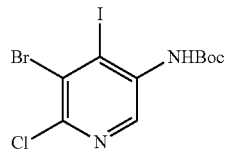

Triethylamine (20.6 mL, 147 mmol) was added to a solution of 5-bromo-6-chloro-4-iodo-nicotinic acid (17.7 g, 49 mmol) and diphenylphosphorazide (15.8 mL, 73 mmol) in toluene (100 mL) and t-BuOH (90 mL) and the resultant solution was heated at 110° C. for 3 h. The reaction mixture was allowed to cool and then concentrated in vacuo and the resultant residue was purified by flash chromatography (silica, 330 g column, ISCO, 0-100% ethyl acetate in cyclohexane) to afford the title compound as a white solid (21.1 g, 90%). $^1$H NMR (DMSO-D$_6$, 400 MHz): 9.04 (s, 1H), 8.25 (s, 1H), 1.47 (s, 9H).

Step 3: 5-Bromo-6-chloro-4-iodo-pyridin-3-ylamine

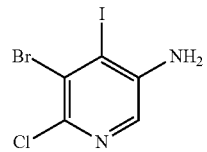

Trifluoroacetic acid (30 mL) was added to a solution of (5-bromo-6-chloro-4-iodo-pyridin-3-yl)-carbamic acid tert-butyl ester (19.0 g, 44 mmol) in DCM (120 mL) and the resultant solution was stirred at ambient temperature for 2 h then concentrated in vacuo. The resultant residue was loaded onto an SCX-2 cartridge (70 g) eluting with acetonitrile (100 mL) then 2N ammonia in methanol (100 mL). The basic fraction was concentrated in vacuo to afford the title compound (11.5 g, 78%). $^1$H NMR (DMSO-D$_6$, 400 MHz): 7.23 (s, 1H), 5.92 (s, 2H).

Step 4: 2-Fluoro-5-(4-piperidin-1-ylmethylphenyl)-pyridine

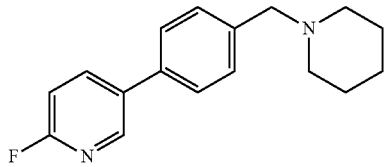 [SMILES: Fc1ccc(-c2ccc(CN3CCCCC3)cc2)cn1]

A degassed mixture of 5-bromo-2-fluoropyridine (578 µL, 5.60 mmol), 4-piperidin-1-ylmethyl-boronic acid (1.23 g, 5.6 mmol), 1,1'-[bis(diphenylphosphino)ferrocene]dichloropalladium(II) (205 mg, 5 mol %) in 1N potassium fluoride solution (4 mL) and acetonitrile (9 mL) was heated under microwave irradiation at 100° C. for 15 min. The resultant crude mixture was diluted with water (10 mL) and extracted with DCM (3×20 mL). The combined organic layer was purified by flash chromatography (silica, 40 g column, ISCO, 0-10% (2N ammonia in MeOH) in DCM) to afford the title compound (1.27 g, 84%). $^1$H NMR (CDCl$_3$, 400 MHz): 8.41 (d, J=2.5 Hz, 1H), 7.96 (td, J=8.5, 2.5 Hz, 1H), 7.48 (d, J=8.0 Hz, 2H), 7.42 (d, J=8.0 Hz, 2H), 6.99 (dd, J=8.5, 3.0 Hz, 1H), 3.52 (s, 2H), 2.40 (br. s, 4H), 1.59 (p, J=6.0 Hz, 4H), 1.44 (t, J=6.0 Hz, 2H). LCMS (Method B): R$_T$=2.05 min, M+H$^+$=271.

Step 5: 2-Fluoro-3-boronic acid-5-(4-piperidin-1-ylmethylphenyl)-pyridine

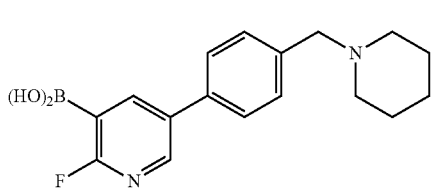 [SMILES: OB(O)c1cc(-c2ccc(CN3CCCCC3)cc2)cnc1F]

Lithium diisopropylamine (7.1 mL, 14.1 mmol) was added to a solution of 2-fluoro-5-(4-piperidin-1-ylmethylphenyl)-pyridine (1.27 g, 4.70 mmol) and triisopropyl borate (3.26 mL, 14.1 mmol) in anhydrous THF (12 mL) at −10° C. The resultant solution was stirred between −10° C. and 0° C. for 1 h, and then quenched by the addition of saturated aqueous ammonium chloride (10 mL). The reaction mixture was diluted with water (20 mL) and extracted with DCM (3×20 mL). The combined organic layer was dried over magnesium sulfate and concentrated in vacuo. The crude oil was triturated with cyclohexane: DCM (3:1) to afford the title compound as a beige solid (677 mg, 46%). $^1$H NMR (DMSO-D$_6$, 300 MHz): 8.53 (s, 1H), 8.35-8.31 (m, 1H), 7.66 (d, J=8.0 Hz, 2H), 7.41 (d, J=8.0 Hz, 2H), 3.54-3.42 (m, 2H), 2.44-2.24 (m, 4H), 1.57-1.45 (m, 4H), 1.44-1.36 (m, 2H), 1.20 (d, J=6.5 Hz, 2H). LCMS (Method B): R$_T$=1.79 min, M+H$^+$=315.

Step 6: 5'-Bromo-6'-chloro-2-fluoro-5-(4-piperidin-1-ylmethyl-phenyl)-[3,4]bipyridinyl-3'-ylamine

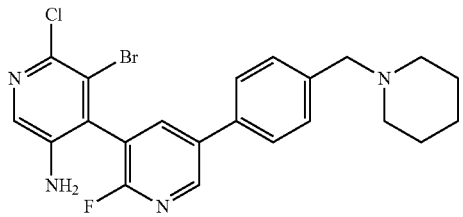 [SMILES: Nc1cnc(Cl)c(Br)c1-c1cc(-c2ccc(CN3CCCCC3)cc2)cnc1F]

A mixture of 2-fluoro-3-boronic acid-5-(4-piperidin-1-ylmethylphenyl)-pyridine (515 mg, 1.6 mmol), 5-bromo-6-chloro-4-iodo-pyridin-3-ylamine (546 mg, 1.6 mmol), 1,1'-[bis(diphenylphosphino)ferrocene]dichloro palladium(II) (60 mg, 5 mol %) in 1N potassium fluoride solution (5 mL) and acetonitrile (15 mL) was heated under microwave irradiation at 110° C. for 20 min. The reaction mixture was allowed to cool to ambient temperature, diluted with water (10 mL) and extracted with DCM (3×20 mL). The combined organic layer was concentrated in vacuo and the residue was purified by flash chromatography (silica, 12 g column, ISCO, 0-10% MeOH in DCM) to afford the title compound (189 mg, 24%). $^1$H NMR (CDCl$_3$, 300 MHz): 8.57 (dd, J=2.5, 1.0 Hz, 1H), 7.96 (s, 1H), 7.90 (dd, J=8.5, 2.5 Hz, 1H), 7.53 (d, J=8.0 Hz, 2H), 7.46 (d, J=8.0 Hz, 2H), 3.72 (s, 2H), 3.54 (s, 2H), 2.41 (br. s, 4H), 1.64-1.58 (m, 4H), 1.48-1.44 (m, 2H). LCMS (Method B): R$_T$=2.41 min, M+H$^+$=475/477.

Step 7: 5-Bromo-6-chloro-3-(4-piperidin-1-ylmethylphenyl)-9H-dipyrido[2,3-b;4',3'-d]pyrrole

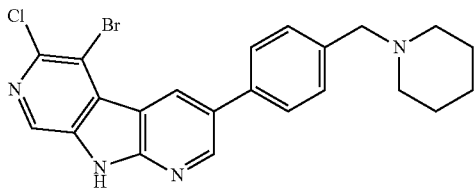 [SMILES: Clc1ncc2[nH]c3ncc(-c4ccc(CN5CCCCC5)cc4)cc3c2c1Br]

Sodium bis(trimethylsilyl)amide (3.9 mL, 3.90 mmol) was added to a solution of 5'-bromo-6'-chloro-2-fluoro-5-(4-piperidin-1-ylmethyl-phenyl)-[3,4]bipyridinyl-3'-ylamine (187 mg, 0.39 mmol) in anhydrous THF (7.0 mL) and the resultant solution stirred at ambient temperature for 20 min. The reaction mixture was diluted with water (20 mL) and extracted with DCM: MeOH (4:1, 3×20 mL). The combined organic layer was dried over anhydrous magnesium sulfate, filtered and concentrated in vacuo. The resultant residue was purified by flash chromatography (silica, 4 g column, ISCO, 0-15% MeOH in DCM) to afford the title compound as a beige powder (30 mg, 17%). $^1$H NMR (CDCl$_3$, 400 MHz): 9.17 (d, J=2.0 Hz, 1H), 8.86 (d, J=2.0 Hz, 1H), 8.67 (s, 1H), 7.65 (d, J=7.5 Hz, 2H), 7.49 (d, J=7.5 Hz, 2H), 3.59 (s, 2H), 2.51-2.47 (m, 4H), 1.68-1.59 (m, 4H), 1.51-1.45 (m, 2H). LCMS (Method A): R$_T$=7.10 min, M+H$^+$=455/457.

Example 315

6-Chloro-3-(4-piperidin-1-ylmethyl-phenyl)-5-vinyl-9H-dipyrido[2,3-b;4',3'-d]pyrrole

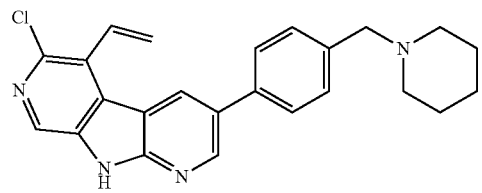 [SMILES: C=Cc1c(Cl)ncc2[nH]c3ncc(-c4ccc(CN5CCCCC5)cc4)cc3c12]

Step 1: 6'-Chloro-2-fluoro-5-(4-piperidin-1-ylmethyl-phenyl)-5'-vinyl-[3,4']bipyridinyl-3'-ylamine

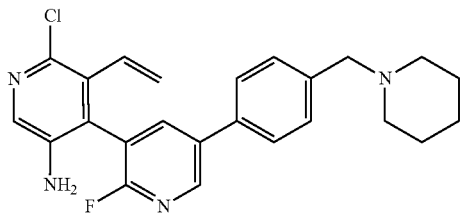 [SMILES: C=Cc1c(Cl)ncc(N)c1-c1cc(-c2ccc(CN3CCCCC3)cc2)cnc1F]

A mixture of 5'-bromo-6'-chloro-2-fluoro-5-(4-piperidin-1-ylmethyl-phenyl)-[3,4]bipyridinyl-3'-ylamine (93 mg, 0.19 mmol), vinyltributyl tin (63 µL, 0.21 mmol), tetrakis (triphenylphosphine)palladium(0) (11 mg, 5 mol %) and lithium chloride (25 mg, 0.59 mmol) in 1,4-dioxane (1.0 mL) was heated under reflux for 3.5 h. The reaction mixture was allowed to cool to ambient temperature, diluted with water (10 mL) and extracted with DCM (3×20 mL). The combined organic layer was concentrated in vacuo and the resultant residue purified by flash chromatography (silica, 4 g column, ISCO, 0-10% MeOH in DCM) to afford the title compound as a beige powder (77 mg, 82%). $^1$H NMR (CDCl$_3$, 400 MHz): 8.50 (dd, J=2.5, 1.0 Hz, 1H), 7.94 (s, 1H), 7.88 (dd, J=8.5, 2.5 Hz, 1H), 7.54-7.47 (m, 4H), 6.53 (dd, J=18.0, 11.5 Hz, 1H), 5.37 (dd, J=11.5, 1.0 Hz, 1H), 5.11 (dd, J=18.0, 1.0 Hz, 1H), 3.60 (s, 2H), 3.55-3.50 (m, 2H), 2.48-2.35 (m, 4H), 1.68-1.58 (m, 4H), 1.50-1.44 (m, 2H). LCMS (Method B): R$_T$=2.32 min, M+H$^+$=423/425.

Step 2: 6-Chloro-3(4-piperidin-1-ylmethyl-phenyl)-5-vinyl-9H-dipyrido[2,3-b;4',3'-d]pyrrole

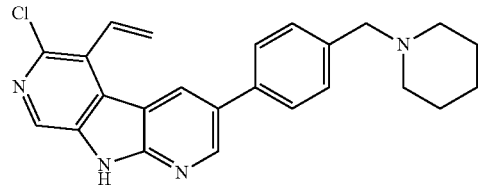 [SMILES: C=Cc1c(Cl)ncc2[nH]c3ncc(-c4ccc(CN5CCCCC5)cc4)cc3c12]

Sodium bis(trimethylsilyl)amide (1.3 mL, 1.3 mmol) was added to a solution of 6'-chloro-2-fluoro-5-(4-piperidin-1-ylmethyl-phenyl)-5'-vinyl-[3,4]bipyridinyl-3'-ylamine (53 mg, 0.13 mmol) in anhydrous THF (1 mL) and the resultant solution stirred at ambient temperature for 20 min. The reaction mixture was diluted with brine (5 mL) and ethyl acetate (5 mL). The resultant precipitate was collected by filtration to afford the title compound as a beige powder (13 mg, 26%). $^1$H NMR (CDCl$_3$, 400 MHz): 8.85 (d, J=2.0 Hz, 1H), 8.77 (d, J=2.0 Hz, 1H), 8.61 (s, 1H), 7.58-7.55 (m, 2H), 7.46 (d, J=8.0 Hz, 2H), 7.22-7.14 (m, 1H), 6.03-6.01 (m, 1H), 5.99-5.97 (m, 1H), 3.56 (s, 2H), 2.47-2.37 (m, 4H), 1.64-1.59 (m, 4H), 1.52-1.44 (m, 2H). LCMS (Method A): R$_T$=6.81 min, M+H$^+$=403/405.

Example 316

5-Ethyl-3-(4-piperidin-1-ylmethylphenyl)-9H-dipyrido[2,3-b;4',3'-d]pyrrole-6-carbonitrile

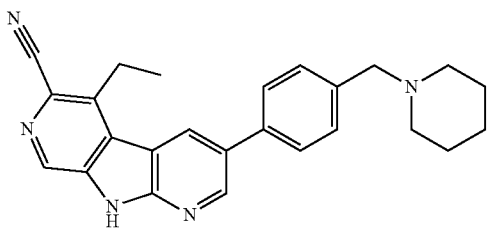 [SMILES: CCc1c(C#N)ncc2[nH]c3ncc(-c4ccc(CN5CCCCC5)cc4)cc3c12]

Step 1: Trifluoromethanesulfonic acid 9-benzenesulfonyl-6-cyano-9H-dipyrido[2,3-b;4',3'-d]pyrrol-5-yl ester

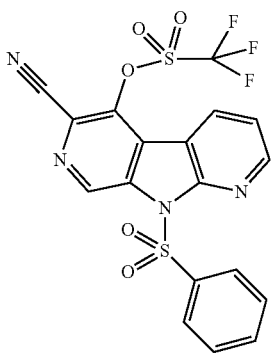 [SMILES: N#Cc1ncc2c(c1OS(=O)(=O)C(F)(F)F)c1cccnc1n2S(=O)(=O)c1ccccc1]

Trifluoromethanesulfonic anhydride (0.91 g, 0.54 mL, 3.22 mmol) was added dropwise to a suspension of 9-benzenesulfonyl-5-hydroxy-9H-dipyrido[2,3-b;4',3'-d]pyrrole-6-carbonitrile (1.03 g, 2.93 mmol) in pyridine (1.2 mL, 14.7 mmol) and dry DCM (20 mL) at 0° C. The reaction mixture was then allowed to warm to ambient temperature and stirred for 2 h. The reaction mixture was treated with 1N hydrochloric acid (10 mL) and the phases were separated. The aqueous phase was extracted with DCM (2×10 mL), the combined organic phase was dried over anhydrous magnesium sulfate and concentrated in vacuo. The resultant residue was purified by chromatography (silica, 5 g column, Si-SPE, DCM) to afford the title compound as a white solid (855 mg, 60%). LCMS (Method B): R$_T$=4.22 min, M+H$^+$=483.

Step 2: 9-Benzenesulfonyl-5-vinyl-9H-dipyrido[2,3-b;4',3'-d]pyrrole-6-carbonitrile

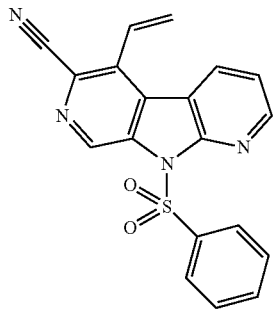 [SMILES: C=Cc1c(C#N)ncc2c1c1cccnc1n2S(=O)(=O)c1ccccc1]

A mixture of trifluoromethanesulfonic acid 9-benzenesulfonyl-6-cyano-9H-dipyrido[2,3-b;4',3'-d]pyrrol-5-yl ester (150 mg, 0.31 mmol), tributyl(vinyl)stannane (102 µL, 0.35 mmol), lithium chloride (40 mg, 0.93 mmol) and tetrakis(triphenylphosphine)palladium(0) (7.0 mg, 6.0 µmol) in dioxane (1.5 mL) was degassed with argon and heated under reflux for 18 h. The reaction mixture was allowed to cool to ambient temperature then diluted with DCM (9 mL) and methanol (1 mL). The resultant residue was purified by chromatography (silica, 2 g column, Si-SPE, 0-2% MeOH in DCM) and triturated with pentane (2×2 mL) to afford the title compound as a white solid (60 mg, 52%). LCMS (Method B): R$_T$=3.73 min, M+H$^+$=361.

Step 3

9-Benzenesulfonyl-5-ethyl-9H-dipyrido[2,3-b;4',3'-d]pyrrole-6-carbonitrile

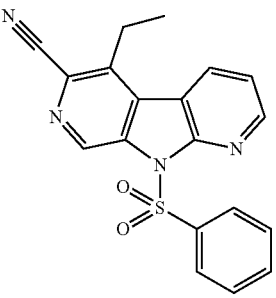 [SMILES: CCc1c(C#N)ncc2c1c1cccnc1n2S(=O)(=O)c1ccccc1]

A mixture of 9-benzenesulfonyl-5-vinyl-9H-dipyrido[2,3-b;4',3'-d]pyrrole-6-carbonitrile (60 mg 0.16 mmol) and 10% palladium on carbon (20 mg) in THF (4 mL) and IMS (3 mL) was stirred under an atmosphere of hydrogen for 3 h. The reaction vessel was then purged with nitrogen then the reaction mixture was filtered through celite. The celite pad was washed with DCM and then ethyl acetate and the combined filtrate was concentrated in vacuo to yield the title compound as a beige solid (60 mg, 99%). LCMS (Method B): R$_T$=3.78 min, M+H$^+$=363.

Step 4: 5-Ethyl-9H-dipyrido[2,3-b;4',3'-d]pyrrole-6-carbonitrile

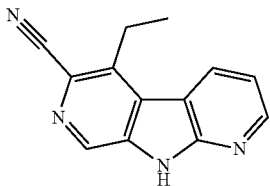 [SMILES: CCc1c(C#N)ncc2[nH]c3ncccc3c12]

A mixture of 9-benzenesulfonyl-5-ethyl-9H-dipyrido[2,3-b;4',3'-d]pyrrole-6-carbonitrile (60 mg, 0.16 mmol), DCM (3.0 mL) and 7N ammonia in methanol (3 mL) was stirred at room temperature for 5 days. The reaction mixture was then concentrated in vacuo and the resultant residue was triturated with methanol (2 mL) and dried in vacuo to give the title compound as an off-white solid (28 mg, 81%). LCMS (Method B): $R_T$=2.81 min, M+H$^+$=223.

Step 5: 3-Bromo-5-ethyl-9H-dipyrido[2,3-b;4',3'-d]pyrrole-6-carbonitrile

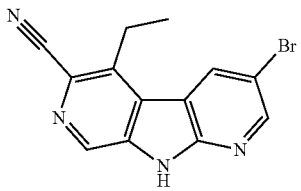 [SMILES: CCc1c(C#N)ncc2[nH]c3ncc(Br)cc3c12]

To a solution of 5-ethyl-9H-dipyrido[2,3-b;4',3'-d]pyrrole-6-carbonitrile (48 mg, 0.21 mmol) in DMF (1 mL) was added NBS (54 mg, 0.30 mmol) then the reaction mixture was stirred for 18 h at ambient temperature. The reaction mixture was then diluted with ethyl acetate (20 mL) and washed with saturated aqueous sodium carbonate (10 mL). The aqueous phase was washed with DCM (2×10 mL), the combined organic phase was washed with saturated brine (2×10 mL) and concentrated in vacuo to afford the title compound as a yellow solid (50 mg, 79%). LCMS (Method B): $R_T$=3.34 min, M+H$^+$=301/303.

Step 6: 5-Ethyl-3-(4-piperidin-1-ylmethyl-phenyl)-9H-dipyrido[2,3-b;4',3'-d]pyrrole-6-carbonitrile

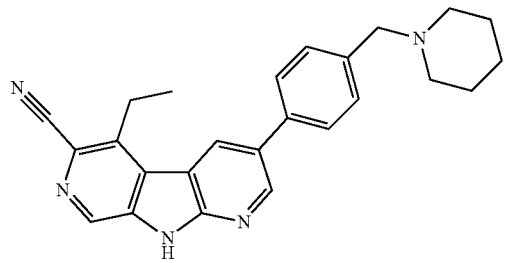 [SMILES: CCc1c(C#N)ncc2[nH]c3ncc(-c4ccc(CN5CCCCC5)cc4)cc3c12]

A mixture of 3-bromo-5-ethyl-9H-dipyrido[2,3-b;4',3'-d]pyrrole-6-carbonitrile (48 mg, 0.16 mmol), 4-piperidin-1-ylmethyl-phenyl boronic acid (56 mg, 0.26 mmol), [1,1'-bis (diphenylphosphino)ferrocene]dichloropalladium(II) (12 mg, 0.016 mmol) in 2N aqueous sodium carbonate (0.5 mL) and acetonitrile (0.63 mL) was heated under microwave irradiation at 140° C. for 35 minutes. The reaction mixture was allowed to cool to ambient temperature, diluted with water (5 mL) and extracted with ethyl acetate (3×5 mL). The combined organic layer was dried over anhydrous magnesium sulfate, filtered and evaporated in vacuo. The resultant residue was purified by flash chromatography (silica, 2 g column, ISCO, 0-5% methanol in DCM) and trituration with diethyl ether (2×1 mL) to afford the title compound as a beige solid (29 mg, 46%). $^1$H NMR (DMSO-D$_6$, 400 MHz): 12.93 (br. s, 1H), 8.99 (d, J=2.2 Hz, 1H), 8.91 (s, 1H), 8.79 (d, J=2.2 Hz, 1H), 7.79 (d, J=8.0 Hz, 2H), 7.46 (d, J=8.0 Hz, 2H), 3.53-3.43 (m, 4H), 2.42-2.33 (m, 4H), 1.55-1.47 (m, 4H), 1.46-1.37 (m, 5H). LCMS (Method A): $R_T$=6.23 min, M+H$^+$=396.

Example 317

5-Hydroxy-3-(4-piperidin-1-ylmethyl-phenyl)-9H-dipyrido[2,3-b;4',3'-d]pyrrole-6-carbonitrile

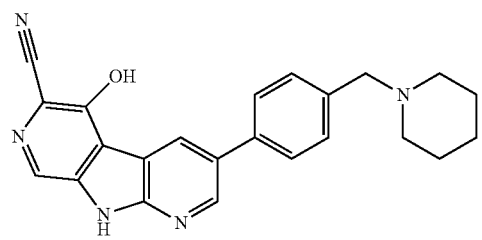 [SMILES: N#Cc1ncc2[nH]c3ncc(-c4ccc(CN5CCCCC5)cc4)cc3c2c1O]

Step 1: 9-Benzenesulfonyl-5-hydroxy-3(4-piperidin-1-ylmethyl phenyl)-9H-dipyrido[2,3-b;4',3'-d]pyrrole-6-carbonitrile

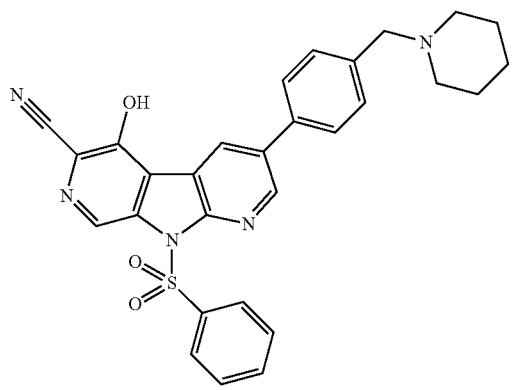 [SMILES: N#Cc1ncc2c(c1O)c1cc(-c3ccc(CN4CCCCC4)cc3)cnc1n2S(=O)(=O)c1ccccc1]

A mixture of 9-benzenesulfonyl-3-bromo-5-hydroxy-9H-dipyrido[2,3-b;4',3'-d]pyrrole-6-carbonitrile (150 mg, 0.35 mmol), 4-piperidin-1-ylmethylphenyl boronic acid (126 mg, 0.6 mmol) and [1,1'-bis(diphenylphosphino) ferrocene] dichloropalladium(II) (27 mg, 0.04 mmol) in 2N aqueous potassium acetate (1.1 mL) and acetonitrile (1.4 mL) was heated under microwave irradiation at 140° C., for 30 minutes. The reaction mixture was diluted with ethyl acetate (10 mL) and water (10 mL) resulting in the formation of a precipitate. The supernatant liquors were decanted and the precipitate was dissolved in 10% methanol in DCM. The decanted liquors were partitioned and the aqueous phase was washed with 10% methanol in DCM (2×10 mL). The combined organic phases were concentrated in vacuo and the resultant residue purified by column chromatography (silica, 2 g cartridge, Si-SPE, 0-20% MeOH in DCM) afforded the crude product which was triturated with acetonitrile (1 mL) and methanol (1 mL) to afford the title compound as a beige solid (60 mg, 31%). LCMS (Method B): $R_T$=2.65 min, M+H$^+$=524.

Step 2: 5-Hydroxy-3-(4-piperidin-1-ylmethylphenyl)-9H-dipyrido[2,3-b;4',3'-d]pyrrole-6-carbonitrile

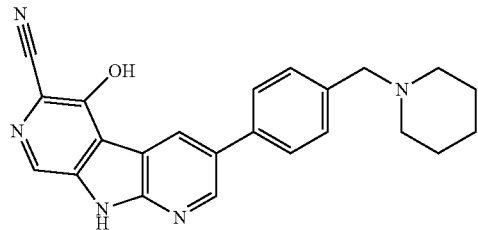 [SMILES: N#Cc1ncc2[nH]c3ncc(-c4ccc(CN5CCCCC5)cc4)cc3c2c1O]

9-Benzenesulfonyl-5-hydroxy-3-(4-piperidin-1-ylmethylphenyl)-9H-dipyrido[2,3-b;4',3'-d]pyrrole-6-carbonitrile (50 mg, 0.01 mmol) was dissolved in 0.15N potassium hydroxide solution in methanol (7 mL). The reaction mixture was stirred for 2.5 h then treated with a solution of monobasic potassium phosphate (136 mg, 1.0 mmol) in water (2 mL). The resultant mixture was concentrated in vacuo and the resultant residue was diluted with water (5 mL). The pH of the aqueous phase was adjusted to 7 by the addition of 1N hydrochloric acid. The aqueous phase was extracted with ethyl acetate, DCM and THF. The combined organic phase was concentrated in vacuo and the residue purified by flash chromatography (silica, 500 mg column, Si-SPE, 10-20% methanol in DCM) to afford the title compound as its hydrochloride salt (25 mg, 63%). $^1$H NMR (DMSO-D$_6$, 400 MHz): 12.91 (s, 1H), 11.86 (br. s, 1H), 10.41 (s, 1H), 9.13 (d, J=2.2 Hz, 1H), 9.00 (d, J=2.2 Hz, 1H), 8.60 (s, 1H), 7.93 (d, J=8.1 Hz, 2H), 7.76 (d, J=8.1 Hz, 2H), 4.33 (d, J=5.2 Hz, 2H), 3.39-3.29 (m, 2H), 2.92-2.83 (m, 2H), 1.85-1.63 (m, 5H), 1.45-1.31 (m, 1H). LCMS (Method A): $R_T$=5.32 min, M+H$^+$=384.

Example 318

5-Ethoxy-3-(4-piperidin-1-ylmethyl-phenyl)-9H-dipyrido[2,3-b;4',3'-d]pyrrole-6-carbonitrile hydrochloride

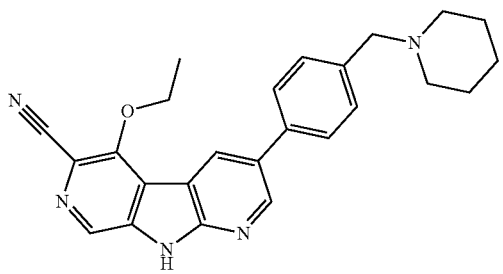 [SMILES: CCOc1c(C#N)ncc2[nH]c3ncc(-c4ccc(CN5CCCCC5)cc4)cc3c12]

Step 1: 9-Benzenesulfonyl-3-bromo-5-ethoxy-9H-dipyrido[2,3-b;4',3'-d]pyrrole-6-carbonitrile

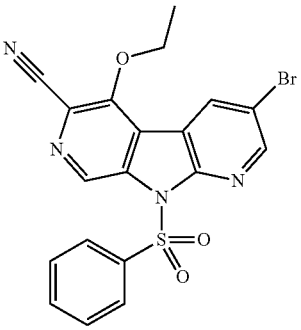 [SMILES: CCOc1c(C#N)ncc2c1c1cc(Br)cnc1n2S(=O)(=O)c1ccccc1]

A solution of 9-benzenesulfonyl-3-bromo-5-hydroxy-9H-dipyrido[2,3-b;4',3'-d]pyrrole-6-carbonitrile (120 mg, 0.28 mmol) in anhydrous THF (5 mL) was cooled to 0° C. and treated with sodium hydride (60% dispersion in mineral oil; 12 mg, 0.30 mmol). After gas evolution had ceased, iodoethane (424 µL, 4.10 mmol) was added and the mixture stirred at ambient temperature overnight then heated at 60° C. for 5 h. The reaction was then allowed to cool, diluted with toluene and concentrated in vacuo. The residue was purified by column chromatography (silica, 2 g column, Si II SPE, 10-100% ethyl acetate in DCM) to afford the title compound as a yellow solid (30 mg, 23%). $^1$H NMR (DMSO-D$_6$, 400 MHz): 8.86 (s, 1H), 8.77 (s, 2H), 8.24-8.22 (m, 1H), 8.22-8.20 (m, 1H), 7.81-7.75 (m, 1H), 7.68-7.61 (m, 2H), 4.75 (q, J=7.2 Hz, 2H), 1.64 (t, J=7.2 Hz, 3H). LCMS (Method B): $R_T$=3.30 min, M+H$^+$=457/459.

Step 2: 5-Ethoxy-3-(4-piperidin-1-ylmethylphenyl)-9H-dipyrido[2,3-b;4',3'-d]pyrrole-6-carbonitrile hydrochloride

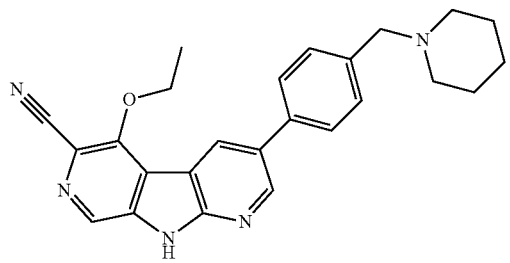 [SMILES: CCOc1c(C#N)ncc2[nH]c3ncc(-c4ccc(CN5CCCCC5)cc4)cc3c12]

A degassed mixture of 9-benzenesulfonyl-3-bromo-5-ethoxy-9H-dipyrido[2,3-b;4',3'd]pyrrole-6-carbonitrile (60 mg, 0.13 mmol), 4-piperidin-1-ylmethylphenyl boronic acid (48 mg, 0.22 mmol) and [1,1'-bis(diphenylphosphino) ferrocene]dichloropalladium(II) (10 mg, 0.013 mmol) in 2N aqueous sodium carbonate (0.42 mL) and acetonitrile (0.53 mL) was heated under microwave irradiation at 140° C. for 30 minutes. The reaction mixture was allowed to cool to ambient temperature, diluted with ethyl acetate (5 mL) and THF (5 mL) and washed with sodium hydrogen carbonate (5 mL). The aqueous phase was extracted with THF (2×5 mL) then the combined organic layer was concentrated in vacuo. The resultant residue was taken up in 1:1 DCM: MeOH containing 0.5 mL 1M hydrochloric acid and purified by flash chromatography (silica, 2 g column, Si-SPE, 5-25% methanol in DCM) and trituration with acetonitrile and 20% MeOH in acetonitrile to afford the title compound as the hydrochloride salt as a brown powder (24 mg, 41%). $^1$H NMR (DMSO-D$_6$, 400 MHz): 8.98 (d, J=2.3 Hz, 1H), 8.94 (d, J=2.3 Hz, 1H), 8.44 (s, 1H), 7.84 (d, J=7.8 Hz, 2H), 7.62 (d, J=7.8 Hz, 2H), 4.64 (q, J=7.2 Hz, 2H), 4.34 (s, 2H), 3.54-3.45 (m, 4H), 3.44-3.26 (m, 1H), 3.02-2.82 (m, 2H), 1.91-1.66 (m, 4H), 1.62 (t, J=7.2 Hz, 3H). LCMS (Method A): R$_T$=4.94 min, M+H$^+$=412.

Example 319

5-(2-Methoxyethoxy)-3-(4-piperidin-1-ylmethyl-phenyl)-9H-dipyrido[2,3-b;4',3'-d]pyrrole-6-carbonitrile

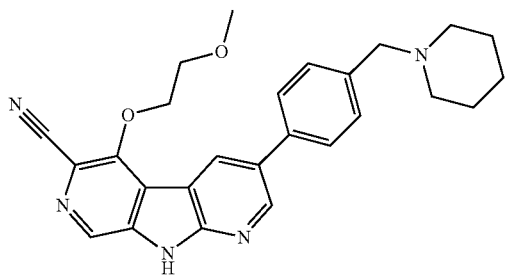 [SMILES: COCCOc1c(C#N)ncc2[nH]c3ncc(-c4ccc(CN5CCCCC5)cc4)cc3c12]

Step 1: 9-Benzenesulfonyl-3-bromo-5-(2-methoxy-ethoxy)-9H-dipyrido[2,3-b;4',3'-d]pyrrole-6-carbonitrile

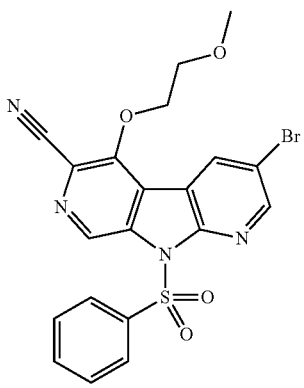 [SMILES: COCCOc1c(C#N)ncc2c1c1cc(Br)cnc1n2S(=O)(=O)c1ccccc1]

A solution of 9-benzenesulfonyl-3-bromo-5-hydroxy-9H-dipyrido[2,3-b;4',3'-d]pyrrole-6-carbonitrile (120 mg, 0.28 mmol), 2-methoxyethanol (128 µL, 1.60 mmol) and triphenylphosphine (315 mg, 1.60 mmol) in anhydrous DMF (1.25 mL) was treated dropwise with diethyl azodicarboxylate (252 µL, 1.60 mmol) and the mixture stirred at ambient temperature for 9 h. The mixture was diluted with ethyl acetate (15 mL) and washed with brine (3×10 mL), dried over anhydrous magnesium sulfate, filtered and evaporated in vacuo. The crude material was purified by column chromatography (silica, 5 g column, Si-SPE, 30-50% DCM in pentane) to afford the title compound (50 mg, 37%). $^1$H NMR (CDCl$_3$, 400 MHz): 9.58 (s, 1H), 8.97 (d, J=2.3 Hz, 1H), 8.76 (d, J=2.3 Hz, 1H), 8.24-8.22 (m, 1H), 8.22-8.00 (m, 1H), 7.66-7.60 (m, 1H), 7.54-7.48 (m, 2H), 4.74-4.69 (m, 2H), 3.87-3.83 (m, 2H), 3.48 (s, 3H). LCMS (Method B): R$_T$=4.25 min, M+H$^+$=487/489.

Step 2: 5-(2-Methoxyethoxy)-3-(4-piperidin-1-ylm-ethylphenyl)-9H-dipyrido[2,3-b;4',3'-d]pyrrole-6-carbonitrile

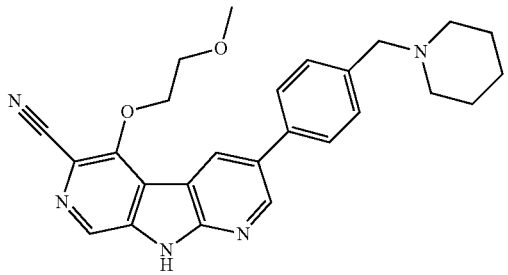 [SMILES: COCCOc1c(C#N)ncc2[nH]c3ncc(-c4ccc(CN5CCCCC5)cc4)cc3c12]

A degassed mixture of 3-bromo-5-(2-methoxy-ethoxy)-9H-dipyrido[2,3-b;4',3'-d]pyrrole-6-carbonitrile (50 mg, 0.10 mmol), 4-piperidin-1-ylmethylphenyl boronic acid (31 mg, 0.14 mmol), [1,1'-bis(diphenylphosphino)ferrocene]dichloropalladium(II) (9 mg, 0.012 mmol) in 2N aqueous sodium carbonate solution (0.42 mL) and acetonitrile (0.53 mL) were heated under microwave irradiation at 140° C. for 30 minutes. The reaction mixture was diluted with water (2 mL) and extracted with 10% MeOH in DCM. The combined organic phase was concentrated in vacuo and the resultant residue was purified by flash chromatography (silica, 500 mg column, Si-SPE, 0-20% methanol in DCM). The resultant residue was dissolved in a solution of 0.15M potassium hydroxide in methanol (7 mL) and stirred for 45 minutes. 1N Potassium dihydrogen phosphate (1 mL) was added then the mixture concentrated in vacuo. The resultant residue was diluted with water and the pH adjusted to 7 by the addition of 1N potassium dihydrogen phosphate. The aqueous phase was extracted with DCM (3×10 mL) and 20% ethanol in DCM (10 mL), the combined organic phase was dried over magnesium sulfate and concentrated in vacuo. The resultant residue was purified by flash chromatography (silica, 500 mg column, Si-SPE, 2-4% methanol in DCM) and trituration with acetonitrile to afford the title compound as a brown solid (14 mg, 32%). $^1$H NMR (CDCl$_3$, 300 MHz): 9.91 (s, 1H), 9.09 (d, J=2.2 Hz, 1H), 8.93 (d, J=2.2 Hz, 1H), 8.80 (s, 1H), 7.67 (d, J=8.1 Hz, 2H), 7.49 (d, J=8.0 Hz, 2H), 4.75-4.69 (m, 2H), 3.95-3.89 (m, 2H), 3.58 (s, 2H), 3.47 (s, 3H), 2.51-2.37 (m, 4H), 1.68-1.54 (m, 4H), 1.52-1.41 (m, 2H). LCMS (Method A): R$_T$=6.27 min, M+H$^+$=442.

Example 320

3-(1-Methyl-1H-pyrazol-4-yl)-5-(pyrrolidin-3-yloxy)-9H-dipyrido[2,3-b;4',3'-d]pyrrole-6-carbonitrile hydrochloride

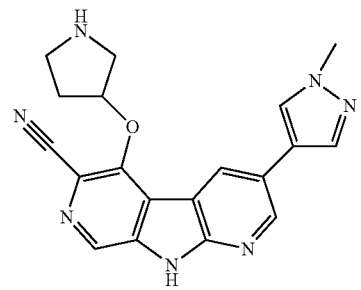 [SMILES: Cn1cc(-c2cnc3[nH]c4cnc(C#N)c(OC5CCNC5)c4c3c2)cn1]

Step 1: 3-(9-Benzenesulfonyl-3-bromo-6-cyano-9H-dipyrido[2,3-b;4',3'-d]pyrrol-5-yloxy)pyrrolidine-1-carboxylic acid tert-butyl ester

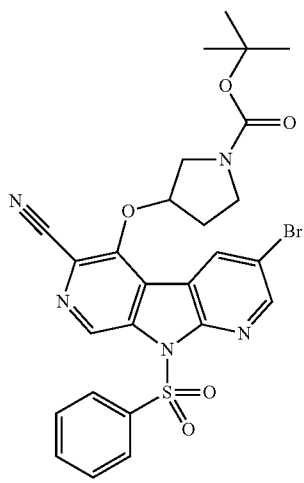 [SMILES: CC(C)(C)OC(=O)N1CCC(Oc2c(C#N)ncc3c2c2cc(Br)cnc2n3S(=O)(=O)c2ccccc2)C1]

A solution of 9-benzenesulfonyl-3-bromo-5-hydroxy-9H-dipyrido[2,3-b;4',3'-d]pyrrole-6-carbonitrile (200 mg, 0.46 mmol), 3-hydroxypyrrolidine-1-carboxylic acid tert-butyl ester (670 mg, 3.56 mmol) and triphenylphosphine (724 mg, 2.76 mmol) in anhydrous DMF (2 mL) was treated dropwise with diethyl azodicarboxylate (0.53 mL, 3.40 mmol) and the mixture stirred at ambient temperature for 3 h then left to stand overnight. The mixture was diluted with ethyl acetate (20 mL) and washed with brine (3×15 mL), dried over magnesium sulfate and concentrated in vacuo. The crude material was purified by flash chromatography (silica, 20 g column, Si-SPE, 0-20% methanol in DCM). Collecting appropriate fractions afforded the title compound (160 mg, 57%). $^1$H NMR (CDCl$_3$, 400 MHz): 9.57 (s, 1H), 8.76 (d, J=2.3 Hz, 1H), 8.46 (d, J=2.3 Hz, 1H), 8.24-8.23 (m, 1H), 8.23-8.21 (m, 1H), 7.71-7.61 (m, 1H), 7.58-7.45 (m, 2H), 5.88-5.83 (m, 1H), 4.36-4.11 (m, 1H), 3.87-3.36 (m, 2H), 2.48-2.26 (m, 2H), 2.13-2.05 (m, 1H), 1.46 (s, 9H). LCMS (Method B): R$_T$=4.51 min, M+H$^+$=598/600.

Step 2: 3-[6-Cyano-3-(1-methyl-1H-pyrazol-4-yl)-9H-dipyrido[2,3-b;4',3'-d]pyrrol-5-yloxy]-pyrrolidine-1-carboxylic acid tert-butyl ester

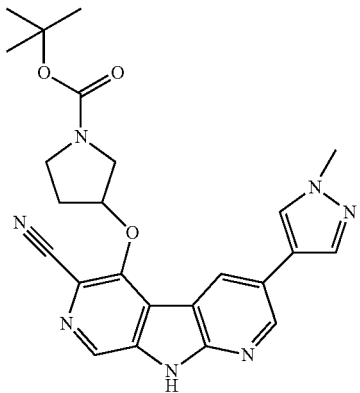 [SMILES: Cn1cc(-c2cnc3[nH]c4cnc(C#N)c(OC5CCN(C(=O)OC(C)(C)C)C5)c4c3c2)cn1]

A degassed mixture of 3-(3-bromo-6-cyano-9H-dipyrido[2,3-b;4',3'-d]pyrrol-5-yloxy)-pyrrolidine-1-carboxylic acid tert-butyl ester (160 mg, 0.20 mmol), 1-methyl-4-(4,4,5,5-tetramethyl-[1,3,2]dioxaborolan-2-yl)-1H-pyrazole (54 mg, 0.26 mmol), [1,1'-bis(diphenylphosphino)ferrocene]dichloropalladium(II) (20 mg, 0.026 mmol) in 1N aqueous potassium fluoride (0.60 mL, 0.60 mmol) and acetonitrile (0.60 mL) was heated at 130° C. under microwave irradiation for 30 minutes. The reaction mixture was allowed to cool to ambient temperature diluted with water (5 mL) and saturated aqueous sodium carbonate (5 mL) then extracted with ethyl acetate (3×10 mL). The combined organic phase was dried over magnesium sulfate and concentrated in vacuo. The resultant was purified by flash chromatography (silica, 2 g column, Si-SPE cartridge, 0-100% ethyl acetate in DCM then methanol) and trituration with acetonitrile to afford the title compound as a white solid (28 mg, 30%). $^1$H NMR (CDCl$_3$, 400 MHz): 8.78-8.71 (m, 2H), 8.46 (s, 1H), 7.90 (s, 1H), 7.85-7.80 (m, 1H), 5.81 (s, 0.5H), 5.73 (s, 0.5H), 4.01 (s, 3H), 3.86-3.57 (m, 3H), 2.58-2.40 (m, 1H), 2.37-2.17 (m, 2H), 1.39 (s, 4H), 1.33 (s, 5H). LCMS (Method B): R$_T$=3.09 min, M+H$^+$=460.

Step 3: 3-(1-Methyl-1H-pyrazol-4-yl)-5-(pyrrolidin-3-yloxy)-9H-dipyrido[2,3-b;4',3'-d]pyrrole-6-carbonitrile, hydrochloride salt

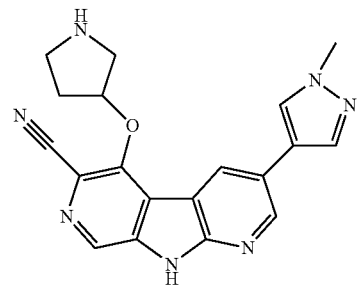 [SMILES: Cn1cc(-c2cnc3[nH]c4cnc(C#N)c(OC5CCNC5)c4c3c2)cn1]

3-[6-Cyano-3-(1-methyl-1H-pyrazol-4-yl)-9H-dipyrido[2,3-b;4',3'-d]pyrrol-5-yloxy]-pyrrolidine-1-carboxylic acid tert-butyl ester (28 mg, 0.06 mmol) was treated with a mixture of acetyl chloride and methanol (2:5, 1 mL). After 1 h the mixture was concentrated in vacuo and the resultant residue was triturated with acetonitrile, the solid collected by filtration and dried in vacuo to afford the compound as a yellow solid (25 mg, 100%). $^1$H NMR (DMSO-D$_6$, 400 MHz): 13.07 (s, 1H), 9.83 (s, 1H), 9.63 (s, 1H), 8.99 (d, J=2.1 Hz, 1H), 8.82 (s, 1H), 8.58 (d, J=2.1 Hz, 1H), 8.45 (s, 1H), 8.11 (d, J=0.8 Hz, 1H), 5.68-5.61 (m, 1H), 3.98-3.88 (m, 5H), 3.62-3.43 (m, 2H), 2.43-2.34 (m, 1H), 2.29-2.17 (m, 1H). LCMS (Method A): R$_T$=4.97 min, M+H$^+$=360.

Example 321

3-(1-Methyl-1H-pyrazol-4-yl)-5-((S)-pyrrolidin-3-yloxy)-9H-dipyrido[2,3-b;4',3'-d]pyrrole-6-carbonitrile Hydrochloride salt

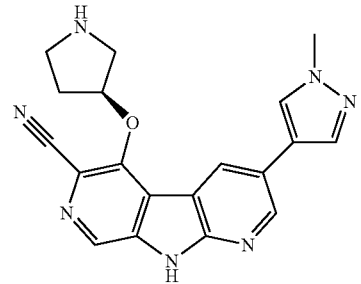 [SMILES: Cn1cc(-c2cnc3[nH]c4cnc(C#N)c(O[C@H]5CCNC5)c4c3c2)cn1]

The title compound was prepared using the procedure described in Example 320 using (R)-3-hydroxy-pyrrolidine-1-carboxylic acid tert-butyl ester. ¹H NMR (DMSO-D₆, 400 MHz): 13.06 (s, 1H), 9.67 (s, 1H), 9.43 (s, 1H), 8.99 (d, J=2.1 Hz, 1H), 8.82 (s, 1H), 8.58 (d, J=2.1 Hz, 1H), 8.41 (s, 1H), 8.09 (d, J=0.8 Hz, 1H), 5.68-5.60 (m, 1H), 3.99-3.89 (m, 4H), 3.80-3.70 (m, 1H), 2.44-2.34 (m, 1H), 2.30-2.17 (m, 1H). LCMS (Method A): R$_T$=5.07 min, M+H⁺=360.

Example 322

3-(1-Methyl-1H-pyrazol-4-yl)-5-((R)-pyrrolidin-3-yloxy)-9H-dipyrido[2,3-b;4',3'-d]pyrrole-6-carbonitrile, hydrochloride salt

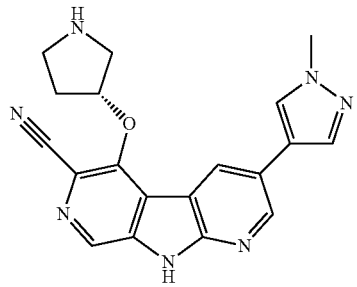 [SMILES: Cn1cc(-c2cnc3[nH]c4cnc(C#N)c(O[C@@H]5CCNC5)c4c3c2)cn1]

The title compound was prepared using the procedure described in Example 320 using (S)-3-hydroxypyrrolidine-1-carboxylic acid tert-butyl ester. ¹H NMR (DMSO-D₆, 400 MHz): 13.07 (s, 1H), 9.83 (s, 1H), 9.63 (s, 1H), 8.99 (d, J=2.1 Hz, 1H), 8.82 (s, 1H), 8.58 (d, J=2.1 Hz, 1H), 8.45 (s, 1H), 8.11 (d, J=0.8 Hz, 1H), 5.68-5.61 (m, 1H), 3.98-3.88 (m, 5H), 3.62-3.43 (m, 2H), 2.43-2.34 (m, 1H), 2.29-2.17 (m, 1H). LCMS (Method A): R$_T$=4.97 min, M+H⁺=360.

Example 323

5-(2-Methoxyethoxy)-3-(1-methyl-1H-pyrazol-4-yl)-9H-dipyrido[2,3-b;4',3'-d]pyrrole-6-carbonitrile

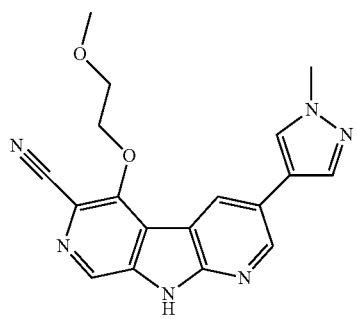 [SMILES: COCCOc1c(C#N)ncc2[nH]c3ncc(-c4cnn(C)c4)cc3c12]

Step 1: 9-Benzenesulfonyl-3-bromo-5-(2-methoxyethoxy)-9H-dipyrido[2,3-b;4',3'-d]pyrrole-6-carbonitrile

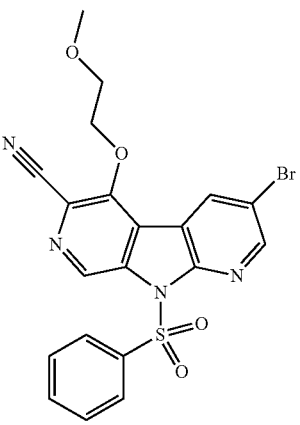 [SMILES: COCCOc1c(C#N)ncc2c1c1cc(Br)cnc1n2S(=O)(=O)c1ccccc1]

A solution of 9-benzenesulfonyl-3-bromo-5-hydroxy-9H-dipyrido[2,3-b;4',3'-d]pyrrole-6-carbonitrile (145 mg, 0.3 mmol), 2-methoxyethanol (158 μL, 2.0 mmol) and triphenylphosphine (525 mg, 2.0 mmol) in anhydrous DMF (1.25 mL) was treated with diethyl azodicarboxylate (0.315 mL, 2.0 mmol) and the mixture stirred at ambient temperature for 30 min then left to stand for 4 days. The mixture was diluted with ethyl acetate (20 mL) and washed with brine (3×10 mL) then the aqueous phase was extracted with ethyl acetate (10 mL). The combined organic phase was dried over magnesium sulfate and concentrated in vacuo. The resultant residue was purified by flash chromatography (silica, 5 g column, Si-SPE, 0-100% ethyl acetate in DCM) to afford the title compound (35 mg, 23%). ¹H NMR (CDCl₃, 300 MHz): 9.58 (s, 1H), 8.97 (d, J=2.3 Hz, 1H), 8.76 (d, J=2.3 Hz, 1H), 8.26-8.18 (m, 2H), 7.68-7.60 (m, 1H), 7.57-7.47 (m, 2H), 4.74-4.69 (m, 2H), 3.89-3.80 (m, 2H), 3.49 (s, 3H).

Step 2: 5-(2-Methoxyethoxy)-3-(1-methyl-1H-pyrazol-4-yl)-9H-dipyrido[2,3-b;4',3'-d]pyrrole-6-carbonitrile

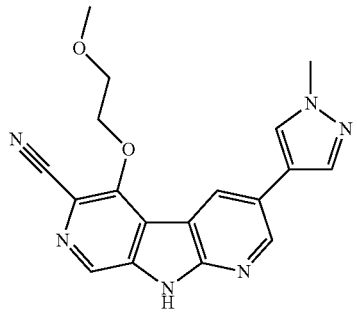 [SMILES: COCCOc1c(C#N)ncc2[nH]c3ncc(-c4cnn(C)c4)cc3c12]

A mixture of 9-benzenesulfonyl-3-bromo-5-(2-methoxyethoxy)-9H-dipyrido[2,3-b;4',3'-d]pyrrole-6-carbonitrile (35 mg, 0.07 mmol), 1-methyl-4-(4,4,5,5-tetramethyl-[1,3,2]dioxaborolan-2-yl)-1H-pyrazole (20 mg, 0.096 mmol), [1,1'-bis(diphenylphosphino) ferrocene]dichloropalladium(II) (7 mg) in 1N aqueous potassium fluoride solution (0.30 mL) and acetonitrile (0.30 mL) was degassed and heated under microwave irradiation at 130° C. for 30 minutes. The reaction mixture was allowed to cool to ambient temperature and ethyl acetate (5 mL) added. The solid was collected by filtration, washed with water (5 mL) and acetonitrile (5 mL) and left to air dry. The resultant solid was purified by flash chromatography (silica, 500 mg column, Si-SPE, 10% MeOH in DCM) and trituration with acetonitrile (2×0.25 mL) to afford the title compound as a grey solid (12 mg, 50%). $^1$H NMR (DMSO-D$_6$, 400 MHz): 12.91 (s, 1H), 8.96 (d, J=2.2 Hz, 1H), 8.81 (d, J=2.2 Hz, 1H), 8.77 (s, 1H), 8.27 (s, 1H), 7.98 (s, 1H), 4.66-4.62 (m, 2H), 3.92 (s, 3H), 3.87-3.83 (m, 2H), 3.36 (s, 3H). LCMS (Method A): R$_T$=7.66 min, M+H$^+$=349.

Example 324

3-(1-Methyl-1H-pyrazol-4-yl)-5-(piperidin-4-ylsulfanyl)-9H-dipyrido[2,3-b;4',3'-d]pyrrole-6-carbonitrile Step 1: 5-Bromo-3-(1-methyl-1H-pyrazol-4-yl)-9H-dipyrido[2,3-b;4',3'-d]pyrrole-6-carbonitrile

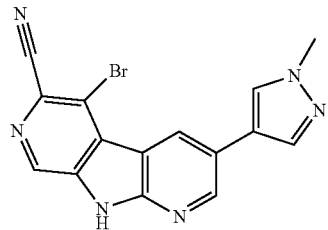 [SMILES: Cn1cc(-c2cnc3[nH]c4cnc(C#N)c(Br)c4c3c2)cn1]

A mixture of 9-benzenesulfonyl-5-bromo-3-(1-methyl-1H-pyrazol-4-yl)-9H-bipyrido[2,3-b;4',3'-d]pyrrole-6-carbonitrile (575 mg, 1.2 mmol) and tetrabutylammonium fluoride (1.0M in THF, 25 mL, 25 mmol) in THF (25 mL) was stirred at ambient temperature for 15 min. The reaction mixture was evaporated in vacuo to afford a residue that was suspended in water and sonicated. The resultant solid was collected by filtration and triturated with methanol to afford the title compound as a white solid (420 mg, 100%). $^1$H NMR (DMSO-D$_6$, 300 MHz): 9.02 (d, J=2.2 Hz, 1H), 8.98 (s, 1H), 8.93 (d, J=2.2 Hz, 1H), 8.33 (s, 1H), 8.02 (s, 1H), 3.92 (s, 3H).

Step 2: 5-Bromo-3-(1-methyl-1H-pyrazol-4-yl)-9-(2-trimethylsilanyl-ethoxymethyl)-9H-dipyrido[2,3-b;4',3'-d]pyrrole-6-carbonitrile

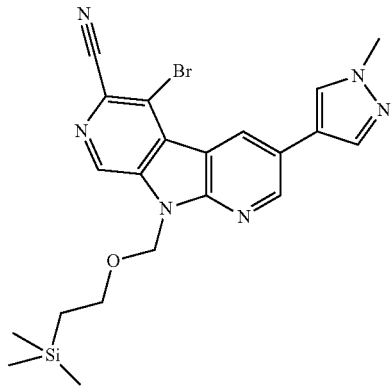 [SMILES: Cn1cc(-c2cnc3c(c2)c2c(Br)c(C#N)ncc2n3COCC[Si](C)(C)C)cn1]

To a solution of 5-bromo-3-(1-methyl-1H-pyrazol-4-yl)-9H-dipyrido[2,3-b;4',3'-d]pyrrole-6-carbonitrile (547 mg, 1.55 mmol) in DMF (25 ml) under a flow of nitrogen was added sodium hydride (93 mg, 60% dispersion in mineral oil, 2.39 mmol). After 20 min, a yellow solution had formed and (2-chloromethoxyethyl)-trimethyl-silane (358 μL, 2.02 mmol) was added. The reaction mixture was stirred at ambient temperature for 3 days, then diluted with water and sonicated. The resultant solid was collected by filtration and triturated with methanol to afford the title compound as a yellow solid (404 mg, 54%). $^1$H NMR (CDCl$_3$, 300 MHz): δ 9.13 (s, 1H), 9.04 (d, J=2.2 Hz, 1H), 8.95 (d, J=2.1 Hz, 1H), 7.93-7.88 (m, 1H), 7.83-7.77 (m, 1H), 6.06 (s, 2H), 4.06 (s, 3H), 3.70-3.59 (m, 2H), 1.03-0.92 (m, 2H), −0.03 (s, 9H).

Step 3: 4-[6-Cyano-3-(1-methyl-1H-pyrazol-4-yl)-9-(2-trimethylsilanylethoxy methyl)-9H-dipyrido[2,3-b;4',3'-d]pyrrol-5-ylsulfanyl]-piperidine-1-carboxylic acid tert-butyl ester

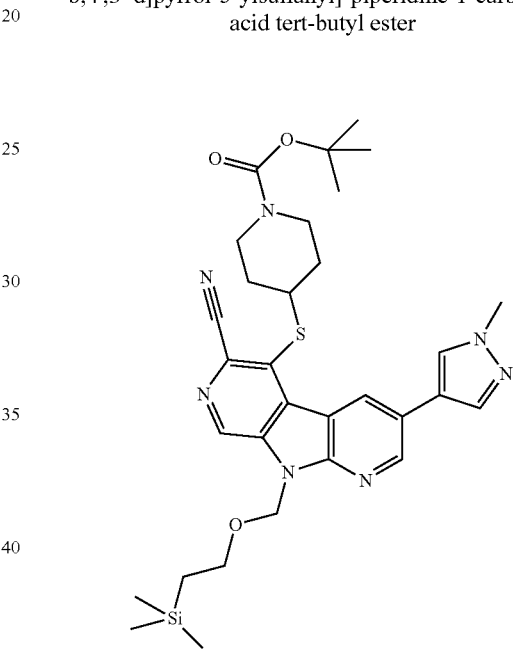

To a degassed suspension of 5-bromo-3-(1-methyl-1H-pyrazol-4-yl)-9-(2-trimethylsilanylethoxymethyl)-9H-dipyrido[2,3-b;4',3'-d]pyrrole-6-carbonitrile (120 mg, 0.25 mmol), 4-mercaptopiperidine-1-carboxylic acid tert-butyl ester (54 mg, 0.25 mmol) and sodium tert-butoxide (26.4 mg, 0.28 mmol) in dimethoxyethane (0.4 mL) in a sealed 5 ml microwave vial was added a degassed solution of palladium (II) acetate (2.2 mg, 0.01 mmol) and (R)-(−)-1-[(S)-2-(dicyclohexylphosphino)ferrocenyl]ethyldi-tert-butylphosphine (5.5 mg, 0.01 mmol) in dimethoxyethane (1.0 mL). The reaction mixture was heated at 100° C. for 22 h then cooled to ambient temperature and concentrated in vacuo. The resultant residue was adsorbed onto HM-N then purified by flash chromatography (silica, 50 g column, Si-SPE, 0-10% (2M ammonia in MeOH) in DCM) to afford the title compound as a yellow solid (106 mg, 68%). $^1$H NMR (DMSO-D$_6$, 300 MHz): 9.33 (s, 1H), 9.11-9.06 (m, 2H), 8.35 (s, 1H), 8.05-8.01 (m, 1H), 6.05 (s, 2H), 3.93 (s, 3H), 3.86-3.73 (m, 2H), 3.64-3.53 (m, 2H), 2.97-2.78 (m, 3H), 1.97-1.83 (m, 2H), 1.64-1.45 (m, 2H), 1.35 (s, 9H), 0.87-0.78 (m, 2H), −0.17 (s, 9H).

379

Step 4: 3-(1-Methyl-1H-pyrazol-4-yl)-5-(piperidin-4-ylsulfanyl)-9H-dipyrido[2,3-b;4'3'-d]pyrrole-6-carbonitrile

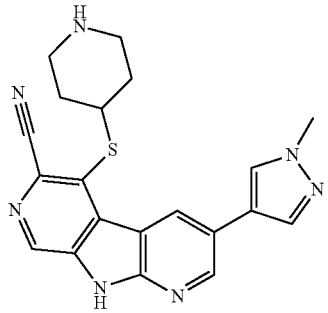 [SMILES: Cn1cc(-c2cnc3[nH]c4cnc(C#N)c(SC5CCNCC5)c4c3c2)cn1]

A mixture of 4-[6-cyano-3-(1-methyl-1H-pyrazol-4-yl)-9-(2-trimethylsilanyl-ethoxymethyl)-9H-dipyrido[2,3-b;4',3'-d]pyrrol-5-ylsulfanyl]-piperidine-1-carboxylic acid tert-butyl ester (106 mg, 0.17 mmol) and trifluoroacetic acid (1 mL) in dichloromethane (9 mL) was stirred at ambient temperature for 22 h. The reaction mixture was concentrated in vacuo and the resultant residue partitioned between dichloromethane (10 mL) and a saturated aqueous solution of sodium hydrogen carbonate (10 mL). The organic phase was concentrated in vacuo and the residue was adsorbed onto HM-N then purified by flash chromatography (silica, 25 g column, Si-SPE, 0-13% (2M ammonia in MeOH) in DCM) to afford the title compound as a pale yellow solid (21.5 mg, 25%). NMR (DMSO-D$_6$, 300 MHz): 9.04 (d, J=2.2 Hz, 1H), 9.02-8.97 (m, 2H), 8.29 (s, 1H), 7.98 (s, 1H), 3.93 (s, 3H), 3.54-3.21 (m, 1H), 2.97-2.86 (m, 2H), 2.49-2.36 (m, 2H), 1.89-1.77 (m, 2H), 1.65-1.47 (m, 2H). LCMS (Method F): R$_T$=7.08 min, M+H$^+$=390.

Example 325

5-(1-Ethyl-piperidin-4-ylmethyl)-9H-dipyrido[2,3-b;4',3'-d]pyrrole-6-carbonitrile

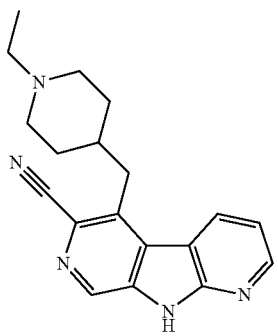 [SMILES: CCN1CCC(Cc2c(C#N)ncc3[nH]c4ncccc4c23)CC1]

380

Step 1: 9-Benzenesulfonyl-5-hydroxy-9H-dipyrido[2,3-b;4'3'-d]pyrrole-6-carbonitrile

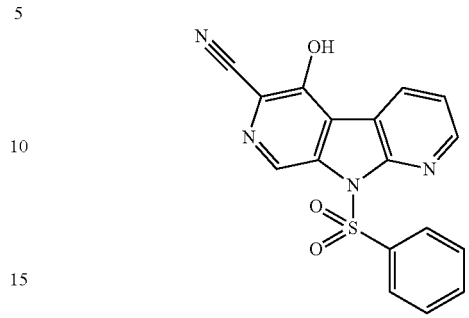

A suspension of 9-benzenesulfonyl-3-bromo-5-hydroxy-9H-dipyrido[2,3-b;4',3'-d]pyrrole-6-carbonitrile (5.0 g, 11.7 mmol) and 10% palladium on carbon (500 mg) in industrial methylated spirits (120 mL), ethyl acetate (25 mL), dimethylformamide (25 mL) and triethylamine (25 mL) was stirred at ambient temperature under an atmosphere of hydrogen for 20 h. The reaction vessel was purged with nitrogen then the reaction mixture was filtered through celite. The filtrate was evaporated in vacuo. The resultant brown residue was suspended in aqueous hydrochloric acid (1M, 40 mL) and sonicated for 20 minutes then filtered to afford the title compound as a beige solid (4.0 g, 98%). $^1$H NMR (DMSO-D$_6$, 300 MHz): 9.27 (d, J=0.8 Hz, 1H), 8.73-8.65 (m, 2H), 8.19 (d, J=7.9 Hz, 2H), 7.78-7.69 (m, 1H), 7.65-7.54 (m, 3H).

Step 2: 1,1,2,2,3,3,4,4,4-Nonafluoro-butane-1-sulfonic acid 9-benzenesulfonyl-6-cyano-9H-dipyrido[2,3-b;4',3'-d]pyrrol-5-yl ester

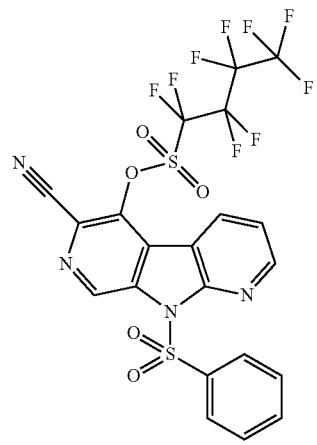 [SMILES: N#Cc1ncc2c(c1OS(=O)(=O)C(F)(F)C(F)(F)C(F)(F)C(F)(F)F)c1cccnc1n2S(=O)(=O)c1ccccc1]

To a suspension of 9-benzenesulfonyl-5-hydroxy-9H-dipyrido[2,3-b;4',3'-d]pyrrole-6-carbonitrile (4.0 g, 11.4 mmol) in dichloromethane (250 ml) was added pyridine (8.9 mL, 114 mmol). The reaction mixture was stirred at ambient temperature for 10 min then cooled to 0° C. and nonafluorobutanesulfonic anhydride (7.01 mL, 22.9 mmol) added over 10 minutes. The mixture was allowed to warm to ambient temperature and stirred for 2.5 h. After this time, the reaction was cooled to 0° C., aqueous hydrochloric acid (1M, 120 mL) was added and the resulting mixture extracted with dichloromethane (3×100 mL). The combined organic phase was dried over sodium sulfate, filtered and concentrated in vacuo. The resultant residue was purified by flash chromatography (silica, 50 g column, Si-SPE, DCM) to afford the title compound as a pale yellow solid (5.34 g, 74%). $^1$H NMR (CDCl$_3$, 300 MHz): 9.93 (s, 1H), 8.84 (dd, J=4.8, 1.65 Hz, 1H), 8.67 (dd, J=8.1, 1.65 Hz, 1H), 8.33-8.28 (m, 2H), 7.71-7.63 (m, 1H), 7.59-7.51 (m, 3H).

Step 3: 9-Benzenesulfonyl-5-bromo-9H-dipyrido[2,3-b;4',3'-d]pyrrole-6-carbonitrile

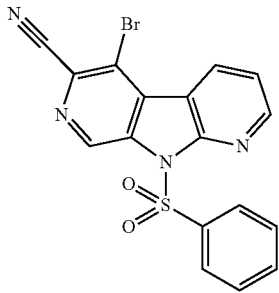 [SMILES: N#Cc1ncc2c(c1Br)c1cccnc1n2S(=O)(=O)c1ccccc1]

A mixture of 1,1,2,2,3,3,4,4,4-nonafluoro-butane-1-sulfonic acid 9-benzenesulfonyl-6-cyano-9H-dipyrido[2,3-b;4',3'-d]pyrrol-5-yl ester (5.43 g, 8.4 mmol) and tetrabutylammonium bromide (10.0 g, 31 mmol) in 1,4-dioxane (175 mL) was heated at 100° C. for 30 min. The reaction mixture was allowed to cool to ambient temperature then evaporated in vacuo to afford the title compound as a white solid (2.38 g, 68%). $^1$H NMR (DMSO-D$_6$, 300 MHz): 9.74 (s, 1H), 9.02 (dd, J=8.1, 1.6 Hz, 1H), 8.84 (dd, J=4.8, 1.6 Hz, 1H), 8.29-8.22 (m, 2H), 7.78-7.68 (m, 2H), 7.67-7.58 (m, 2H).

Step 4: 9-Benzenesulfonyl-5-(1-ethyl-piperidin-4-ylmethyl)-9H-dipyrido[2,3-b;4',3'-d]pyrrole-6-carbonitrile

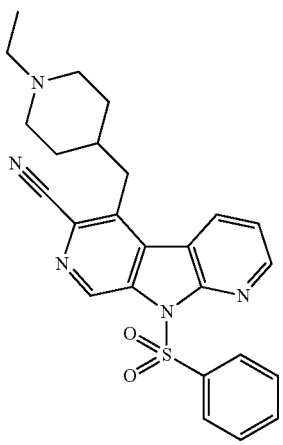 [SMILES: CCN1CCC(Cc2c(C#N)ncc3c2c2cccnc2n3S(=O)(=O)c2ccccc2)CC1]

A mixture of 1-ethyl-4-methylene-piperidine (540 mg, 4.32 mmol) and 9-borabicyclo[3.3.1]nonane (0.5M in THF, 8.0 mL, 4.0 mmol) was heated at 65° C. for 3.5 h. The resultant cooled solution was then added portionwise to a degassed suspension of 9-benzenesulfonyl-5-bromo-9H-dipyrido[2,3-b;4',3'-d]pyrrole-6-carbonitrile (420 mg, 1 mmol), bis(diphenylphosphino)ferrocene dichloropalladium (II) (90 mg, 0.11 mmol) and potassium carbonate (180 mg, 1.3 mmol) in water (1 mL) and dimethylformamide (10 mL). The resultant orange solution was heated at 65° C. for 2 h then allowed to cool to ambient temperature and partitioned between dichloromethane (20 mL) and a saturated aqueous solution of sodium chloride (15 mL). The aqueous phase was extracted with dichloromethane (3×10 mL) and the combined organic phase was washed with a saturated aqueous solution of sodium chloride (20 mL), dried over magnesium sulfate and concentrated in vacuo. The resultant residue was purified by flash chromatography (silica, 10 g column, Si-SPE, 0-20% MeOH in DCM) to afford the title compound (200 mg, 43%). $^1$H NMR (CDCl$_3$, 400 MHz): 9.81 (s, 1H), 8.76 (dd, J=4.8, 1.5 Hz, 1H), 8.66 (d, J=8.0 Hz, 1H), 8.29-8.24 (m, 2H), 7.66-7.60 (m, 1H), 7.58-7.48 (m, 3H), 3.41 (d, J=7.2 Hz, 2H), 2.89 (q, J=7.3 Hz, 2H), 2.56-2.44 (m, 2H), 2.33-2.08 (m, 3H), 1.94-1.74 (m, 4H), 1.35 (t, J=7.3 Hz, 3H). LCMS (Method G): R$_T$=3.01 min, M+H$^+$=460.

Step 5: 5-(1-Ethyl-piperidin-4-ylmethyl)-9H-dipyrido[2,3-b;4',3'-d]pyrrole-6-carbonitrile

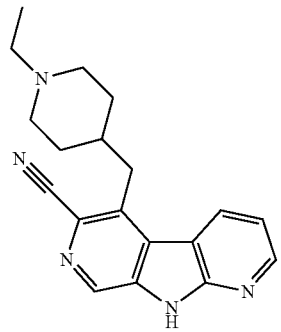 [SMILES: CCN1CCC(Cc2c(C#N)ncc3[nH]c4ncccc4c23)CC1]

A solution of 9-benzenesulfonyl-5-(1-ethyl-piperidin-4-ylmethyl)-9H-dipyrido[2,3-b;4',3'-d]pyrrole-6-carbonitrile (200 mg, 0.4 mmol) and triethylamine (4 mL) in methanol (40 mL) was stirred at ambient temperature for 6 days. The mixture was concentrated in vacuo and the residue purified by flash chromatography (silica, 2 g column, Si-SPE, 0-20% MeOH in DCM). The resultant material was triturated with acetonitrile and methanol to afford the title compound as a white solid (65 mg, 51%). $^1$H NMR (DMSO-D$_6$, 400 MHz): 12.85 (s, 1H), 8.90 (s, 1H), 8.70 (dd, J=4.8, 1.5 Hz, 1H), 8.65 (dd, J=8.0, 1.6 Hz, 1H), 7.46 (dd, J=8.0, 4.8 Hz, 1H), 2.86-2.77 (m, 2H), 2.24 (q, J=7.2 Hz, 2H), 1.84-1.58 (m, 5H), 1.54-1.40 (m, 2H), 0.95 (t, J=7.1 Hz, 3H). LCMS (Method H): R$_T$=4.56 min, M+H$^+$=320.

Example 326

6-Cyano-5-(1-ethylpiperidin-4-yloxy)-9H-dipyrido[2,3-b;4',3'-d]pyrrole-3-carboxylic acid methyl ester

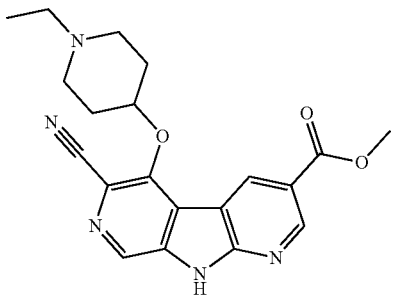 [SMILES: CCN1CCC(Oc2c(C#N)ncc3[nH]c4ncc(C(=O)OC)cc4c23)CC1]

9-Benzenesulfonyl-3-bromo-5-(1-ethylpiperidin-4-yloxy)-9H-dipyrido[2,3-b;4',3'-d]pyrrole-6-carbonitrile (150 mg, 0.278 mmol), molybdenum hexacarbonyl (73 mg, 0.278 mmol), Herman's catalyst (trans-di(μ-acetato)bis[(2-di-o-tolylphosphino)benzyl]dipalladium(II), 26 mg, 0.028 mmol)

and tri-tert-butylphosphonium tetrafluoroborate (20 mg, 0.069 mmol) were placed in a 5 mL microwave vial. Dioxane (3 mL), methanol (1.5 mL) followed by 1,8-diazabicyclo(5.4.0)undec-7-ene (0.12 mL, 0.833 mmol) were added to the mixture, the tube sealed and heated under microwave irradiation at 150° C. for 15 min. The cooled reaction mixture was diluted with water and extracted into ethyl acetate (4×50 mL). The combined organic phase was washed with brine, dried over sodium sulfate and concentrated in vacuo to afford a residue that was purified by flash chromatography (silica, 12 g column, ISCO, 0-10% MeOH in DCM). The resultant material was triturated with MeOH and collected by filtration to afford the title compound as a pale yellow powder (29 mg, 28%). $^1$H NMR (CDCl$_3$, 300 MHz): 9.35 (d, J=2.1 Hz, 1H), 9.23 (s, 1H), 8.83 (s, 1H), 5.21-5.06 (m, 1H), 4.05 (s, 3H), 3.07-2.88 (m, 2H), 2.59-2.44 (m, 2H), 2.41-2.06 (m, 6H), 1.20-1.07 (m, 3H). LCMS (Method H): R$_T$=6.56 min, M+H$^+$=380.

Example 327

5-(1-Ethylpiperidin-4-yloxy)-3-isopropyl-9H-dipyrido[2,3-b;4',3'-d]pyrrole-6-carbonitrile

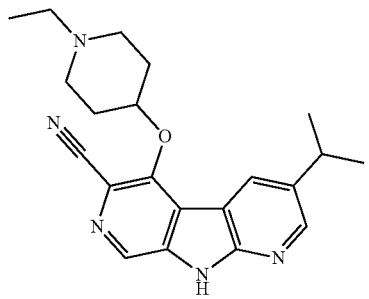 [SMILES: CCN1CCC(Oc2c(C#N)ncc3[nH]c4ncc(C(C)C)cc4c23)CC1]

Step 1: 5-(1-Ethylpiperidin-4-yloxy)-3-isopropenyl-9H-dipyrido[2,3-b;4',3'-d]pyrrole-6-carbonitrile

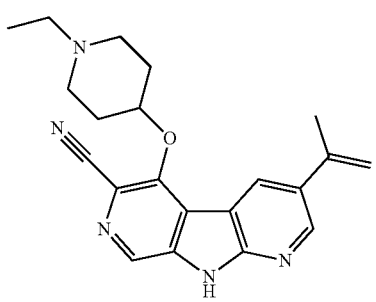 [SMILES: C=C(C)c1cnc2[nH]c3cnc(C#N)c(OC4CCN(CC)CC4)c3c2c1]

9-Benzenesulfonyl-3-bromo-5-(1-ethyl-piperidin-4-yloxy)-9H-dipyrido[2,3-b;4',3'-d]pyrrole-6-carbonitrile (147 mg, 0.272 mmol) and [1,1'-bis(diphenylphosphino)ferrocene]dichloropalladium(II) (11 mg, 0.014 mmol) were dissolved in THF (9 mL) and 1N aqueous sodium carbonate (3 mL) added followed by isopropenylboronic acid pinacol ester (0.076 mL, 0.408 mmol) and placed under an argon atmosphere. The reaction mixture was heated under microwave irradiation at 140° C. for 50 min. The cooled reaction mixture was diluted with saturated aqueous sodium hydrogen carbonate solution (20 mL) and extracted into ethyl acetate (4×20 mL). The combined organic phase was washed with brine (20 mL), dried over sodium sulfate and concentrated in vacuo to afford the title compound as a brown solid (163 mg) which was used without further purification in the next step. $^1$H NMR (CDCl$_3$, 300 MHz): 12.05 (br s, 1H), 8.81 (d, J=2.2 Hz, 1H), 8.77 (s, 1H), 8.64 (d, J=2.2 Hz, 1H), 5.48 (s, 1H), 5.28-5.24 (m, 1H), 5.09-4.97 (m, 1H), 3.02-2.91 (m, 2H), 2.49 (q, J=7.2 Hz, 2H), 2.35-2.20 (m, 7H), 2.19-2.07 (m, 2H), 1.12 (t, J=7.2 Hz, 3H).

Step 2: 5-(1-Ethylpiperidin-4-yloxy)-3-isopropyl-9H-dipyrido[2,3-b;4',3'-d]pyrrole-6-carbonitrile

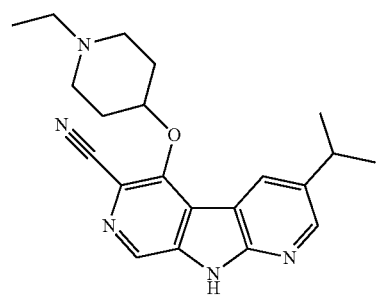 [SMILES: CCN1CCC(Oc2c(C#N)ncc3[nH]c4ncc(C(C)C)cc4c23)CC1]

A suspension of 5-(1-ethylpiperidin-4-yloxy)-3-isopropenyl-9H-dipyrido[2,3-b;4',3'-d]pyrrole-6-carbonitrile (98 mg, 0.271 mmol), 10% palladium on carbon (50 mg) and triethylamine (0.5 mL) in IMS (5 mL) was stirred at ambient temperature under a hydrogen atmosphere for 18 h. The mixture was filtered through a PTFE filter and the filtrate concentrated in vacuo to give a brown solid. The resultant solid was purified by flash chromatography (silica, 12 g column, ISCO, 0-5% MeOH in DCM) to afford the title compound as a white solid (27 mg, 27%). $^1$H NMR (DMSO-D$_6$, 300 MHz): 12.96 (s, 1H), 8.82 (s, 1H), 8.68 (s, 1H), 8.32 (s, 1H), 5.11-4.77 (m, 1H), 3.65-3.48 (m, 2H), 3.28-3.18 (m, 2H), 3.14-2.90 (m, 3H), 2.42-2.18 (m, 4H), 1.37 (d, J=6.9 Hz, 6H), 1.29-1.17 (m, 3H). LCMS (Method H): R$_T$=7.10 min, M+H$^+$=364.

Example 328

5-(1-Ethylpiperidin-4-yloxy)-9H-dipyrido[2,3-b;4',3'-d]pyrrole-3,6-dicarbonitrile

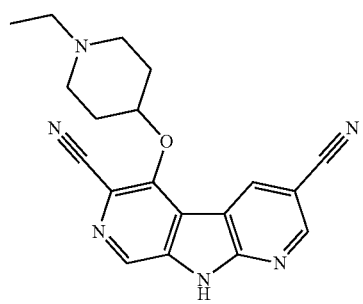 [SMILES: CCN1CCC(Oc2c(C#N)ncc3[nH]c4ncc(C#N)cc4c23)CC1]

DMF (8 mL) was added to a mixture of 9-benzenesulfonyl-3-bromo-5-(1-ethyl-piperidin-4-yloxy)-9H-dipyrido[2,3-b;4',3'-d]pyrrole-6-carbonitrile (200 mg, 0.37 mmol), zinc cyanide (217 mg, 1.85 mmol) and tetrakis(triphenylphosphine)

palladium(0) (43 mg, 0.04 mmol) and the reaction mixture heated under microwave irradiation at 150° C. for 30 min. Triethylamine (2 mL) was then added and the reaction mixture heated at 50° C. for 24 h. The mixture was diluted with saturated aqueous sodium bicarbonate solution (100 mL) and extracted into 10% MeOH in DCM (2×25 mL). The combined organic phase was adsorbed onto HM-N then purified by flash chromatography (silica, 12 g column, ISCO, 0-10% MeOH in DCM) to afford the title compound as a cream solid (6 mg, 5%). $^1$H NMR (DMSO-D$_6$, 400 MHz): 9.07 (d, J=2.0 Hz, 1H), 8.99 (d, J=1.9 Hz, 1H), 8.84 (s, 1H), 4.86-4.76 (m, 1H), 2.97-2.87 (m, 2H), 2.42 (q, J=7.2 Hz, 2H), 2.23-2.13 (m, 2H), 2.12-1.94 (m, 4H), 1.03 (t, J=7.2 Hz, 3H). LCMS (Method H): R$_T$=5.27 min, M+H$^+$=347.

Example 329

5-[1-(2,2,2-Trifluoroethyl)-piperidin-4-ylmethyl]-9H-dipyrido[2,3-b;4',3'-d]pyrrole-6-carbonitrile

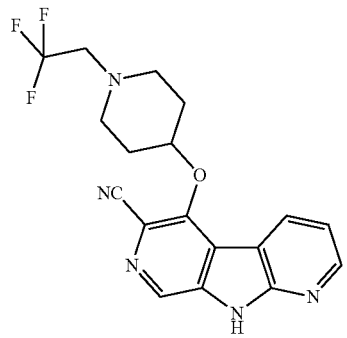

Step 1: 4-(9-Benzenesulfonyl-6-cyano-9H-dipyrido[2,3-b;4',3'-d]pyrrol-5-ylmethyl)-piperidine-1-carboxylic acid tert-butyl ester

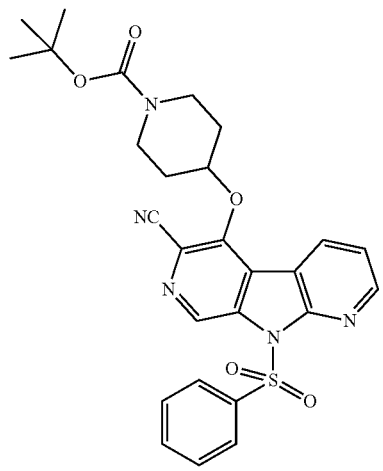 [SMILES: CC(C)(C)OC(=O)N1CCC(Oc2c(C#N)ncc3c2c2cccnc2n3S(=O)(=O)c2ccccc2)CC1]

A mixture of 4-methylene-piperidine-1-carboxylic acid tert-butyl ester (0.70 g, 3.55 mmol) and 9-borabicyclo[3,3,1]nonane (0.5M solution in THF, 7 mL, 3.5 mmol) were heated at reflux for 1.5 h. The reaction mixture was cooled and added to a degassed mixture of 9-benzenesulfonyl-5-bromo-9H-dipyrido[2,3-b;4',3'-d]pyrrole-6-carbonitrile (0.41 g, 1.0 mmol), [1,1-bis(diphenylphosphino) ferrocene]dichloropalladium(II) (0.090 g, 0.11 mmol) and potassium carbonate (0.18 g, 1.3 mmol) in water (1 mL) and DMF (10 mL) and the reaction mixture was then heated at 65° C. for 1.25 h. After cooling to ambient temperature the reaction mixture was then diluted with water (5 mL) and dichloromethane (10 mL). The aqueous phase was extracted with dichloromethane (2×15 mL) and the combined organic phase was washed with brine (15 mL), dried over magnesium sulfate, filtered and concentrated in vacuo. The residue was triturated with pentane (10 mL) and the resultant material was purified by flash chromatography (silica, 5 g column, SPE-Si II, 0-2% methanol in DCM) to afford title compound as a yellow solid (202 mg, 38%). $^1$H NMR (CDCl$_3$, 400 MHz): 9.81 (s, 1H), 8.79 (dd, J=4.8, 1.6 Hz, 1H), 8.33-8.27 (m, 3H), 7.66-7.60 (m, 1H), 7.55-7.46 (m, 3H), 4.22-4.01 (m, 2H), 3.34-3.27 (m, 2H), 2.62-2.50 (m, 2H), 1.97-1.76 (m, 2H), 1.72-1.46 (m, 3H), 1.45 (s, 9H).

Step 2: 9-Benzenesulfonyl-5-piperidin-4-ylmethyl-9H-dipyrido[2,3-b;4',3'-d]pyrrole-6-carbonitrile

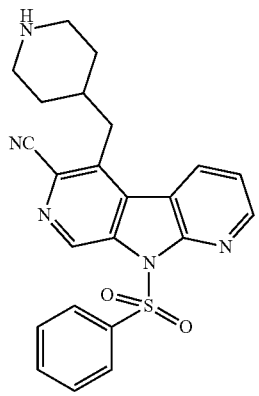 [SMILES: N#Cc1ncc2c(c1CC1CCNCC1)c1cccnc1n2S(=O)(=O)c1ccccc1]

A solution of 4-(9-benzenesulfonyl-6-cyano-9H-dipyrido[2,3-b;4',3'-d]pyrrol-5-ylmethyl)-piperidine-1-carboxylic acid tert-butyl ester (202 mg, 0.38 mmol) in dichloromethane (6 mL) was treated with trifluoroacetic acid (2 mL) and the resultant mixture stirred for 1 h then concentrated in vacuo. The residue was purified by flash chromatography (silica, 5 g column, SPE-NH$_2$, 0-8% methanol in DCM) to give title compound as an off white solid (150 mg, 80%). LCMS (Method G): R$_T$=3.07 min, M+H$^+$=432.

Step 3: 9-Benzenesulfonyl-5-[1-(2,2,2-trifluoroethyl)-piperidin-4-ylmethyl]-9H-dipyrido[2,3-b;4',3'-d]pyrrole-6-carbonitrile

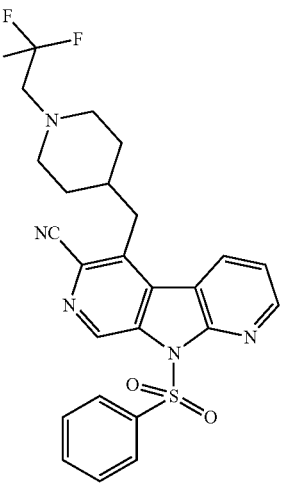

N,N-Diisopropylethylamine (100 mg, 0.77 mmol) and trifluoromethane sulfonic acid 2,2,2-trifluoroethyl ester (100 mg, 0.43 mmol) in THF (1 mL) were added to a solution of 9-benzenesulfonyl-5-piperidin-4-ylmethyl-9H-dipyrido[2,3-b;4',3'-d]pyrrole-6-carbonitrile in THF (4 mL) and resultant mixture stirred at ambient temperature for 30 min. The mixture was then filtered through a 2 g SiII SPE cartridge, eluting with THF. The THF washings were concentrated in vacuo and the resultant residue was purified by flash chromatography (silica, 2 g column, Si H SPE, 0-20% ethyl acetate in DCM) to afford title compound as a white solid (0.16 g, 85%). $^1$H NMR (CDCl$_3$, 400 MHz): 9.81 (d, J=2.9 Hz, 1H), 8.81-8.75 (m, 1H), 8.34 (d, J=8.1 Hz, 1H), 8.28 (d, J=7.9 Hz, 2H), 7.66-7.59 (m, 1H), 7.55-7.45 (m, 3H), 3.35-3.27 (m, 2H), 3.02-2.88 (m, 5H), 2.32-2.21 (m, 2H), 1.86-1.60 (m, 4H).

Step 4: 5-[1-(2,2,2-Trifluoroethyl)-piperidin-4-ylmethyl]-9H-dipyrido[2,3-b;4',3'-d]pyrrole-6-carbonitrile

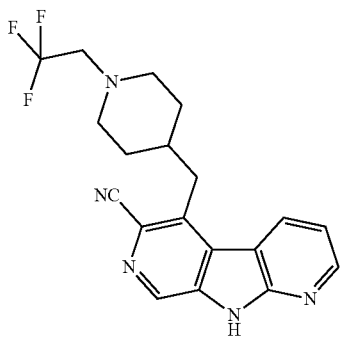 [SMILES: N#Cc1ncc2[nH]c3ncccc3c2c1CC1CCN(CC(F)(F)F)CC1]

9-Benzenesulfonyl-5-[1-(2,2,2-trifluoroethyl)-piperidin-4-ylmethyl]-9H-dipyrido[2,3-b;4',3'-d]pyrrole-6-carbonitrile (0.16 g, 0.3 mmol) was dissolved in tetrabutylammonium fluoride (1M in THF, 5 mL, 5 mmol) and stirred at ambient temperature for 24 h. The solution was filtered through 2 g NH$_2$ cartridge, eluting with 1:1 methanol/dichloromethane. The filtrate was concentrated in vacuo and the residue diluted with water (10 mL) and the resultant precipitate collected by filtration. Purification of the solid by flash chromatography (silica, 5 g column, SPE Si-II, 0-6% methanol in DCM) afforded the title compound as a white solid (90 mg, 80%). $^1$H NMR (DMSO-D$_6$, 400 MHz): 12.88 (s, 1H), 8.91 (s, 1H), 8.72-8.64 (m, 2H), 7.46 (dd, J=8.0, 4.8 Hz, 1H), 3.09 (q, J=10.3 Hz, 2H), 2.92-2.83 (m, 2H), 2.25-2.15 (m, 2H), 1.85-1.72 (m, 1H), 1.66-1.58 (m, 2H), 1.57-1.43 (m, 2H). LCMS (Method H): R$_T$=9.20 min, M+H$^+$=374.

Example 330

5-(Azetidin-3-yloxy)-3-(1-methyl-1H-pyrazol-4-yl)-9H-dipyrido[2,3-b;4',3'-d]pyrrole-6-carbonitrile

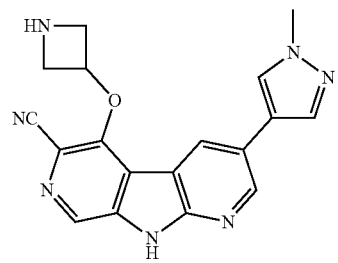 [SMILES: Cn1cc(-c2cnc3[nH]c4cnc(C#N)c(OC5CNC5)c4c3c2)cn1]

Step 1: 9-Benzenesulfonyl-5-(1-benzhydrylazetidin-3-yloxy)-3-(1-methyl-1H-pyrazol-4-yl)-9H-dipyrido[2,3-b;4',3'-d]pyrrole-6-carbonitrile

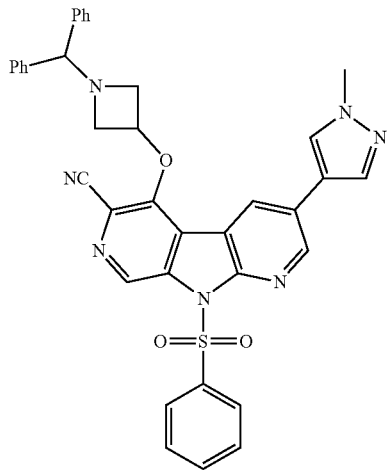 [SMILES: Cn1cc(-c2cnc3c(c2)c2c(OC4CN(C(c5ccccc5)c5ccccc5)C4)c(C#N)ncc2n3S(=O)(=O)c2ccccc2)cn1]

A mixture of 9-benzenesulfonyl-5-hydroxy-3-(1-methyl-1H-pyrazol-4-yl)-9H-dipyrido[2,3-b;4',3'-d]pyrrole-6-carbonitrile (210 mg, 0.50 mmol), cesium carbonate (320 mg, 0.98 mmol) and sodium iodide (37 mg, 0.24 mmol) in DMF (10 mL) were heated at 130° C. for 10 minutes. After cooling to ambient temperature the reaction mixture was then diluted with water (5 mL) and ethyl acetate (3×10 mL). The combined organic phase was washed with brine (15 mL), dried over magnesium sulfate, filtered and concentrated in vacuo. Purification of the residue by flash chromatography (silica, 12 g column, SPE Si-II, 0-10% methanol in DCM) afforded the title compound as a white solid (240 mg, 76%). LCMS (Method G): R$_T$=4.12 min, M+H$^+$=652.

Step 2: 5-(Azetidin-3-yloxy)-3-(1-methyl-1H-pyrazol-4-yl)-9H-dipyrido[2,3-b;4',3'-d]pyrrole-6-carbonitrile

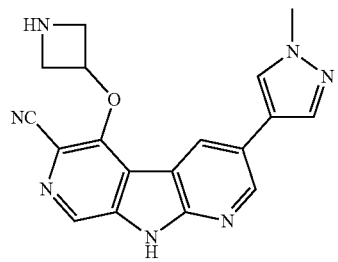 [SMILES: Cn1cc(-c2cnc3[nH]c4cnc(C#N)c(OC5CNC5)c4c3c2)cn1]

To a stirred solution of 9-benzenesulfonyl-5-(1-benzhydrylazetidin-3-yloxy)-3-(1-methyl-1H-pyrazol-4-yl)-9H-dipyrido[2,3-b;4',3'-d]pyrrole-6-carbonitrile (238 mg, 0.37 mmol) in methanol (10 mL) at 0° C. was added a solution of 1-chloroethyl chloroformate (120 μL, 1.1 mmol) in DCM (10 mL). The reaction mixture was allowed to warm to ambient temperature then heated at 40° C. for 4 h. The reaction was cooled to ambient temperature and then concentrated in vacuo. Purification of the residue by flash chromatography (silica, 11 g column, SPE NH$_2$, 0-20% methanol in DCM) afforded the title compound as a white solid (5 mg, 5%). $^1$H NMR (CDCl$_3$ plus CD$_3$OD, 400 MHz): 8.85 (s, 1H), 8.74-

8.69 (m, 2H), 8.08 (s, 1H), 7.93 (s, 1H), 5.73-5.64 (m, 1H), 4.19-4.05 (m, 4H), 4.01 (s, 3H). LCMS (Method G): $R_T$=5.59 min, M+H$^+$=346.

The compounds of the Examples in Table 16 were prepared using the methods described above from commercially available starting materials and the general Suzuki Methods.

TABLE 16

| Example | Structure/Name | Suzuki Coupling Method | Purification Method (s) | LCMS $R_T$, M + H$^+$, Method | $^1$H NMR (ppm) |
|---|---|---|---|---|---|
| 331 | 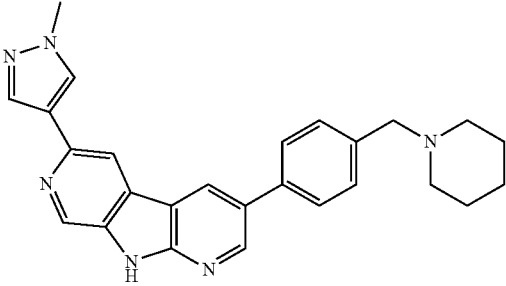<br>6-(1-Methyl-1H-pyrazol-4-yl)-3-(4-piperidin-1-ylmethyl-phenyl)-9H-dipyrido[2,3-b;4′,3′-d]pyrrole | I | B$^1$ | 4.7, 423, A | (CD$_3$OD, 300 MHz): 8.85 (d, J = 1.1 Hz, 1H), 8.81 (d, J = 2.2 Hz, 1H), 8.77 (d, J = 2.2 Hz, 1H), 8.31 (d, J = 1.1 Hz, 1H), 8.07 (s, 1H), 8.05 (s, 1H), 7.69 (d, J = 8.0 Hz, 2H), 7.49 (d, J = 8.0 Hz, 2H), 4.01 (s, 3H), 3.60 (s, 2H), 2.56-2.44 (m, 4H), 1.71-1.58 (m, 4H), 1.55-1.45 (m, 2H). |
| 332 | 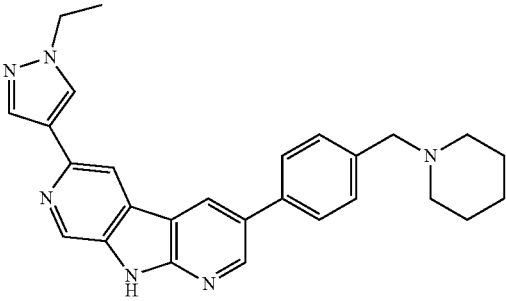<br>6-(1-Ethyl-1H-pyrazol-4-yl)-3-(4-piperidin-1-ylmethyl-phenyl)-9H-dipyrido[2,3-b;4′,3′-d]pyrrole | I | C, B, E, D | 4.9, 437, A | (DMSO-D$_6$, 400 MHz): 12.12 (s, 1H), 8.92 (d, J = 2.3 Hz, 1H), 8.90 (d, J = 2.3 Hz, 1H), 8.85 (d, J = 1.1 Hz, 1H), 8.51 (d, J = 1.1 Hz, 1H), 8.26 (d, J = 0.7 Hz, 1H), 8.00 (d, J = 0.7 Hz, 1H), 7.76 (d, J = 8.0 Hz, 2H), 7.45 (d, J = 7.9 Hz, 2H), 4.21 (q, J = 7.3 Hz, 2H), 3.50 (s, 2H), 2.41-2.34 (m, 4H), 1.58-1.48 (m, 4H), 1.47-1.37 (m, 5H). |
| 333 | 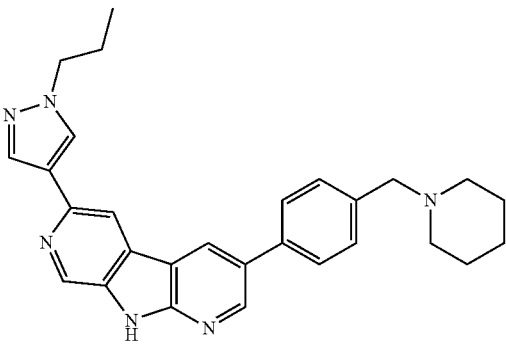<br>3-(4-Piperidin-1-ylmethyl-phenyl)-6-(1-propyl-1H-pyrazol-4-yl)-9H-dipyrido[2,3-b;4′,3′-d]pyrrole | I | C, B, D | 951, 451, A | (DMSO-D$_6$, 400 MHz): 12.13 (s, 1H), 8.93 (d, J = 2.3 Hz, 1H), 8.90 (d, J = 2.3 Hz, 1H), 8.86 (d, J = 1.1 Hz, 1H), 8.52 (d, J = 1.1 Hz, 1H), 8.25 (d, J = 0.7 Hz, 1H), 8.01 (d, J = 0.7 Hz, 1H), 7.76 (d, J = 8.0 Hz, 2H), 7.45 (d, J = 8.0 Hz, 2H), 4.14 (t, J = 6.9 Hz, 2H), 3.49 (s, 2H), 2.40-2.34 (m, 4H), 1.91-1.80 (m, 2H), 1.56-1.48 (m, 4H), 1.43-1.38 (m, 2H), 0.88 (t, J = 7.4 Hz, 3H). |

TABLE 16-continued

| Example | Structure/Name | Suzuki Coupling Method | Purification Method (s) | LCMS $R_T$, M + H$^+$, Method | $^1$H NMR (ppm) |
|---|---|---|---|---|---|
| 334 | 6-(1-Isobutyl-1H-pyrazol-4-yl)-3-(4-piperidin-1-ylmethyl-phenyl)-9H-dipyrido[2,3-b;4',3'-d]pyrrole | J | B | 5.5, 465, A | (CD$_3$OD, 300 MHz): 8.85 (d, J = 1.0 Hz, 1H), 8.81 (d, J = 2.2 Hz, 1H), 8.78 (d, J = 2.2 Hz, 1H), 8.32 (d, J = 1.1 Hz, 1H), 8.08 (s, 1H), 8.07 (s, 1H), 7.72 (d, J = 8.0 Hz, 2H), 7.51 (d, J = 8.0 Hz, 2H), 4.02 (d, J = 7.3 Hz, 2H), 3.74 (s, 2H), 2.70-2.58 (m, 4H), 2.35-2.19 (m, 1H), 1.73-1.64 (m, 4H), 1.59-1.48 (m, 2H), 0.98 (d, J = 6.7 Hz, 6H). |
| 335 | 6-(1-Benzyl-1H-pyrazol-4-yl)-3-(4-piperidin-1-ylmethyl-phenyl)-9H-dipyrido[2,3-b;4',3'-d]pyrrole | J | N, O, P, Q$^3$ | 5.8, 499, A | (CD$_3$OD, 300 MHz): 8.84 (d, J = 1.1 Hz, 1H), 8.81 (d, J = 2.2 Hz, 1H), 8.77 (d, J = 2.2 Hz, 1H), 8.33 (d, J = 1.1 Hz, 1H), 8.13 (d, J = 0.7 Hz, 1H), 8.12 (d, J = 0.8 Hz, 1H), 7.69 (d, J = 8.1 Hz, 2H), 7.48 (d, J = 8.0 Hz, 2H), 7.42-7.29 (m, 5H), 5.42 (s, 2H), 3.60 (s, 2H), 2.55-2.45 (m, 4H), 1.68-1.60 (m, 4H), 1.53-1.47 (m, 2H). |
| 336 | 6-(1,5-Dimethyl-1H-pyrazol-4-yl)-3-(4-piperidin-1-ylmethyl-phenyl)-9H-dipyrido[2,3-b;4',3'-d]pyrrole | J | O | 4.7, 437, A | (CD$_3$OD, 300 MHz): 8.93 (d, J = 1.1 Hz, 1H), 8.81 (d, J = 2.2 Hz, 1H), 8.75 (d, J = 2.2 Hz, 1H), 8.15 (d, J = 1.1 Hz, 1H), 7.82 (s, 1H), 7.68 (d, J = 8.0 Hz, 2H), 7.47 (d, J = 8.0 Hz, 2H), 3.89 (s, 3H), 3.59 (s, 2H), 2.60 (s, 3H), 2.52-2.45 (m, 4H), 1.69-1.59 (m, 4H), 1.54-1.45 (m, 2H). |
| 337 | 3-(4-Piperidin-1-ylmethyl-phenyl)-6-thiazol-5-yl-9H-dipyrido[2,3-b;4',3'-d]pyrrole | | | 6.02, 426, A | (CDCl$_3$ plus CD$_3$OD, 300 MHz): 8.93 (d, J = 1.1 Hz, 1H), 8.92 (d, J = 0.7 Hz, 1H), 8.85 (d, J = 2.2 Hz, 1H), 8.82 (d, J = 2.2 Hz, 1H), 8.56 (d, J = 1.1 Hz, 1H), 8.43 (d, J = 0.7 Hz, 1H), 7.75-7.70 (m, 2H), 7.55-7.49 (m, 2H), 3.71 (s, 2H), 2.67-2.53 (m, 4H), 1.74-1.63 (m, 4H), 1.59-1.47 (m, 2H) plus one exchangeable not observed. |

Example 338

3-(4-Piperidin-1-ylmethyl-phenyl)-9H-dipyrido[2,3-b;4',3'-d]pyrrole

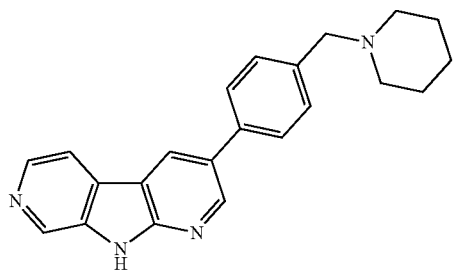 [SMILES: c1cc2c(cn1)[nH]c1ncc(-c3ccc(CN4CCCCC4)cc3)cc12]

Step 1: 5-Bromo-2-fluoro-[3,4']bipyridinyl-3'-ylamine

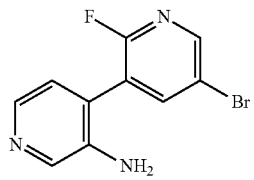 [SMILES: Nc1cnccc1-c1cc(Br)cnc1F]

A mixture of 4-iodo-pyridin-3-ylamine (1.027 g, 4.67 mmol), 2-fluoro-5-bromopyridine-3-boronic acid (2.05 g, 9.33 mmol), and [1,1'-bis(diphenylphosphino)ferrocene]dichloropalladium(II) complex with dichloromethane (1:1) (191 mg, 0.233 mmol) in acetonitrile (12 mL) and 1N aqueous potassium fluoride solution (12 mL) was heated at 95° C. for 3 h. The reaction mixture was allowed to cool, treated with additional portions of the boronic acid (0.5 eq) and of catalyst (5.0 mol %), and heated under reflux overnight under a nitrogen atmosphere. The mixture was allowed to cool, diluted with DCM and water, and filtered to remove the solids. The filtrate layers were separated and the aqueous phase was extracted into DCM, and the combined organic phase concentrated in vacuo. The resultant residue was redissolved in 20% methanol in DCM and absorbed onto silica gel for purification by flash chromatography (silica, 100 g column, Biotage, 1-20% methanol in DCM) to afford the title compound as a brown solid (861 mg, 69%). $^1$H NMR (DMSO-D$_6$, 400 MHz): 8.43 (d, J=1.1 Hz, 1H), 8.18 (dd, J=8.3 Hz, 2.5 Hz, 1H) 8.11 (s, 1H), 7.81 (d, J=4.8 Hz, 1H), 7.01 (d, J=4.8 Hz, 1H), 5.37 (s, 2H). LCMS (Method B): R$_T$=0.95 min, M+H$^+$=268/270.

Step 2: 5-(4-Piperidin-1-ylmethyl-phenyl)-2-fluoro-[3,4]bipyridinyl-3'-ylamine

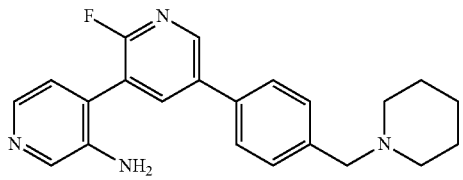 [SMILES: Nc1cnccc1-c1cc(-c2ccc(CN3CCCCC3)cc2)cnc1F]

A degassed mixture of 5-bromo-2-fluoro-[3,4]bipyridinyl-3'-ylamine (861 mg, 3.21 mmol), 4-piperidin-1-ylmethyl-phenyl boronic acid (816 mg, 3.72 mmol) and bis(triphenylphosphine)palladium(II) chloride (169 mg, 0.241 mmol) in acetonitrile (14 mL) and 1N aqueous potassium fluoride solution (8.0 mL) was heated under microwave irradiation at 100° C. for 25 minutes. The cooled reaction mixture was diluted with water and 20% methanol in DCM, the layers separated, and the aqueous phase extracted into 20% methanol in DCM. The combined organic phase was concentrated in vacuo, and the resultant residue dissolved in DCM/methanol, absorbed onto celite, and purified by flash chromatography (silica, 100 g column, Biotage, 0-20% methanol in DCM) to afford the title compound as a dark orange foam (753 mg, 65%). $^1$H NMR (DMSO-D$_6$, 400 MHz): 8.58 (s, 1H), 8.20 (d, J=7.1 Hz, 1H), 8.13 (s, 1H), 7.84 (d, J=4.8 Hz, 1H), 7.74 (m, 2H), 7.43 (m, 2H), 7.07 (d, J=4.9 Hz, 1H), 5.31 (s, 2H), 3.29 (s, 2H), 2.35 (m, 4H), 1.51 (m, 4H), 1.40 (m, 2H). LCMS (Method B): R$_T$=1.27 min, M+H$^+$=363.

Step 3: 3-(4-Piperidin-1-ylmethyl-phenyl)-9H-dipyrido[2,3-b;4',3'-d]pyrrole

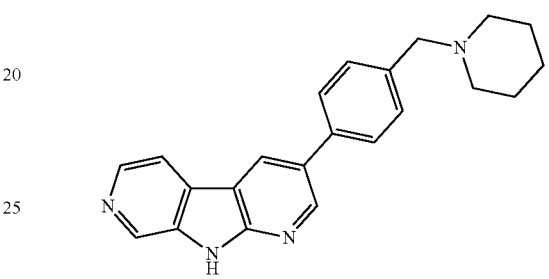

A 1N solution of bis(trimethylsilyl)amide in THF (2.78 mL, 2.80 mmol) was added dropwise to a solution of 5-(4-piperidin-1-ylmethyl-phenyl)-2-fluoro-[3,4]bipyridinyl-3'-ylamine (101 mg, 0.278 mmol) in THF (5.0 mL) at ambient temperature. The mixture was stirred for 1 h at ambient temperature and then treated with water. The resultant brown solution was partitioned between DCM and water, the layers separated, and the aqueous phase extracted into 20% methanol in DCM. The combined organic phase was concentrated in vacuo. The resultant residue was absorbed onto silica gel, and purified by flash chromatography (silica, 1-20% methanol in DCM) to provide a light orange-yellow solid (39.9 mg, 42%). $^1$H NMR. (DMSO-D$_6$, 500 MHz): 12.24 (s, 1H), 8.99 (d, J=1.8 Hz, 1H), 8.93 (s, 1H), 8.92 (d, J=1.8 Hz, 1H), 8.45 (d, J=5.2 Hz, 1H), 8.22 (d, J=5.2 Hz, 1H), 7.77 (d, J=7.5 Hz, 2H), 7.45 (d, J=7.5 Hz, 2H), 3.49 (s, 2H), 2.36 (m, 4H), 1.52 (m 4H), 1.41 (m, 2H). LCMS (Method D): R$_T$=4.64 min, M+H$^+$=343.

Example 339

3-[4-(4-Methylpiperazin-1-yl)-phenyl]-9H-dipyrido[2,3-b;4',3'-d]pyrrole-6-carboxylic acid

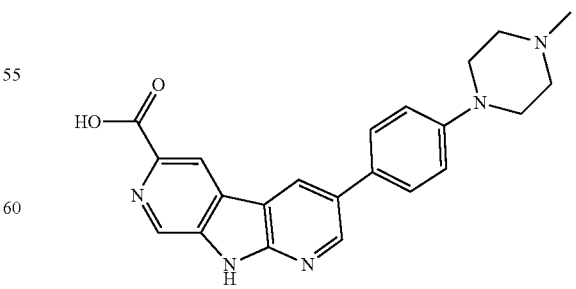

A degassed mixture of 3-bromo-9H-dipyrido[2,3-b;4',3'-d]pyrrole-6-carboxylic acid (37.7 mg, 0.13 mmol), 4-(4-methylpiperazin-1-yl)phenylboronic acid, pinacol ester (58.5 mg, 0.194 mmol) and bis(triphenylphosphine)palladium(II) dichloride (4.5 mg, 6.4 µmol) in acetonitrile (2 mL) and aqueous sodium carbonate solution (2 mL) was heated under microwave irradiation at 140° C. for 10 minutes. The cooled reaction mixture was acidified with 10% aqueous sulfuric acid, filtered, and the crude solution was purified by preparative HPLC (0-30% MeCN over 30 min, 35 mL/min) to afford the title compound. $^1$H NMR (DMSO-D$_6$, 400 MHz): 12.62 (s, 1H), 9.66 (s, 1H), 9.14-8.95 (m, 4H), 7.77 (d, J=8.7 Hz, 2H), 7.18 (d, J=8.9 Hz, 2H), 3.97 (d, J=13.4 Hz, 2H), 3.55 (d, J=11.6 Hz, 2H), 3.20 (q, J=11.1 Hz, 2H), 3.04 (t, J=11.9 Hz, 2H), 2.89 (s, 3H). LCMS (Method D): R$_T$=5.09 min, M+H$^+$=388.

Example 340

3-(1-Methyl-1H-pyrazol-4-yl)-9H-dipyrido[2,3-b;4',3'-d]pyrrole-6-carboxylic acid

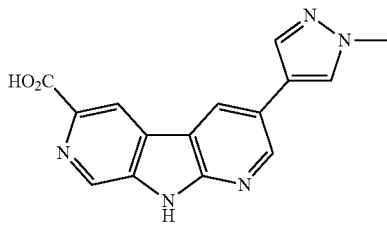 [SMILES: Cn1cc(-c2cnc3[nH]c4cnc(C(=O)O)cc4c3c2)cn1]

A degassed mixture of 3-bromo-9H-dipyrido[2,3-b;4',3'-d]pyrrole-6-carboxylic acid methyl ester (30.4 mg, 99.3 µmol), 1-methyl-4-(4,4,5,5-tetramethyl-1,3,2-dioxaborolan-2-yl)-1H-pyrazole (31.0 mg, 0.149 mmol), and bis(triphenylphosphine)palladium(II) dichloride (3.5 mg, 5.0 µmol) in acetonitrile (2.5 mL) and 2N aqueous sodium carbonate solution (2.5 mL) was heated under microwave irradiation at 140° C. for 10 minutes. The cooled reaction mixture was acidified with 10% aqueous sulfuric acid, the solid removed by filtration and the resultant filtrate purified by preparative HPLC (0-30% MeCN over 30 min, 35 mL/min) to afford the title compound. $^1$H NMR (DMSO-D$_6$, 500 MHz): 12.84 (s, 1H), 9.04 (d, J=2.1 Hz, 1H), 8.95 (s, 2H), 8.91 (d, J=2.1 Hz, 1H), 8.25 (s, 1H), 8.00 (s, 1H), 6.48 (s, 1H), 3.92 (s, 3H). LCMS (Method D): R$_T$=5.24 min, M+H$^+$=294.

Example 341

3-(3-Trifluoromethylphenyl)-9H-dipyrido[2,3-b;4',3'-d]pyrrole-6-carboxylic acid

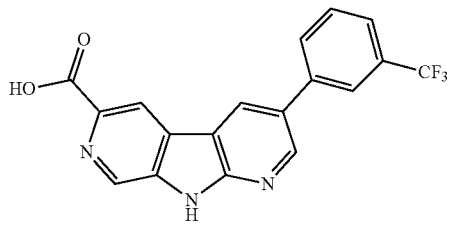 [SMILES: O=C(O)c1cc2c(cn1)[nH]c1ncc(-c3cccc(C(F)(F)F)c3)cc12]

A degassed mixture of 3-bromo-9H-dipyrido[2,3-b;4',3'-d]pyrrole-6-carboxylic acid (20.0 mg, 68.5 µmol), 3-(trifluoromethyl)phenylboronic acid (19.5 mg, 0.103 mmol), and bis(triphenylphosphine)palladium(II) dichloride (2.4 mg, 3.4 µmol) in acetonitrile (0.3 mL) and 2N aqueous sodium carbonate solution (0.3 mL) was heated under microwave irradiation at 140° C. for 10 minutes. The cooled reaction mixture was acidified with 10% aqueous sulfuric acid. The solid was removed by filtration and the resultant filtrate was purified by preparative HPLC (5-45% MeCN over 45 min, 35 mL/min) to afford the title compound. $^1$H NMR (DMSO-D$_6$, 400 MHz): 12.75 (s, 1H), 9.38-9.00 (m, 3 1H), 8.21 (m, 1H), 7.78 (m, 2H), 7.65-7.60 (m, 2H). LCMS (Method D): R$_T$=10.76 min, M+H$^+$=358.

Example 342

3-(3-{N-[(4-Methoxyphenyl)methyl]aminocarbonyl}phenyl)-9H-dipyrido[2,3-b;4',3'-d]pyrrole-6-carboxylic acid

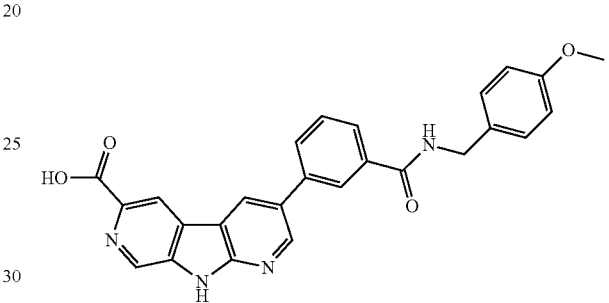

Step 1: 3-{N-[(4-Methoxyphenyl)methyl]aminocarbonyl}phenylboronic acid

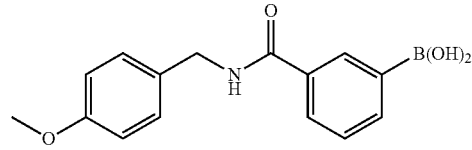 [SMILES: COc1ccc(CNC(=O)c2cccc(B(O)O)c2)cc1]

3-Carboxyphenylboronic acid (140 mg, 0.84 mmol), PyBOP (376 mg, 0.72 mmol) and HOBt (97.7 mg, 0.72 mmol) were dissolved in DMF (3.18 mL) and treated with DIPEA (420 µL, 2.41 mmol). After 5 min at ambient temperature, 4-methoxybenzenemethanamine (78 µL, 0.60 mmol) was added. The homogeneous reaction mixture was stirred at ambient temperature for 16 h, the solvent was removed under reduced pressure, and the residue purified by preparative HPLC (5-40% MeCN over 40 min, 35 mL/min) to afford the product as a white solid.

Step 2: 3-(3-{N-[(4-Methoxyphenyl)methyl]aminocarbonyl}phenyl)-9H-dipyrido[2,3-b;4',3'-d]pyrrole-6-carboxylic acid A degassed mixture of 3-bromo-9H-dipyrido[2,3-b;4',3'-d]pyrrole-6-carboxylic acid methyl ester (40.4 mg, 0.13 mmol), N-[(4-methoxyphenyl)methyl]aminocarbonyl}phenylboronic acid (41.4 mg, 0.15 mmol) and bis(triphenylphosphine)palladium(II) dichloride (4.6 mg, 66 mmol) in acetonitrile (3.3 mL) and 2N aqueous sodium carbonate solution (3.3 mL) was heated under microwave irradiation at 140° C. for 10 minutes. The cooled reaction mixture was acidified with 10% aqueous sulfuric acid. The solid was removed by filtration, and the resultant filtrate was purified by preparative HPLC (5-40% MeCN over 40 min, 35 mL/min) to afford the title compound. $^1$H NMR (DMSO-D$_6$, 400 MHz): 12.74 (s, 1H), 9.28 (m, 1H), 9.13 (m, 1H), 9.07 (m, 1H), 9.00 (m, 1H), 8.35 (m, 1H), 8.02 (d, J=7.8 Hz, 1H), 7.93 (d, J=7.7 Hz, 1H), 7.65 (t, J=7.7 Hz, 1H), 7.30 (q, J=8.6 Hz, 2H), 6.91 (q, J=8.6 Hz, 2H), 4.48 (d, J=5.8 Hz, 2H), 3.73 (s, 3H). LCMS (Method D): R$_T$=9.61 min, M+H$^+$=423.

Example 343

3-(4-Piperidin-1-ylmethyl-phenyl)-9H-dipyrido[2,3-b;4',3'-d]pyrrole-6-carboxamide

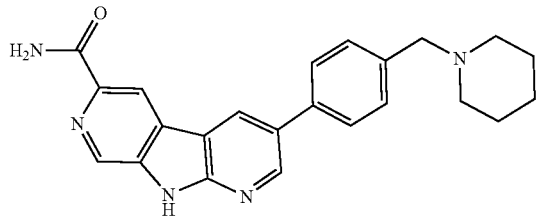 [SMILES: NC(=O)c1cc2c(cn1)[nH]c1ncc(-c3ccc(CN4CCCCC4)cc3)cc12]

A solution of 3-(4-piperidin-1-ylmethyl-phenyl)-9H-dipyrido[2,3-b;4',3'-d]pyrrole-6-carboxylic acid methyl ester (67.3 mg, 0.168 mmol) in 7M ammonia in methanol (8.0 mL) was heated to 70° C. for 24 h in a sealed tube. The mixture was allowed to cool and concentrated in vacuo. The residue was dissolved in DMSO and purified by preparative HPLC (2-60% MeCN/water modified with 0.1% ammonium hydroxide) to afford a light-yellow fluffy solid (10.3 mg, 16%). $^1$H NMR (DMSO-D$_6$, 500 MHz): 12.56 (s, 1H), 9.18 (d, J=2.2 Hz, 1H), 9.00 (s, 1H), 8.96 (d, J=2.1 Hz, 1H), 8.90 (s, 1H), 8.10 (s, 1H), 7.79 (d, J=8.1 Hz, 2H), 7.53 (s, 1H), 7.44 (d, J=8.1 Hz, 2H), 3.49 (s, 2H), 2.36 (m, 4H), 1.56-1.47 (m, 4H), 1.40 (m, 2H). LCMS (Method D): R$_T$=5.88 min, M+H$^+$=386.

Example 344

N-Ethyl-3-(4-piperidin-1-ylmethyl-phenyl)-9H-dipyrido[2,3-b;4',3'-d]pyrrole-6-carboxamide

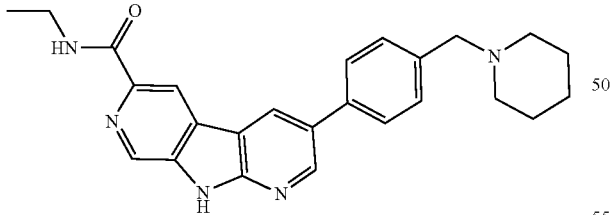

A solution of 3-(4-piperidin-1-ylmethyl-phenyl)-9H-dipyrido[2,3-b;4',3'-d]pyrrole-6-carboxylic acid methyl ester (152 mg, 0.380 mmol) in 2M ethylamine in THF (8.0 mL) was heated to 80° C. for 4 days in a sealed tube. The mixture was allowed to cool and concentrated in vacuo. The residue was redissolved in DMSO and purified by preparative HPLC [2-60% MeCN/water modified with 0.1% ammonium hydroxide] to afford a dark brown solid (74.9 mg, 48%). $^1$H NMR (DMSO-D$_6$, 500 MHz): 9.19 (d, J=2.2 Hz, 1H), 8.99 (s, 1H), 8.97 (d, J=2.2 Hz, 1H), 8.91 (s, 1H), 8.72 (m, 1H), 8.24 (s, 1H), 7.81 (d, J=8.1 Hz, 2H), 7.45 (d, J=8.1 Hz, 2H), 3.47-3.33 (m, 2H), 2.38 (m, 4H), 1.53 (m, 4H), 1.42 (m, 2H), 1.18 (t, J=7.2 Hz, 3H). LCMS (Method E): R$_T$=3.30 min, M+H$^+$=414.

Example 345

N-(2-Aminoethyl)-3-(4-piperidin-1-ylmethyl-phenyl)-9H-dipyrido[2,3-b;4',3'-d]pyrrole-6-carboxamide

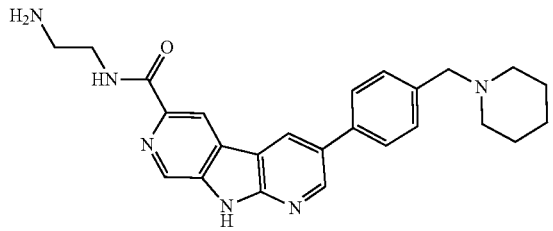 [SMILES: NCCNC(=O)c1cc2c(cn1)[nH]c1ncc(-c3ccc(CN4CCCCC4)cc3)cc12]

A solution of 3-(4-piperidin-1-ylmethyl-phenyl)-9H-dipyrido[2,3-b;4',3'-d]pyrrole-6-carboxylic acid methyl ester (152 mg, 0.380 mmol) in ethylenediamine (8.0 mL) was heated to 80° C. for 16 h in a sealed tube. The mixture was allowed to cool and concentrated in vacuo. The residue was dissolved in DMSO and purified by preparative HPLC (2-60% MeCN/water modified with 0.1% ammonium hydroxide) to afford a light brown solid (45.4 mg, 28%). $^1$H NMR (DMSO-D$_6$, 400 MHz): 9.19 (d, J=2.1 Hz, 1H), 8.99 (s, 1H), 8.96 (d, J=2.2 Hz, 1H), 8.92 (s, 1H), 8.74 (m, 1H), 7.80 (d, J=8.1 Hz, 2H), 7.45 (d, J=8.1 Hz, 2H), 3.50 (s, 2H), 3.41-3.33 (m, 2H), 2.76 (t, J=6.4 Hz, 2H), 2.38 (m, 4H), 1.52 (m, 4H), 1.41 (m, 2H). LCMS (Method D): R$_T$=6.45 min, M+H$^+$=429.

Example 346

3-[4-(4-Methylpiperazin-1-yl)-phenyl]-9H-dipyrido[2,3-b;4',3'-d]pyrrole-6-carboxylic acid amide

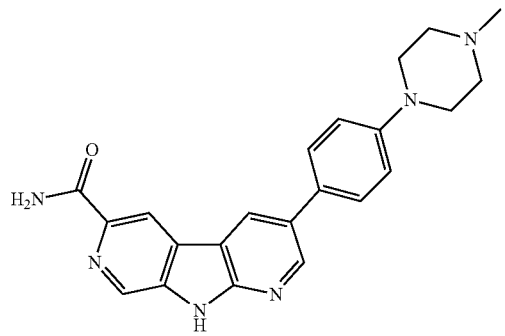 [SMILES: CN1CCN(c2ccc(-c3cnc4[nH]c5cnc(C(N)=O)cc5c4c3)cc2)CC1]

DIPEA (14 µL, 77 µmol) was added to a solution of 3-[4-(4-methylpiperazin-1-yl)-phenyl]-9H-dipyrido[2,3-b;4',3'-d]pyrrole-6-carboxylic acid (20.0 mg, 51.6 µmol), PyBOP (28.2 mg, 54.2 µmol) and HOBt (8.4 mg, 62 µmol) in DMF (1 mL). After 10 min at ambient temperature, a solution of 0.5M ammonia in 1,4-dioxane (500 µL, 0.258 mmol) was added to the reaction mixture. After 30 min the reaction mixture was acidified with 10% aqueous sulfuric acid and made homogeneous with the addition of DMSO. The crude solution was purified by preparative HPLC (0-30% MeCN over 30 min, 35 mL/min) to afford the title compound. $^1$H NMR (DMSO-D$_6$, 400 MHz): 12.48 (s, 1H), 9.11-8.89 (m, 4H), 7.77 (d, J=8.9 Hz, 2H), 7.18 (d, J=8.9 Hz, 2H), 3.97 (d, J=13.5 Hz, 2H), 3.55

(q, J=12.2 Hz, 2H), 3.20 (q, J=11.4 Hz, 2H), 3.03 (t, J=12.0 Hz, 2H), 2.89 (s, 3H). LCMS (Method D): $R_T$=6.35 min, M+H$^+$=387.

Example 347

3-[4-(4-Methylpiperazin-1-yl)-phenyl]-9H-dipyrido[2,3-b;4',3'-d]pyrrole-6-carboxylic acid dimethylamide

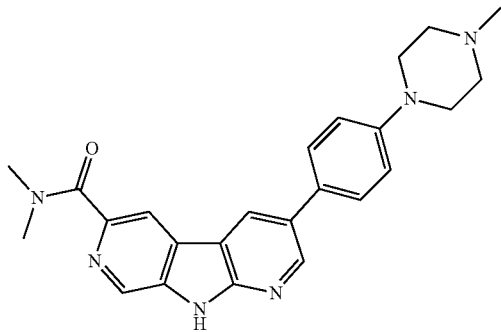

DIPEA (14 µL, 77 µmol) was added to a solution of 3-[4-(4-methylpiperazin-1-yl)-phenyl]-9H-dipyrido[2,3-b;4',3'-d]pyrrole-6-carboxylic acid (20.0 mg, 51.6 µmol), PyBOP (28.2 mg, 54.2 µmol) and HOBt (8.4 mg, 62 µmol) in DMF (0.6 mL). After 10 min at ambient temperature, dimethylamine hydrochloride (20.0 mg, 0.258 mmol) and DIPEA (45 µL, 0.26 mmol) were added to the reaction mixture. After 30 min the reaction mixture was acidified with 10% aqueous sulfuric acid, the solid removed by filtration and the resultant filtrate was purified by preparative HPLC (0-30% MeCN over 30 min, 35 mL/min) to afford the title compound. $^1$H NMR (DMSO-D$_6$, 400 MHz): 12.40 (s, 1H), 9.03 (m, 1H), 8.92 (m, 1H), 8.89 (m, 1H), 8.55 (m, 1H), 7.75 (d, J=8.9 Hz, 2H), 7.18 (d, J=8.9 Hz, 2H), 3.97 (d, J=12.2 Hz, 2H), 3.56 (d, J=12.2 Hz, 2H), 3.21 (m, 2H), 3.08 (m, 6H), 3.02 (m, 2H), 2.98 (s, 3H). LCMS (Method D): $R_T$=6.19 min, M+H$^+$=415.

Example 348

3-[4-(4-Methylpiperazin-1-yl)-phenyl]-9H-dipyrido[2,3-b;4',3'-d]pyrrole-6-carboxylic acid (2-hydroxyethyl)amide

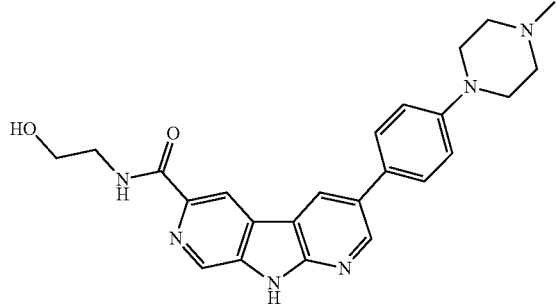 [SMILES: CN1CCN(c2ccc(-c3cnc4[nH]c5cnc(C(=O)NCCO)cc5c4c3)cc2)CC1]

DIPEA (13.5 µL, 77.4 µmol) was added to a solution of 3-[4-(4-methylpiperazin-1-yl)-phenyl]-9H-dipyrido[2,3-b;4',3'-d]pyrrole-6-carboxylic acid (20.0 mg, 51.6 PyBOP (28.2 mg, 54.2 µmol) and HOBt (8.4 mg, 62 µmol) in DMF (0.6 mL). After 10 min at ambient temperature, ethanolamine (16 µL, 0.26 mmol) was added to the reaction mixture. After 30 min the resultant mixture was acidified with 10% aqueous sulfuric acid and concentrated in vacuo. The resultant residue was dissolved in DMF, water and 10% aqueous sulfuric acid and purified by preparative HPLC (0-30% MeCN over 30 min, 35 mL/min) to afford the title compound. $^1$H NMR (DMSO-D$_6$, 400 MHz): 12.49 (s, 1H), 9.71 (br.s, 1H), 9.14 (d, J=2.1 Hz, 1H), 8.90 (s, 1H), 8.94 (d, J=2.2 Hz, 1H), 8.66 (t, J=5.8 Hz, 1H), 7.77 (d, J=8.7 Hz, 2H), 7.17 (d, J=8.8 Hz, 2H), 3.97 (d, J=13.4 Hz, 2H), 3.57 (m, 4H), 3.45 (m, 2H), 3.20 (m, 2H), 3.04 (m, 2H), 2.89 (s. 3H), LCMS (Method D): $R_T$=6.31 min, M+H$^+$=431.

Example 349

6-(Pyrrolidinylcarbonyl)-3-[4-(4-methylpiperizin-1-yl)-phenyl]-9H-dipyrido[2,3-b;4',3'-d]pyrrole

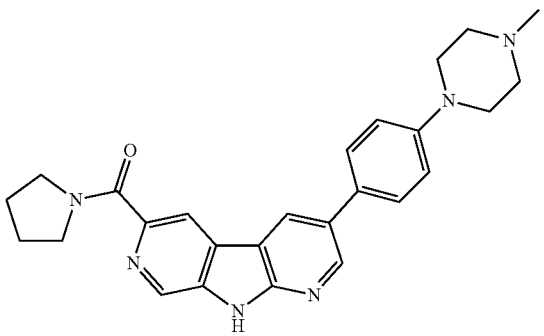 [SMILES: CN1CCN(c2ccc(-c3cnc4[nH]c5cnc(C(=O)N6CCCC6)cc5c4c3)cc2)CC1]

Step 1: 6-(Pyrrolidinylcarbonyl)-3-bromo-9H-dipyrido[2,3-b;4',3'-d]pyrrole

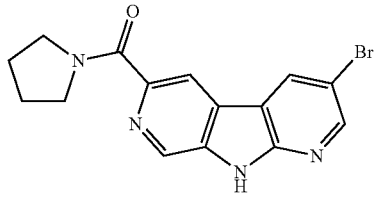 [SMILES: O=C(c1cc2c(cn1)[nH]c1ncc(Br)cc12)N1CCCC1]

3-Bromo-9H-dipyrido[2,3-b;4',3'-d]pyrrole-6-carboxylic acid methyl ester (140 mg, 0.458 mmol) was dissolved in pyrrolidine (6 mL) and the mixture heated to reflux for 2 h. The mixture was allowed to cool and concentrated in vacuo to afford a bright orange oily solid. The residue was used without purification.

Step 2: 6-(Pyrrolidinylcarbonyl)-3-[4-(4-methylpiperizin-1-yl)-phenyl]-9H-dipyrido[2,3-b;4',3'-d]pyrrole

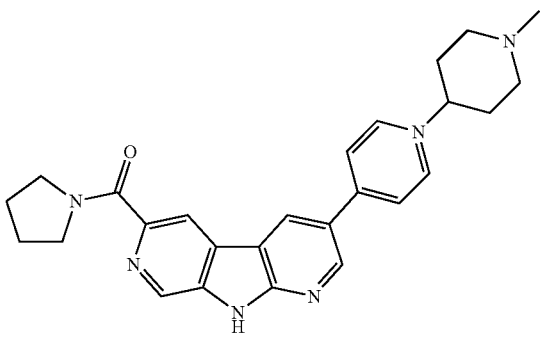

A degassed mixture of 6-(pyrrolidinylcarbonyl)-3-bromo-9H-dipyrido[2,3-b;4',3'-d]pyrrole (158 mg, 0.457 mmol), 4-(4-methylpiperizin-1-yl)-phenyl-1-boronic acid, pinacol ester (597 mg, 1.98 mmol), and bis(triphenylphosphine)palladium(II) chloride (69.0 mg, 99.0 µmol, 5.0 mol %) in acetonitrile (2.5 mL) and 1.0M aqueous sodium carbonate (2.5 mL) was heated under microwave irradiation at 120° C. for 10 minutes, allowed to cool, and partitioned between ethyl acetate and water. The organic layer was dried over sodium sulfate filtered and concentrated in vacuo. The resultant residue was purified by preparative HPLC (0-30% MeCN/water modified with 0.1% formic acid) to afford an off-white solid (10.0 mg, 5%). $^1$H NMR (DMSO-D$_6$, 400 MHz) 12.39-12.29 (s, 1H), 9.01 (d, J=2.2 Hz, 1H), 8.88 (d, J=2.2 Hz, 31), 8.86 (s, 1H), 8.70 (s, 1H), 7.69 (d, J=8.7 Hz, 2H), 7.08 (d, J=8.8 Hz, 2H), 3.78 (t, J=6.2 Hz, 2H), 3.57 (t, J=6.2 Hz, 2H), 3.25-3.18 (m, 4H), 2.47 (m, 311), 2.24 (m, 4H), 1.87 (m, 4H). LCMS (Method D): R$_T$=7.36 min, M+H$^+$=441.

Example 350

3-(4-Piperidin-1-ylmethyl-phenyl)-9H-dipyrido[2,3-b;4',3'-d]pyrrole-6-methanol

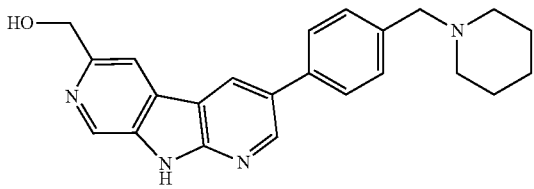 [SMILES: OCc1cc2c(cn1)[nH]c1ncc(-c3ccc(CN4CCCCC4)cc3)cc12]

A 1M solution of lithium aluminum hydride in THF (1.2 mL, 1.2 mmol) was slowly added to a suspension of 3-(4-piperidin-1-ylmethyl-phenyl)-9H-dipyrido[2,3-b;4',3'-d] pyrrole-6-carboxylic acid methyl ester (48.0 mg, 0.120 mmol) in THF at 0° C. The mixture was slowly warmed to ambient temperature. A further portion of 1M solution of lithium aluminum hydride in THF (1.2 mL, 1.2 mmol) was added slowly to the bright orange-yellow, homogeneous mixture at ambient temperature. After 1 h, the mixture was treated with aqueous ammonium chloride, and diluted with water and 50% DCM/methanol. The resulting mixture was treated with Rochelle's salt and allowed to stir vigorously for 2 h. The solids were removed by filtration, and the filtrate layers were separated. The aqueous phase was extracted with 20% methanol in DCM and the combined organic phase concentrated in vacuo. The residue was dissolved in DMSO and purified by preparative HPLC (2-60% MeCN/water modified with 0.1% ammonium hydroxide) to provide a light-yellow solid (7.1 mg, 16%). $^1$H NMR (DMSO-D$_6$, 400 MHz): 12.10 (s, 1H), 9.02 (m, 1H), 8.90 (m, 1H), 8.82 (m, 1H), 8.28 (m, 1H), 7.79 (m, 2H), 7.46 (m, 2H), 5.40 (t, J=5.7 Hz, 1H), 4.74 (d, J=5.6 Hz, 2H), 3.59-3.41 (m, 2H), 2.38 (m, 4H), 1.54 (m, 4H), 1.42 (m, 2H). LCMS (Method D): R$_T$=4.48 min, M+H$^+$=373.

Example 351

{3-[4-(4-Methylpiperazin-1-yl)-phenyl]-9H-dipyrido[2,3-b;4',3'-d]pyrrol-6-yl}-methanol

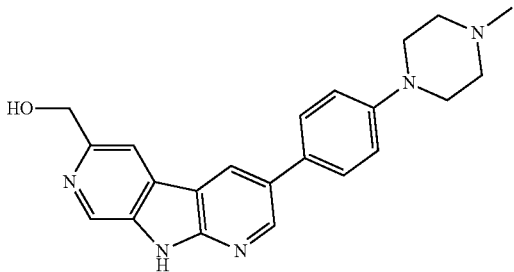 [SMILES: CN1CCN(c2ccc(-c3cnc4[nH]c5cnc(CO)cc5c4c3)cc2)CC1]

Step 1: 3-Bromo-9H-dipyrido[2,3-b;4',3'-d]pyrrole-6-methanol

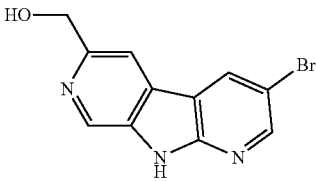 [SMILES: OCc1cc2c(cn1)[nH]c1ncc(Br)cc12]

Lithium aluminium hydride (1M solution in THF, 16.3 mL, 16.3 mmol) was added dropwise to a suspension of 3-bromo-9H-dipyrido[2,3-b;4',3'-d]pyrrole-6-carboxylic acid methyl ester (500 mg, 1.63 mmol) in THF (10 mL). After 10 minutes the reaction mixture was quenched with a solution of saturated ammonium chloride, diluted with DCM and water and the solid removed by filtration. The layers of the resultant filtrate were separated and the aqueous phase was further extracted with DCM. The combined organic layer was concentrated in vacuo and purified by flash chromatography (silica, 1-15% methanol in DCM).

Step 2: {3-[4-(4-Methylpiperazin-1-yl)-phenyl]-9H-dipyrido[2,3-b;4',3'-d]pyrrol-6-yl}-methanol

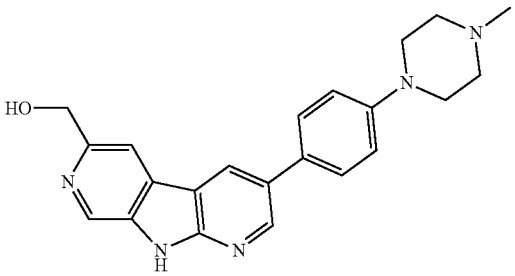 [SMILES: CN1CCN(c2ccc(-c3cnc4[nH]c5cnc(CO)cc5c4c3)cc2)CC1]

A suspension of 3-bromo-9H-dipyrido[2,3-b;4',3'-d]pyrrole-6-methanol (40.7 mg, 0.146 mmol), 4-(4-methylpiperazin-1-yl)phenylboronic acid pinacol ester (46.4 mg, 0.154 mmol) and bis(triphenylphosphine)palladium(II) dichloride (5.1 mg, 7.3 µmol) in acetonitrile (0.73 mL) and 2N aqueous sodium carbonate solution (0.73 mL) was heated at 150° C. under microwave irradiation for 20 minutes. The cooled reaction mixture was diluted with THF, the solid removed by filtration, and washed with THF and DCM. The combined filtrate was concentrated in vacuo and the resultant residue purified by flash chromatography (silica, 1-15% (2N ammonia methanol) in DCM) to afford the title compound. $^1$H NMR (DMSO-D$_6$, 400 MHz): 12.46 (s, 1H), 9.76 (s, 1H), 9.07 (d, J=1.8 Hz, 1H), 8.97 (d, J=1.8 Hz, 1H), 8.50 (s, 1H), 7.76 (d, J=8.7 Hz, 2H), 7.17 (d, J=8.7 Hz, 2H), 4.13 (s, 2H), 3.38-3.30 (m, 8H), 2.89 (s, 3H). LCMS (Method D): R$_T$=5.24 min, M+H$^+$=374.

Example 352

2-{3-[4-(4-Methylpiperazin-1-yl)-phenyl]-9H-dipyrido[2,3-b;4',3'-d]pyrrol-6-yl}-propan-2-ol

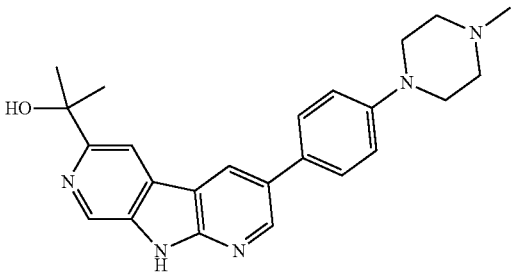 [SMILES: CN1CCN(c2ccc(-c3cnc4[nH]c5cnc(C(C)(C)O)cc5c4c3)cc2)CC1]

Step 1: 3-[4-(4-Methyl-piperazin-1-yl)-phenyl]-9H-dipyrido[2,3-b;4',3'-d]pyrrole-6-carboxylic acid methyl ester

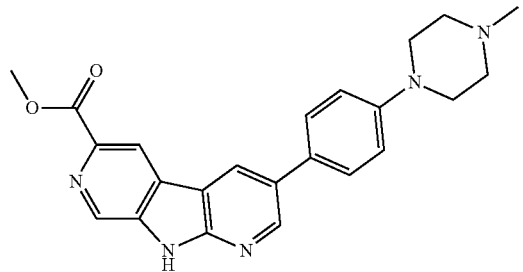

3-Bromo-9H-dipyrido[2,3-b;4',3'-d]pyrrole-6-carboxylic acid methyl ester (100 mg, 0.327 mmol), 4-(4-methylpiperazin-1-yl)phenylboronic acid, pinacol ester (104 mg, 0.343 mmol) and bis(triphenylphosphine)palladium(II) dichloride (11.5 mg, 0.016 mmol) were suspended in acetonitrile (1.8 mL) and 1N aqueous potassium acetate solution (1.8 mL) and heated under microwave irradiation at 140° C. for 30 minutes. The cooled reaction mixture was diluted with saturated sodium bicarbonate solution and DCM, and the solid removed by filtration. The layers of the resultant filtrate were separated and the aqueous phase was further extracted with DCM. The combined organic phase was dried over sodium sulfate, filtered and concentrated in vacuo. The resultant residue was purified by flash chromatography (silica, 0-20% (MeOH containing 1% triethylamine) in DCM).

Step 2: 2-{3-[4-(4-Methyl-piperazin-1-yl)-phenyl]-9H-dipyrido[2,3-b;4',3'-d]pyrrol-6-yl}-propan-2-ol

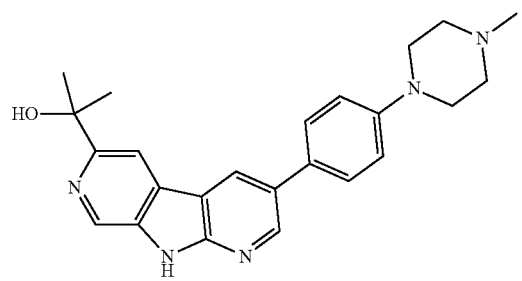 [SMILES: CN1CCN(c2ccc(-c3cnc4[nH]c5cnc(C(C)(C)O)cc5c4c3)cc2)CC1]

A solution of 3N methylmagnesium chloride in THF (545 µL, 1.6 mmol) was added to a suspension of 3-[4-(4-methylpiperazin-1-yl)-phenyl]-9H-dipyrido[2,3-b;4',3'-d]pyrrole-6-carboxylic acid methyl ester (54.7 mg, 0.136 mmol) in THF (4 mL) at ambient temperature. After 5 minutes the reaction mixture was quenched with saturated ammonium chloride solution and diluted with DCM and water. The layers were separated and the aqueous phase was further extracted with DCM. The combined organic phase was dried over sodium sulfate, filtered, and concentrated in vacuo. The resultant residue was dissolved in water, DMF, and 10% aqueous sulfuric acid and purified by preparative HPLC (0-30% MeCN over 40 min, 35 mL/min) to afford the title compound. $^1$H NMR (DMSO-D$_6$, 400 MHz): 12.85 (s, 1H), 9.78 (s, 1H), 9.15-8.84 (m, 4H), 7.78 (d, J=8.7 Hz, 2H), 7.19 (d, J=8.7 Hz, 2H), 3.98 (d, J=13.6 Hz, 2H), 3.60 (m, 2H), 3.20 (q, J=10.0 Hz, 2H), 3.03 (t, J=12.4 Hz, 2H), 2.89 (s, 3H), 1.65 (s, 6H). LCMS (Method D): R$_T$=2.91 min, M+H$^+$=402.

Example 353

6-Bromo-3-(4-piperidin-1-ylmethyl-phenyl)-9H-dipyrido[2,3-b;4',3'-d]pyrrole

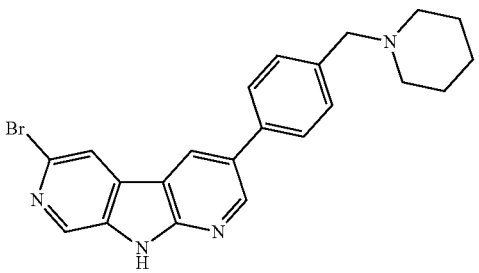

Method 1: Step 1: 6'-Bromo-2-fluoro-5-(4-piperidin-1-ylmethyl-phenyl)-[3,4']bipyridinyl-3'-ylamine

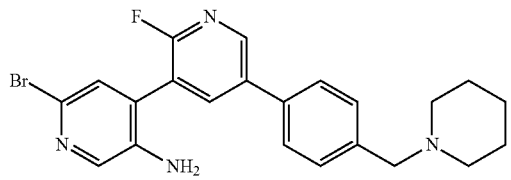 [SMILES: Nc1cnc(Cl)cc1-c1cc(-c2ccc(CN3CCCCC3)cc2)cnc1F]

A mixture of 6-bromo-4-iodopyridin-3-amine (3.3 g, 8.0 mmol), 2-fluoro-3-boronic acid-5-(4-piperidin-1-ylmethylphenyl)pyridine (3.2 g, 10.0 mmol), and 1,1'-[bis(diphenylphosphino)ferrocene]dichloropalladium(II) (360 mg, 0.44 mmol) in 1N aqueous potassium fluoride (21 mL) and acetonitrile (45 mL) was heated at 90° C. for 4 h. The cooled reaction was diluted with water (100 mL) and extracted with DCM (3×50 mL). The combined organic layer was dried over sodium sulfate, filtered, and evaporated to afford a residue which was purified by flash chromatography (silica, 25 g column, Biotage, 0-10% methanol in (DCM containing 1% 2M ammonia in methanol)) to afford the title compound as a yellow/orange solid (3.2 g, 91%). $^1$H NMR (DMSO-D$_6$, 500 MHz,): 8.62 (s, 1H), 8.25 (d, J=7.3 Hz, 1H), 7.90 (s, 1H), 7.74 (d, J=6.5 Hz, 2H), 7.42 (d, J=6.5 Hz), 7.35 (s, 1H), 5.57 (s, 2H), 3.47 (s, 2H), 2.34 (s, 4H), 1.51 (s, 4H), 1.40 (s, 2H).

Step 2: 6-Bromo-3-(4-piperidin-1-ylmethyl-phenyl)-9H-dipyrido[2,3-b;4',3'-d]pyrrole To a solution of 6'-bromo-2-fluoro-[3,4']bipyridinyl-3'-ylamine (1.5 g, 3.4 mmol) in anhydrous tetrahydrofuran (41 mL) was added sodium bis(trimethylsilyl)amide (1N solution in THF, 10.5 mL, 10 mmol) under a flow of nitrogen. The reaction mixture was left to stir at room temperature for 1 h then quenched by the addition of acetic acid (1 mL). The reaction mixture was evaporated in vacuo to afford a residue that was purified by flash chromatography (silica, 25 g column, Biotage, 0-10% methanol in (DCM containing 1% 2M ammonia in methanol) to afford the title compound as an off-white solid (620 mg, 43%). $^1$H NMR (DMSO-D$_6$, 400 MHz) 12.37 (s, 1H), 9.03 (d, J=2.5 Hz, 1H), 8.95 (d, J=2.5 Hz, 1H), 8.71 (s, 1H), 8.52 (s, 1H), 7.75 (d, J=8.0 Hz, 2H), 7.45 (d, J=8.0 Hz, 2H), 3.51 (s, 2H), 2.38 (s, 4H), 1.52 (m, 4H), 1.41 (m, 2H). LCMS (Method D): $R_T$=8.63 min, M+H$^+$=422/424.

Method 2: Step 1: 6'-Chloro-2-fluoro-5-(4-piperidin-1-ylmethyl-phenyl)-[3,4']bipyridinyl-3'-ylamine

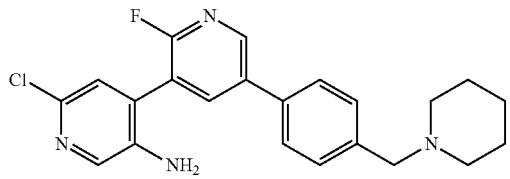

A degassed mixture of 5-bromo-6'-chloro-2-fluoro-[3,4'] bipyridinyl-3'-ylamine (1.35 g, 4.46 mmol), 4-(piperidin-1-ylmethyl)phenylboronic acid hydrobromide (2.28 g, 7.59 mmol) and bis(triphenylphosphine)palladium(II) chloride (0.29 g, 0.35 mmol) in acetonitrile (70 mL) and 1N aqueous potassium fluoride solution (12 mL) was heated under microwave irradiation at 100° C. for 30 minutes. The cooled reaction was diluted with water (100 mL) and extracted with DCM (3×50 mL). The combined organic layer was dried over sodium sulfate, filtered, and evaporated to afford a residue which was purified by flash chromatography (silica, 25 g column, Biotage, 0-10% methanol in (DCM containing 1% 2M ammonia in methanol)) to afford the title compound as a yellow/orange solid (0.95 g, 54%).

Step 2: 6-Bromo-3-(4-piperidin-1-ylmethyl-phenyl)-9H-dipyrido[2,3-b;4',3'-d]pyrrole

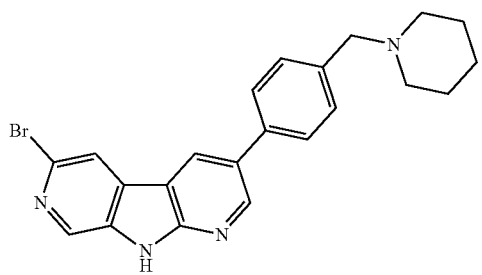

To a solution of 6'-chloro-2-fluoro-5-(4-piperidin-1-ylmethyl-phenyl)-[3,4]bipyridinyl-3'-ylamine (1.6 g, 0.004 mol) in 1,4-dioxane (30 mL) was added bromotrimethylsilane (27 mL, 0.2 mol) which immediately produced a white precipitate. The reaction was heated at 100° C. for 48 h. The solid from the cooled reaction mixture was collected by filtration and washed with ethyl acetate (2×20 mL). The resultant solid was then purified by flash chromatography (silica, 25 g column, Biotage, 040% methanol in (DCM containing 1% 2M ammonia in methanol)) to afford the title compound as an off-white solid (1.1 g, 45%). $^1$H NMR (DMSO-D$_6$, 500 MHz,): 8.62 (s, 1H), 8.25 (d, J=7.3 Hz, 1H), 7.90 (s, 1H), 7.74 (d, J=6.5 Hz, 2H), 7.42 (d, J=6.5 Hz, 2H), 7.35 (s, 1H), 5.57 (s, 2H), 3.47 (s, 2H), 2.34 (s, 4H), 1.51 (s, 4H), 1.40 (s, 2H).

Example 354

6-Chloro-3-(4-piperidin-1-ylmethyl-phenyl)-9H-dipyrido[2,3-b;4',3'-d]pyrrole

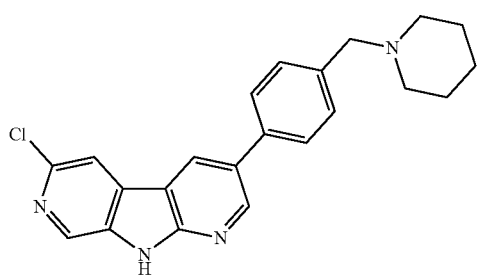 [SMILES: Clc1cc2c(cn1)[nH]c1ncc(-c3ccc(CN4CCCCC4)cc3)cc12]

A degassed mixture of 3-bromo-6-chloro-9H-dipyrido[2,3-b;4',3'-d]pyrrole (1.00 g, 3.55 mmol), 1-[4-(4,4,5,5-tetramethyl-[1,3,2]dioxaborolan-2-yl)-benzyl]-piperidine hydrochloride (1.24 g, 3.67 mmol) and 1,1'-[bis(diphenylphosphino) ferrocene]dichloro palladium(II) (0.29 g, 0.35 mmol) in acetonitrile (20 mL) and 2N aqueous potassium fluoride solution (10 mL) was heated under microwave irradiation at 140° C. for 30 minutes. The cooled reaction mixture was concentrated under reduced pressure and taken up in DCM/methanol and loaded onto an SCX-2 cartridge (20 g) which was then washed with methanol (50 mL) then 2N ammonia in methanol (50 mL). The combined basic fractions were concentrated in vacuo and the residue purified by flash chromatography (silica, 80 g column, ISCO, 0-10% methanol in DCM) to afford the title compound as a pink solid (0.87 g, 66%). $^1$H NMR (DMSO-D$_6$, 400 MHz): 12.38 (s, 1H), 9.03 (d, J=2.3 Hz, 1H), 8.95 (d, J=2.3 Hz, 1H), 8.71 (d, J=1.0 Hz, 1H), 8.38 (d, J=0.9 Hz, 1H), 7.75 (d, J=7.9 Hz, 2H), 7.44 (d, J=7.9 Hz, 2H), 3.49 (s, 2H), 2.39-2.33 (m, 4H), 1.56-1.48 (m, 4H), 1.45-1.37 (m, 2H). LCMS (Method B): $R_T$=2.27 min, M+H$^+$=377.

Example 355

6-Chloro-3-[4-(4-methylpiperazin-1-yl)-phenyl]-9H-dipyrido[2,3-b;4',3'-d]pyrrole

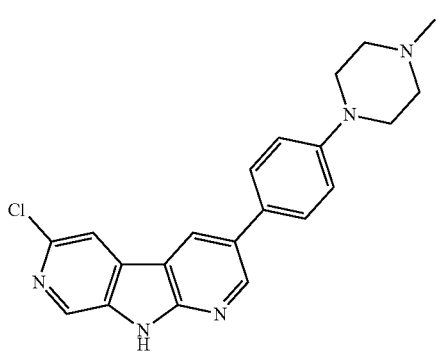 [SMILES: CN1CCN(c2ccc(-c3cnc4[nH]c5cnc(Cl)cc5c4c3)cc2)CC1]

A degassed mixture of 3-bromo-6-chloro-9H-dipyrido[2,3-b;4',3'-d]pyrrole (43.0 mg, 0.152 mmol), 4-(4-methylpiperizin-1-yl)-phenyl-1-boronic acid, pinacol ester (48.2 mg, 0.159 mmol) and bis(triphenylphosphine)palladium(II) chloride (5.3 mg, 7.6 μmol, 5.0 mol %) in acetonitrile (0.63 mL)

and 1M aqueous potassium acetate (0.63 mL) was heated under microwave irradiation at 140° C. for 30 minutes, allowed to cool and concentrated in vacuo. The residue was dissolved in water, DMF, and 10% sulfuric acid and purified by preparative HPLC (0-30% MeCN/water modified with 0.1% formic acid) to afford a light yellow solid (21.3 mg, 35%). $^1$H NMR (DMSO-D$_6$, 400 MHz): 12.34 (s, 1H), 8.96 (d, J=2.2 Hz, 1H), 8.90 (d, J=2.2 Hz, 1H), 8.70 (s, 1H), 8.38 (s, 1H), 7.66 (d, J=8.7, 3H), 7.09 (d, J=8.8, 3H), 3.26-3.17 (m, 4H), 2.47 (m, 4H), 2.24 (s, 3H). LCMS (Method D): R$_T$=8.90 min, M+H$^+$=378.

Example 356

6-Chloro-3-(1-methylpyrazol-4-yl)-phenyl]-9H-dipyrido[2,3-b;4',3'-d]pyrrole

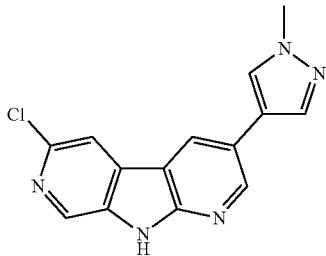 [SMILES: Cn1cc(-c2cnc3[nH]c4cnc(Cl)cc4c3c2)cn1]

A degassed mixture of 3-bromo-6-chloro-9H-dipyrido[2,3-b;4',3'-d]pyrrole (34.6 mg, 0.122 mmol), 1-methyl-4-(4,4,5,5-tetramethyl-1,3,2-dioxaborolan-2-yl)-1H-pyrazole (26.8 mg, 0.129 mmol), and bis(triphenylphosphine)palladium(II) chloride (4.3 mg, 6.1 μmol, 5.0 mol %) in acetonitrile (0.51 mL) and 1M aqueous potassium acetate (0.51 mL) was heated under microwave irradiation at 140° C. for 30 minutes, allowed to cool and concentrated in vacuo. The residue was dissolved in water, DMF, and 10% sulfuric acid and purified by preparative HPLC (0-30% MeCN/water modified with 0.1% formic acid) to afford an off-white solid (15.4 mg, 44%). $^1$H NMR (DMSO-D$_6$, 400 MHz): 12.32 (s, 1H), 8.89 (s, 2H), 8.69 (d, J=0.7 Hz, 1H), 8.28 (d, J=0.7 Hz, 1H), 8.22 (s, 1H), 7.96 (s, 1H), 3.90 (s, 3H). LCMS (Method D): R$_T$=9.61 min, M+H$^+$=284.

Example 357

6-Fluoro-3-(4-piperidin-1-ylmethylphenyl)-9H-dipyrido[2,3-b;4',3'-d]pyrrole

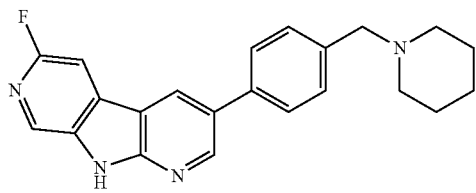 [SMILES: Fc1cc2c(cn1)[nH]c1ncc(-c3ccc(CN4CCCCC4)cc3)cc12]

Step 1: 6-Fluoro-4-iodopyridin-3-ylamine

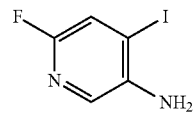

(6-Fluoro-4-iodopyridin-3-yl)-carbamic acid tert-butyl ester (1.75 g, 5.18 mmol) was dissolved in DCM (25 mL) and TFA (5 mL) added. The mixture was stirred at ambient temperature for 1 h and then evaporated in vacuo. The resultant residue was treated with saturated aqueous sodium hydrogen carbonate solution (25 mL), diluted with water (100 mL) and extracted into ethyl acetate (2×100 mL). The organic layer was separated, dried over sodium sulfate, filtered and evaporated in vacuo to afford the title compound as an orange oil, which crystallized on standing (1.23 g, 99%). $^1$H NMR (CDCl$_3$, 300 MHz): 7.61 (d, J=1.6 Hz, 1H), 7.28-7.25 (m, 1H), 3.99 (s, 2H). LCMS (Method B): R$_T$=2.52 min, M+H$^+$=239.

Step 2: 5-Bromo-2,6'-difluoro-[3,4]bipyridinyl-3'-ylamine

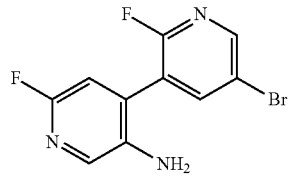 [SMILES: Nc1cnc(F)cc1-c1cc(Br)cnc1F]

A mixture of 6-fluoro-4-iodopyridin-3-ylamine (1.57 g, 6.59 mmol), 2-fluoro-5-bromopyridine-3-boronic acid (2.17 g, 9.89 mmol) and 1,1'-[bis(diphenylphosphino)ferrocene]dichloropalladium(II) (0.43 g, 0.53 mmol) in acetonitrile (25 mL) and 1N aqueous potassium fluoride solution (25 mL) was degassed with nitrogen for 20 minutes. The reaction mixture was heated at 80° C. for 3 h, allowed to cool to ambient temperature and then partitioned between ethyl acetate (100 mL) and water (75 mL). The organic layer was separated, dried over sodium sulfate, filtered and evaporated in vacuo. The resultant residue was purified by flash chromatography (silica, 40 g column, ISCO, 0-50% ethyl acetate in cyclohexane) to afford the title compound as an brown solid (0.54 g, 29%). $^1$H NMR (CDCl$_3$, 300 MHz): 8.37 (dd, J=2.5, 1.4 Hz, 1H), 7.99 (dd, J=8.1, 2.5 Hz, 1H), 7.79 (d, J=1.5 Hz, 1H), 6.74 (d, J=2.8 Hz, 1H), 3.62 (s, 2H). LCMS (Method B): R$_T$=3.01 min, M+H$^+$=286/288.

Step 3: 3-Bromo-6-fluoro-9H-dipyrido[2,3-b;4',3'-d]pyrrole

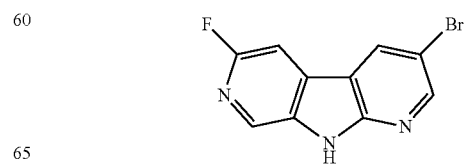

A solution of 5-bromo-2,6'-difluoro-[3,4']bipyridinyl-3'-ylamine (0.79 g, 2.76 mmol) in THF (15 mL) was added dropwise over 10 minutes to sodium bis(trimethylsilyl)amide (1N solution in THF, 5.5 mL, 5.52 mmol). The reaction mixture was left to stir for 20 minutes then quenched by the addition of water (2 mL). The resultant black solution was partitioned between ethyl acetate (75 mL) and water (50 mL) and the layers separated. The organic phase was dried over sodium sulfate, filtered and evaporated in vacuo to give an off white solid. The resultant solid was triturated with ethyl acetate (30 mL), collected by filtration, washed with diethyl ether (5 mL) and left to air dry to afford the title compound as an off white solid (0.51 g, 65%). $^1$H NMR (DMSO-D$_6$, 300 MHz): 9.00 (d, J=2.3 Hz, 1H), 8.69 (d, J=2.3 Hz, 1H), 8.51 (dd, J=1.7, 0.9 Hz, 1H), 7.95 (dd, J=2.4, 0.9 Hz, 1H). LCMS (Method B): R$_T$=3.10 min, M+H$^+$=266/268.

Step 4: 6-Fluoro-3-(4-piperidin-1-ylmethyl-phenyl)-9H-dipyrido[2,3-b;4',3'-d]pyrrole

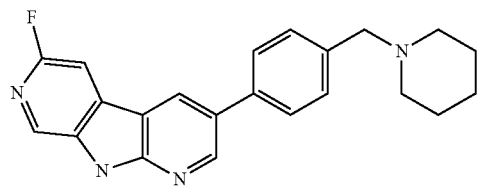 [SMILES: Fc1cc2c(cn1)[nH]c1ncc(-c3ccc(CN4CCCCC4)cc3)cc12]

A mixture of 3-bromo-6-fluoro-9H-dipyrido[2,3-b;4',3'-d]pyrrole (100 mg, 0.38 mmol), 4-benzylpiperidine boronic acid (123 mg, 0.56 mmol) and 1,1'-[bis(diphenylphosphino)ferrocene]dichloropalladium(II) (31 mg, 0.038 mmol) in acetonitrile (1.5 mL) and 2N aqueous potassium fluoride solution (1.5 mL) was degassed with nitrogen for 20 minutes. The reaction mixture was then heated under microwave irradiation at 150° C. for 30 minutes, allowed to cool to ambient temperature and diluted with water (3 mL). The resultant precipitate was collected by filtration, washed with water (5 mL) and ethyl acetate (10 mL). The resultant solid residue was purified by flash chromatography (silica, 4 g column, ISCO, 0-20% methanol in DCM) to afford the title compound as an off white solid (90 mg, 67%). $^1$H NMR (DMSO-D$_6$, 300 MHz): 12.27 (s, 1H), 9.00 (d, J=2.3 Hz, 1H), 8.93 (d, J=2.3 Hz, 1H), 8.49 (d, J=1.5 Hz, 1H), 7.98 (d, J=2.3 Hz, 1H), 7.74 (d, J=8.0 Hz, 2H), 7.43 (d, J=7.9 Hz, 2H), 3.48 (s, 2H), 2.42-2.29 (m, 4H), 1.54-1.47 (m, 4H), 1.44-1.34 (m, 2H). LCMS (Method A): R$_T$=5.87 min, M+H$^+$=361.

Example 358

6-Oxo-3-(4-piperidin-1-ylmethyl-phenyl)-6,7-dihydro-9H-dipyrido[2,3-b;4',3'-d]pyrrole

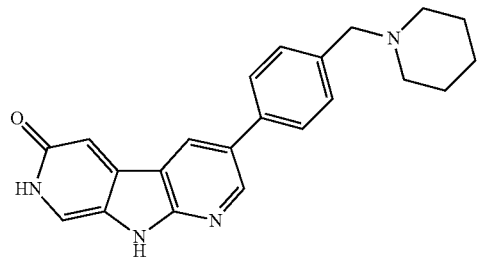 [SMILES: O=c1cc2c(c[nH]1)[nH]c1ncc(-c3ccc(CN4CCCCC4)cc3)cc12]

To 6-methoxy-3-(4-piperidin-1-ylmethyl-phenyl)-9H-dipyrido[2,3-b;4',3'-d]pyrrole (200 mg, 0.5 mmol) was added HBr (33% in acetic acid, 5 mL) and the reaction was heated at 100° C. for 16 h. The cooled reaction mixture was then evaporated in vacuo to afford a residue that was purified by preparative HPLC [0-30% MeCN in water (0.1% formic acid) over 30 min, 35 mL/min] to afford the title compound as a bright yellow solid (50 mg, 30%). $^1$H NMR (DMSO-D$_6$, 400 MHz): 11.51 (s, 1H), 8.91-8.74 (m, 2H), 8.28 (s, 1H), 7.72 (d, J=8.2 Hz, 2H), 7.41 (d, J=8.1 Hz, 2H), 7.29 (s, 1H), 6.68-6.44 (s, 1H), 3.48 (s, 2H), 2.36 (s, 4H), 1.51 (m, 4H), 1.40 (m, 2H). LCMS (Method D): R$_T$=4.97 min, M+H$^+$=359.

Example 359

6-Methoxy-3-(4-piperidin-1-ylmethyl-phenyl)-9H-dipyrido[2,3-b;4',3'-d]pyrrole

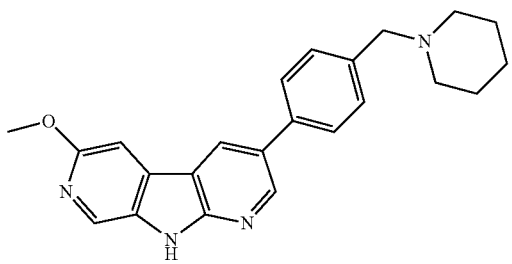 [SMILES: COc1cc2c(cn1)[nH]c1ncc(-c3ccc(CN4CCCCC4)cc3)cc12]

Step 1: tert-Butyl 6-methoxypyridin-3-ylcarbamate

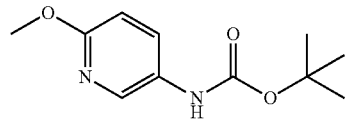 [SMILES: COc1ccc(NC(=O)OC(C)(C)C)cn1]

A mixture of 6-methoxypyridin-3-amine (14 g, 0.11 mol) and di-tert-butyldicarbonate (32 g, 0.15 mol) in 1,4-dioxane (100 mL) was heated at 75° C. for 16 h. The cooled reaction mixture was diluted with ethyl acetate (200 mL) and washed with water (150 mL). The organic phase was separated, dried over sodium sulfate, filtered and evaporated in vacuo to afford a residue that was purified by flash chromatography (silica, 120 g column, ISCO, 0-40% ethyl acetate in hexanes) to afford the title compound as a pink solid (20 g, 80%).

Step 2: (6-Methoxy-4-iodo-pyridin-3-yl)-carbamic acid tert-butyl ester

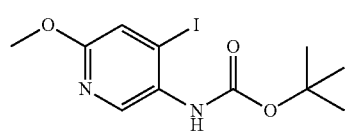 [SMILES: COc1cc(I)c(NC(=O)OC(C)(C)C)cn1]

n-Butyllithium (2.5M in hexanes, 100 mL, 240 mmol) was added dropwise over 1 h to a cooled (−78° C.) mixture of tert-butyl-6-methoxypyridin-3-ylcarbamate (16 g, 71 mmol) and N,N,N',N'-tetramethylethylenediamine (34 mL, 221 mmol) in diethyl ether (100 mL). The reaction was stirred at −78° C. for 30 minutes, then warmed to −20° C. and left stirring for 3 h. The reaction mixture was transferred via cannula over fifteen minutes to a cold (−78° C.) solution of 1-chloro-2-iodoethane (48 g, 243 mmol) in diethyl ether (50 mL). On complete addition, the reaction mixture was allowed to warm to room temperature and left stirring at this temperature for 16 h. The reaction was quenched with saturated aqueous ammonium chloride (30 mL) and water (200 mL) then extracted with ethyl acetate (2×100 mL). The combined organic layer was washed with saturated sodium sulfite (50 mL), 1N hydrochloric acid (100 mL), water (100 mL), saturated sodium bicarbonate solution (100 mL) and brine (50 mL), dried over sodium sulfate, and evaporated to give a residue which was purified by flash chromatography (silica, 120 g column, ISCO, 0-40% ethyl acetate in hexanes) to afford the title compound as a white cyrstaline solid (18 g, 72%).

Step 3: 6-Methoxy-4-iodopyridin-3-amine

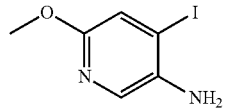

A solution of (6-methoxy-4-iodo-pyridin-3-yl)-carbamic acid tert-butyl ester (18 g, 51 mmol) in DCM (50 mL) and TFA (50 mL) was stirred at ambient temperature for 1 h and then evaporated in vacuo. The resultant residue was treated with saturated aqueous sodium hydrogen carbonate solution (25 mL), diluted with water (100 mL) and extracted into ethyl acetate (2×100 mL). The organic layer was separated, dried over sodium sulfate, filtered and evaporated in vacuo to afford the title compound as a brown foam (10 g, 60%).

Step 4: 5-Bromo-6'-methoxy-2-fluoro-[3,4']bipyridinyl-3'-ylamine

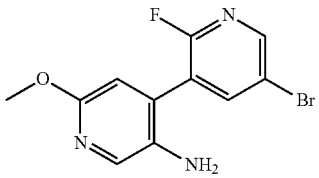 [SMILES: COc1cc(-c2cc(Br)cnc2F)c(N)cn1]

A mixture of 6-methoxy-4-iodopyridin-3-amine (9.5 g, 38 mmol), 5-bromo-2-fluoropyridin-3-ylboronic acid (16.7 g, 76 mmol), and 1,1'-[bis(diphenylphosphino)ferrocene]dichloropalladium(II) (1.5 g, 2 mmol) in 1N aqueous potassium fluoride (95 mL) and acetonitrile (200 mL) was heated at 95° C. for 16 h. The cooled reaction mixture was diluted with water (100 mL) and extracted with DCM (3×100 mL). The combined organic layer was dried over sodium sulfate, filtered, and evaporated to afford a residue which was purified by flash chromatagraphy (silica, 120 g column, ISCO, 0-40% ethyl acetate in hexanes) to afford the title compound as a yellow/orange solid (8.0 g, 71%).

Step 5: 6'-Methoxy-2-fluoro-5-(4-piperidin-1-ylmethyl-phenyl)-[3,4']bipyridinyl-3'-ylamine

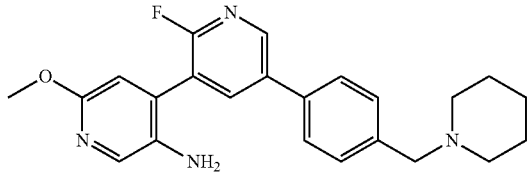 [SMILES: COc1cc(-c2cc(-c3ccc(CN4CCCCC4)cc3)cnc2F)c(N)cn1]

A mixture of 6'-methoxy-2-fluoro-[3,4]bipyridinyl-3'-ylamine (1.0 g, 3.4 mmol), 4-(piperidin-1-ylmethyl)phenylboronic acid hydrobromide (1.7 g, 5.7 mmol), and bis(triphenylphosphine)palladium(II) dichloride (0.18 g, 0.25 mmol) in 1N aqueous potassium fluoride (8.4 mL) and acetonitrile (12 mL) was heated under microwave irradiation at 100° C. for 25 minutes. The cooled reaction was diluted with water (100 mL) and extracted with DCM (3×50 mL). The combined organic layer was, dried over sodium sulfate, filtered, and purified by flash chromatography (silica, 25 g column, Biotage, 0-10% methanol in (DCM containing 1% 2M ammonia in methanol)) to afford the title compound as a yellow/orange solid (1.0 g, 77%). $^1$H NMR (DMSO-D$_6$, 500 MHz): 8.59 (s, 1H), 8.22 (d, J=8.0 Hz, 1H), 7.74 (s, 3H), 7.42 (s, 2H), 6.65 (s, 1H), 4.71 (s, 2H), 3.77 (s, 3H), 3.47 (s, 2H), 2.34 (s, 4H), 1.51 (s, 4H), 1.40 (s, 2H).

Step 6: 6-Methoxy-3-(4-piperidin-1-ylmethyl-phenyl)-9H-dipyrido[2,3-b;4',3'-d]pyrrole

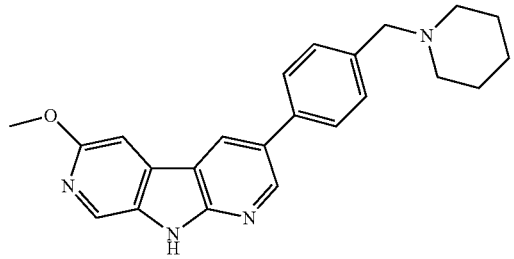 [SMILES: COc1cc2c(cn1)[nH]c1ncc(-c3ccc(CN4CCCCC4)cc3)cc12]

To a solution of 6'-methoxy-2-fluoro-[3,4']bipyridinyl-3'-ylamine (43 mg, 0.11 mmol) in anhydrous tetrahydrofuran (1.8 mL) was added sodium bis(trimethylsilyl)amide (1N solution in THF, 0.33 mL, 0.332 mmol) under a flow of nitrogen. The reaction was left to stir at room temperature for 1 h then quenched with acetic acid (1 mL). The reaction mixture was evaporated in vacuo to afford a residue that was purified by preparative HPLC [0-30% MeCN in water (0.1% formic acid) over 30 min, 35 mL/min] to afford the title compound as a beige solid (10 mg, 20%). $^1$H NMR (DMSO-D$_6$, 400 MHz): 11.82 (s, 1H), 8.92 (d, J=2.1 Hz, 1H), 8.85 (d, J=2.3 Hz, 1H), 8.47 (s, 1H), 7.73 (d, J=8.2 Hz, 2H), 7.64 (s, 1H), 7.42 (d, J=8.2 Hz, 2H), 3.92 (s, 3H), 3.48 (s, 2H), 2.36 (s, 4H), 1.51 (m, 4H), 1.40 (m, 2H). LCMS (Method E): R$_T$=2.40, M+H$^+$=373.

Example 360

6-Methoxy-3-[4-(4-methylpiperazin-1-yl)-phenyl]-9H-dipyrido[2,3-b;4',3'-d]pyrrole

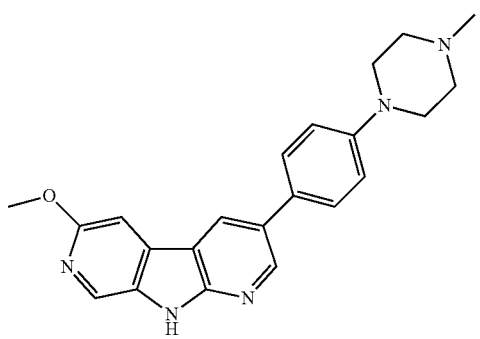

Step 1: 6-Methoxy-3-bromo-9H-dipyrido[2,3-b;4',3'-d]pyrrole

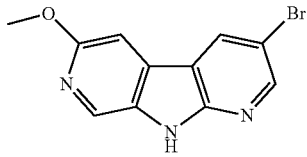 [SMILES: COc1cc2c(cn1)[nH]c1ncc(Br)cc12]

A 1N solution of bis(trimethylsilyl)amide in THF (6.81 mL, 6.81 mmol) was added dropwise to a solution of 5-bromo-2-fluoro-6'-methoxy-[3,4']bipyridinyl-3'-ylamine (203 mg, 0.681 mmol) in THF (12.0 mL). The reaction mixture was stirred for 30 minutes at ambient temperature, diluted with water, and extracted into ethyl acetate. The organic phase was dried over sodium sulfate, filtered, and concentrated in vacuo. The crude residue was dissolved in ethyl acetate and methanol, absorbed onto silica gel, and purified by flash chromatography (silica, 12 g column, ISCO, 0-100% ethyl acetate in hexanes) to provide the title compound as an orange-tan solid (89.0 mg, 47%). $^1$H NMR (DMSO-D$_6$, 400 MHz): 12.44-12.12 (m, 1H), 7.79 (d, J=2.6 Hz, 1H), 7.66 (d, J=3.5 Hz, 2H), 6.56 (s, 1H), 3.75 (s, 3H). LCMS (Method B): $R_T$=1.83 min, M+H$^+$=278/280.

Step 2: 6-Methoxy-3-[4-(4-methylpiperazin-1-yl)-phenyl]-9H-dipyrido[2,3-b;4',3'-d]pyrrole

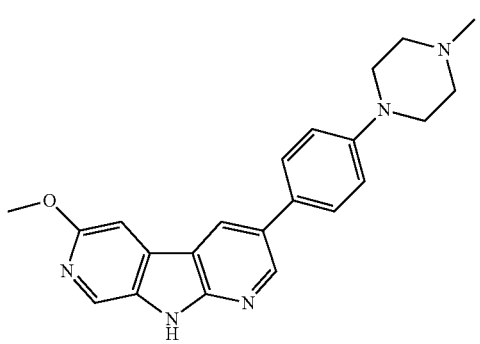

A degassed mixture of 6-methoxy-3-bromo-9H-dipyrido [2,3-b;4',3'-d]pyrrole (89.0 mg, 0.320 mmol), 4-(4-methylpiperazin-1-yl)-phenyl-1-boronic acid, pinacol ester (102 mg, 0.336 mmol) and bis(triphenylphosphine)palladium(II) chloride (11.2 mg, 16.0 umol, 5.0 mol %) in acetonitrile (1.3 mL) and 1M aqueous potassium acetate (1.3 mL) was heated under microwave irradiation at 140° C. for 30 minutes, allowed to cool to room temperature and concentrated. The residue was dissolved in water, DMF, and 10% sulfuric acid and purified by preparative HPLC [0-25% MeCN/water modified with 0.1% formic acid] to afford a light yellow solid (17.3 mg, 15%). $^1$H NMR (DMSO-D$_6$, 500 MHz): 11.72 (s, 1H), 8.83 (d, J=2.2 Hz, 1H), 8.80 (d, J=2.3 Hz, 1H), 8.46 (m, 1H), 7.65 (d, J=8.8 Hz, 2H), 7.63 (s, 1H), 7.09 (d, J=8.8 Hz, 2H), 3.92 (s, 3H), 3.28 (s, 3H), 2.71 (m, 4H), 2.41 (m, 4H). LCMS (Method D): $R_T$=6.70 min, M+H$^+$=374.

Example 361

3,6-Bis(1-methyl-4-pyrazolyl)-9H-dipyrido[2,3-b;4',3'-d]pyrrole

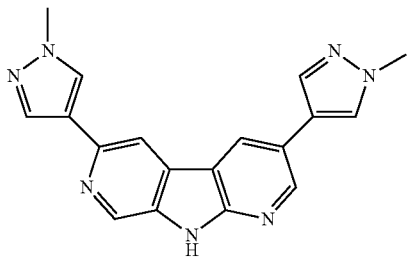 [SMILES: Cn1cc(-c2cnc3[nH]c4cnc(-c5cnn(C)c5)cc4c3c2)cn1]

Step 1: 3-Bromo-9H-dipyrido[2,3-b;4',3'-d]pyrrole-6-carboxylic acid hydrazide

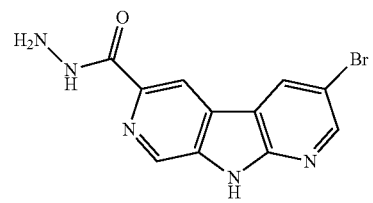 [SMILES: NNC(=O)c1cc2c(cn1)[nH]c1ncc(Br)cc12]

A solution of 3-bromo-9H-dipyrido[2,3-b;4',3'-d]pyrrole-6-carboxylic acid methyl ester (582 mg, 1.90 mmol) and hydrazine hydrate (2.29 mL, 47.0 mmol) in ethanol (4.6 mL) was heated under reflux in an inert atmosphere. After 1 h, the reaction mixture was allowed to cool to ambient temperature. The resultant precipitate was collected by filtration, washed with ethanol, and left to air-dry to afford the title compound as a tan-yellow solid.

Step 2: 3-Bromo-9H-dipyrido[2,3-b;4',3'-d]pyrrole-6-carboxylic acid azide

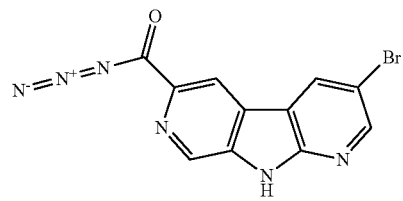 [SMILES: [N-]=[N+]=NC(=O)c1cc2c(cn1)[nH]c1ncc(Br)cc12]

Hydrogen chloride (3.0 mL, 90 mmol) was added dropwise to a suspension of 3-bromo-9H-dipyrido[2,3-b;4',3'-d]pyrrole-6-carboxylic acid hydrazide (530 mg, 1.73 mmol) in water (12.4 mL). Once homogeneous, the solution was cooled to 0° C. and a solution of 3N sodium nitrite in water (0.60 mL, 2.0 mmol) was added to the mixture. After 1 h, added another 1.03 eq. of 3N sodium nitrite in water (0.60 mL, 2.0 mmol) and allowed the reaction to warm to ambient temperature over night. After 17 h at room temperature, the reaction was cooled to 0° C. and a solution of 3N sodium nitrite in water (0.60 mL, 2.0 mmol) was added and then warmed to room temperature. The reaction was made basic with a solution of saturated sodium bicarbonate, and the solid precipitate was collected by filtration, washed with water, and dried in a dessicator under vacuum to provide a solid material that was 70% pure by LCMS analysis.

Step 3: 6-Amino-3-bromo-9H-dipyrido[2,3-b;4'3'-d]pyrrole

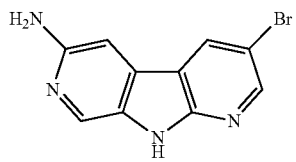 [SMILES: Nc1cc2c(cn1)[nH]c1ncc(Br)cc12]

A suspension of 3-bromo-9H-dipyrido[2,3-b;4',3'-d]pyrrole-6-carboxylic acid azide (1.09 g, 3.44 mmol) in a mixture of 1:1 water-acetic acid (3.52 mL) was heated under reflux for 1 h. The reaction was allowed to cool to ambient temperature and the mixture concentrated in vacuo. The resultant residue was purified by flash chromatography (silica, 1-20% (MeOH containing 1% of 2N ammonia in MeOH) in DCM) and recrystallized from pyridine to afford the title compound.

Step 4: 3,6-Dibromo-9H-dipyrido[2,3-b;4',3'-d]pyrrole

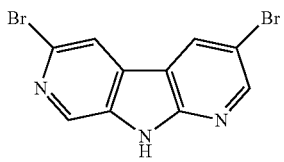

A solution of hydrogen bromide (33%) in acetic acid (1.10 mL, 6.08 mmol) was added to 6-amino-3-bromo-9H-dipyrido[2,3-b;4',3'-d]pyrrole (80.1 mg, 0.304 mmol) at 0° C. To the resulting suspension was added bromine (18 µL, 0.34 mmol), and then a 1N solution of sodium nitrite in water (0.43 mL, 0.43 mmol), and the mixture was allowed to warm to ambient temperature. After 1 h, the reaction mixture was diluted with concentrated ammonium hydroxide-water (1:1) and DCM, filtered to remove the solid, and the filtrate layers separated. The aqueous phase was extracted into DCM and the combined organic phase was concentrated in vacuo. The residue was purified by flash chromatography (silica, 0-100% ethyl acetate in hexanes).

Step 5: 3,6-Bis(1-Methyl-4-pyrazolyl)-9H-dipyrido[2,3-b;4',3'-d]pyrrole

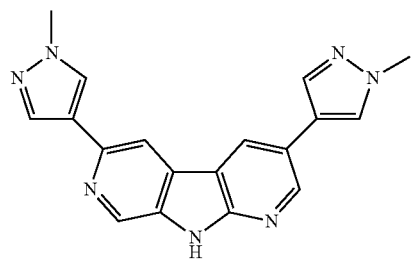 [SMILES: Cn1cc(-c2cnc3[nH]c4cnc(-c5cnn(C)c5)cc4c3c2)cn1]

A suspension of 3,6-dibromo-9H-dipyrido[2,3-b;4',3'-d]pyrrole (9.3 mg, 28 µmol), 1-methyl-4-(4,4,5,5-tetramethyl-1,3,2-dioxaborolan-2-yl)-1H-pyrazole (17.8 mg, 85.3 µmol) and bis(triphenylphosphine)palladium(II) dichloride (1.0 mg, 14 µmol) in acetonitrile (0.18 mL) and 2N aqueous sodium carbonate solution was heated under microwave irradiation at 140° C. for 20 minutes. The reaction mixture was allowed to cool to ambient temperature and the resultant precipitate collected by filtration, and the solid washed sequentially with water, DCM, and 20% MeOH in DCM. The filtrate was combined, the layers separated, and the aqueous phase extracted into 20% MeOH inDCM. The combined organic phase was concentrated in vacuo and the resultant residue purified by flash chromatography (silica, 0-20% MeOH in DCM) to afford the title compound. $^1$H NMR (DMSO-D$_6$, 400 MHz): 12.01 (s, 1H), 8.83 (m, 2H), 8.78 (m, 1H), 8.39 (s, 1H), 8.21 (d, J=9.4 Hz, 2H), 7.97 (d, J=7.0 Hz, 2H), 3.98-3.91 (s, 6H). LCMS (Method D): R$_T$=7.53 min, M+H$^+$=330.

Example 362

3-(4-Piperidin-1-ylmethyl-phenyl)-9H-dipyrido[2,3-b;4',3'-d]pyrrole-6-amine

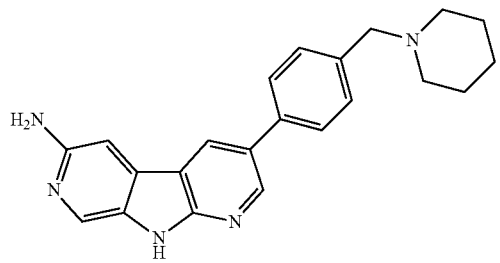 [SMILES: Nc1cc2c(cn1)[nH]c1ncc(-c3ccc(CN4CCCCC4)cc3)cc12]

Step 1: tert-Butyl-{3-bromo-9H-dipyrido[2,3-b;4',3'-d]pyrrol-6-yl}-carbamate

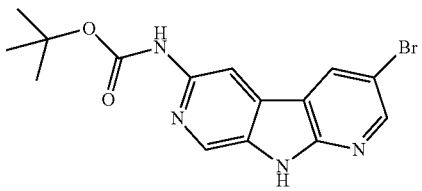 [SMILES: CC(C)(C)OC(=O)Nc1cc2c(cn1)[nH]c1ncc(Br)cc12]

A suspension of 3-bromo-9H-dipyrido[2,3-b;4',3'-d]pyrrole-6-carbonyl azide (50.0 mg, 0.158 mmol) in toluene (3.0 mL) was treated with tert-butyl alcohol (1.00 mL, 10.4 mmol) and heated under reflux for 1 h under a nitrogen atmosphere. The solution was allowed to cool to ambient temperature and the resulting precipitate was collected by filtration, washed with DCM, and dried under vacuum to afford an orange solid (55.9 mg, 98%). The solid was used without purification. $^1$H NMR (DMSO-D$_6$, 400 MHz): 12.12 (s, 1H), 9.57 (s, 1H), 8.99 (d, J=2.2 Hz, 1H), 8.62 (d, J=2 Hz2, 1H), 8.59 (s, 1H), 8.49 (s, 1H), 1.51 (s, 9H).

Step 2: tert-Butyl-{3-(4-piperidin-1-ylmethyl-phenyl)-9H-dipyrido[2,3-b;4',3'-d]pyrrol-6-yl}-carbamate

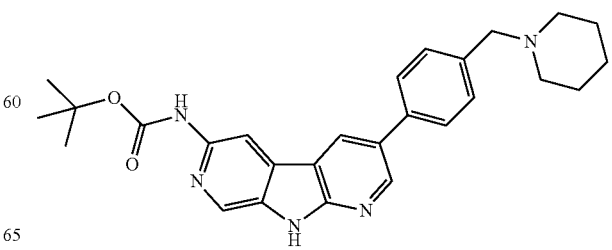

A degassed mixture of tert-butyl-{3-bromo-9H-dipyrido[2,3-b;4',3'-d]pyrrol-6-yl}-carbamate (229 mg, 0.631 mmol), 4-piperidin-1-ylmethyl-phenyl boronic acid (207 mg, 0.946 mmol), and [1,1'-bis(diphenylphosphino)ferrocene]dichloropalladium(II) complex with dichloromethane (1:1) (51.5 mg, 6.31 µmol, 10.0 mol %) in 1,4-dioxane (12.4 mL) and 2M aqueous cesium carbonate (1.32 mL) was heated under reflux for 5 h. The mixture was allowed to cool to room temperature, diluted with DCM and water, and filtered to remove the precipitate. The filtrate layers were separated and the aqueous phase was extracted with DCM, and the combined organic phase concentrated in vacuo. The resultant residue was dissolved in 20% methanol in DCM and absorbed onto silica gel for purification by flash chromatography (silica, 11 g column, Biotage, 1-20% methanol in DCM) to afford the title compound as a beige solid (86.9 mg, 30%). $^1$H NMR (DMSO-D$_6$, 400 MHz): 11.96 (s, 1H), 9.55 (s, 1H), 8.99 (d, J=1.9 Hz, 1H), 8.88 (d, J=2.2 Hz, 1H), 8.57 (d, J=7.8 Hz, 2H), 7.80 (d, J=8.1 Hz, 2H), 7.42 (d, J=8.1 Hz, 2H), 3.50 (s, 2H), 2.35 (m, 4H), 1.55-1.45 (m, 4H), 1.52 (s, 9H), 1.39 (m, 2H). LCMS (Method D): R$_T$=9.11 min, M+H$^+$=458.

Step 3: 3-(4-Piperidin-1-ylmethyl-phenyl)-9H-dipyrido[2,3-b;4',3'-d]pyrrole-6-amine

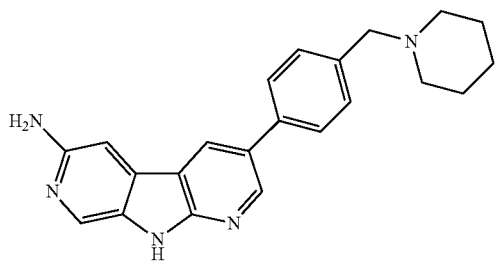 [SMILES: Nc1cc2c(cn1)[nH]c1ncc(-c3ccc(CN4CCCCC4)cc3)cc12]

A degassed mixture of tert-butyl-{3-Bromo-9H-dipyrido[2,3-b;4',3'-d]pyrrol-6-yl}-carbamate (105 mg, 0.290 mmol), 4-piperidin-1-ylmethyl-phenyl boronic acid (73.7 mg, 0.336 mmol), and [1,1'-bis(diphenylphosphino)ferrocene]dichloropalladium(II) complex with dichloromethane (1:1) (17.8 mg, 2.18 µmol, 7.5 mol %) in acetonitrile (1.3 mL) and 1M aqueous potassium acetate (1.3 mL) was heated under microwave irradiation at 140° C. for 30 minutes. The cooled reaction mixture was diluted with 20% MeOH in DCM and water, and filtered to remove the solids. The filtrate layers were separated and the aqueous phase was extracted into 20% MeOH in DCM, and the combined organic phase concentrated in vacuo. The resultant residue was purified by preparative HPLC (0-30% MeCN in water (0.1% formic acid) over 30 min, 35 mL/min) to afford the title compound as a yellow solid (41 mg, 40%). $^1$H NMR (DMSO-D$_6$, 400 MHz): 11.47 (s, 1H), 8.77 (d, J=2.0 Hz, 1H), 8.73 (d, J=2.0 Hz, 1H), 8.30 (s, 1H), 8.16 (s, 1H), 7.73 (d, J=8.1 Hz, 2H), 7.41 (d, J=8.1 Hz, 2H), 7.18 (s, 1H), 3.48 (s, 2H), 2.38 (m, 4H), 1.57-1.47 (m, 4H), 1.41 (m, 2H). LCMS (Method D): R$_T$=6.20 min, M+H$^+$=358.

Example 363

N-{3-(4-Piperidin-1-ylmethyl-phenyl)-9H-dipyrido[2,3-b;4',3'-d]pyrrol-6-yl-methanesulfonamide

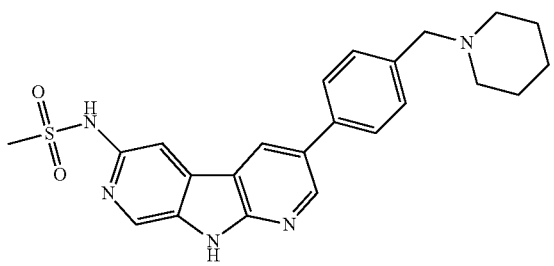 [SMILES: CS(=O)(=O)Nc1cc2c(cn1)[nH]c1ncc(-c3ccc(CN4CCCCC4)cc3)cc12]

A solution of 3-(4-piperidin-1-ylmethyl-phenyl)-9H-dipyrido[2,3-b;4',3'-d]pyrrol-6-amine (82.1 mg, 0.230 mmol) in pyridine (8.2 mL) was treated with methanesulfonyl chloride (58.7 µL, 0.758 mmol) and heated at 50° C. for 15 h. The cooled reaction mixture was treated with saturated sodium bicarbonate solution and diluted with 20% MeOH in DCM and water. The layers were separated, the aqueous phase extracted into 20% MeOH in DCM, and the combined organic phases were dried over sodium sulfate and concentrated in vacuo. The resultant residue was purified by preparative HPLC (0-30% MeCN in water (0.1% formic acid) over 30 min, 35 mL/min) to afford the title compound as a tan solid (38 mg, 38%). $^1$H NMR (DMSO-D$_6$, 400 MHz): 12.03 (s, 1H), 8.96 (d, J=2.1 Hz, 1H), 8.88 (d, J=2.1 Hz, 1H), 8.64 (s, 1H), 7.85 (s, 1H), 7.77 (d, J=8.1 Hz, 2H), 7.42 (d, J=8.1 Hz, 2H), 3.48 (s, 2H), 3.22 (s, 3H), 2.36 (m, 4H), 1.55-1.46 (m, 4H), 1.41 (m, 2H). LCMS (Method D): R$_T$=7.37 min, M+H$^+$=436.

Example 364

1-Ethyl-3-{3-(4-piperidin-1-ylmethyl-phenyl)-9H-dipyrido[2,3-b;4',3'-d]pyrrol-6-yl}-urea

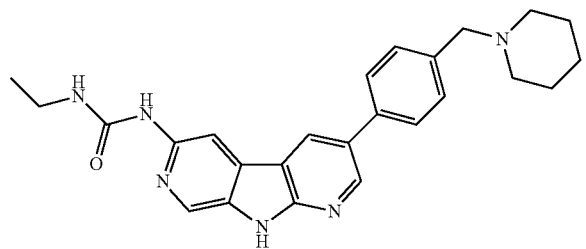 [SMILES: CCNC(=O)Nc1cc2c(cn1)[nH]c1ncc(-c3ccc(CN4CCCCC4)cc3)cc12]

A suspension of 3-(4-piperidin-1-ylmethyl-phenyl)-9H-dipyrido[2,3-b;4',3'-d]pyrrol-6-amine (91.6 mg, 0.256 mmol) in DCM (9.1 mL) was treated with pyridine (22.8 µL, 0.282 mmol) and ethylisocyanate (33.2 µL, 0.423 mmol) and then the reaction mixture was heated under reflux for 5 h. The cooled reaction mixture was treated with saturated sodium bicarbonate and diluted with 20% MeOH in DCM and water. The layers were separated, the aqueous phase extracted into 20% MeOH in DCM, and the combined organic phases were dried over sodium sulfate and concentrated in vacuo. The resultant residue was purified by preparative HPLC (0-30% MeCN in water (0.1% formic acid) over 30 min, 35 mL/min)

to afford the title compound as a yellow solid (34 mg, 31%). $^1$H NMR (DMSO-D$_6$, 400 MHz): 9.66 (t, J=5.4 Hz, 1H), 9.19 (s, 1H), 8.96 (d, J=2.1 Hz, 1H), 8.91 (d, J=2.1 Hz, 1H), 7.80 (d, J=8.1 Hz, 2H), 7.45 (d, J=8.1 Hz, 2H), 7.20 (s, 1H), 3.53-3.44 (m, 4H), 2.36 (m, 4H), 1.58-1.46 (m, 4H), 1.41 (m, 2H), 1.31-1.21 (m, 3H). LCMS (Method D): R$_T$=8.06 min, M+H$^+$=429.

Example 365

N-{3-(4-Piperidin-1-ylmethyl-phenyl)-9H-dipyrido[2,3-b;4',3'-d]pyrrol-6-yl}-isobutyramide

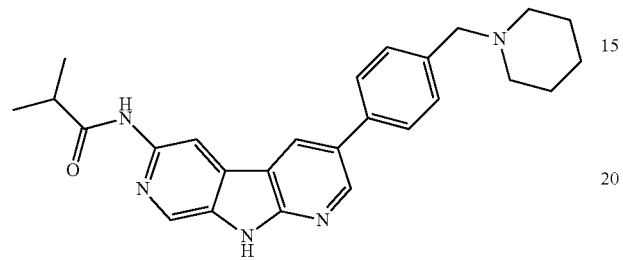

A suspension of 3-(4-piperidin-1-ylmethyl-phenyl)-9H-dipyrido[2,3-b;4',3'-d]pyrrol-6-amine (80.9 mg, 0.226 mmol) in DCM (1.8 mL) was treated with isobutyryl chloride (26.3 µL, 0.249 mmol) and DIPEA (118 µL, 0.679 mmol). The reaction mixture was treated with saturated sodium bicarbonate and diluted with 20% MeOH in DCM and water. The layers were separated, the aqueous phase extracted into 20% MeOH in DCM, and the combined organic phase was dried over sodium sulfate and concentrated in vacuo. The resultant residue was dissolved in DCM/methanol, absorbed onto celite, and purified by preparative HPLC (0-30% MeCN/water modified with 0.1% formic acid) to afford an off-white solid (12 mg, 12%). $^1$H NMR (DMSO-D$_6$, 400 MHz): 12.03 (s, 1H), 10.32 (s, 1H), 8.95 (d, J=2.2 Hz, 1H), 8.90-8.85 (m, 2H), 8.62 (s, 1H), 7.79 (d, J=8.1 Hz, 2H), 7.42 (d, J=8.1 Hz, 2H), 3.48 (s, 2H), 2.79 (dt, J=6.7, 13.5 Hz, 1H), 2.36 (m, 4H), 1.58-1.46 (m, 4H), 1.41 (m, 2H), 1.14 (d, J=6.8 Hz, 6H). LCMS (Method D): R$_T$=7.73 min, M+H$^+$=428.

Example 366

3-(4-Piperidin-1-ylmethyl-phenyl)-6-(1H-imidazol-1-yl)-9H-dipyrido[2,3-b;4',3'-d]pyrrole

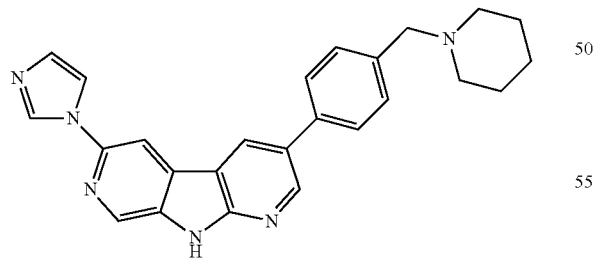

A mixture of 3-(4-piperidin-1-ylmethyl-phenyl)-9H-dipyrido[2,3-b;4',3'-d]pyrrol-6-amine (101.1 mg, 0.283 mmol), paraformaldehyde (9.65 µL, 0.283 mmol), glyoxal (13.0 µL, 0.283 mmol) and 0.17M aqueous ammonium chloride (5.0 mL) in 1,4-dioxane (8.4 mL) and water (8.4 mL) was heated at 100° C. for 18 h. The cooled reaction mixture was treated with saturated sodium bicarbonate and diluted with 20% MeOH in DCM and water. The layers were separated, the aqueous phase extracted into 20% MeOH in DCM, and the combined organic phase was dried over sodium sulfate and concentrated in vacuo. The resultant residue was purified by preparative HPLC (0-30% MeCN in water (0.1% formic acid) over 30 min, 35 mL/min) to afford the title compound as a white solid (20 mg, 17%). NMR (DMSO-D$_6$, 400 MHz): 12.37 (s, 1H), 8.96 (s, 2H), 8.82 (s, 1H), 8.67 (s, 1H), 8.49 (s, 1H), 7.94 (s, 1H), 7.76 (d, J=8.1 Hz, 2H), 7.46 (d, J=8.0 Hz, 2H), 7.16 (s, 1H), 3.50 (s, 2H), 2.37 (m, 4H), 1.58-1.46 (m, 4H), 1.41 (m, 2H). LCMS (Method D): R$_T$=6.62 min, M+H$^+$=409

Example 367

3-(4-piperidin-1-ylmethyl-phenyl)-6-(4H-1,2,4-triazol-4-yl)-9H-dipyrido[2,3-b;4',3'-d]pyrrole

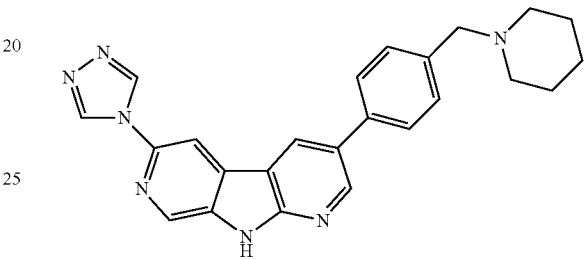

A mixture of 3-(4-piperidin-1-ylmethyl-phenyl)-9H-dipyrido[2,3-b;4',3'-d]pyrrol-6-amine (22.3 mg, 62.4 µmol), 1,2-diformylhydrazine (16.5 mg, 0.187 mmol), chloro-trimethylsilane (119 µL, 0.936 mmol) in triethylamine (60.9 µL, 0.437 mmol) and pyridine (340 µL) was heated under reflux for 30 minutes. The cooled reaction mixture was diluted with water, DCM, methanol and water. The layers were separated; the aqueous phase extracted with 20% MeOH in DCM, and the combined organic phase was concentrated in vacuo. The resultant residue was purified by preparative HPLC (0-30% MeCN in water (0.1% formic acid) over 30 min, 35 mL/min) to afford the title compound as a yellow solid (21 mg, 81%). $^1$H NMR (DMSO-D$_6$, 400 MHz): 12.50 (s, 1H), 9.25 (s, 2H), 8.99 (d, J=2.1 Hz, 1H), 8.94 (d, J=2.2 Hz, 1H), 8.86 (s, 1H), 8.73 (s, 1H), 7.76 (d, J=8.1 Hz, 2H), 7.46 (d, J=8.1 HZ, 2H), 3.50 (s, 2H), 2.35 (m, 4H), 1.58-1.46 (m, 4H), 1.41 (m, 2H). LCMS (Method D): R$_T$=7.46 min, M+H$^+$=410.

Example 368

6-(1-Methyl-1H-1,2,3-triazol-5-yl)-3-(4-piperidin-1-ylmethyl-phenyl)-9H-dipyrido[2,3-b;4',3'-d]pyrrole

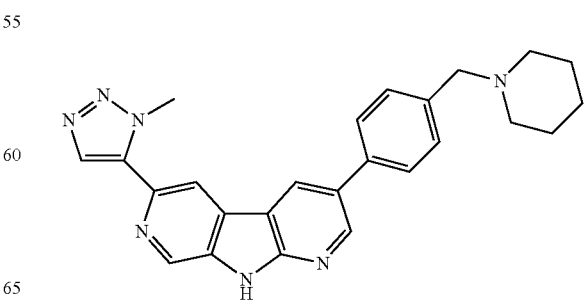

421

Step 1: 6-Iodo-3-(4-piperidin-1-ylmethyl-phenyl)-9H-dipyrido[2,3-b;4',3'-d]pyrrole

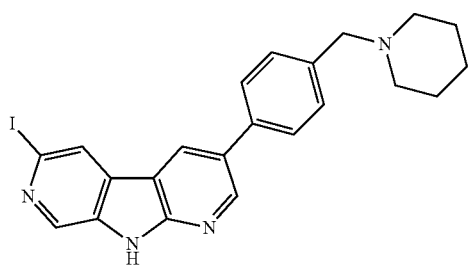 [SMILES: Ic1cc2c(cn1)[nH]c1ncc(-c3ccc(CN4CCCCC4)cc3)cc12]

A mixture of 6-bromo-3-(4-piperidin-1-ylmethyl-phenyl)-9H-dipyrido[2,3-b;4',3'-d]pyrrole (250 mg, 0.6 mmol), copper (I) iodide (23 mg, 0.12 mmol), N,N'-dimethyl-1,2-ethanediamine (0.013 mL, 0.12 mmol), and sodium iodide (360 mg, 2.4 mmol) in 1,4-dioxane was heated at 110° C. for 3 days. The reaction was diluted with dichloromethane (20 mL), filtered, and concentrated to afford a residue that was purified by flash chromatography (silica, 10 g column, Biotage, 0-10% methanol in (DCM containing 1% 2M ammonia in methanol)) to afford the title compound as an orange solid (280 mg, 100%).

Step 2: 6-(1-Methyl-1H-1,2,3-triazol-5-yl)-3-(4-piperidin-1-ylmethyl-phenyl)-9H-dipyrido[2,3-b;4',3'-d]pyrrole

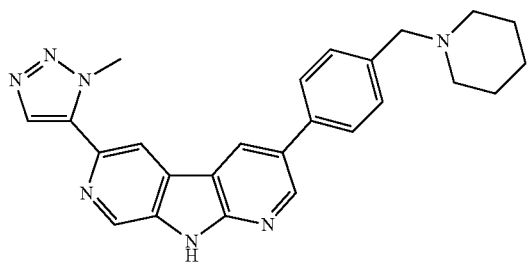 [SMILES: Cn1nncc1-c1cc2c(cn1)[nH]c1ncc(-c3ccc(CN4CCCCC4)cc3)cc12]

A degassed mixture of 6-iodo-3-(4-piperidin-1-ylmethyl-phenyl)-9H-dipyrido[2,3-b;4',3'-d]pyrrole (100 mg, 0.21 mmol), 1-methyl-5-(trimethylstannyl)-1H-1,2,3-triazole (158 mg, 0.64 mmol) and bis(triphenylphosphine)palladium (II) dichloride (15 mg, 0.021 mmol) in N,N-diisopropylethylamine (0.74 mL, 0.43 mmol) in 1,4-dioxane (1.7 mL) was heated at 100° C. for 1 h. The cooled reaction mixture was diluted with DCM (20 mL) and methanol (2 mL) and washed with water (15 mL). The organic phase was separated, dried over sodium sulfate, filtered and evaporated in vacuo to afford a residue that was purified by preparative HPLC (20-60% MeCN in water (0.1% ammonium hydroxide) over 30 min, 35 mL/min) to afford the title compound as a pale yellow solid (20 mg, 20%). $^1$H NMR (DMSO-D$_6$, 400 MHz): 12.47 (s, 1H), 9.05 (s, 1H), 9.04 (d, J=2.2 Hz, 1H), 8.96 (d, J=2.2 Hz, 1H), 8.78 (s, 1H), 8.18 (s, 1H), 7.77 (d, J=8.1 Hz, 2H), 7.45 (d, J=8.1 Hz, 2H), 4.37 (s, 3H), 3.50 (s, 2H), 2.35 (s, 4H), 1.52 (m, 4H), 1.41 (m, 2H). LCMS (method D): R$_T$=8.04 min, M+H$^+$=424.

422

Example 369

6-((5-1H-1,2,3-Triazol-4-yl)methanol)-3-(4-piperidin-1-ylmethyl-phenyl)-9H-dipyrido[2,3-b;4',3'-d]pyrrole

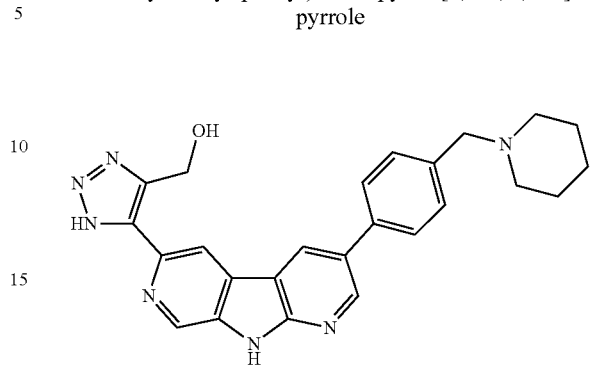

Step 1: 6-(1-Benzyl-4-((tert-butyldimethylsilyloxy)methyl)-1H-1,2,3-triazol-5-yl)-3-(4-piperidin-1-ylmethyl-phenyl)-9H-dipyrido[2,3-b;4',3'-d]pyrrole

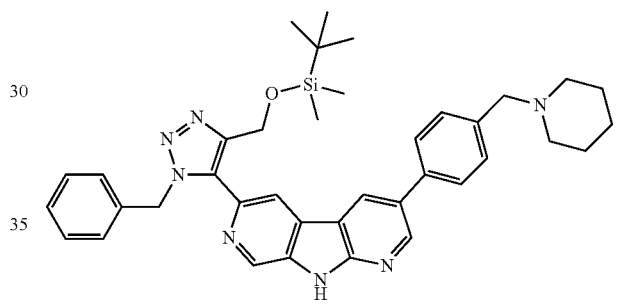

The title compound was prepared following a similar procedure to Example 368 using 1-benzyl-4-((tert-butyldimethylsilyloxy)methyl)-5-(trimethylstannyl)-1H-1,2,3-triazole. The crude reaction mixture was purified by flash chromotagraphy (silica, 10 g column, Biotage, 0-10% methanol in DCM containing 1% 7M ammonia in methanol) to afford a residue that was used in the next step without further purification.

Step 2: 6-((5-1H-1,2,3-Triazol-4-yl)methanol)-3-(4-piperidin-1-ylmethyl-phenyl)-9H-dipyrido[2,3-b;4',3'-d]pyrrole

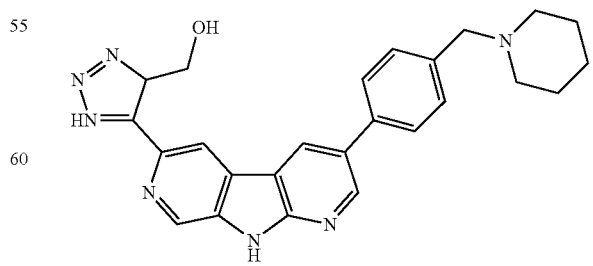

A solution of 6-(1-benzyl-4-((tert-butyldimethylsilyloxy)methyl)-1H-1,2,3-triazol-5-yl)-3-(4-piperidin-1-ylmethylphenyl)-9H-dipyrido[2,3-b;4',3'-d]pyrrole in 48% aqueous hydrobromic acid (1.5 mL) was heated at 110° C. in a sealed tube for 7 h. The cooled reaction mixture was then neutralized by dropwise addition of 6N sodium hydroxide solution. The solvent was evaporated to afford a residue that was dissolved in DMF and purified by preparative HPLC (20-60% MeCN in water (0.1% ammonium hydroxide) over 30 min, 35 mL/min) to afford the title compound as a pale yellow solid (20 mg, 20%). $^1$H NMR (DMSO-D$_6$, 400 MHz): 12.29 (s, 1H), 9.13 (d, J=2.1 Hz, 1H), 8.97 (s, 1H), 8.95-8.91 (m, 2H), 7.80 (d, J=8.1 Hz, 2H), 7.44 (d, J=8.1 Hz, 2H), 6.00 (s, 1H), 4.90 (s, 2H), 3.49 (s, 2H), 2.35 (m, 4H), 1.52 (m, 4H), 1.41 (m, 2H). LCMS (method D): R$_T$=6.83 min, M+H$^+$=440.

Example 370

3-(5-Ethyl-4,5,6,7-tetrahydrothieno[3,2-c]pyridin-2-yl)-6-(1-methyl-1H-pyrazol-4-yl)-9H-dipyrido[2,3-b;4',3'-d]pyrrole

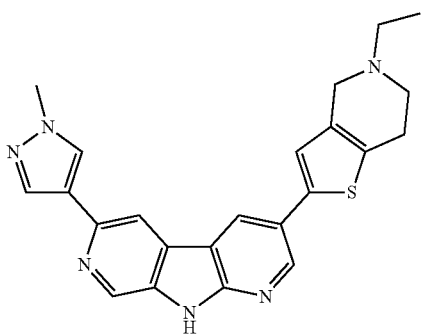 [SMILES: CCN1CCc2sc(-c3cnc4[nH]c5cnc(-c6cnn(C)c6)cc5c4c3)cc2C1]

Step 1: 6'-Chloro-2-fluoro-5-(4,4,5,5-tetramethyl-[1,3,2]dioxaborolan-2-yl)-[3,4']bipyridinyl-3'-ylamine

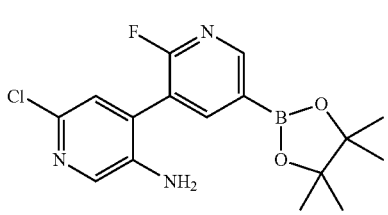 [SMILES: CC1(C)OB(c2cnc(F)c(-c3cc(Cl)ncc3N)c2)OC1(C)C]

A degassed mixture of 5-bromo-6'-chloro-2-fluoro-[3,4']bipyridinyl-3'-ylamine (2.0 g, 6.60 mmol), bis(pinacolato) diborane (1.84 g, 7.30 mmol), 1,1'-[bis(diphenylphosphino) ferrocene]dichloropalladium(II) (270 mg, 0.33 mmol) and potassium acetate (1.94 g, 19.8 mmol) in dioxane (20 mL) and DMSO (2 mL) was heated under microwave irradiation at 150° C. for 30 minutes. The cooled reaction mixture was diluted with ethyl acetate (50 mL) the solid removed by filtration and the filtrate was washed with water (75 mL). The organic phase was dried over sodium sulfate, filtered and evaporated in vacuo to afford a residue that was purified by flash chromatography (silica, 40 g column, ISCO, 0-50% ethyl acetate in DCM) to afford the title compound as a white solid (737 mg, 32%). NMR (CDCl$_3$, 300 MHz): 8.67 (dd, J=2.0, 0.8 Hz, 1H), 8.18 (dd, J=10.0, 2.0 Hz, 1H), 7.97 (d, J=0.5 Hz, 1H), 7.10 (s, 1H), 1.36 (s, 12H).

Step 2: 6'-Chloro-5-(5-ethyl-4,5,6,7-tetrahydrothieno[3,2-c]pyridin-2-yl)-2-fluoro-[3,4']bipyridinyl-3'-ylamine

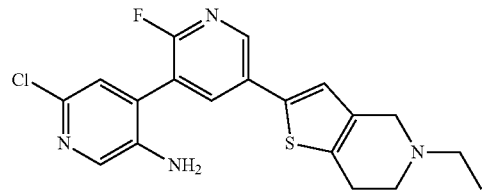 [SMILES: CCN1CCc2sc(-c3cnc(F)c(-c4cc(Cl)ncc4N)c3)cc2C1]

A degassed mixture of 6'-chloro-2-fluoro-5-(4,4,5,5-tetramethyl-[1,3,2]dioxaborolan-2-yl)-[3,4']bipyridinyl-3'-ylamine (1.99 g, 5.70 mmol), 2-bromo-5-ethyl-4,5,6,7-tetrahydrothieno[3,2-c]pyridine (1.54 g, 6.30 mmol), 1,1'-[bis(diphenylphosphino) ferrocene]dichloropalladium(II) (466 mg, 0.57 mmol) in 1N aqueous potassium fluoride solution (22.5 mL) and acetonitrile (22.5 mL) was heated under microwave irradiation at 100° C. for 30 minutes. The cooled reaction mixture was loaded onto an SCX-2 cartridge (50 g) and eluted with 2N ammonia in methanol to afford impure product as a brown solid. The resultant brown residue was purified by flash chromatography (silica, 40 g column, ISCO, 0-10% methanol in DCM) to afford the title compound as an off-white solid (1.05 g, 47%). $^1$H NMR (DMSO-D$_6$, 300 MHz): 8.48 (d, J=2.4 Hz, 1H), 8.12 (dd, J=9.0, 2.6 Hz, 1H), 7.89 (s, 1H), 7.36 (s, 1H), 7.21 (s, 1H), 5.54 (s, 2H), 3.45 (s, 2H), 2.86-2.79 (m, 2H), 2.75-2.68 (m, 2H), 2.58-2.51 (m, 2H), 1.08 (t, J=7.1 Hz, 3H).

Step 3: 5-(5-Ethyl-4,5,6,7-tetrahydrothieno[3,2-c]pyridin-2-yl)-2-fluoro-6'-(1-methyl-1H-pyrazol-4-yl)-[3,4']bipyridinyl-3'-ylamine

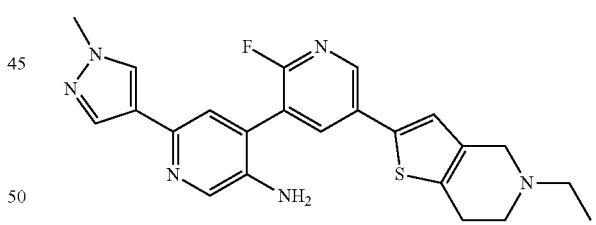

A degassed mixture of 6'-chloro-5-(5-ethyl-4,5,6,7-tetrahydro thieno[3,2-c]pyridin-2-yl)-2-fluoro-[3,4']bipyridinyl-3'-ylamine (1.05 g, 2.70 mmol), 1-methyl-4-(4,4,5,5-tetramethyl-1,3,2-dioxaborolan-2-yl)-1H-pyrazole (842 mg, 4.10 mmol), 1,1'-[bis(diphenylphosphino)ferrocene]dichloropalladium(II) (221 mg, 0.27 mmol) in 1N aqueous potassium fluoride solution (9 mL) and acetonitrile (9 mL) was heated under microwave irradiation at 120° C. for 20 minutes. The cooled reaction mixture was diluted with ethyl acetate (100 mL) then washed with water (75 mL). The organic phase was dried over sodium sulfate, filtered and evaporated in vacuo to afford a residue that was purified by flash chromatography (silica, 40 g column, ISCO, 0-10% methanol in DCM) to afford the title compound as a white solid (641 mg, 55%). NMR (CDCl$_3$ plus CD$_3$OD, 300 MHz): 8.44 (dd, J=2.5, 1.1 Hz, 1H), 8.13 (d, J=0.6 Hz, 1H), 8.07 (dd, J=8.7, 2.5 Hz, 1H), 7.89 (s, 1H), 7.85 (d, J=0.8 Hz, 1H), 7.32 (s, 1H), 7.12 (s, 1H), 3.94 (s, 3H), 3.61 (s, 2H), 3.00-2.94 (m, 2H), 2.93-2.85 (m, 2H), 2.68 (q, J=7.2 Hz, 2H), 1.21 (t, J=7.2 Hz, 3H).

Step 4: 3-(5-Ethyl-4,5,6,7-tetrahydrothieno[3,2-c]pyridin-2-yl)-6-(1-methyl-1H-pyrazol-4-yl)-9H-dipyrido[2,3-b;4',3'-d]pyrrole

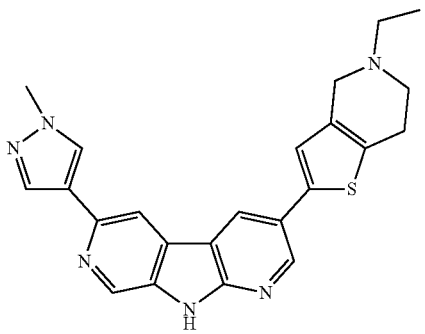 [SMILES: CCN1CCc2sc(-c3cnc4[nH]c5cnc(-c6cnn(C)c6)cc5c4c3)cc2C1]

A solution of sodium bis(trimethylsilyl)amide (1N solution in THF, 4.5 mL, 4.5 mmol) was added dropwise over 10 minutes to a solution of 5-(5-ethyl-4,5,6,7-tetrahydrothieno[3,2-c]pyridin-2-yl)-2-fluoro-6'-(1-methyl-1H-pyrazol-4-yl)-[3,4']bipyridinyl-3'-ylamine (638 mg, 1.50 mmol) in anhydrous THF (26 mL). After 30 minutes, the reaction was quenched by the addition of aqueous saturated aqueous potassium fluoride solution (10 mL). The resultant brown solution was partitioned between DCM (75 mL) and brine (50 mL). The organic phase was separated, dried over sodium sulfate, filtered and evaporated in vacuo to afford a residue that was purified by flash chromatography (silica, 50 g column, Biotage, 0-15% methanol in DCM) to afford the title compound as a white solid (96 mg, 16%). $^1$H NMR (CDCl$_3$ plus CD$_3$OD, 300 MHz): 8.82 (s, 1H), 8.76 (d, J=2.2 Hz, 1H), 8.66 (d, J=2.2 Hz, 1H), 8.29 (s, 1H), 8.07 (s, 1H), 8.05 (s, 1H), 7.11 (s, 1H), 4.00 (s, 3H), 3.64 (s, 2H), 3.02-2.95 (m, 2H), 2.93-2.86 (m, 2H), 2.70 (q, J=7.2 Hz, 2H), 1.24 (t, J=7.2 Hz, 3H).

Example 371

3-(3,5-Dimethoxy-4-piperidin-1-ylmethylphenyl)-6-(1-methyl-1H-pyrazol-4-yl)-9H-dipyrido[2,3-b;4',3'-d]pyrrole

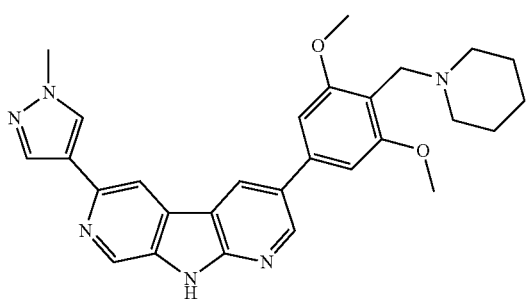 [SMILES: COc1cc(-c2cnc3[nH]c4cnc(-c5cnn(C)c5)cc4c3c2)cc(OC)c1CN1CCCCC1]

Step 1: 6'-Chloro-5-(3,5-dimethoxy-4-piperidin-1-ylmethylphenyl)-2-fluoro-[3,4']bipyridinyl-3'-ylamine

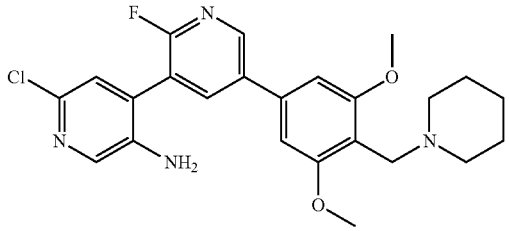 [SMILES: COc1cc(-c2cnc(F)c(-c3cc(Cl)ncc3N)c2)cc(OC)c1CN1CCCCC1]

A degassed mixture of 6'-chloro-2-fluoro-5-(4,4,5,5-tetramethyl-[1,3,2]dioxaborolan-2-yl)-[3,4']bipyridinyl-3'-ylamine (630 mg, 1.80 mmol), trifluoromethanesulfonic acid 3,5-dimethoxy-4-piperidin-1-ylmethylphenyl ester (1.06 g, 1.98 mmol), 1,1'-[bis(diphenylphosphino)ferrocene]dichloropalladium(II) (147 mg, 0.18 mmol) in 1N aqueous potassium fluoride solution (10 mL) and acetonitrile (8 mL) was heated under microwave irradiation at 100° C. for 30 minutes. The cooled reaction mixture was partitioned between DCM (50 mL) and brine (50 mL). The organic phase was separated, dried over sodium sulfate, filtered and evaporated in vacuo to afford a residue that was purified by flash chromatography (silica, 20 g column, ISCO, 0-10% methanol in DCM) to afford the title compound as a white solid (830 mg, 76%). $^1$H NMR (CDCl$_3$ plus CD$_3$OD, 300 MHz): 8.52-8.57 (m, 1H), 8.12-8.19 (m, 1H), 7.98 (s, 1H), 7.19 (s, 1H), 6.91 (s, 2H), 4.34 (s, 2H), 4.01 (s, 6H), 2.87-3.64 (v br m, 4H), 1.63-2.02 (s, 6H).

Step 2: 5-(3,5-Dimethoxy-4-piperidin-1-ylmethylphenyl)-2-fluoro-6'-(1-methyl-1H-pyrazol-4-yl)-[3,4']bipyridinyl-3'-ylamine

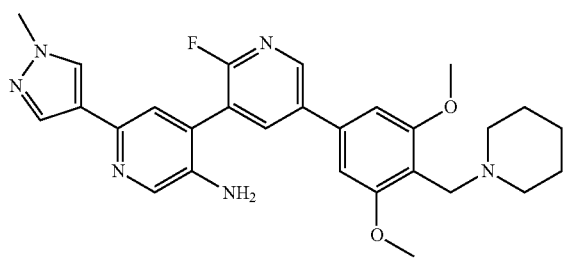 [SMILES: COc1cc(-c2cnc(F)c(-c3cc(-c4cnn(C)c4)ncc3N)c2)cc(OC)c1CN1CCCCC1]

A degassed mixture of 6'-chloro-5-(3,5-dimethoxy-4-piperidin-1-ylmethylphenyl)-2-fluoro-[3,4']bipyridinyl-3'-ylamine (830 mg, 1.40 mmol), 1-methyl-4-(4,4,5,5-tetramethyl-1,3,2-dioxaborolan-2-yl)-1H-pyrazole (577 mg, 2.78 mmol), 1,1'-[bis(diphenylphosphino)ferrocene]dichloropalladium(II) (151 mg, 0.19 mmol) in 1N aqueous potassium fluoride solution (10 mL) and acetonitrile (6 mL) was heated under microwave irradiation at 100° C. for 20 minutes. The cooled reaction mixture was diluted with ethyl acetate (100 mL) then washed with water (75 mL). The organic phase was separated, dried over sodium sulfate, filtered and evaporated in vacuo to afford a residue that was purified by flash chromatography (silica, 20 g column, ISCO, 0-10% methanol in DCM) to afford the title compound as a white solid (494 mg, 54%). $^1$H NMR (CDCl$_3$ plus CD$_3$OD, 300 MHz): 8.55 (dd, J=2.5, 1.0 Hz, 1H), 8.22 (dd, J=8.8, 2.5 Hz, 1H), 8.16 (d, J=0.6 Hz, 1H), 7.92 (s, 1H), 7.85 (d, J=0.8 Hz, 1H), 7.37 (s, 1H), 6.95 (s, 2H), 4.35 (s, 2H), 4.01 (s, 6H), 3.95 (s, 3H), 3.61-3.22 (br m, 2H), 3.19-2.90 (br m, 2H), 2.02-1.47 (br m, 6H).

Step 3: 3-(3,5-Dimethoxy-4-piperidin-1-ylmethyl-phenyl)-6-(1-methyl-1H-pyrazol-4-yl)-9H-dipyrido[2,3-b;4',3'-d]pyrrole

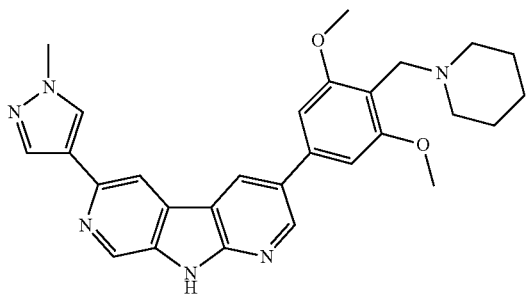 [SMILES: COc1cc(-c2cnc3[nH]c4cnc(-c5cnn(C)c5)cc4c3c2)cc(OC)c1CN1CCCCC1]

A solution of 5-(3,5-dimethoxy-4-piperidin-1-ylmethyl-phenyl)-2-fluoro-6'-(1-methyl-1H-pyrazol-4-yl)-[3,4']bipyridinyl-3'-ylamine (490 mg, 0.98 mmol) in anhydrous THF (16.7 mL) was added dropwise over 10 minutes to a solution of sodium bis(trimethylsilyl)amide (1N solution in THF, 2.9 mL, 2.9 mmol). After 30 minutes, the reaction was quenched by the addition of saturated aqueous potassium fluoride solution (5 mL) and concentrated under reduced pressure to afford a brown residue. The resultant brown residue was partitioned between ethyl acetate (75 mL) and water (50 mL). The organic phase was separated, dried over sodium sulfate, filtered and evaporated in vacuo to afford a residue that was purified by flash chromatography (silica, 50 g column, Biotage, 0-20% methanol in DCM) to afford the title compound as an off-white solid (69 mg, 15%). ¹H NMR (CDCl₃ plus CD₃OD, 300 MHz): 8.86 (d, J=1.1 Hz, 1H), 8.84-8.80 (m, 2H), 8.37 (d, J=1.1 Hz, 1H), 8.09 (s, 1H), 8.06 (d, J=0.8 Hz, 1H), 6.91 (s, 2H), 4.01 (s, 3H), 3.96 (s, 6H), 3.74 (s, 2H), 2.64-2.50 (m, 4H), 1.65-1.56 (m, 4H), 1.49-1.37 (m, 2H).

Example 372

3-[4-(4,4-Dimethylpiperidin-1-ylmethyl)-phenyl]-6-(1-methyl-1H-pyrazol-4-yl)-9H-dipyrido[2,3-b;4',3'-d]pyrrole

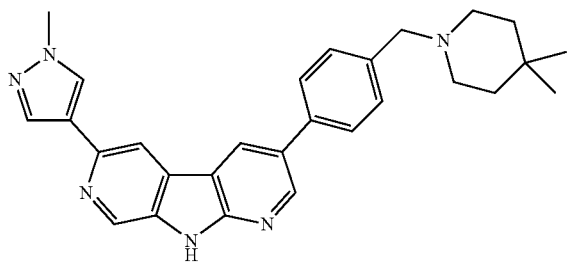 [SMILES: Cn1cc(-c2cc3c(cn2)[nH]c2ncc(-c4ccc(CN5CCC(C)(C)CC5)cc4)cc23)cn1]

Step 1: 6-Bromo-3-[4-(4,4-dimethylpiperidin-1-ylmethyl)-phenyl]-9H-dipyrido[2,3-b;4',3'-d]pyrrole

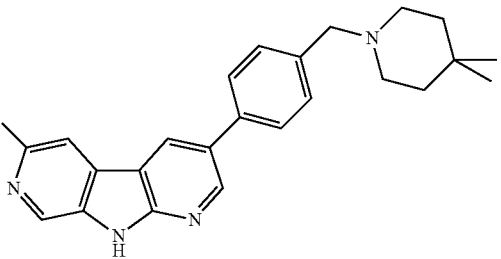

A degassed mixture of 4,4-dimethyl-1-[4-(4,4,5,5-tetramethyl-[1,3,2]dioxaborolan-2-yl)-benzyl]-piperidine (836 mg, 2.5 mmol), 3-iodo-6-bromo-9H-dipyrido[2,3-b;4',3'-d]pyrrole (500 mg, 1.3 mmol), 1,1'-[bis(diphenylphosphino)ferrocene]dichloropalladium(II) (109 mg, 0.13 mmol) in 1N aqueous potassium fluoride solution (25 mL) and acetonitrile (25 mL) was heated at 80° C. for 18 h. The cooled reaction mixture was diluted with ethyl acetate (100 mL) then washed with water (75 mL). The organic phase was separated, dried over sodium sulfate, filtered and evaporated in vacuo to afford a residue that was purified by flash chromatography (silica, 120 g column, ISCO, 0-15% methanol in DCM) to afford the title compound as an off-white solid (190 mg, 33%). ¹H NMR (CDCl₃ plus CD₃OD, 300 MHz): 8.85 (d, J=2.2 Hz, 1H), 8.76 (d, J=2.2 Hz, 1H), 8.70 (d, J=0.9 Hz, 1H), 8.32 (d, J=0.9 Hz, 1H), 7.73 (d, J=8.0 Hz, 2H), 7.54 (d, J=8.0 Hz, 2H), 3.82 (s, 2H), 2.77-2.63 (m, 4H), 1.52 (t, J=5.6 Hz, 4H), 1.00 (s, 6H).

Step 2: 3-[4-(4,4-Dimethylpiperidin-1-ylmethyl)-phenyl]-6-(1-methyl-1H-pyrazol-4-yl)-9H-dipyrido[2,3-b;4',3'-d]pyrrole

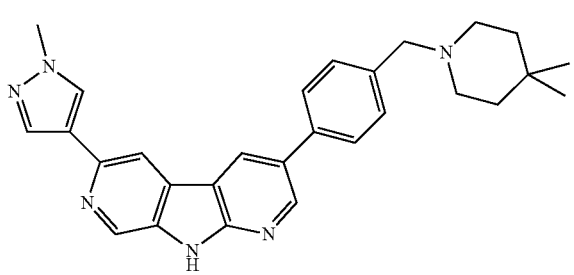 [SMILES: Cn1cc(-c2cc3c(cn2)[nH]c2ncc(-c4ccc(CN5CCC(C)(C)CC5)cc4)cc23)cn1]

A degassed mixture of 6-bromo-3-[4-(4,4-dimethylpiperidin-1-ylmethyl)-phenyl]-9H-dipyrido[2,3-b;4',3'-d]pyrrole (200 mg, 0.45 mmol), 1-methyl-4-(4,4,5,5-tetramethyl-1,3,2-dioxaborolan-2-yl)-1H-pyrazole (185 mg, 0.89 mmol), 1,1'-[bis(diphenylphosphino)ferrocene]dichloropalladium (II) (37 mg, 0.05 mmol) in 2N aqueous sodium carbonate solution (5 mL) and acetonitrile (5 mL) was heated under microwave irradiation at 130° C. for 20 minutes. The cooled reaction mixture was diluted with ethyl acetate (100 mL) and washed with water (75 mL). The organic phase was separated, dried over sodium sulfate, filtered and evaporated in vacuo to afford a residue that was purified by flash chromatography (silica, 10 g column, Biotage, 0-15% methanol in DCM) to afford the title compound as a white solid (78 mg, 38%). ¹H NMR (CDCl₃ plus CD₃OD, 300 MHz): 8.85 (d, J=1.1 Hz, 1H), 8.81 (d, J=2.2 Hz, 1H), 8.79 (d, J=2.2 Hz, 1H), 8.33 (d, J=1.1 Hz, 1H), 8.08 (s, 1H), 8.06 (d, J=08 Hz, 1H), 7.70 (d, J=8.1 Hz, 2H), 7.49 (d, J=8.1 Hz, 2H), 4.00 (s, 3H), 3.63 (s, 2H), 2.51 (t, J=5.0 Hz, 4H), 1.46 (t, J=5.6 Hz, 4H), 0.96 (s, 6H).

Example 373

3-[4-((2S,6R)-2,6-Dimethyl-piperidin-1-ylmethyl)-phenyl]-6-(1-methyl-1H-pyrazol-4-yl)-9H-dipyrido[2,3-b;4',3'-d]pyrrole

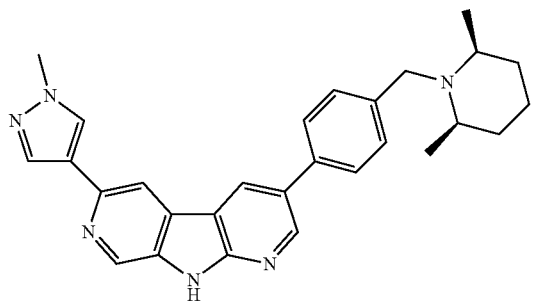 [SMILES: C[C@@H]1CCC[C@H](C)N1Cc1ccc(-c2cnc3[nH]c4cnc(-c5cnn(C)c5)cc4c3c2)cc1]

Step 1: 6-Bromo-3-[4(2S,6R)-2,6-dimethylpiperidin-1-ylmethyl)-phenyl]-9H-dipyrido[2,3-b;4',3'-d]pyrrole

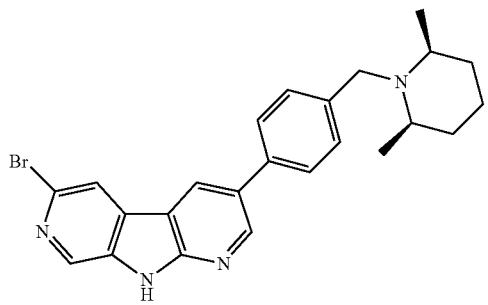 [SMILES: C[C@@H]1CCC[C@H](C)N1Cc1ccc(-c2cnc3[nH]c4cnc(Br)cc4c3c2)cc1]

A degassed mixture of (2S,6R)-2,6-dimethyl-1-[4-(4,4,5,5-tetramethyl-[1,3,2]dioxaborolan-2-yl)benzyl]piperidine (685 mg, 2.08 mmol), 3-iodo-6-bromo-9H-dipyrido[2,3-b;4',3'-d]pyrrole (389 mg, 1.04 mmol), 1,1'[bis(diphenylphosphino)ferrocene]dichloropalladium(II) (127 mg, 0.16 mmol) in saturated sodium carbonate solution (1 mL) and THF (10 mL) was heated under reflux for 18 h. The cooled reaction mixture was diluted with DCM (50 mL) and washed with water (25 mL). The organic phase was separated, dried over sodium sulfate, filtered and evaporated in vacuo to afford a residue that was purified by flash chromatography (silica, 40 g column, ISCO, 0-15% methanol in DCM) to afford the title compound as an off-white solid (181 mg, 39%). ¹H NMR (CDCl₃ plus CD₃OD, 300 MHz): 8.85 (d, J=2.2 Hz, 1H), 8.72 (d, J=2.2 Hz, 1H), 8.69 (d, J=0.9 Hz, 1H), 8.29 (d, J=0.9 Hz, 1H), 7.68-7.63 (d, J=8.1 Hz, 2H), 7.56-7.50 (m, 2H), 4.00 (s, 2H), 2.65-2.51 (m, 2H), 1.72-1.56 (m, 4H), 1.46-1.30 (m, 2H), 1.25 (d, J=6.2 Hz, 6H).

Step 2: 3-[4-(2S,6R)-2,6-Dimethylpiperidin-1-ylmethyl)-phenyl]-6-(1-methyl-1H-pyrazol-4-yl)-9H-dipyrido[2,3-b;4',3'-d]pyrrole

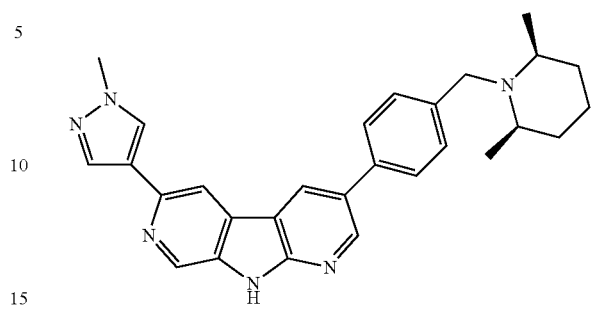

A degassed mixture of 6-bromo-3-[4-((2S,6R)-2,6-dimethyl-piperidin-1-ylmethyl)-phenyl]-9H-dipyrido[2,3-b;4',3'-d]pyrrole (223 mg, 0.50 mmol), 1-methyl-4-(4,4,5,5-tetramethyl-1,3,2-dioxaborolan-2-yl)-1H-pyrazole (208 mg, 1.0 mmol), 1,1'-[bis(diphenylphosphino)ferrocene]dichloropalladium(II) (41 mg, 0.05 mmol) in 2N aqueous sodium carbonate solution (6 mL) and acetonitrile (6 mL) was heated under microwave irradiation at 130° C. for 20 minutes. The cooled reaction mixture was diluted with ethyl acetate (100 mL) and washed with water (75 mL). The organic phase was separated, dried over sodium sulfate, filtered and evaporated in vacuo to afford a residue that was purified by flash chromatography (silica, 25 g column, Biotage, 0-15% methanol in DCM) to afford the title compound as a white solid (70 mg, 31%). ¹H NMR (CDCl₃ plus CD₃OD, 300 MHz): 8.85 (d, J=1.1 Hz, 1H), 8.82-8.77 (m, 2H), 8.33 (d, J=1.1 Hz, 1H), 8.08 (s, 1H), 8.06 (d, J=0.8 Hz, 1H), 7.71-7.65 (m, 2H), 7.56-7.51 (m, 2H), 4.00 (d, J=1.9 Hz, 5H), 2.65-2.52 (m, 2H), 1.72-1.60 (m, 3H), 1.47-1.30 (m, 3H), 1.25 (d, J=6.2 Hz, 6H).

Example 374

6-(1-Methyl-1H-pyrazol-4-yl)-3-(4-morpholin-4-ylmethyl-phenyl)-9H-dipyrido[2,3-b;4',3'-d]pyrrole

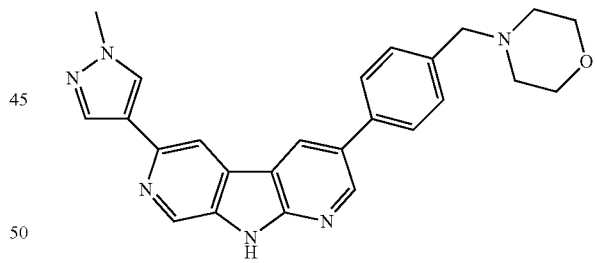

Step 1: 6-Bromo-3-(4-morpholin-4-ylmethylphenyl)-9H-dipyrido[2,3-b;4',3'-d]pyrrole

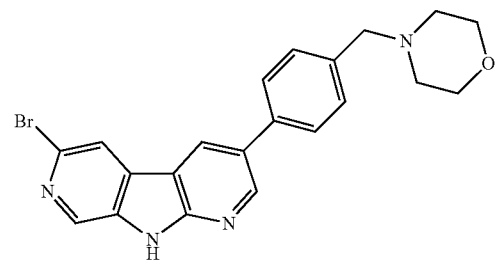 [SMILES: Brc1cc2c(cn1)[nH]c1ncc(-c3ccc(CN4CCOCC4)cc3)cc12]

A degassed mixture of 4-(4-morpholinomethyl)phenylboronic acid pinacol ester (486 mg, 1.61 mmol), 3-iodo-6-bromo-9H-dipyrido[2,3-b;4',3'-d]pyrrole (400 mg, 1.07 mmol), 1,1'-[bis(diphenylphosphino)ferrocene]dichloropalladium(II) (131 mg, 0.16 mmol) in 2N aqueous sodium carbonate solution (8 mL) and 2-methyltetrahyrdofuran (16 mL) was heated at 85° C. for 18 h. The cooled reaction mixture was diluted with ethyl acetate (100 mL) and washed with water (75 mL). The organic phase was separated, dried over sodium sulfate, filtered and evaporated in vacuo to afford a residue that was purified by flash chromatography (silica, 50 g column, Biotage, 0-15% methanol in DCM) to afford the title compound as an off-white solid (137 mg, 30%). $^1$H NMR (CDCl$_3$, 300 MHz): 12.41 (s, 1H), 9.04 (d, J=2.3 Hz, 1H), 8.95 (d, J=2.3 Hz, 1H), 8.72 (d, J=1.0 Hz, 1H), 8.53 (s, 1H), 7.76 (d, J=8.0 Hz, 2H), 7.47 (d, J=8.0 Hz, 2H), 3.65-3.56 (m, 4H), 3.53 (s, 2H), 2.44-2.29 (m, 4H).

Step 2: 6-(1-Methyl-1H-pyrazol-4-yl)-3-(4-morpholin-4-ylmethyl-phenyl)-9H-dipyrido[2,3-b;4',3'-d]pyrrole

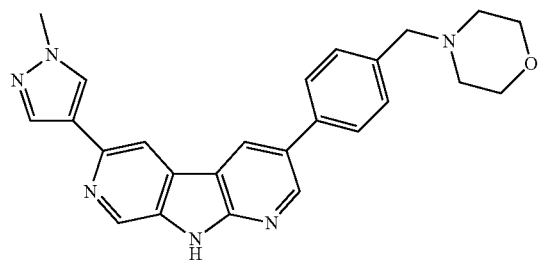 [SMILES: Cn1cc(-c2cc3c(cn2)[nH]c2ncc(-c4ccc(CN5CCOCC5)cc4)cc23)cn1]

A degassed mixture of 6-bromo-3-(4-morpholin-4-ylmethyl-phenyl)-9H-dipyrido[2,3-b;4',3'-d]pyrrole (245 mg, 0.58 mmol), 1-methyl-4-(4,4,5,5-tetramethyl-1,3,2-dioxaborolan-2-yl)-1H-pyrazole (241 mg, 1.16 mmol), 1,1'-[bis(diphenylphosphino)ferrocene]dichloropalladium(II) (47 mg, 0.06 mmol) in 2N aqueous sodium carbonate solution (7 mL) and acetonitrile (7 mL) was heated under microwave irradiation at 130° C. for 20 minutes. The cooled reaction mixture was diluted with ethyl acetate (75 mL) and washed with water (50 mL). The organic phase was separated, dried over sodium sulfate, filtered and evaporated in vacuo to afford a residue that was purified by flash chromatography (silica, 10 g column, Biotage, 0-10% methanol in DCM) to afford the title compound as a white solid (61 mg, 25%). $^1$H NMR (CDCl$_3$, 300 MHz): 8.86 (d, J=1.1 Hz, 1H), 8.81 (d, J=2.2 Hz, 1H), 8.77 (d, J=2.2 Hz, 1H), 8.31 (d, J=1.1 Hz, 1H), 8.07 (s, 1H), 8.05 (d, J=0.8 Hz, 1H), 7.73-7.67 (m, 2H), 7.54-7.48 (m, 2H), 4.01 (s, 3H), 3.80-3.73 (m, 4H), 3.63 (s, 2H), 2.60-2.52 (m, 4H).

Example 375

6-(1-Methyl-1H-pyrazol-4-yl)-3-[4-(4-trifluoromethylpiperidin-1-ylmethyl)-phenyl]-9H-dipyrido[2,3-b;4',3'-d]pyrrole

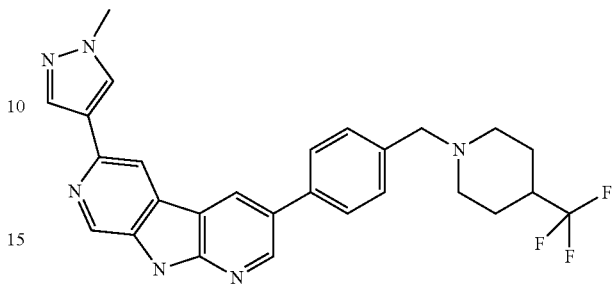

Step 1: 1-[4-(4,4,5,5-Tetramethyl-[1,3,2]dioxaborolan-2-yl)-benzyl]-4-trifluoromethylpiperidine

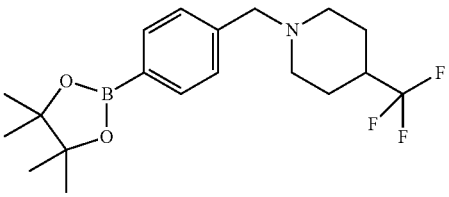 [SMILES: CC1(C)OB(c2ccc(CN3CCC(C(F)(F)F)CC3)cc2)OC1(C)C]

A degassed mixture of 1-(4-bromobenzyl)-4-trifluoromethylpiperidine (1.0 g, 3.1 mmol), bis(pinacolato)diborane (0.95 g, 3.7 mmol), 1,1'-[bis(diphenylphosphino)ferrocene]dichloropalladium(II) (0.13 g, 0.16 mmol) and potassium acetate (0.91 g, 9.3 mmol) in 1,4-dioxane (15 mL) and DMSO (1 mL) was heated under microwave irradiation at 150° C. for 30 minutes. The cooled reaction mixture was partitioned between ethyl acetate and water and the organic phase was separated, dried over sodium sulfate, filtered and evaporated to afford the title compound as a black oil (1.9 g) which was used without further purification. $^1$H NMR (CDCl$_3$, 300 MHz): 7.79-7.74 (m, 2H), 7.32 (d, J=7.7 Hz, 2H), 3.71 (s, 2H), 3.01-2.91 (m, 2H), 2.04-1.90 (m, 3H), 1.85-1.76 (m, 2H), 1.72-1.60 (m, 2H), 1.34 (s, 12H). LCMS (Method B): R$_T$=2.53 min, M+H$^+$=370.

Step 2: 6-Bromo-3-[4-(4-trifluoromethylpiperidin-1-ylmethyl)-phenyl]-9H-dipyrido[2,3-b;4',3'-d]pyrrole

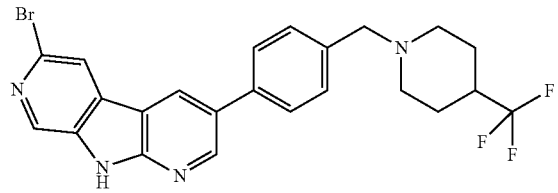 [SMILES: FC(F)(F)C1CCN(Cc2ccc(-c3cnc4[nH]c5cnc(Br)cc5c4c3)cc2)CC1]

A degassed mixture of 6-bromo-3-iodo-9H-dipyrido[2,3-b;4',3'-d]pyrrole (0.64 g, 1.7 mmol), 1-[4-(4,4,5,5-tetramethyl-[1,3,2]dioxaborolan-2-yl)-benzyl]-4-trifluoromethyl piperidine (1.14 g, 3.1 mmol) and 1,1'-[bis(diphenyl phosphino)ferrocene]dichloropalladium(II) (0.21 g, 0.26 mmol) in 2-methyl-THF (26 mL) and saturated aqueous sodium carbonate solution (12 mL) was heated at 85° C. for 16 h. The cooled reaction mixture was filtered through celite and partitioned between DCM and water and the phases were separated. The organic phase was dried over sodium sulfate, filtered and evaporated then the residue was purified by flash chromatography (silica, 40 g column, ISCO, 0-15% methanol in DCM). Trituration of the resultant residue with acetonitrile afforded the title compound as a tan solid (57 mg, 7%). NMR (CD$_3$OD, 300 MHz): 8.84 (d, J=2.2 Hz, 1H), 8.70-8.67 (m, 2H), 8.27 (d, J=1.0 Hz, 1H), 7.67 (d, J=8.0 Hz, 2H), 7.49 (d, J=8.0 Hz, 2H), 3.63 (s, 2H), 3.11-3.02 (m, 2H), 2.14-2.02 (m, 3H), 1.94-1.84 (m, 2H), 1.76-1.59 (m, 2H. LCMS (Method B): R$_T$=2.55 min, M+H$^+$=489.

Step 3: 6-(1-Methyl-1H-pyrazol-4-yl)-3-[4-(4-trifluoromethylpiperidin-1-ylmethyl)-phenyl]-9H-dipyrido[2,3-b;4',3'-d]pyrrole

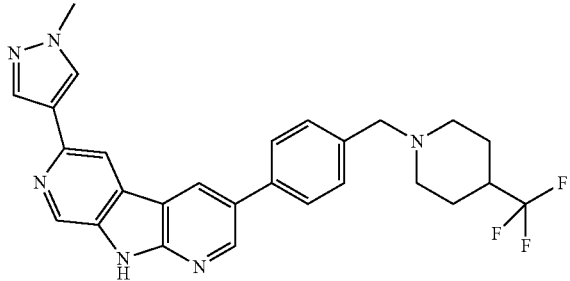 [SMILES: Cn1cc(-c2cc3c(cn2)[nH]c2ncc(-c4ccc(CN5CCC(C(F)(F)F)CC5)cc4)cc23)cn1]

A degassed mixture of 6-bromo-3-[4-(4-trifluoromethylpiperidin-1-ylmethyl)-phenyl]-9H-dipyrido[2,3-b;4',3'-d]pyrrole (0.15 g, 0.30 mmol), 1-methyl-4-(4,4,5,5-tetramethyl-[1,3,2]dioxaborolan-2-yl)-1H-pyrazole (0.13 g, 0.60 mmol) and 1,1'-[bis(diphenyl phosphino)ferrocene]dichloropalladium(II)(25 mg, 0.03 mmol) in acetonitrile (3 mL) and saturated aqueous sodium carbonate solution (3 mL) was heated under microwave irradiation at 130° C. for 30 minutes. The cooled reaction mixture was partitioned between DCM and water then separated on a hydrophobic frit. The organic phase was evaporated then the resultant residue was purified by flash chromatography (silica, 12 g column, ISCO, 0-10% methanol in DCM) to afford a residue which was purified by HPLC (C18 column, 50-98% MeCN in water (plus 20 mM triethylamine) to afford the title compound (46 mg, 31%). $^1$H NMR (DMSO-D$_6$, 400 MHz): 12.15 (s, 1H), 8.94-8.88 (m, 2H), 8.86 (d, J=1.1 Hz, 1H), 8.51 (d, J=1.1 Hz, 1H), 8.21 (s, 1H), 7.99 (d, J=0.8 Hz, 1H), 7.78 (d, J=8.0 Hz, 2H), 7.46 (d, J=8.0 Hz, 2H), 3.92 (s, 3H), 3.56 (s, 2H), 2.99-2.88 (m, 2H), 2.39-2.19 (m, 1H), 2.00 (t, J=1.5 Hz, 2H), 1.85-1.94 (m, 2H), 1.57-1.38 (m, 2H). LCMS (Method A): R$_T$=5.22 min, M+H$^+$=491.

Example 376

3-[4-(4-Methoxypiperidin-1-ylmethyl)-phenyl]-6-(1-methyl-1H-pyrazol-4-yl)-9H-dipyrido[2,3-b;4',3'-d]pyrrole

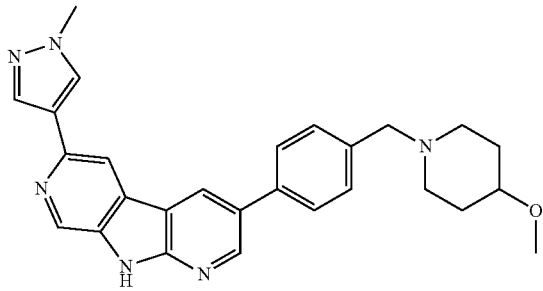 [SMILES: COC1CCN(Cc2ccc(-c3cnc4[nH]c5cnc(-c6cnn(C)c6)cc5c4c3)cc2)CC1]

Step 1: 4-Methoxy-1-[4-(4,4,5,5-tetramethyl-[1,3,2]dioxaborolan-2-yl)-benzyl]-piperidine

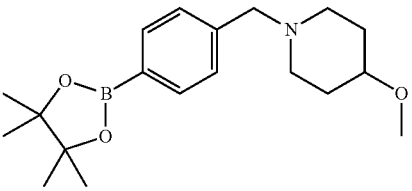

A degassed mixture of 1-(4-bromobenzyl)-4-methoxypiperidine (0.90 g, 3.18 mmol), bis(pinacolato)diborane (0.89 g, 3.5 mmol), 1,1'-[bis(diphenyl phosphino)ferrocene]dichloropalladium(II) (0.13 g, 0.16 mmol) and potassium acetate (0.94 g, 9.5 mmol) in 1,4-dioxane (16 mL) was heated under microwave irradiation at 150° C. for 30 minutes. The cooled reaction mixture was partitioned between ethyl acetate and water, the organic phase was separated, dried over sodium sulfate, filtered through celite and evaporated to afford the title compound as a brown oil (1.07 g) which was used without further purification. $^1$H NMR (CDCl$_3$, 300 MHz): 7.78 (d, J=7.5 Hz, 2H), 7.38 (d, J=7.5 Hz, 2H), 3.71 (s, 2H), 3.64 (br s, 1H), 3.31 (s, 3H), 2.83-2.71 (m, 2H), 2.34 (br s, 2H), 1.98 (br s, 2H), 1.69 (br s, 2H), 1.34 (s, 12H). LCMS (Method G): R$_T$=3.00 min, M+H$^+$=332.

Step 2: 6-Bromo-3-[4-(4-methoxypiperidin-1-ylmethyl)-phenyl]-9H-dipyrido[2,3-b;4',3'-d]pyrrole

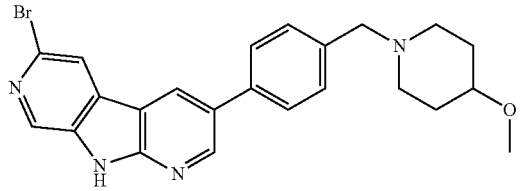 [SMILES: COC1CCN(Cc2ccc(-c3cnc4[nH]c5cnc(Br)cc5c4c3)cc2)CC1]

A degassed mixture of 6-bromo-3-iodo-9H-dipyrido[2,3-b;4',3'-d]pyrrole (0.50 g, 1.3 mmol), 4-methoxy-1-[4-(4,4,5,5-tetramethyl-[1,3,2]dioxaborolan-2-yl)-benzyl]-piperidine (0.80 g, 2.4 mmol) and 1,1'-[bis(diphenylphosphino)ferrocene]dichloropalladium(II) (0.16 g, 0.2 mmol) in 2-methyl THF (20 mL) and saturated aqueous sodium carbonate (10 mL) was heated at 85° C. for 3 h. The material was partitioned between DCM, water and methanol and the phases were separated. The organic phase was separated, dried over sodium sulfate, filtered and evaporated to afford a residue which was purified by flash chromatography (silica, 50 g column, Biotage, 0-10% methanol in DCM). The resultant material was triturated with methanol to afford the title compound as a tan solid (0.165 g, 28%). $^1$H NMR (CDCl$_3$ plus CD$_3$OD, 300 MHz): 8.84 (d, J=2.2 Hz, 1H), 8.73 (d, J=2.2 Hz, 1H), 8.69 (d, J=0.9 Hz, 1H), 8.30 (d, J=1.0 Hz, 1H), 7.68 (d, J=8.0 Hz, 2H), 7.49 (d, J=8.0 Hz, 2H), 3.63 (s, H), 2.89-2.76 (m, 2H), 2.37-2.22 (m, 2H), 2.02-1.89 (m, 2H), 1.73-1.56 (m, 2H). LCMS (Method G): R$_T$=3.30 min, M+H$^+$=451.

Step 3: 3-[4-(4-Methoxypiperidin-1-ylmethyl)-phenyl]-6-(1-methyl-1H-pyrazol-4-yl)-9H-dipyrido[2,3-b;4',3'-d]pyrrole

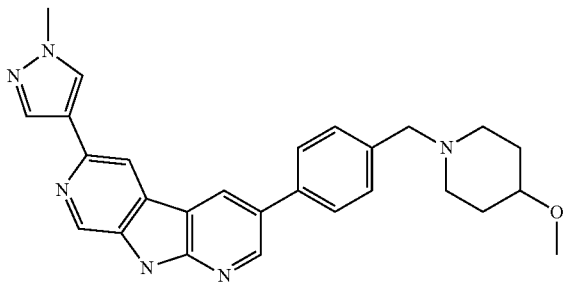 [SMILES: COC1CCN(Cc2ccc(-c3cnc4[nH]c5cnc(-c6cnn(C)c6)cc5c4c3)cc2)CC1]

A degassed mixture of 6-bromo-3-[4-(4-methoxypiperidin-1-ylmethyl)-phenyl]-9H-dipyrido[2,3-b;4',3'-d]pyrrole (0.16 g, 0.36 mmol), 1-methyl-4-(4,4,5,5-tetramethyl-[1,3,2]dioxaborolan-2-yl)-1H-pyrazole (0.15 g, 0.72 mmol) and 1,1'-[bis(diphenyl phosphino)ferrocene]dichloropalladium (II) (29 mg, 0.036 mmol) in acetonitrile (3.6 mL) and saturated aqueous sodium carbonate solution (3.6 mL). The reaction mixture was heated under microwave irradiation at 130° C. for 20 minutes. The cooled reaction mixture was partitioned between DCM and water. The organic phase was dried over sodium sulfate, filtered and evaporated and the resultant residue was purified by flash chromatography (silica, 12 g column, ISCO, 0-15% methanol in DCM) to afford the title compound as a yellow solid (68 mg, 42%). $^1$H NMR (CDCl$_3$ plus CD$_3$OD, 300 MHz): 8.86 (d, J=1.1 Hz, 1H), 8.81 (d, J=2.2 Hz, 1H), 8.77 (d, J=2.2 Hz, 1H), 8.30 (d, J=1.1 Hz, 1H), 8.06-8.04 (m, 2H), 7.71 (d, J=7.9 Hz, 2H), 7.52 (d, J=2.0 Hz, 2H), 4.01 (s, 3H), 3.74-3.63 (m, 2H), 2.94-2.79 (m, 2H), 2.47-2.25 (m, 2H), 2.04-1.90 (m, 2H), 1.78-1.58 (m, 2H). LCMS (Method A): R$_T$=4.76 min, M+H$^+$=453.

Example 377

3-(3-Methoxy-4-piperidin-1-ylmethyl-phenyl)-6-(1-methyl-1H-pyrazol-4-yl)-9H-dipyrido[2,3-b;4',3'-d]pyrrole

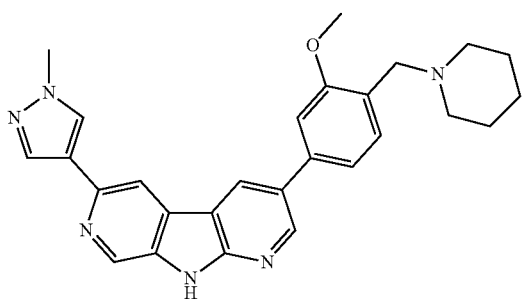 [SMILES: COc1cc(-c2cnc3[nH]c4cnc(-c5cnn(C)c5)cc4c3c2)ccc1CN1CCCCC1]

Step 1: 6-Bromo-3-(3-methoxy-4-piperidin-1-ylmethylphenyl)-9H-dipyrido[2,3-b;4',3'-d]pyrrole

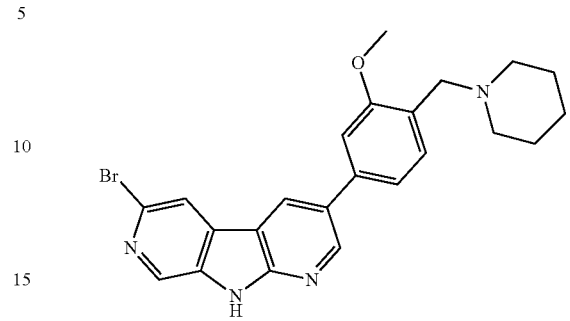

A degassed mixture of 1-[2-methoxy-4-(4,4,5,5-tetramethyl-[1,3,2]dioxaborolan-2-yl)-benzyl]-piperidine (885 mg, 2.7 mmol), 3-iodo-6-bromo-9H-dipyrido[2,3-b;4',3'-d]pyrrole (500 mg, 1.3 mmol), 1,1'-[bis(diphenylphosphino)-ferrocene]dichloropalladium(II) (163 mg, 0.2 mmol) in 2N aqueous sodium carbonate solution (10 mL) and 2-methyltetrahydrofuran (20 mL) was heated at 85° C. for 18 h. The cooled reaction mixture was diluted with DCM (100 mL) and washed with water (75 mL). The organic phase was separated, dried over sodium sulfate, filtered and evaporated in vacuo to afford a residue (357 mg, 61%) that was used in the next step without purification. $^1$H NMR (CDCl$_3$, 300 MHz): 8.83 (d, J=2.0 Hz, 1H), 8.70 (s, 1H), 8.63 (d, J=2.0 Hz, 1H), 8.24 (s, 1H), 7.45 (d, J=7.8 Hz, 1H), 7.25 (d, J=7.8 Hz, 1H), 7.14 (s, 1H), 3.96 (s, 3H), 3.65 (s, 2H), 2.56-2.48 (m, 4H), 1.67-1.59 (m, 4H), 1.52-1.41 (m, 2H).

Step 2: 3-(3-Methoxy-4-piperidin-1-ylmethylphenyl)-6-(1-methyl-1H-pyrazol-4-yl)-9H-dipyrido[2,3-b;4',3'-d]pyrrole

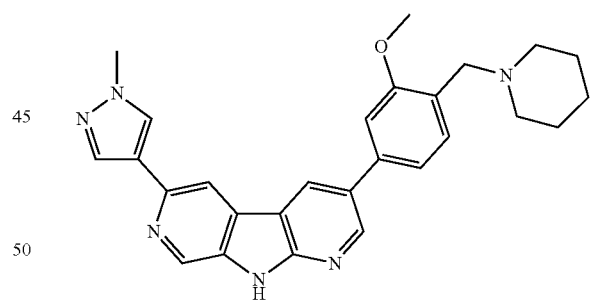

A degassed mixture of 6-bromo-3-(3-methoxy-4-piperidin-1-ylmethylphenyl)-9H-dipyrido[2,3-b;4',3'-d]pyrrole (350 mg, 0.78 mmol), 1-methyl-4-(4,4,5,5-tetramethyl-1,3,2-dioxaborolan-2-yl)-1H-pyrazole (242 mg, 1.16 mmol), 1,1'-[bis(diphenylphosphino)ferrocene]dichloropalladium (II) (64 mg, 0.08 mmol) in 2N aqueous sodium carbonate solution (8 mL) and acetonitrile (8 mL) was heated under microwave irradiation at 130° C. for 20 minutes. The cooled reaction mixture was diluted with ethyl acetate (75 mL) and washed with water (50 mL). The organic phase was separated, dried over sodium sulfate, filtered and evaporated in vacuo to afford a residue that was purified by flash chromatography (silica, 50 g column, Biotage, 0-25% methanol in DCM) to afford the title compound as an off-white solid (61 mg, 17%).

¹H NMR (DMSO-D₆, 300 MHz): 8.95-8.92 (m, 2H), 8.85 (d, J=1.0 Hz, 1H), 8.49 (d, J=1.1 Hz, 1H), 8.22 (s, 1H), 8.00 (s, 1H), 7.44 (d, J=7.7 Hz, 1H), 7.38-7.33 (m, 2H), 3.93 (s, 3H), 3.91 (s, 3H), 3.48 (s, 2H), 2.44-2.34 (m, 4H), 1.55-1.48 (m, 4H), 1.45-1.37 (m, 2H).

Example 378

6-(Oxazol-5-yl)-3-(4-piperidin-1-ylmethyl-phenyl)-9H-dipyrido[2,3-b;4',3'-d]pyrrole

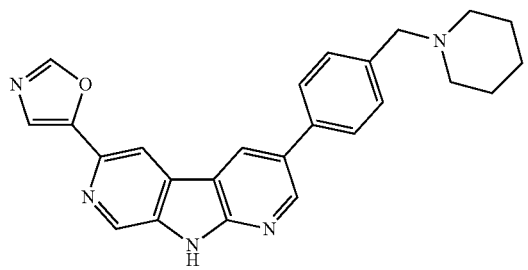

A mixture of 6-bromo-3-(4-piperidin-1-ylmethyl-phenyl)-9H-dipyrido[2,3-b;4',3'-d]pyrrole (150 mg, 0.36 mmol), 5-(4,4,5,5-tetramethyl-1,3,2-dioxaborolan-2-yl)oxazole (140 mg, 0.71 mmol), 1,1'-[bis(diphenylphosphino)-ferrocene]dichloropalladium(II) (29 mg, 0.004 mmol) in saturated aqueous sodium carbonate solution (0.5 mL) and acetonitrile (5 mL) was heated under microwave irradiation at 130° C. for 30 minutes. The cooled reaction mixture was diluted with DCM (20 mL) and methanol (2 mL) and washed with water (15 mL). The organic phase was separated, dried over sodium sulfate, filtered and evaporated in vacuo to afford a residue that was purified by preparative HPLC [20-60% MeCN in water (0.1% ammonium hydroxide) over 30 min, 35 mL/min] to afford the title compound as an off-white solid (42 mg, 29%). ¹H NMR (DMSO-D₆, 400 MHz): 12.42 (s, 1H), 9.12 (d, J=2.2 Hz, 1H), 8.96 (s, 1H), 8.94 (d, J=2.2 Hz, 1H), 8.67 (s, 1H), 8.52 (s, 1H), 7.78 (d, J=8.1 Hz, 2H), 7.66 (s, 1H), 7.44 (d, J=8.1 Hz, 2H), 3.50 (s, 2H), 2.37 (s, 4H), 1.51 (m, 4H), 1.40 (m, 2H). LCMS (Method D): $R_T$=7.76 min, M+H⁺=410.

Example 379

6-(1-Methyl-1H-pyrazol-5-yl)-3-(4-piperidin-1-ylmethyl-phenyl)-9H-dipyrido[2,3-b;4',3'-d]pyrrole

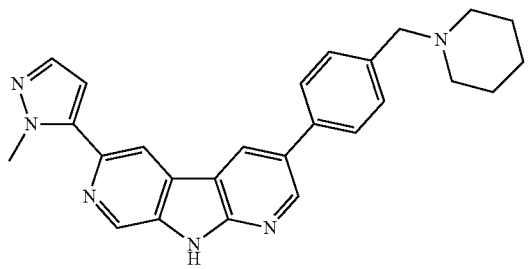 [SMILES: Cn1nccc1-c1cc2c(cn1)[nH]c1ncc(-c3ccc(CN4CCCCC4)cc3)cc12]

The title compound was prepared following a similar procedure to the previous example using 1-methyl-5-(4,4,5,5-tetramethyl-1,3,2-dioxaborolan-2-yl)-1H-pyrazole to yield a yellow/orange solid (20%). ¹H NMR (DMSO-D₆, 400 MHz): 12.34 (s, 1H), 9.05 (d, J=2.2 Hz, 1H), 9.00 (s, 1H), 8.94 (d, J=2.3 Hz, 1H), 8.65 (s, 1H), 7.77 (d, J=8.2 Hz, 2H), 7.50 (d, J=1.9 Hz, 1H), 7.45 (d, J=8.2 Hz, 2H), 6.72 (d, J=1.9 Hz, 1H), 4.17 (s, 3H), 3.49 (s, 2H), 2.35 (s, 4H), 1.51 (m, 4H), 1.42 (m, 2H). LCMS (Method D): $R_T$=6.48 min, M+H⁺=423.

Example 380

6-(1-Methyl-1H-imidazol-5-yl)-3-(4-piperidin-1-ylmethylphenyl)-9H-dipyrido[2,3-b;4',3'-d]pyrrole

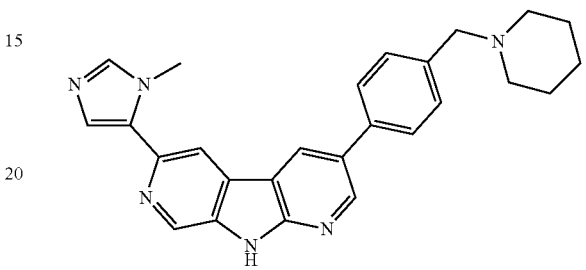

A mixture of 6-bromo-3-(4-piperidin-1-ylmethyl-phenyl)-9H-dipyrido[2,3-b;4',3'-d]pyrrole (100 mg, 0.16 mmol), 1-methyl-5-(tributylstannyl)-1H-imidazole (120 mg, 0.32 mmol), tetrakis(triphenylphosphine)palladium(0) (18 mg, 0.016 mmol) and lithium chloride (68 mg, 1.6 mmol) in 1,4-dioxane (3 mL) was degassed and flushed with nitrogen and the reaction heated at 100° C. for 16 h. The cooled reaction mixture was diluted with DCM (20 mL) and methanol (2 mL) and washed with water (15 mL). The organic phase was separated, dried over sodium sulfate, filtered and evaporated in vacuo to afford a residue that was purified by flash chromatography (silica, 10 g column, Biotage, 0-10% methanol in (DCM containing 1% 7M ammonia in methanol)) to afford a residue that was purified by preparative HPLC [20-60% MeCN in water (0.1% ammonium hydroxide) over 30 min, 35 mL/min] to afford the title compound as a pale orange solid (13 mg, 20%). NMR (DMSO-D₆, 400 MHz): 12.26 (s, 1H), 9.04 (d, J=2.2 Hz, 1H), 8.95 (d, J=0.9 Hz, 1H), 8.92 (d, J=2.2 Hz, 1H), 8.58 (d, J=0.9 Hz, 1H), 7.77 (d, J=8.2 Hz, 2H), 7.72 (s, 1H), 7.44 (d, J=8.1 Hz, 2H), 7.39 (d, J=1.0 Hz, 1H), 3.96 (s, 3H), 3.49 (s, 2H), 2.36 (s, 4H), 1.57-1.47 (m, 4H), 1.40 (m, 2H). LCMS (Method D): $R_T$=6.54 min, M+H⁺=423.

Example 381

6-(Thiazol-5-yl)-3-(4-piperidin-1-ylmethylphenyl)-9H-dipyrido[2,3-b;4',3'-d]pyrrole

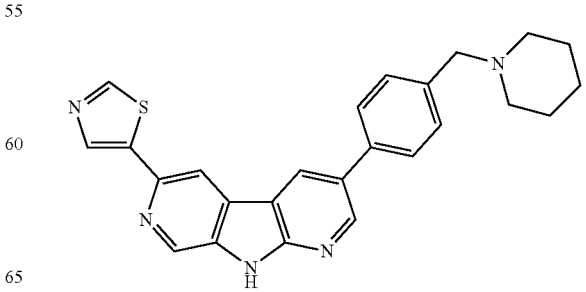

The title compound was prepared following a similar procedure as to the previous example using 5-(4,4,5,5-tetramethyl-1,3,2-dioxaborolan-2-yl)thiazole to yield a beige solid (21%). $^1$H NMR (DMSO-D$_6$, 400 MHz): 12.32 (s, 1H), 9.08 (s, 1H), 9.00 (d, J=2.4 Hz, 1H), 8.95 (d, J=2.4 Hz, 1H), 8.92 (s, 1H), 8.89 (s, 1H), 8.49 (s, 1H), 8.25 (s, 2H), 7.78 (d, J=8.2 Hz, 2H), 7.46 (d, J=8.1 Hz, 3H), 3.50 (s, 2H), 2.37 (s, 4H), 1.53 (m, 4H), 1.40 (m, 2H). LCMS (Method D): R$_T$=8.36 min, M+H$^+$=426.

Example 382

6-(Isoxazol-4-yl)-3-(4-piperidin-1-ylmethylphenyl)-9H-dipyrido[2,3-b;4',3'-d]pyrrole

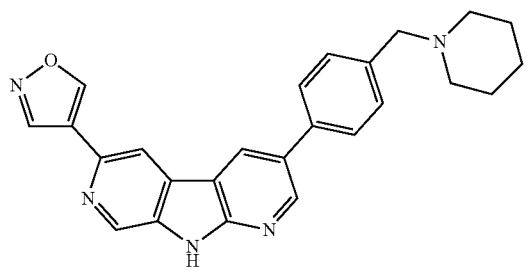 [SMILES: c1cc(-c2cnc3[nH]c4cnc(-c5cnoc5)cc4c3c2)ccc1CN1CCCCC1]

A mixture of 6-bromo-3-(4-piperidin-1-ylmethylphenyl)-9H-dipyrido[2,3-b;4',3'-d]pyrrole (130 mg, 0.18 mmol), 4-(4,4,5,5-tetramethyl-1,3,2-dioxaborolan-2-yl)isoxazole (140 mg, 0.74 mmol), 1,1'-[bis(diphenylphosphino)ferrocene]-dichloropalladium(II) (18 mg, 0.002 mmol) in 1N aqueous potassium acetate solution (0.62 mL) and acetonitrile (3 mL) was heated under microwave irradiation at 85° C. for 18 minutes. The cooled reaction mixture was diluted with DCM (20 mL) and methanol (2 mL) and washed with water (15 mL). The organic phase was separated, dried over sodium sulfate, filtered and evaporated in vacuo to afford a residue that was purified by preparative HPLC [0-30% MeCN in water (0.1% formic acid) over 30 min, 35 mL/min] to afford the title compound as a beige solid (10 mg, 10%). $^1$H NMR (DMSO-D$_6$, 400 MHz): 12.32 (s, 1H), 9.47 (s, 1H), 9.18 (s, 1H), 8.95 (s, 1H), 8.94 (d, J=2.3 Hz, 1H), 8.89 (d, J=2.2 Hz, 1H), 8.68 (s, 1H), 7.76 (d, J=8.1 Hz, 2H), 7.45 (d, J=8.1 Hz, 2H), 3.50 (s, 2H), 2.37 (s, 4H), 1.52 (m, 4H), 1.41 (m, 2H). LCMS (Method D): R$_T$=6.55 min, M+H$^+$=410.

Example 383

6-(3,5-Dimethylisoxazol-4-yl)-3-(4-piperidin-1-ylmethylphenyl)-9H-dipyrido[2,3-b;4',3'-d]pyrrole

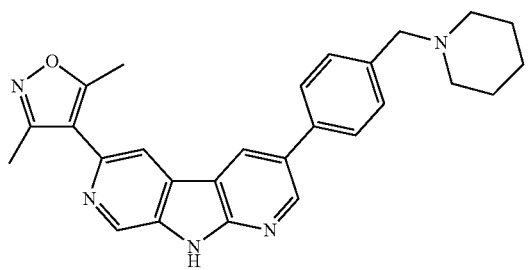 [SMILES: Cc1noc(C)c1-c1cc2c(cn1)[nH]c1ncc(-c3ccc(CN4CCCCC4)cc3)cc12]

The title compound was prepared following a similar procedure to the previous example using 3,5-dimethyl-4-(4,4,5,5-tetramethyl-1,3,2-dioxaborolan-2-yl)isoxazole to yield an off-white solid (20%). $^1$H NMR (DMSO-D$_6$, 500 MHz): 12.32 (s, 1H), 9.09 (d, J=2.3 Hz, 1H), 9.00 (d, J=1.0 Hz, 1H), 8.93 (d, J=2.3 Hz, 1H), 8.41 (s, 1H), 7.77 (d, J=8.2 Hz, 2H), 7.45 (d, J=8.2 Hz, 2H), 3.49 (s, 2H), 2.63 (s, 3H), 2.45 (s, 3H), 2.36 (s, 4H), 1.51 (m, 4H), 1.40 (m, 2H). LCMS (Method D): R$_T$=6.44 min, M+H$^+$=438.

Example 384

6-(2-Methylthiazol-5-yl)-3-(4-piperidin-1-ylmethylphenyl)-9H-dipyrido[2,3-b;4',3'-d]pyrrole

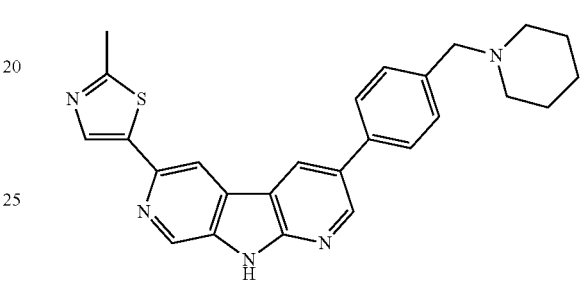

The title compound was prepared following a similar procedure to the previous example using 2-methyl-5-(trimethylstannyl)thiazole to yield a pale yellow solid (20%). $^1$H NMR (DMSO-D$_6$, 400 MHz): 12.35 (s, 1H), 8.99 (d, J=2.2 Hz, 1H), 8.94 (d, J=2.2 Hz, 1H), 8.89 (s, 1H), 8.82 (s, 1H), 8.21 (s, 1H), 7.77 (d, J=8.2 Hz, 2H), 7.45 (d, J=8.1 Hz, 2H), 3.49 (s, 2H), 2.69 (s, 3H), 2.36 (s, 4H), 1.57-1.47 (m, 4H), 1.41 (m, 2H). LCMS (Method D): R$_T$=7.42 min, M+H$^+$=440.

Example 385

6-(1,2-Dimethyl-1H-imidazol-5-yl)-3-(4-piperidin-1-ylmethyl-phenyl)-9H-dipyrido[2,3-b;4',3'-d]pyrrole

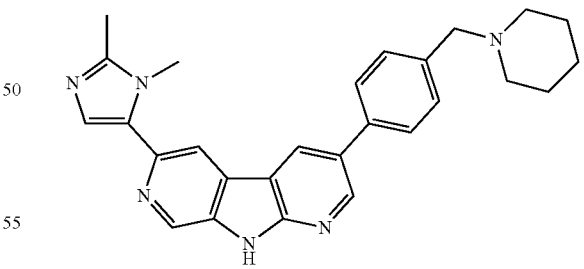

The title compound was prepared following a similar procedure to the previous example using 1,2-dimethyl-5-(tributylstannyl)-1H-imidazole to yield a pale yellow solid (20%). $^1$H NMR (DMSO-D$_6$, 500 MHz): 12.25 (s, 1H), 9.04 (d, J=2.1 Hz, 1H), 8.95 (s, 1H), 8.92 (d, J=2.1 Hz, 1H), 8.51 (s, 1H), 7.77 (d, J=8.0 Hz, 2H), 7.44 (d, J=8.0 Hz, 2H), 7.21 (s, 1H), 3.86 (s, 3H), 3.49 (s, 2H), 2.38 (s, 3H), 2.36 (s, 4H), 1.51 (m, 4H), 1.40 (m, 2H). LCMS (Method D): R$_T$=6.72 min, M+H$^+$=437.

Example 386

6-(1,3,4-Thiadiazol-2-yl)-3-(4-piperidin-1-ylmethyl-phenyl)-9H-dipyrido[2,3-b;4',3'-d]pyrrole

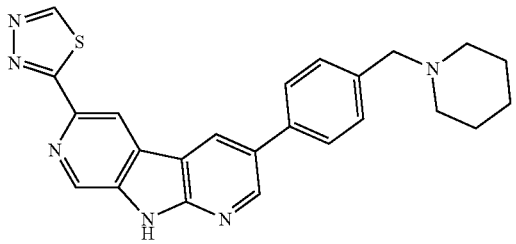 [SMILES: c1nnc(-c2cc3c(cn2)[nH]c2ncc(-c4ccc(CN5CCCCC5)cc4)cc23)s1]

Step 1: 3-(4-Piperidin-1-ylmethylphenyl)-9H-dipyrido[2,3-b;4',3'-d]pyrrole-6-carbohydrazide

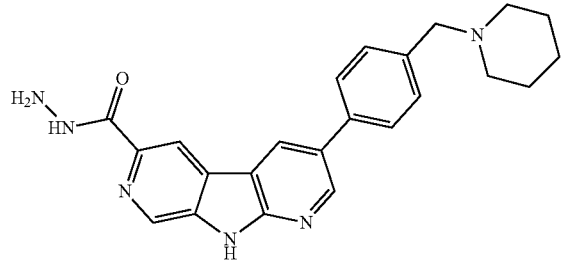 [SMILES: NNC(=O)c1cc2c(cn1)[nH]c1ncc(-c3ccc(CN4CCCCC4)cc3)cc12]

A solution of 3-(4-piperidin-1-ylmethylphenyl)-9H-dipyrido[2,3-b;4',3'-d]pyrrole-6-carboxylic acid methyl ester (425 mg, 1.06 mmol) and hydrazine hydrate (1.29 mL, 26.5 mmol) in ethanol (4.6 mL) was heated under reflux for 1 h under a nitrogen atmosphere. The solution was allowed to cool to ambient temperature and the resulting precipitate was collected by filtration, washed with ethanol, and dried under vacuum to afford a yellow solid (337 mg, 79%). The solid was used without purification.

Step 2: 6-(1,3,4-Thiadiazol-2-yl)-3-(4-piperidin-1-ylmethylphenyl)-9H-dipyrido[2,3-b;4',3'-d]pyrrole

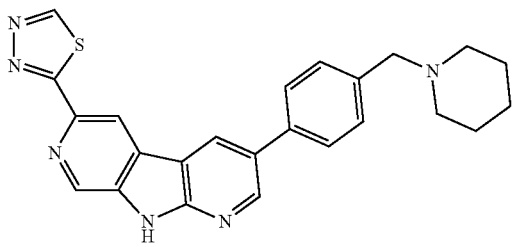 [SMILES: c1nnc(-c2cc3c(cn2)[nH]c2ncc(-c4ccc(CN5CCCCC5)cc4)cc23)s1]

A solution of 3-(4-piperidin-1-ylmethylphenyl)-9H-dipyrido[2,3-b;4',3'-d]pyrrole-6-carbohydrazide (87.3 mg, 0.218 mmol) in formic acid (1.0 mL) was heated under reflux for 30 minutes then allowed to cool to room temperature, diluted with xylenes (4.4 mL) and treated with phosphorus pentasulfide (174 mg, 0.392 mmol). The mixture was heated under reflux under a nitrogen atmosphere for 24 h, then allowed to cool to ambient temperature and treated with additional phosphorus pentasulfide (116 mg, 0.263 mmol) and formic acid (1.0 mL). The mixture was heated under reflux for an additional 24 h, allowed to cool, and concentrated in vacuo. The resulting residue was purified by preparative HPLC (2-60% MeCN/water modified with 0.1% ammonium hydroxide) to afford the title compound as an orange fluffy solid (9.5 mg, 10%). $^1$H NMR (DMSO-D$_6$, 400 MHz): 12.63-12.59 (s, 1H), 9.62 (s, 1H), 9.26 (s, 1H), 9.24 (d, J=2.2 Hz, 1H), 9.02 (s, 1H), 8.98 (d, J=2.2 Hz, 1H), 7.81 (d, J=8.1 Hz, 2H), 7.45 (d, J=8.1 Hz, 2H), 3.50 (s, 2H), 2.38 (m, 4H), 1.52 (m, 4H), 1.41 (m, 2H). LCMS (Method D): R$_T$=8.71 min, M+H$^+$=427.

Example 387

6-(1,3,4-Oxadiazol-2-yl)-3-(4-piperidin-1-ylmethylphenyl)-9H-dipyrido[2,3-b;4',3'-d]pyrrole

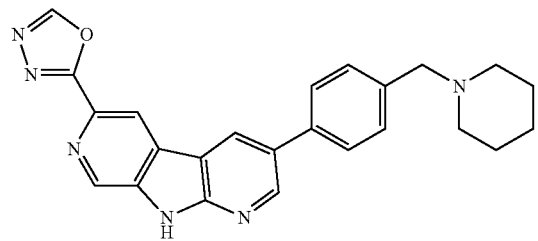 [SMILES: c1nnc(-c2cc3c(cn2)[nH]c2ncc(-c4ccc(CN5CCCCC5)cc4)cc23)o1]

A solution of 3-(4-piperidin-1-ylmethylphenyl)-9H-dipyrido[2,3-b;4',3'-d]pyrrole-6-carbohydrazide (53.8 mg, 0.134 mmol) and trimethoxymethane (1.21 mL, 11.0 mmol) in DMF (0.81 mL) was heated at 120° C. for 24 h. The mixture was cooled, treated with trimethoxymethane (1.0 mL) and a few drops of acetic acid and heated under reflux for 48 h. The mixture was allowed to cool, treated with saturated aqueous sodium bicarbonate solution, and the resultant white precipitate collected by filtration and washed with water. The filtrate was extracted with DCM, 20% methanol in DCM, and the combined organic phases dried over sodium sulfate, combined with the isolated solid and concentrated in vacuo. The resultant residue was purified by preparative HPLC [2-60% MeCN/water modified with 0.1% ammonium hydroxide] to afford a light-yellow flaky solid (6.0 mg, 27%). $^1$H NMR (DMSO-D$_6$, 400 MHz): 12.77-12.69 (s, 1H), 9.41 (s, 1H), 9.26 (d, J=2.2 Hz, 1H), 9.18 (s, 1H), 9.08 (s, 1H), 9.00 (d, J=2.2 Hz, 1H), 8.31 (s, 1H), 7.80 (d, J=8.1 Hz, 2H), 7.46 (d, J=8.1 Hz, 2H), 3.50 (s, 2H), 2.37 (m, 4H), 1.52 (m, 4H), 1.41 (m, 2H). LCMS (Method D): R$_T$=7.69 min, M+H$^+$=411.

Example 388

6-(1-Benzyl-1H-1,2,3-triazol-4-yl)-3-(4-piperidin-1-ylmethyl-phenyl)-9H-dipyrido[2,3-b;4',3'-d]pyrrole

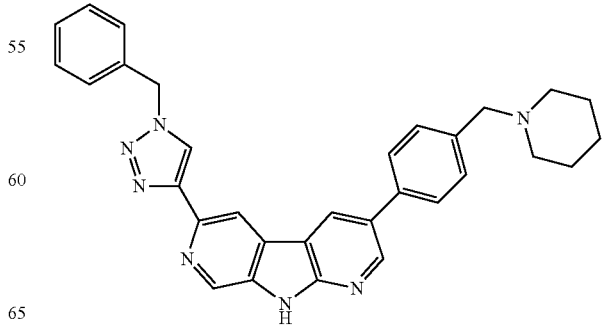

Step 1: 6-((Trimethylsilyl)ethynyl)-3-(4-piperidin-1-ylmethylphenyl)-9H-dipyrido[2,3-b;4',3'-d]pyrrole

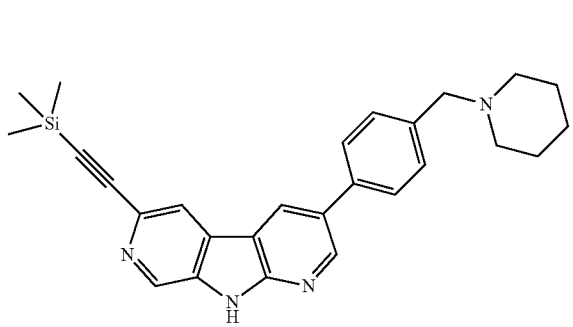 [SMILES: C[Si](C)(C)C#Cc1cc2c(cn1)[nH]c1ncc(-c3ccc(CN4CCCCC4)cc3)cc12]

A mixture of 6-bromo-3-(4-piperidin-1-ylmethylphenyl)-9H-dipyrido[2,3-b;4',3'-d]pyrrole (170 mg, 0.40 mmol), copper(I) iodide (7.7 mg, 0.04 mmol), and N,N-diisopropylethylamine (0.21 mL, 1.2 mmol) in anhydrous 1,4-dioxane (3 mL) was degassed and flushed with nitrogen. Tetrakis(triphenylphosphine)palladium(0) (47 mg, 0.04 mmol) and (trimethylsilyl)acetylene (0.34 mL, 2.4 mmol) were added and the reaction mixture heated at 110° C. for 1 h. The cooled reaction mixture was diluted with DCM (20 mL) and methanol (2 mL) and washed with water (15 mL). The organic phase was separated, dried over sodium sulfate, filtered and evaporated in vacuo to afford a residue that was purified by flash chromatography (silica, 10 g column, Biotage, 0-10% methanol in (DCM containing 1% 7M ammonia in methanol) to afford a brown residue that was taken to the next step without further purification.

Step 2: 6-Ethynyl-3-(4-piperidin-1-ylmethylphenyl)-9H-dipyrido[2,3-b;4',3'-d]pyrrole

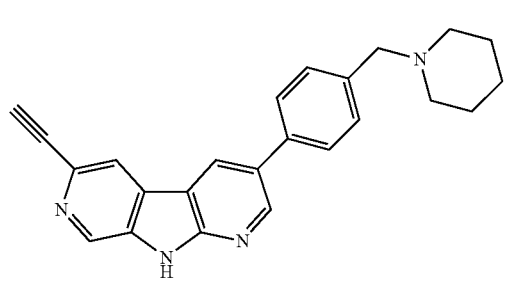 [SMILES: C#Cc1cc2c(cn1)[nH]c1ncc(-c3ccc(CN4CCCCC4)cc3)cc12]

A mixture of 6-((trimethylsilyl)ethynyl)-3-(4-piperidin-1-ylmethylphenyl)-9H-dipyrido[2,3-b;4',3'-d]pyrrole (120 mg, 0.3 mmol) and potassium carbonate (170 mg, 1.2 mmol) in methanol (2 mL) was stirred at ambient temperature for 1 h. The reaction mixture was diluted with DCM (20 mL) and methanol (2 mL) and washed with water (15 mL). The organic phase was separated, dried over sodium sulfate, filtered and evaporated in vacuo to afford a brown residue that was taken to the next step without purification.

Step 3: 6-(1-Benzyl-1H-1,2,3-triazol-4-yl)-3-(4-piperidin-1-ylmethylphenyl)-9H-dipyrido[2,3-b;4',3'-d]pyrrole

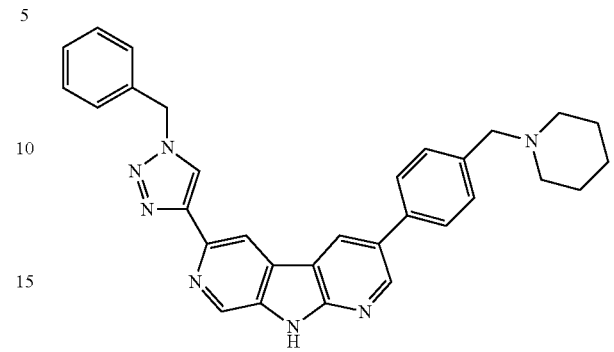

A mixture of 6-ethynyl-3-(4-piperidin-1-ylmethylphenyl)-9H-dipyrido[2,3-b;4',3'-d]pyrrole (90 mg, 0.2 mmol), copper (I) iodide (4.7 mg, 0.02 mmol), and azidomethyl-benzene (36 mg, 0.27 mmol) in N,N-dimethylformamide (2 mL) was heated at 60° C. for 2 h. The cooled reaction mixture was diluted with DCM (20 mL) and methanol (2 mL) and washed with water (15 mL). The organic phase was separated, dried over sodium sulfate, filtered and evaporated in vacuo to afford a residue that was purified by preparative HPLC [20-60% MeCN in water (0.1% ammonium hydroxide) over 30 min, 35 mL/min] to afford the title compound as an off-white solid (20 mg, 20%). $^1$H NMR (DMSO-D$_6$, 400 MHz): 12.30 (s, 1H), 9.16 (d, J=2.2 Hz, 1H), 8.93 (s, 2H), 8.91 (s, 1H), 8.61 (s, 1H), 7.80 (d, J=8.1 Hz, 2H), 7.40 (m, 7H), 5.69 (s, 2H), 3.49 (s, 2H), 2.36 (s, 4H), 1.57-1.46 (m, 4H), 1.40 (m, 2H). LCMS (Method D): R$_T$=9.35 min, M±H$^+$=500.

Example 389

6-(1H-1,2,3-Triazol-4-yl)-3-(4-piperidin-1-ylmethylphenyl)-9H-dipyrido[2,3-b;4',3'-d]pyrrole

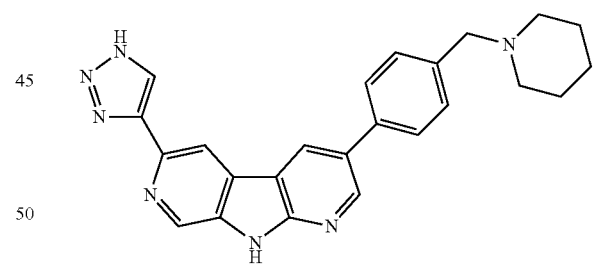

Step 1: 6'-((Trimethylsilyl)ethynyl)-2-fluoro-5-(4-piperidin-1-ylmethylphenyl)-[3,4']bipyridinyl-3'-ylamine

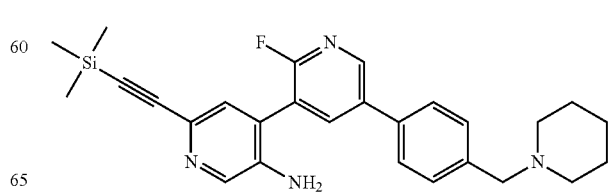

A mixture of 6'-bromo-2-fluoro-5-(4-piperidin-1-ylmethylphenyl)-[3,4']bipyridinyl-3'-ylamine (100 mg, 0.23 mmol), copper (I) iodide (4.3 mg, 0.02 mmol), and N,N-diisopropylethylamine (0.08 mL, 0.45 mmol) in anhydrous 1,4-dioxane (2.5 mL) was degassed and flushed with nitrogen. Tetrakis(triphenylphosphine)palladium(0) (26 mg, 0.02 mmol) and (trimethylsilyl)acetylene (0.16 mL, 1:1 mmol) were added and the reaction was heated at 100° C. for 5 h. The cooled reaction mixture was diluted with DCM (20 mL) and methanol (2 mL) and washed with water (15 mL). The organic phase was separated, dried over sodium sulfate, filtered and evaporated in vacuo to afford a residue that was purified by flash chromatography (silica, 10 g column, Biotage, 0-10% methanol in (DCM containing 1% 7M ammonia in ammonia)) to afford a brown residue that was taken to the next step without further purification.

Step 2: 6'-Ethynyl-2-fluoro-5-(4-piperidin-1-ylmethylphenyl)-[3,4']bipyridinyl-3'-ylamine

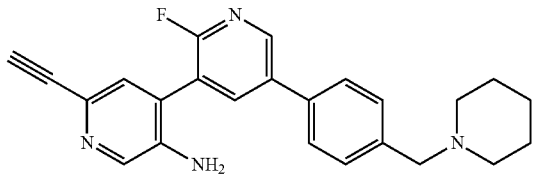 [SMILES: C#Cc1cc(-c2cc(-c3ccc(CN4CCCCC4)cc3)cnc2F)c(N)cn1]

A mixture of 6'-((trimethylsilyl)ethynyl)-2-fluoro-5-(4-piperidin-1-ylmethyl-phenyl)-[3,4']bipyridinyl-3'-ylamine (90 mg, 0.2 mmol) and potassium carbonate (150 mg, 1.1 mmol) in methanol (2 mL) was stirred at ambient temperature for 1 h. The cooled reaction mixture was diluted with DCM (20 mL) and methanol (2 mL) and washed with water (15 mL). The organic phase was separated, dried over sodium sulfate, filtered and evaporated in vacuo to afford a brown residue that was taken to the next step without purification.

Step 3: 6-(1-Benzyl-1H-1,2,3-triazol-4-yl)-3-(4-piperidin-1-ylmethylphenyl)-9H-dipyrido[2,3-b;4',3'-d]pyrrole

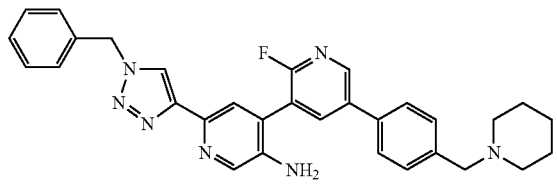 [SMILES: Nc1cnc(-c2cn(Cc3ccccc3)nn2)cc1-c1cc(-c2ccc(CN3CCCCC3)cc2)cnc1F]

A mixture of 6'-ethynyl-2-fluoro-5-(4-piperidin-1-ylmethylphenyl)-[3,4]bipyridinyl-3'-ylamine (60 mg, 0.16 mmol), copper (I) iodide (3.0 mg, 0.016 mmol), and azidomethylbenzene (29 mg, 0.22 mmol) in N,N-dimethylformamide (2 mL) was heated at 60° C. for 2 h. The cooled reaction mixture was diluted with DCM (20 mL) and methanol (2 mL) and washed with water (15 mL). The organic phase was separated, dried over sodium sulfate, filtered and evaporated in vacuo to afford a brown residue that was taken to the next step without purification.

Step 4: 6-(1H-1,2,3-Triazol-4-yl)-3-(4-piperidin-1-ylmethylphenyl)-9H-dipyrido[2,3-b;4',3'-d]pyrrole

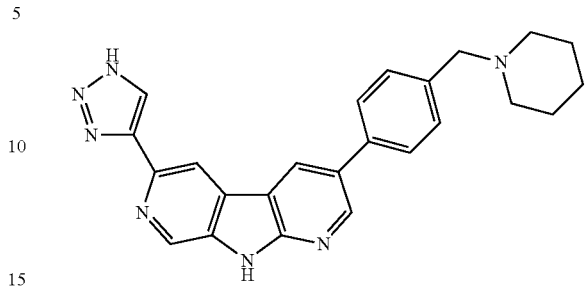

To a solution of 6'-(1-benzyl-1H-1,2,3-triazol-4-yl)-2-fluoro-5-(4-piperidin-1-ylmethylphenyl)[3,4']bipyridinyl-3'-ylamine (80 mg, 0.16 mmol) in anhydrous tetrahydrofuran (2 mL) was added sodium bis(trimethylsilyl)amide (1N solution in THF, 0.46 mL, 0.46 mmol) under a flow of nitrogen and the reaction mixture was stirred at room temperature for 2 h. The reaction mixture was then evaporated in vacuo to afford a residue that was purified by preparative HPLC (20-60% MeCN in water (0.1% ammonium hydroxide) over 30 min, 35 mL/min) to afford the title compound as an orange solid (10 mg, 10%). NMR (DMSO-$D_6$, 500 MHz): 12.33 (s, 1H), 9.12 (s, 1H), 8.95 (s, 1H), 8.94 (d, J=2.2 Hz, 1H), 8.88 (s, 1H), 8.31 (s, 1H), 7.80 (d, J=8.1 Hz, 2H), 7.44 (d, J=8.0 Hz, 2H), 3.49 (s, 2H), 2.36 (s, 4H), 1.52 (m, 4H), 1.41 (m, 2H), triazole NH not observed. LCMS (Method D): $R_T$=6.68 min, M+H$^+$=410.

Example 390

6-(Tetrazol-5-yl)-3-(4-piperidin-1-ylmethylphenyl)-9H-dipyrido[2,3-b;4',3'-d]pyrrole

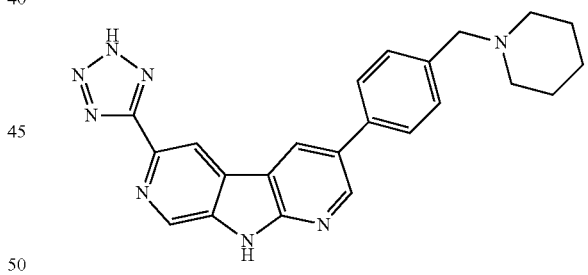

A mixture of 6-carbonitrile-3-(4-piperidin-1-ylmethylphenyl)-9H-dipyrido[2,3-b;4',3'-d]pyrrole (269 mg, 0.732 mmol) and azidotrimethyltin(IV) (1.51 g, 7.32 mmol) in a mixture of N,N-dimethylacetamide (5 mL) and toluene (24 mL) was heated 110° C. for 24 hours. The reaction mixture was allowed to cool and concentrated in vacuo. The resultant residue was dissolved in 20% methanol in DCM, absorbed onto celite in vacuo, and purified by flash chromatography (Amino Silica, Snap KP-NH, Biotage, 1-20% methanol in (DCM containing 0 1% 7M ammonia in methanol) to yield a dark yellow solid (80.5 mg). The solid was further purified by preparative HPLC (2-60% MeCN/water containing 0.1% ammonium hydroxide) to afford the title compound as a pale yellow solid (36.9 mg, 12%). $^1$H NMR (DMSO-$D_6$, 400 MHz): 12.52 (s, 1H), 9.22 (d, J=2.2 Hz, 1H), 9.10 (s, 1H), 9.02 (s, 1H), 8.98 (d, J=2.2 Hz, 1H), 7.83 (d, J=8.2 Hz, 2H), 7.48 (d, J=8.1 Hz, 2H), 3.69 (s, 2H), 2.55 (m, 4H), 1.58 (m, 4H), 1.44 (m, 2H). LCMS (Method E): $R_T$=3.04 min, M+H$^+$=411.

Example 391

6-Pyridin-3-yl-3-[4-(4-trifluoromethylpiperidin-1-ylmethyl)-phenyl]-9H-dipyrido[2,3-b;4',3'-d]pyrrole

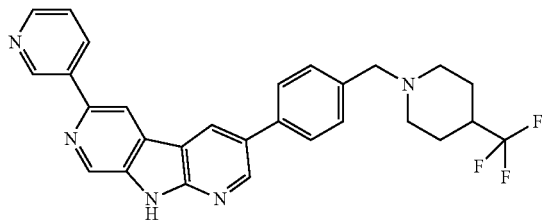 [SMILES: FC(F)(F)C1CCN(Cc2ccc(-c3cnc4[nH]c5cnc(-c6cccnc6)cc5c4c3)cc2)CC1]

To a mixture of pyridine-2-boronic acid (27 mg, 0.22 mmol), 6-bromo-3-[4-(4-trifluoromethyl-piperidin-1-ylmethyl)-phenyl]-9H-dipyrido[2,3-b;4',3'-d]pyrrole (55 mg, 0.11 mmol) and 1,1'-[bis(diphenylphosphino)ferrocene]-dichloropalladium(II) (9 mg, 0.011 mmol) in acetonitrile (1 mL) and saturated aqueous sodium carbonate solution (1 mL) was heated under microwave irradiation at 140° C. for 30 minutes. The cooled reaction mixture was partitioned between DCM and water and the phases were separated using a hydrophobic frit and the organic phase evaporated. The residue was purified HPLC (C18 column, 50-98% MeCN in water (containing 20 mM triethylamine) over 30 minutes and the fractions containing pure product combined and concentrated then freeze-dried to afford the title compound (6 mg, 11%). $^1$H NMR (CDCl$_3$ plus CD$_3$OD, 400 MHz): 9.22 (dd, J=2.3, 0.8 Hz, 1H), 9.05 (d, J=1.1 Hz, 1H), 8.86-8.83 (m, 2H), 8.59-8.56 (m, 2H), 8.48-8.44 (m, 1H), 7.73-7.69 (m, 2H), 7.58-7.54 (m, 1H), 7.50 (d, J=8.0 Hz, 2H), 3.64 (s, 2H), 3.11-3.03 (m, 2H), 2.17-2.04 (m, 3H), 1.93-1.85 (m, 2H), 1.74-1.61 (m, 2H). LCMS (Method A): $R_T$=5.43 min, M+H$^+$=488.

Example 392

6-(Pyridin-3-yl)-3-(4-piperidin-1-ylmethylphenyl)-9H-dipyrido[2,3-b;4',3'-d]pyrrole

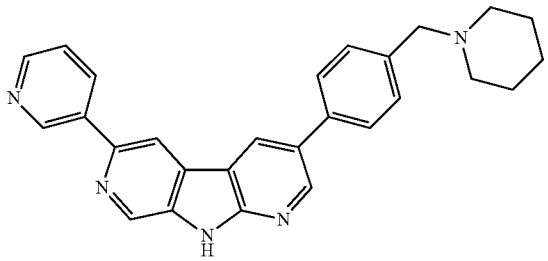 [SMILES: c1cncc(-c2cc3c(cn2)[nH]c2ncc(-c4ccc(CN5CCCCC5)cc4)cc23)c1]

The title compound was prepared following a similar procedure to the previous example using 3-(1,3,2-dioxaborinan-2-yl)pyridine to yield a beige solid (40%). $^1$H NMR (DMSO-D$_6$, 400 MHz): 12.30 (s, 1H), 9.36 (d, J=2.0 Hz, 1H), 9.05 (d, J=2.3 Hz, 1H), 9.04 (s, 1H), 8.99 (s, 1H), 8.94 (d, J=2.2 Hz, 1H), 8.60 (dd, J=1.6 Hz, 3.2, 1H), 8.50 (dt, J=8.0, 2.0 Hz, 1H), 7.78 (d, J=8.2 Hz, 2H), 7.55 (s, 1H), 7.46 (d, J=8.1 Hz, 2H), 3.51 (s, 2H), 2.38 (s, 4H), 1.53 (m, 4H), 1.41 (m, 2H). LCMS (Method D): $R_T$=6.92 min, M+H$^+$=420.

Example 393

6-(Pyridin-3-yl)-3-(4-piperidin-1-ylmethylphenyl)-9H-dipyrido[2,3-b;4',3'-d]pyrrole

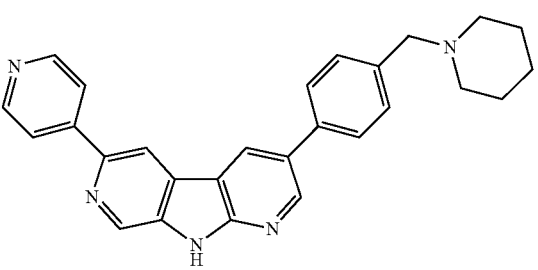 [SMILES: c1cc(-c2cc3c(cn2)[nH]c2ncc(-c4ccc(CN5CCCCC5)cc4)cc23)ccn1]

The title compound was prepared following a similar procedure to the previous example using pyridin-4-ylboronic acid to yield a beige solid (40%). $^1$H NMR (DMSO-D$_6$, 400 MHz): 12.48 (s, 1H), 9.10 (s, 1H), 9.07 (d, J=2.2 Hz, 1H), 9.06 (s, 1H), 8.96 (d, J=2.2 Hz, 1H), 8.70 (d, J=6.1 Hz, 2H), 8.15 (d, J=6.1 Hz, 2H), 7.78 (d, J=8.1 Hz, 2H), 7.46 (d, J=8.1 Hz, 2H), 3.50 (s, 2H), 2.37 (s, 4H), 1.58-1.47 (m, 4H), 1.41 (m, 2H). LCMS (Method D): $R_T$=7.01 min, M+H$^+$=420.

Example 394

6-(4-Methoxypyridin-3-yl)-3-(4-piperidin-1-ylmethylphenyl)-9H-dipyrido[2,3-b;4',3'-d]pyrrole

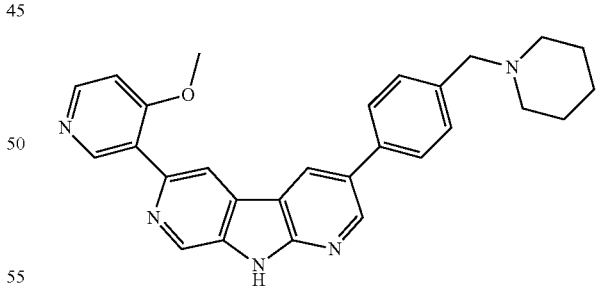

The title compound was prepared following a similar procedure to the previous example using 5-4-methoxypyridin-3-ylboronic acid to yield a beige solid (20%). $^1$H NMR (DMSO-D$_6$, 500 MHz): 12.36 (s, 1H), 9.05 (d, J=2.2 Hz, 1H), 9.03 (s, 1H), 8.93 (d, J=2.1 Hz, 1H), 8.87 (s, 1H), 8.71 (s, 1H), 8.48 (d, J=5.7 Hz, 1H), 7.79 (d, J=8.1 Hz, 2H), 7.44 (d, J=8.1 Hz, 2H), 7.24 (d, J=5.8 Hz, 1H), 3.99 (s, 3H), 3.49 (s, 2H), 2.36 (s, 4H), 1.57-1.47 (m, 4H), 1.40 (m, 2H). LCMS (Method D): $R_T$=6.56 min, M+H$^+$=450.

Example 395

6-(5-Methoxypyridin-3-yl)-3-(4-piperidin-1-ylmethylphenyl)-9H-dipyrido[2,3-b;4',3'-d]pyrrole

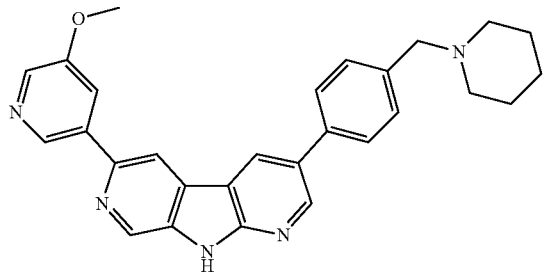 [SMILES: COc1cncc(-c2cc3c(cn2)[nH]c2ncc(-c4ccc(CN5CCCCC5)cc4)cc23)c1]

The title compound was prepared following a similar procedure to the previous example using 3-methoxy-5-(4,4,6,6-tetramethyl-1,3,2-dioxaborinan-2-yl)pyridine to afford a beige solid (20%). $^1$H NMR (DMSO-D$_6$, 500 MHz): 12.39 (s, 1H), 9.05 (d, J=2.5 Hz, 1H), 9.04 (s, 1H), 9.03 (s, 1H), 8.99 (s, 1H), 8.95 (d, J=2.5 Hz, 1H), 8.32 (d, J=2.8 Hz, 1H), 8.08 (s, 1H), 7.78 (d, J=8.1 Hz, 2H), 7.46 (d, J=8.1 Hz, 2H), 3.96 (s, 3H), 3.50 (s, 2H), 2.36 (s, 4H), 1.52 (m, 4H), 1.41 (m, 2H). LCMS (Method D): R$_T$=7.68 min, M+H$^+$=450.

Example 396

3-(1-Methyl-1H-pyrazol-4-yl)-6-[4-(piperidin-4-yloxy)-pyridin-3-yl]-9H-dipyrido[2,3-b;4',3'-d]pyrrole

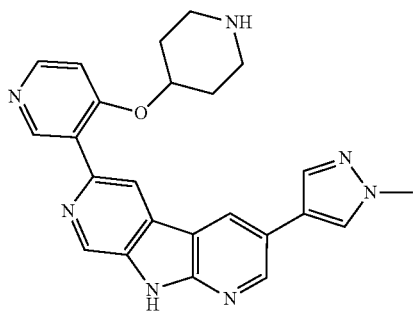 [SMILES: Cn1cc(-c2cnc3[nH]c4cnc(-c5cnccc5OC5CCNCC5)cc4c3c2)cn1]

Step 1: 6-Iodo-3-(1-methyl-1H-pyrazol-4-yl)-9-(2-trimethylsilanyl-ethoxymethyl)-9H-dipyrido[2,3-b;4',3'-d]pyrrole

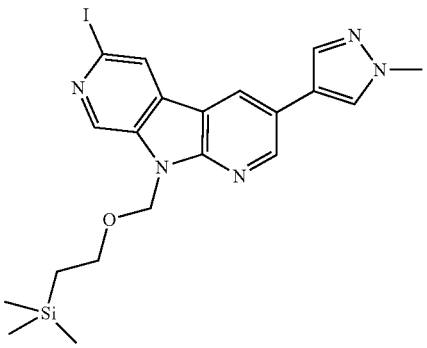

A degassed mixture of 6-bromo-(1-methyl-1H-pyrazol-4-yl)-9-(2-trimethylsilanyl ethoxymethyl)-9H-dipyrido[2,3-b;4',3'-d]pyrrole (0.20 g, 0.44 mmol), copper (I) iodide (8.9 mg, 0.044 mmol), N,N'-dimethylethylenediamine (9.4 µL, 0.088 mmol) and sodium iodide (0.264 mg, 1.76 mmol) in 1,4-dioxane (2 mL) was heated at 110° C. for 3 days. The cooled reaction mixture was partitioned between water and ethyl acetate, the organic layer was separated, dried over sodium sulfate, filtered and evaporated to afford the title compound as a yellow solid (0.205 g, 92%). $^1$H NMR (CDCl$_3$, 300 MHz): 8.88 (d, J=0.9 Hz, 1H), 8.78 (d, J=2.1 Hz, 1H), 8.41-8.36 (m, 2H), 7.84 (s, 1H), 7.71 (s, 1H), 5.92 (s, 2H), 4.02 (s, 3H), 3.58 (t, J=8.2 Hz, 2H), 0.92 (t, J=8.2 Hz, 2H), −0.09 (s, 9H).

Step 2: 6-(4-Chloro-pyridin-3-yl)-3-(1-methyl-1H-pyrazol-4-yl)-9-(2-trimethylsilanylethoxymethyl)-9H-dipyrido[2,3-b;4',3'-d]pyrrole

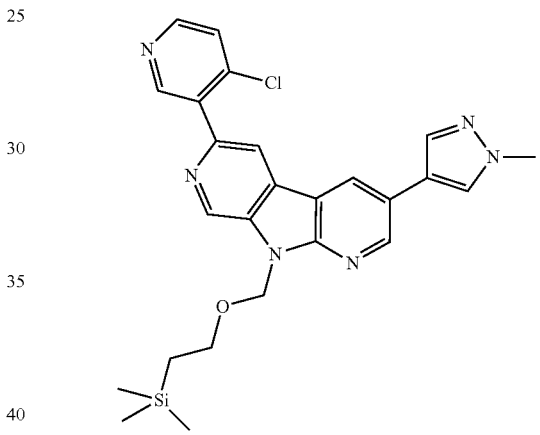

6-Iodo-3-(1-methyl-1H-pyrazol-4-yl)-9-(2-trimethylsilanylethoxymethyl)-9H-dipyrido[2,3-b;4',3'-d]pyrrole (0.21 g, 0.41 mmol), 4-chloro-3-(4,4,5,5-tetramethyl-[1,3,2]dioxaborolan-2-yl)-pyridine (0.15 g, 0.615 mmol), 1,1'-[bis(diphenylphosphino)ferrocene]dichloro palladium(II) (17 mg, 0.021 mmol) in saturated aqueous sodium carbonate solution (1 mL) and acetonitrile (4 mL) were placed under an atmosphere of argon and heated with microwave irradiation at 100° C. for 45 minutes. The cooled reaction mixture was diluted with water and extracted with ethyl acetate. The organic layer was separated, dried over sodium sulfate, filtered and evaporated to afford a residue which was purified by flash chromatography (silica, 12 g column, ISCO, 0-10% methanol in DCM) to afford the title compound as a yellow oil (0.13 g, 66%). $^1$H NMR (CDCl$_3$, 400 MHz): 9.22 (d, J=1.1 Hz, 1H), 8.91 (d, J=0.5 Hz, 1H), 8.79 (d, J=2.1 Hz, 1H), 8.53 (d, J=5.4 Hz, 1H), 8.48 (d, J=2.1 Hz, 1H), 8.32 (d, J=1.1 Hz, 1H), 7.86 (d, J=0.8 Hz, 1H), 7.73 (s, 1H), 7.48 (dd, J=5.4, 0.5 Hz, 1H), 6.01 (s, 2H), 4.01 (s, 3H), 3.70-3.63 (m, 2H), 1.02-0.94 (m, 2H), −0.06 (s, 9H). LCMS (Method G): R$_T$=4.8 min, M+H$^+$=491.

Step 3: 4-{3-[3-(1-Methyl-1H-pyrazol-4-yl)-9-(2-trimethylsilanyl-ethoxymethyl)-9H-dipyrido[2,3-b;4',3'-d]pyrrol-6-yl]-pyridin-4-yloxy}-piperidine-1-carboxylic acid tert-butyl ester

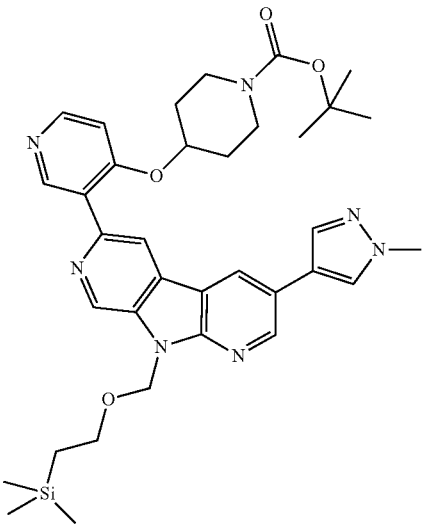

Sodium hydride (60% dispersion in mineral oil, 42 mg, 1.06 mmol) was added to a solution of tert-butyl-4-hydroxy-1-piperidinecarboxaldehyde (0.16 g, 0.795 mmol) in DMF (2.5 mL) and the reaction mixture was stirred at ambient temperature for 30 minutes. 6-(4-Chloro-pyridin-3-yl)-3-(1-methyl-1H-pyrazol-4-yl)-9-(2-trimethylsilanyl-ethoxymethyl)-9H-dipyrido[2,3-b;4',3'-d]pyrrole (0.13 g, 0.265 mmol) was added as a solution in DMF (2.5 mL) and the reaction mixture was heated at 80° C. for 1.5 h. The material was partitioned between water and ethyl acetate. The organic layer was separated, dried over sodium sulfate, filtered and evaporated in vacuo. The resultant residue was purified by flash chromatography (silica, 12 g column, ISCO, 0-10% methanol in DCM) to afford the title compound as a yellow oil which crystallised on standing (0.1 g, 58%). $^1$H NMR (CDCl$_3$, 400 MHz): 9.19 (d, J=1.1 Hz, 1H), 9.01 (s, 1H), 8.79 (d, J=2.1 Hz, 1H), 8.51 (d, J=5.7 Hz, 1H), 8.45 (d, J=1.1 Hz, 1H), 8.38 (d, J=2.1 Hz, 1H), 7.85 (s, 1H), 7.76 (s, 1H), 6.97 (d, J=5.8 Hz, 1H), 6.01 (s, 2H), 4.84-4.73 (br s, 1H), 4.02 (s, 3H), 3.71-3.62 (m, 2H), 3.60-3.39 (m, 4H), 1.97 (br s, 2H), 1.88 (br s, 2H), 1.41 (s, 9H), 1.01-0.93 (m, 2H), −0.07 (s, 9H).

Step 4: 3-(1-Methyl-1H-pyrazol-4-yl)-6-[4-(piperidin-4-yloxy)-pyridin-3-yl]-9H-dipyrido[2,3-b;4',3'-d]pyrrole

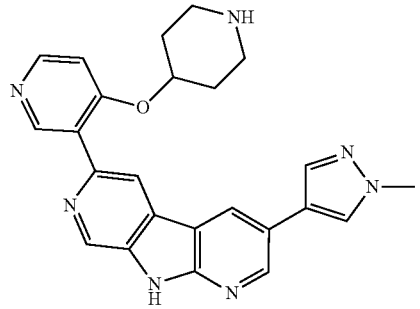 [SMILES: Cn1cc(-c2cnc3[nH]c4cnc(-c5cnccc5OC5CCNCC5)cc4c3c2)cn1]

A mixture of 4-{3-[3(1-methyl-1H-pyrazol-4-yl)-9-(2-trimethylsilanylethoxy methyl)-9H-dipyrido[2,3-b;4',3'-d]pyrrol-6-yl]-pyridin-4-yloxy}-piperidine-1-carboxylic acid tert-butyl ester (0.1 g, 0.15 mmol) in TBAF (1N in THF, 10 mL) was heated at 50° C. for 19 h. The cooled reaction mixture was partitioned between water and ethyl acetate. The organic layer was separated, dried over sodium sulfate, filtered and concentrated in vacuo, to afford a residue which was purified by flash chromatography (silica, 12 g column, ISCO, 0-10% methanol in DCM). This resultant residue was dissolved in DCM (5 mL) and TFA (1 mL) and left to stir for 30 minutes. The mixture was diluted with DCM and water. The aqueous layer was separated, evaporated and the resultant residue was loaded onto an SCX-2 cartridge and washed with methanol and 2M ammonia in methanol. The combined basic fraction was purified by HPLC (C18 column, eluting with 5-60% MeCN in water (with 20 mM triethylamine) over 20 minutes) to afford the title compound as a white solid (25 mg, 39%). $^1$H NMR (MeOD, 400 MHz): 8.97 (s, 1H), 8.83-8.78 (m, 2H), 8.72 (s, 1H), 8.58 (s, 1H), 8.43 (d, J=5.9 Hz, 1H), 8.12 (s, 1H), 7.98 (s, 1H), 7.28 (d, J=6.0 Hz, 1H), 4.91-4.80 (m, 1H), 3.98 (s, 3H), 3.01-2.91 (m, 2H), 2.80-2.70 (m, 2H), 2.11-2.00 (m, 2H), 1.83-1.73 (m, 2H) plus 2 exchangeables not observed. LCMS (Method A): R$_T$=4.0 min, M+H$^+$=426.

Example 397

6-[4-(1-Ethyl-piperidin-4-yloxy)-pyridin-3-yl]-3-(1-methyl-1H-pyrazol-4-yl)-9H-dipyrido[2,3-b;4',3'-d]pyrrole

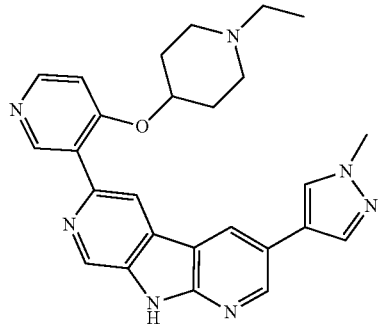 [SMILES: CCN1CCC(Oc2ccncc2-c2cc3c(cn2)[nH]c2ncc(-c4cnn(C)c4)cc23)CC1]

Sodium hydride (60% dispersion in mineral oil, 0.133 g, 3.32 mmol) was added to a solution of 1-ethyl-piperidin-4-ol (0.306 g, 2.37 mmol) in DMF (5 mL) and the reaction mixture was stirred at ambient temperature for 45 minutes. 6-(4-Chloro-pyridin-3-yl)-3-(1-methyl-1H-pyrazol-4-yl)-9H-dipyrido[2,3-b;4',3'-d]pyrrole (0.121 g, 0.474 mmol) was added and the reaction mixture was heated at 80° C. for 5 h. The material was partitioned between water and ethyl acetate. The solid suspended in the aqueous layer was removed by filtration then the aqueous layer was separated, adsorbed onto HM-N and purified by flash chromatography (silica, 12 g column, ISCO, 0-10% (2N ammonia in methanol) in DCM). The resultant residue was triturated with ethyl acetate and cyclohexane to afford the title compound as a yellow solid (28 mg, 13%). $^1$H NMR (MeOD, 400 MHz): 8.97 (d, J=1.1 Hz, 1H), 8.83-8.80 (m, 2H), 8.73 (s, 1H), 8.60 (d, J=1.1 Hz, 1H); 8.43 (d, J=5.9 Hz, 1H), 8.11 (s, 1H), 7.97 (d, J=0.8 Hz, 1H), 7.28 (d, J=6.0 Hz, 1H), 3.98 (s, 3H), 2.65-2.54 (m, 2H), 2.53-2.43 (m, 2H), 2.39 (q, J=7.3 Hz, 2H), 2.13-2.03 (m, 2H), 1.97-1.86 (m, 2H), 1.02 (t, J=7.2 Hz, 3H). LCMS (Method A): R$_T$=4.0 min, M+H$^+$=454.

Example 398

Dimethyl-(2-{3-[3-(1-methyl-1H-pyrazol-4-yl)-9H-dipyrido[2,3-b;4',3'-d]pyrrol-6-yl]-pyridin-4-yloxy}-ethyl)-amine

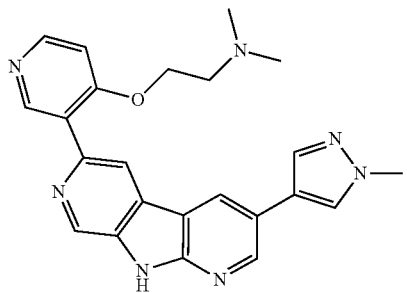 [SMILES: CN(C)CCOc1ccncc1-c1cc2c(cn1)[nH]c1ncc(-c3cnn(C)c3)cc12]

Sodium hydride (60% dispersion in mineral oil, 38 mg, 0.96 mmol) was added to a solution of N,N-dimethylethanolamine (63 mg, 0.71 mmol) in DMF (5 mL) and the mixture stirred at ambient temperature for 75 minutes. 6-(4-chloropyridin-3-yl)-3-(1-methyl-1H-pyrazol-4-yl)-9H-dipyrido[2,3-b;4',3'-d]pyrrole (85 mg, 0.24 mmol) was added and the reaction mixture was stirred at ambient temperature for 26 h then at 80° C. for 2 h. After this time, the reaction mixture was added to a solution of N,N-dimethylethanolamine (0.48 mL) and sodium hydride (60% dispersion in mineral oil, 288 mg) in DMF (2 mL), which had been pre-stirred for 15 minutes. The reaction mixture was stirred at 80° C. overnight before being poured onto water and the resultant solid collected by filtration. The material was purified by flash chromatography (silica, 12 g column, ISCO, 0-20% methanol in DCM then 20% (2N ammonia in methanol) in DCM) to afford the title compound as a yellow oil which crystallised on standing (0.1 g, 58%). $^1$H NMR (CD$_3$OD, 400 MHz): 8.94 (d, J=1.1 Hz, 1H), 8.81-8.77 (m, 2H), 8.71 (s, 1H), 8.58 (d, J=1.1 Hz, 1H), 8.48 (d, J=5.9 Hz, 1H), 8.09 (s, 1H), 7.94 (s, 1H), 7.28 (d, J=5.9 Hz, 1H), 4.42 (t, J=5.2 Hz, 2H), 3.98 (s, 3H), 3.03 (t, J=5.1 Hz, 2H), 2.42 (s, 6H). LCMS (Method A): R$_T$=3.93 min, M+H$^+$=414.

Example 399

6-(Pyrazin-2-yl)-3-(4-piperidin-1-ylmethyl-phenyl)-9H-dipyrido[2,3-b;4',3'-d]pyrrole

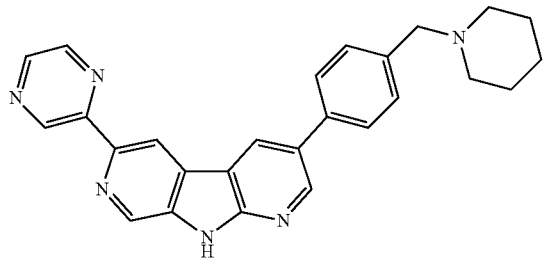 [SMILES: c1cnc(-c2cc3c(cn2)[nH]c2ncc(-c4ccc(CN5CCCCC5)cc4)cc23)cn1]

The title compound was prepared following a similar procedure to the previous example using 2-(tributylstannyl)pyrazine to yield a pale orange solid (20%). $^1$H NMR (DMSO-D$_6$, 500 MHz): 12.43 (s, 1H), 9.62 (d, J=1.4 Hz, 1H), 9.28 (s, 1H), 9.19 (d, J=2.3 Hz, 1H), 9.06 (s, 1H), 8.95 (d, J=2.2 Hz, 1H), 8.78-8.72 (m, 1H), 8.66 (d, J=2.5 Hz, 1H), 7.81 (d, J=8.2 Hz, 2H), 7.44 (d, J=8.1 Hz, 2H), 3.50 (s, 2H), 2.37 (s, 4H), 1.58-1.48 (m, 4H), 1.41 (m, 2H). LCMS (Method E): R$_T$=2.93 min, M+H$^+$=421.

Example 400

6-(Pyridazin-4-yl)-3-(4-piperidin-1-ylmethylphenyl)-9H-dipyrido[2,3-b;4',3'-d]pyrrole

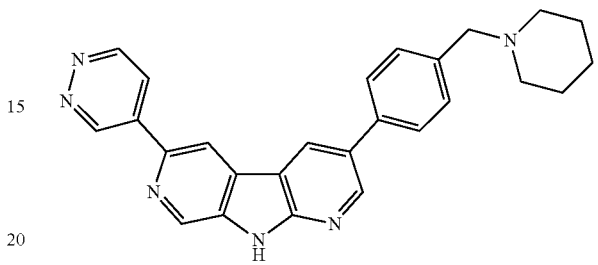

Step 1: 6'-(Pyridazin-4-yl)-2-fluoro-5-(4-piperidin-1-ylmethylphenyl)-[3,4']bipyridinyl-3'-ylamine

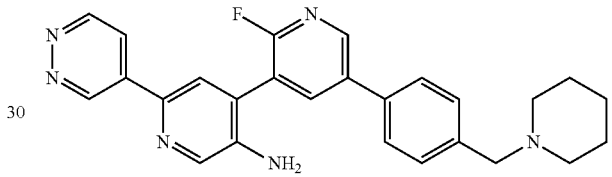

A mixture of 6'-bromo-2-fluoro-5-(4-piperidin-1-ylmethylphenyl)-[3,4']bipyridinyl-3'-ylamine (200 mg, 0.45 mmol), 4-(tributylstannyl)pyridazine (334 mg, 0.91 mmol) and lithium chloride (192 mg, 4.5 mmol) in 1,4-dioxane (5 mL) was degassed and flushed with nitrogen. Tetrakis(triphenylphosphine)-palladium(0) (39 mg, 0.034 mmol) was added and the reaction was heated at 110° C. for 24 h. The cooled reaction mixture was diluted with DCM (20 mL) and methanol (2 mL) and washed with water (15 mL). The organic phase was separated, dried over sodium sulfate, filtered and evaporated in vacuo to afford a residue that was purified by flash chromatagraphy (silica, 10 g column, Biotage, 0-10% methanol in DCM containing 0 1% ammonia) to afford a brown residue that was taken to the next step without further purification.

Step 2: 6-(Pyridazin-4-yl)-3-(4-piperidin-1-ylmethylphenyl)-9H-dipyrido[2,3-b;4',3'-d]pyrrole

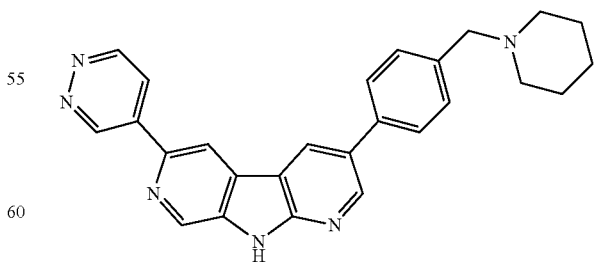

To a solution of 6'-(pyridazin-4-yl)-2-fluoro-[3,4]bipyridinyl-3'-ylamine (120 mg, 0.27 mmol) in anhydrous tetrahydrofuran (5 mL) was added sodium bis-(trimethylsilyl)amide (1N solution in THF, 1.4 mL, 1.4 mmol) under a flow of nitrogen. The reaction was left to stir at room temperature for 5 h then quenched with acetic acid (1 mL). The reaction mixture was then evaporated in vacuo to afford a residue that was purified by preparative HPLC [20-60% MeCN in water (0.1% ammonium hydroxide) over 30 min, 35 mL/min] to afford the title compound as a pale orange solid (37 mg, 20%). $^1$H NMR (DMSO-D$_6$, 400 MHz): 12.58 (s, 1H), 10.01 (s, 1H), 9.35 (d, J=5.4 Hz, 1H), 9.25 (s, 1H), 9.12 (s, 1H), 9.05 (d, J=2.1 Hz, 1H), 8.98 (d, J=2.1 Hz, 1H), 8.34 (m, 1H), 7.78 (d, J=8.1 Hz, 2H), 7.47 (d, J=8.1 Hz, 2H), 3.52 (s, 2H), 2.38 (s, 4H), 1.53 (m, 4H), 1.41 (m, 2H). LCMS (Method D): R$_T$=7.78 min, M+H$^+$=421.

Example 401

6-(pyrimidin-5-yl)-3-(4-piperidin-1-ylmethylphenyl)-9H-dipyrido[2,3-b;4',3'-d]pyrrole

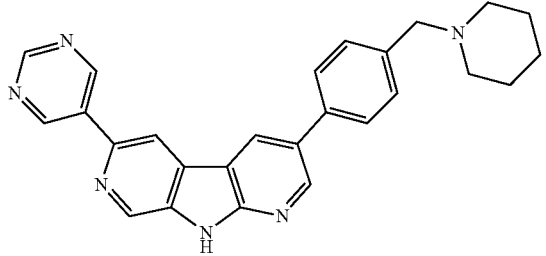 [SMILES: c1cc(-c2cc3c(cn2)[nH]c2ncc(-c4ccc(CN5CCCCC5)cc4)cc23)cnn1]

A mixture of 6-chloro-3-(4-piperidin-1-ylmethylphenyl)-9H-dipyrido[2,3-b;4',3'-d]pyrrole (40 mg, 0.08 mmol), pyrimidin-5-yl boronic acid (20 mg, 0.16 mmol), 1,1'-[bis(diphenylphosphino)ferrocene]dichloropalladium(II) (3.2 mg, 0.004 mmol) in saturated aqueous sodium carbonate solution (0.15 mL) and acetonitrile (1.50 mL) was heated under microwave irradiation at 130° C. for 30 minutes. The cooled reaction mixture was diluted with DCM (20 mL) and methanol (2 mL) and washed with water (15 mL). The organic phase was separated, dried over sodium sulfate, filtered and evaporated in vacuo to afford a residue that was purified by preparative HPLC [0-30% MeCN in water (0.1% formic acid) over 30 min, 35 mL/min] to afford the title compound as a yellow/orange solid (10 mg, 23%). $^1$H NMR (DMSO-D$_6$, 400 MHz): 12.44 (s, 1H), 9.52 (s, 2H), 9.21 (s, 1H), 9.08 (d, J=1.7 Hz, 2H), 9.02 (d, J=2.2 Hz, 1H), 8.96 (d, J=2.2 Hz, 1H), 7.77 (d, J=8.2 Hz, 2H), 7.46 (d, J=8.1 Hz, 2H), 3.50 (s, 2H), 2.37 (s, 4H), 1.53 (m, 4H), 1.41 (m, 2H). LCMS (Method D): R$_T$=6.84 min, M+H$^+$=421.

Example 402

6-(2-Aminopyrimidin-5-yl)-3-(4-piperidin-1-ylmethylphenyl)-9H-dipyrido[2,3-b;4',3'-d]pyrrole

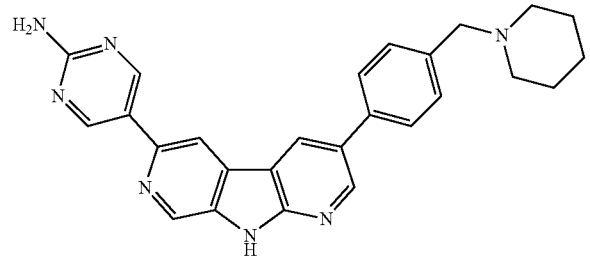 [SMILES: Nc1ncc(-c2cc3c(cn2)[nH]c2ncc(-c4ccc(CN5CCCCC5)cc4)cc23)cn1]

A degassed mixture of 6-chloro-3-(4-piperidin-1-ylmethylphenyl)-9H-dipyrido[2,3-b;4',3'-d]pyrrole (74.4 mg, 0.197 mmol), 2-aminopyrimidine-5-boronic acid, pinacol ester (45.8 mg, 0.207 mmol), and [1,1'-bis(diphenylphosphino)ferrocene]dichloropalladium(II) complex with dichloromethane (1:1) (8.1 mg, 9.87 umol, 5.0 mol %) in acetonitrile (0.74 mL) and 1M aqueous potassium carbonate solution (0.74 mL) was heated under microwave irradiation (140° C.) for 30 minutes. Further portions of the boronate ester (1.0 eq) and catalyst (5 mol %), acetonitrile (0.74 mL), and 1M aqueous potassium carbonate solution (0.74 mL) were added and the mixture heated under microwave irradiation (140° C.) for an additional 30 minutes. The mixture was concentrated in vacuo and the residue dissolved in water and DMF, and acidified with 10% (v/v) sulfuric acid. The resultant solid was removed by filtration and the filtrate concentrated in vacuo. The resultant residue was dissolved in DMSO and purified by preparative HPLC [0-30% MeCN/water modified with 0.1% formic acid] to afford an orange fluffy solid (5.1 mg, 14%). LCMS (Method E): R$_T$=5.45 min, M+H$^+$=436.

Example 403

6-(Imidazo[1,2-a]pyrimidin-3-yl)-3-(4-piperidin-1-ylmethyl-phenyl)-9H-dipyrido[2,3-b;4',3'-d]pyrrole

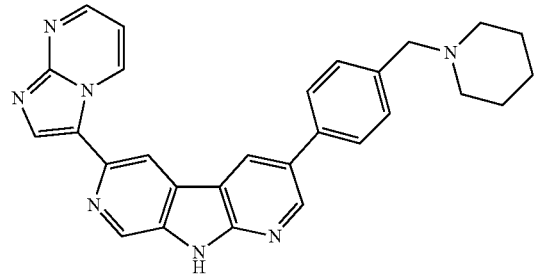 [SMILES: c1cnc2ncc(-c3cc4c(cn3)[nH]c3ncc(-c5ccc(CN6CCCCC6)cc5)cc34)n2c1]

The title compound was prepared following a similar procedure to the previous example using 3-(trimethylstannyl)imidazo[1,2-a]pyrimidine to yield a pale yellow solid (20%). $^1$H NMR (DMSO-D$_6$, 400 MHz): 12.34 (s, 1H), 10.23 (dd, J=6.8, 2.0 Hz, 1H), 9.05 (s, 1H), 9.04 (d, J=2.4 Hz, 1H), 8.97 (d, J=2.4 Hz, 1H), 8.95 (s, 1H), 8.64 (s, 1H), 8.46 (s, 1H), 7.79 (d, J=8.1 Hz, 2H), 7.47 (d, J=8.1 Hz, 2H), 7.25 (s, 1H), 3.52 (s, 2H), 2.39 (s, 4H), 1.54 (m, 4H), 1.42 (m, 2H). LCMS (Method D): R$_T$=7.32 min, M+H$^+$=460.

Example i

Chk1 and Chk2 Assays (Chk Primary Assays)

Full length human mutant recombinant protein, histidine tagged and expressed in insect cells is used as source of enzymatic activity (Invitrogen, chk1 from product PV3982 and chk2 from product PV3983).

The chk1 AlphaScreen assay is carried out for 30 minutes in the presence of 10 μM ATP using biotinylated Akt substrate-1 peptide (Cell Signalling Technology, product #1065) as a substrate. Phosphorylation of the substrate is detected and quantified using AlphaScreen technology. This consists of an anti-phospho-Akt substrate-1 antibody (Cell Signalling technology Product #9611) and two AlphaScreen beads (Perkin Elmer), one product coated with Protein A which binds the antibody Ig chain (Product 6760137), and one coated with Streptavidin which binds the biotin on the biotinylated Akt substrate peptide-1 (Product 6760002). Chk1 activity results in the production of phosphorylated Akt substrate peptide-1 an event which causes the two bead species to be brought into close proximity in the presence of antibody leading to the generation of luminescence which is detected on a Perkin Elmer reader (Fusion).

The ATP Radiometric ChK1 assay is carried out by incubation for 30 minutes in the presence of 10 μM ATP containing 0.3 μCi $^{33}$P-ATP per sample and using ChKTide (peptide sequence KKKVSRSGLYRSPSMPENLNRPR) as a substrate. Following acidification with 1% phosphoric acid and washing to remove unincorporated ATP, phosphorylation of the substrate is detected and quantified by measurement of radioactivity incorporated using a Perkin Elmer Topcount.

The chk2 AlphaScreen assay is carried out for 30 minutes in the presence of 30 μM ATP using biotinylated tyrosine hydroxylase (ser 40) peptide (Cell Signalling Technology, product #1132) as a substrate. Phosphorylation of the substrate is detected and quantified using AlphaScreen technology. This consists of an anti-phospho-tyrosine hydroxylase (ser 40) peptide antibody (Cell Signalling technology Product #2791) and two AlphaScreen beads (Perkin Elmer), one product coated with Protein A which binds the antibody Ig chain (Product 6760137), and one coated with Streptavidin which binds the biotin on the biotinylated tyrosine hydroxylase (ser 40) peptide (Product 6760002). Chk2 activity results in the production of phosphorylated tyrosine hydroxylase peptide an event which causes the two bead species to be brought into close proximity in the presence of antibody leading to the generation of luminescence which is detected on a Perkin Elmer reader (Fusion).

The ATP Radiometric ChK2 assay is carried out by incubation for 30 minutes in the presence of 30 μM ATP containing 0.3 μCi $^{33}$P-ATP per sample and using ChKTide (peptide sequence KKKVSRSGLYRSPSMPENLNRPR) as a substrate. Following acidification with 1% phosphoric acid and washing to remove unincorporated ATP, phosphorylation of the substrate is detected and quantified by measurement of radioactivity incorporated using a Perkin Elmer Topcount.

Test compounds are diluted in DMSO prior to addition to assay buffer, the final DMSO concentration in the assay is 1%.

The $IC_{50}$ is defined as the concentration at which a given test compound achieved 50% inhibition of the control. $IC_{50}$ values are calculated using the XLfit software package (version 2.0.5).

Title compounds of EXAMPLES 1-119, 121-141, 143, 145-146, 148-171, 173, 175-178, 180-181, 184, and 186-403 exhibited an $IC_{50}$ of less than 5 μM in the assays described in EXAMPLE i against chk1.

Example ii

Cellular Assay (Checkpoint Abrogation)

Compounds are tested in a cellular assay using the human colorectal adenocarcinoma derived cell line HT-29 (ATCC HTB-38).

The cell line is maintained in DMEM/F12 (1:1) media (Invitrogen Gibco, #31331) supplemented with 10% FCS at 37° C. in a 5% $CO_2$ humidified incubator.

Cells are seeded in 96-well plates at 30,000 cells/well and after 24 h they are exposed to 20 nM SN-38 in 0.4% DMSO. One column of 8 wells on each plate was used to generate a maximum signal control. These cells are treated with 0.4% DMSO without SN-38. Cells are grown for a further 16 h, then the media containing DMSO plus or minus SN-38 is removed and replaced with media containing 300 nM nocodazole alone (to determine baseline) or in combination with ten concentrations of chk1 inhibitor (final DMSO concentration is 0.4%). Cells are grown for a further 24 h. The media is removed and replaced with 50 μl lysis buffer containing protease inhibitors and phosphatase inhibitors. This buffer contains detergent to bring about cellular disruption. Following complete cellular disruption, 25 μl lysate is transferred to a MesoScale 96 well 4-spot plate coated with an antibody to Histone H3 (MesoScale Discovery (MSD) Product K110EWA-3) which have been previously blocked with 3% bovine serum albumin in Tris buffered saline. Following the transfer of lysate to the MSD plate, Histone H3 in the lysate is captured on the coated antibody by incubation at room temperature for 2 h. Following the capture step the plate is washed and then incubated with an antibody to phosphorylated Histone H3 which is conjugated with a Sulfo-Tag. This tag gives a signal when in proximity to the electrode on the base of the MSD plate. Binding the tagged antibody to the captured protein allow detection on a MSD reader.

The $EC_{50}$ is defined as the concentration at which a given compound achieves 50% decrease of the measured levels of phospho-Histone H3 within the range of a normal sigmoidal dose response curve compared to the signal generated by 300 nM nocodazole alone. $EC_{50}$ values are calculated using the XLfit software package (version 2.0.5) or Graphpad Prism, (version 3.03) fitting a sigmoidal curve with a variable slope.

Title compounds of EXAMPLES 1, 4-7, 9-13, 15-30, 32-41, 43-46, 48-55, 58-62, 64-77, 80, 84-90, 93-117, 119, 125, 127, 130-133, 135, 138, 157, 160, 166, 176, 180, 186, 188, 190, 194-195, 198-209, 211-212, 214, 216-282, 284-316, 319-322, 324-338, 343-344, 350-351, 353-362, 366, 368, 370-389, 391-395, 397-402 exhibited an $EC_{50}$ of less than 10 μM in the assay described in EXAMPLE ii.

We claim:

1. A method of treating colorectal cancer in a mammal comprising administering to said mammal a therapeutically effective amount of a compound of formula (I), or a salt thereof:

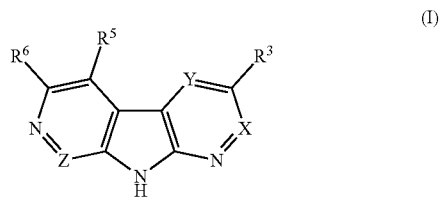

(I)

X is $CR^2$ or N;
Y is $CR^4$ or N;
Z is $CR^8$ or N; provided that no more than one of X, Y and Z is N at the same time;
$R^2$ is H, halo, CN, $CF_3$, —$OCF_3$, OH, —$NO_2$, $C_1$-$C_5$ alkyl, —O($C_1$-$C_5$ alkyl), —S($C_1$-$C_5$ alkyl), or $N(R^{22})_2$;
$R^3$ is H, halo, CN, —O—$R^9$, —N($R^{22}$)—$R^9$, —S(O)$_p$—$R^9$, or $R^9$;
p is 0, 1 or 2;
$R^4$ is H, halo, CN, $CF_3$, —$OCF_3$, OH, —$NO_2$, —$(CR^{14}R^{15})_n$C(=Y')$OR^{11}$, —$(CR^{14}R^{15})_n$C(=Y') $NR^{11}R^{12}$, —$(CR^{14}R^{15})_n$$NR^{11}R^{12}$, —$(CR^{14}R^{15})_n$$OR^{11}$, —$(CR^{14}R^{15})_n$S(O)$_p$$R^{11}$, —$(CR^{14}R^{15})_n$$NR^{12}$C(=Y') $R^{11}$, —$(CR^{14}R^{15})_n$$NR^{12}$C(=Y')$OR^{11}$, —$(CR^{14}R^{15})_n$ $NR^{12}$C(=Y')$NR^{11}R^{12}$, —$(CR^{14}R^{15})_n$$NR^{12}SO_2R^{11}$, —$(CR^{14}R^{15})_n$OC(=Y')$R^{11}$, —$(CR^{14}R^{15})_n$OC(=Y') $NR^{11}R^{12}$, —$(CR^{14}R^{15})_n$S(O)$_2$$NR^{11}R^{12}$, alkyl, alkenyl, alkynyl, cycloalkyl, heterocyclyl, aryl, or heteroaryl wherein said alkyl, alkenyl, alkynyl, cycloalkyl, heterocyclyl, aryl and heteroaryl are optionally substituted with one to four $R^{13}$ groups;

each n is independently 0-5;

$R^5$ is H, halo, CN, $CF_3$, $-OCF_3$, OH, $-NO_2$, $-(CR^{14}R^{15})_nC(=Y')OR^{11}$, $-(CR^{14}R^{15})_nC(=Y')NR^{11}R^{12}$, $-(CR^{14}R^{15})_nNR^{12}C(=Y')R^{11}$, $-(CR^{14}R^{15})_nNR^{11}R^{12}$, $-(CR^{14}R^{15})_nOR^{11}$, $-(CR^{14}R^{15})_nS(O)_pR^{11}$, $-(CR^{14}R^{15})_nNR^{12}C(=Y')OR^{11}$, $-(CR^{14}R^{15})_nNR^{12}C(=Y')NR^{11}R^{12}$, $-(CR^{14}R^{15})_nNR^{12}SO_2R^{11}$, $-(CR^{14}R^{15})_nOC(=Y')R^{11}$, $-(CR^{14}R^{15})_nOC(=Y')NR^{11}R^{12}$, $-(CR^{14}R^{15})_nS(O)_2NR^{11}R^{12}$, alkyl, alkenyl, alkynyl, cycloalkyl, heterocyclyl, aryl, heteroaryl wherein the said alkyl, alkenyl, alkynyl, cycloalkyl, heterocyclyl, aryl and heteroaryl are optionally substituted with one to four $R^{13}$ groups;

$R^6$ is CN, $-CF_3$, $-OCF_3$, halo, $-C(=Y')NR^{11}R^{12}$, $-OR^{11}$, $-OC(=Y')R^{11}$, $-NR^{11}R^{12}$, $-NR^{12}C(=Y')R^{11}$, $-NR^{12}C(=Y')NR^{11}R^{12}$, $-NR^{12}S(O)_qR^{11}$, $-SR^{11}$, $-S(O)R^{11}$, $-S(O)_2R^{11}$, $-OC(=Y')NR^{11}R^{12}$, $-S(O)_2NR^{11}R^{12}$, alkyl, alkenyl, alkynyl, cycloalkyl, heterocyclyl, aryl, or heteroaryl wherein said alkyl, alkenyl, alkynyl, cycloalkyl, heterocyclyl, aryl and heteroaryl are optionally substituted by one to four $R^{13}$ groups;

$R^8$ is H, halo, CN, $NO_2$, $N(R^{22})_2$, OH, $O(C_1-C_3$ alkyl), or $C_1-C_3$ alkyl, wherein each said alkyl is optionally substituted with one to three fluoro groups;

each $R^9$ is independently alkyl, alkenyl, alkynyl, cycloalkyl, heterocyclyl, aryl, heteroaryl, wherein each member of $R^9$ is independently substituted with one to three $R^{10}$ groups;

each $R^{10}$ is independently H, CN, $-CF_3$, $-OCF_3$, $-NO_2$, halo, $R^{11}$, $-OR^{11}$, $-NR^{12}C(=Y')^{11}$, $-NR^{12}C(NR^{12})R^{11}$, $-NR^{12}S(O)_qR^{11}$, $-SR^{11}$, $-NR^{11}R^{12}$, oxo, $-C(=Y')OR^{11}$, $-C(=Y')NR^{11}R^{12}$, $-S(O)_qR^{11}$, $-NR^{12}C(=Y')OR^{11}$, $-NR^{12}C(=Y')NR^{11}R^{12}$, $-OC(=Y')R^{11}$, $-OC(=Y')NR^{11}R^{12}$, or $-S(O)_2NR^{11}R^{12}$;

each q independently is 1 or 2;

$R^{11}$ and $R^{12}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{13}$ groups, wherein two geminal $R^{13}$ groups are optionally taken together with the atom to which they are attached to form a 3-6 membered ring having additional 0-2 heteroatoms selected from O, S, and N, said ring being optionally substituted with one to four $R^{18}$ groups;

$R^{11}$ and $R^{12}$ are optionally taken together with the attached N atom to form a 4-7 membered ring having additional 0-2 heteroatoms selected from O, S, and N, said ring being optionally substituted with one to four $R^{13}$ groups;

each $R^{13}$ is independently halo, CN, $CF_3$, $-OCF_3$, $-NO_2$, oxo, $-(CR^{14}R^{15})_nC(=Y')R^{16}$, $-(CR^{14}R^{15})_nC(=Y')OR^{16}$, $-(CR^{14}R^{15})_nC(=Y')NR^{16}R^{17}$, $-(CR^{14}R^{15})_nNR^{16}R^{17}$, $-(CR^{14}R^{15})_nOR^{16}$, $-(CR^{14}R^{15})_nSR^{16}$, $-(CR^{14}R^{15})_nNR^{16}C(=Y')R^{17}$, $-(CR^{14}R^{15})_nNR^{16}C(=Y')OR^{17}$, $-(CR^{14}R^{15})_nNR^{17}C(=Y')NR^{16}R^{17}$, $-(CR^{14}R^{15})_nNR^{17}SO_2R^{16}$, $-(CR^{14}R^{15})_nOC(=Y')R^{16}$, $-(CR^{14}R^{15})_nOC(=Y')NR^{16}R^{17}$, $-(CR^{14}R^{15})_nS(O)R^{16}$, $-(CR^{14}R^{15})_nS(O)_2R^{16}$, $-(CR^{14}R^{15})_nS(O)_2NR^{16}R^{17}$, or $R^{16}$;

$R^{14}$ and $R^{15}$ are independently selected from H, alkyl, cycloalkyl, heterocyclyl, aryl or heteroaryl, wherein said alkyl, cycloalkyl, heterocyclyl, aryl and heteroaryl are optionally substituted with one to four $R^{18}$ groups;

$R^{16}$ and $R^{17}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{18}$ groups;

$R^{16}$ and $R^{17}$ are optionally taken together with the attached N atom to form a 5-6 membered ring having additional 0-2 heteroatoms selected from O, S, and N, said ring being optionally substituted with one to four $R^{18}$ groups;

each $R^{18}$ is independently H, alkyl, cycloalkyl, heterocyclyl, aryl, heteroaryl, halo, CN, $CF_3$, $-OCF_3$, $-NO_2$, oxo, $-(CR^{19}R^{20})_nC(=Y')R^{23}$, $-(CR^{19}R^{20})_nC(=Y')OR^{23}$, $-(CR^{19}R^{20})_nC(=Y')NR^{23}R^{24}$, $-(CR^{19}R^{20})_nNR^{23}R^{24}$, $-(CR^{19}R^{20})_nOR^{23}$, $-(CR^{19}R^{20})_nSR^{23}$, $-(CR^{19}R^{20})_nNR^{24}C(=Y')R^{23}$, $-(CR^{19}R^{20})_nNR^{24}C(=Y')OR^{23}$, $-(CR^{19}R^{20})_nNR^{22}C(=Y')NR^{23}R^{24}$, $-(CR^{19}R^{20})_nNR^{24}SO_2R^{23}$, $-(CR^{19}R^{20})_nOC(=Y')R^{23}$, $-(CR^{19}R^{20})_nOC(=Y')NR^{23}R^{24}$, $-(CR^{19}R^{20})_nS(O)R^{23}$, $-(CR^{19}R^{20})_nS(O)_2R^{23}$, or $-(CR^{19}R^{20})_nS(O)_2NR^{23}R^{24}$, wherein said alkyl, cycloalkyl, heterocyclyl, aryl, and heteroaryl are optionally substituted with one to four $R^{21}$ groups;

$R^{19}$ and $R^{20}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{25}$ groups;

$R^{23}$ and $R^{24}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{21}$ groups;

$R^{23}$ and $R^{24}$ are optionally taken together with the attached N atom to form a 5-6 membered ring having additional 0-2 heteroatoms selected from O, S, and N, said ring being optionally substituted with one to four $R^{21}$ groups;

each $R^{21}$ is independently H, alkyl, cycloalkyl, heterocyclyl, aryl, heteroaryl, halo, CN, $CF_3$, $-OCF_3$, $-NO_2$, oxo, $-C(=Y')R^{25}$, $-C(=Y')OR^{25}$, $-C(=Y')NR^{25}R^{26}$, $-NR^{25}R^{26}$, $-OR^{25}$, $-SR^{25}$, $-NR^{26}C(=Y')R^{25}$, $-NR^{26}C(=Y')OR^{25}$, $-NR^{22}C(=Y')NR^{25}R^{26}$, $-NR^{26}SO_2R^{25}$, $-OC(=Y')R^{25}$, $-OC(=Y')NR^{25}R^{26}$, $-S(O)R^{25}$, $-S(O)_2R^{25}$, or $-S(O)_2NR^{25}R^{26}$, wherein said alkyl, cycloalkyl, heterocyclyl, aryl, and heteroaryl are optionally substituted with one to four $R^{25}$ groups;

each $R^{25}$ and $R^{26}$ is independently H, alkyl, cycloalkyl, heterocyclyl, aryl, or heteroaryl, wherein said alkyl, cycloalkyl, heterocyclyl, aryl, or heteroaryl is optionally substituted with one to four groups selected from halo, $-CN$, $-OCF_3$, $-CF_3$, $-NO_2$, $-C_1-C_6$ alkyl, $-OH$, oxo, $-SH$, $-O(C_1-C_6$ alkyl), $-S(C_1-C_6$ alkyl), $-NH_2$, $-NH(C_1-C_6$ alkyl), $-N(C_1-C_6$ alkyl)$_2$, $-SO_2(C_1-C_6$ alkyl), $-CO_2H$, $-CO_2(C_1-C_6$ alkyl), $-C(O)NH_2$, $-C(O)NH(C_1-C_6$ alkyl), $-C(O)N(C_1-C_6$ alkyl)$_2$, $-N(C_1-C_6$ alkyl)$C(O)(C_1-C_6$ alkyl), $-NHC(O)(C_1-C_6$ alkyl), $-NHSO_2(C_1-C_6$ alkyl), $-N(C_1-C_6$ alkyl)$SO_2(C_1-C_6$ alkyl), $-SO_2NH_2$, $-SO_2NH(C_1-C_6$ alkyl), $-SO_2N(C_1-C_6$ alkyl)$_2$, $-OC(O)NH_2$, $-OC(O)NH(C_1-C_6$ alkyl), $-OC(O)N(C_1-C_6$ alkyl)$_2$, $-NHC(O)NH(C_1-C_6$ alkyl), $-NHC(O)N(C_1-C_6$ alkyl)$_2$, $-N(C_1-C_6$ alkyl)$C(O)NH(C_1-C_6$ alkyl), $-N(C_1-C_6$ alkyl)$C(O)N(C_1-C_6$ alkyl)$_2$, $-NHC(O)NH(C_1-C_6$ alkyl), $-NHC(O)N(C_1-C_6$ alkyl)$_2$, $-NHC(O)O(C_1-C_6$ alkyl), and $-N(C_1-C_6$ alkyl)$C(O)O(C_1-C_6$ alkyl);

$R^{25}$ and $R^{26}$ are optionally taken together with the attached N atom to form a 5-6 membered ring having additional 0-2 heteroatoms selected from O, S, and N, said ring being optionally substituted with one to four groups selected from halo, $-CN$, $-OCF_3$, $CF_3$, $-NO_2$, $-C_1-$ $C_6$ alkyl, —OH, oxo, —SH, —O($C_1$-$C_6$ alkyl), —S($C_1$-$C_6$ alkyl), —NH$_2$, —NH($C_1$-$C_6$ alkyl), —N($C_1$-$C_6$ alkyl)$_2$, —SO$_2$($C_1$-$C_6$ alkyl), —CO$_2$H, —CO$_2$($C_1$-$C_6$ alkyl), —C(O)NH$_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —SO$_2$NH$_2$, —SO$_2$NH($C_1$-$C_6$ alkyl), —SO$_2$N($C_1$-$C_6$ alkyl)$_2$, —OC(O)NH$_2$, —OC(O)NH($C_1$-$C_6$ alkyl), —OC(O)N($C_1$-$C_6$ alkyl)$_2$, —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);

Y' is independently O, NR$^{22}$, or S; and each R$^{22}$ is independently H or $C_1$-$C_5$ alkyl.

2. The method of claim 1, wherein the compounds of formula (I) are those wherein X is CR$^2$.

3. The method of claim 1, wherein the compounds of formula (I) are those wherein R$^2$ is H.

4. The method of claim 1, wherein the compounds of formula (I) are those wherein Y is CR$^4$.

5. The method of claim 1, wherein the compounds of formula (I) are those wherein R$^4$ is H.

6. The method of claim 1, wherein the compounds of formula (I) are those wherein Z is CR$^8$.

7. The method of claim 1, wherein the compounds of formula (I) are those wherein R$^8$ is H.

8. The method of claim 1, wherein the compounds of formula (I) are those wherein R$^3$ is Br.

9. The method of claim 1, wherein the compounds of formula (I) are those wherein R$^3$ is H.

10. The method of claim 1, wherein the compounds of formula (I) are those wherein R$^3$ is R$^9$.

11. The method of claim 1, wherein the compounds of formula (I) are those wherein R$^9$ is $C_1$-$C_6$ alkyl, $C_2$-$C_3$ alkynyl, $C_6$ aryl, or 5-6 membered monocyclic or 8-10-membered bicyclic heteroaryl having 1 to 2 ring atoms selected from N, O and S; and wherein each member of R$^9$ is independently substituted with one to two R$^{10}$ groups.

12. The method of claim 1, wherein the compounds of formula (I) are those wherein R$^9$ is isopropyl, propynyl, phenyl, pyrazolyl, furanyl, thienyl, pyridyl, imidazolyl, pyrimidinyl, benzothienyl, thiazolyl, tetrahydrothienopyridinyl, tetrahydrothiazolopyridinyl, isothiazolyl, tetrahydropyridinyl, tetrahydroisoquinolinyl, triazolyl, dihydrobenzodioxinyl, dihydroindolyl, oxazolyl, or tetrahydrobenzothienyl, wherein each member of R$^9$ is independently substituted with one to two R$^{10}$ groups.

13. The method of claim 1, wherein the compounds of formula (I) are those wherein R$^{10}$ is halo, R$^{11}$, —OR$^{11}$, CN, —CF$_3$, —OCF$_3$, —NR$^{12}$C(=O)R$^{11}$, —NR$^{12}$S(O)$_q$R$^{11}$, —SR$^{11}$, —NR$^{11}$R$^{12}$, —C(=O)NR$^{11}$R$^{12}$, oxo, —S(O)$_q$R$^{11}$, —S(O)$_2$NR$^{11}$R$^{12}$, or —C(=O)OR$^{11}$ wherein R$^{11}$ and R$^{12}$ are optionally taken together with the attached N atom to form a 4-7 membered ring having additional 0-2 heteroatoms selected from O, S, and N, said ring being optionally substituted with one to four R$^{13}$ groups.

14. The method of claim 1, wherein the compounds of formula (I) are those wherein R$^{10}$ is R$^{11}$.

15. The method of claim 1, wherein the compounds of formula (I) are those wherein R$^{11}$ is $C_1$-$C_6$ alkyl, or 4-6 membered monocyclic or 8-10 membered bicyclic heterocyclyl having 1 to 2 heteroatoms selected from N and O, wherein said alkyl and heterocyclyl are optionally substituted with one to four R$^{13}$ groups, wherein two geminal R$^{13}$ groups are optionally taken together with the atom to which they are attached to form a six-membered ring having 0-2 heteroatom selected from O, S, and N, said ring being optionally substituted with one to four R$^{18}$ groups.

16. The method of claim 1, wherein the compounds of formula (I) are those wherein R$^{11}$ is $C_1$-$C_6$ alkyl, wherein alkyl is optionally substituted with one to two R$^{13}$ groups and wherein each R$^{13}$ is independently halo, CN, CF$_3$, —OCF$_3$, oxo, —(CR$^{14}$R$^{15}$)$_n$C(O)OR$^{16}$, —(CR$^{14}$R$^{15}$)$_n$C(O)NR$^{16}$R$^{17}$, —(CR$^{14}$R$^{15}$)$_n$—NR$^{16}$R$^{17}$, —(CR$^{14}$R$^{15}$)$_n$OR$^{16}$, —(CR$^{14}$R$^{15}$)$_n$NR$^{16}$C(O)R$^{17}$, —(CR$^{14}$R$^{15}$)$_n$S(O)$_2$NR$^{16}$R$^{17}$, or R$^{16}$.

17. The method of claim 1, wherein the compounds of formula (I) are those wherein R$^{11}$ is 4-6 membered monocyclic or 8-10 membered bicyclic heterocyclyl having 1 to 2 heteroatoms selected from N and O, wherein said alkyl and heterocyclyl are optionally substituted with one to two R$^{13}$ groups and wherein each R$^{13}$ is independently halo, CN, CF$_3$, —OCF$_3$, oxo, —(CR$^{14}$R$^{15}$)$_n$C(O)OR$^{16}$, —(CR$^{14}$R$^{15}$)$_n$C(O)NR$^{16}$R$^{17}$, —(CR$^{14}$R$^{15}$)$_n$NR$^{16}$R$^{17}$, —(CR$^{14}$R$^{15}$)$_n$OR$^{16}$, —(CR$^{14}$R$^{15}$)$_n$NR$^{16}$C(O)R$^{17}$, —(CR$^{14}$R$^{15}$)$_n$S(O)$_2$NR$^{16}$R$^{17}$, or R$^{16}$.

18. The method of claim 1, wherein the compounds of formula (I) are those wherein R$^{10}$ is —OR$^{11}$.

19. The method of claim 1, wherein the compounds of formula (I) are those wherein R$^{11}$ is H, $C_1$-$C_4$ alkyl, or 4-6 membered monocyclic or 8-10 membered bicyclic heterocyclyl having 1 to 2 nitrogen atoms, wherein said alkyl or heterocyclyl is optionally substituted with one to two R$^{13}$ groups, wherein each R$^{13}$ is independently halo, CN, CF$_3$, —OCF$_3$, oxo, —(CR$^{14}$R$^{15}$)—C(O)OR$^{16}$, —(CR$^{14}$R$^{15}$)$_n$C(O)NR$^{16}$R$^{17}$, —(CR$^{14}$R$^{15}$)$_n$NR$^{16}$R$^{17}$, —(CR$^{14}$R$^{15}$)$_n$OR$^{16}$, —(CR$^{14}$R$^{15}$)$_n$NR$^{16}$C(O)R$^{17}$, —(CR$^{14}$R$^{15}$)$_n$S(O)$_2$NR$^{16}$R$^{17}$, or R$^{16}$.

20. The method of claim 1, wherein the compounds of formula (I) are those wherein R$^5$ is H.

21. The method of claim 1, wherein the compounds of formula (I) are those wherein R$^5$ is —(CR$^{14}$R$^{15}$)$_n$C(O)NR$^{11}$R$^{12}$, —(CR$^{14}$R$^{15}$)$_n$NR$^{12}$C(O)R$^{11}$, —(CR$^{14}$R$^{15}$)$_n$NR$^{11}$R$^{12}$, —(CR$^{14}$R$^{15}$)$_n$OR$^{11}$, $C_1$-$C_6$alkyl, or 4-6 membered monocyclic or 7-10 membered bicyclic heterocyclyl having 1 to 2 nitrogen atoms, wherein said alkyl or heterocyclyl is optionally substituted with one to two R$^{13}$ groups; wherein R$^{14}$ and R$^{15}$ are H; n is 0-2; each R$^{11}$ is independently H, $C_1$-$C_4$ alkyl, or 5-6 membered monocyclic heterocyclyl having 1 to 2 nitrogen atoms, wherein said alkyl or heterocyclyl is optionally substituted with one to two R$^{13}$ groups; and R$^{13}$ is OH, O($C_1$-$C_3$ alkyl), or $C_1$-$C_3$ alkyl.

22. The method of claim 1, wherein the compounds of formula (I) are those wherein R$^6$ is CN, halo, —C(O)NR$^{11}$R$^{12}$, —OR$^{11}$, —NR$^{11}$R$^{12}$, —NR$^{12}$C(O)R$^{11}$, $C_1$-$C_3$ alkyl, $C_3$-$C_6$ cycloalkyl, 5-6 membered heterocyclyl having 1 to 2 heteroatoms, $C_6$ aryl, or 5-6 membered heteroaryl having 1 to 2 heteroatoms; wherein said alkyl is substituted with one to two R$^{13}$ groups except H; and said cycloalkyl, aryl, heterocyclyl or heteroaryl is optionally substituted by one to two R$^{13}$ groups; wherein heteroatoms are selected from N, O and S; wherein each R$^{12}$ is H or $C_1$-$C_3$ alkyl and each R$^{11}$ is independently H or $C_1$-$C_3$ alkyl optionally substituted by one to two R$^{13}$ groups.

23. The method of claim 1, wherein the compounds of formula (I) are those wherein R$^6$ is CN.

24. The method of claim 1, wherein the compounds of formula (I) are selected from the group consisting of:

463
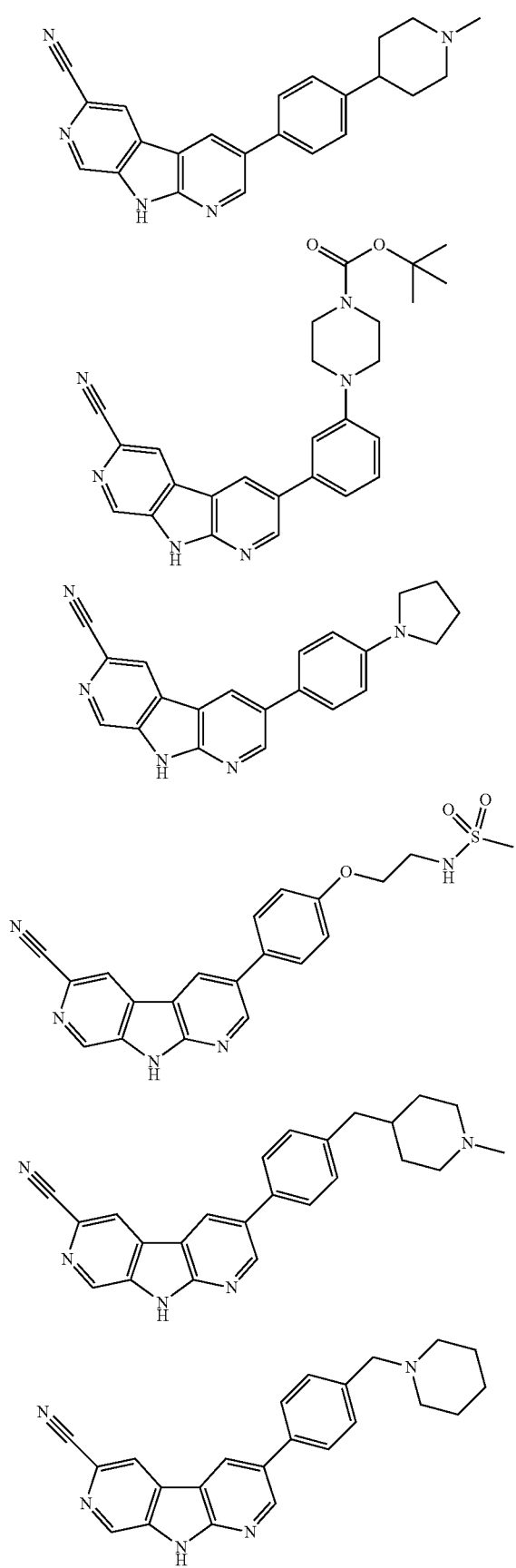
464
-continued
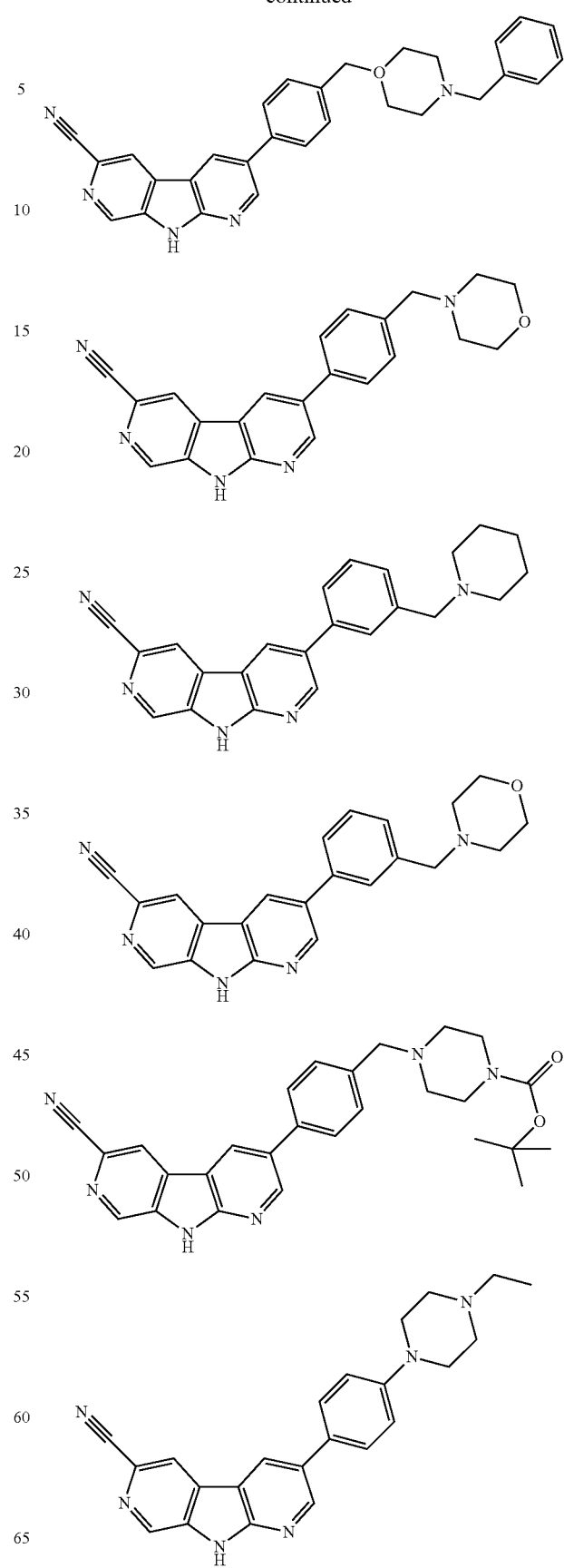

465
-continued
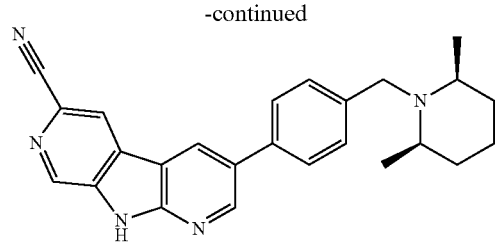
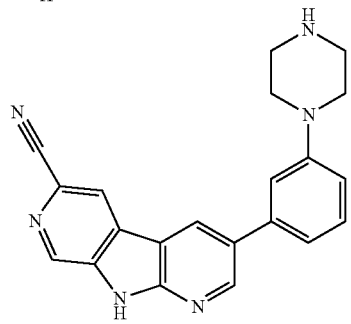
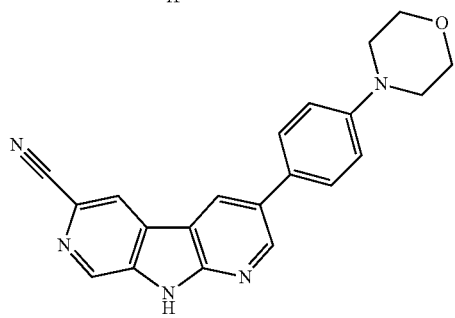
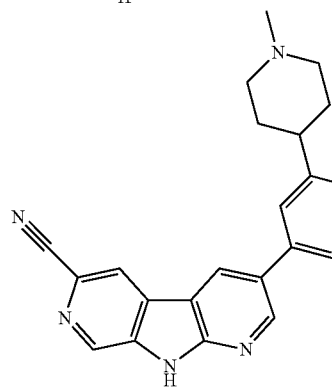
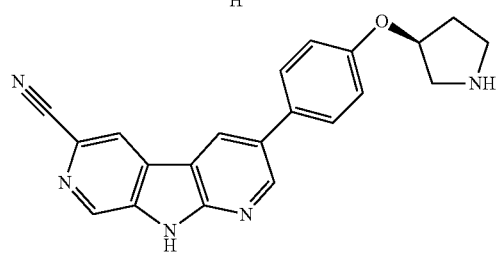
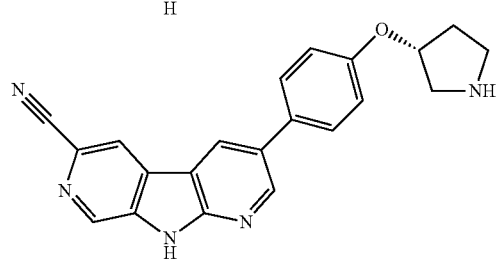
466
-continued
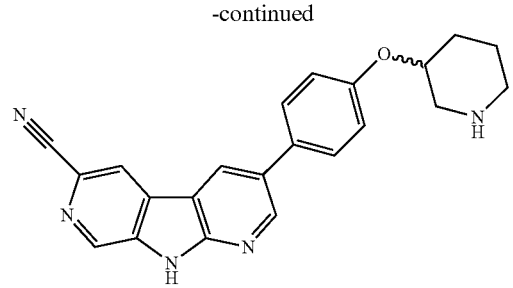
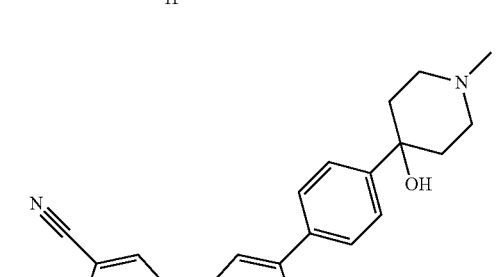
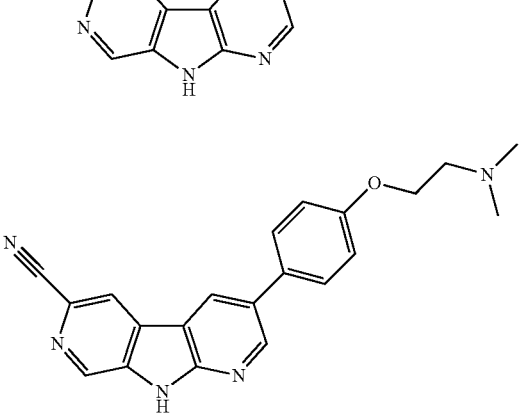
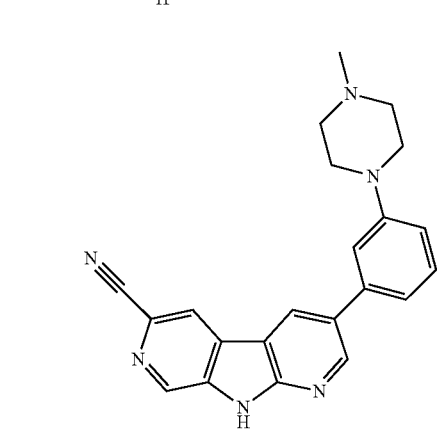
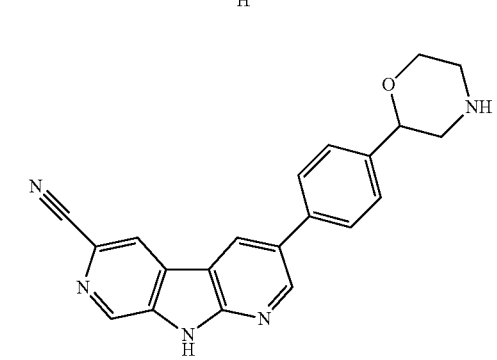

467
-continued
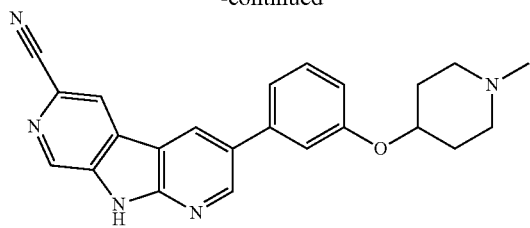
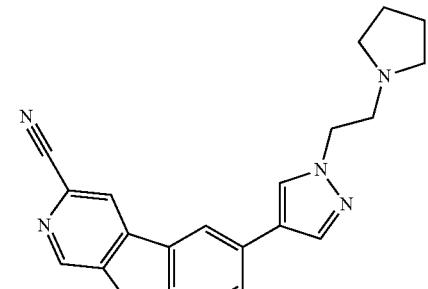
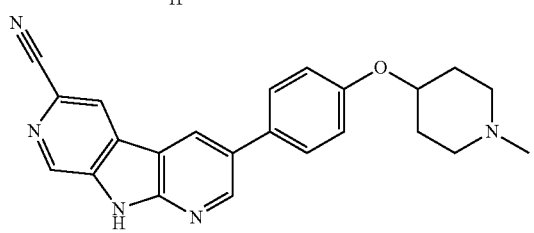
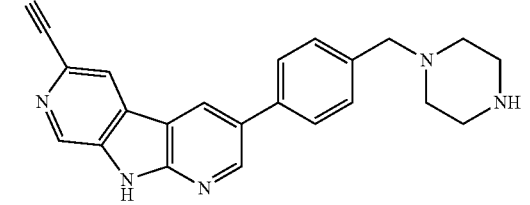
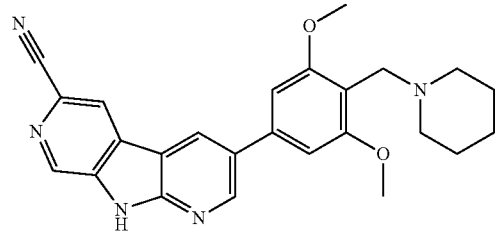
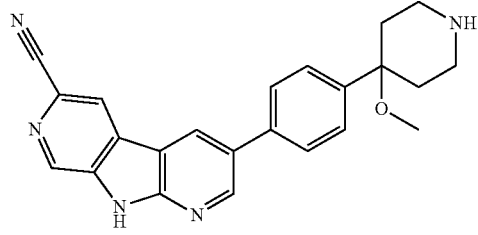
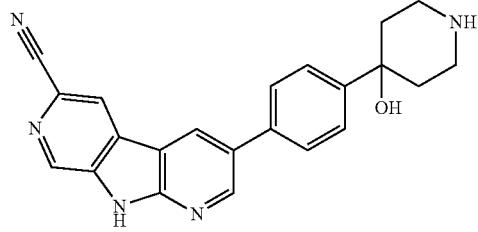
468
-continued
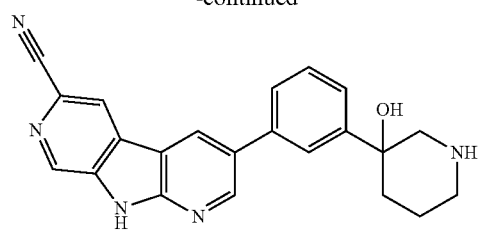
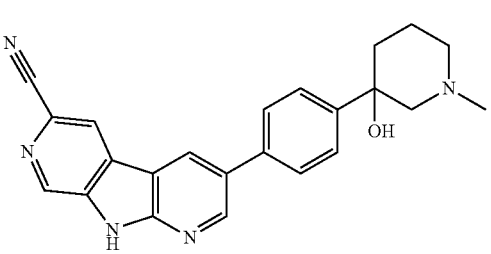
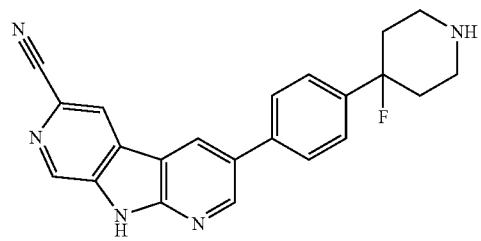
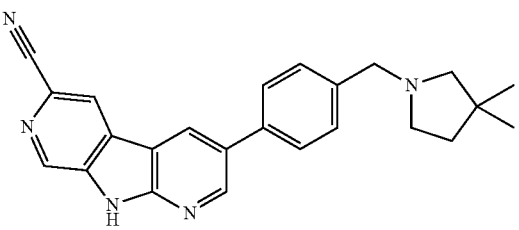
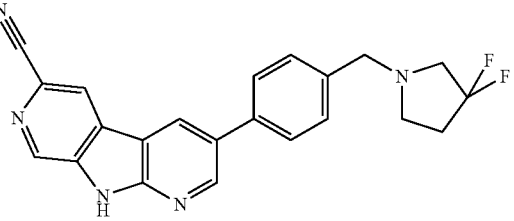
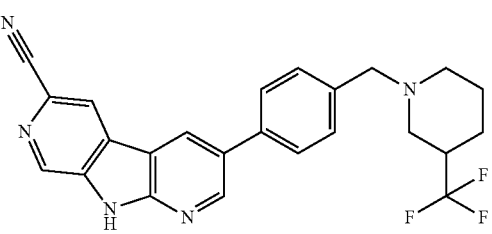
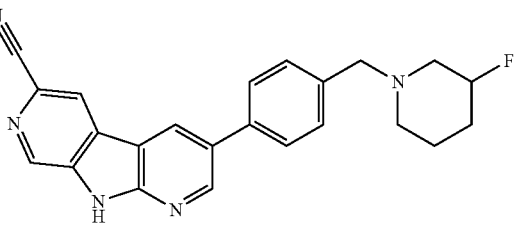

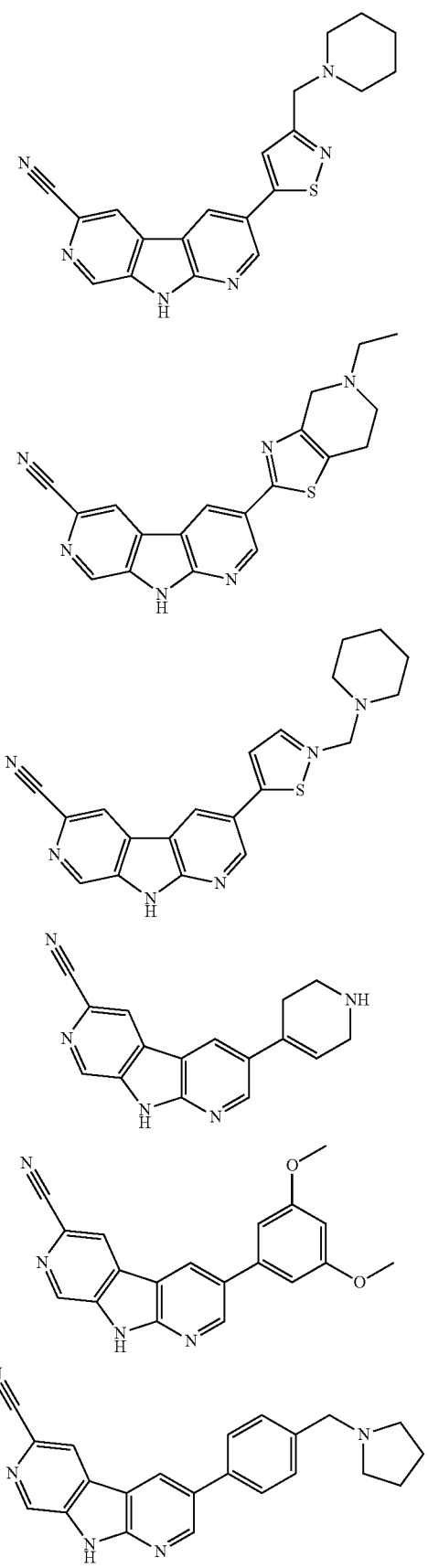
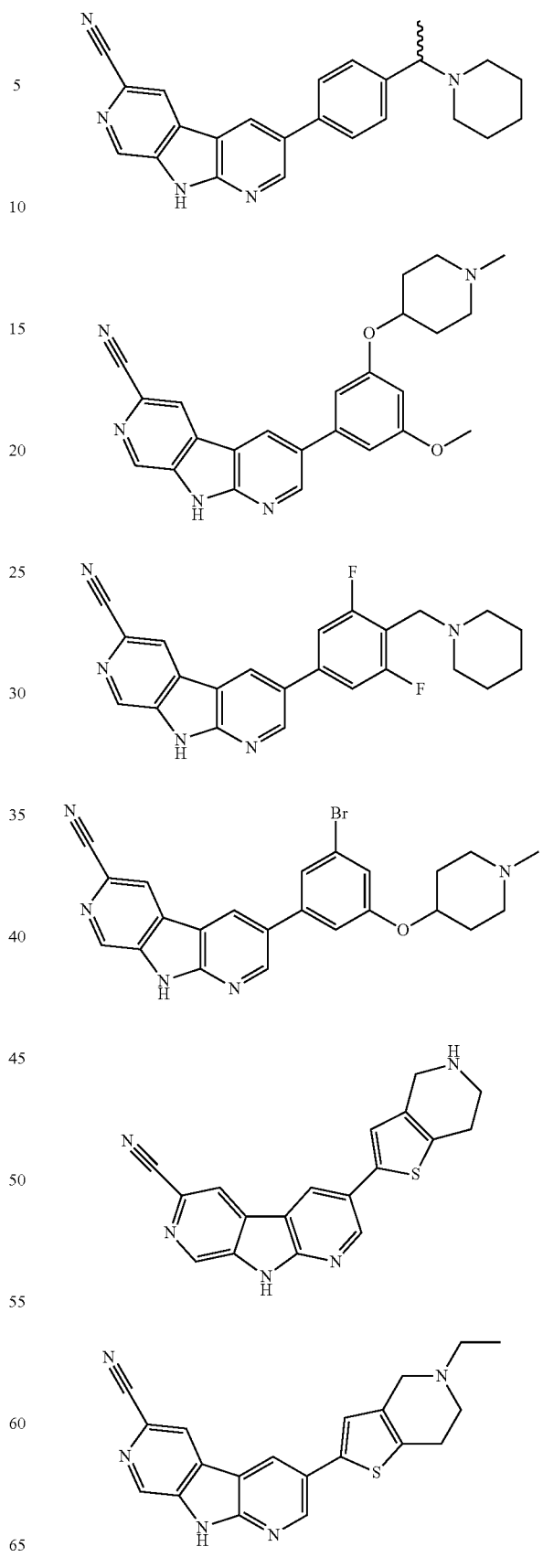

471
-continued
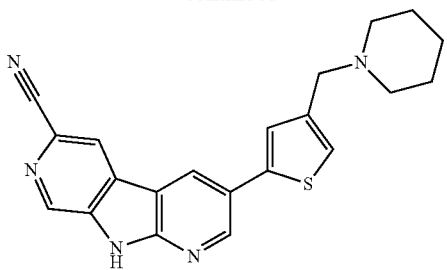
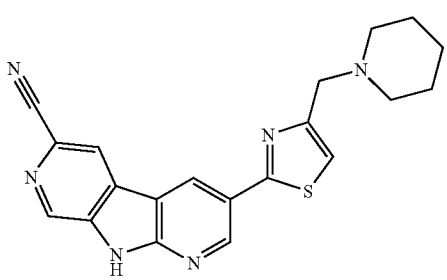
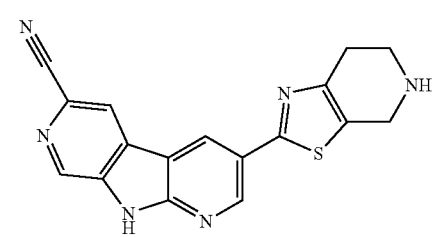
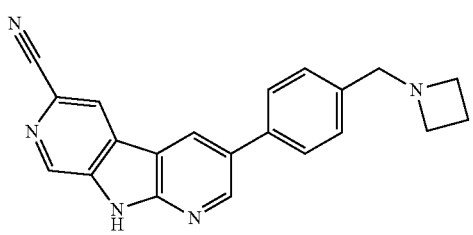
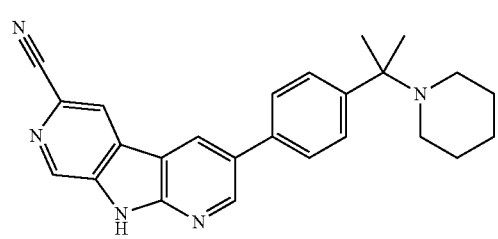
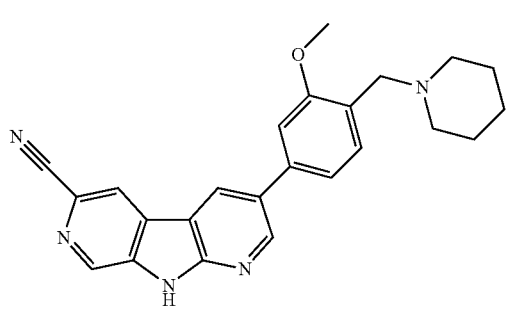
472
-continued
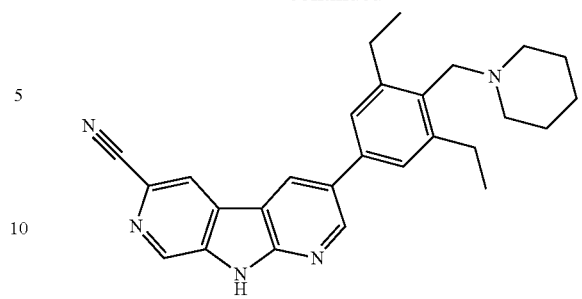
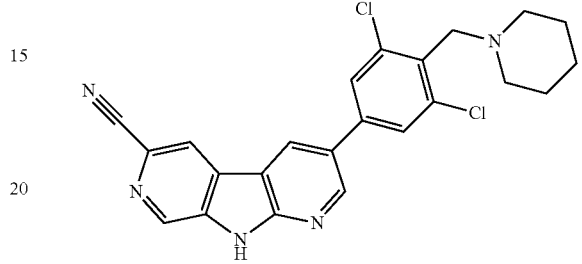
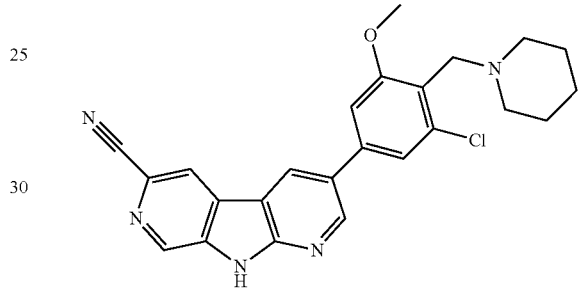
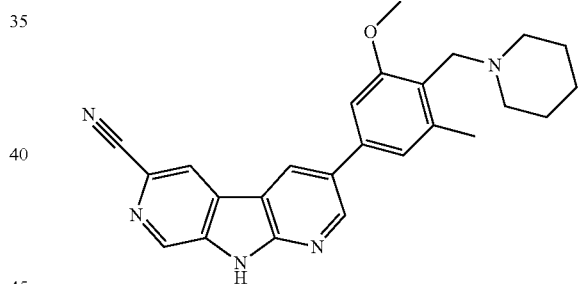
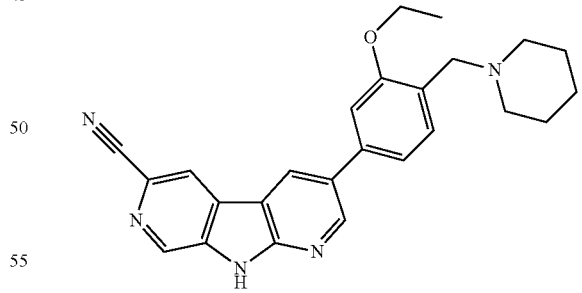
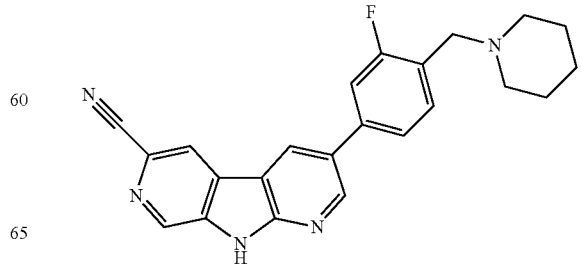

473
-continued
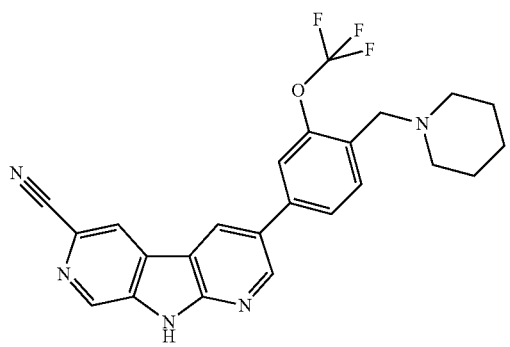
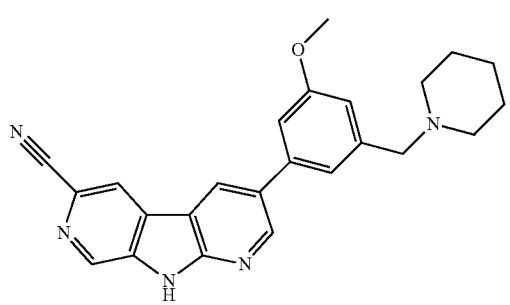
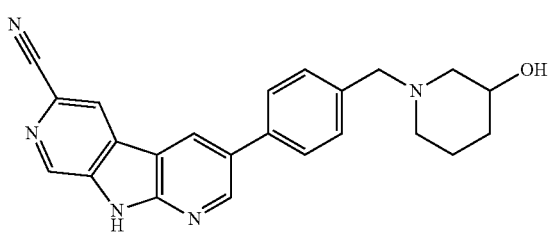
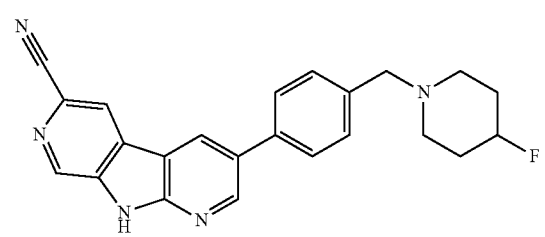
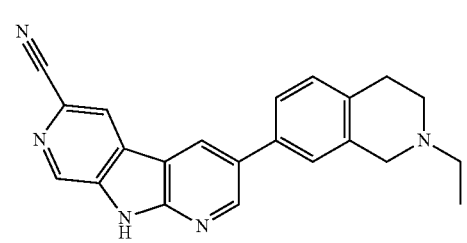
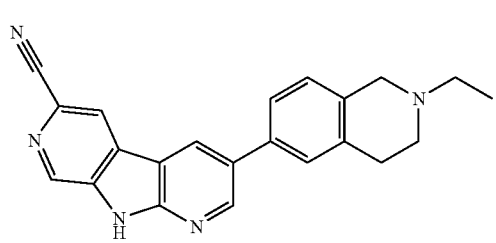
474
-continued
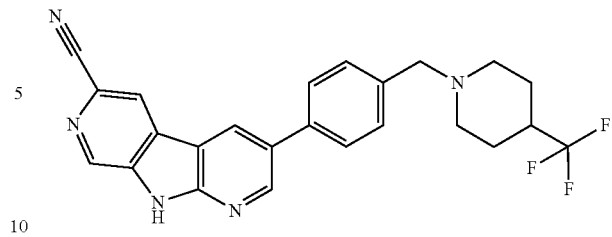
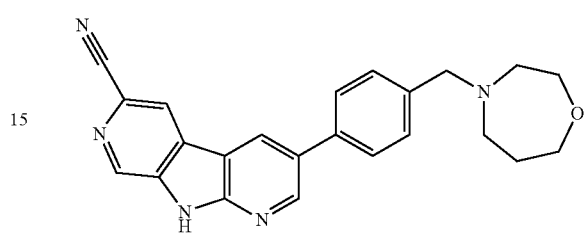
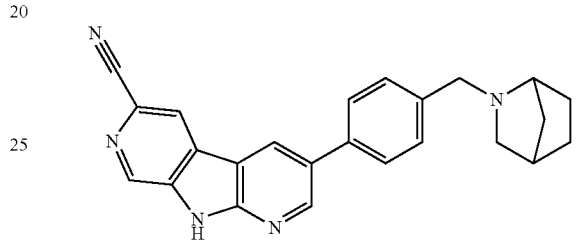
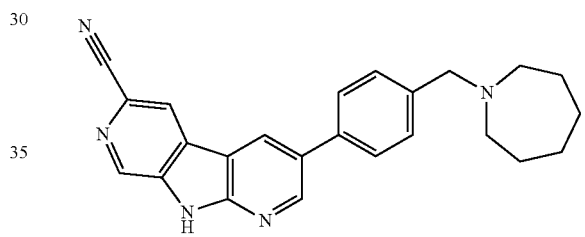
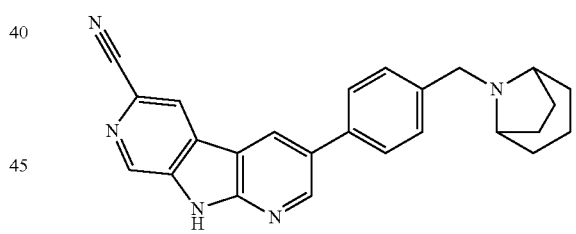
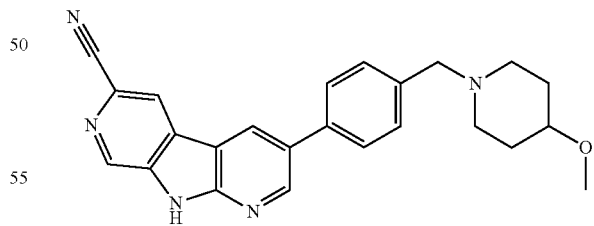
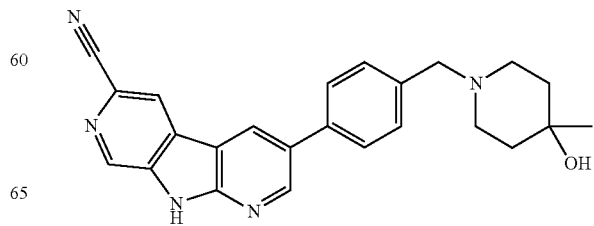

475
-continued
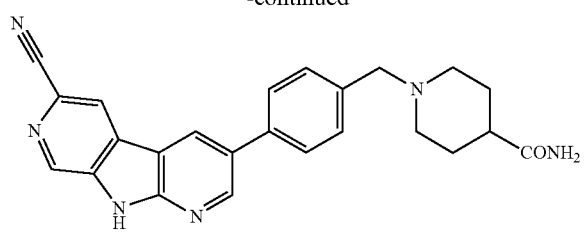
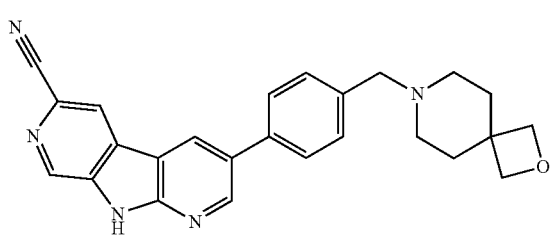
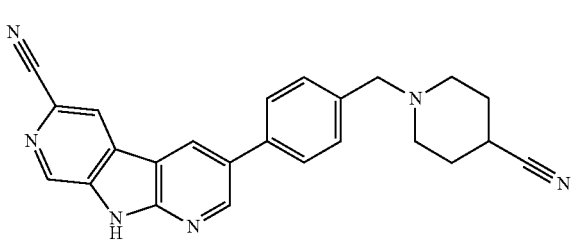
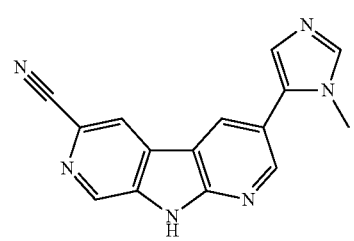
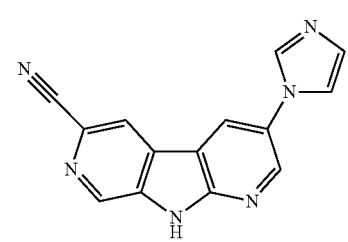
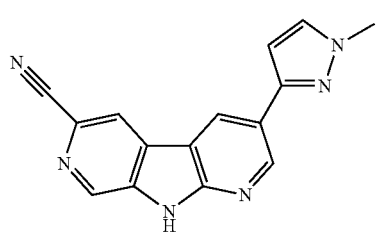
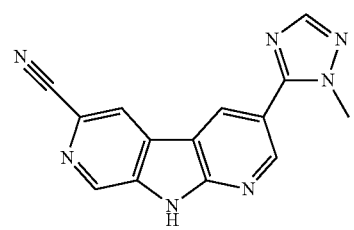
476
-continued
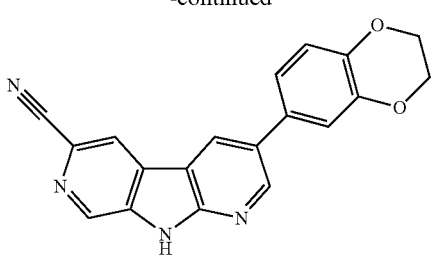
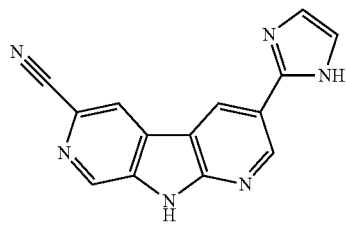
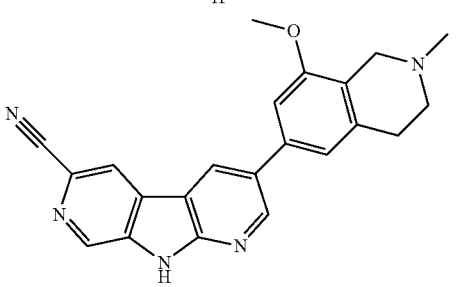
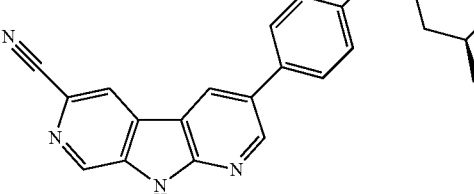
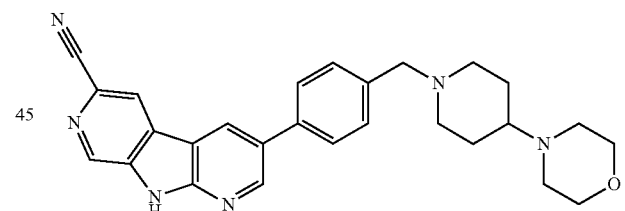
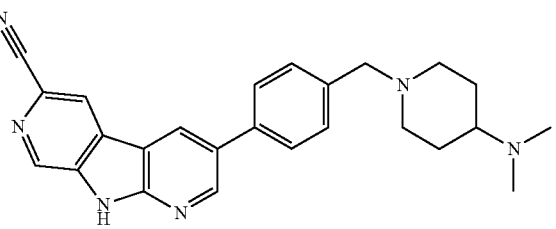
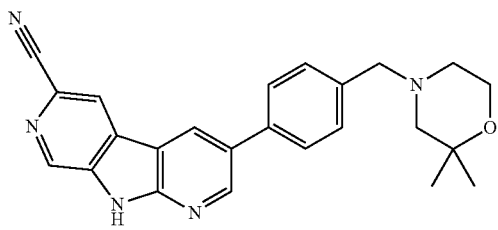

477
-continued
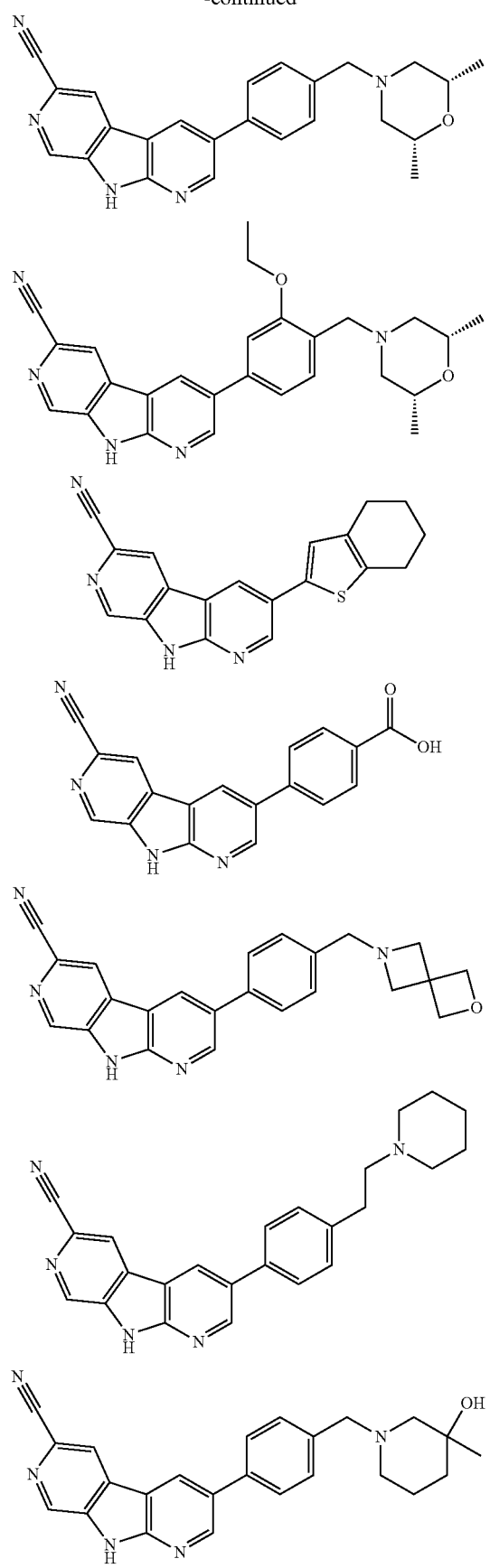
478
-continued
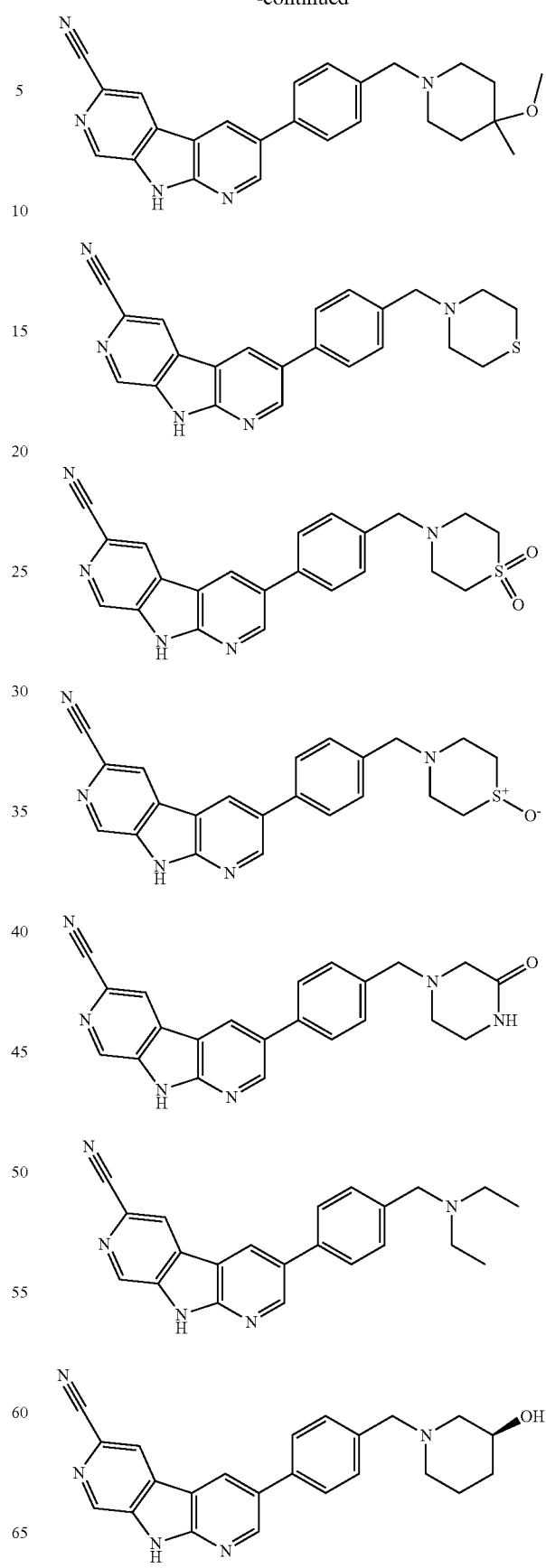

479
-continued
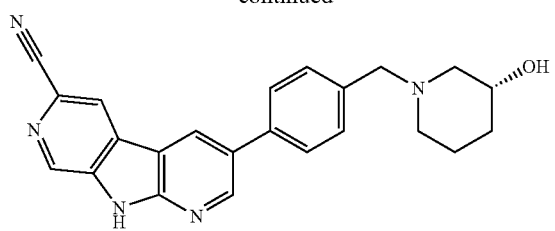
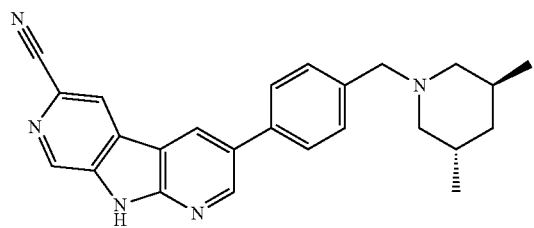
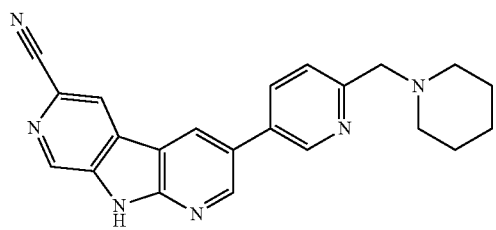
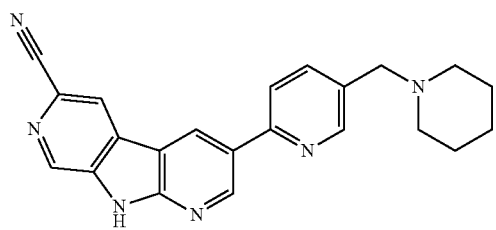
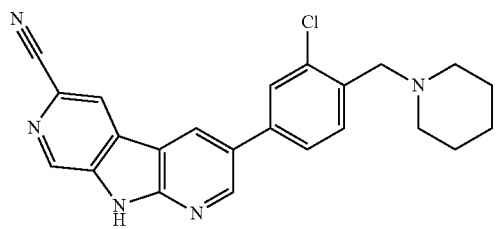
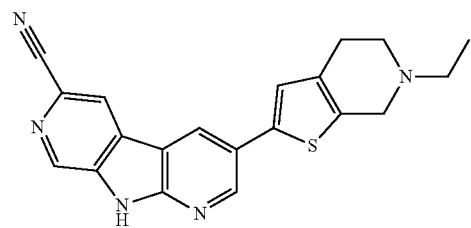
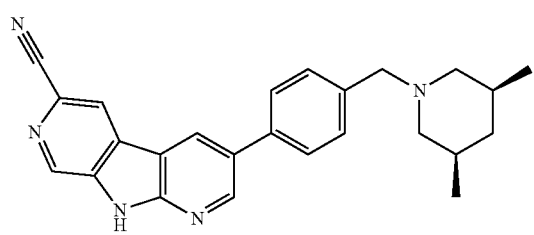
480
-continued
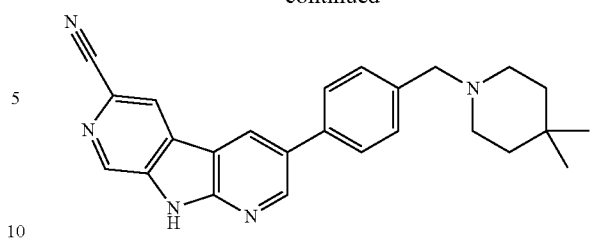
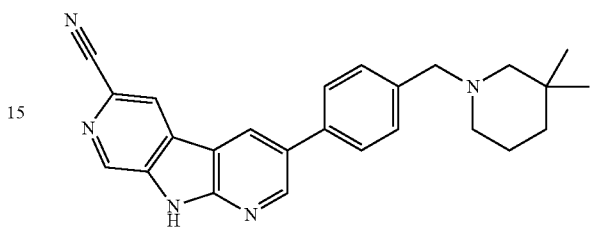
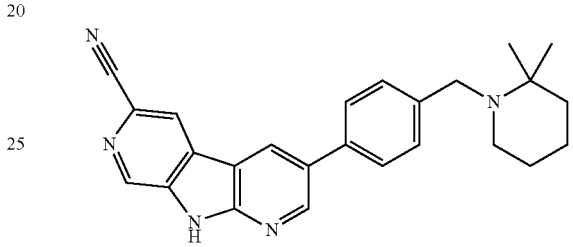
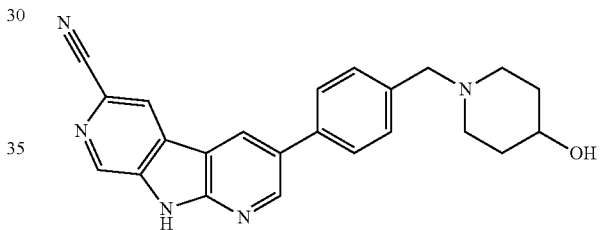
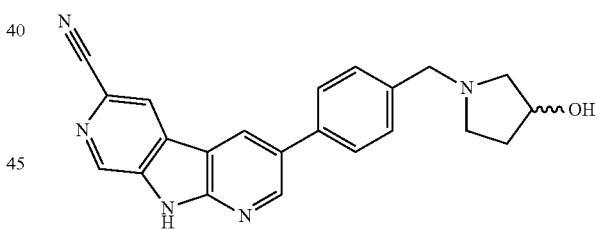
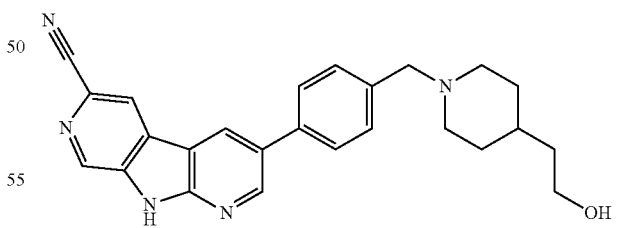
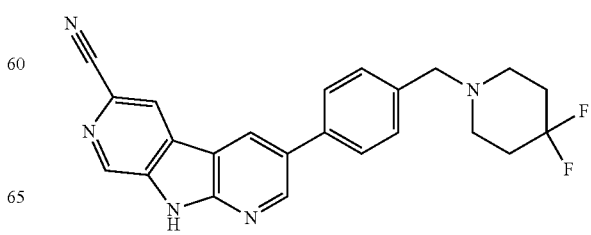

481
-continued
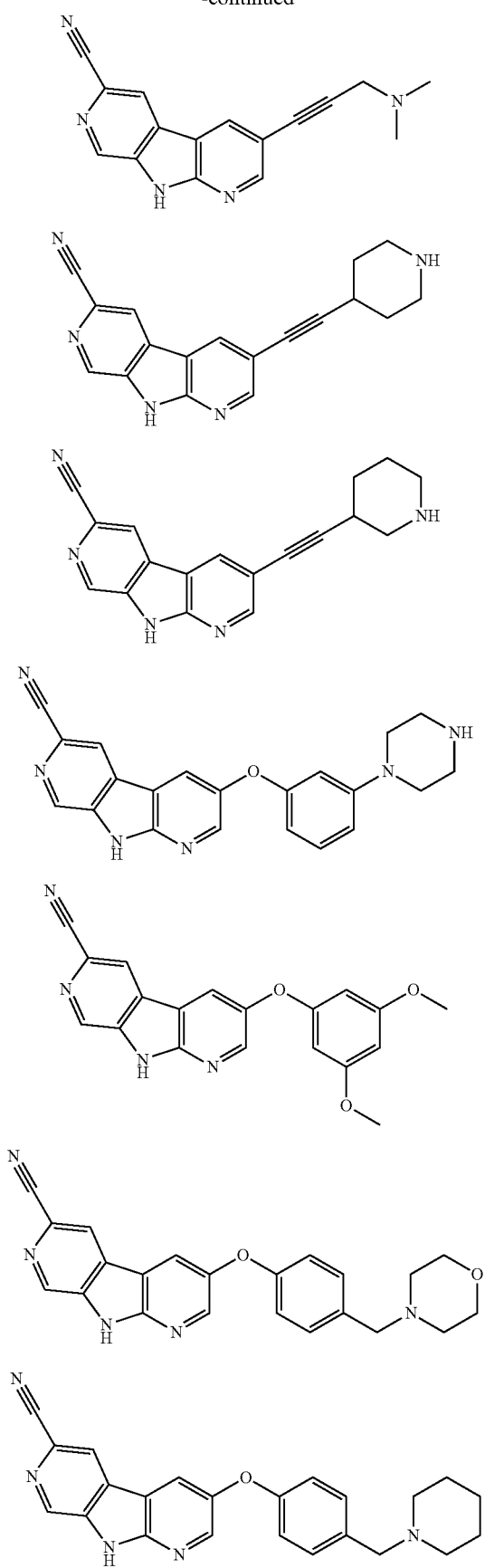
482
-continued
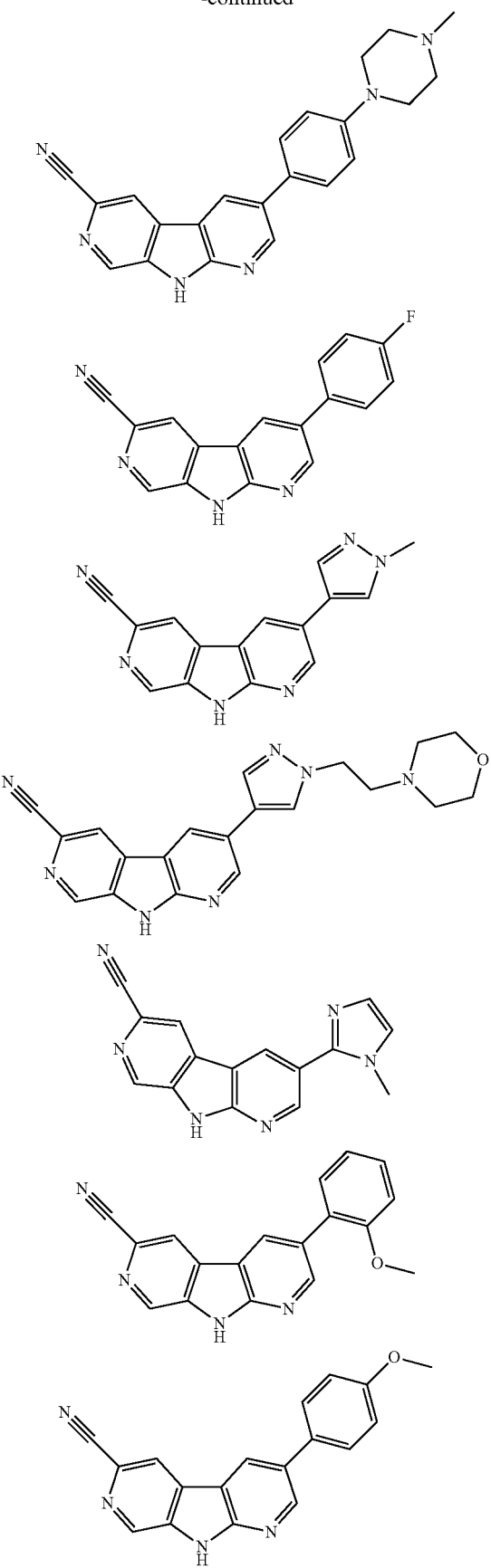

483
-continued
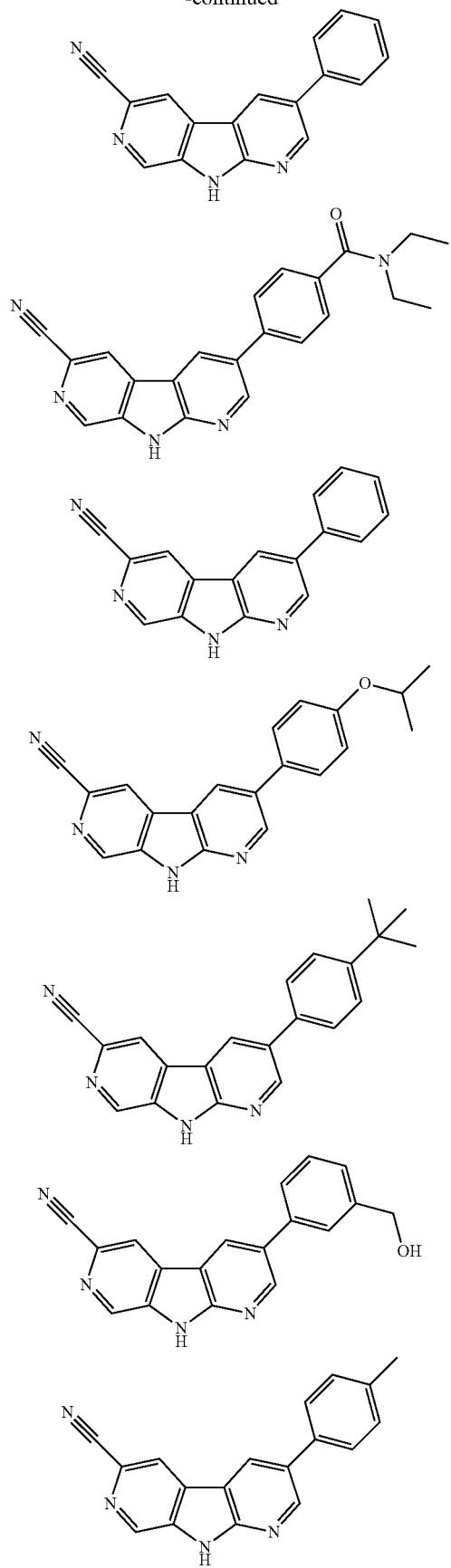
484
-continued
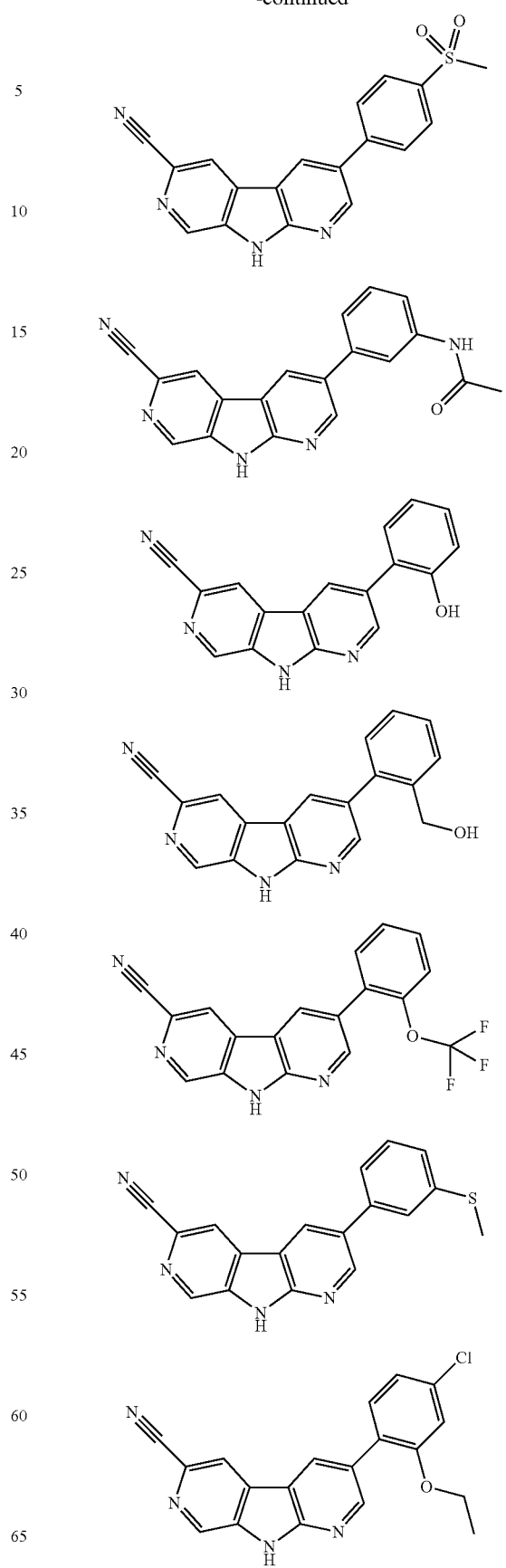

485
-continued
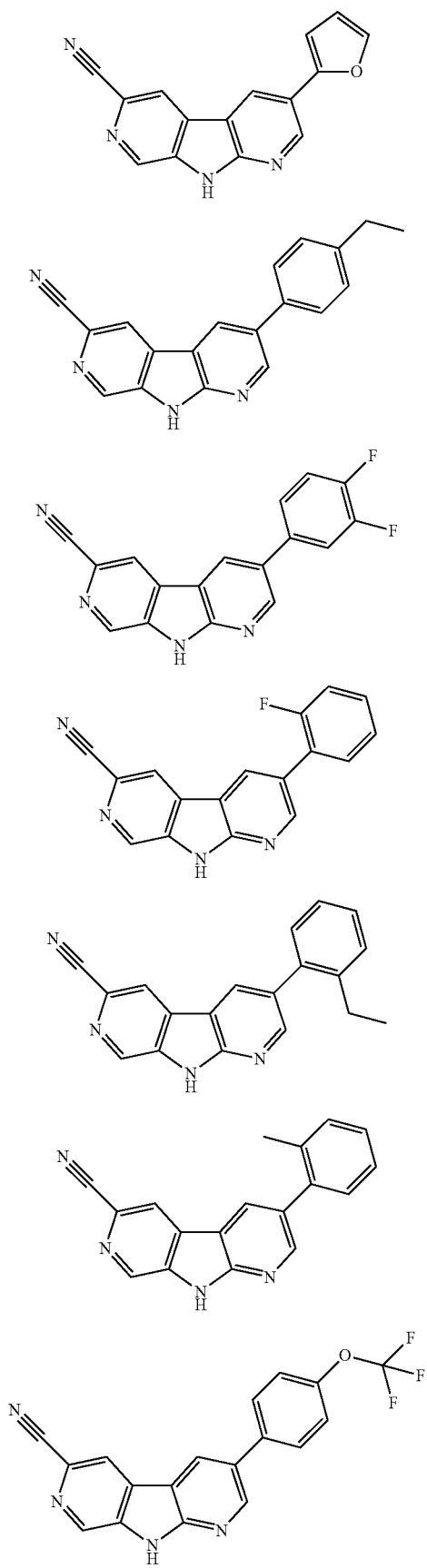
486
-continued
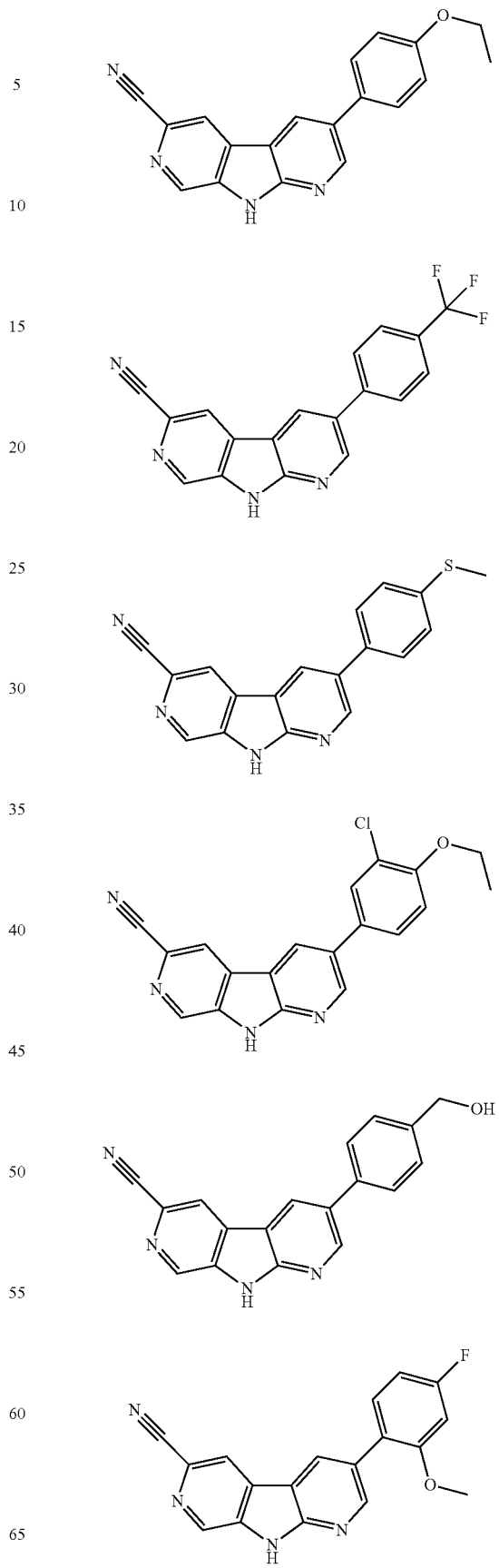

487
-continued
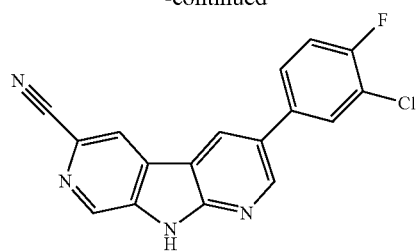
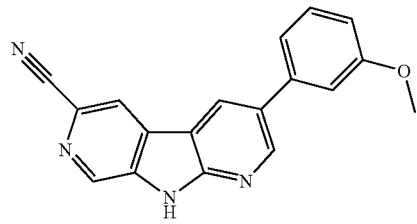
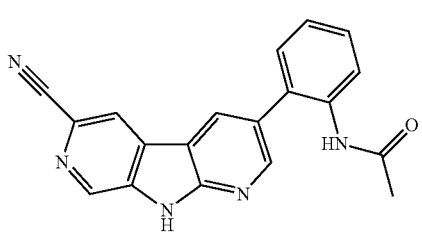
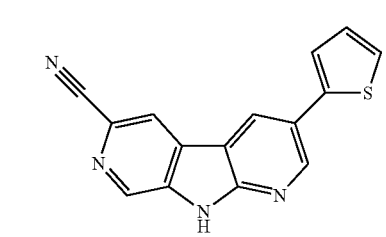
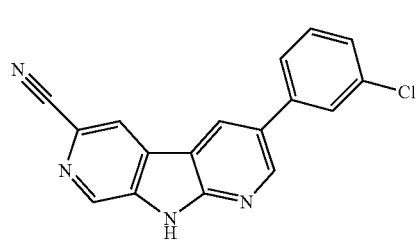
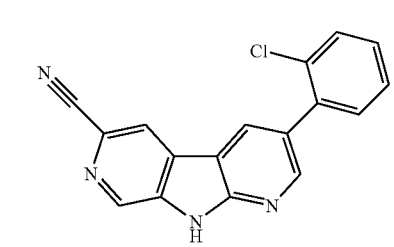
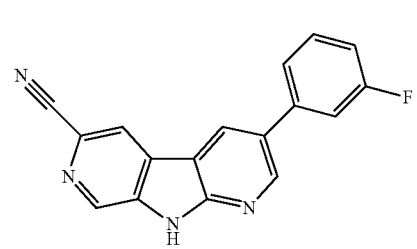
488
-continued
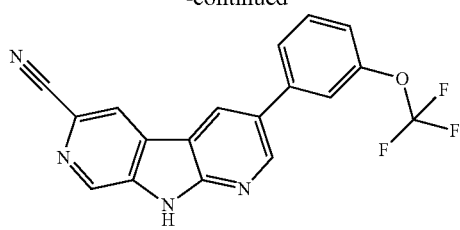
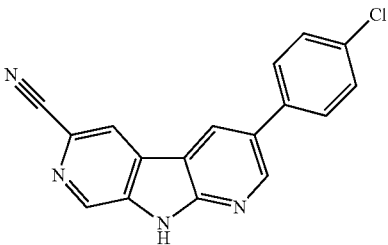
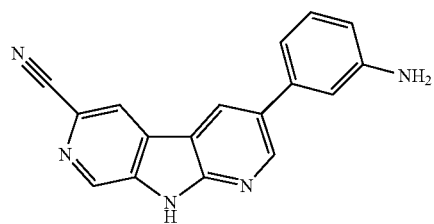
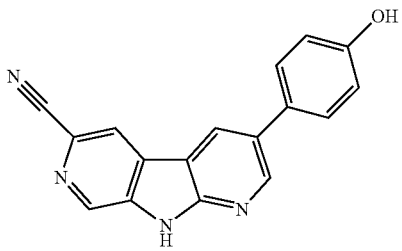
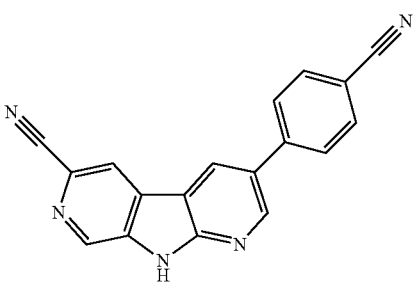
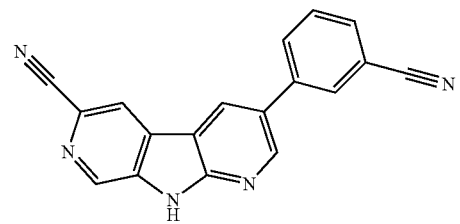
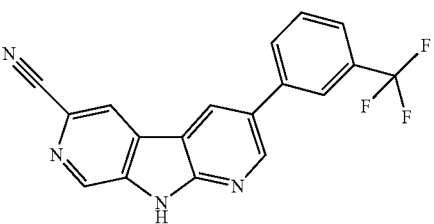

489
-continued
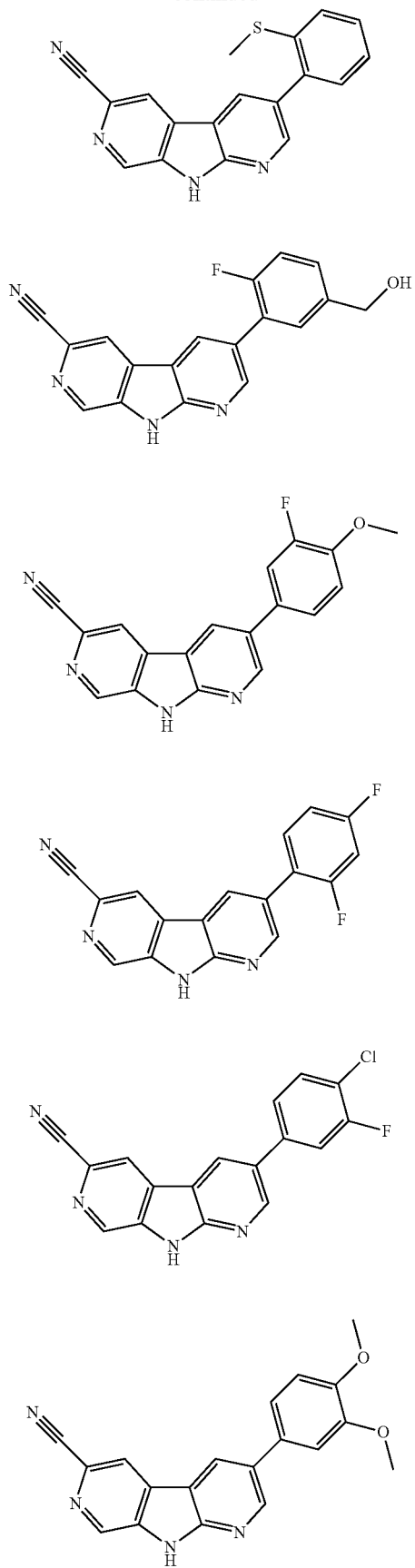
490
-continued
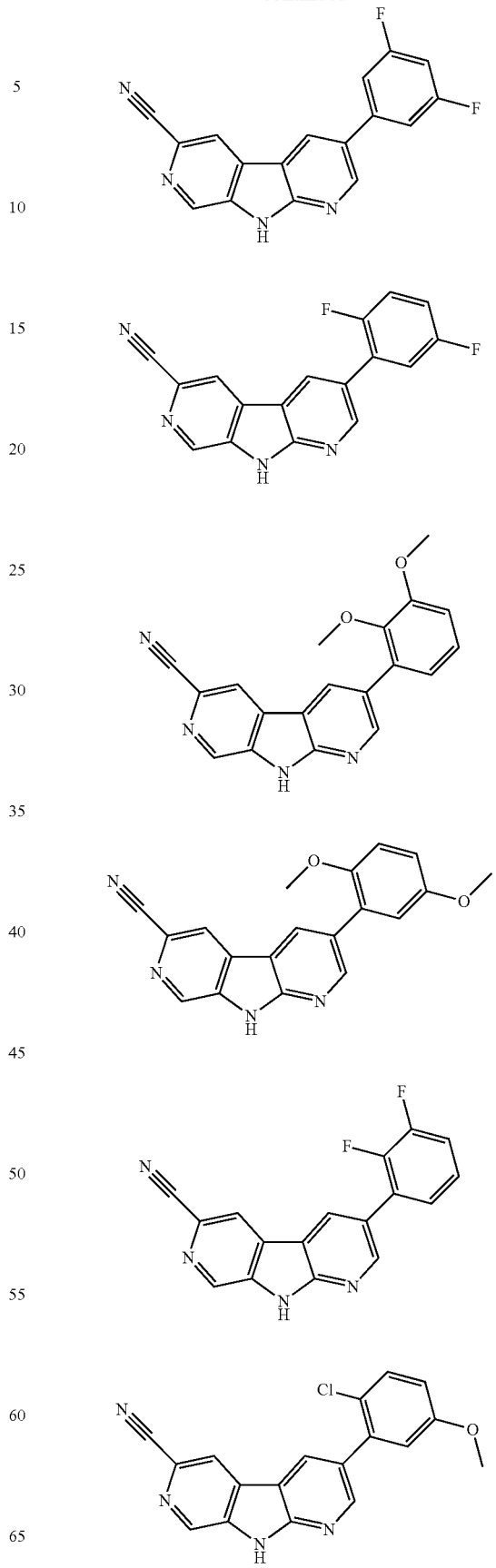

491
-continued
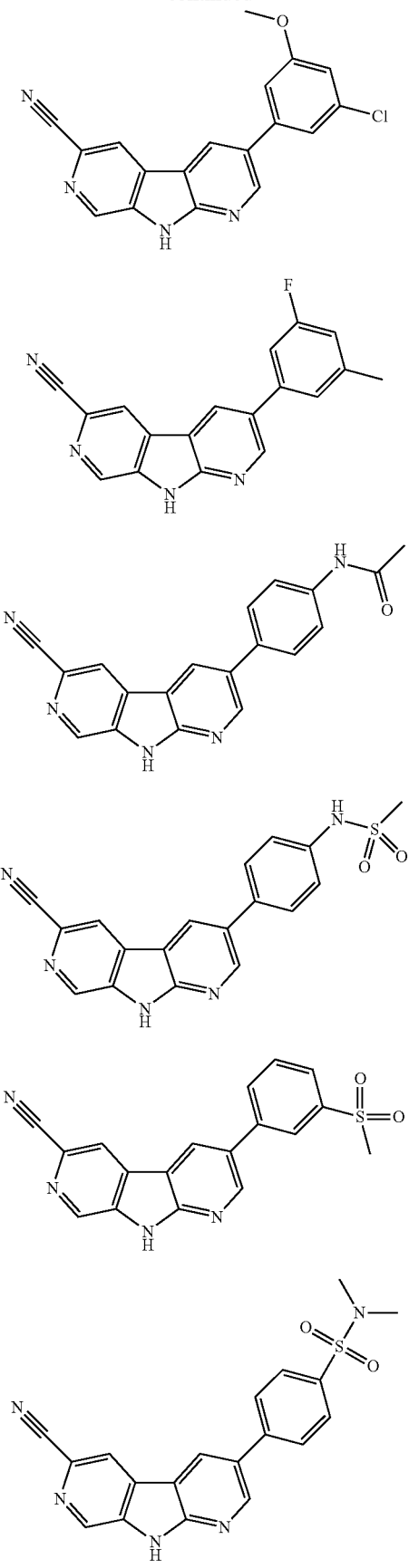
492
-continued
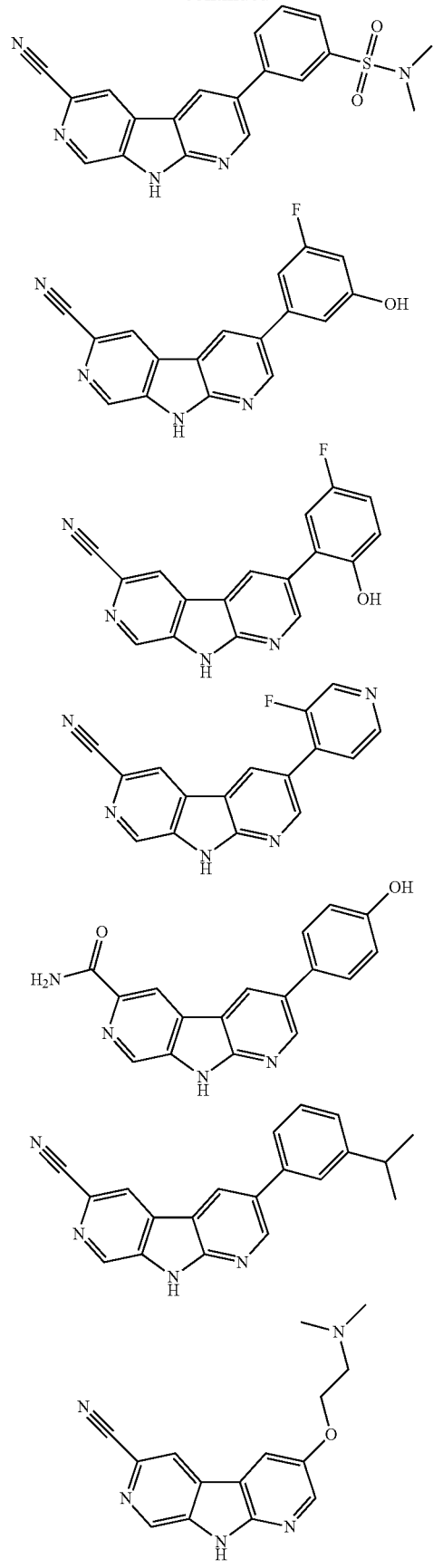

493
-continued
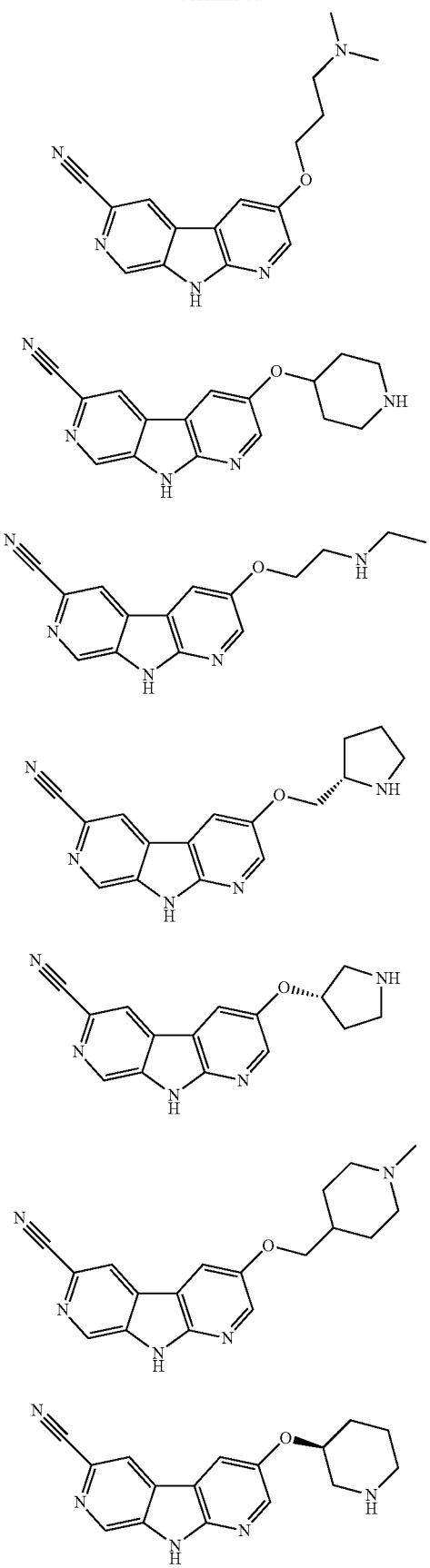
494
-continued
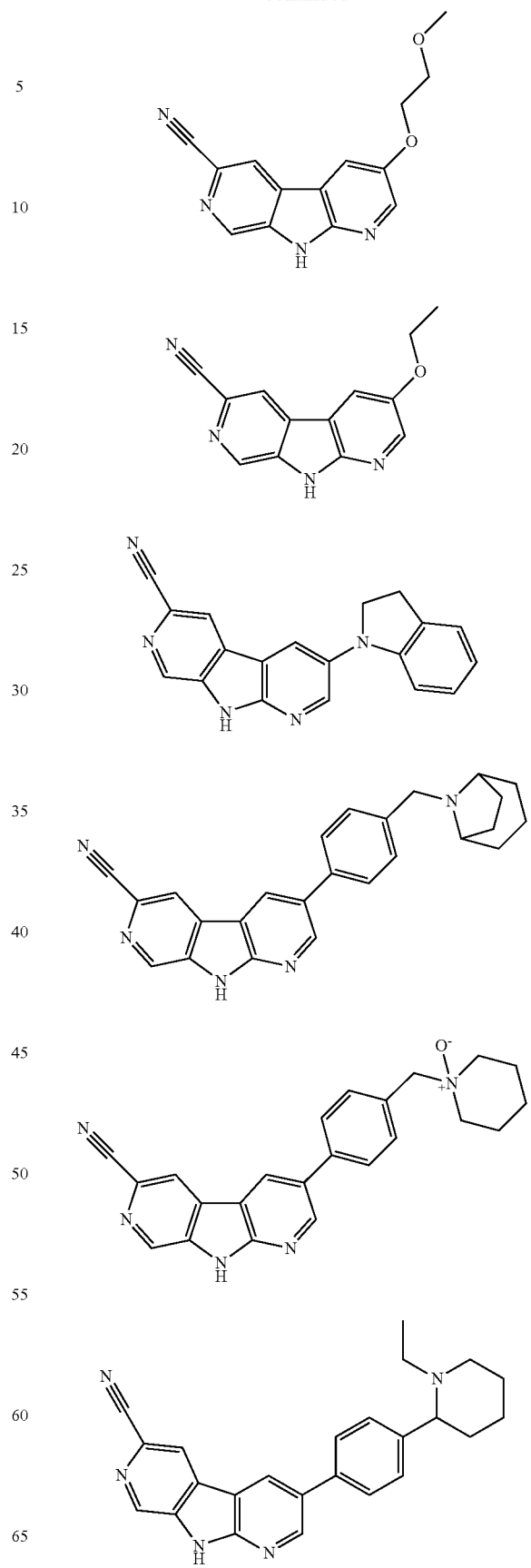

495
-continued
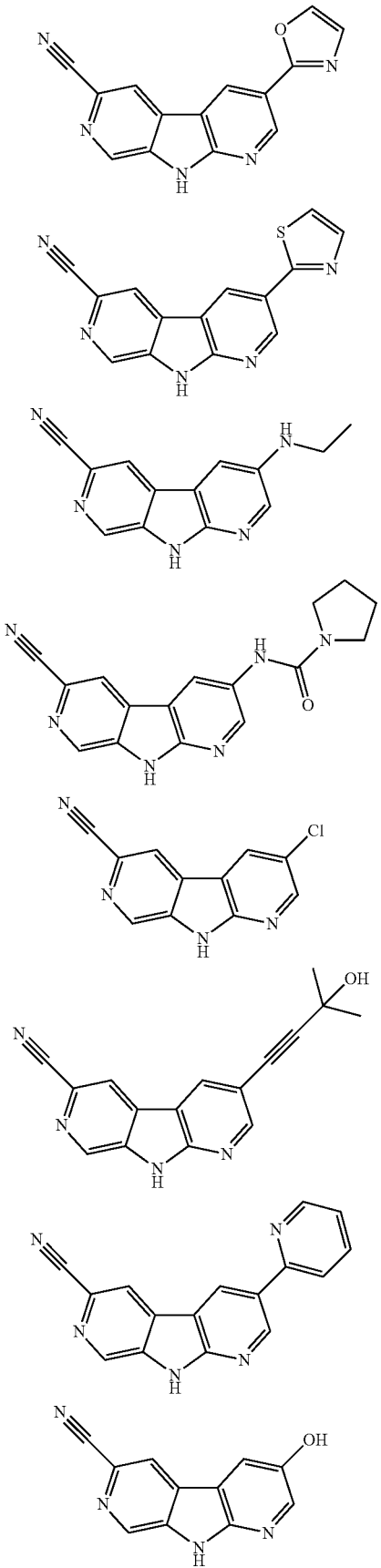
496
-continued
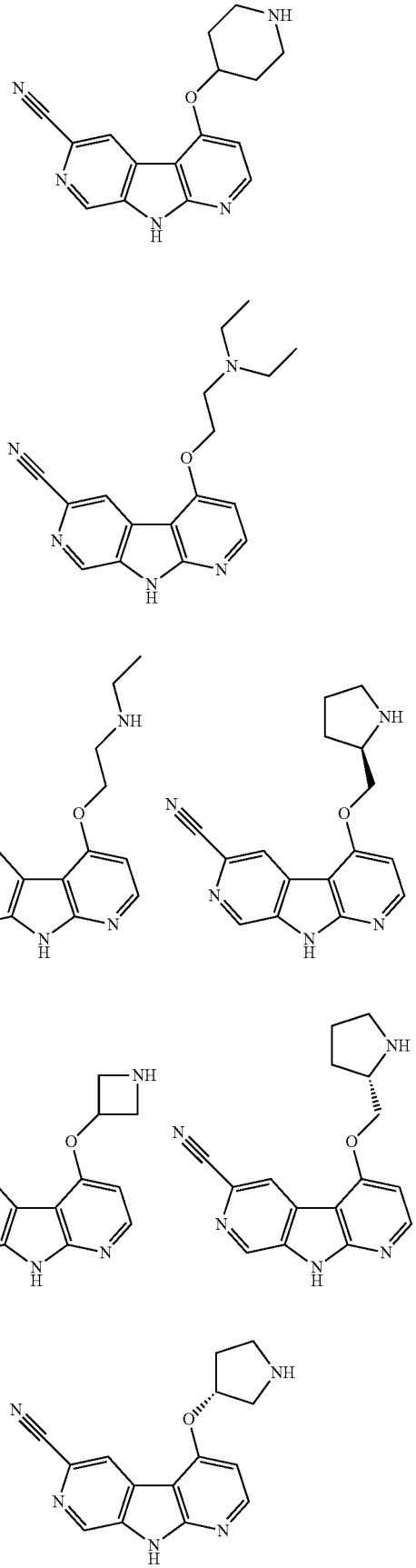

497
-continued
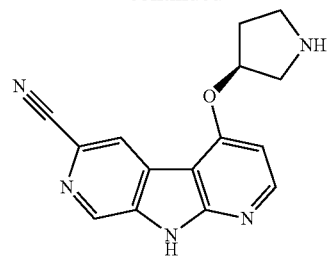
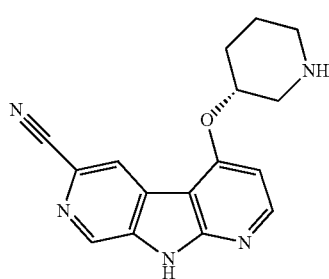
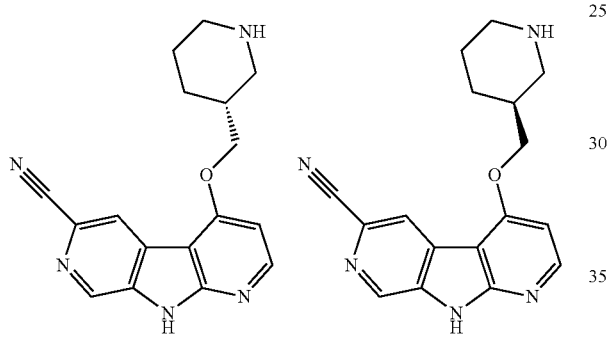
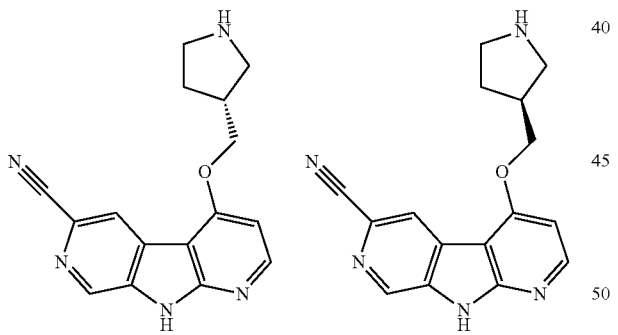
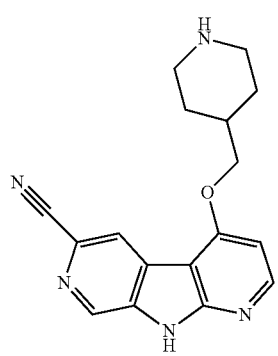
498
-continued
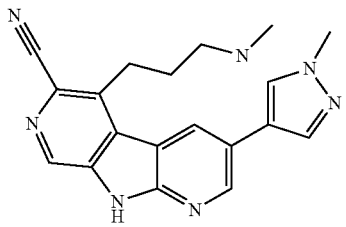
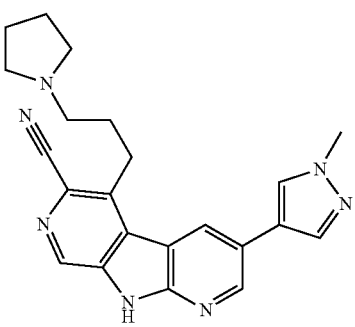
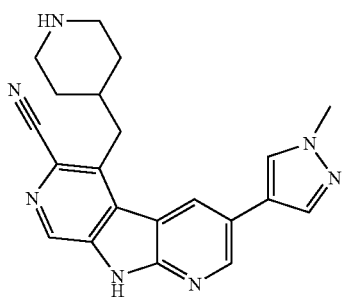
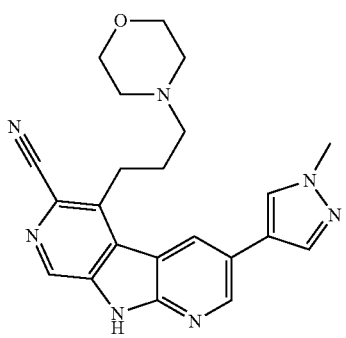
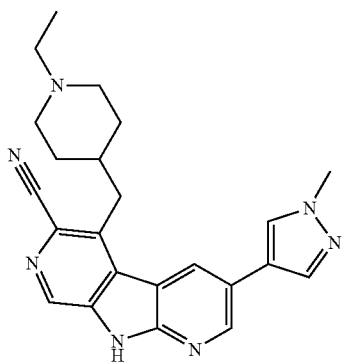

499
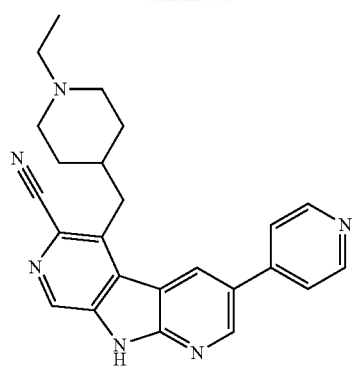
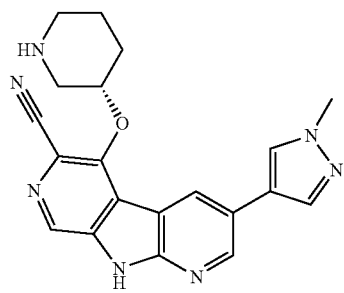
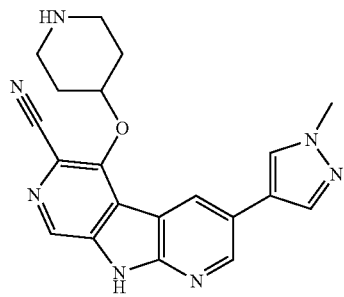
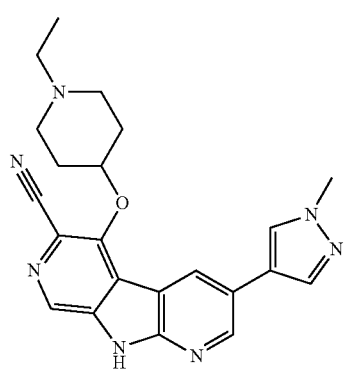
500
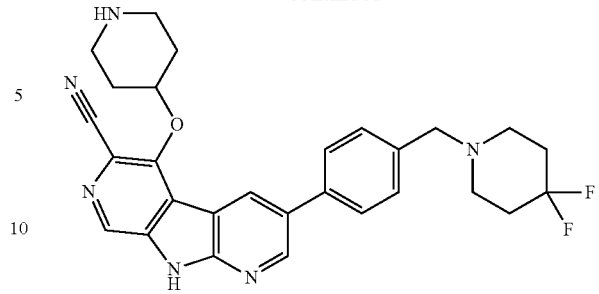
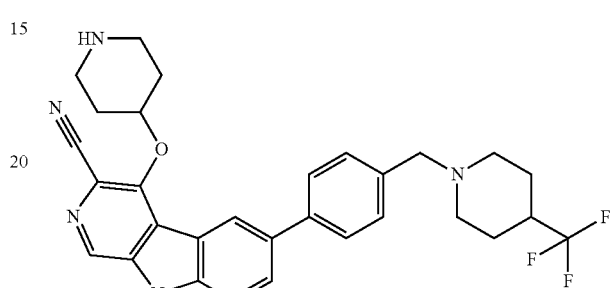
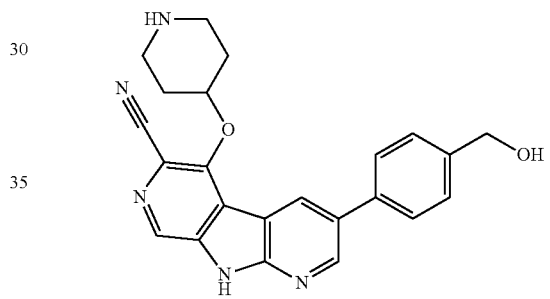
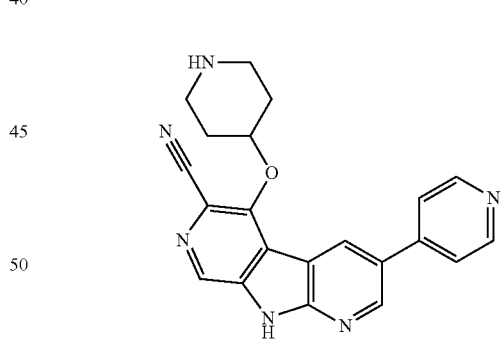
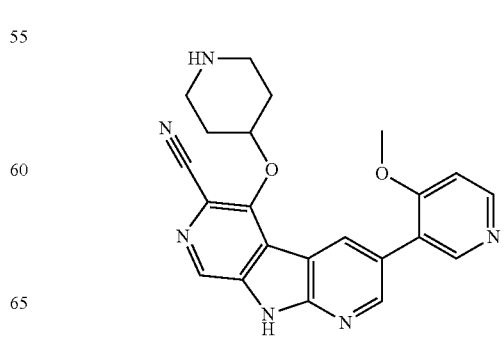

501
-continued
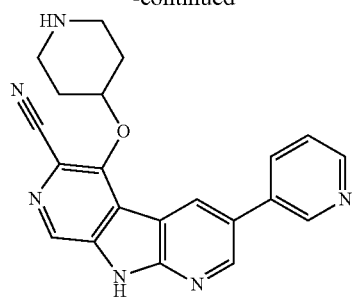
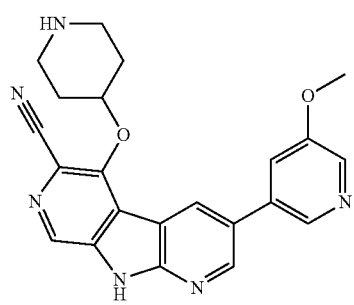
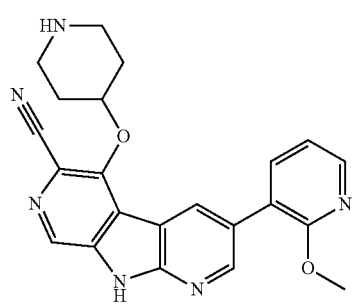
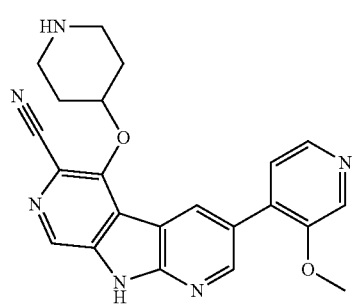
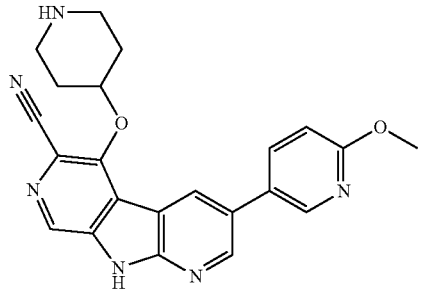
502
-continued
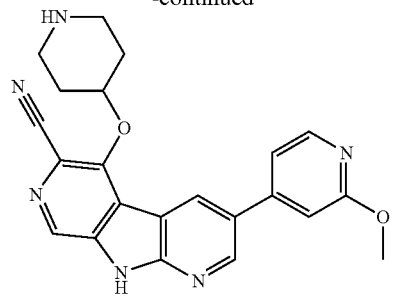
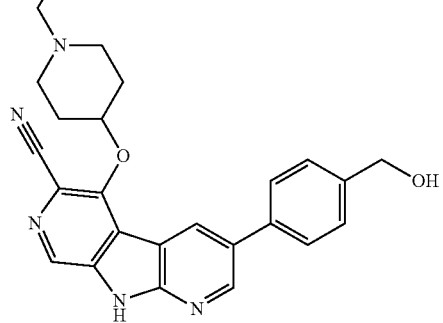
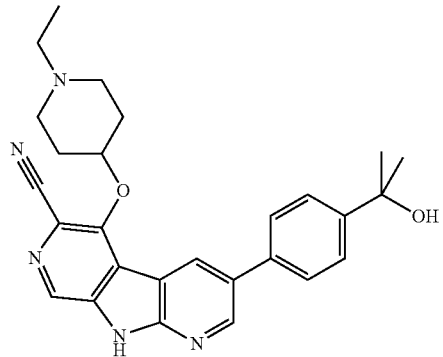
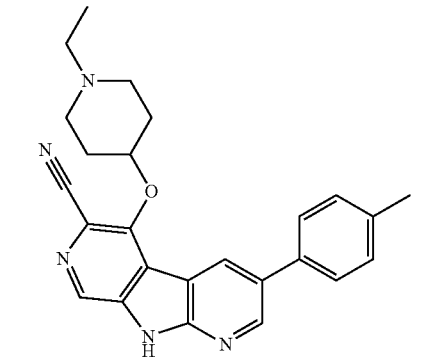
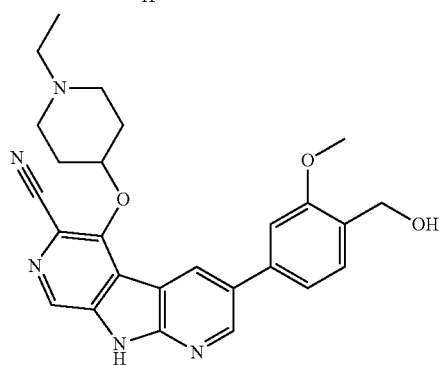

503
-continued
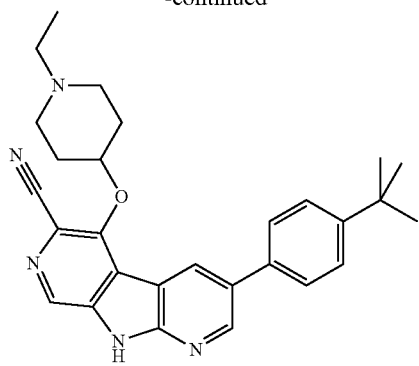
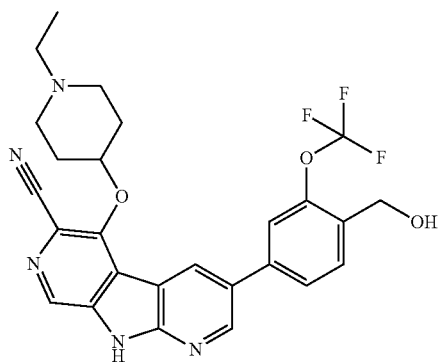
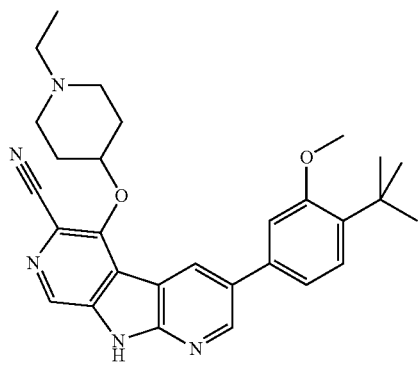
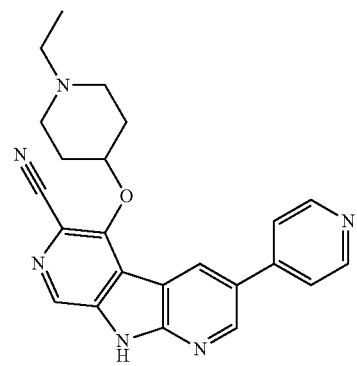
504
-continued
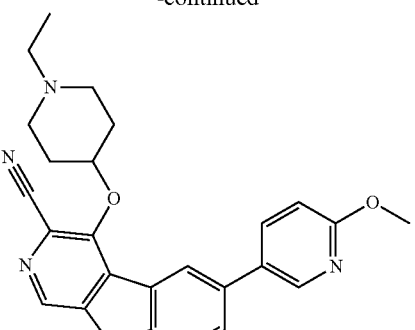
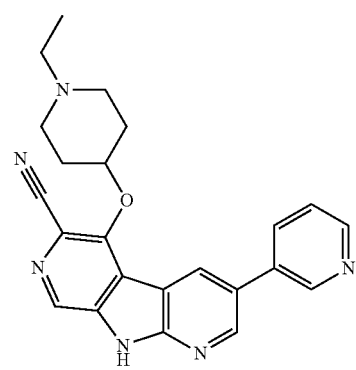
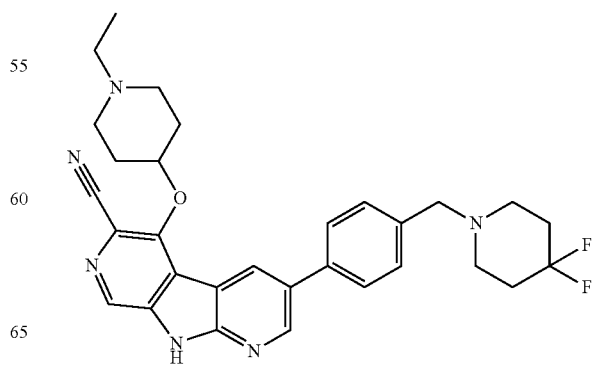

505
-continued
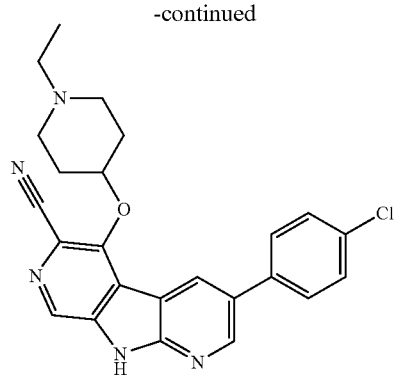
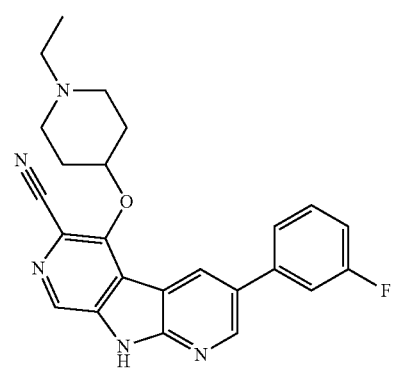
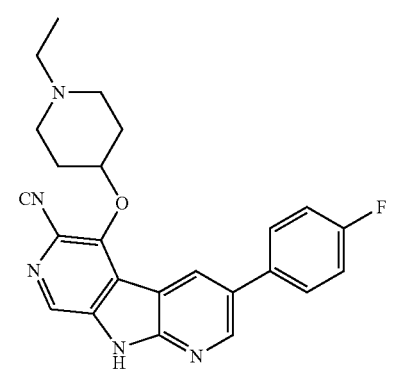
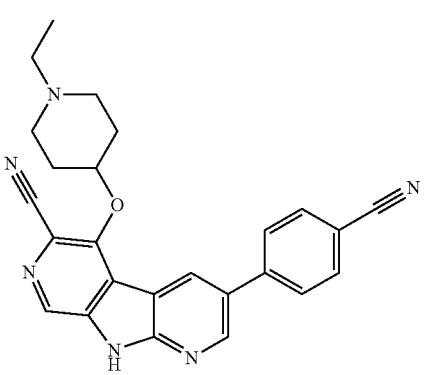
506
-continued
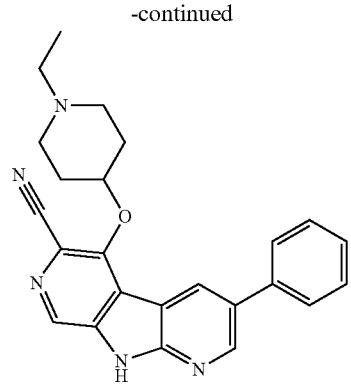
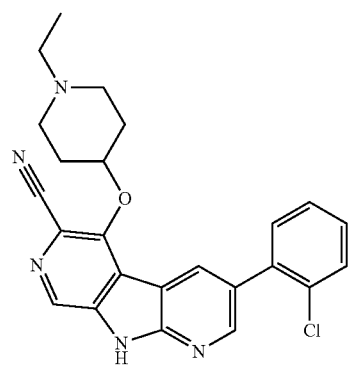
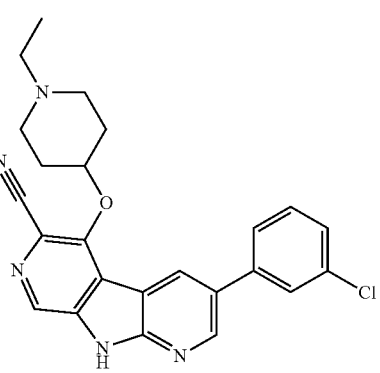
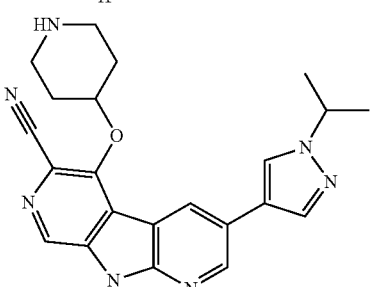
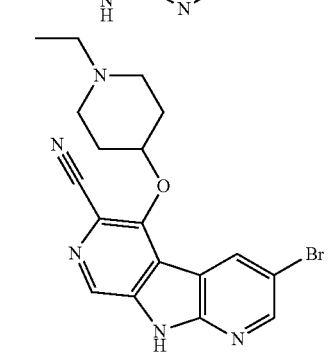

507
-continued
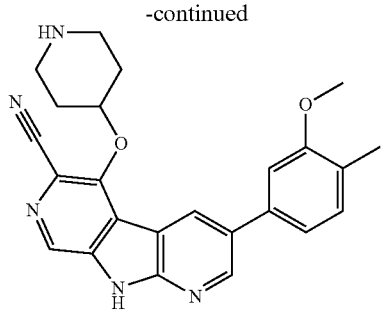
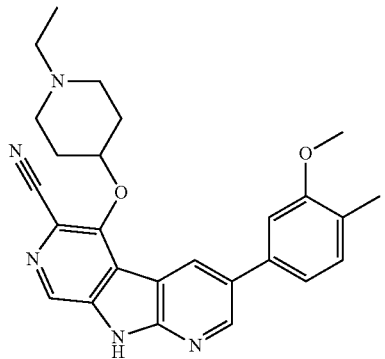
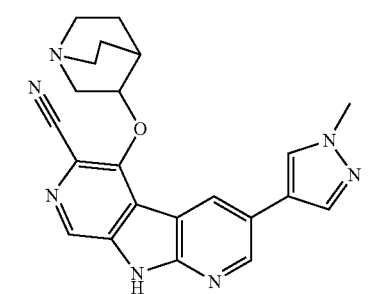
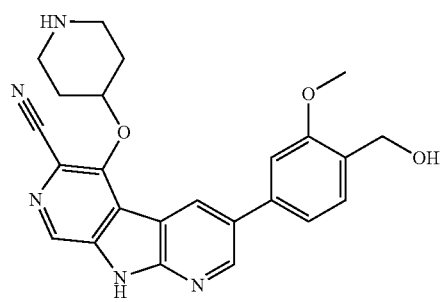
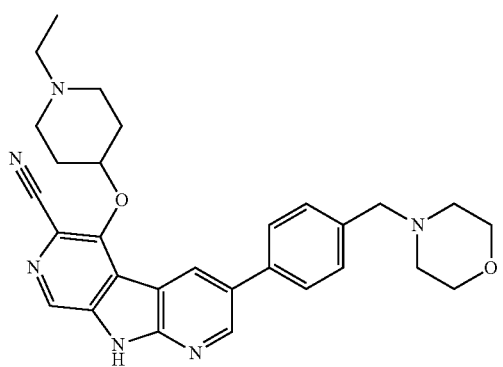
508
-continued
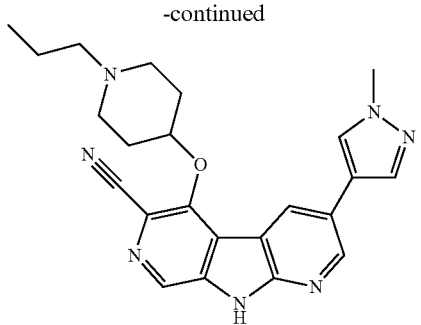
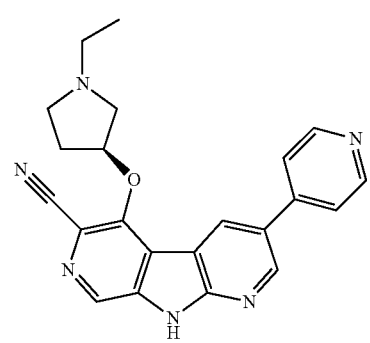
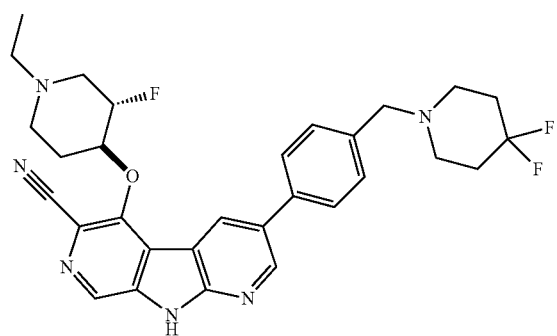
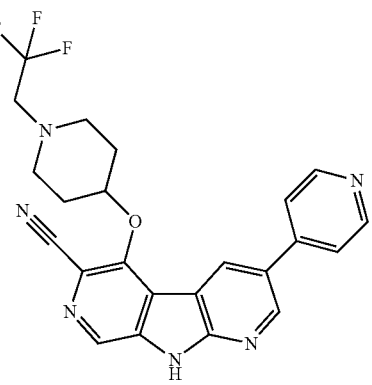
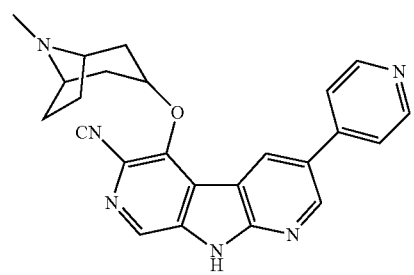

509
-continued
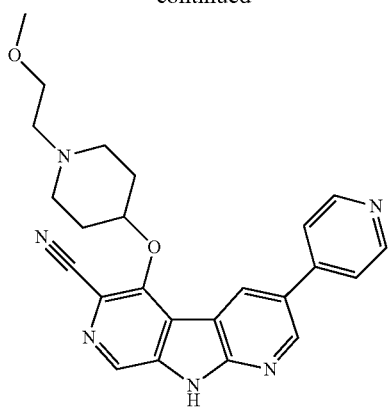
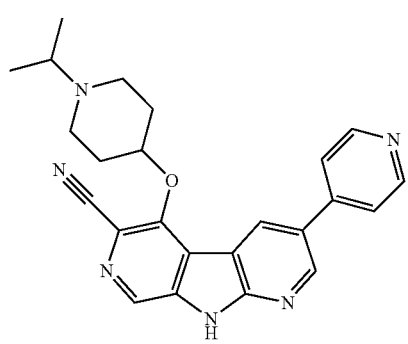
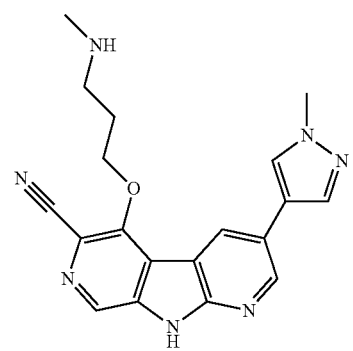
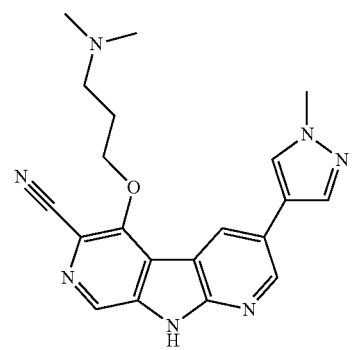
510
-continued
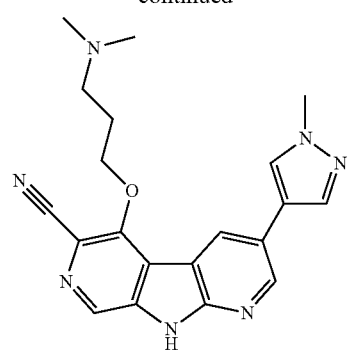
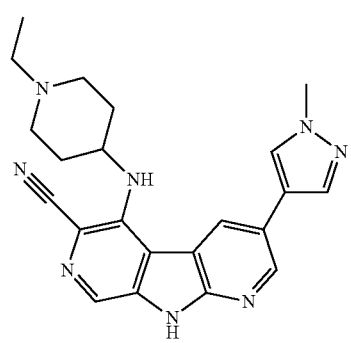
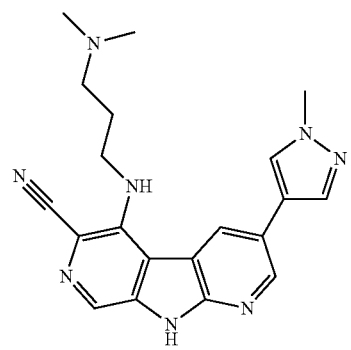
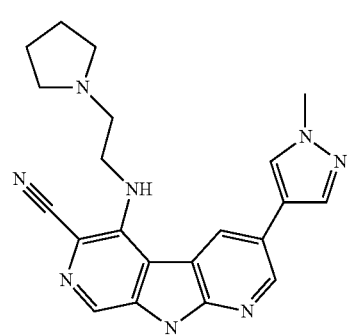
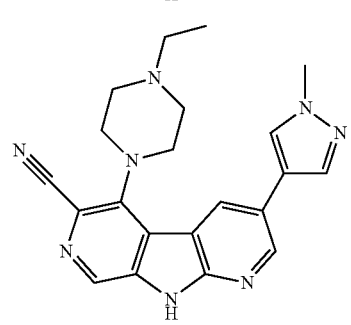

511
-continued
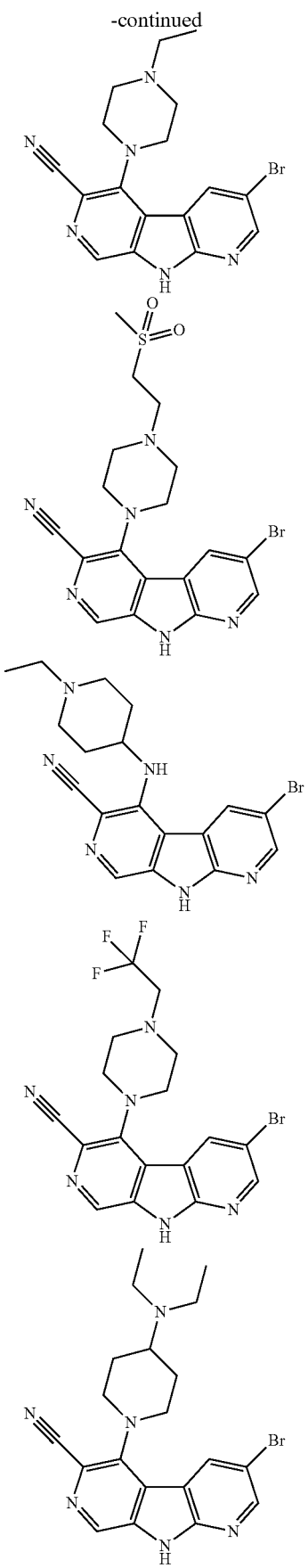
512
-continued
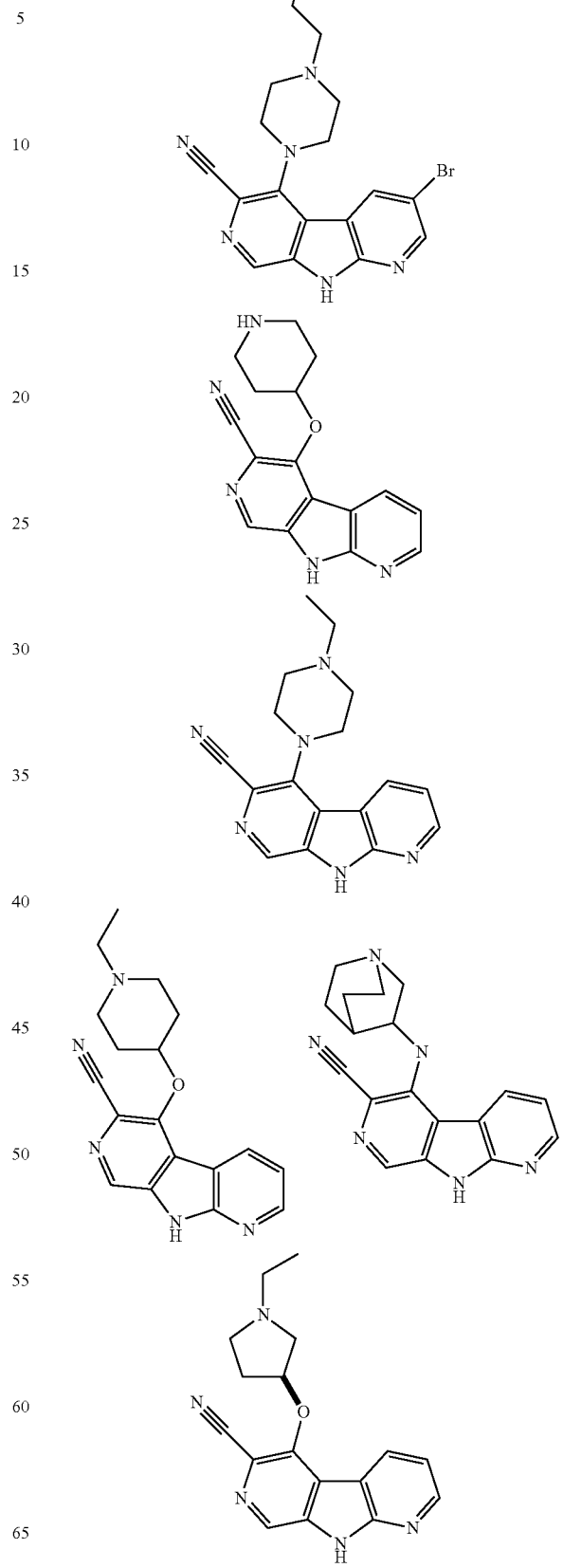

513
-continued
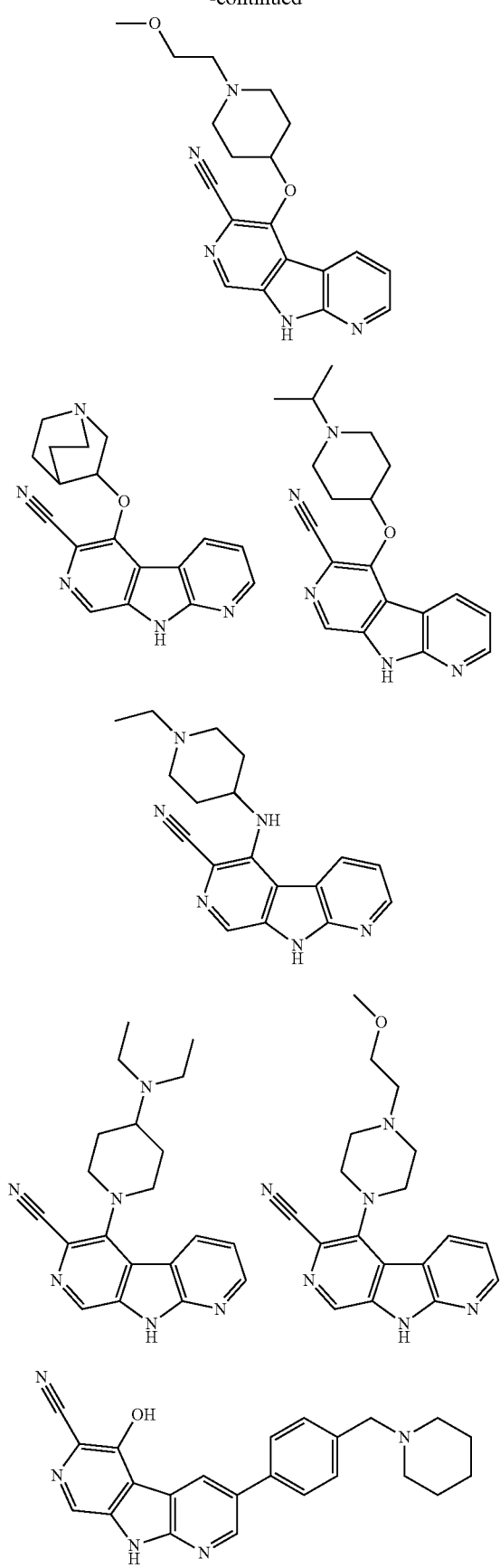
514
-continued
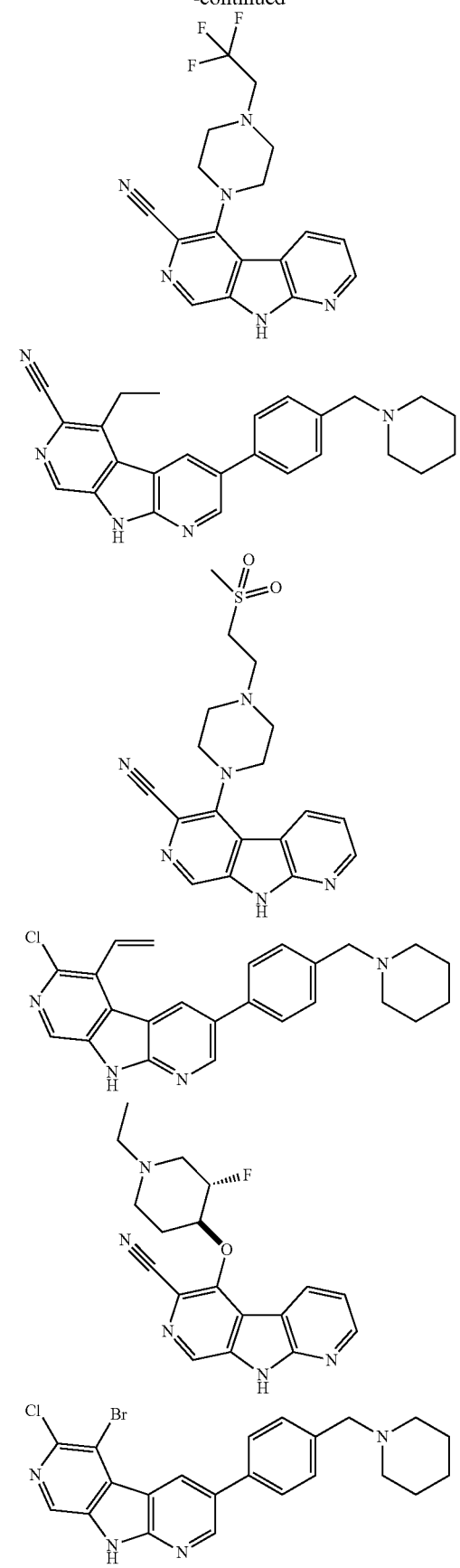

515
-continued
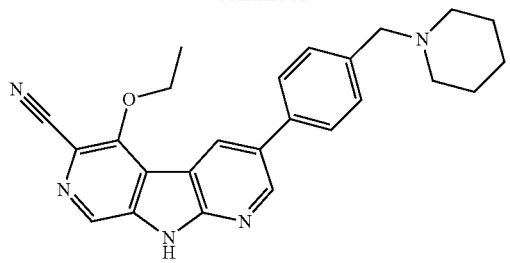
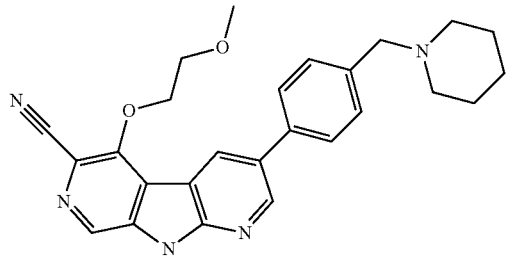
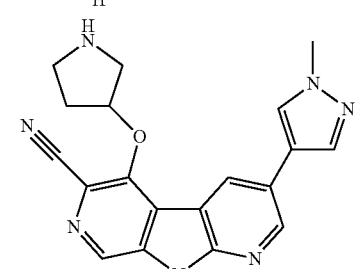
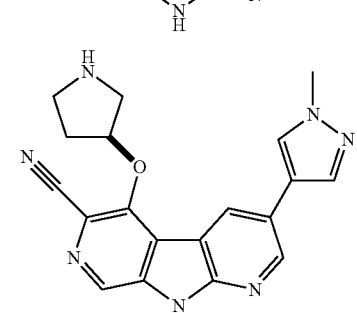
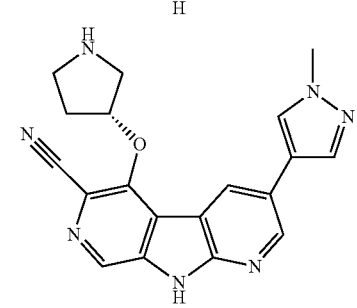
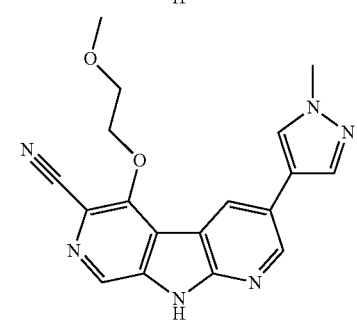
516
-continued
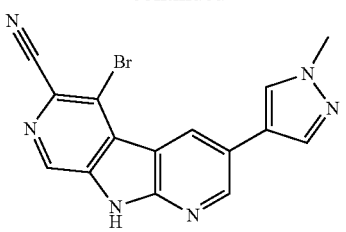
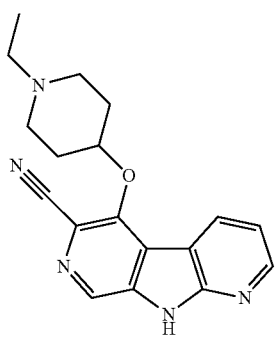
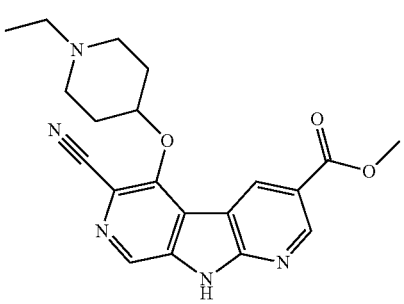
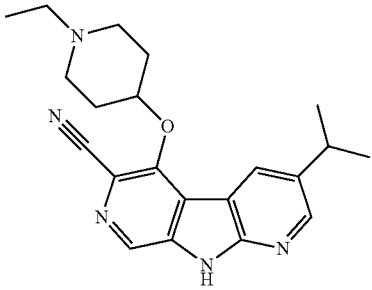
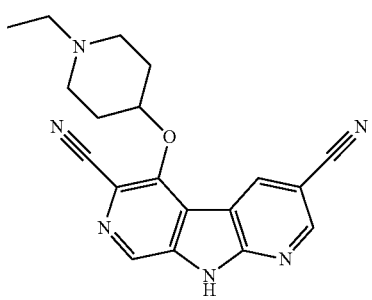

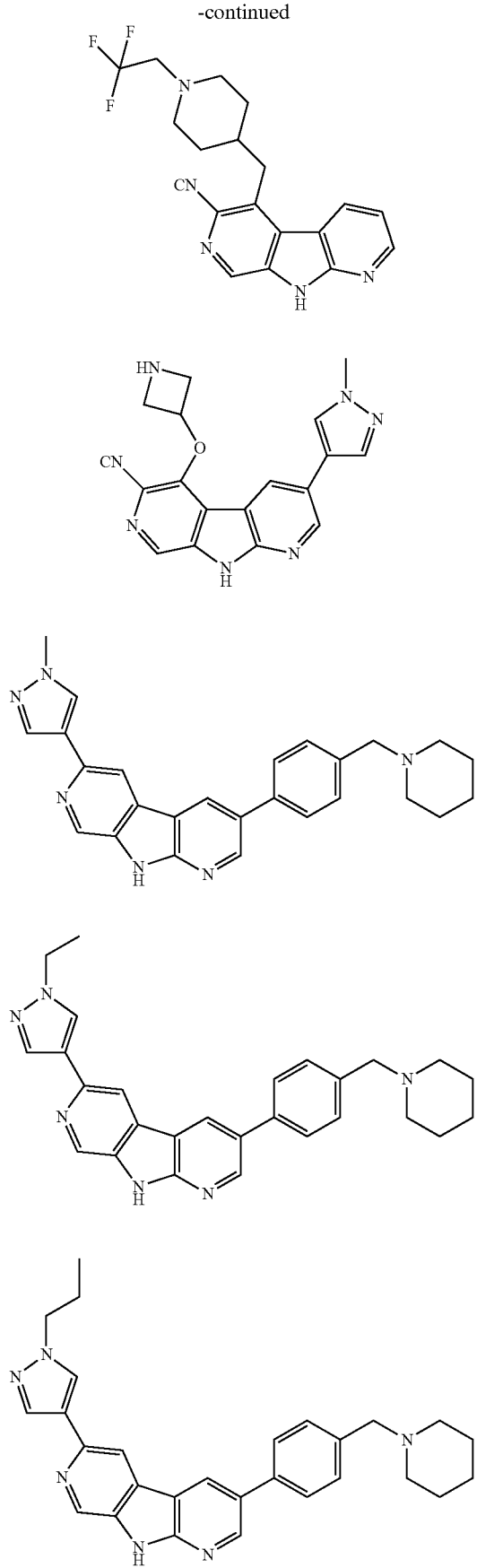

519
-continued
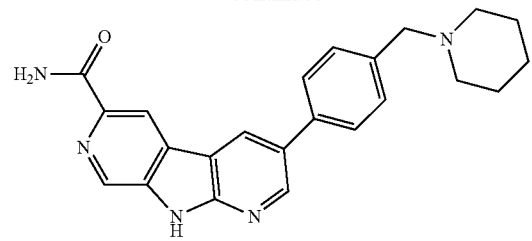
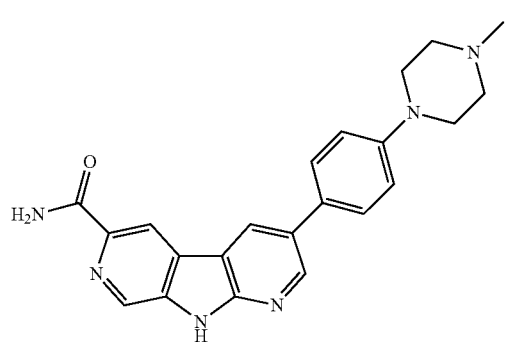
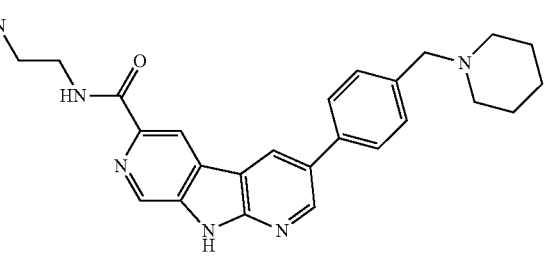
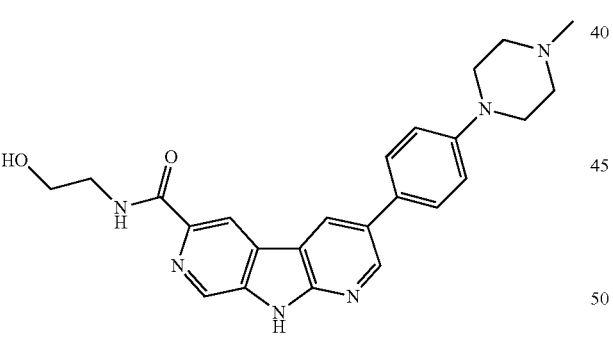
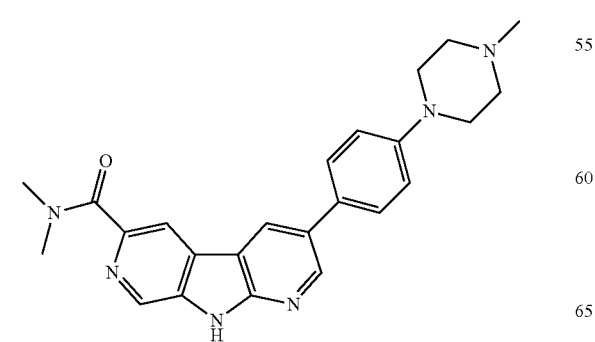
520
-continued
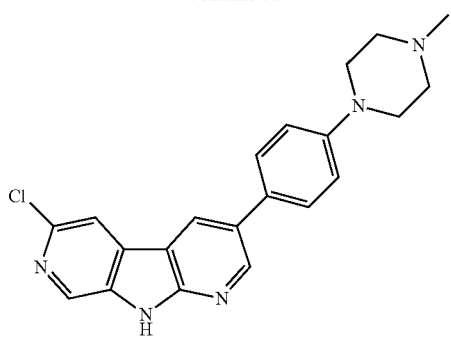
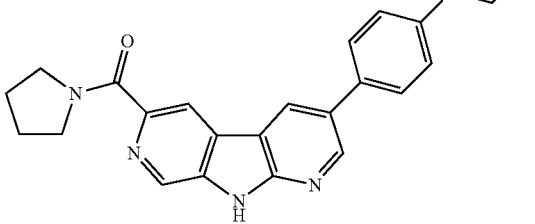
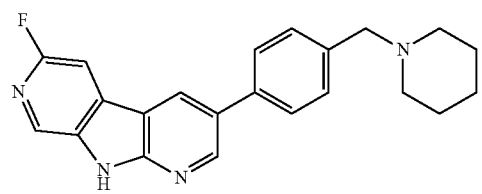
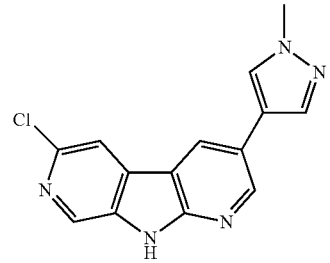
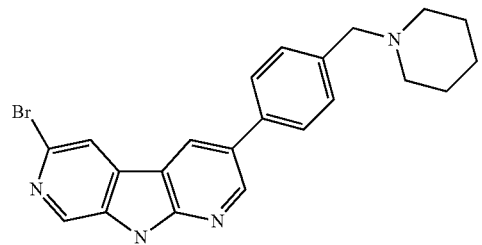
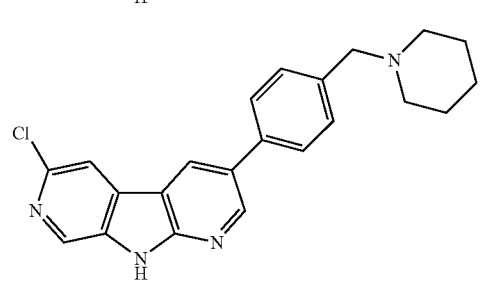

521
-continued
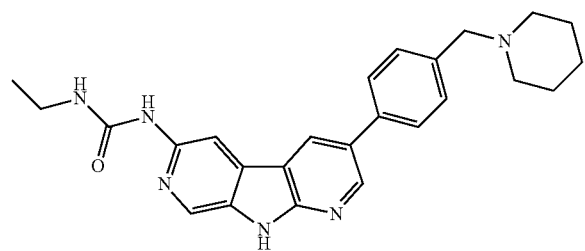
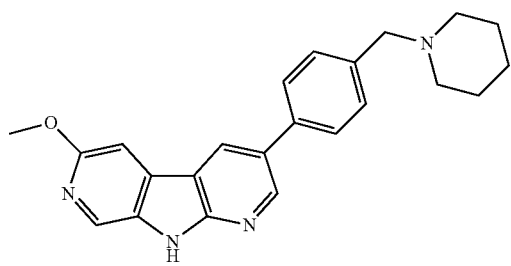
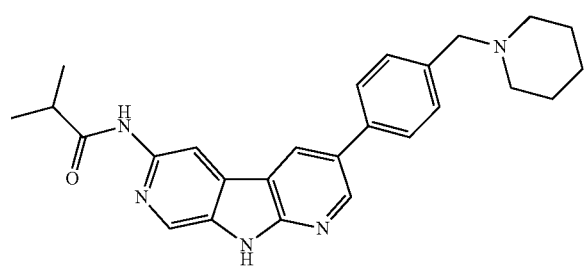
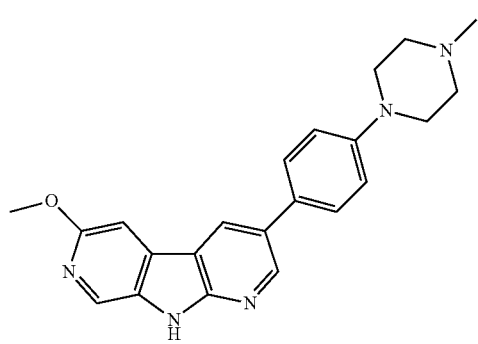
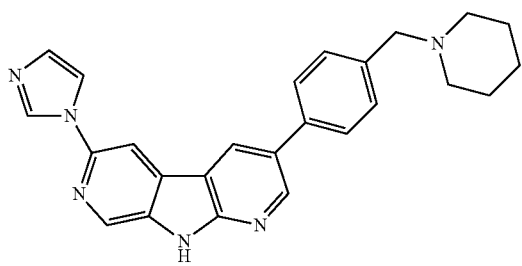
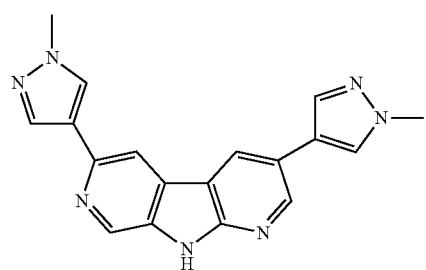
522
-continued
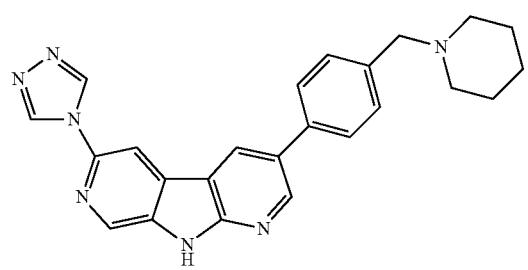
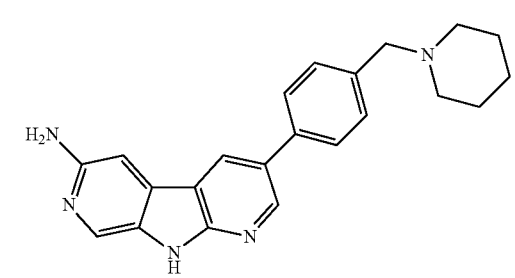
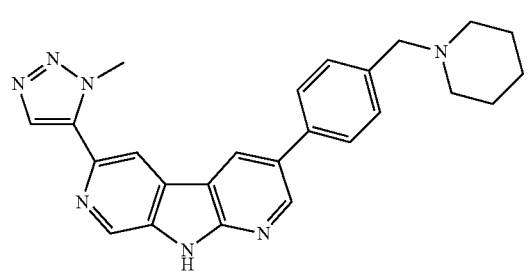
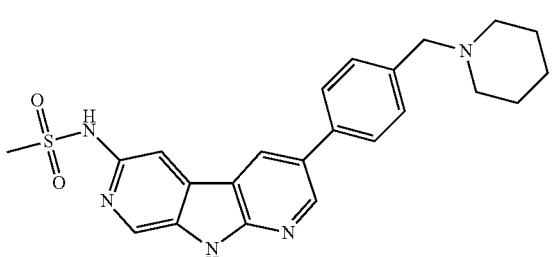
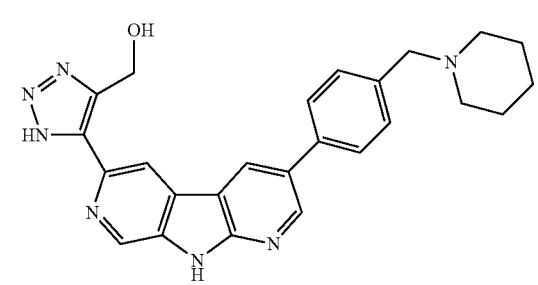
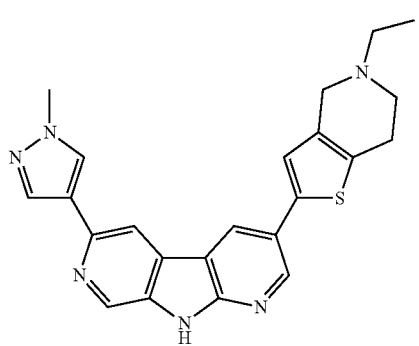

523
-continued
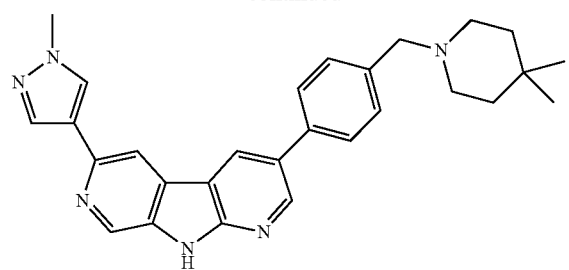
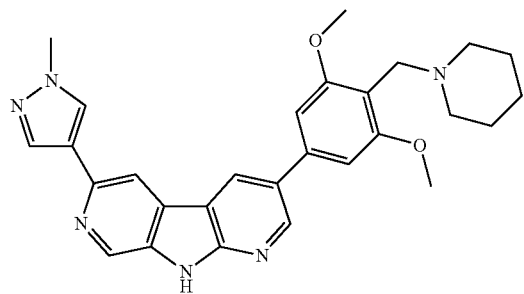
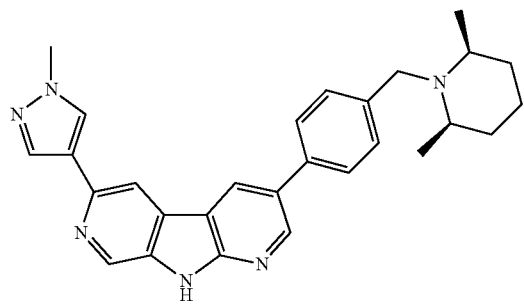
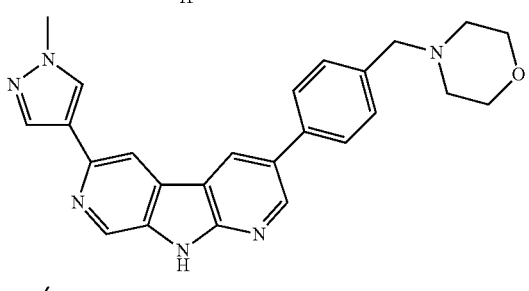
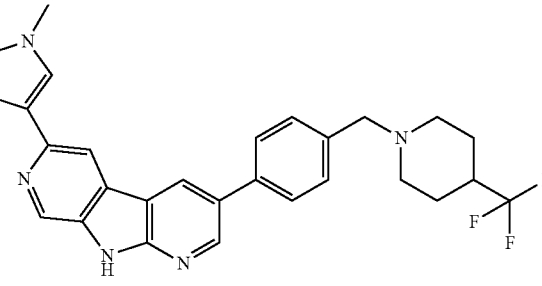
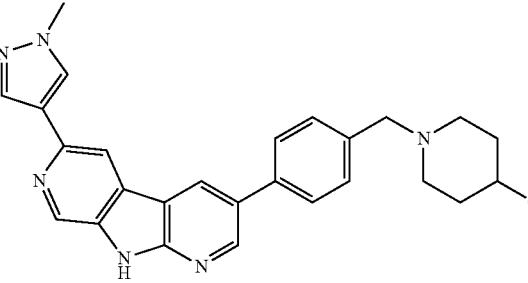
524
-continued
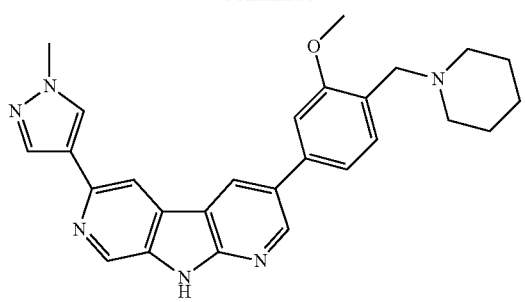
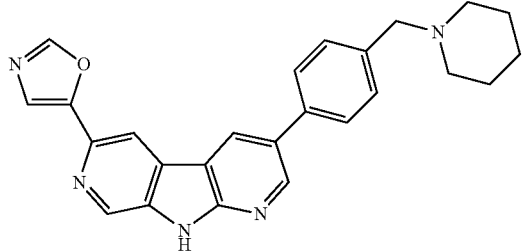
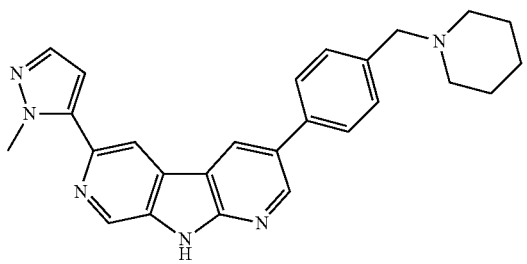
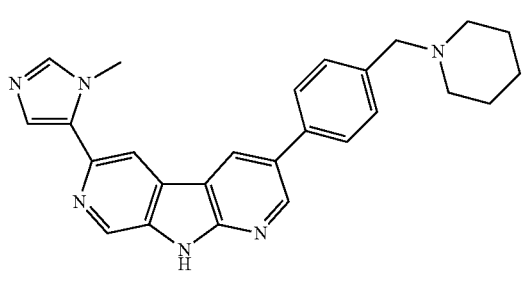
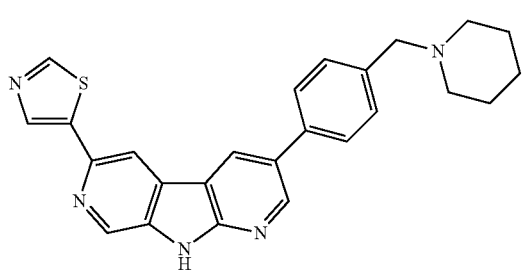
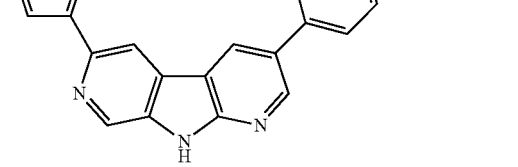

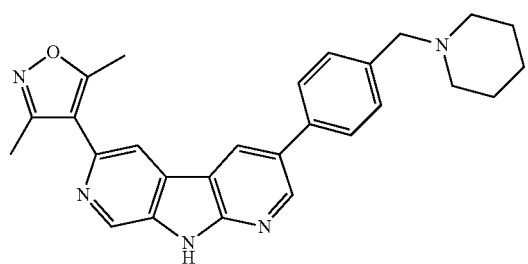
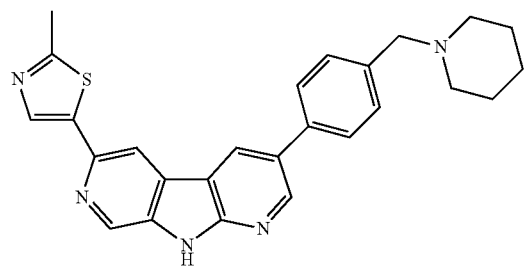
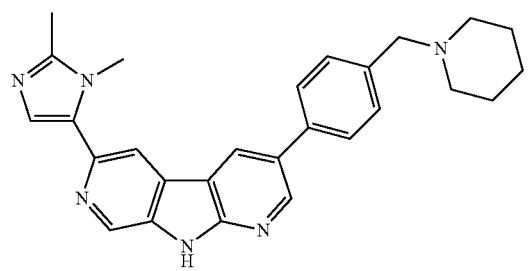
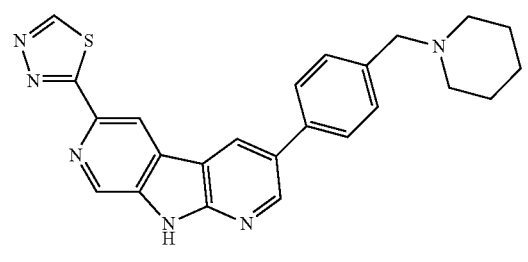
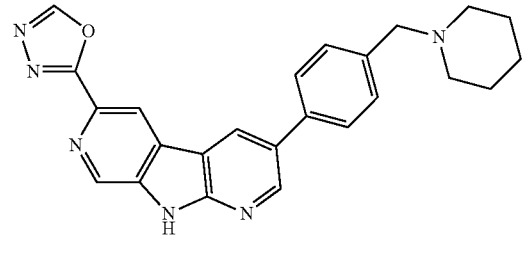
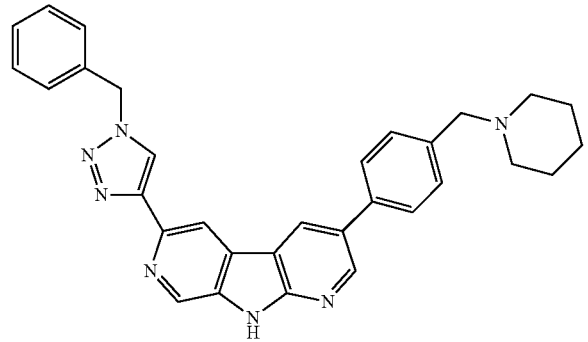
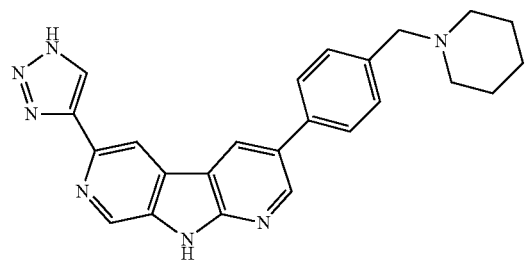
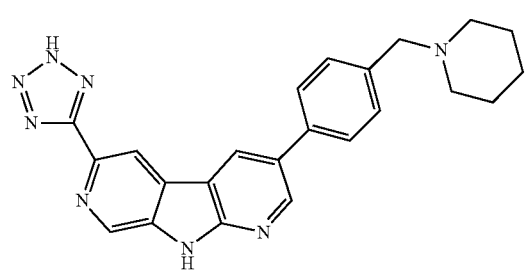
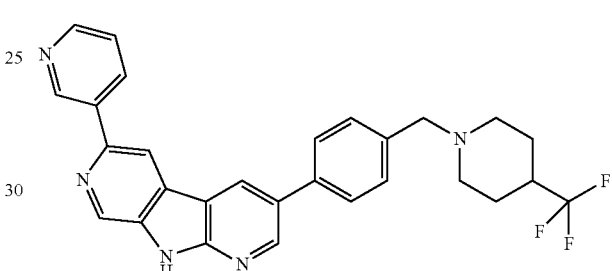
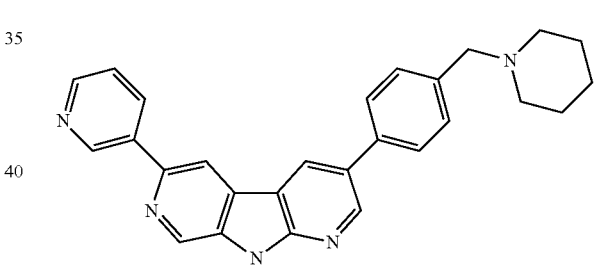
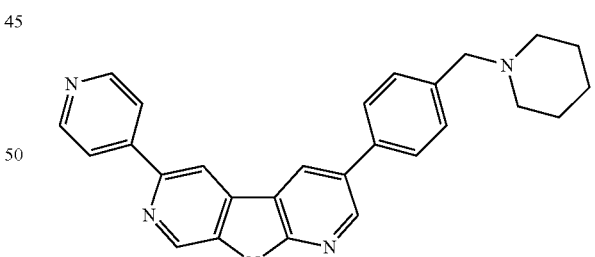
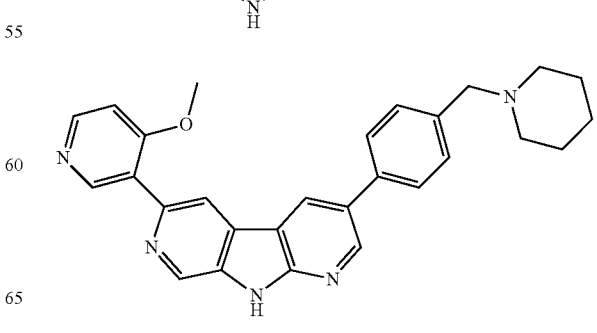

527
-continued
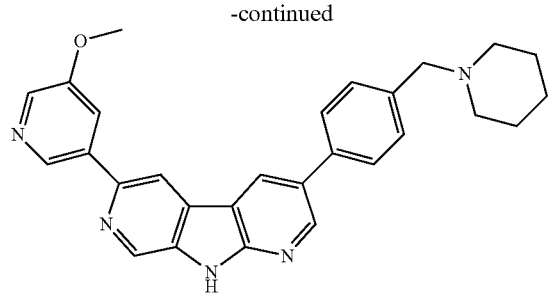
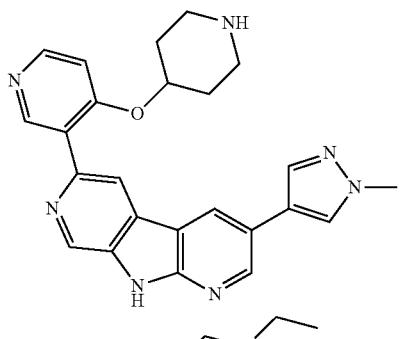
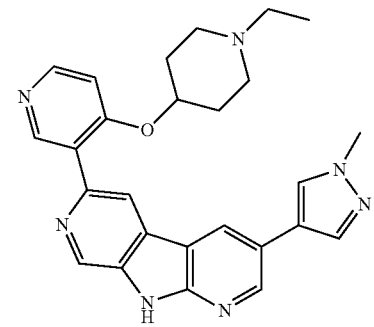
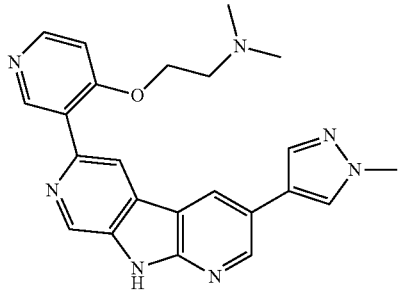
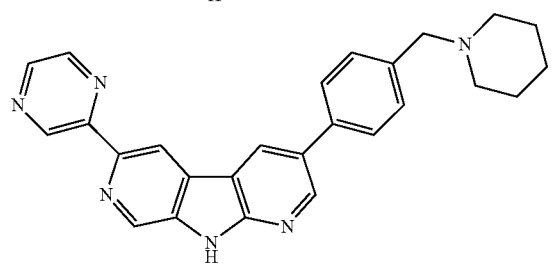
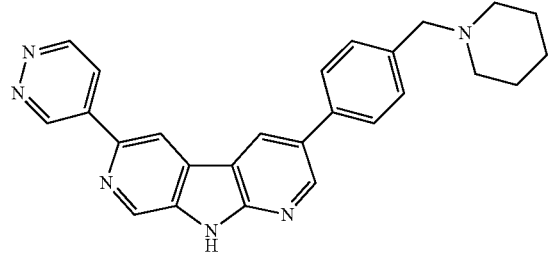
528
-continued
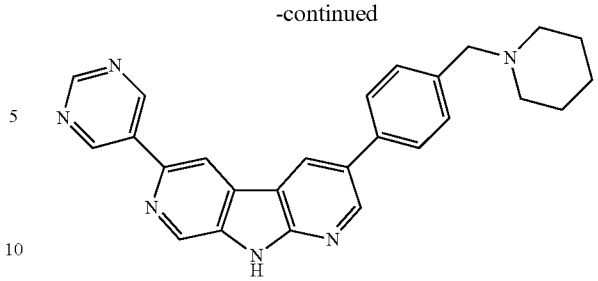
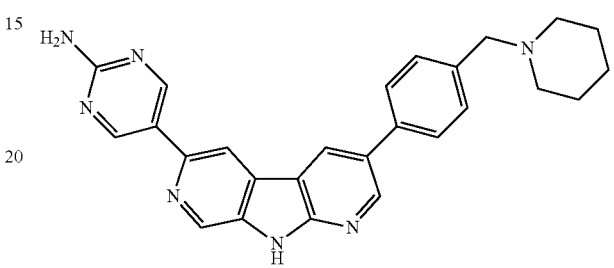
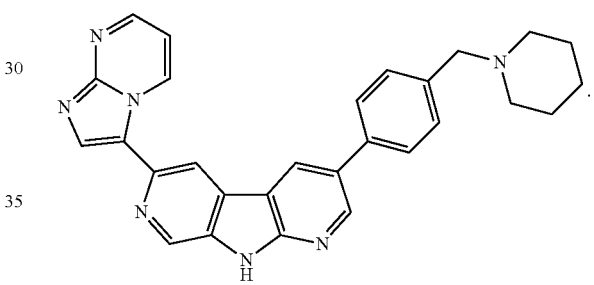
25. The method of claim 1, wherein the compound of formula (I) is:
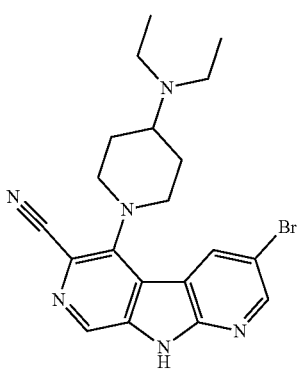 [SMILES: CCN(CC)C1CCN(c2c(C#N)ncc3[nH]c4ncc(Br)cc4c23)CC1]
or a pharmaceutically acceptable salt thereof.
26. The method of claim 1, wherein the compound of formula (I) is:

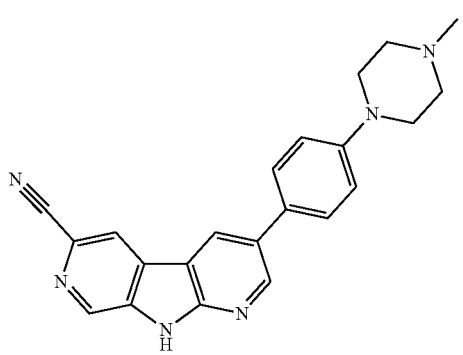 [SMILES: CN1CCN(c2ccc(-c3cnc4[nH]c5cnc(C#N)cc5c4c3)cc2)CC1]

or a pharmaceutically acceptable salt thereof.

27. The method of claim 1, wherein the compound of formula (I) is:

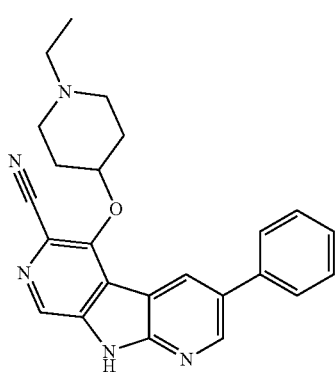 [SMILES: CCN1CCC(Oc2c(C#N)ncc3[nH]c4ncc(-c5ccccc5)cc4c23)CC1]

or a pharmaceutically acceptable salt thereof.

28. The method of claim 1, wherein the compound of formula (I) is:

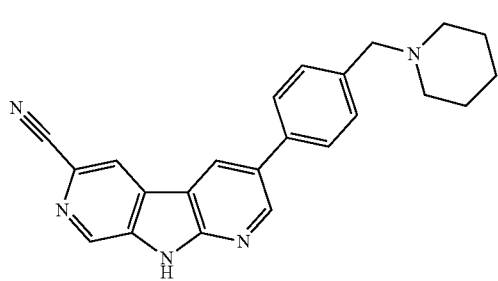 [SMILES: N#Cc1cc2c(cn1)[nH]c1ncc(-c3ccc(CN4CCCCC4)cc3)cc12]

or a pharmaceutically acceptable salt thereof.

29. The method of claim 1, wherein the compound of formula (I) is:

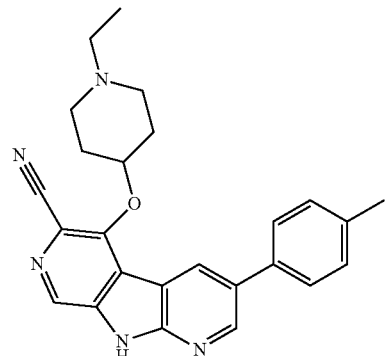

or a pharmaceutically acceptable salt thereof.

30. The method of claim 1, wherein the compound of formula (I) is:

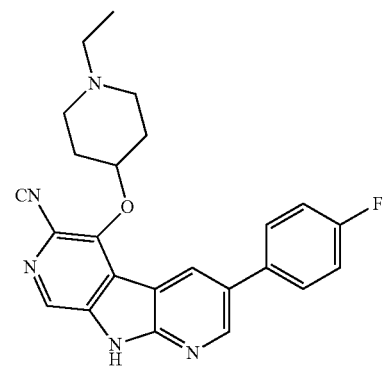

or a pharmaceutically acceptable salt thereof.

31. The method of claim 1, wherein the compound of formula (I) is:

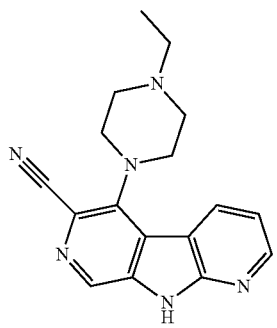 [SMILES: CCN1CCN(c2c(C#N)ncc3[nH]c4ncccc4c23)CC1]

or a pharmaceutically acceptable salt thereof.

32. The method of claim 1, wherein the compound of formula (I) is:

531

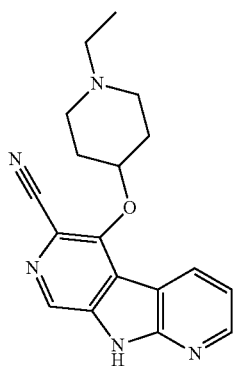 [SMILES: CCN1CCC(Oc2c(C#N)ncc3[nH]c4ncccc4c23)CC1]

or a pharmaceutically acceptable salt thereof.

33. The method of claim 1, wherein the compound of formula (I) is:

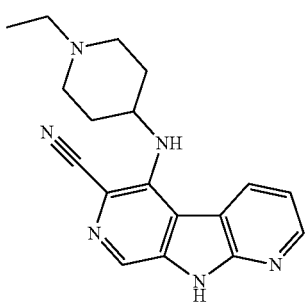 [SMILES: CCN1CCC(Nc2c(C#N)ncc3[nH]c4ncccc4c23)CC1]

or a pharmaceutically acceptable salt thereof.

34. The method of claim 1, wherein the compound of formula (I) is:

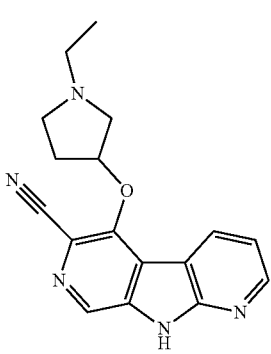 [SMILES: CCN1CCC(Oc2c(C#N)ncc3[nH]c4ncccc4c23)C1]

or a pharmaceutically acceptable salt thereof.

35. The method of claim 1, wherein the compound of formula (I) is:

532

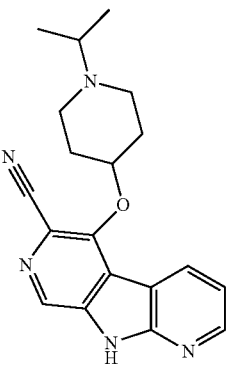 [SMILES: CC(C)N1CCC(Oc2c(C#N)ncc3[nH]c4ncccc4c23)CC1]

or a pharmaceutically acceptable salt thereof.

36. The method of claim 1, wherein the compound of formula (I) is:

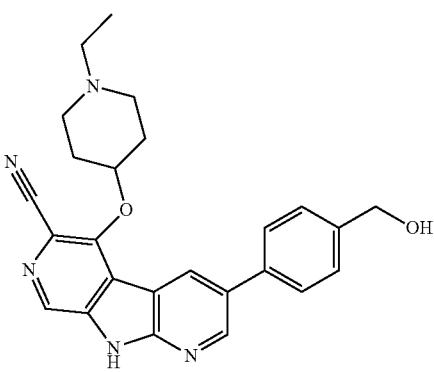 [SMILES: CCN1CCC(Oc2c(C#N)ncc3[nH]c4ncc(-c5ccc(CO)cc5)cc4c23)CC1]

or a pharmaceutically acceptable salt thereof.

37. A method of treating colorectal cancer in a mammal comprising administering to said mammal a therapeutically effective amount of a compound selected from the group consisting of:

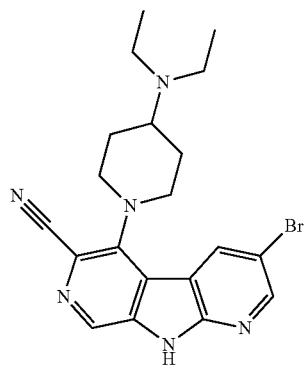

533
-continued
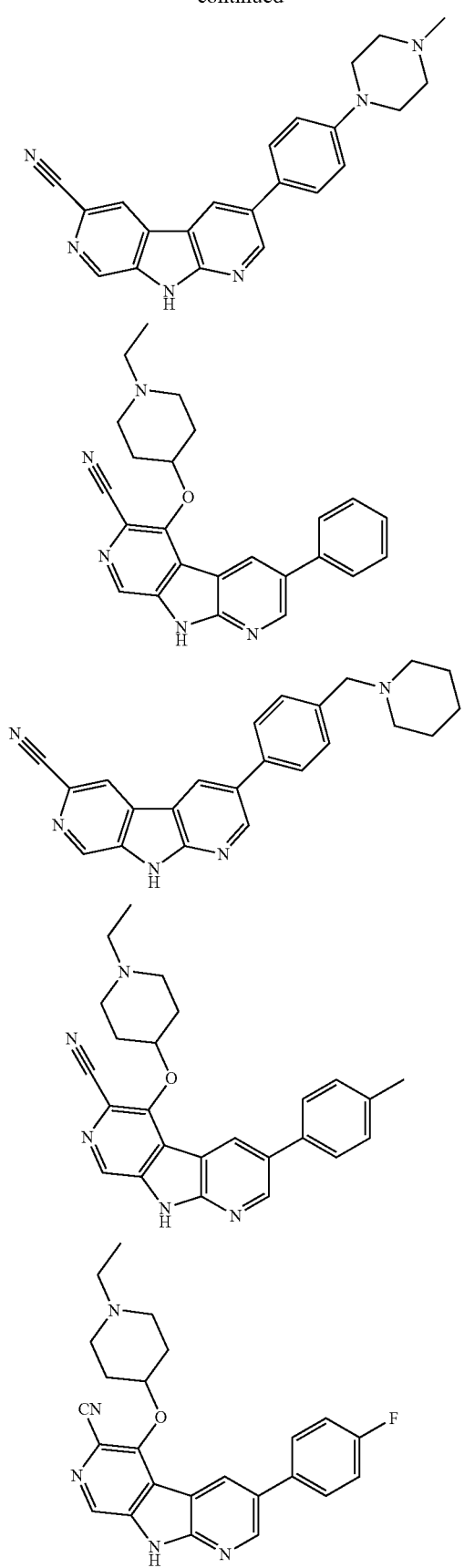
534
-continued
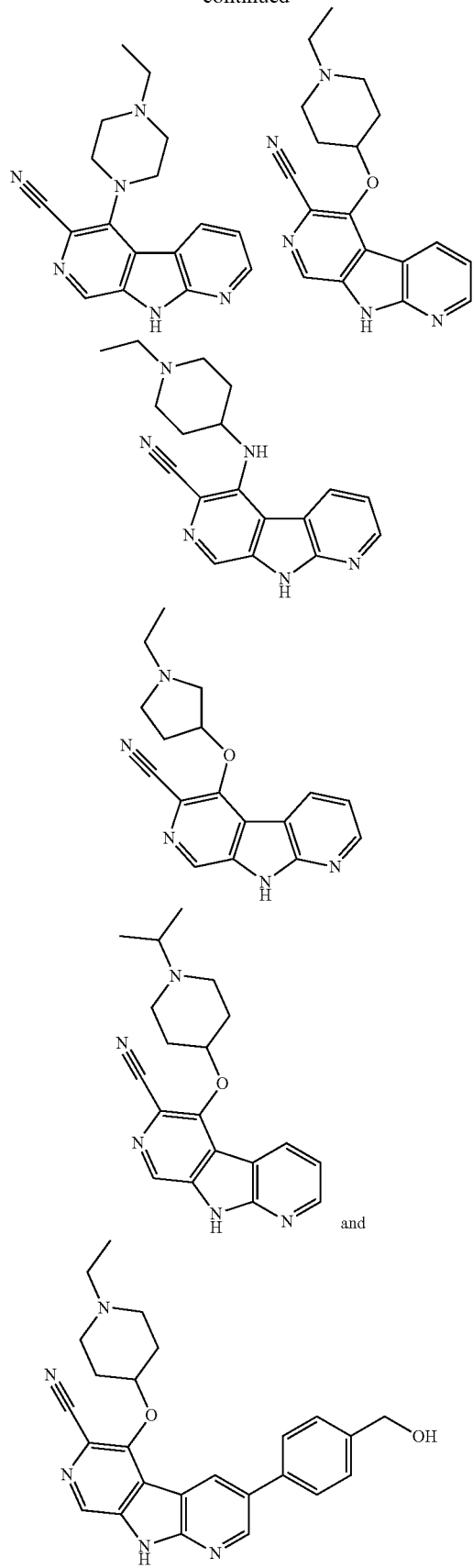
and or a pharmaceutically acceptable salt thereof and a second chemotherapeutic agent selected from the group consisting of Gemcitabine, Irinotecan, SN-38, arabinoside ("Ara-C") and a topoisomerase inhibitor 1 or 2.

* * * * *